(12) United States Patent
Hay et al.

(10) Patent No.: US 7,989,451 B2
(45) Date of Patent: Aug. 2, 2011

(54) TRICYCLIC 1,2,4-TRIAZINE OXIDES AND COMPOSITIONS FOR THERAPEUTIC USE IN CANCER TREATMENTS

(75) Inventors: Michael Patrick Hay, Auckland (NZ); Adrian Blaser, Auckland (NZ); William Alexander Denny, Auckland (NZ); Kevin Owen Hicks, Auckland (NZ); Ho Huat Lee, Auckland (NZ); Karin Pchalek, Auckland (NZ); Frederik Bastiaan Pruijn, Auckland (NZ); Bronwyn Gae Siim, Auckland (NZ); William Robert Wilson, Waiuku (NZ); Shangjin Yang, Auckland (NZ)

(73) Assignee: Auckland Uniservices Limited, Auckland (NZ)

( * ) Notice: Subject to any disclaimer, the term of this patent is extended or adjusted under 35 U.S.C. 154(b) by 630 days.

(21) Appl. No.: 11/887,368

(22) PCT Filed: Mar. 31, 2006

(86) PCT No.: PCT/NZ2006/000064
§ 371 (c)(1), (2), (4) Date: Jun. 27, 2008

(87) PCT Pub. No.: WO2006/104406
PCT Pub. Date: Oct. 5, 2006

(65) Prior Publication Data
US 2009/0186886 A1    Jul. 23, 2009

(30) Foreign Application Priority Data

Mar. 31, 2005 (NZ) ........................... 539152
Sep. 22, 2005 (NZ) ........................... 542556

(51) Int. Cl.
*A01N 43/64* (2006.01)
*A01N 43/62* (2006.01)
*A61K 31/53* (2006.01)
*A61K 31/55* (2006.01)
*C07D 253/08* (2006.01)
*C07D 487/00* (2006.01)

(52) U.S. Cl. ......... 514/243; 514/218; 544/183; 544/184

(58) Field of Classification Search ............... 514/243, 514/218; 544/183, 184
See application file for complete search history.

(56) References Cited

FOREIGN PATENT DOCUMENTS
EP    649 658 A1    4/1995

OTHER PUBLICATIONS

Nagasawa, H., et al; "Design, synthesis and biological activities of antiangiogenic hypoxic cytotoxin, triazine-N-oxide derivatives"; *Comparative Biochemistry and Physiology Part A*; vol. 132; pp. 33-40 (2002).
Hay, M.P., et al; "Structure-activity relationships of 1,2,4-benzotriazine 1,4-dioxides as hypoxia-selective analogues of Tirapazamine"; *J. Med Chem*; vol. 46, pp. 169-182 (2003).
Rauth, A.M., et al; "Bioreductive therapies: an overview of drugs and their mechanisms of action"; *Int. J. Radiation Oncology Biol Phys*; vol. 42, No. 4; pp. 755-762 (1998).

*Primary Examiner* — Sreeni Padmanabhan
*Assistant Examiner* — Samira Jean-Louis
(74) *Attorney, Agent, or Firm* — Nixon & Vanderhye

(57) ABSTRACT

The invention relates to novel tricyclic 1,2,4-triazine-1-oxides and novel tricyclic 1,2,4-triazine-1,4-dioxides of formula I Formula I

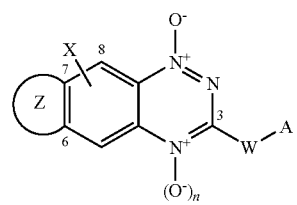

and to related analogues, to their preparation, and to their use as hypoxia-selective drugs and radiosensitizers for cancer therapy, both alone or in combination with radiation and/or other anticancer drugs.

30 Claims, 3 Drawing Sheets

Figure 2:
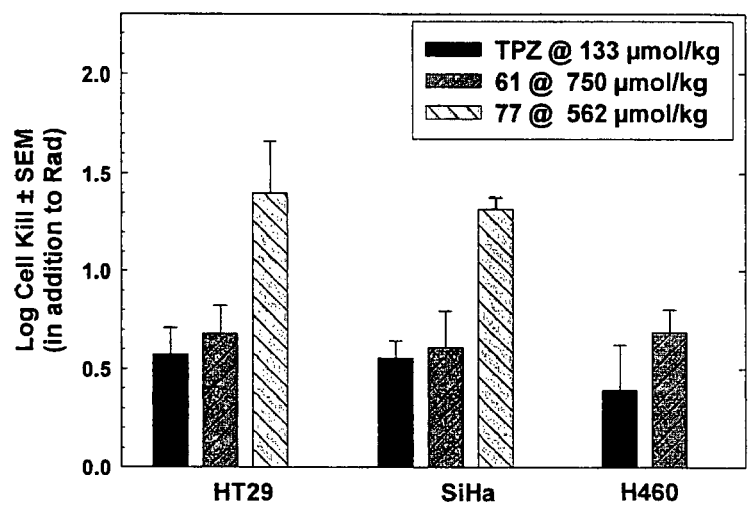

Figure 2. Activity of single dose (0.75 x MTD) TPZ and compounds 61 and 77 against hypoxic cells in three human tumour xenograft models: HT29, human colon carcinoma; SiHa, human cervical carcinoma; H460, non-small cell lung carcinoma.

Figure 3:
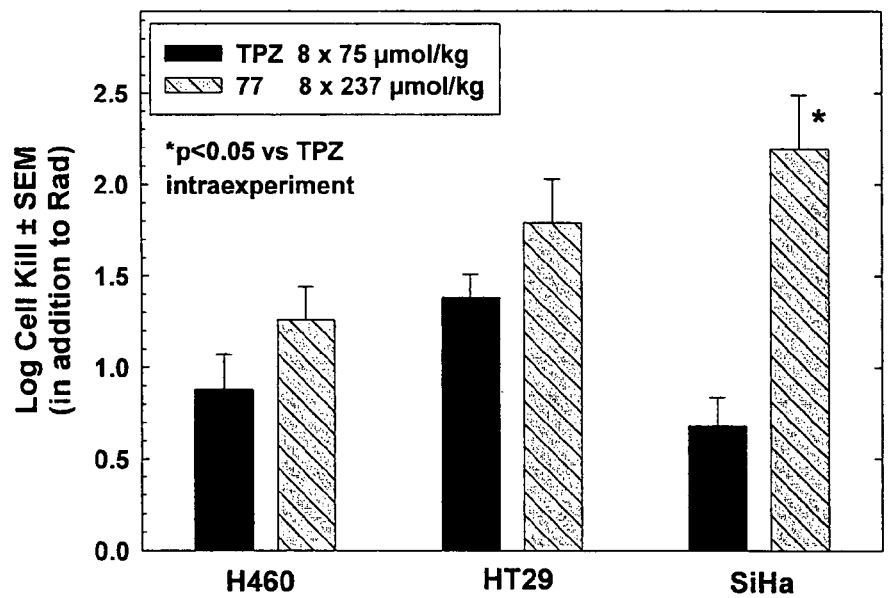

Figure 3. Activity of fractionated dose TPZ and compound 77 against hypoxic cells in three human tumour xenograft models: H460, non-small cell lung carcinoma; HT29, human colon carcinoma; SiHa, human cervical carcinoma. Drugs (1.0 x fractionated MTD) were administered 30 min before each of 8 x 2.5 Gy doses of radiation.

TRICYCLIC 1,2,4-TRIAZINE OXIDES AND COMPOSITIONS FOR THERAPEUTIC USE IN CANCER TREATMENTS

REFERENCE TO GOVERNMENT CONTRACT

This invention was made with government support under grant number PO1 CA 082566, awarded by National Institutes of Health (NIH). The government has certain rights to this invention.

This application is the U.S. National Phase of International Application PCT/NZ2006/000064, filed 31 Mar. 2006, which designated the U.S. PCT/)NZ2006/000064 claims priority to New Zealand Application No. 539152, filed 31 Mar. 2005, and New Zealand Application No. 542556, filed 22 Sep. 2005. The entire content of these applications are incorporated herein by reference.

TECHNICAL FIELD

The present invention relates to novel tricyclic 1,2,4-triazine-1-oxides and novel tricyclic 1,2,4-triazine-1,4-dioxides and related analogues, to their preparation, and to their use as hypoxia-selective drugs and radiosensitizers for cancer therapy, both alone or in combination with radiation and/or other anticancer drugs.

BACKGROUND TO THE INVENTION

Hypoxic cells in tumours are resistant to ionising radiation, and are a major cause of treatment failure in radiation therapy (Movsas et al., *Cancer* 2000, 89, 2018; Rudaf et al., *Radiother. Oncol.* 2000, 57, 31). Hypoxic cells are also considered to compromise response of solid tumours to cytotoxic chemotherapy (Brown and Giaccia, *Cancer Res.* 1998, 58, 1408). The 1,2,4-benzotriazine di-N-oxide tirapazamine (TPZ) is selectively toxic to hypoxic cells because of its metabolic activation to a cytotoxic species by one-electron reduction (Baker et al., *Cancer Res.* 1988, 48, 5947; Laderoute et al., *Biochem. Pharmacol.* 1988, 37, 1487; Brown, *Br. J. Cancer* 1993, 67, 1163). As shown below, the initial one-electron reduction product TPZ* is reoxidised to the starting compound by dioxygen, thereby preventing cytotoxicity in oxic cells.

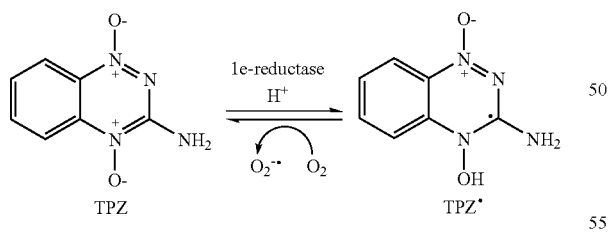

TPZ is therefore of interest for killing hypoxic cells in tumours, thereby improving overall response during radiation therapy. TPZ also has potential for combination with standard cytotoxic chemotherapy (Dorie and Brown, *Cancer Res.* 1993, 53, 4633; Langmuir et al., *Cancer Res.* 1994, 54, 2845; Dorie and Brown, *Cancer Chemother. Pharmacol.* 1997, 39, 361), with (at least) two mechanisms of therapeutic synergy. The first mechanism is the killing of resistant hypoxic cells (analogous to the mechanism of interaction with radiotherapy), and the second is the interference with repair of chemotherapy-induced DNA damage in hypoxic cells as has been demonstrated for cisplatin (Kovacs et al., *Br. J. Cancer* 1999, 80, 1245; Peters et al., *Cancer Res.* 2001, 61, 5425).

TPZ has already demonstrated significant antitumour activity in early phase human clinical trials in combination with ionising radiation and/or cisplatin chemotherapy (for a review, see Denny and Wilson, *Exp. Opin. Invest. Drugs* 2000, 9, 2889), and a multicentre phase III trial of TPZ in combination with cisplatin and radiation for treatment of head and neck tumours is in progress (Rischin et al., *J. Clin. Oncol.* 2005, 23, 79-87). While TPZ shows promising indications of clinical activity, it also displays considerable toxicity, such as neutropenia, thrombocytopenia, nausea, vomiting, diarrhea and muscle cramping. These toxicity limitations preclude administration of doses that are either high enough or sufficient enough to exploit hypoxia fully during cancer treatment. Although the mechanisms of TPZ toxicity towards normal tissues are not fully understood, it is considered that the toxicity arises at least in part because of redox cycling (Elwell et al., *Biochem. Pharmacol.* 1997, 54, 249; Wouters et al., *Cancer Res.* 2001, 61, 145), and is therefore considered to be distinct from the mechanism of hypoxic cell killing.

There have been only limited structure-activity studies on analogues of TPZ. Kelson et al (*Anti-Cancer Drug Design* 1998, 13, 575-592) disclosed compounds of type A, where X was H or an electron-withdrawing group, n was 2 or 3, and R was Me or Et. The main conclusion from this paper was that compounds with dialkylaminoalkyl side chains showed decreased hypoxic selectivity in vitro and comparable but not superior activity to TPZ in vivo. There was no clear relationship between the electron-withdrawing capability of the 7-substituent on the benzo ring and biological activity. Hay and Denny (*Tet. Lett.* 2002, 43, 9569-9571) and Kelson et al (*Anti-Cancer Drug Design* 1998, 13, 575-592) described compounds of type B, where X is H or hydroxyalkyl, n is 2 or 3, and R is OH or OMe, but did not describe any biological activity. Finally, Hay et al. (*J. Med. Chem.* 2003, 46, 169-182) showed, for compounds of type C, where X is $NEt_2$, $NMe_2$, OMe, Me, Cl, F, $CF_3$, $MeSO_2$, $nBuSO_2$, and $NO_2$, that oxic cytotoxicity in SCCVII cells in vitro correlated with one-electron reduction potential [E(1)], but there was not a clear relationship between in vitro hypoxic cytotoxicity and E(1). Further, there was no clear relationship between hypoxia-selectivity and E(1) and none of the compounds displayed improved in vitro activity compared to TPZ.

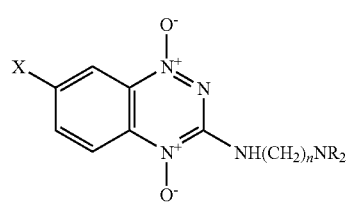

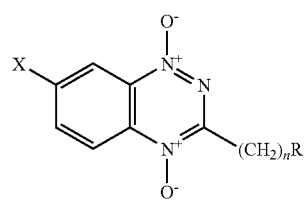

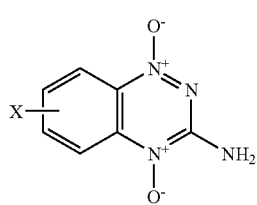

To a large extent the above efforts to identify analogues of TPZ with improved therapeutic activity have focused on compounds with higher reduction potentials, with the expectation that such compounds will be metabolically activated more rapidly than TPZ under hypoxic conditions and will therefore have improved activity against hypoxic cells in tumours.

In the present invention the inventors have unexpectedly found that certain tricyclic triazine compounds of the invention have activity against hypoxic tumor cells in vivo despite having lower reduction potentials than the corresponding compounds in the literature (Kelson et al, *Anti-Cancer Drug Design* 1998, 13, 575-592).

It is an object of the present invention to provide a range of novel tricyclic 1,2,4-triazine-1-oxides and novel tricyclic 1,2,4-triazine-1,4-dioxides and their related analogues, and to provide for their use as potentiators of the cytotoxicity of anticancer drugs and as radiosensitizers and as hypoxia-selective cytotoxins for cancer therapy in combination with radiation and/or with other anticancer agents, or to at least provide the public with a useful choice.

DISCLOSURE OF THE INVENTION

In a first aspect, the present invention provides a compound of Formula I or a pharmacologically acceptable salt thereof,

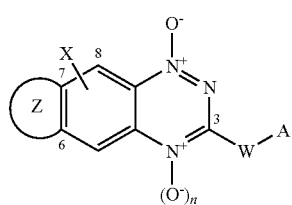

Formula I wherein
n=0 or 1; and
each X at one or more of the available carbons 5-8 on the benzo ring is independently selected from the following groups, H, halo, R, OH, OR, OC(O)H, OC(O)R, OC(O)NH$_2$, OC(O)NHR, OC(O)NRR, OP(O)(OH)$_2$, OP(O)(OR)$_2$, NO$_2$, NH$_2$, NHR, NRR, NHC(O)H, NHC(O)R, NRC(O)R, NHC(O)NH$_2$, NHC(O)NRR, NRC(O)NHR, SH, SR, S(O)H, S(O)R, SO$_2$R, SO$_2$NH$_2$, SO$_2$NHR, SO$_2$NRR, CF$_3$, CN, CO$_2$H, CO$_2$R, CHO, C(O)R, C(O)NH$_2$, C(O)NHR, C(O)NRR, CONHSO$_2$H, CONHSO$_2$R, CONHSO$_2$R, cyclic C$_3$-C$_7$ alkylamino, imidazolyl, C$_1$-C$_6$-alkylpiperazinyl and morpholinyl;

wherein each R is independently selected from an optionally substituted C$_{1-6}$ alkyl, an optionally substituted C$_{2-4}$ alkenyl group or an optionally substituted C$_{3-7}$ cyclic alkyl group, and wherein the one or more optional substituents are each independently selected from; halo, OH, OR$^1$, OC(O)R$^1$, OC(O)NH$_2$, OC(O)NHR$^1$, OC(O)NR$^1$R$^1$, OP(O)(OH)$_2$, OP(O)(OR$^1$)$_2$, NO$_2$, NH$_2$, NHR$^1$, NR$^1$R$^1$, N$^+$(—O$^-$)R$^1$R$^1$, NHC(O)H, NHC(O)R$^1$, NR$^1$C(O)R$^1$, NHC(O)NH$_2$, NHC(O)NR$^1$R$^1$, NR$^1$C(O)NHR$^1$, SH, SR$^1$, S(O)H, S(O)R$^1$, SO$_2$R$^1$, SO$_2$NH$_2$, SO$_2$NHR$^1$, SO$_2$NR$^1$R$^1$, CF$_3$, CN, CO$_2$H, CO$_2$R$^1$, CHO, C(O)R$^1$, C(O)NH$_2$, C(O)NHR$^1$, C(O)NR$^1$R$^1$, C(O)NHSO$_2$R$^1$, C(O)NR$^1$SO$_2$R$^1$, cyclic C$_3$-C$_7$ alkylamino, imidazolyl, piperazinyl, morpholinyl, piperidinyl, azepanyl, pyrrolidinyl and azetidinyl; wherein each of the groups imidazolyl, piperazinyl, morpholinyl, piperidinyl, azepanyl, pyrrolidinyl and azetidinyl are optionally substituted by one or more R$^1$ groups, halo, OH, OR$^1$, OC(O)R$^1$, OC(O)NH$_2$, OC(O)NHR$^1$, OC(O)NR$^1$R$^1$, OP(O)(OH)$_2$, OP(O)(OR$^1$)$_2$, NO$_2$, NH$_2$, NHR$^1$, NR$^1$R$^1$, N$^+$(—O$^-$)R$^1$R$^1$, NHC(O)H, NHC(O)R$^1$, NR$^1$C(O)R$^1$, NHC(O)NH$_2$, NHC(O)NR$^1$R$^1$, NR$^1$C(O)NHR$^1$, SH, SR$^1$, S(O)H, S(O)R$^1$, SO$_2$R$^1$, SO$_2$NH$_2$, SO$_2$NHR$^1$, SO$_2$NR$^1$R$^1$, CF$_3$, CN, CO$_2$H, CO$_2$R$^1$, CHO, C(O)R$^1$, C(O)NH$_2$, C(O)NHR$^1$, C(O)NR$^1$R$^1$, CONHSO$_2$H, C(O)NHSO$_2$R$^1$ and C(O)NR$^1$SO$_2$R$^1$;

R can also represent an optionally substituted C$_{4-8}$ aryl or an optionally substituted heteroaryl group having up to 12 carbon atoms, and wherein the one or more optional substituents are each independently selected from; halo, OH, OR$^1$, OC(O)R$^1$, OC(O)NH$_2$, OC(O)NHR$^1$, OC(O)NR$^1$R$^1$, OP(O)(OH)$_2$, OP(O)(OR$^1$)$_2$, NO$_2$, NH$_2$, NHR$^1$, NR$^1$R$^1$, N$^+$(—O$^-$)R$^1$R$^1$, NHC(O)H, NHC(O)R$^1$, NR$^1$C(O)R$^1$, NHC(O)NH$_2$, NHC(O)NR$^1$R$^1$, NR$^1$C(O)NHR$^1$, SH, SR$^1$, S(O)H, S(O)R$^1$, SO$_2$R$^1$, SO$_2$NH$_2$, SO$_2$NHR$^1$, SO$_2$NR$^1$R$^1$, CF$_3$, CN, CO$_2$H, CO$_2$R$^1$, CHO, C(O)R$^1$, C(O)NH$_2$, C(O)NHR$^1$, C(O)NR$^1$R$^1$, C(O)NHSO$_2$R$^1$, C(O)NR$^1$SO$_2$R$^1$, cyclic C$_3$-C$_7$ alkylamino, imidazolyl, piperazinyl, morpholinyl, piperidinyl, azepanyl, pyrrolidinyl and azetidinyl; wherein each of the groups imidazolyl, piperazinyl, morpholinyl, piperidinyl, azepanyl, pyrrolidinyl and azetidinyl are optionally substituted by one or more R$^1$ groups, halo, OH, OR$^1$, OC(O)R$^1$, OC(O)NH$_2$, OC(O)NHR$^1$, OC(O)NR$^1$R$^1$, OP(O)(OH)$_2$, OP(O)(OR$^1$)$_2$, NO$_2$, NH$_2$, NHR$^1$, NR$^1$R$^1$, N$^+$(—O$^-$)R$^1$R$^1$, NHC(O)H, NHC(O)R$^1$, NR$^1$C(O)R$^1$, NHC(O)NH$_2$, NHC(O)NR$^1$R$^1$, NR$^1$C(O)NHR$^1$, SH, SR$^1$, S(O)H, S(O)R$^1$, SO$_2$R$^1$, SO$_2$NH$_2$, SO$_2$NHR$^1$, SO$_2$NR$^1$R$^1$, CF$_3$, CN, CO$_2$H, CO$_2$R$^1$, CHO, C(O)R$^1$, C(O)NH$_2$, C(O)NHR$^1$, C(O)NR$^1$R$^1$, CONHSO$_2$H, C(O)NHSO$_2$R$^1$ and C(O)NR$^1$SO$_2$R$^1$; and wherein each heteroaryl group contains one or more heteroatoms in its ring system which are each independently selected from O, N or S;

wherein each R$^1$ is independently selected from an optionally substituted C$_{1-6}$ alkyl or an optionally substituted C$_{2-6}$ alkenyl group and wherein the one or more optional substituents are each independently selected from; halo, OH, OR$^2$, OC(O)R$^2$, OC(O)NH$_2$, OC(O)NHR$^2$, OC(O)NR$^2$R$^2$, OP(O)(OH)$_2$, OP(O)(OR$^2$)$_2$, NO$_2$, NH$_2$, NHR$^2$, NR$^2$R$^2$, N$^+$(—O$^-$)R$^2$R$^2$, NHC(O)H, NHC(O)R$^2$, NR$^2$C(O)R$^2$, NHC(O)NH$_2$, NHC(O)NR$^2$R$^2$, NR$^2$C(O)NHR$^2$, SH, SR$^2$, S(O)H, S(O)R$^2$, SO$_2$R$^2$, SO$_2$NH$_2$, SO$_2$NHR$^2$, SO$_2$NR$^2$R$^2$, CF$_3$, CN, CO$_2$H, CO$_2$R$^2$, CHO, C(O)R$^2$, C(O)NH$_2$, C(O)NHR$^2$, C(O)NR$^2$R$^2$, C(O)NHSO$_2$R$^2$, C(O)NR$^2$SO$_2$R$^2$, cyclic C$_3$-C$_7$ alkylamino, imidazolyl, piperazinyl, morpholinyl, piperidinyl, azepanyl, pyrrolidinyl and azetidinyl; wherein each of the groups imidazolyl, piperazinyl, morpholinyl, piperidinyl, azepanyl, pyrrolidinyl and azetidinyl are optionally substituted by one or more R$^2$ groups, halo, OH, OR$^2$, OC(O)R$^2$, OC(O)NH$_2$, OC(O)NHR$^2$, OC(O)NR$^2$R$^2$, OP(O)(OH)$_2$, OP(O)(OR$^2$)$_2$, NO$_2$, NH$_2$, NHR$^2$, $NR^2R^2$, $N^+(-O^-)R^2R^2$, $NHC(O)H$, $NHC(O)R^2$, $NR^2C(O)R^2$, $NHC(O)NH_2$, $NHC(O)NR^2R^2$, $NR^2C(O)NHR^2$, $SH$, $SR^2$, $S(O)H$, $S(O)R^2$, $SO_2R^2$, $SO_2NH_2$, $SO_2NHR^2$, $SO_2NR^2R^2$, $CF_3$, $CN$, $CO_2H$, $CO_2R^2$, $CHO$, $C(O)R^2$, $C(O)NH_2$, $C(O)NHR^2$, $C(O)NR^2R^2$, $CONHSO_2H$, $C(O)NHSO_2R^2$ and $C(O)NR^2SO_2R^2$;

wherein each $R^2$ is independently selected from $C_{1-6}$ alkyl, $C_{2-6}$ alkenyl, OH, OMe, $NO_2$, $NH_2$, $CF_3$, CN, $CO_2H$ or SH; and wherein W represents NH, NMe, $CH_2$, SO, $SO_2$, or O; and A represents H or an optionally substituted $C_{1-6}$ alkyl group or an optionally substituted $C_{2-6}$ alkenyl group or an optionally substituted $C_{3-7}$ cyclic alkyl group wherein the one or more optional substituents are each independently selected from halo, OH, $OR^3$, $OC(O)R^3$, $OC(O)NH_2$, $OC(O)NHR^3$, $OC(O)NR^3R^3$, $OP(O)(OH)_2$, $OP(O)(OR^3)_2$, $NO_2$, $NH_2$, $NHR^3$, $NR^3R^3$, $N^+(-O^-)R^3R^3$, $NHC(O)H$, $NHC(O)R^3$, $NR^2C(O)R^3$, $NHC(O)NH_2$, $NHC(O)NR^3R^3$, $NR^2C(O)NHR^3$, SH, $SR^3$, $S(O)H$, $S(O)R^3$, $SO_2R^3$, $SO_2NH_2$, $SO_2NHR^3$, $SO_2NR^3R^3$, $CF_3$, CN, $CO_2H$, $CO_2R$, CHO, $C(O)R^3$, $C(O)NH_2$, $C(O)NHR^3$, $C(O)NR^3R^3$, $CONHSO_2H$, $C(O)NHSO_2R^3$, $C(O)NR^3SO_2R^3$, cyclic $C_3$-$C_7$ alkylamino, imidazolyl, piperazinyl, morpholinyl, piperidinyl, azepanyl, pyrrolidinyl and azetidinyl; wherein each of the groups imidazolyl, piperazinyl, morpholinyl, piperidinyl, azepanyl, pyrrolidinyl and azetidinyl are optionally substituted by one or more $R^3$ groups, halo, OH, $OR^3$, $OC(O)R^3$, $OC(O)NH_2$, $OC(O)NHR^3$, $OC(O)NR^3R^3$, $OP(O)(OH)_2$, $OP(O)(OR^3)_2$, $NO_2$, $NH_2$, $NHR^3$, $NR^3R^3$, $N^+(-O^-)R^3R^3$, $NHC(O)H$, $NHC(O)R^3$, $NR^3C(O)R^3$, $NHC(O)NH_2$, $NHC(O)NR^3R^3$, $NR^3C(O)NHR^3$, SH, $SR^3$, $S(O)H$, $S(O)R^3$, $SO_2R^3$, $SO_2NH_2$, $SO_2NHR^3$, $SO_2NR^3R^3$, $CF_3$, CN, $CO_2H$, $CO_2R^3$, CHO, $C(O)R^3$, $C(O)NH_2$, $C(O)NHR^3$, $C(O)NR^3R^3$, $CONHSO_2H$, $C(O)NHSO_2R^3$, and $C(O)NR^3SO_2R^3$; or A represents an optionally substituted $C_4$-$C_8$ aryl or an optionally substituted heteroaryl group having up to 12 carbon atoms, and wherein the one or more optional substituents are each independently selected from; halo, OH, $OR^3$, $OC(O)R^3$, $OC(O)NH_2$, $OC(O)NHR^3$, $OC(O)NR^3R^3$, $OP(O)(OH)_2$, $OP(O)(OR^3)_2$, $NO_2$, $NH_2$, $NHR^3$, $NR^3R^3$, $N^+(-O^-)R^3R^3$, $NHC(O)H$, $NHC(O)R^3$, $NR^2C(O)R^3$, $NHC(O)NH_2$, $NHC(O)NR^3R^3$, $NR^2C(O)NHR^3$, SH, $SR^3$, $S(O)H$, $S(O)R^3$, $SO_2R^3$, $SO_2NH_2$, $SO_2NHR^3$, $SO_2NR^3R^3$, $CF_3$, CN, $CO_2H$, $CO_2R$, CHO, $C(O)R^3$, $C(O)NH_2$, $C(O)NHR^3$, $C(O)NR^3R^3$, $CONHSO_2H$, $C(O)NHSO_2R^3$, $C(O)NR^3SO_2R^3$, cyclic $C_3$-$C_7$ alkylamino, imidazolyl, piperazinyl, morpholinyl, piperidinyl, azepanyl, pyrrolidinyl and azetidinyl; wherein each of the groups imidazolyl, piperazinyl, morpholinyl, piperidinyl, azepanyl, pyrrolidinyl and azetidinyl are optionally substituted by one or more $R^3$ groups, halo, OH, $OR^3$, $OC(O)R^3$, $OC(O)NH_2$, $OC(O)NHR^3$, $OC(O)NR^3R^3$, $OP(O)(OH)_2$, $OP(O)(OR^3)_2$, $NO_2$, $NH_2$, $NHR^3$, $NR^3R^3$, $N^+(-O^-)R^3R^3$, $NHC(O)H$, $NHC(O)R^3$, $NR^3C(O)R^3$, $NHC(O)NH_2$, $NHC(O)NR^3R^3$, $NR^3C(O)NHR^3$, SH, $SR^3$, $S(O)H$, $S(O)R^3$, $SO_2R^3$, $SO_2NH_2$, $SO_2NHR^3$, $SO_2NR^3R^3$, $CF_3$, CN, $CO_2H$, $CO_2R^3$, CHO, $C(O)R^3$, $C(O)NH_2$, $C(O)NHR^3$, $C(O)NR^3R^3$, $CONHSO_2H$, $C(O)NHSO_2R^3$ and $C(O)NR^3SO_2R^3$; and each heteroaryl group includes one or more heteroatoms in its ring system which are each independently selected from O, N or S;

wherein each $R^3$ is independently selected from an optionally substituted $C_{1-6}$ alkyl or an optionally substituted $C_{2-6}$ alkenyl group and wherein the one or more optional substituents are each independently selected from; halo, OH, $OR^4$, $OC(O)R^4$, $OC(O)NH2$, $OC(O)NHR^4$, $OC(O)NR^4R^4$, $OP(O)(OH)_2$, $OP(O)(OR^4)_2$, $NO_2$, $NH_2$, $NHR^4$, $NR^4R^4$, $N^+(-O^-)R^4R^4$, $NHC(O)H$, $NHC(O)R^4$, $NR^4C(O)R^4$, $NHC(O)NH_2$, $NHC(O)NR^4R^4$, $NR^4C(O)NHR^4$, SH, $SR^4$, $S(O)H$, $S(O)R^4$, $SO_2R^4$, $SO_2NH_2$, $SO_2NHR^4$, $SO_2NR^4R^4$, $CF_3$, CN, $CO_2H$, $CO_2R$, CHO, $C(O)R^4$, $C(O)NH_2$, $C(O)NHR^4$, $C(O)NR^4R^4$, $CONHSO_2H$, $C(O)NHSO_2R^4$, $C(O)NR^4SO_2R^4$, cyclic $C_3$-$C_7$ alkylamino, imidazolyl, piperazinyl, morpholinyl, piperidinyl, azepanyl, pyrrolidinyl and azetidinyl; wherein each of the groups imidazolyl, piperazinyl, morpholinyl, piperidinyl, azepanyl, pyrrolidinyl and azetidinyl are optionally substituted by one or more $R^4$ groups, halo, OH, $OR^4$, $OC(O)R^4$, $OC(O)NH2$, $OC(O)NHR^4$, $OC(O)NR^4R^4$, $OP(O)(OH)_2$, $OP(O)(OR^4)_2$, $NO_2$, $NH_2$, $NHR^4$, $NR^4R^4$, $N^+(-O^-)R^4R^4$, $NHC(O)H$, $NHC(O)R^4$, $NR^4C(O)R^4$, $NHC(O)NH_2$, $NHC(O)NR^4R^4$, $NR^4C(O)NHR^4$, SH, $SR^4$, $S(O)H$, $S(O)R^4$, $SO_2R^4$, $SO_2NH_2$, $SO_2NHR^4$, $SO_2NR^4R^4$, $CF_3$, CN, $CO_2H$, $CO_2R$, CHO, $C(O)R^4$, $C(O)NH_2$, $C(O)NHR^4$, $C(O)NR^4R^4$, $CONHSO_2H$, $C(O)NHSO_2R^4$ and $C(O)NR^4SO_2R^4$; wherein each $R^4$ is independently selected from $C_{1-4}$ alkyl, $C_{2-4}$ alkenyl, halo, OH, $OC_1$-$C_4$, $NO_2$, $NH_2$, $CF_3$, CN, $CO_2H$, COCN or SH;

or wherein W and A together represent H or halo;

Z represents an optionally substituted 4-8 membered saturated ring system fused to the benzo ring in the 6,7-positions or the 7,8-positions;

wherein the one or more optional substituents of the ring system are each independently selected from halo, $R^5$, OH, $OR^5$, $OC(O)R^5$, $OC(O)NH_2OC(O)NHR^5$, $OC(O)NR^5R^5$, $OP(O)(OH)_2$, $OP(O)(OR^5)_2$, $NO_2$, $NH_2$, $NHR^5$, $NR^5R^5$, $N^+(-O^-)R^5R^5$, $NHC(O)H$, $NHC(O)R^5$, $NR^5C(O)R^5$, $NHC(O)NH_2$, $NHC(O)NR^5R^5$, $NR^5C(O)NHR^5$, SH, $SR^5$, $S(O)H$, $S(O)R^5$, $SO_2R^5$, $SO_2NH_2$, $SO_2NHR^5$, $SO_2NR^5R^5$, $CF_3$, CN, $CO_2H$, $CO_2R$, CHO, $C(O)R^5$, $C(O)NH_2$, $C(O)NHR^5$, $C(O)NR^5R^5$, $C(O)NHSO_2H$, $C(O)NHSO_2R^5$, $C(O)NR^5SO_2R^5$, cyclic $C_3$-$C_7$ alkylamino, imidazolyl, piperazinyl, morpholinyl, piperidinyl, azepanyl, pyrrolidinyl and azetidinyl; wherein each of the groups imidazolyl, piperazinyl, morpholinyl, piperidinyl, azepanyl, pyrrolidinyl and azetidinyl are optionally substituted by one or more $R^5$ groups halo, $R^5$, OH, $OR^5$, $OC(O)R^5$, $OC(O)NH_2OC(O)NHR^5$, $OC(O)NR^5R^5$, $OP(O)(OH)_2$, $OP(O)(OR^5)_2$, $NO_2$, $NH_2$, $NHR^5$, $NR^5R^5$, $N^+(-O^-)R^5R^5$, $NHC(O)H$, $NHC(O)R^5$, $NR^5C(O)R^5$, $NHC(O)NH_2$, $NHC(O)NR^5R^5$, $NR^5C(O)NHR^5$, SH, $SR^5$, $S(O)H$, $S(O)R^5$, $SO_2R^5$, $SO_2NH_2$, $SO_2NHR^5$, $SO_2NR^5R^5$, $(R^5)_3SiO$, $CF_3$, CN, $CO_2H$, $CO_2R$, CHO, $C(O)R^5$, $C(O)NH_2$, $C(O)NHR^5$, $C(O)NR^5R^5$, $C(O)NHSO_2H$, $C(O)NHSO_2R^5$ and $C(O)NR^5SO_2R^5$ wherein each $R^5$ is independently selected from an optionally substituted $C_{1-4}$ alkyl or an optionally substituted $C_{2-6}$ alkenyl group or an optionally substituted $C_{3-7}$ cyclic alkyl group and wherein the one or more optional substituents are each independently selected from; halo, $R^6$, OH, $OR^6$, $OC(O)R^6$, $OC(O)NHR^6$, $OC(O)NR^6R^6$, $OP(O)(OH)_2$, $OP(O)(OR^6)_2$, $NO_2$, $NH_2$, $NHR^6$, $NR^6R^6$, $N^+(-O^-)R^6R^6$, $NHC(O)R^6$, $NR^6C(O)R^6$, $NHC(O)NR^6R^6$, $NR^6C(O)NHR^6$, SH, $SR^8$, $S(O)R^6$, $SO_2R^6$, $SO_2NHR^6$, $SO_2NR^6R^6$, $CF_3$, CN, $CO_2H$, $CO_2R$, CHO, $C(O)R^6$, $C(O)NH_2$, $C(O)NHR^6$, $C(O)NR^6R^6$, $C(O)NHSO_2R^6$, $C(O)NR^6SO_2R^6$, cyclic $C_3$-$C_7$ alkylamino, imidazolyl, piperazinyl, morpholinyl, piperidinyl, azepanyl, pyrrolidinyl and azetidinyl; wherein each of the groups imidazolyl, piperazinyl, morpholinyl, piperidinyl, azepanyl, pyrrolidinyl and azetidinyl are optionally substituted by one or more $R^6$ groups, halo, OH, $OR^6$, $OC(O)R^6$, $OC(O)NH_2$, $OC(O)NHR^6$, $OC(O)NR^6R^6$, $OP(O)(OH)_2$, $OP(O)(OR^6)_2$, $NO_2$, $NH_2$, $NHR^6$, $NR^6R^6$, $N^+(-O^-)R^6R^6$, $NHC(O)H$, $NHC(O)R^6$, $NR^6C(O)R^6$, $NHC(O)NH_2$, $NHC(O)NR^6R^6$, $NR^6C(O)NHR^6$, SH, $SR^6$, $S(O)H$, $S(O)R^6$, $SO_2R^6$, $SO_2NH_2$, $SO_2NHR^6$, $SO_2NR^6R^6$, $CF_3$, CN, $CO_2H$, $CO_2R^6$, CHO, $C(O)R^6$, $C(O)NH_2$, $C(O)NHR^6$, $C(O)NR^6R^6$, $C(O)NHSO_2H$, $C(O)NHSO_2R^6$ and $C(O)NR^6SO_2R^6$ wherein each $R^6$ is independently selected from $C_{1-6}$ alkyl, $C_{2-6}$ alkenyl, halo, OH, OMe, $NO_2$, $NH_2$, $CF_3$, CN, $CO_2H$ or SH; and wherein the optionally substituted 4-8 membered ring system includes one or more carbon atoms and/or one or more ring system moieties selected from O, NH, $NR^7$, CONH, $CONR^7$, NHCO, $NR^7CO$, wherein each $R^7$ is independently selected from an optionally substituted $C_{1-6}$ alkyl, an optionally substituted $C_{2-6}$ alkenyl group or an optionally substituted $C_{3-7}$ cyclic alkyl group and wherein the one or more optional substituents are each independently selected from halo, $R^8$, OH, $OR^8$, $OC(O)R^8$, $OC(O)NH_2$, $OC(O)NHR^8$, $OC(O)NR^8R^8$, $OP(O)(OH)_2$, $OP(O)(OR^5)_2$, $NO_2$, $NH_2$, $NHR^8$, $NR^8R^8$, $N^+(—O^-)R^8R^8$, NHC(O)H, $NHC(O)R^8$, $NR^8C(O)R^8$, $NHC(O)NH_2$, $NHC(O)NR^8R^8$, $NR^8C(O)NHR^8$, SH, $SR^8$, S(O)H, $S(O)R^8$, $SO_2R^8$, $SO_2NH_2$, $SO_2NHR^6$, $SO_2NR^8R^8$, $CF_3$, CN, $CO_2H$, $CO_2R$, CHO, $C(O)R^8$, $C(O)NH_2$, $C(O)NHR^8$, $C(O)NR^8R^8$, $C(O)NHSO_2H$, $C(O)NHSO_2R^8$, $C(O)NR^8SO_2R^8$, cyclic $C_{3-7}$ alkylamino, imidazolyl, piperazinyl, morpholinyl, piperidinyl, azepanyl, pyrrolidinyl and azetidinyl; wherein each of the groups imidazolyl, piperazinyl, morpholinyl, piperidinyl, azepanyl, pyrrolidinyl and azetidinyl are optionally substituted by one or more $R^8$ groups, halo, $R^8$, OH, $OR^8$, $OC(O)R^8$, $OC(O)NH_2$, $OC(O)NHR^8$, $OC(O)NR^8R^8$, $OP(O)(OH)_2$, $OP(O)(OR^5)_2$, $NO_2$, $NH_2$, $NHR^8$, $NR^8R^8$, $N^+(—O^-)R^8R^8$, NHC(O)H, NHC(O)$R^8$, $NR^8C(O)R^8$, $NHC(O)NH_2$, $NHC(O)NR^8R^8$, $NR^8C(O)NHR^8$, SH, $SR^8$, S(O)H, $S(O)R^8$, $SO_2R^8$, $SO_2NH_2$, $SO_2NHR^8$, $SO_2NR^8R^8$, $CF_3$, CN, $CO_2H$, $CO_2R$, CHO, $C(O)R^8$, $C(O)NH_2$, $C(O)NHR^8$, $C(O)NR^8R^8$, $C(O)NHSO_2H$, $C(O)NHSO_2R^8$ and $C(O)NR^8SO_2R^8$; wherein each $R^8$ is independently selected from an optionally substituted $C_{1-6}$ alkyl, an optionally substituted $C_{2-6}$ alkenyl group or an optionally substituted $C_{3-7}$ cyclic alkyl group and wherein the one or more optional substituents is each independently selected from; halo, OH, $OR^9$, $OC(O)R^9$, $OC(O)NH_2$, $OC(O)NHR^9$, $OC(O)NR^9R^9$, $OP(O)(OH)_2$, $OP(O)(OR^9)_2$, $NO_2$, $NH_2$, $NHR^9$, $NR^9R^9$, $N^+(—O^-)R^9R^9$, NHC(O)H, NHC(O)$R^9$, $NR^9C(O)R^9$, $NHC(O)NH_2$, $NHC(O)NR^9R^9$, $NR^9C(O)NHR^9$, SH, $SR^9$, S(O)H, $S(O)R^9$, $SO_2R^9$, $SO_2NH_2$, $SO_2NHR^9$, $SO_2NR^9R^9$, $CF_3$, CN, $CO_2H$, $CO_2R$, CHO, $C(O)R^9$, $C(O)NH_2$, $C(O)NHR^9$, $C(O)NR^9R^9$, $C(O)NHSO_2H$, $C(O)NHSO_2R^9$, $C(O)NR^9SO_2R^9$, cyclic $C_{3-7}$ alkylamino, imidazolyl, piperazinyl, morpholinyl, piperidinyl, azepanyl, pyrrolidinyl and azetidinyl; wherein each of the groups imidazolyl, piperazinyl, morpholinyl, piperidinyl, azepanyl, pyrrolidinyl and azetidinyl are optionally substituted by one or more $R^9$ groups, halo, OH, $OR^9$, $OC(O)R^9$, $OC(O)NH_2$, $OC(O)NHR^9$, $OC(O)NR^9R^9$, $OP(O)(OH)_2$, $OP(O)(OR^9)_2$, $NO_2$, $NH_2$, $NHR^9$, $NR^9R^9$, $N^+(—O^-)R^9R^9$, NHC(O)H, NHC(O)$R^9$, $NR^9C(O)R^9$, $NHC(O)NH_2$, $NHC(O)NR^9R^9$, $NR^9C(O)NHR^9$, SH, $SR^9$, S(O)H, $S(O)R^9$, $SO_2R^9$, $SO_2NH_2$, $SO_2NHR^9$, $SO_2NR^9R^9$, $CF_3$, CN, $CO_2H$, $CO_2R$, CHO, $C(O)R^9$, $C(O)NH_2$, $C(O)NHR^9$, $C(O)NR^9R^9$, $C(O)NHSO_2H$, $C(O)NHSO_2R^9$, and $C(O)NR^9SO_2R^9$; wherein each $R^9$ is independently selected from $C_{1-6}$ alkyl, $C_{2-6}$ alkenyl, halo, OH, OMe, $NO_2$, $NH_2$, $CF_3$, CN, $CO_2H$ or SH.

Preferably each X on the benzo ring is H.

Preferably Z represents an optionally substituted 5-7 membered saturated ring system fused to the benzo ring in the 6,7-positions or the 7,8-positions; wherein the one or more optional substituents of the ring system are each independently selected from halo, $C_1-C_6$ alkyl, OH, $OC_1-C_6$alkyl, $OC(O)C_1-C_6$alkyl, $OC(O)NH_2$, $OC(O)NHC_1-C_6$alkyl, $OC(O)N(C_1-C_6alkyl)_2$, $OP(O)(OH)_2$, $OP(O)(OC_1-C_6 alkyl)_2$, $NO_2$, $NH_2$, $NHC_1-C_6alkyl$, $N(C_1-C_6alkyl)_2$, $N^+(—O^-)(C_1-C_6 alkyl)_2$, NHC(O)H, $NHC(O)C_1-C_6alkyl$, $N(C_1-C_6alkyl)C(O)C_1-C_6$ alkyl, $NHC(O)NH_2$, $NHC(O)N(C_1-C_6alkyl)_2$, $NC_1-C_6$ alkylC(O)NHC$_1-C_6$ alkyl, SH, $SC_1-C_6$ alkyl, S(O)H, $S(O)C_1-C_6alkyl$, $SO_2C_1-C_6alkyl$, $SO_2NH_2$, $SO_2NHC_1-C_6$ alkyl, $SO_2N(C_1-C_6 alkyl)_2$, $(C_1-C_6)_3SiO$, $CF_3$, CN, $CO_2H$, $CO_2C_1-C_6$ alkyl, CHO, $C(O)C_1-C_6$ alkyl, $C(O)NH_2$, $C(O)NHC_1-C_6alkyl$, $C(O)N(C_1-C_6$ alkyl$)_2$, $C(O)NHSO_2H$, $C(O)NHSO_2C_1-C_6$alkyl, $C(O)N(C_1-C_6 alkyl)SO_2$ $(C_1-C_6$ alkyl), cyclic $C_3-C_7$ alkylamino, imidazolyl, piperazinyl, morpholinyl, piperidinyl, azepanyl, pyrrolidinyl and azetidinyl; wherein each of the substituents are optionally substituted by one or more halo, $C_1-C_6$ alkyl, OH, $OC_1-C_6$ alkyl, and wherein the optionally substituted ring system includes one or more carbon atoms and/or one or more ring system moieties selected from O, NH, $N(C_1-C_6$ alkyl), CONH, $CON(C_1-C_6$ alkyl), NHCO, $N(C_1-C_6$ alkyl)CO, wherein each $C_1-C_6$ alkyl is optionally substituted with one or more halo, $C_1-C_6$ alkyl, OH, $OC_1-C_6$ alkyl, $OP(O)(OH)_2$, $OP(O)(OC_1-C_6$ alkyl$)_2$, $NO_2$, $NH_2$, $NHC_1-C_6$ alkyl, $N(C_1-C_6$ alkyl$)_2$, SH, $S(C_1-C_6$ alkyl), S(O)H, $S(O)C_1-C_6$ alkyl, $SO_2C_1-C_6$ alkyl, $SO_2NH_2$, $CF_3$, CN, $CO_2H$, $CO_2R$, CHO, $C(O)C_1-C_6$ alkyl, $C(O)NH_2$, $C(O)NHC_1-C_6$ alkyl, $C(O)N(C_1-C_6$ alkyl$)_2$, $C(O)NHSO_2H$, $C(O)NHSO_2R^8$, $C(O)NR^8SO_2R^8$, cyclic $C_3-C_7$ alkylamino, imidazolyl, piperazinyl, morpholinyl, piperidinyl, azepanyl, pyrrolidinyl and azetidinyl; wherein each of the groups imidazolyl, piperazinyl, morpholinyl, piperidinyl, azepanyl, pyrrolidinyl and azetidinyl.

Preferably, Z represents a 5, 6 or 7 membered ring, optionally substituted with one or more substituents selected from $C_{1-6}$ alkyl wherein the alkyl is optionally substituted with one or more OH; NH and $N(C_1-C_6$ alkyl$)_2$, and wherein the ring optionally includes one or more O, NH or $N(C_1-C_6$ alkyl) moieties.

More preferably, Z represents a 5, 6 or 7 membered ring, optionally substituted with $CH_3$, $CH_2OH$, $N(CH_3)_2$, $CH_2CH_3$, $(CH_2)_2OH$, and wherein the ring optionally includes one or more O, NH or $N(C_1-C_6$ alkyl) moieties.

Preferably, Z represents a 5 or 6 membered ring optionally substituted with $CH_3$, $CH_2OH$, $N(CH_3)_2$, $CH_2CH_3$, $(CH_2)_2$OH, and wherein the 5 or 6 membered ring is selected from the following:

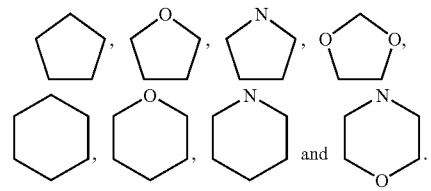

Preferably, Z represents an unsubstituted 5 membered carbon ring.

Preferably W represents —NH, or —$CH_2$.

Preferably A represents H or an optionally substituted $C_{1-6}$alkyl group or an optionally substituted $C_{2-6}$ alkenyl group wherein the one or more optional substituents are each independently selected from halo, OH, $OC_{1-6}$ alkyl, $OC(O)C_{1-6}$alkyl, $OC(O)NH_2$, $OC(O)NH$ $C_{1-6}$ alkyl, $OC(O)N(C_{1-6}$ alkyl$)_2$, $OP(O)(OH)_2$, $OP(O)(OC_{1-6}$ alkyl$)_2$, $NO_2$, $NH_2$, $NHC_{1-6}$ alkyl, $N(C_{1-6}alkyl)_2$, NHC(O)H, $NHC(O)C_{1-6}$alkyl, $NR^2C(O)C_{1-6}$alkyl, $NHC(O)NH_2$, $NHC(O)N(C_{1-6}$ alkyl$)_2$, $N(C_{1-6}$ alkyl$)C(O)NHC_{1-6}$alkyl, $CF_3$, CN, $CO_2H$, $CO_2C_{1-6}$ alkyl, CHO, $C(O)C_{1-6}$alkyl, $C(O)NH_2$, $C(O)NHC_{1-6}$alkyl, C(O)N(C$_{1-6}$ alkyl)$_2$, CONHSO$_2$H, C(O)NHSO$_2$C$_{1-6}$ alkyl, C(O)NC$_{1-6}$alkylSO$_2$C$_{1-6}$alkyl, cyclic C$_3$-C$_7$ alkylamino, imidazolyl, piperazinyl, morpholinyl, piperidinyl, azepanyl, pyrrolidinyl and azetidinyl; wherein each of the groups imidazolyl, piperazinyl, morpholinyl, piperidinyl, azepanyl, pyrrolidinyl and azetidinyl are optionally substituted by one or more groups selected from halo, OH, OC$_{1-6}$alkyl, OC(O) C$_{1-6}$ alkyl, OC(O)NH$_2$, OC(O)NHC$_{1-6}$ alkyl, OC(O)N(C$_{1-6}$ alkyl)$_2$, OP(O)(OH)$_2$, OP(O)(OC$_{1-6}$alkyl)$_2$, NO$_2$, NH$_2$, NHC$_{1-6}$alkyl, N(C$_{1-6}$alkyl)$_2$, NHC(O)H, NHC(O)C$_{1-6}$alkyl, NC$_{1-6}$alkylC(O)C$_{1-6}$ alkyl, NHC(O)NH$_2$, NHC(O)N(C$_{1-6}$ alkyl)$_2$, NC$_{1-6}$alkylC(O)NHC$_{1-6}$alkyl, CF$_3$, CN, CO$_2$H, CO$_2$C$_{1-6}$ alkyl, CHO, C(O)C$_{1-6}$ alkyl, C(O)NH$_2$, C(O) NHC$_{1-6}$ alkyl, C(O)N(C$_{1-6}$ alkyl), CONHSO$_2$H, C(O) NHSO$_2$(C$_{1-6}$alkyl), and C(O)NC$_{1-6}$ alkylSO$_2$C$_{1-6}$alkyl.

Preferably A represents an optionally substituted —C$_1$-C$_6$alkyl, C$_1$-C$_6$alkyl OH, —N(C$_1$-C$_6$alkyl)$_2$, —N(C$_1$-C$_6$alkyl)OC$_1$-C$_6$alkyl, —C$_1$-C$_6$alkylN(C$_1$-C$_6$alkyl)$_2$, —C$_1$-C$_6$alkylN(C$_1$-C$_6$alkyl) C$_1$-C$_6$alkylOC$_1$-C$_6$alkyl, —C$_1$-C$_6$alkylOC$_1$-C$_6$alkyl, —C$_1$-C$_6$alkylNazetidine, —C$_1$-C$_6$alkyl OP(O)(OH)$_2$, —C$_1$-C$_6$alkylNpyrrolidine, —C$_1$-C$_6$alkylNpiperidine, —C$_1$-C$_6$alkyl N(2,6-(di C$_1$-C$_6$alkyl) piperidine), —C$_1$-C$_6$alkylNmorpholine, —C$_1$-C$_6$alkylazepane, —C$_1$-C$_6$alkylNoxazepine, C$_1$-C$_6$alkylOC (O)C$_1$-C$_6$alkylN(C$_1$-C$_6$alkyl)$_2$, C$_1$-C$_6$alkylOC(O)C$_1$-C$_6$alkyl(NCO$_2$C$_1$-C$_6$alkyl) C$_1$-C$_6$alkyl, wherein the one or more substituents are each independently selected from OH, C$_1$-C$_6$alkyl, OC$_1$-C$_6$alkyl or CN.

Preferably W and A together represent H, halo, NH$_2$, NHCH$_2$CH$_3$, —CH$_2$CH$_2$CH$_2$NMe$_2$, —CH$_2$CH$_2$CH$_2$OH, —NH(CH$_2$)$_2$N(Me)$_2$, —NHCH$_2$CH$_2$OH, —NHCH$_2$CH$_2$NEt$_2$, —NHCH$_2$CH$_2$NPr$_2$, —CHCH$_2$CH$_2$N (Me)CH$_2$CH$_2$OMe, —N(CH$_2$CH$_2$OMe)$_2$, —NHCH$_2$CH$_2$N (Me)CH$_2$CH$_2$CH$_2$OMe, —NHCH$_2$CH$_2$Nazetidine-3-OMe, —CH$_2$CH$_2$CH$_2$OP(O)(OH)$_2$, —CH$_2$CH$_2$CH$_2$Npyrrolidine, —NHCH$_2$CH$_2$Npiperidine, —NHCH$_2$CH$_2$N-(2,6-diMepiperidine), —CH$_2$CH$_2$CH$_2$Nazetidine-3-OMe, —NHCH$_2$CH$_2$CH$_2$Npiperidine-3-OMe, —NHCH$_2$CH$_2$Npiperidine-4-OMe, —CH$_2$CH$_2$CH$_2$Npiperidine, —NHCH$_2$CH$_2$Nmorpholine, —NHCH$_2$CH$_2$Nazepane, —NHCH$_2$CH$_2$Noxazepine, —NHCH$_2$CH$_2$CH$_2$OH, —NHCH$_2$CH$_2$CH$_2$N(Me) CH$_2$CH$_2$OMe, —NHCH$_2$CH$_2$CH$_2$NazetidineOMe —NHCH$_2$CH$_2$CH$_2$N(pyrrolidine-3-CN), —NHCH$_2$CH$_2$CH$_2$Npiperidine-4-OMe, —NHCH$_2$CH$_2$CH$_2$Nmorpholine, —NHCH$_2$CH$_2$CH$_2$CH$_2$Nmorpholine, —CH$_2$CH$_2$CH$_2$OC (O)CH$_2$CH$_2$CHN(Me)$_2$, and —CH$_2$CH$_2$CH$_2$OC(O)CH (NHCO$_2$tBu)CH$_2$Me$_2$.

Preferably, W and A together represent halo, —NHCH$_2$CH$_2$CH$_2$Nmorpholine, NHCH$_2$CH$_2$N(Me)$_2$ or —CH$_2$CH$_2$CH$_2$NMe$_2$.

Preferably the compound is selected from one or more of the following:

8,9-Dihydro-7H-indeno[5,4-e][1,2,4]triazin-3-amine 1-oxide;

3-Chloro-8,9-dihydro-7H-indeno[5,4-e][1,2,4]triazine 1-oxide;

N$^1$,N$^1$-Dimethyl-N$^2$-(1-oxido-8,9-dihydro-7H-indeno[5, 4-e][1,2,4]triazin-3-yl)-1,2-ethanediamine;

N$^1$,N$^1$-Dimethyl-N$^2$-(1,4-dioxido-8,9-dihydro-7H-indeno [5,4-e][1,2,4]triazin-3-yl)-1,2-ethanediamine;

N$^1$,N$^1$-Diethyl-N$^2$-(1-oxido-8,9-dihydro-7H-indeno[5,4-e] [1,2,4]triazin-3-yl)-1,2-ethanediamine;

N$^1$,N$^1$-Diethyl-N$^2$-(1,4-dioxido-8,9-dihydro-7H-indeno[5, 4-e][1,2,4]triazin-3-yl)-1,2-ethanediamine;

N$^1$-(1-Oxido-8,9-dihydro-7H-indeno[5,4-e][1,2,4]triazin-3-yl)-N$^2$,N$^2$-dipropyl-1,2-ethanediamine;

N$^1$-(1-Oxido-8,9-dihydro-7H-indeno[5,4-e][1,2,4]triazin-3-yl)-N$^2$,N$^2$-dipropyl-1,2-ethanediamine;

N-[2-(1-Piperidinyl)ethyl]-8,9-dihydro-7H-indeno[5,4-e][1, 2,4]triazin-3-amine 1-oxide;

N-[2-(1-Piperidinyl)ethyl]-8,9-dihydro-7H-indeno[5,4-e][1, 2,4]triazin-3-amine 1,4-dioxide;

N-[3-(1-Morpholinyl)propyl]-8,9-dihydro-7H-indeno[5,4-e][1,2,4]triazin-3-amine 1-oxide;

N-[3-(1-Morpholinyl)propyl]-8,9-dihydro-7H-indeno[5,4-e][1,2,4]triazin-3-amine 1,4-dioxide;

7,8-Dihydro-6H-indeno[5,6-e][1,2,4]triazin-3-amine 1-oxide;

7,8-Dihydro-6H-indeno[5,6-e][1,2,4]triazin-3-amine 1,4-dioxide;

3-Chloro-7,8-dihydro-6H-indeno[5,6-e][1,2,4]triazine 1-oxide;

N$^1$,N$^1$-Dimethyl-N$^2$-(1-oxido-7,8-dihydro-6H-indeno[5,6-e][1,2,4]triazin-3-yl)-1,2-ethanediamine;

N$^1$-(1,4-Dioxido-7,8-dihydro-6H-indeno[5,6-e][1,2,4]triazin-3-yl)-N$^2$,N$^2$-dimethyl-1,2-ethanediamine;

2-[(1-Oxido-7,8-dihydro-6H-indeno[5,6-e][1,2,4]triazin-3-yl)amino]ethanol;

2-[(1,4-Dioxido-7,8-dihydro-6H-indeno[5,6-e][1,2,4]triazin-3-yl)amino]ethanol;

N$^1$-(1-Oxido-7,8-dihydro-6H-indeno[5,6-e][1,2,4]triazin-3-yl)-N$^2$,N$^2$-diethyl-1,2-ethanediamine;

N$^1$-(1,4-Dioxido-7,8-dihydro-6H-indeno[5,6-e][1,2,4]triazin-3-yl)-N$^2$,N$^2$-diethyl-1,2-ethanediamine;

N$^1$-(1-Oxido-7,8-dihydro-6H-indeno[5,6-e][1,2,4]triazin-3-yl)-N$^2$,N$^2$-dipropyl-1,2-ethanediamine;

N$^1$-(1,4-Dioxido-7,8-dihydro-6H-indeno[5,6-e][1,2,4]triazin-3-yl)-N$^2$,N$^2$-dipropyl-1,2-ethanediamine;

N$^1$-(1-Oxido-7,8-dihydro-6H-indeno[5,6-e][1,2,4]triazin-3-yl)-N$^2$-(2-methoxyethyl)-N$^2$-methyl-1,2-ethanediamine;

N$^1$-(1,4-dioxido-7,8-dihydro-6H-indeno[5,6-e][1,2,4]triazin-3-yl)-N$^2$-(2-methoxyethyl)-N$^2$-methyl-1,2-ethanediamine;

N$^1$-(3-Methoxypropyl)-N$^1$-methyl-N$^2$-(1-oxido-7,8-dihydro-6H-indeno[5,6-e][1,2,4]triazin-3-yl)-1,2-ethanediamine;

N$^1$-(1,4-Dioxido-7,8-dihydro-6H-indeno[5,6-e][1,2,4]triazin-3-yl)-N$^2$-(3-methoxypropyl)-N$^2$-methyl-1,2-ethanediamine;

N-[2-(3-Methoxy-1-azetidinyl)ethyl]-7,8-dihydro-6H-indeno[5,6-e][1,2,4]triazin-3-amine 1-oxide;

N-[2-(3-Methoxy-1-azetidinyl)ethyl]-7,8-dihydro-6H-indeno[5,6-e][1,2,4]triazin-3-amine 1,4-dioxide;

N-[2-(1-Piperidinyl)ethyl]-7,8-dihydro-6H-indeno[5,6-e][1, 2,4]triazin-3-amine 1-oxide;

N-[2-(1-Piperidinyl)ethyl]-7,8-dihydro-6H-indeno[5,6-e][1, 2,4]triazin-3-amine 1,4-dioxide;

N-[2-(2,6-Dimethyl-1-piperidinyl)ethyl]-7,8-dihydro-6H-indeno[5,6-e][1,2,4]triazin-3-amine 1-oxide;

N-[2-(2,6-Dimethyl-1-piperidinyl)ethyl]-7,8-dihydro-6H-indeno[5,6-e][1,2,4]triazin-3-amine 1,4-dioxide;

N-[2-(3-Methoxy-1-piperidinyl)ethyl]-7,8-dihydro-6H-indeno[5,6-e][1,2,4]triazin-3-amine 1-oxide;

N-[2-(3-Methoxy-1-piperidinyl)ethyl]-7,8-dihydro-6H-indeno[5,6-e][1,2,4]triazin-3-amine 1,4-dioxide;

N-[2-(4-Methoxy-1-piperidinyl)ethyl]-7,8-dihydro-6H-indeno[5,6-e][1,2,4]triazin-3-amine 1-oxide;

N-[2-(4-Methoxy-1-piperidinyl)ethyl]-7,8-dihydro-6H-indeno[5,6-e][1,2,4]triazin-3-amine 1,4-dioxide;

N-[2-(4-Morpholinyl)ethyl]-7,8-dihydro-6H-indeno[5,6-e] [1,2,4]triazin-3-amine 1-oxide;

N-[2-(4-Morpholinyl)ethyl]-7,8-dihydro-6H-indeno[5,6-e][1,2,4]triazin-3-amine 1,4-dioxide;

N-[2-(1-Azepanyl)ethyl]-7,8-dihydro-6H-indeno[5,6-e][1,2,4]triazin-3-amine 1-oxide;

N-[2-(1-Azepanyl)ethyl]-7,8-dihydro-6H-indeno[5,6-e][1,2,4]triazin-3-amine 1,4-dioxide;

N-[2-(1,4-Oxazepan-4-yl)ethyl]-7,8-dihydro-6H-indeno[5,6-e][1,2,4]triazin-3-amine 1-oxide;

N-[2-(1,4-Oxazepan-4-yl)ethyl]-7,8-dihydro-6H-indeno[5,6-e][1,2,4]triazin-3-amine 1,4-dioxide;

3-[(1-Oxido-7,8-dihydro-6H-indeno[5,6-e][1,2,4]triazin-3-yl)amino]-1-propanol;

3-[(1,4-Dioxido-7,8-dihydro-6H-indeno[5,6-e][1,2,4]triazin-3-yl)amino]-1-propanol;

$N^1$-(1-Oxido-7,8-dihydro-6H-indeno[5,6-e][1,2,4]triazin-3-yl)-$N^3$-(2-methoxyethyl)-$N^3$-methyl-1,3-propanediamine;

$N^1$-(1,4-Dioxido-7,8-dihydro-6H-indeno[5,6-e][1,2,4]triazin-3-yl)-$N^3$-(2-methoxyethyl)-$N^3$-methyl-1,3-propanediamine;

N-[3-(3-Methoxy-1-azetidinyl)propyl]-7,8-dihydro-6H-indeno[5,6-e][1,2,4]triazin-3-amine 1-oxide;

N-[3-(3-Methoxy-1-azetidinyl)propyl]-7,8-dihydro-6H-indeno[5,6-e][1,2,4]triazin-3-amine 1,4-dioxide;

1-{3-[(1-Oxido-7,8-dihydro-6H-indeno[5,6-e][1,2,4]triazin-3-yl)amino]propyl}-3-pyrrolidinecarbonitrile;

1-{3-[(1,4-Dioxido-7,8-dihydro-6H-indeno[5,6-e][1,2,4]triazin-3-yl)amino]propyl}-3-pyrrolidinecarbonitrile;

N-[3-(4-Methoxy-1-piperidinyl)propyl]-7,8-dihydro-6H-indeno[5,6-e][1,2,4]triazin-3-amine 1-oxide;

N-[3-(4-Methoxy-1-piperidinyl)propyl]-7,8-dihydro-6H-indeno[5,6-e][1,2,4]triazin-3-amine 1,4-dioxide;

N-[3-(4-Morpholinyl)propyl]-7,8-dihydro-6H-indeno[5,6-e][1,2,4]triazin-3-amine 1-oxide;

N-[3-(4-Morpholinyl)propyl]-7,8-dihydro-6H-indeno[5,6-e][1,2,4]triazin-3-amine 1,4-dioxide;

N-[4-(4-Morpholinyl)butyl]-7,8-dihydro-6H-indeno[5,6-e][1,2,4]triazin-3-amine 1-oxide;

N-[4-(4-Morpholinyl)butyl]-7,8-dihydro-6H-indeno[5,6-e][1,2,4]triazin-3-amine 1,4-dioxide;

7,8-Dihydro-6H-indeno[5,6-e][1,2,4]triazine 1-oxide;

7,8-Dihydro-6H-indeno[5,6-e][1,2,4]triazine 1,4-dioxide;

3-Iodo-7,8-dihydro-6H-indeno[5,6-e][1,2,4]triazine 1-oxide;

Ethyl-7,8-dihydro-6H-indeno[5,6-e][1,2,4]triazine 1-oxide;

3-Ethyl-7,8-dihydro-6H-indeno[5,6-e][1,2,4]triazine 1,4-dioxide;

3-Allyl-7,8-dihydro-6H-indeno[5,6-e][1,2,4]triazine 1-oxide;

3-(1-Oxido-7,8-dihydro-6H-indeno[5,6-e][1,2,4]triazin-3-yl)-1-propanol;

3-(1,4-Dioxido-7,8-dihydro-6H-indeno[5,6-e][1,2,4]triazin-3-yl)-1-propanol;

3-(3-(Di-tert-butoxyphosphoryloxy)propyl)-7,8-dihydro-6H-indeno[5,6-e][1,2,4]triazine 1-oxide;

3-(3-(Di-tert-butoxyphosphoryloxy)propyl)-7,8-dihydro-6H-indeno[5,6-e][1,2,4]triazine 1,4-dioxide;

3-(1,4-Dioxido-7,8-dihydro-6H-indeno[5,6-e][1,2,4]triazin-3-yl)propyl dihydrogen phosphate;

3-[3-(4-Morpholinyl)propyl]-7,8-dihydro-6H-indeno[5,6-e][1,2,4]triazine 1-oxide;

3-[3-(4-Morpholinyl)propyl]-7,8-dihydro-6H-indeno[5,6-e][1,2,4]triazine 1,4-dioxide;

N,N-Dimethyl-3-(1-oxido-7,8-dihydro-6H-indeno[5,6-e][1,2,4]triazin-3-yl)-1-propanamine;

N-[3-(1,4-Dioxido-7,8-dihydro-6H-indeno[5,6-e][1,2,4]triazin-3-yl)propyl]-N,N-dimethylamine;

N,N-Bis(2-methoxyethyl)-3-(1-oxido-7,8-dihydro-6H-indeno[5,6-e][1,2,4]triazin-3-yl)-1-propanamine;

N-[3-(1,4-Dioxido-7,8-dihydro-6H-indeno[5,6-e][1,2,4]triazin-3-yl)propyl]-N,N-bis(2-methoxyethyl)amine;

3-[3-(3-Methoxy-1-azetidinyl)propyl]-7,8-dihydro-6H-indeno[5,6-e][1,2,4]triazine 1-oxide;

3-[3-(3-Methoxy-1-azetidinyl)propyl]-7,8-dihydro-6H-indeno[5,6-e][1,2,4]triazine 1,4-dioxide;

3-[3-(1-Pyrrolidinyl)propyl]-7,8-dihydro-6H-indeno[5,6-e][1,2,4]triazine 1-oxide;

3-[3-(1-Pyrrolidinyl)propyl]-7,8-dihydro-6H-indeno[5,6-e][1,2,4]triazine 1,4-dioxide;

3-[3-(1-Piperidinyl)propyl]-7,8-dihydro-6H-indeno[5,6-e][1,2,4]triazine 1-oxide;

3-[3-(1-Piperidinyl)propyl]-7,8-dihydro-6H-indeno[5,6-e][1,2,4]triazine 1,4-dioxide;

7-Methyl-7,8-dihydro-6H-indeno[5,6-e][1,2,4]triazin-3-amine 1-oxide;

3-Chloro-7-methyl-7,8-dihydro-6H-indeno[5,6-e][1,2,4]triazine 1-oxide;

$N^1,N^1$-Dimethyl-$N^2$-(7-methyl-1-oxido-7,8-dihydro-6H-indeno[5,6-e][1,2,4]triazin-3-yl)-1,2-ethanediamine;

$N^1,N^1$-Dimethyl-$N^2$-(7-methyl-1,4-dioxido-7,8-dihydro-6H-indeno[5,6-e][1,2,4]triazin-3-yl)-1,2-ethanediamine;

7-Methyl-N-[3-(4-morpholinyl)propyl]-7,8-dihydro-6H-indeno[5,6-e][1,2,4]triazin-3-amine 1-oxide;

7-Methyl-N-[3-(4-morpholinyl)propyl]-7,8-dihydro-6H-indeno[5,6-e][1,2,4]triazin-3-amine 1,4-dioxide;

3-Iodo-7-methyl-7,8-dihydro-6H-indeno[5,6-e][1,2,4]triazine 1-oxide;

3-(7-Methyl-1-oxido-7,8-dihydro-6H-indeno[5,6-e][1,2,4]triazin-3-yl)propanal;

7-Methyl-3-[3-(4-morpholinyl)propyl]-7,8-dihydro-6H-indeno[5,6-e][1,2,4]triazine 1-oxide;

7-Methyl-3-[3-(4-morpholinyl)propyl]-7,8-dihydro-6H-indeno[5,6-e][1,2,4]triazine 1,4-dioxide;

3-(7-Methyl-1,4-dioxido-7,8-dihydro-6H-indeno[5,6-e][1,2,4]triazin-3-yl)-1-propanol;

$N^7,N^7$-Dimethyl-7,8-dihydro-6H-indeno[5,6-e][1,2,4]triazine-3,7-diamine 1-oxide;

3-Chloro-N,N-dimethyl-7,8-dihydro-6H-indeno[5,6-e][1,2,4]triazin-7-amine 1-oxide;

$N^3$-Ethyl-$N^7,N^7$-dimethyl-7,8-dihydro-6H-indeno[5,6-e][1,2,4]triazine-3,7-diamine 1-oxide;

$N^3$-Ethyl-$N^7,N^7$-dimethyl-7,8-dihydro-6H-indeno[5,6-e][1,2,4]triazine-3,7-diamine 1,4-dioxide;

7-(Dimethylamino)-3-ethyl-7,8-dihydro-6H-indeno[5,6-e][1,2,4]triazine 1-oxide;

7-(Dimethylamino)-3-ethyl-7,8-dihydro-6H-indeno[5,6-e][1,2,4]triazine 1,4-dioxide;

(3-Amino-1-oxido-7,8-dihydro-6H-indeno[5,6-e][1,2,4]triazin-7-yl)methanol;

(3-Bromo-1-oxido-7,8-dihydro-6H-indeno[5,6-e][1,2,4]triazin-7-yl)methanol;

[3-(Ethylamino)-1-oxido-7,8-dihydro-6H-indeno[5,6-e][1,2,4]triazin-7-yl]methanol;

[3-(Ethylamino)-1,4-dioxido-7,8-dihydro-6H-indeno[5,6-e][1,2,4]triazin-7-yl]methanol;

7-({[tert-Butyl(dimethyl)silyl]oxy}methyl)-7,8-dihydro-6H-indeno[5,6-e][1,2,4]triazin-3-amine 1-oxide;

7-({[tert-Butyl(dimethyl)silyl]oxy}methyl)-3-iodo-7,8-dihydro-6H-indeno[5,6-e][1,2,4]triazine 1-oxide;

7-({[tert-Butyl(dimethyl)silyl]oxy}methyl)-3-ethyl-7,8-dihydro-6H-indeno[5,6-e][1,2,4]triazine 1-oxide;

(3-Ethyl-1,4-dioxido-7,8-dihydro-6H-indeno[5,6-e][1,2,4]triazin-7-yl)methanol;

3-Allyl-7-({[tert-butyl(dimethyl)silyl]oxy}methyl)-7,8-dihydro-6H-indeno[5,6-e][1,2,4]triazine 1-oxide;
3-[7-({[tert-Butyl(dimethyl)silyl]oxy}methyl)-1-oxido-7,8-dihydro-6H-indeno[5,6-e][1,2,4]triazin-3-yl]-1-propanol;
7-({[tert-Butyl(dimethyl)silyl]oxy}methyl)-3-[3-(4-morpholinyl)propyl]-7,8-dihydro-6H-indeno[5,6-e][1,2,4]triazine 1-oxide;
{3-[3-(4-Morpholinyl)propyl]-1-oxido-7,8-dihydro-6H-indeno[5,6-e][1,2,4]triazin-7-yl}methanol;
{3-[3-(4-Morpholinyl)propyl]-1,4-dioxido-7,8-dihydro-6H-indeno[5,6-e][1,2,4]triazin-7-yl}methanol,
(3-Ethyl-1-oxido-7,8-dihydro-6H-indeno[5,6-e][1,2,4]triazin-7-yl)methanol;
3-Ethyl-7-(4-morpholinylmethyl)-7,8-dihydro-6H-indeno[5,6-e][1,2,4]triazine 1-oxide;
3-Ethyl-7-(4-morpholinylmethyl)-7,8-dihydro-6H-indeno[5,6-e][1,2,4]triazine 1,4-dioxide;
2-(3-Amino-1-oxido-7,8-dihydro-6H-indeno[5,6-e][1,2,4]triazin-7-yl)ethanol;
2-(3-Iodo-1-oxido-7,8-dihydro-6H-indeno[5,6-e][1,2,4]triazin-7-yl)ethanol;
3-Iodo-7-(2-(tetrahydro-2H-pyran-2-yloxy)ethyl)-7,8-dihydro-6H-indeno[5,6-e][1,2,4]triazine 1-oxide;
3-Ethyl-7-(2-(tetrahydro-2H-pyran-2-yloxy)ethyl)-7,8-dihydro-6H-indeno[5,6-e][1,2,4]triazine 1-oxide;
2-(3-Ethyl-1-oxido-7,8-dihydro-6H-indeno[5,6-e][1,2,4]triazin-7-yl)ethanol;
2-(3-Ethyl-1,4-dioxido-7,8-dihydro-6H-indeno[5,6-e][1,2,4]triazin-7-yl)ethanol;
3-Ethyl-7-[2-(4-morpholinyl)ethyl]-7,8-dihydro-6H-indeno[5,6-e][1,2,4]triazine 1-oxide;
3-Ethyl-7-[2-(4-morpholinyl)ethyl]-7,8-dihydro-6H-indeno[5,6-e][1,2,4]triazine 1,4-dioxide;
7,8,9,10-Tetrahydronaphtho[2,1-e][1,2,4]triazine-3-amine 1-oxide;
3-Chloro-7,8,9,10-tetrahydronaphtho[2,1-e][1,2,4]triazine 1-oxide;
$N^1,N^1$-Dimethyl-$N^2$-(1-oxido-7,8,9,10-tetrahydronaphtho[2,1-e][1,2,4]triazin-3-yl)-1,2-ethanediamine;
$N^1$-(1,4-Dioxido-7,8,9,10-tetrahydronaphtho[2,1-e][1,2,4]triazin-3-yl)-$N^2,N^2$-dimethyl-1,2-ethanediamine;
6,7,8,9-Tetrahydronaphtho[2,3-e][1,2,4]triazine-3-amine 1-oxide;
3-Chloro-6,7,8,9-tetrahydronaphtho[2,3-e][1,2,4]triazine 1-oxide;
$N^1$-(1-Oxido-6,7,8,9-tetrahydronaphtho[2,3-e][1,2,4]triazin-3-yl)-$N^2,N^2$-dimethyl-1,2-ethanediamine;
$N^1$-(1,4-Dioxido-6,7,8,9-tetrahydronaphtho[2,3-e][1,2,4]triazin-3-yl)-$N^2,N^2$-dimethyl-1,2-ethanediamine;
N-[3-(4-Morpholinyl)propyl]-6,7,8,9-tetrahydronaphtho[2,3-e][1,2,4]triazin-3-amine 1-oxide;
N-[3-(4-Morpholinyl)propyl]-6,7,8,9-tetrahydronaphtho[2,3-e][1,2,4]triazin-3-amine 1,4-dioxide;
7,8,9,10-Tetrahydro-6H-cyclohepta[g][1,2,4]benzotriazin-3-amine 1-oxide;
3-Chloro-7,8,9,10-tetrahydro-6H-cyclohepta[g][1,2,4]benzotriazine 1-oxide;
$N^1,N^1$-Dimethyl-$N^2$-(1-oxido-7,8,9,10-tetrahydro-6H-cyclohepta[g][1,2,4]benzotriazin-3-yl)-1,2-ethanediamine;
$N^1$-(1,4-Dioxido-7,8,9,10-tetrahydro-6H-cyclohepta[g][1,2,4]benzotriazin-3-yl)-$N^2,N^2$-dimethyl-1,2-ethanediamine;
6,7-Dihydrofuro[3,2-g][1,2,4]benzotriazin-3-amine 1-oxide;
3-Chloro-6,7-dihydrofuro[3,2-g][1,2,4]benzotriazine 1-oxide;
$N^1,N^1$-Dimethyl-$N^2$-(1-oxido-6,7-dihydrofuro[3,2-g][1,2,4]benzotriazin-3-yl)-1,2-ethanediamine;
$N^1$-(1,4-Dioxido-6,7-dihydrofuro[3,2-g][1,2,4]benzotriazin-3-yl)-$N^2,N^2$-dimethyl-1,2-ethanediamine;
N-[3-(4-Morpholinyl)propyl]-6,7-dihydrofuro[3,2-g][1,2,4]benzotriazin-3-amine 1-oxide;
N-[3-(4-Morpholinyl)propyl]-6,7-dihydrofuro[3,2-g][1,2,4]benzotriazin-3-amine 1,4-dioxide;
3-Amino-7,8-dihydrobenzofuro[6,5-e][1,2,4]triazine 1-oxide;
1,4-Dioxido-7,8-dihydrofuro[2,3-g][1,2,4]benzotriazin-3-ylamine;
3-Chloro-7,8-dihydro-6H-indeno[5,6-e][1,2,4]triazine 1-oxide;
$N^1$-(1-Oxido-7,8-dihydrofuro[2,3-g][1,2,4]benzotriazin-3-yl)-$N^2,N^2$-dimethyl-1,2-ethanediamine;
$N^1$-(1,4-Dioxido-7,8-dihydrofuro[2,3-g][1,2,4]benzotriazin-3-yl)-$N^2,N^2$-dimethyl-1,2-ethanediamine;
$N^1$-(1-Oxido-7,8-dihydrofuro[2,3-g][1,2,4]benzotriazin-3-yl)-$N^2,N^2$-diethyl-1,2-ethanediamine;
$N^1$-(1,4-Dioxido-7,8-dihydrofuro[2,3-g][1,2,4]benzotriazin-3-yl)-$N^2,N^2$-diethyl-1,2-ethanediamine;
N-[3-(4-Morpholinyl)propyl]-7,8-dihydrofuro[2,3-g][1,2,4]benzotriazin-3-amine 1-oxide;
N-[3-(4-Morpholinyl)propyl]-7,8-dihydrofuro[2,3-g][1,2,4]benzotriazin-3-amine 1,4-dioxide;
3-Iodo-7,8-dihydrobenzofuro[6,5-e][1,2,4]triazine 1-oxide;
3-(1-Oxido-7,8-dihydrofuro[2,3-g][1,2,4]benzotriazin-3-yl)propanal;
3-[3-(4-Morpholinyl)propyl]-7,8-dihydrofuro[2,3-g][1,2,4]benzotriazine 1-oxide;
3-[3-(4-Morpholinyl)propyl]-7,8-dihydrofuro[2,3-g][1,2,4]benzotriazine 1,4-dioxide;
[1,3]Dioxolo[4,5-g][1,2,4]benzotriazin-3-amine 1-oxide;
3-Chloro[1,3]dioxolo[4,5-g][1,2,4]benzotriazine 1-oxide;
$N^1,N^1$-Dimethyl-$N^2$-(1-oxido[1,3]dioxolo[4,5-g][1,2,4]benzotriazin-3-yl)-1,2-ethanediamine;
$N^1$-(1,4-Dioxido[1,3]dioxolo[4,5-g][1,2,4]benzotriazin-3-yl)-$N^2,N^2$-dimethyl-1,2-ethanediamine;
9,10-Dihydro-8H-chromeno[6,5-e][1,2,4]triazin-3-amine 1-oxide;
3-Chloro-9,10-dihydro-8H-chromeno[6,5-e][1,2,4]triazine 1-oxide;
$N^1,N^1$-Dimethyl-$N^2$-(1-oxido-9,10-dihydro-8H-chromeno[6,5-e][1,2,4]triazin-3-yl)-1,2-ethanediamine;
$N^1$-(1,4-Dioxido-9,10-dihydro-8H-chromeno[6,5-e][1,2,4]triazin-3-yl)-$N^2,N^2$-dimethyl-1,2-ethanediamine;
7,8-Dihydro-6H-chromeno[6,7-e][1,2,4]triazin-3-amine 1-oxide;
3-Chloro-7,8-dihydro-6H-chromeno[6,7-e][1,2,4]triazine 1-oxide;
$N^1,N^1$-Dimethyl-$N^2$-(1-oxido-7,8-dihydro-6H-chromeno[6,7-e][1,2,4]triazin-3-yl)-1,2-ethanediamine;
$N^1$-(1,4-Dioxido-7,8-dihydro-6H-chromeno[6,7-e][1,2,4]triazin-3-yl)-$N^2,N^2$-dimethyl-1,2-ethanediamine;
N-[3-(4-Morpholinyl)propyl]-7,8-dihydro-6H-chromeno[6,7-e][1,2,4]triazin-3-amine 1-oxide;
N-[3-(4-Morpholinyl)propyl]-7,8-dihydro-6H-chromeno[6,7-e][1,2,4]triazin-3-amine 1,4-dioxide;
7-Ethyl-1-oxido-7,8-dihydro-6H-[1,2,4]triazino[5,6-f]isoindol-3-ylamine;
7-Ethyl-1,4-dioxido-7,8-dihydro-6H-[1,2,4]triazino[5,6-f]isoindol-3-ylamine;
7-Methyl-6,7,8,9-tetrahydro[1,2,4]triazino[6,5-g]isoquinolin-3-amine 1-oxide;
3-Chloro-7-methyl-6,7,8,9-tetrahydro[1,2,4]triazino[6,5-g]isoquinoline 1-oxide;
N-Ethyl-7-methyl-6,7,8,9-tetrahydro[1,2,4]triazino[6,5-g]isoquinolin-3-amine 1-oxide;

N-Ethyl-7-methyl-6,7,8,9-tetrahydro[1,2,4]triazino[6,5-g]
isoquinolin-3-amine 1,4-dioxide;
3-Ethyl-7-methyl-6,7,8,9-tetrahydro[1,2,4]triazino[6,5-g]
isoquinoline 1-oxide;
3-Ethyl-7-methyl-6,7,8,9-tetrahydro[1,2,4]triazino[6,5-g]
isoquinoline 1,4-dioxide;
9-Methyl-7,8,9,10-tetrahydro[1,2,4]triazino[5,6-h]isoquinolin-3-amine 1-oxide;
3-Chloro-9-methyl-7,8,9,10-tetrahydro[1,2,4]triazino[5,6-h]isoquinoline 1-oxide;
3-Ethyl-9-methyl-7,8,9,10-tetrahydro[1,2,4]triazino[5,6-h]
isoquinoline 1-oxide;
3-Ethyl-9-methyl-7,8,9,10-tetrahydro[1,2,4]triazino[5,6-h]
isoquinoline 1,4-dioxide;
3-(3-(4-(Dimethylamino)butanoyloxy)propyl)-7,8-dihydro-6H-indeno[5,6-e][1,2,4]triazine 1-oxide; and
3-(3-(2-(tert-Butoxycarbonylamino)-3-methylbutanoyloxy)
propyl)-7,8-dihydro-6H-indeno[5,6-e][1,2,4]triazine
1-oxide.

More preferably, the compound of Formula I is 3-[3-(4-Morpholinyl)propyl]-7,8-dihydro-6H-indeno[5,6-e][1,2,4]
triazine 1,4-Dioxide or N-[3-(4-Morpholinyl)propyl]-7,8-dihydro-6H-indeno[5,6-e][1,2,4]triazin-3-amine 1,4-dioxide.

In a second aspect the invention provides a method of therapy for treating cancers including the step of administering a compound of Formula I as defined above in a therapeutically effective amount to tumour cells in a subject.

Preferably the tumour cells are in a hypoxic environment.

It is preferred that the method of therapy further includes the step of administering radiotherapy to the tumor cells before, during or after the administration of the compound of Formula I as defined above to the tumour cells.

It is preferred that the method of therapy further includes the step of administering one or more chemotherapeutic agents to the tumor cells before, during or after the administration of the compound of Formula I as defined above to the tumour cells.

While these compounds will typically be used in cancer therapy of human subjects, they can be used to target tumor cells in other warm blooded animal subjects such as other primates, farm animals such as cattle, and sports animals and pets such as horses, dogs, and cats.

A "therapeutically effective amount", is to be understood as an amount of a compound of Formula I as defined above that is sufficient to show benefit to a patient. The actual amount, rate and time-course of administration, will depend on the nature and severity of the disease being treated. Prescription of treatment is within the responsibility of general practitioners and other medical doctors.

A hypoxic environment is to be understood as either an in vitro environment with an oxygen concentration less than 10 μM, or an in vivo environment having a lower oxygen tension than normal tissues.

It is to be understood that the compound of Formula I can be administered alone or in combination with other chemotherapeutic agents or treatments, especially radiotherapy, either simultaneously or sequentially dependent upon the condition to be treated.

Preferred chemotherapeutic agents can be selected from:
Cisplatin or other platinum-based derivatives,
Temozolomide or other DNA methylating agents,
Cyclophosphamide or other DNA alkylating agents,
Doxorubicin, mitoxantrone, camptothecin or other topoisomerase inhibitors,
Methotrexate, gemcitabine or other antimetabolites and
Docetaxel or other taxanes.

In a third aspect of the present invention there is provided a pharmaceutical composition including a therapeutically effective amount of a compound of formula I, a pharmaceutically acceptable excipient, adjuvant, carrier, buffer or stabiliser.

The pharmaceutically acceptable excipient, adjuvant, carrier, buffer or stabiliser should be non-toxic and should not interfere with the efficacy of the active ingredient. The precise nature of the carrier or other material will depend on the route of administration, which can be oral, or by injection, such as cutaneous, subcutaneous, or intravenous injection.

Pharmaceutical compositions for oral administration can be in tablet, capsule, powder or liquid form. A tablet can comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included. A capsule can comprise a solid carrier such as gelatin.

For intravenous, cutaneous or subcutaneous injection, the active ingredient will be in the form of a parenterally acceptable aqueous solution which is pyrogen-free and has a suitable pH, isotonicity and stability. Those of relevant skill in the art are well able to prepare suitable solutions using, for example, isotonic vehicles such as Sodium Chloride injection, Ringer's injection, Lactated Ringer's injection. Preservatives, stabilisers, buffers antioxidants and/or other additives can be included as required.

In a fourth aspect of the present invention there is provided a method of making a compound of Formula I or a pharmacologically acceptable salt thereof, Formula I

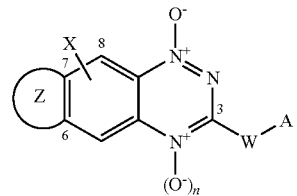

wherein n, X, Z, W and A are as defined above;

the method including the steps of reacting a nitroaniline compound of Formula II Formula II

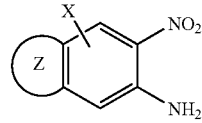

wherein X and Z are as defined above for a compound of Formula I, with cyanamide followed by a cyclisation step under basic conditions to give a mono-oxide compound of Formula I where n represents 0 and of optionally oxidising the mono-oxide compound of Formula I to form a dioxide compound of Formula I where n represents 1.

In a further embodiment, the method may include the steps of converting a monoxide of Formula III

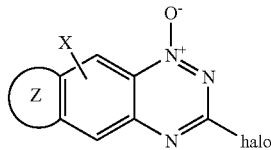

Formula III wherein X and Z are as defined above for a compound of Formula I; to a mono-oxide compound of Formula IV

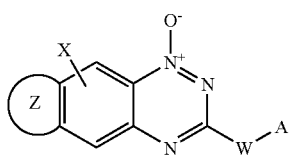

Formula IV wherein X and Z are as defined above for a compound of Formula III and W and A are as defined above for a compound of Formula I and together represent other than halo; and of optionally oxidising the resulting mono-oxide compound to form a dioxide compound of Formula I

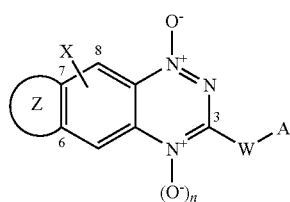

Formula I where n represents 1 and X, Z, W and A are as defined above for a compound of Formula I.

In the method defined above the halo of formula III represents chloro, bromo or iodo.

In a further aspect there is provided a method of making a compound of Formula I as defined above including the step of reacting a nitroaniline compound of Formula II Formula II

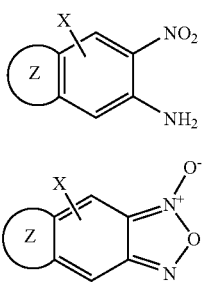

Formula V wherein X and Z are as defined above for a compound of Formula I, with sodium hypochlorite in the presence of a base to form a furoxan of Formula V wherein X and Z are as defined above for a compound of Formula I, and reacting the compound of Formula V with a substituted cyanamide to give a dioxide compound of Formula I where n represents 1.

In a further aspect there is provided a compound of Formula I obtained by the methods defined above.

In another aspect there is provided a method of improving the response of tumours to radiotherapy, comprising the steps of:

(a) administering to the subject a pharmaceutical composition in an amount sufficient to kill or radiosensitive hypoxic cells in tumours, the composition comprising a compound of Formula I as defined above and (b) subjecting the tumour to radiation either before or after administration of the said pharmaceutical composition.

In another aspect, there is provided the use in the manufacture of a medicament of a therapeutically effective amount of compound of Formula I as defined above for the treatment of tumour cells in a subject.

Preferably, the tumour cells are in a hypoxic environment.

It is to be recognised that certain compounds of the present invention may exist in one or more different enantiomeric or diastereomeric forms. It is to be understood that the enantiomeric or diasteriomeric forms are included in the above aspects of the invention.

The term halo or halogen group used throughout the specification is to be taken as meaning a fluoro, chloro, bromo or iodo group.

It is to be understood that where variables of the Formula I to V as defined above are optionally substituted by one or more imidazolyl, piperazinyl, morpholinyl, piperidinyl, azepanyl, pyrrolidinyl and azetidinyl groups that the linkage to the relevant variable may be through either one of the available nitrogen or carbon ring atoms of these groups.

It is to be understood that where reference is made throughout the specification to a $C_1$-$C_6$ alkyl or $C_2$-$C_6$ alkenyl group, these groups may be unbranched or branched. For example it is intended that reference to a $C_1$-$C_6$ alkyl would include a tertbutyl $(Me)_3C$— group.

The term pharmacologically acceptable salt used throughout the specification is to be taken as meaning any acid or base derived salt formed from hydrochloric, sulfuric, phosphoric, acetic, citric, oxalic, malonic, salicylic, malic, fumaric, succinic, ascorbic, maleic, methanesulfonic, isoethonic acids and the like and potassium carbonate sodium or potassium hydroxide ammonia, triethylamine, triethanolamine and the like.

Figure 1:
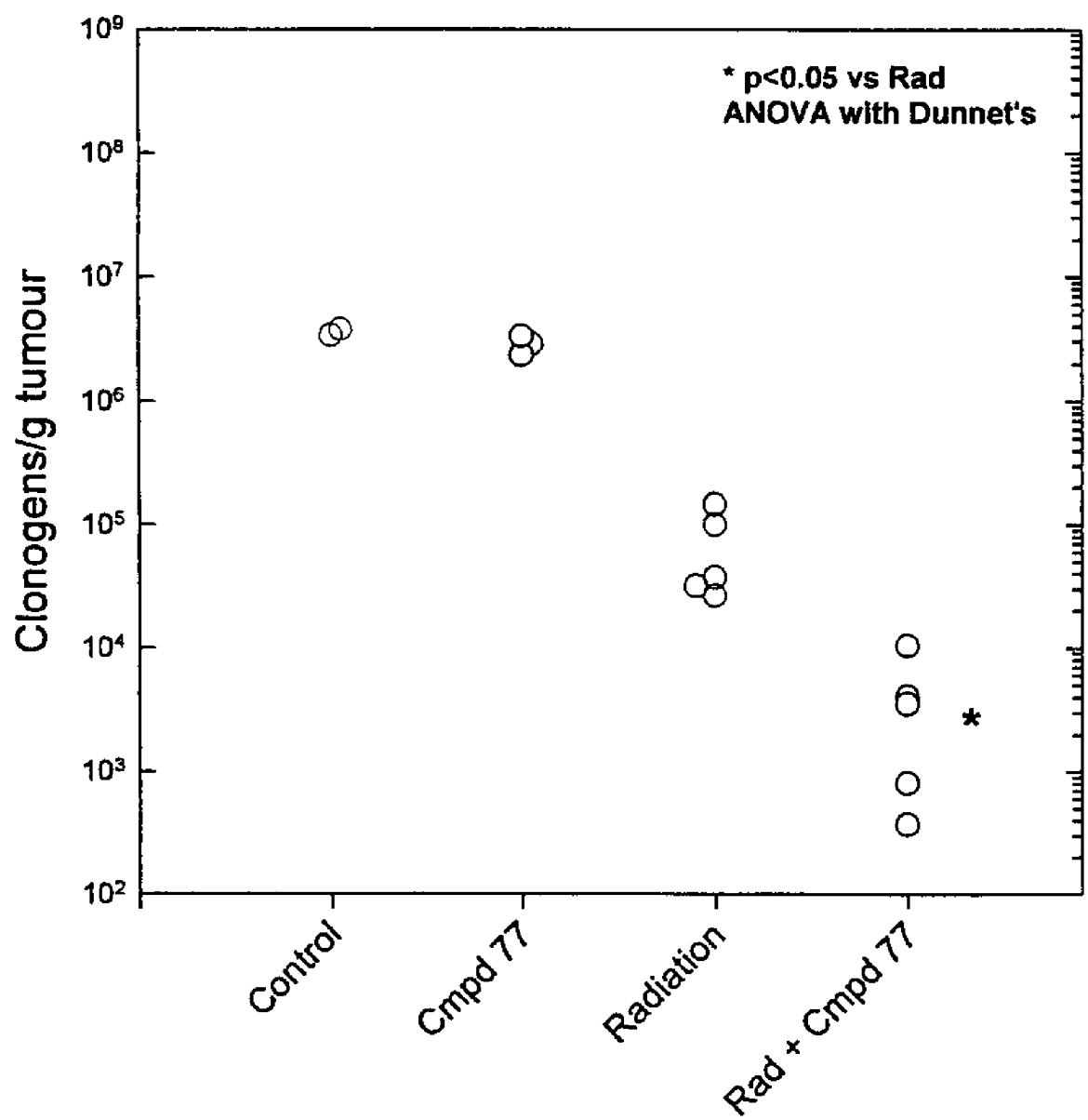

Further aspects of the present invention will become apparent from the following description given by way of example only and with reference to the accompanying synthetic schemes and figures in which:

FIG. 1 illustrates the activity of compound 77 against hypoxic cells in HT29 tumours, FIG. 2 illustrates by way of a plot the activity of a single dose (0.75×MTD) TPZ and compounds 61 and 77 against hypoxic cells in three human tumour xenograft models: HT29, human colon carcinoma; SiHa, human cervical carcinoma; H460, non-small cell lung carcinoma.

FIG. 3 illustrates by way of a plot the activity of fractionated dose TPZ and compound 77 against hypoxic cells in three human tumour xenograft models: H460, non-small cell lung carcinoma; HT29, human colon carcinoma; SiHa, human cervical carcinoma. Drugs (1.0× fractionated MTD) were administered 30 min before each of 8×2.5 Gy doses of radiation.

DETAILED DESCRIPTION OF THE INVENTION

Methods for Preparing Compounds of Formula I of the Invention

Acetylation of 5-aminoindan (1) followed by nitration, separation of the acetanilides and hydrolysis gave the nitroanilines 2 and 3 (Scheme 1). Treatment of nitroaniline 3 with cyanamide under acidic conditions followed by cyclisation under basic conditions gave amine 4. Diazotisation and chlorination of 4 gave chloride 5. Reaction of the chloride 5 with N,N-dimethylethylenediamine gave 1-oxide 6, which was selectively oxidised to 1,4-dioxide 7 using the trifluoroacetate salt of the aliphatic amine as a protecting group.

Scheme 1

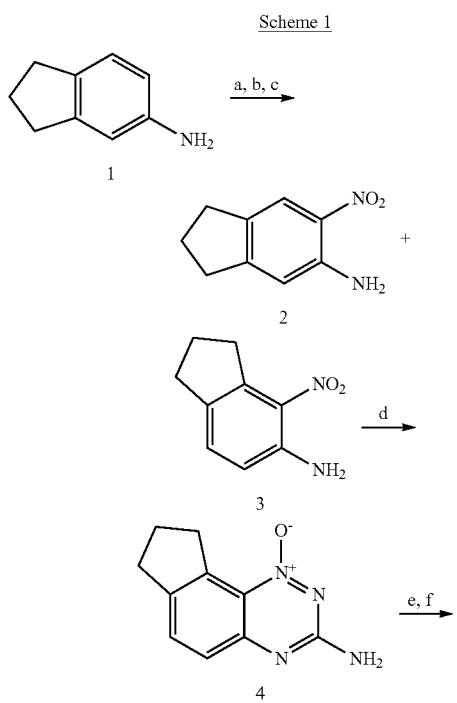

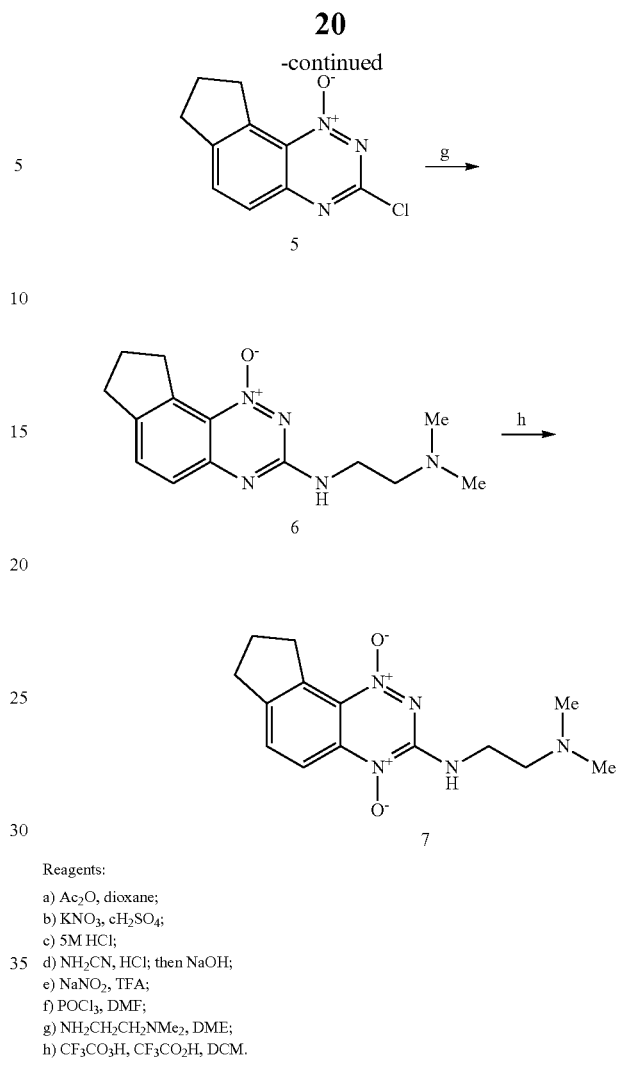

Reagents:
a) Ac$_2$O, dioxane;
b) KNO$_3$, cH$_2$SO$_4$;
c) 5M HCl;
d) NH$_2$CN, HCl; then NaOH;
e) NaNO$_2$, TFA;
f) POCl$_3$, DMF;
g) NH$_2$CH$_2$CH$_2$NMe$_2$, DME;
h) CF$_3$CO$_3$H, CF$_3$CO$_2$H, DCM.

Similarly, reaction of 5 with a variety of amines gave 1-oxides 8, 10, 12, and 14 that were oxidised to the corresponding 1,4-dioxides 9, 11, 13, and 15 (Scheme 2).

Scheme 2

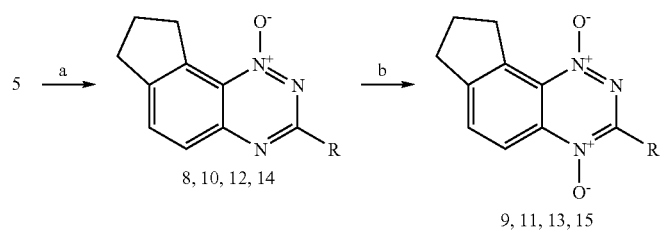

| Reagent | 1-oxide | 1,4-dioxide | R = |
|---|---|---|---|
| NH$_2$CH$_2$CH$_2$NEt$_2$ | 8 | 9 | —NHCH$_2$CH$_2$NEt$_2$ |
| NH$_2$CH$_2$CH$_2$NPr$_2$ | 10 | 11 | —NHCH$_2$CH$_2$NPr$_2$ |
| NH$_2$CH$_2$CH$_2$Npiperidine | 12 | 13 | —NHCH$_2$CH$_2$Npiperidine |
| NH$_2$CH$_2$CH$_2$CH$_2$Nmorpholine | 14 | 15 | —NHCH$_2$CH$_2$CH$_2$Nmorpholine |

Reagents:
a) amine, DME;
b) CF$_3$CO$_3$H, CF$_3$CO$_2$H, DCM.

In an alternative preparation of nitroaniline 2, acetylation of 5-aminoindan (1) gave acetamide 16 (Scheme 3). Nitration of acetamide 16 with nitric acid in acetic acid gave predominantly 6-nitroacetanilide 17 with minor amounts of 4-nitroacetanilide 18. Hydrolysis of nitroacetanilide 17 with cHCl in EtOH gave nitroaniline 2. Treatment of nitroaniline 2 with cyanamide under acidic conditions followed by cyclisation under basic conditions gave 1-oxide 19. Oxidation of 1-oxide 19 gave 1,4-dioxide 20. Diazotisation and chlorination of 1-oxide 19 gave chloride 21. Reaction of the chloride 21 with N,N-dimethylethylenediamine gave 1-oxide 22 which was oxidised to 1,4-dioxide 23.

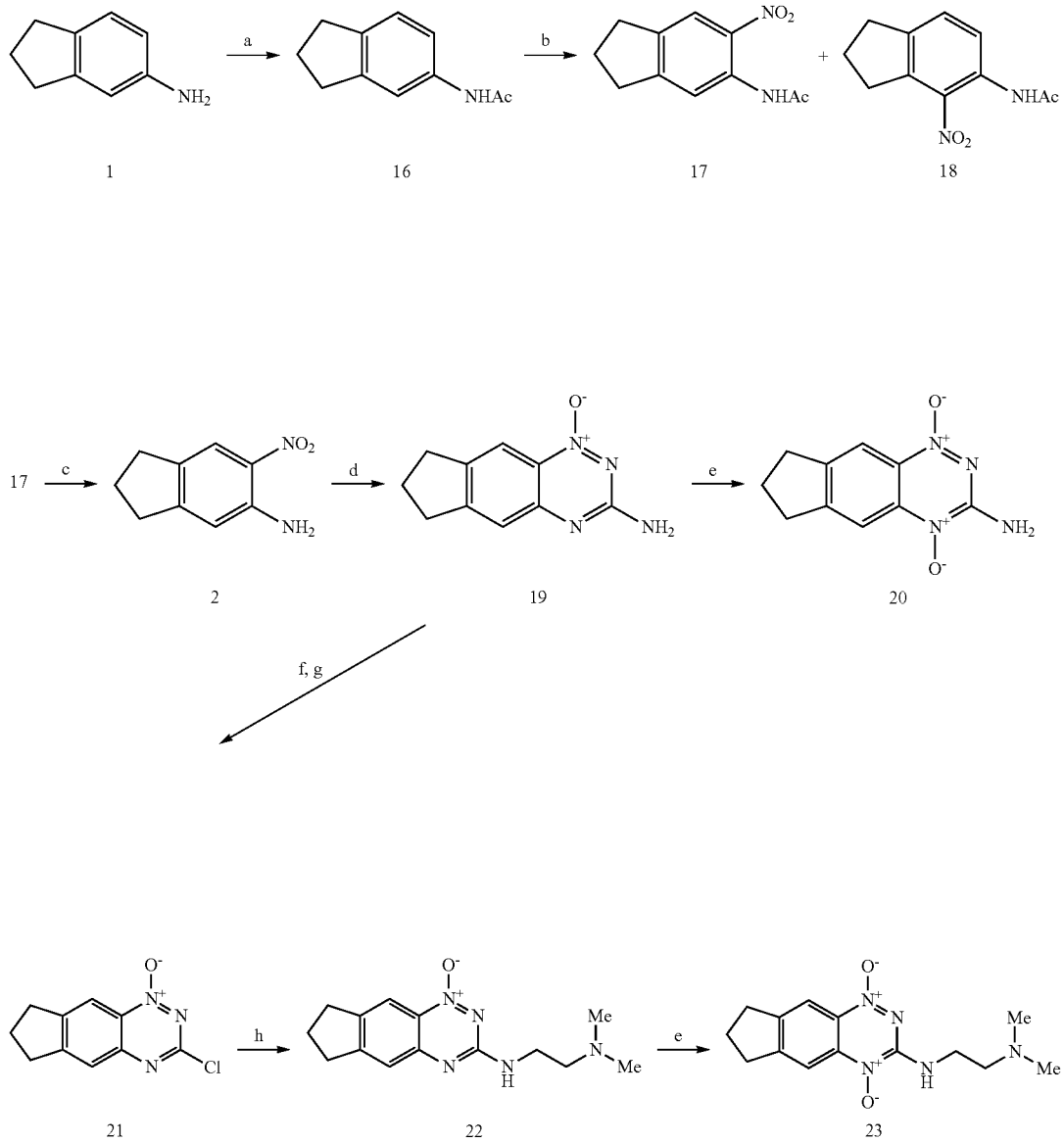

Scheme 3

Reagents:

a) Ac₂O, dioxane;
b) cHNO₃, HOAc;
c) cHCl; EtOH;
d) NH₂CN, HCl; then NaOH;
e) CF₃CO₃H, CF₃CO₂H, DCM;
f) NaNO₂, TFA;
g) POCl₃, DMF;
h) NH₂CH₂CH₂NMe₂, DME.

Similarly, reaction of 21 with a variety of amines gave 1-oxides 24, 26, 28, 30, 32, 34, 36, 38, 40, 42, 44, 46, 48, 50, 52, 54, 56, 58, 60, and 62 which were oxidised to the corresponding 1,4-dioxides 25, 27, 29, 31, 33, 35, 37, 39, 41, 43, 45, 47, 49, 51, 53, 55, 57, 59, 61, and 63 (Scheme 4).

Scheme 4

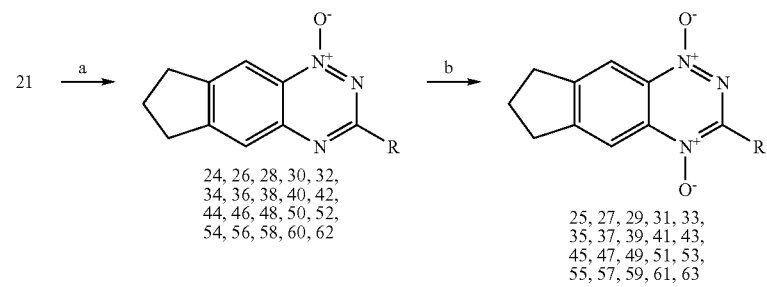

21 —a→ (24, 26, 28, 30, 32, 34, 36, 38, 40, 42, 44, 46, 48, 50, 52, 54, 56, 58, 60, 62) —b→ (25, 27, 29, 31, 33, 35, 37, 39, 41, 43, 45, 47, 49, 51, 53, 55, 57, 59, 61, 63)

| Reagent | 1-oxide | 1,4-dioxide | R = |
|---|---|---|---|
| $NH_2CH_2CH_2OH$ | 24 | 25 | $-NHCH_2CH_2OH$ |
| $NH_2CH_2CH_2NEt_2$ | 26 | 27 | $-NHCH_2CH_2NEt_2$ |
| $NH_2CH_2CH_2NPr_2$ | 28 | 29 | $-NHCH_2CH_2NPr_2$ |
| $NH_2CH_2CH_2N(Me)CH_2CH_2OMe$ | 30 | 31 | $-NHCH_2CH_2N(Me)CH_2CH_2OMe$ |
| $NH_2CH_2CH_2N(Me)CH_2CH_2CH_2OMe$ | 32 | 33 | $-NHCH_2CH_2N(Me)CH_2CH_2CH_2OMe$ |
| $NH_2CH_2CH_2Nazetidine-3-OMe$ | 34 | 35 | $-NHCH_2CH_2Nazetidine-3-OMe$ |
| $NH_2CH_2CH_2Npiperidine$ | 36 | 37 | $-NHCH_2CH_2Npiperidine$ |
| $NH_2CH_2CH_2N-(2,6-diMepiperidine)$ | 38 | 39 | $-NHCH_2CH_2N-(2,6-diMepiperidine)$ |
| $NH_2CH_2CH_2CH_2Npiperidine-3-OMe$ | 40 | 41 | $-NHCH_2CH_2CH_2Npiperidine-3-OMe$ |
| $NH_2CH_2CH_2Npiperidine-4-OMe$ | 42 | 43 | $-NHCH_2CH_2Npiperidine-4-OMe$ |
| $NH_2CH_2CH_2Nmorpholine$ | 44 | 45 | $-NHCH_2CH_2Nmorpholine$ |
| $NH_2CH_2CH_2Nazepane$ | 46 | 47 | $-NHCH_2CH_2Nazepane$ |
| $NH_2CH_2CH_2Noxazepine$ | 48 | 49 | $-NHCH_2CH_2Noxazepine$ |
| $NH_2CH_2CH_2CH_2OH$ | 50 | 51 | $-NHCH_2CH_2CH_2OH$ |
| $NH_2CH_2CH_2CH_2N(Me)CH_2CH_2OMe$ | 52 | 53 | $-NHCH_2CH_2CH_2N(Me)CH_2CH_2OMe$ |
| $NH_2CH_2CH_2CH_2NazetidineOMe$ | 54 | 55 | $-NHCH_2CH_2CH_2NazetidineOMe$ |
| $NH_2CH_2CH_2CH_2N(pyrrolidine-3-CN)$ | 56 | 57 | $-NHCH_2CH_2CH_2N(pyrrolidine-3-CN)$ |
| $NH_2CH_2CH_2CH_2Npiperidine-4-OMe$ | 58 | 59 | $-NHCH_2CH_2CH_2Npiperidine-4-OMe$ |
| $NH_2CH_2CH_2CH_2Nmorpholine$ | 60 | 61 | $-NHCH_2CH_2CH_2Nmorpholine$ |
| $NH_2CH_2CH_2CH_2CH_2Nmorpholine$ | 62 | 63 | $-NHCH_2CH_2CH_2CH_2Nmorpholine$ |

Reagents:
a) amine, DME; or amine, $Et_3N$, DME;
b) $CF_3CO_3H$, $CF_3CO_2H$, DCM.

Reaction of amine 19 with tert-butyl nitrite in DMF gave the 1-oxide 64, which was oxidised to 1,4-dioxide 65 (Scheme 5).

Scheme 5

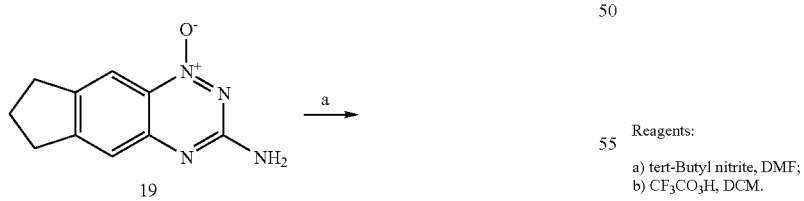

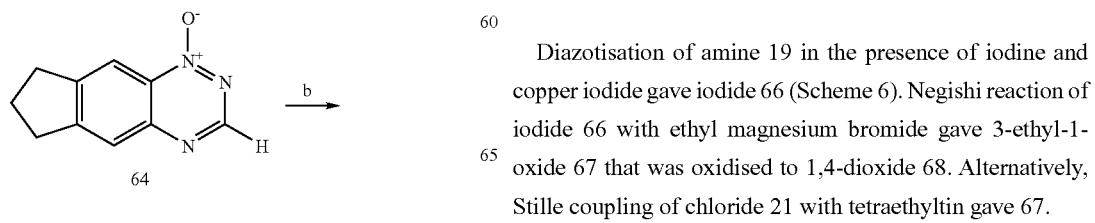

Reagents:
a) tert-Butyl nitrite, DMF;
b) $CF_3CO_3H$, DCM.

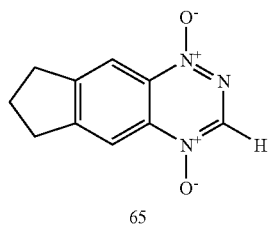

Diazotisation of amine 19 in the presence of iodine and copper iodide gave iodide 66 (Scheme 6). Negishi reaction of iodide 66 with ethyl magnesium bromide gave 3-ethyl-1-oxide 67 that was oxidised to 1,4-dioxide 68. Alternatively, Stille coupling of chloride 21 with tetraethyltin gave 67.

Scheme 6

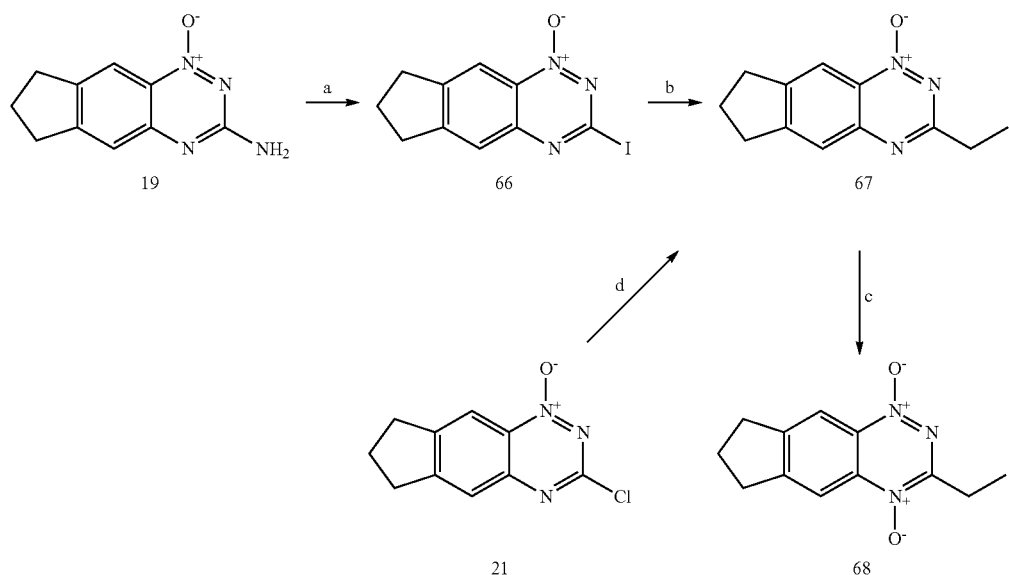

Reagents:
a) tert-BuNO₂, CH₂I₂, CuI, THF;
b) EtMgBr, ZnCl₂·Et₂O, Pd(PPh₃)₄, THF;
c) CF₃CO₃H, DCM
d) Et₄Sn, Pd(dppf)Cl₂, THF.

Stille coupling of iodide 66 with allyltributyltin gave alkene 69 which underwent hydroboration to give alcohol 70 (Scheme 7). Alternatively, reaction of iodide 66 with allyl alcohol using Heck conditions followed by reduction of the intermediate aldehyde gave alcohol 70. Oxidation of alcohol 70 gave 1,4-dioxide 71.

Scheme 7

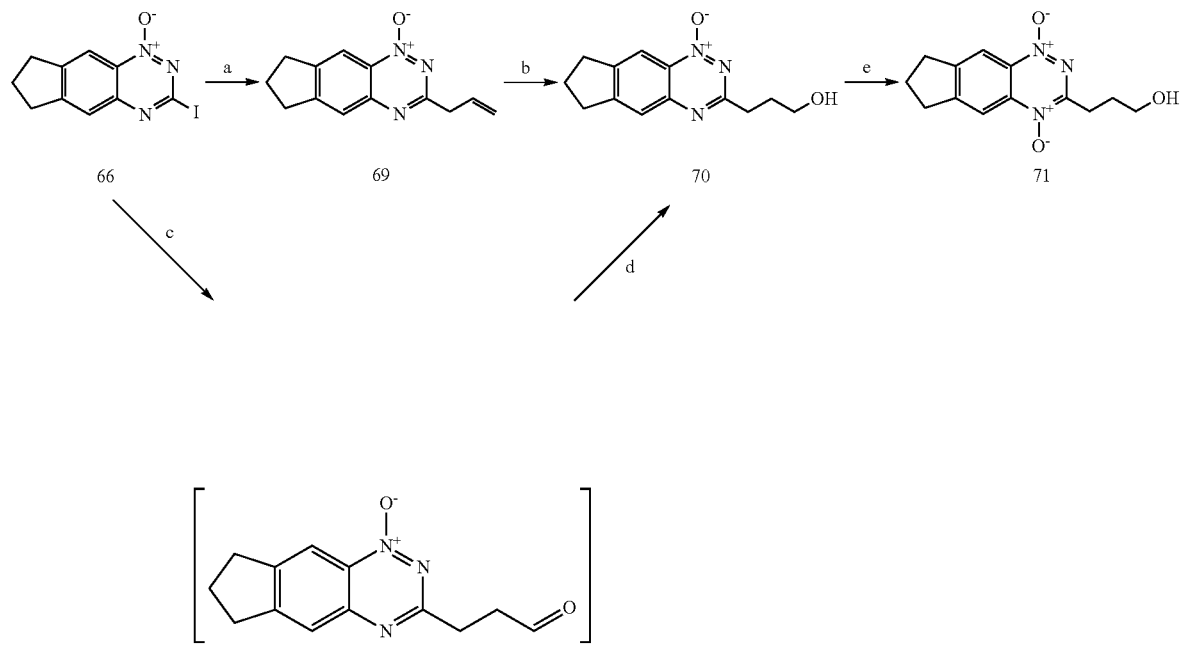

Reagents:
a) AllylSnBu₃, Pd(PPh₃)₄, THF;
b) 9-BBN, THF; NaOH, H₂O₂;
c) Allyl alcohol, Pd(OAc)₂, nBu₄NCl, NaHCO₃, MeCN;
d) NaBH₄, MeOH, -40° C.
e) CF₃CO₃H, DCM.

Reaction of the alcohol 70 with di-tert-butyldiethylphosphoramidite in the presence of tetrazole with subsequent oxidation of the intermediate phosphite gave phosphate ester 72 (Scheme 8). Oxidation of ester 72 gave 1,4-dioxide 73, which was deprotected to give phosphate 74.

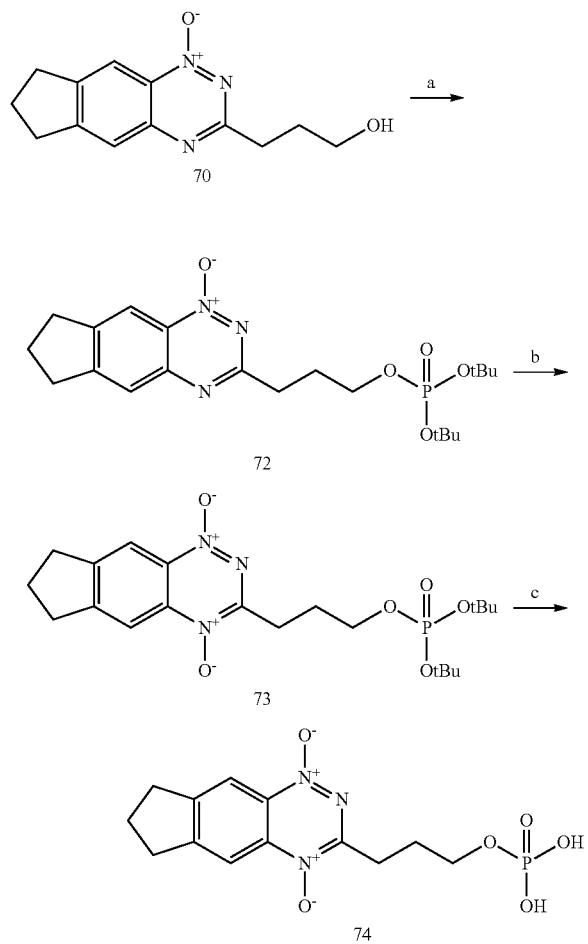

Reagents:
a) Di-tert-butyldiethylphosphoramidite, tetrazole, THF, then MCPBA;
b) MCPBA, NaHCO₃, DCM;
c) CF₃CO₂H, DCM.

Heck reaction of iodide 66 with allyl alcohol gave the unstable aldehyde 75 that was converted to 1-oxide 76 by reductive amination with morpholine and sodium cyanoborohydride (Scheme 9). Oxidation of 1-oxide 76 with trifluoroperacetic acid gave 1,4-dioxide 77.

Scheme 9

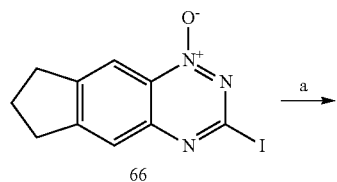

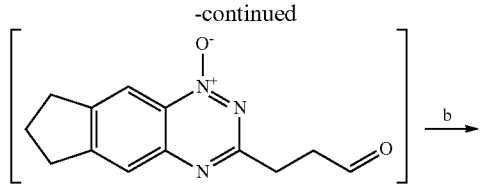

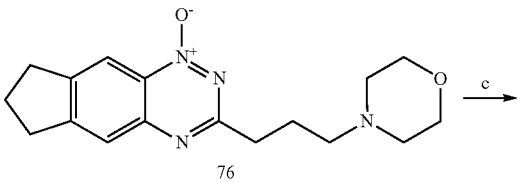

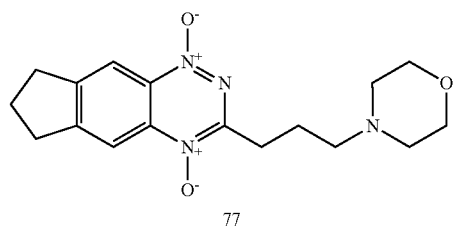

Reagents:
a) Allyl alcohol, Pd(OAc)₂, nBu₄NBr, NAHCO₃, DMF;
b) Morpholine, NaBH₃CN, EtOH; then HOAc;
c) CF₃CO₃H, CF₃CO₂H, DCM.

A similar sequence of reactions converted 66 to 1-oxides 78, 82, 82, 84, and 86, which were oxidised to the corresponding 1,4-dioxides 79, 81, 83, 85, and 87 (Scheme 10).

Scheme 10

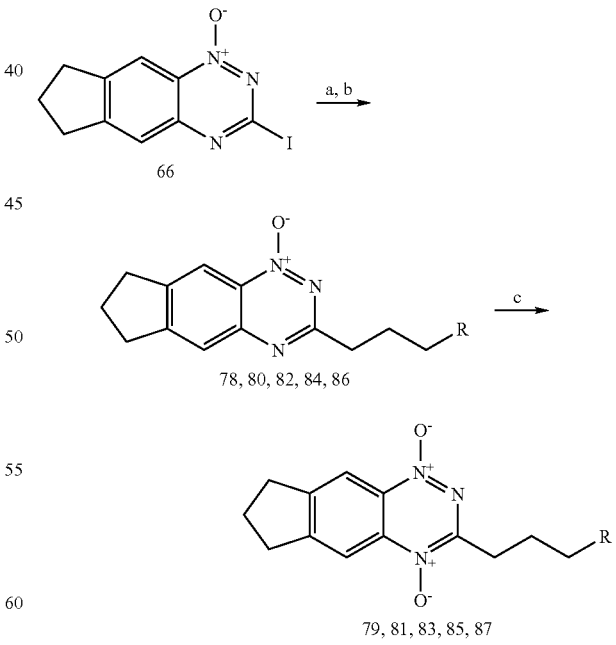

| Reagent | 1-oxide | 1,4-dioxide | R = |
|---|---|---|---|
| HNMe₂ | 78 | 79 | —NMe₂ |
| HN(CH₂CH₂OMe)₂ | 80 | 81 | —N(CH₂CH₂OMe)₂ |
| Azetidine-3-OMe | 82 | 83 | —Nazetidine-3-OMe |

| | | | |
|---|---|---|---|
| Pyrrolidine | 84 | 85 | —Npyrrolidine |
| Piperidine | 86 | 87 | —Npiperidine |

Reagents:
a) Allyl alcohol, Pd(OAc)$_2$, nBu$_4$NBr, NaHCO$_3$, DMF;
b) Amine, NaBH$_3$CN, EtOH; then HOAc;
c) CF$_3$CO$_3$H, CF$_3$CO$_2$H, DCM.

Nitration of 2-methyl-1-indanone (88) gave a mixture of nitroindanones 89 and 90 (Scheme 11). Reduction of nitroindanone 90 and acetylation gave acetamide 91 that was nitrated to give nitroacetamide 92. Hydrolysis of 92 gave the nitroaniline 93. Treatment of nitroaniline 93 with cyanamide under acidic conditions followed by cyclisation under basic conditions gave 1-oxide 94. Diazotisation and chlorination of 1-oxide 94 gave chloride 95. Reaction of chloride 95 with N,N-dimethylethylenediamine gave 1-oxide 96 which was oxidised to 1,4-dioxide 97.

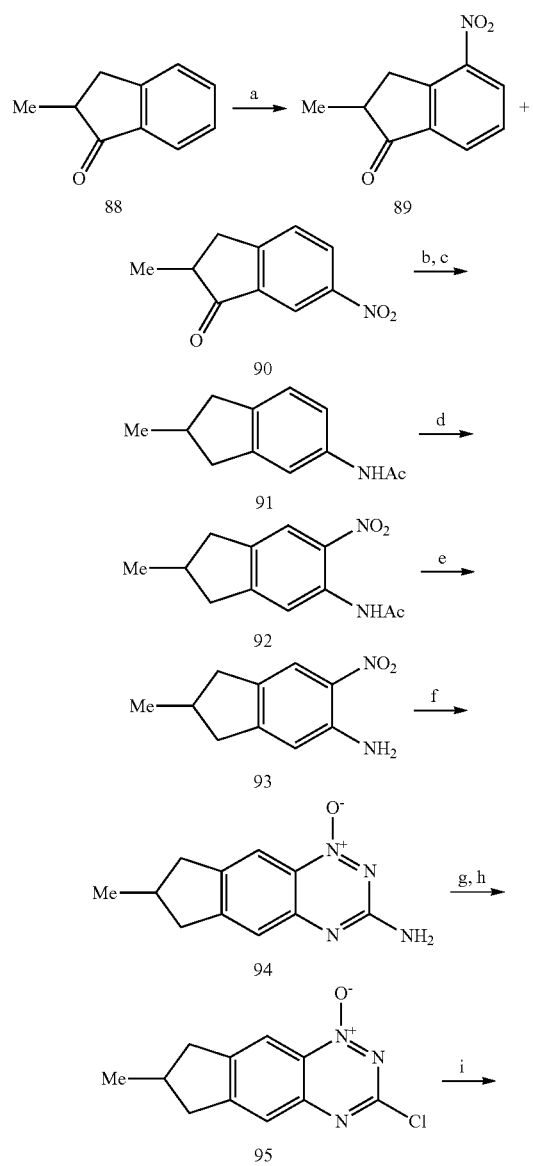

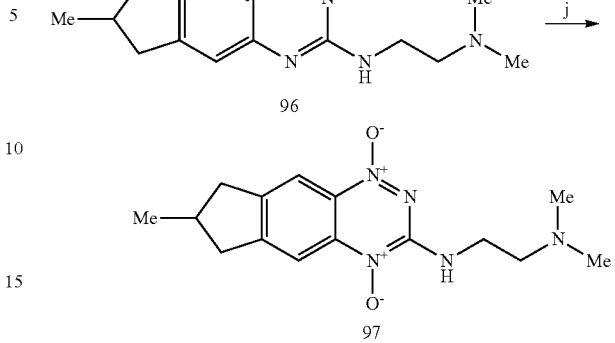

Reagents:
a) fHNO$_3$;
b) H$_2$, Pd/C, EtOH, aq HCl;
c) Ac$_2$O, dioxane;
d) HNO$_3$, CF$_3$CO$_2$H;
e) cHCl, EtOH;
f) NH$_2$CN, HCl; then NaOH;
g) NaNO$_2$, TFA;
h) POCl$_3$, DMF;
i) NH$_2$CH$_2$CH$_2$NMe$_2$, DME;
j) CF$_3$CO$_3$H, CF$_3$CO$_2$H, DCM.

Similarly, reaction of chloride 95 with 3-(4-morpholinyl)propylamine gave 1-oxide 98 which was oxidised to 1,4-dioxide 99 (Scheme 12).

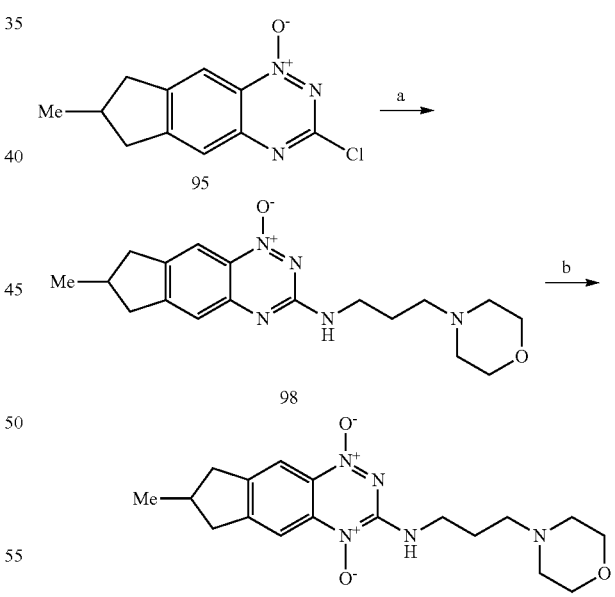

Reagents:
a) NH$_2$CH$_2$CH$_2$CH$_2$Nmorpholine, Et$_3$N, DME;
b) CF$_3$CO$_3$H, CF$_3$CO$_2$H, DCM.

Diazotisation of amine 94 in the presence of diiodomethane gave iodide 100 (Scheme 13). Heck coupling of iodide 100 with allyl alcohol gave the unstable aldehyde 101 which underwent reductive amination with morpholine to give 1-oxide 102. Alcohol 103 was also isolated from the reaction mixture. Oxidation of 1-oxides 102 and 103 gave 1,4-dioxides 104 and 105, respectively.

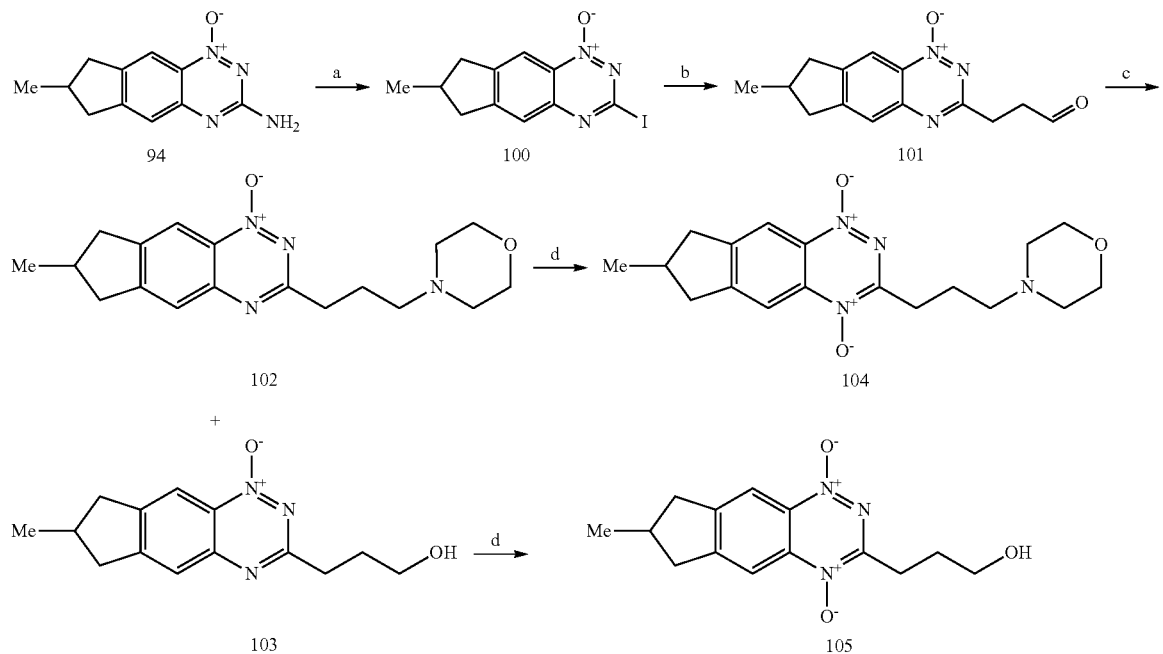

Reagents:
a) tBuNO$_2$, CH$_2$I$_2$, CuI, THF;
b) Allyl alcohol, Pd(OAc)$_2$, nBu$_4$NBr, NaHCO$_3$, DMF;
c) Morpholine, NaBH$_3$CN, EtOH; then HOAc;
d) CF$_3$CO$_3$H, CF$_3$CO$_2$H, DCM.

Mesylation of 2-indanol (106) and displacement of the mesylate with methylamine gave the indanamine 107 (Scheme 14). Nitration of indanamine 107 with nitric acid in trifluoroacetic acid gave predominantly the 5-nitroindanamine 108 which was reduced by catalytic hydrogenation and subsequent acetylation to give acetamide 109. Nitration of acetamide 109 with nitric acid in trifluoroacetic acid gave a 6:1 mixture of 6-nitro:4-nitroacetamide isomers which was hydrolysed with ethanolic HCl and recrystallised to give pure 6-nitro-5-aniline 110. Treatment of nitroaniline 110 with cyanamide under acidic conditions followed by cyclisation under basic conditions gave amine 111. Diazotisation and chlorination of 111 gave chloride 112. Reaction of chloride 112 with aqueous ethylamine gave 1-oxide 113, which was oxidised to 1,4-dioxide 114.

Scheme 14

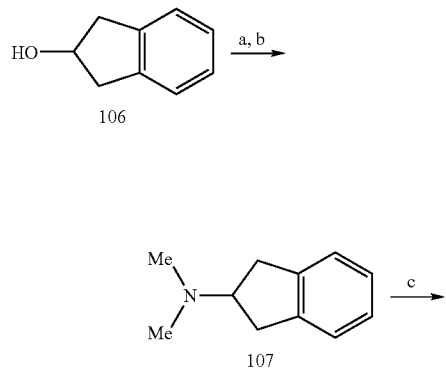

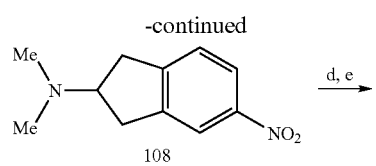

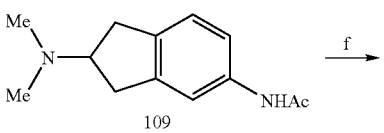

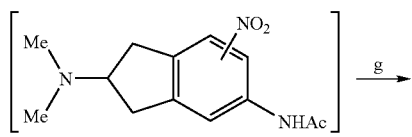

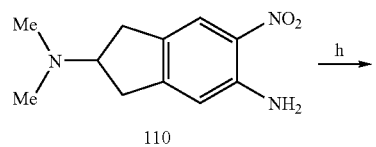

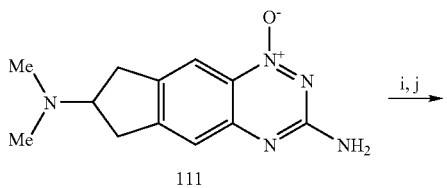

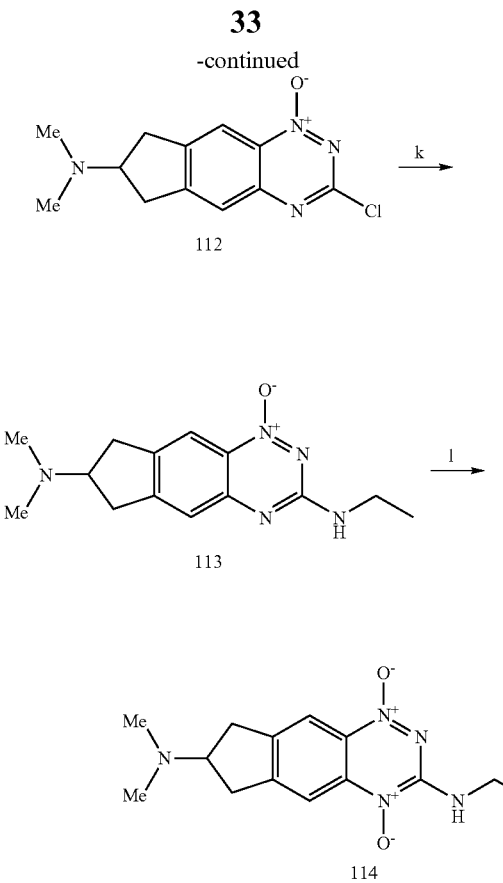

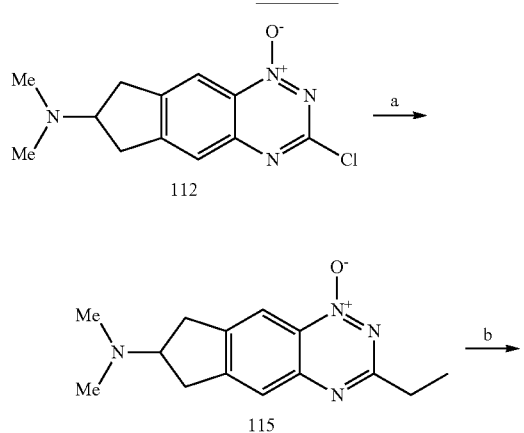

Reagents:
a) MsCl, iPr$_2$NEt, DCM;
b) aq. HNMe$_2$, DMF;
c) cHNO$_3$, CF$_3$CO$_2$H;
d) H$_2$, Pd/C, EtOH;
e) Ac$_2$O, dioxane;
f) cHNO$_3$, CF$_3$CO$_2$H;
g) cHCl, EtOH;
h) NH$_2$CN, HCl; then NaOH;
i) NaNO$_2$, TFA;
j) POCl$_3$, DMF;
k) aq. EtNH$_2$, DME;
l) CF$_3$CO$_3$H, DCM.

Stille coupling of chloride 112 with tetraethyltin gave 1-oxide 115, which was oxidised to 1,4-dioxide 116 (Scheme 15).

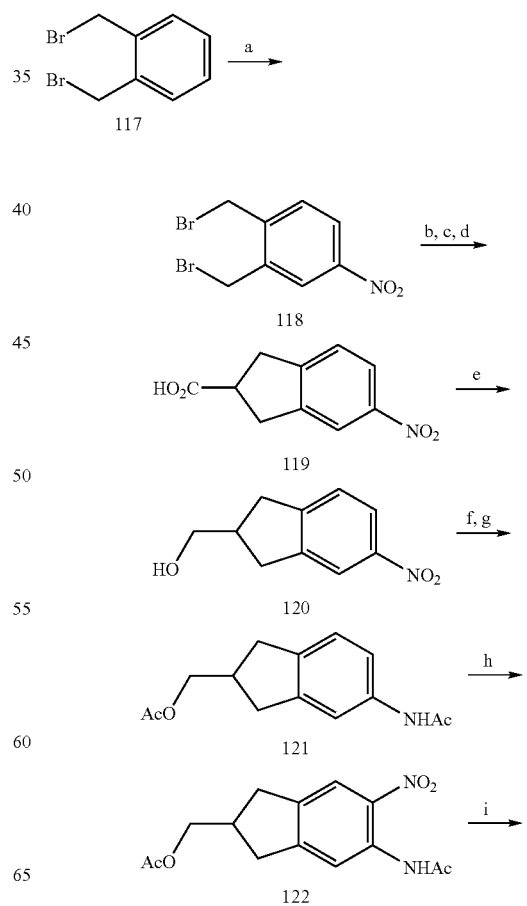

Reagents:
a) Et$_4$Sn, Pd(PPh$_3$)$_4$, DME;
b) CF$_3$CO$_3$H, CF$_3$CO$_2$H, DCM.

Nitration of 1,2-bis(bromomethyl)benzene (117) gave 4-nitrobenzene 118 (Scheme 16). Condensation of 118 with diethylmalonate gave the acid 119, which was reduced to alcohol 120 with diborane. Catalytic hydrogenation of 120 followed by acetylation with acetic anhydride gave acetamide 121. Nitration of acetamide 121 gave the 5-nitroisomer 122 which was hydrolysed under acidic conditions to give nitroaniline 123. Treatment of nitroaniline 123 with cyanamide under acidic conditions followed by cyclisation under basic conditions gave amine 124. Diazotisation and bromination of 124 gave bromide 125. Reaction of the bromide 125 with aqueous ethylamine gave 1-oxide 126 that was oxidised to 1,4-dioxide 127.

Scheme 16

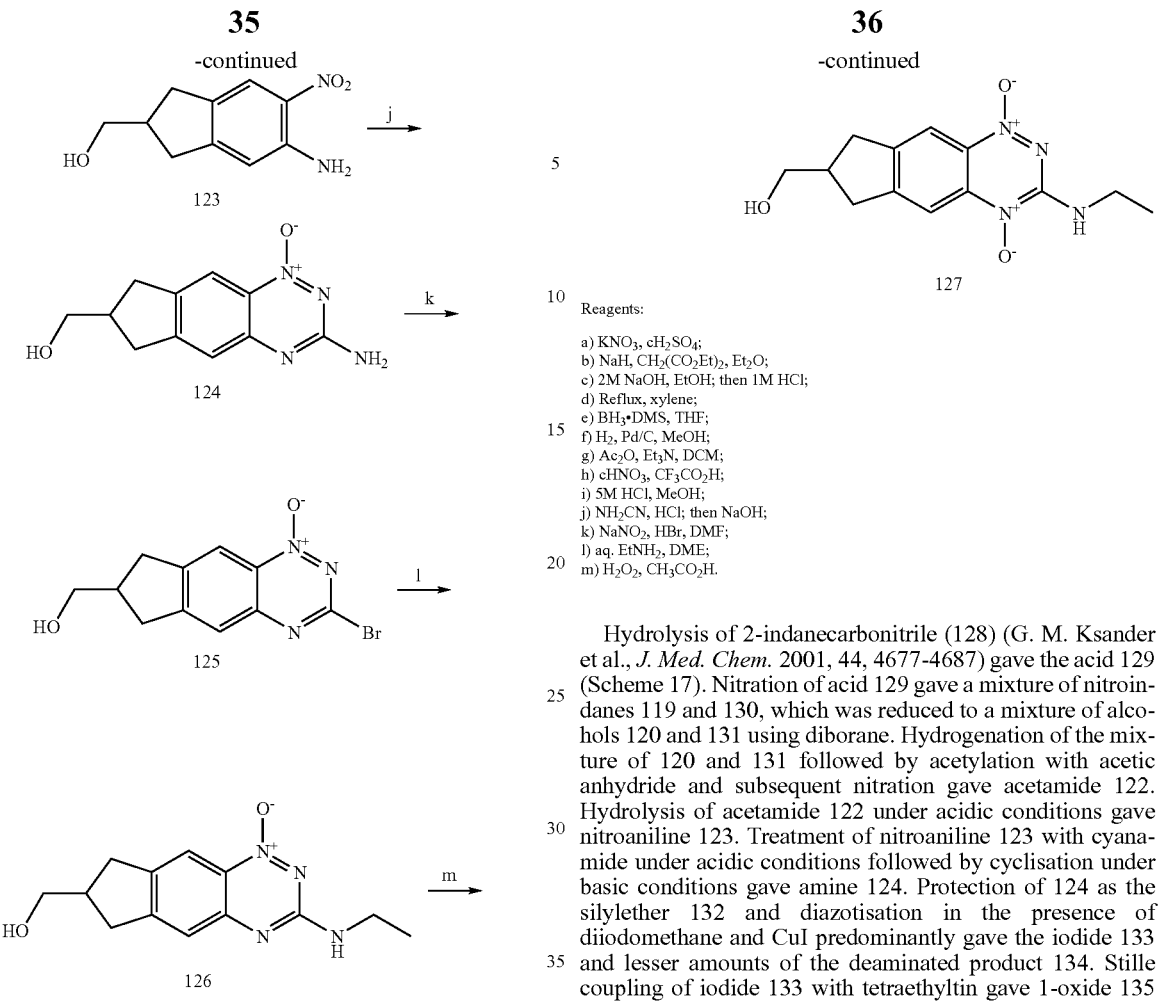

Reagents:

a) $KNO_3$, $cH_2SO_4$;
b) NaH, $CH_2(CO_2Et)_2$, $Et_2O$;
c) 2M NaOH, EtOH; then 1M HCl;
d) Reflux, xylene;
e) $BH_3$·DMS, THF;
f) $H_2$, Pd/C, MeOH;
g) $Ac_2O$, $Et_3N$, DCM;
h) $cHNO_3$, $CF_3CO_2H$;
i) 5M HCl, MeOH;
j) $NH_2CN$, HCl; then NaOH;
k) $NaNO_2$, HBr, DMF;
l) aq. $EtNH_2$, DME;
m) $H_2O_2$, $CH_3CO_2H$.

Hydrolysis of 2-indanecarbonitrile (128) (G. M. Ksander et al., *J. Med. Chem.* 2001, 44, 4677-4687) gave the acid 129 (Scheme 17). Nitration of acid 129 gave a mixture of nitroindanes 119 and 130, which was reduced to a mixture of alcohols 120 and 131 using diborane. Hydrogenation of the mixture of 120 and 131 followed by acetylation with acetic anhydride and subsequent nitration gave acetamide 122. Hydrolysis of acetamide 122 under acidic conditions gave nitroaniline 123. Treatment of nitroaniline 123 with cyanamide under acidic conditions followed by cyclisation under basic conditions gave amine 124. Protection of 124 as the silylether 132 and diazotisation in the presence of diiodomethane and CuI predominantly gave the iodide 133 and lesser amounts of the deaminated product 134. Stille coupling of iodide 133 with tetraethyltin gave 1-oxide 135 that was oxidised to give 1,4-dioxide 136.

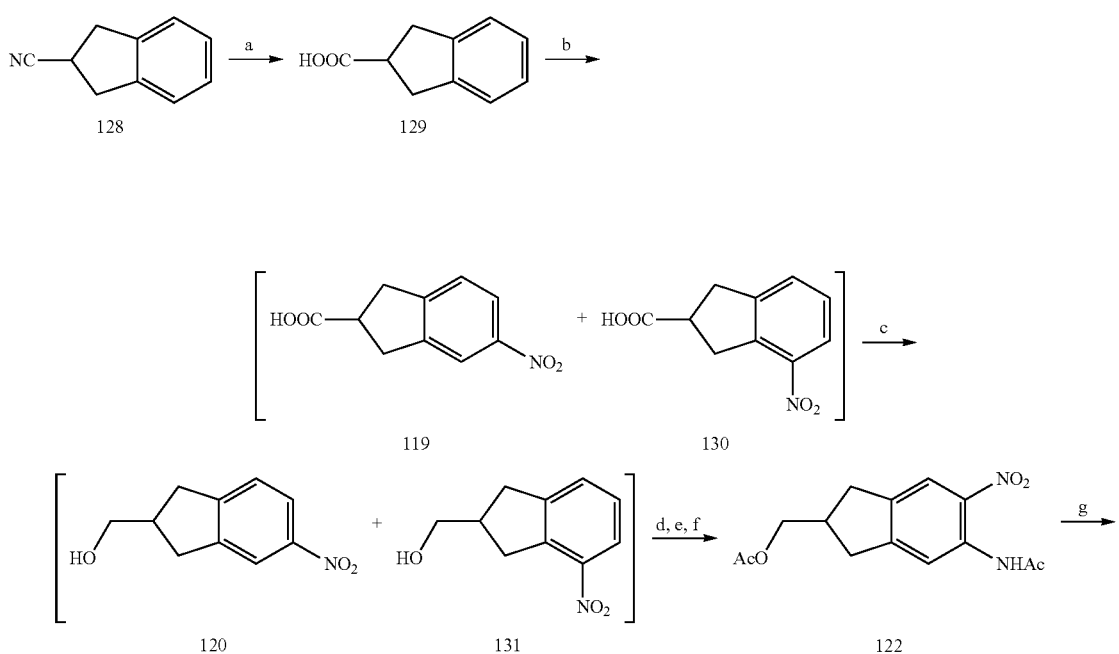

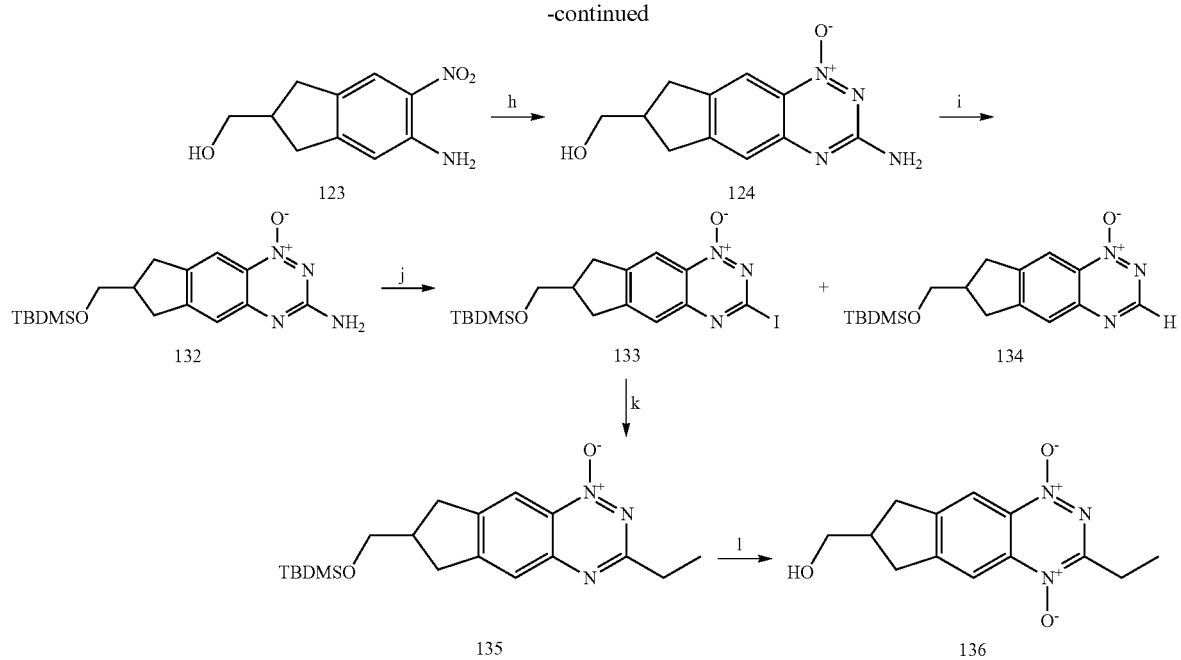

Reagents:

a) cHCl, dioxane;
b) cHNO₃, CF₃CO₂H;
c) BH₃·DMS, THF;
d) H₂, Pd/C, MeOH;
e) Ac₂O, Et₃N, DCM;
f) cHNO₃, CF₃CO₂H;
g) 5M HCl, MeOH;
h) NH₂CN, HCl; then NaOH;
i) TBDMSCl, iPr₂NEt, DMF;
j) tert-BuNO₂, CH₂I₂, CuI, THF;
k) Et₄Sn, Pd(PPh₃)₄, DME;
l) H₂O₂, CH₃CO₂H.

Stille coupling of iodide 133 with allyltributyltin gave alkene 137, which underwent hydroboration with 9-BBN to give alcohol 138 (Scheme 18). Mesylation and displacement of alcohol 138 with morpholine gave 1-oxide 139 that was deprotected to give alcohol 140 and oxidised to give 1,4-dioxide 141.

Scheme 18

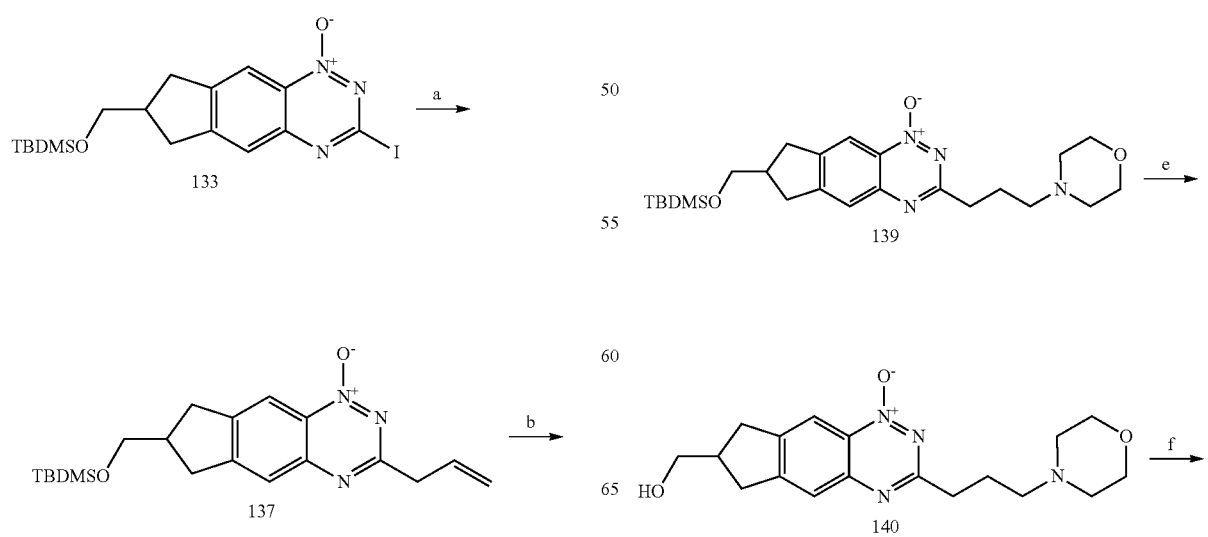

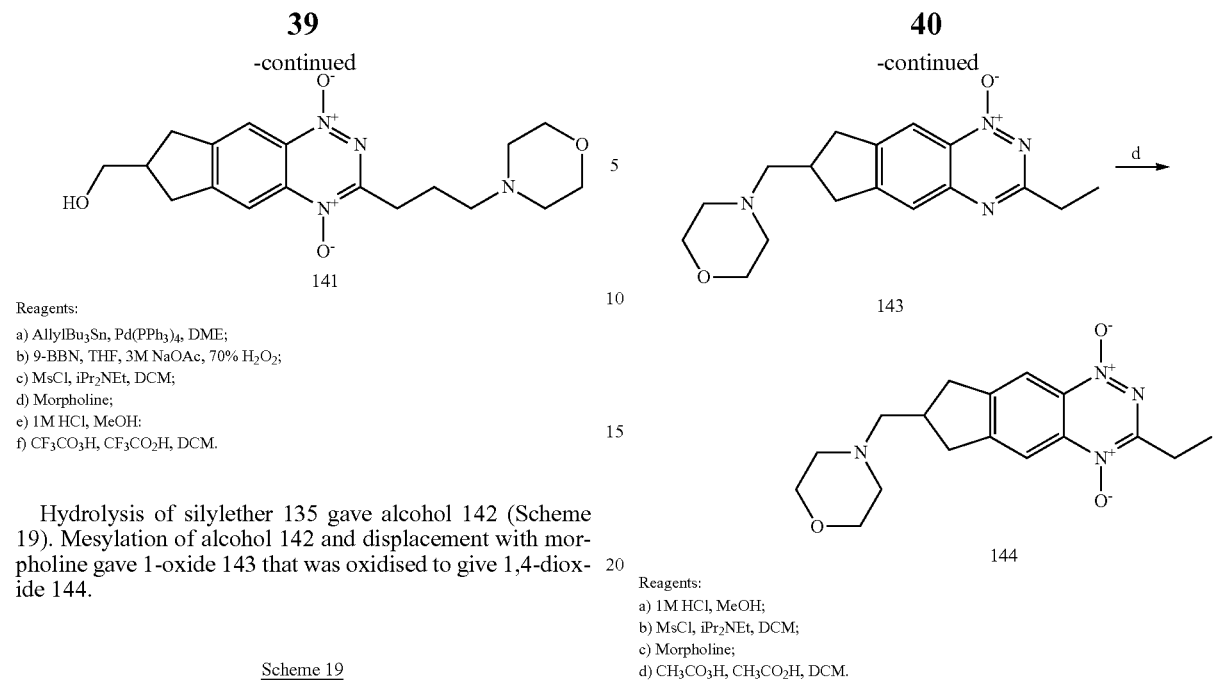

Reagents:
a) AllylBu$_3$Sn, Pd(PPh$_3$)$_4$, DME;
b) 9-BBN, THF, 3M NaOAc, 70% H$_2$O$_2$;
c) MsCl, iPr$_2$NEt, DCM;
d) Morpholine;
e) 1M HCl, MeOH:
f) CF$_3$CO$_3$H, CF$_3$CO$_2$H, DCM.

Hydrolysis of silylether 135 gave alcohol 142 (Scheme 19). Mesylation of alcohol 142 and displacement with morpholine gave 1-oxide 143 that was oxidised to give 1,4-dioxide 144.

Reagents:
a) 1M HCl, MeOH;
b) MsCl, iPr$_2$NEt, DCM;
c) Morpholine;
d) CH$_3$CO$_3$H, CH$_3$CO$_2$H, DCM.

Scheme 19

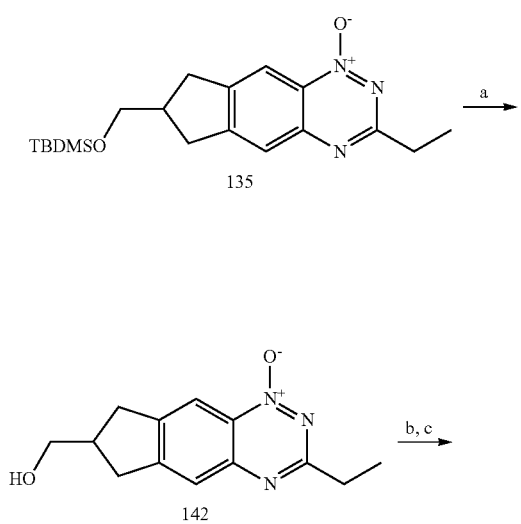

Condensation of 1-indanone (145) with glyoxylic acid gave unsaturated acid 146 that was reduced by catalytic hydrogenation to indane acetic acid 147 (Scheme 20) (Nagasawa, et al., Japanese Patent 4338358, 1992). Esterification of acid 147 gave ester 148 which was reduced to alcohol 149 with LiAlH$_4$. Acetylation of alcohol 149 gave acetate 150 that was nitrated to give an inseparable mixture of nitroindanes 151 and 152. The mixture was reduced by catalytic hydrogenation and acetylated with acetic anhydride to give a mixture of acetanilides 153 and 154. The mixture of 153 and 154 was nitrated with cHNO$_3$ in trifluoroacetic acid and a single isomer, nitroacetanilide 155, was isolated by crystallisation. Hydrolysis of nitroacetanilide 155 gave nitroaniline 156. Treatment of nitroaniline 156 with cyanamide under acidic conditions followed by cyclisation under basic conditions gave amine 157. Diazotisation of amine 157 in the presence of iodine and CuI gave iodide 158 that was protected as the tetrahydropyranyl ether 159. Stille coupling of iodide 159 with tetraethyltin gave 1-oxide 160, which was deprotected to give alcohol 161 and then oxidised to give 1,4-dioxide 162.

Scheme 20

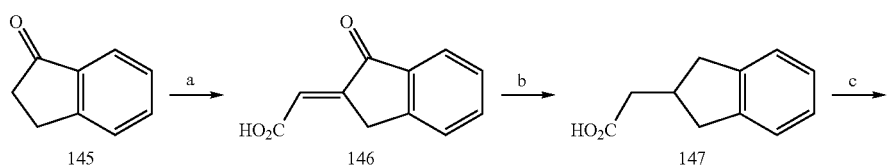

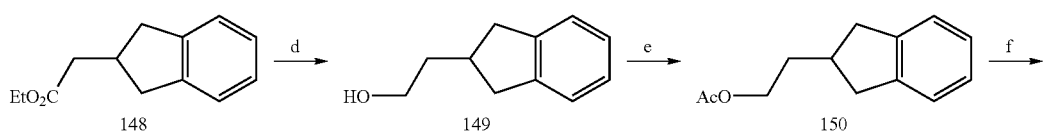

-continued
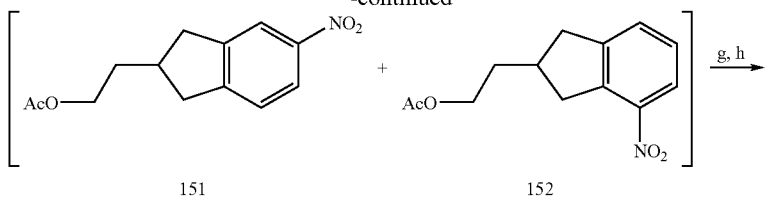
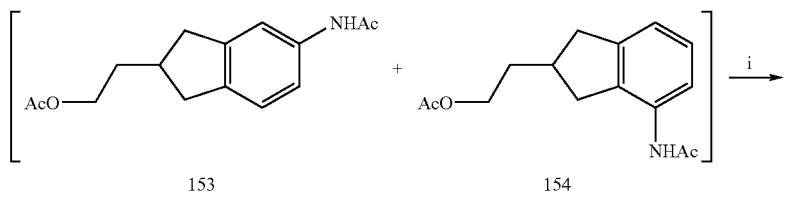
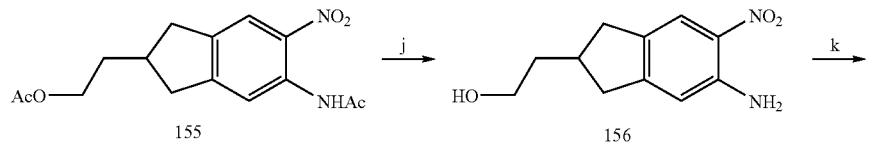
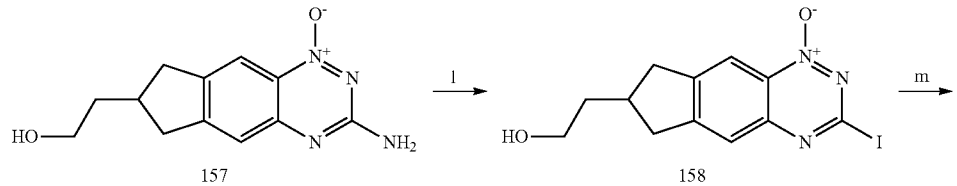
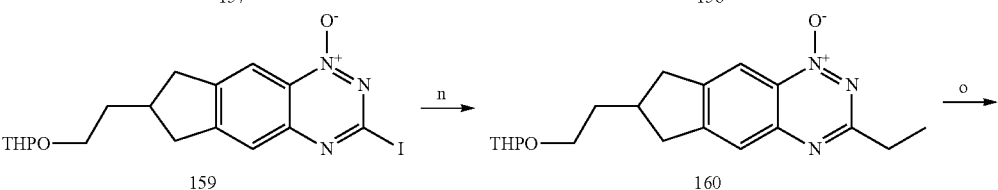
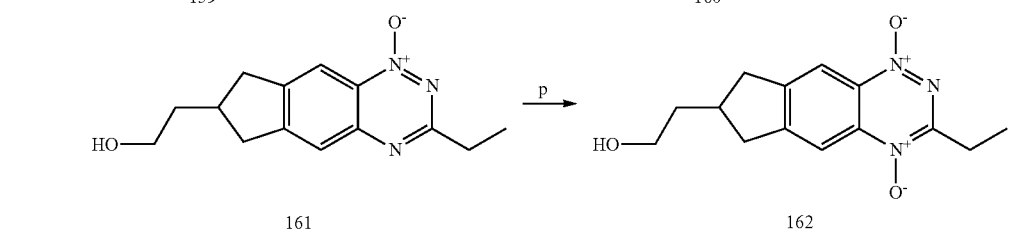
Reagents:
a) aq. glyoxylic acid, cH$_2$SO$_4$;
b) H$_2$, Pd/C, MeOH, dioxane;
c) cH$_2$SO$_4$, EtOH;
d) LiAlH$_4$, THF;
e) Ac$_2$O, pyridine, DMAP, DCM;
f) Ac$_2$O, Cu(NO$_3$)$_2$·3H$_2$O, DCM;
g) H$_2$, Pd/C, MeOH;
h) Ac$_2$O, dioxane;
i) cHNO$_3$, CF$_3$CO$_2$H;
j) 5M HCl, MeOH;
k) NH$_2$CN, HCl; then NaOH;
l) tert-BuNO$_2$, I$_2$, CuI, THF;
m) Dihydropyran, PPTS, DCM;
n) Et$_4$Sn, Pd(PPh$_3$)$_4$, DME;
o) MeSO$_3$H, MeOH;
p) CF$_3$CO$_2$H, DCM.

Mesylation of alcohol 161 and displacement with morpholine gave 1-oxide 163 that was oxidised to give 1,4-dioxide 164 (Scheme 21).

Scheme 21

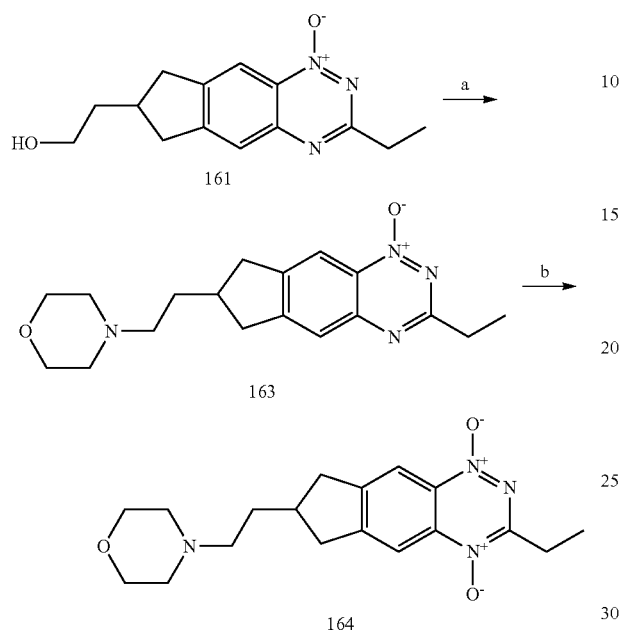

Reagents:
a) MsCl, NEt₃, DCM;
b) morpholine;
c) CF₃CO₃H, CF₃CO₂H, DCM.

Nitration of 1-tetralone (165) followed by reduction and acetylation gave acetamide 166 (Scheme 22). Further nitration gave a mixture of isomers including 157 and 168. Hydrolysis of 168 gave nitroaniline 169, which was treated with cyanamide under acidic conditions followed by cyclisation under basic conditions to give amine 170. Diazotisation and chlorination of 170 gave chloride 171. Reaction of the chloride 171 with N,N-dimethylethylenediamine gave 1-oxide 172 which was oxidised to 1,4-dioxide 173.

Scheme 22

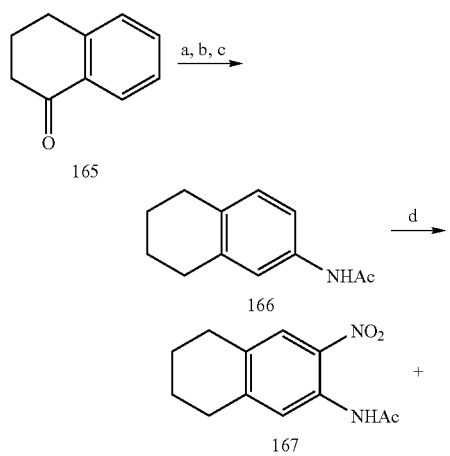

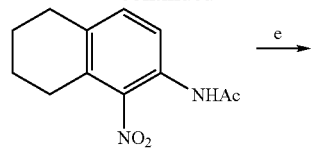

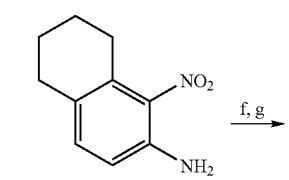

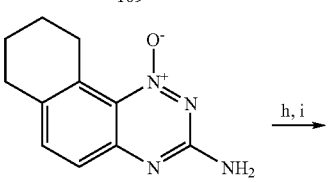

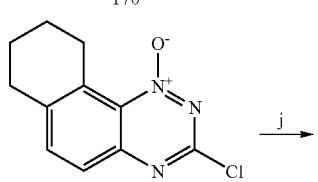

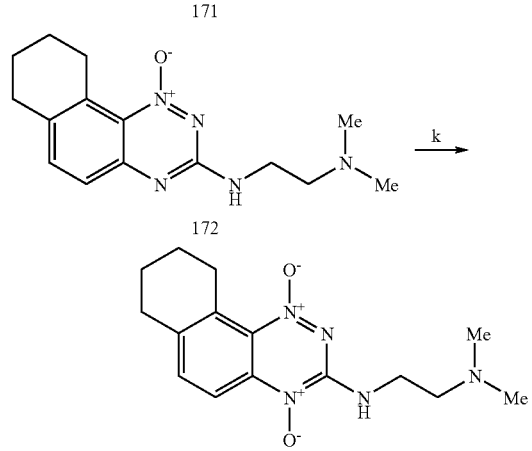

Reagents:
a) KNO₃, cH₂SO₄;
b) H₂, Pd/C, EtOH, EtOAc, HCl;
c) Ac₂O, dioxane;
d) KNO₃, cH₂SO₄;
e) 6M HCl;
f) NH₂CN, HCl;
g) NaOH;
h) NaNO₂, TFA;
i) POCl₃, DMF;
j) NH₂CH₂CH₂NMe₂, DME;
k) CF₃CO₃H, CF₃CO₂H, DCM.

Deprotection of acetamide 167 under acidic conditions gave nitroaniline 174 (Scheme 23). Treatment of nitroaniline 174 with cyanamide under acidic conditions followed by cyclisation under basic conditions gave 1-oxide 175. Diazotisation and chlorination of 175 gave chloride 176. Reaction of the chloride 176 with N,N-dimethylethylendiamine gave 1-oxide 177 which was oxidised to 1,4-dioxide 178.

Scheme 23

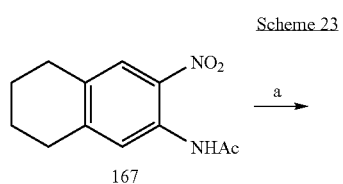

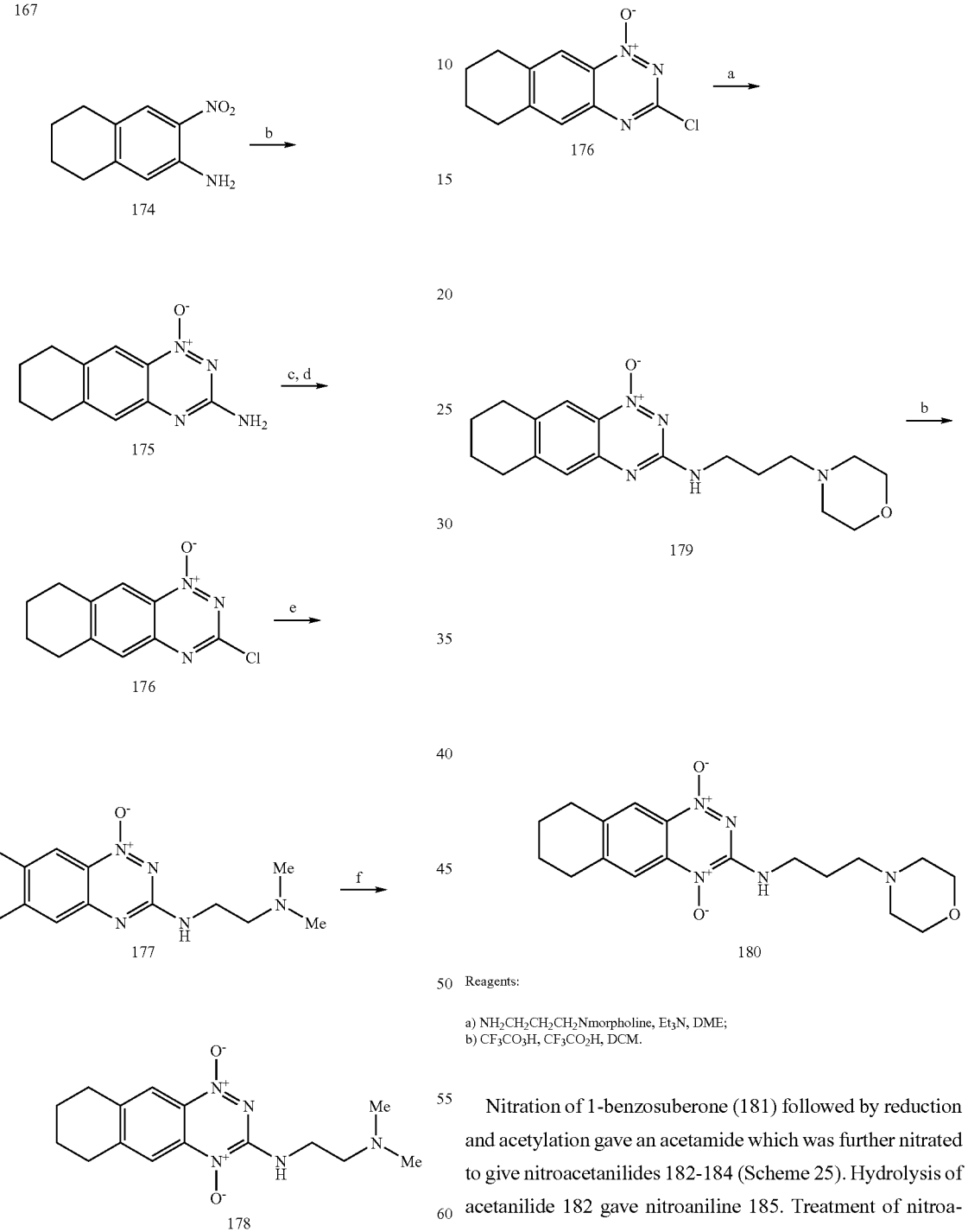

Reagents:
a) HCl;
b) NH₂CN, HCl; then NaOH;
c) NaNO₂, TFA;
d) POCl₃, DMF;
e) NH₂CH₂CH₂NMe₂, DME;
f) CF₃CO₃H, CF₃CO₂H, DCM.

Similarly, reaction of chloride 176 with 3-(4-morpholinyl)propylamine gave 1-oxide 179 which was oxidised to 1,4-dioxide 180 (Scheme 24).

Reagents:
a) NH₂CH₂CH₂CH₂Nmorpholine, Et₃N, DME;
b) CF₃CO₃H, CF₃CO₂H, DCM.

Nitration of 1-benzosuberone (181) followed by reduction and acetylation gave an acetamide which was further nitrated to give nitroacetanilides 182-184 (Scheme 25). Hydrolysis of acetanilide 182 gave nitroaniline 185. Treatment of nitroaniline 185 with cyanamide under acidic conditions followed by cyclisation under basic conditions gave amine 186. Diazotisation and chlorination of 186 gave chloride 187. Reaction of chloride 187 with N,N-dimethylethylendiamine gave 1-oxide 188 which was oxidised to 1,4-dioxide 189.

Scheme 25

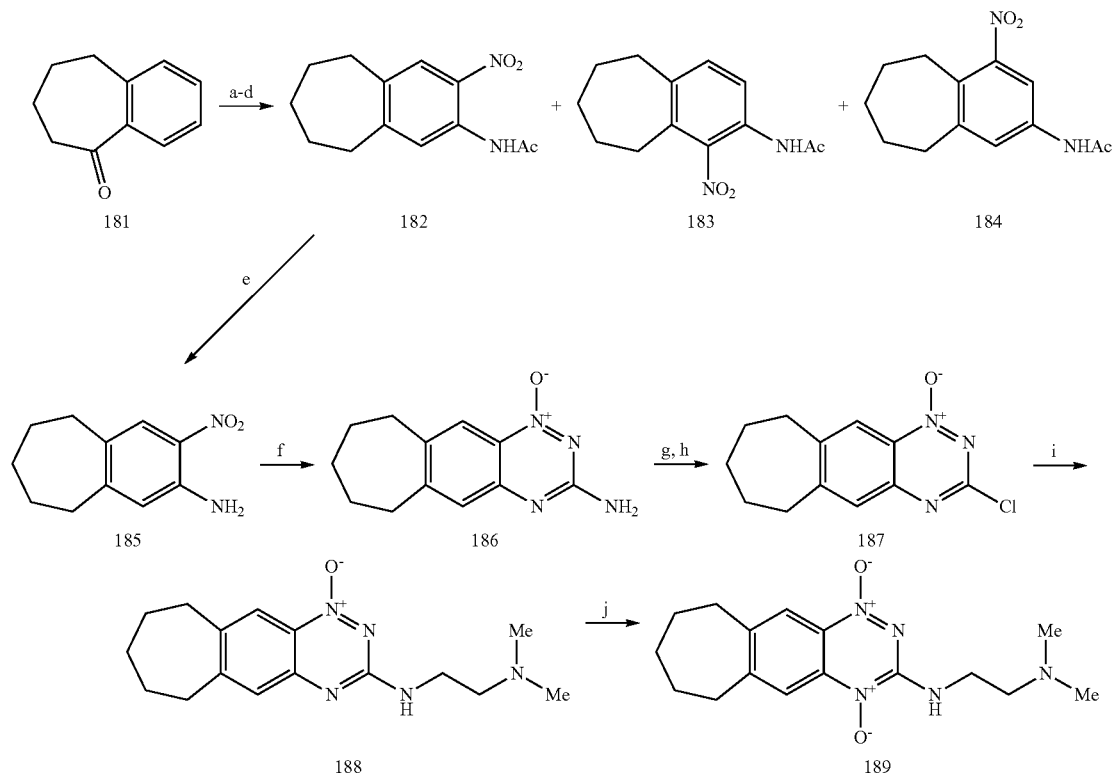

Reagents:

a) fHNO₃, cH₂SO₄;
b) H₂, Pd/C, EtOH/EtOAc;
c) Ac₂O, dioxane;
d) KNO₃, cH₂SO₄;
e) 5M HCl;
f) NH₂CN, HCl; then NaOH;
g) NaNO₂, TFA;
h) POCl₃, DMF;
i) NH₂CH₂CH₂NMe₂, DME;
j) CF₃CO₃H, CF₃CO₂H, DCM.

Friedel-Crafts acylation of 2,3-dihydrobenzofuran (190) gave ketone 191 which was converted to the oxime and underwent Beckmann rearrangement to the acetamide 192 (Scheme 26). Nitration of acetamide 192 gave nitroacetamide 193, which was hydrolysed to give nitroaniline 194. Treatment of nitroaniline 194 with cyanamide under acidic conditions followed by cyclisation under basic conditions gave amine 195. Diazotisation and chlorination of 195 gave chloride 196. Reaction of the chloride 196 with N,N-dimethylethylenediamine gave 1-oxide 197 which was oxidised to 1,4-dioxide 198.

Scheme 26

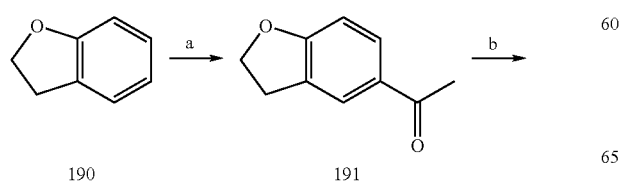

-continued

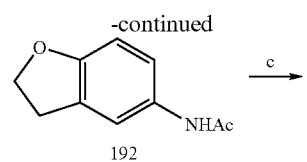

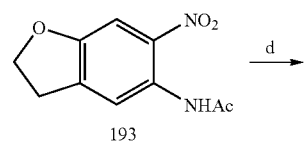

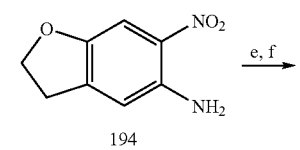

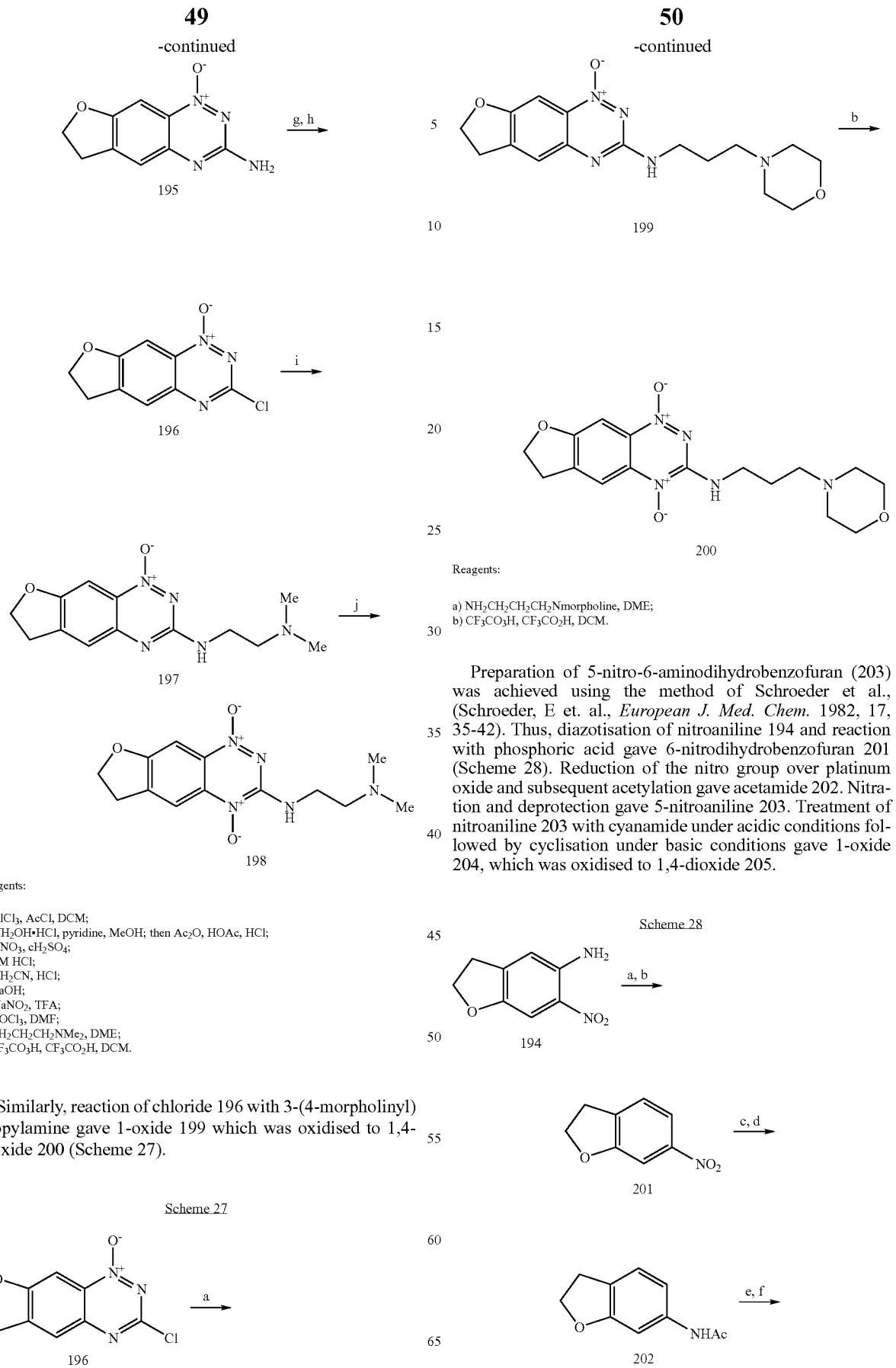

Reagents:

a) AlCl₃, AcCl, DCM;
b) NH₂OH·HCl, pyridine, MeOH; then Ac₂O, HOAc, HCl;
c) KNO₃, cH₂SO₄;
d) 5M HCl;
e) NH₂CN, HCl;
f) NaOH;
g) NaNO₂, TFA;
h) POCl₃, DMF;
i) NH₂CH₂CH₂NMe₂, DME;
j) CF₃CO₃H, CF₃CO₂H, DCM.

Similarly, reaction of chloride 196 with 3-(4-morpholinyl)propylamine gave 1-oxide 199 which was oxidised to 1,4-dioxide 200 (Scheme 27).

Reagents:

a) NH₂CH₂CH₂CH₂CH₂Nmorpholine, DME;
b) CF₃CO₃H, CF₃CO₂H, DCM.

Preparation of 5-nitro-6-aminodihydrobenzofuran (203) was achieved using the method of Schroeder et al., (Schroeder, E et. al., *European J. Med. Chem.* 1982, 17, 35-42). Thus, diazotisation of nitroaniline 194 and reaction with phosphoric acid gave 6-nitrodihydrobenzofuran 201 (Scheme 28). Reduction of the nitro group over platinum oxide and subsequent acetylation gave acetamide 202. Nitration and deprotection gave 5-nitroaniline 203. Treatment of nitroaniline 203 with cyanamide under acidic conditions followed by cyclisation under basic conditions gave 1-oxide 204, which was oxidised to 1,4-dioxide 205.

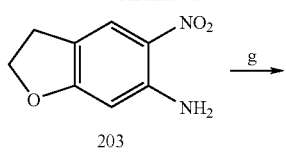

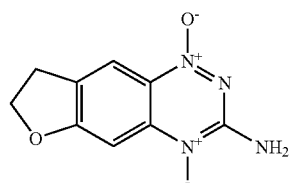

Reagents:

a) NaNO$_2$, cH$_2$SO$_4$;
b) 50% aq. H$_3$PO$_2$;
c) H$_2$, PtO$_2$, EtOH;
d) Ac$_2$O, dioxane;
e) 70% HNO$_3$, HOAc;
f) cHCl, EtOH;
g) NH$_2$CN, HCl; then NaOH;
h) CF$_3$CO$_3$H, CF$_3$CO$_2$H, DCM.

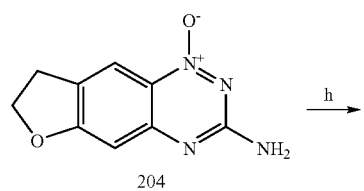

Diazotisation and chlorination of amine 204 gave chloride 206 (Scheme 29). Reaction of chloride 206 with a variety of amines gave 1-oxides 207, 209, and 211, which were oxidised to the corresponding 1,4-dioxides 208, 210, and 212.

Scheme 29

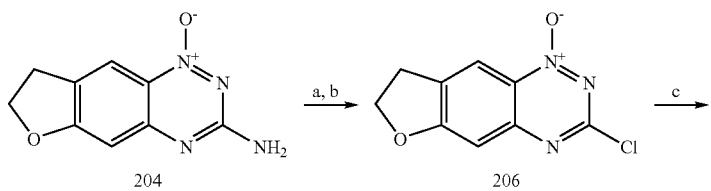

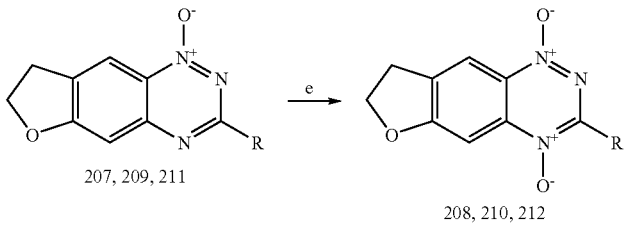

| Reagent | 1-oxide | 1,4-dioxide | R = |
|---|---|---|---|
| NH$_2$CH$_2$CH$_2$NMe$_2$ | 207 | 208 | —NHCH$_2$CH$_2$NMe$_2$ |
| NH$_2$CH$_2$CH$_2$NEt$_2$ | 209 | 210 | —NHCH$_2$CH$_2$NEt$_2$ |
| NH$_2$CH$_2$CH$_2$CH$_2$Nmorpholine | 211 | 212 | —NH$_2$CH$_2$CH$_2$CH$_2$Nmorpholine |

Reagents:

a) NaNO$_2$, TFA;

b) POCl$_3$, DMF;

c) Amine, DME;

d) CF$_3$CO$_3$H, CF$_3$CO$_2$H, DCM.

Diazotisation of amine 204 in the presence of diiodomethane and CuI gave iodide 213 (Scheme 30). Heck coupling of iodide 213 with allyl alcohol gave the unstable aldehyde 214 which underwent reductive amination with morpholine to give 1-oxide 215. Oxidation of 1-oxide 215 gave 1,4-dioxide 216.

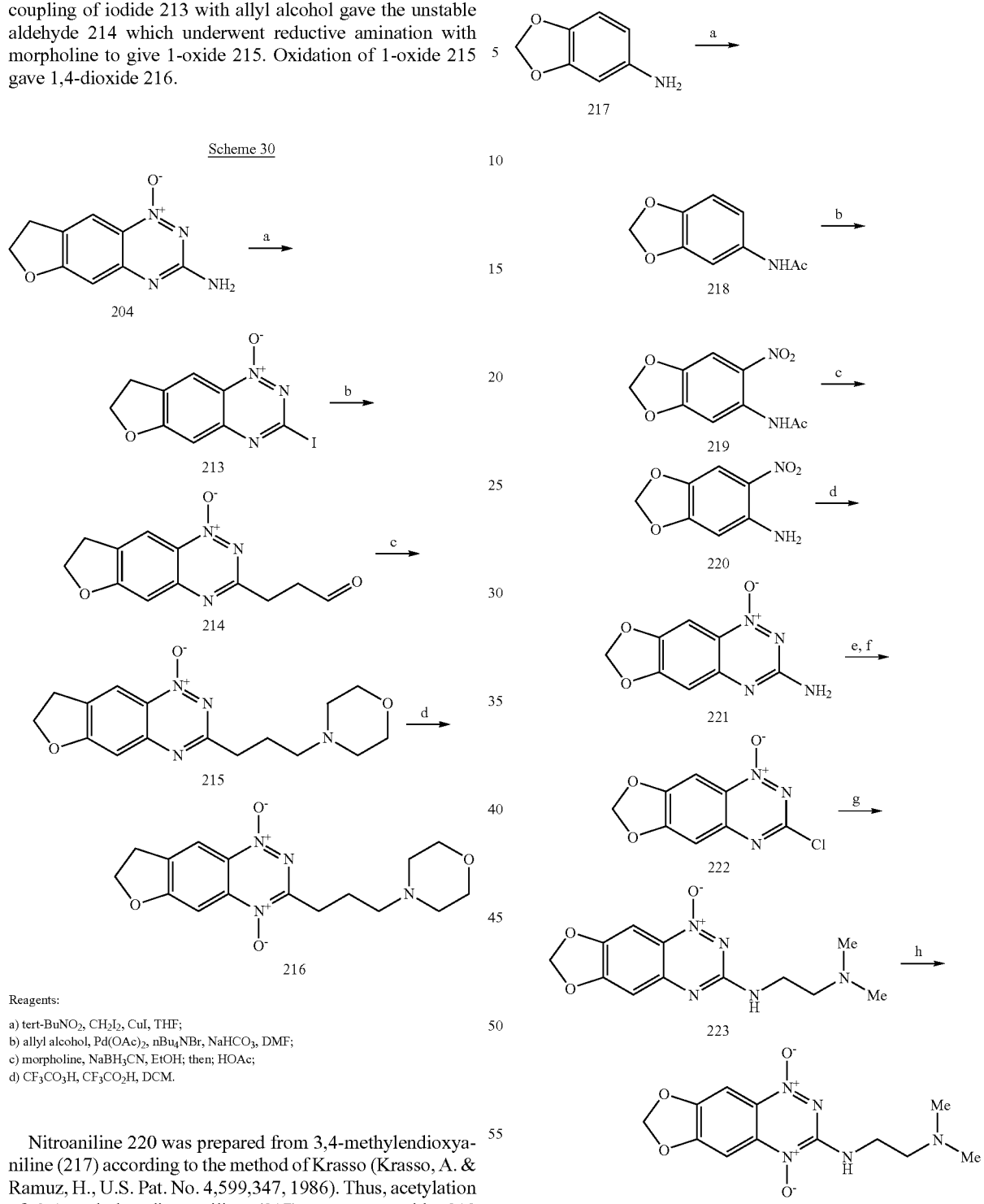

Reagents:
a) tert-BuNO$_2$, CH$_2$I$_2$, CuI, THF;
b) allyl alcohol, Pd(OAc)$_2$, nBu$_4$NBr, NaHCO$_3$, DMF;
c) morpholine, NaBH$_3$CN, EtOH; then; HOAc;
d) CF$_3$CO$_3$H, CF$_3$CO$_2$H, DCM.

Nitroaniline 220 was prepared from 3,4-methylendioxyaniline (217) according to the method of Krasso (Krasso, A. & Ramuz, H., U.S. Pat. No. 4,599,347, 1986). Thus, acetylation of 3,4-methylenedioxyaniline (217) gave acetamide 218 (Scheme 31). Nitration of acetamide 218 gave nitroacetamide 219, which was hydrolysed to give nitroaniline 220. Treatment of nitroaniline 220 with cyanamide under acidic conditions followed by cyclisation under basic conditions gave amine 221. Diazotisation and chlorination of 221 gave chloride 222. Reaction of the chloride 222 with N,N-dimethylethylenediamine gave 1-oxide 223, which was oxidised to 1,4-dioxide 224.

Reagents:
a) Ac$_2$O, dioxane;
b) cHNO$_3$, HOAc;
c) NaOMe, MeOH;
d) NH$_2$CN, HCl, then NaOH;
e) NaNO$_2$, TFA;
f) POCl$_3$, DMF;
g) NH$_2$CH$_2$CH$_2$NMe$_2$, DME;
h) CF$_3$CO$_3$H, CF$_3$CO$_2$H, DCM.

Nitration of 4-chromanone (225) gave nitrochromanone isomers 226 and 227 (Scheme 32). Reduction of nitrochromanone 227 and acetylation gave acetamide 228. Alternatively, reduction of chromanone 225 gave chroman 229 which underwent Friedel-Crafts acylation to give ketone 230. Reaction of ketone 230 with hydroxylamine gave the oxime which underwent Beckmann rearrangement to give acetamide 228.

Further nitration of 228 gave nitroacetamides 231 and 232. Hydrolysis of acetamide 231 gave nitroaniline 233. Treatment of nitroaniline 233 with cyanamide under acidic conditions followed by cyclisation under basic conditions gave amine 234. Diazotisation and chlorination of 234 gave chloride 235. Reaction of chloride 235 with N,N-dimethylethylendiamine gave 1-oxide 236 which was oxidised to 1,4-dioxide 237.

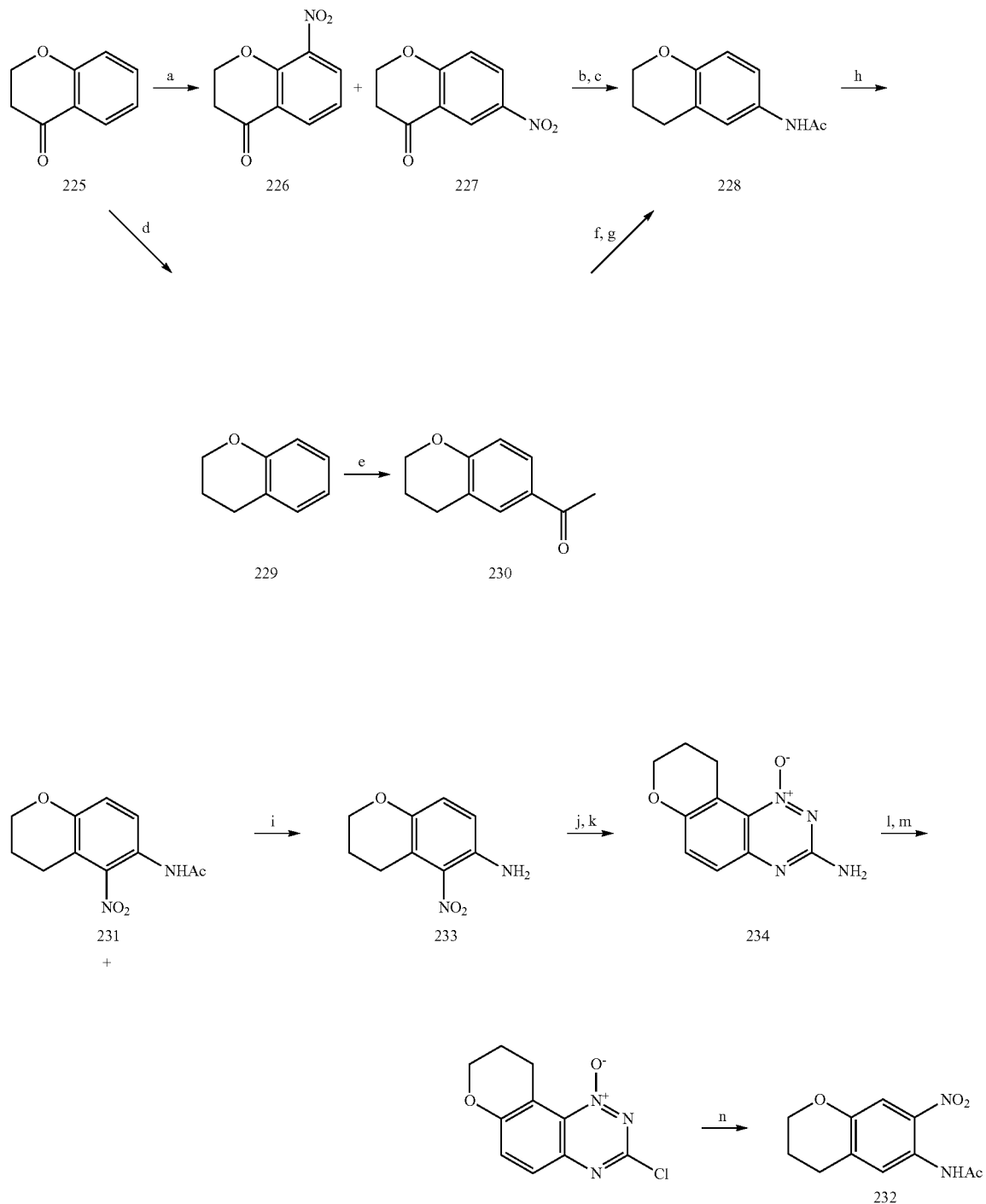

Scheme 32

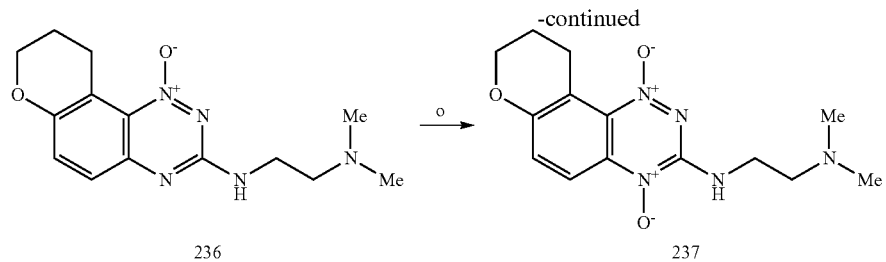

Reagents:

a) KNO₃, cH₂SO₄;
b) H₂, Pd/C, EtOH/EtOAc, HCl;
c) Ac₂O, dioxane;
d) Zn, HOAc;
e) AlCl₃, AcCl, DCM;
f) NH₂OH·HCl, pyridine, MeOH;
g) Ac₂O, HOAc, HCl;
h) KNO₃, cH₂SO₄;
i) NaOH, aq EtOH;
j) NH₂CN, HCl;
k) NaOH;
l) NaNO₂, TFA;
m) POCl₃, DMF;
n) NH₂CH₂CH₂NMe₂, DME;
o) CF₃CO₃H, CF₃CO₂H, DCM.

Hydrolysis of acetamide 232 gave nitroaniline 238 (Scheme 33). Treatment of nitroaniline 238 with cyanamide under acidic conditions followed by cyclisation under basic conditions gave amine 239. Diazotisation and chlorination of 239 gave chloride 240. Reaction of chloride 240 with N,N-dimethylethylendiamine gave 1-oxide 241 which was oxidised to 1,4-dioxide 242. Similarly, reaction of the chloride 240 with 3-(4-morpholinyl)propylamine gave 1-oxide 243 which was oxidised to 1,4-dioxide 244.

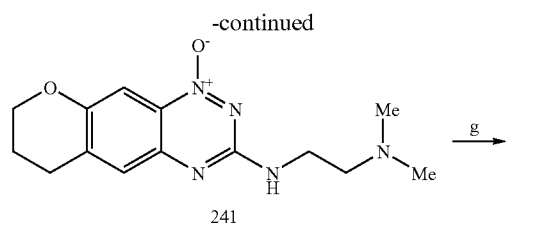

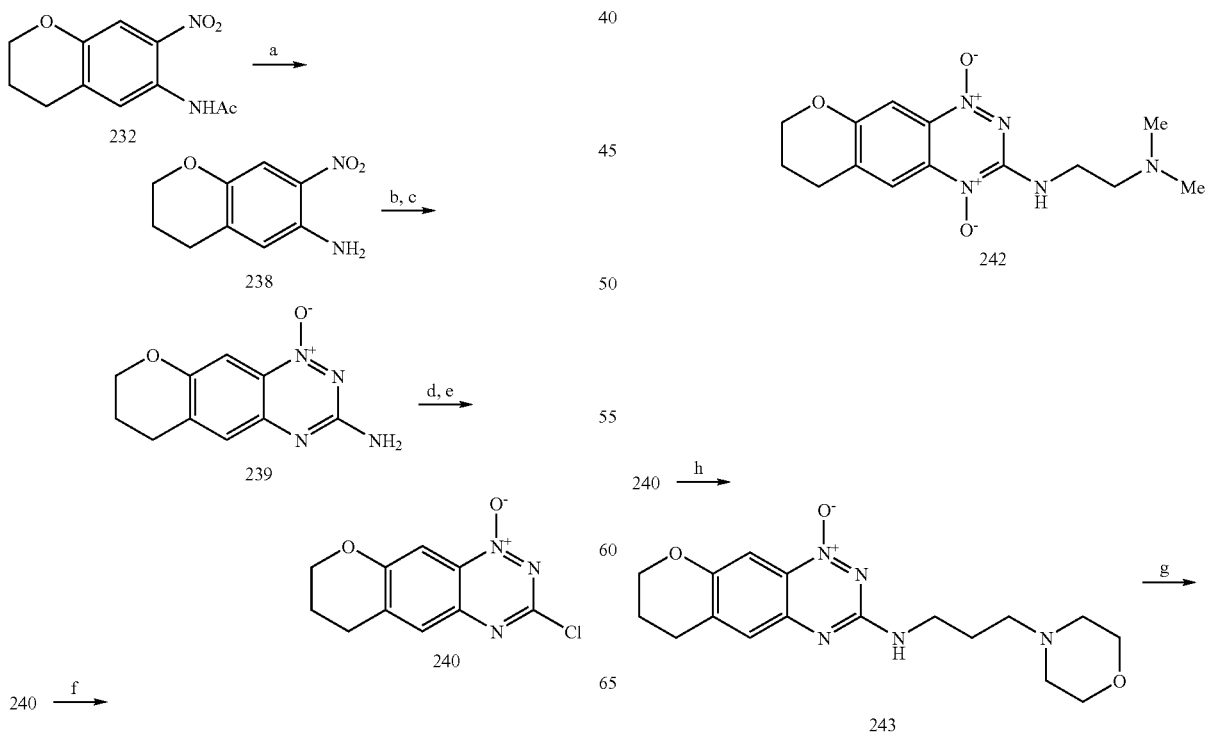

-continued

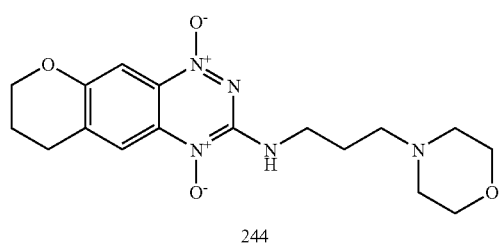

244

Reagents:

a) HCl, aq EtOH;
b) NH$_2$CN, HCl;
c) NaOH;
d) NaNO$_2$, TFA;
e) POCl$_3$, DMF;
f) NH$_2$CH$_2$CH$_2$NMe$_2$, DME;
g) CF$_3$CO$_3$H, CF$_3$CO$_2$H, DCM;
h) NH$_2$CH$_2$CH$_2$CH$_2$Nmorpholine, DME.

Reaction of dibromide 118 with ethylamine gave nitroisoindole 245 (Scheme 34). Catalytic hydrogenation of 245 followed by acetylation gave acetamide 246. Further nitration of 246 gave nitroacetanilide 247 which was hydrolysed to give nitroaniline 248. Treatment of nitroaniline 248 with cyanamide under acidic conditions followed by cyclisation under basic conditions gave amine 249, which was oxidised to 1,4-dioxide 250.

-continued

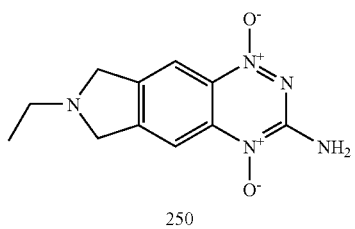

250

Reagents:

a) EtNH$_2$, Et$_3$N, DMF;
b) H$_2$, Pd/C, MeOH;
c) Ac$_2$O, dioxane;
d) KNO$_3$, cH$_2$SO$_4$;
e) 5M HCl;
f) NH$_2$CN, HCl; then NaOH;
g) H$_2$O$_2$, CF$_3$CO$_2$H, DCM.

Reductive alkylation of tetrahydroisoquinoline 251 gave amine 252 (Scheme 35). Catalytic hydrogenation of 252 followed by acetylation gave acetamide 253. Nitration of acetamide 253 gave a mixture of nitroacetamides which was hydrolysed under acidic conditions and purified by chromatography to give 8-nitroaniline 254 and 6-nitroaniline 255. Treatment of nitroaniline 255 with cyanamide under acidic conditions followed by cyclisation under basic conditions gave amine 256. Diazotisation and chlorination of 256 gave chloride 257. Reaction of the chloride 257 with ethylamine gave 1-oxide 258 which was oxidised to 1,4-dioxide 259.

Scheme 34

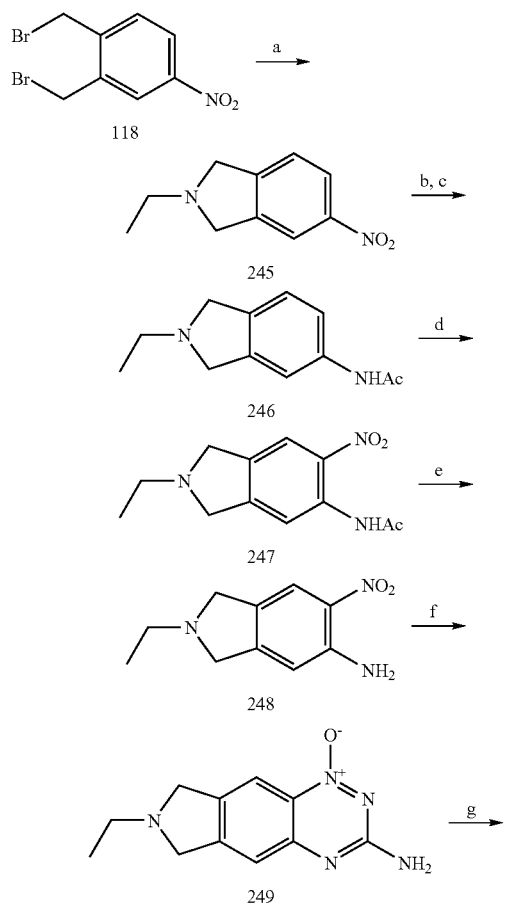

Scheme 35

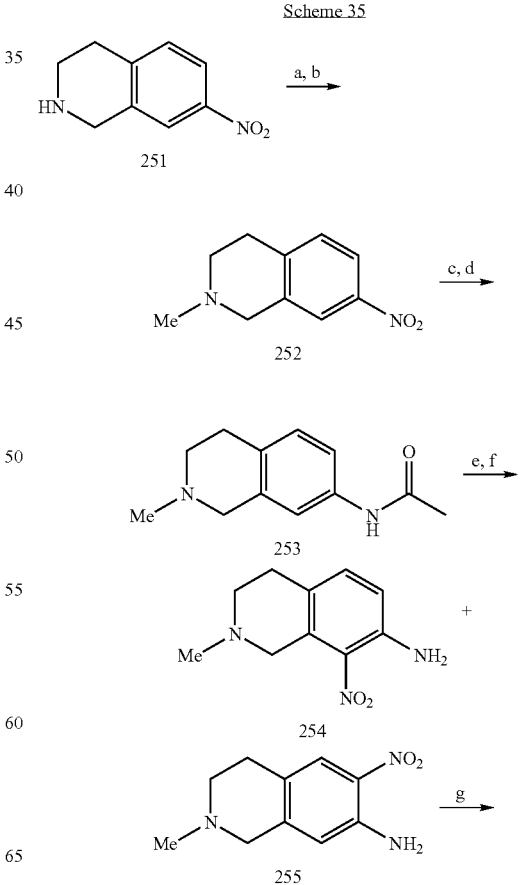

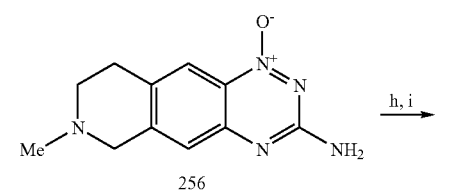

256

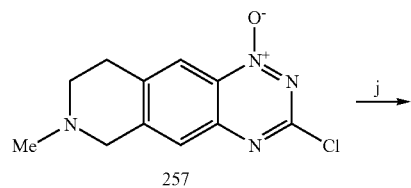

257

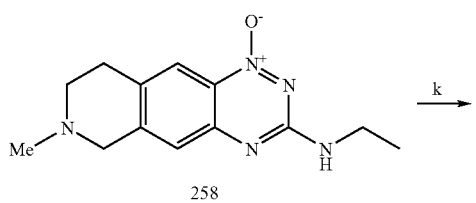

258

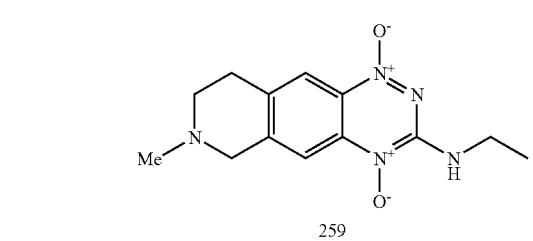

259

Reagents:

a) Ac₂O, HCO₂H, THF;
b) BH₃·DMS, THF;
c) H₂, Pd/C, EtOH;
d) Ac₂O, dioxane;
e) KNO₃, cH₂SO₄;
f) 5M HCl;
g) NH₂CN, HCl; then NaOH;
h) NaNO₂, TFA;
i) POCl₃, DMF;
j) EtNH₂, DME;
k) CF₃CO₃H, CF₃CO₂H, DCM.

Stille coupling of chloride 257 with tetraethyltin gave 1-oxide 260, which was oxidised to 1,4-dioxide 261 (Scheme 36).

Scheme 36

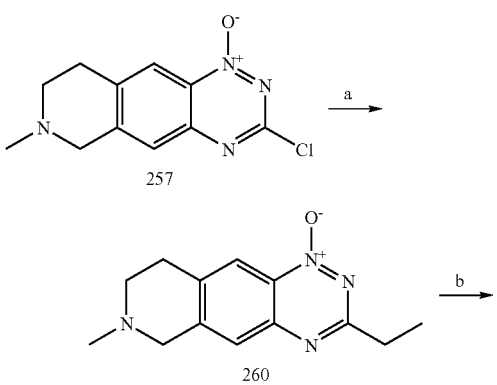

257

260

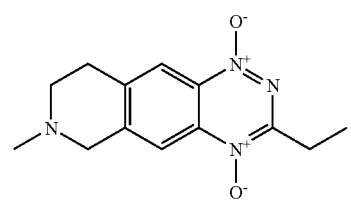

261

Reagents:

a) Et₄Sn, Pd(PPh₃)₄, DME;
b) CF₃CO₃H, CF₃CO₂H, DCM.

Treatment of nitroaniline 254 with cyanamide under acidic conditions followed by cyclisation under basic conditions gave amine 262 (Scheme 37). Diazotisation and chlorination of 262 gave chloride 263. Stille coupling of chloride 263 with tetraethyltin gave 1-oxide 264, which was oxidised to 1,4-dioxide 265.

Scheme 37

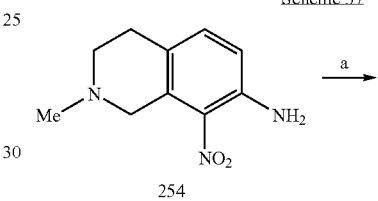

254

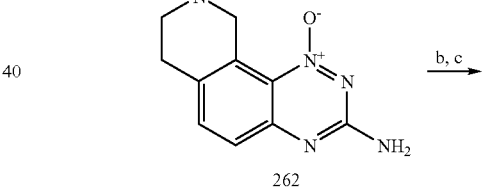

262

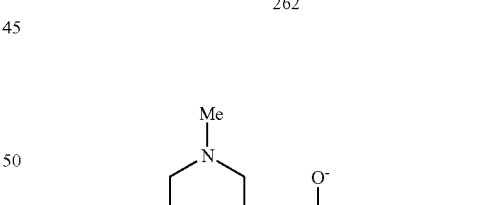

263

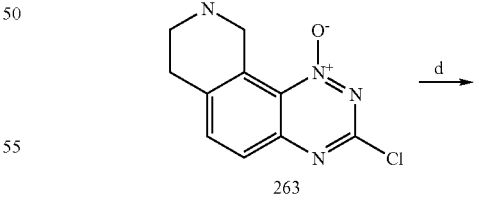

264

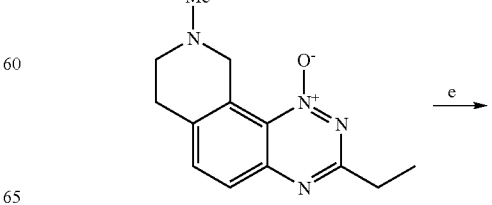

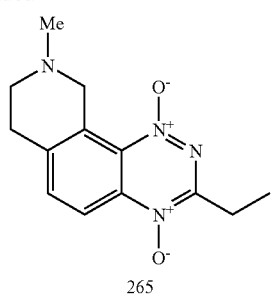

265

Reagents:

a) NH$_2$CN, HCl; then NaOH;
b) NaNO$_2$, TFA;
c) POCl$_3$, DMF;
d) Et$_4$Sn, Pd(PPh$_3$)$_4$, DME;
e) CF$_3$CO$_3$H, CF$_3$CO$_2$H, DCM.

Two general methods were used to synthesize amine sidechains which coupled to various chlorides described above. In the first method, the addition of an amine to an aqueous solution of glycolonitrile gave a nitrile, which was reduced to the diamine. Thus, reaction of amine 266 with glycolonitrile gave nitrile 267, which was reduced using Raney Nickel and H$_2$ to give diamine 268 (Scheme 38).

Scheme 38

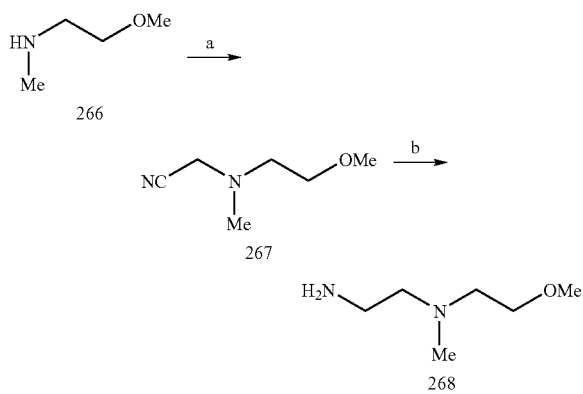

Reagents:

a) aq. Glycolonitrile;
b) H$_2$, Raney Nickel, cNH$_3$, EtOH.

Protection of amine 269 as the carbamate 270, followed by O-alkylation to give ether 271 and deprotection gave amine 272. Reaction of amine 272 with glycolonitrile gave nitrile 273 which was reduced to diamine 274 (Scheme 39).

Scheme 39

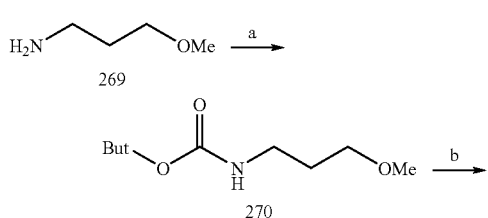

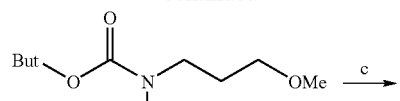

271

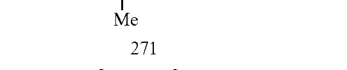

272

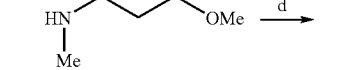

273

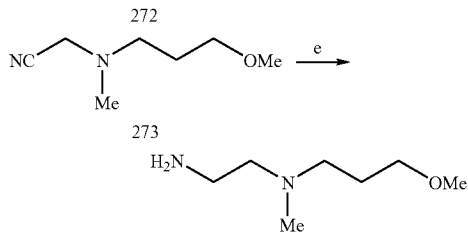

274

Reagents:

a) Di-tert-butyl dicarbonate, CHCl$_3$;
b) KOH, MeI;
c) HCl, dioxane;
d) aq. Glyocolonitrile, Et$_3$N;
e) H$_2$, Raney Nickel, cNH$_3$, EtOH.

Reaction of amine 275 with glycolonitrile gave nitrile 276, which was reduced using Raney Nickel and H$_2$ to give diamine 277 (Scheme 40).

Scheme 40

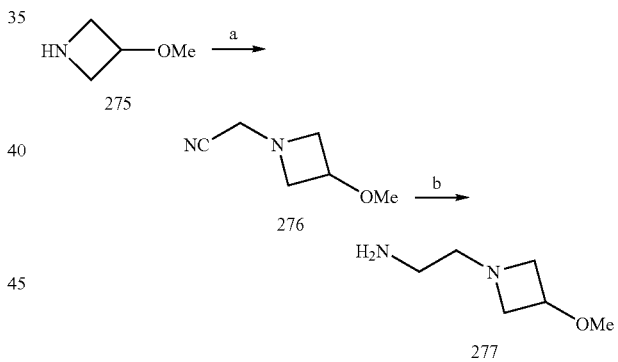

Reagents:

a) aq. Glycolonitrile;
b) H$_2$, Raney Nickel, cNH$_3$, EtOH.

Reaction of amine 278 with glycolonitrile gave nitrile 279, which was reduced using Raney Nickel and H$_2$ to give diamine 280 (Scheme 41).

Scheme 41

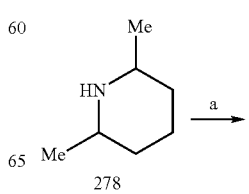

278

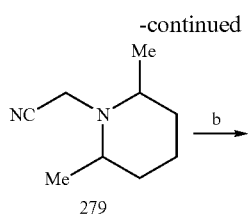

Reagents:

a) aq. Glycolonitrile;
b) H₂, Raney Nickel, cNH₃, EtOH.

Reaction of amine 281 with glycolonitrile gave nitrile 282, which was reduced using Raney Nickel and H₂ to give diamine 283 (Scheme 42).

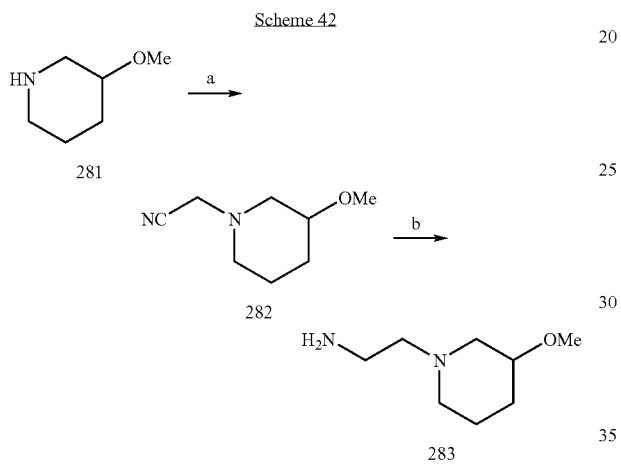

Reagents:

a) aq. Glycolonitrile; Et₃N;
b) H₂, Raney Nickel, cNH₃, EtOH.

Reaction of amine 286, prepared by O-alkylation of the carbamate 284, to give ether 285 which was deprotected, gave nitrile 287 which was reduced to diamine 288 (Scheme 43).

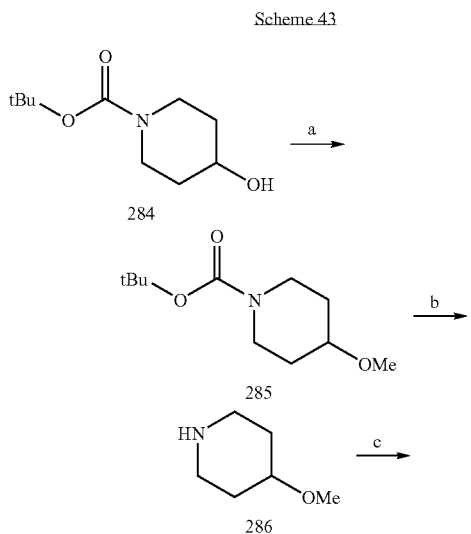

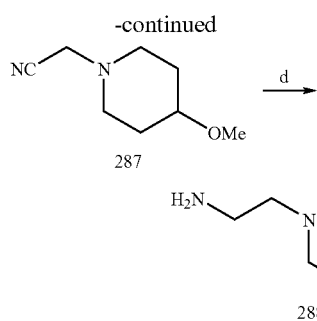

Reagents:

a) KOH, MeI, DMSO;
b) HCl, dioxane;
c) aq. Glycolonitrile;
d) H₂, Raney Nickel, cNH₃, EtOH.

Reaction of azepane (289) with glycolonitrile gave nitrile 290, which was reduced using Raney Nickel and H₂ to give diamine 291 (Scheme 44).

Scheme 44

Reagents:

a) aq. Glycolonitrile;
b) H₂, Raney Nickel, cNH₃, EtOH.

Reaction of oxazepane (292) with glycolonitrile gave nitrile 293, which was reduced using Raney Nickel and H₂ to give diamine 294 (Scheme 45).

Scheme 45

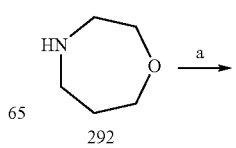

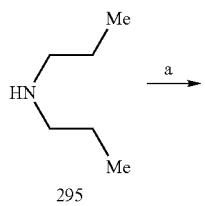

-continued

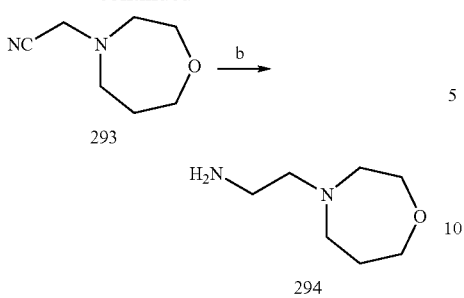

Reagents:

a) aq. Glycolonitrile;
b) H$_2$, Raney Nickel, cNH$_3$, EtOH.

In the alternative method for synthesizing the amine sidechains the appropriate bromoalkylphthalimide was condensed with a secondary amine and then reduced with hydrazine to give the diamine. Thus, reaction of bromoethylphthalimide with N,N-dipropylamine (295) gave phthalimide 296, which was reduced with hydrazine hydrate in EtOH to give diamine 297 (Scheme 46).

Scheme 46

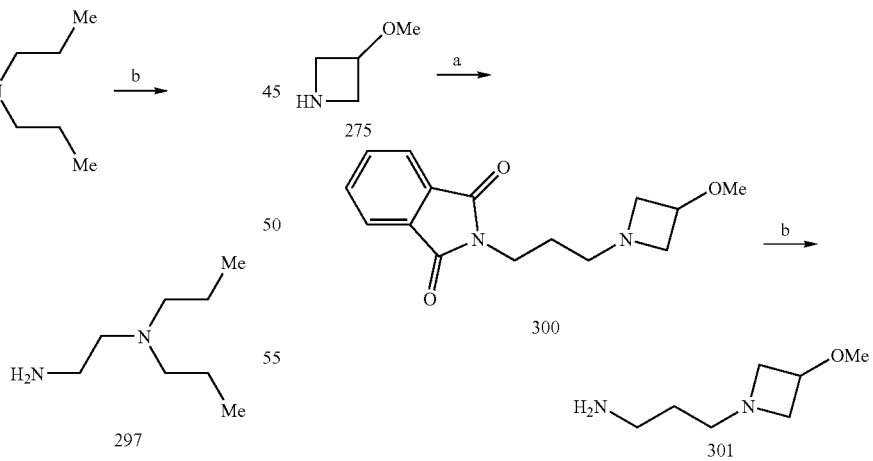

Reagents:

a) N-(2-Bromoethyl)phthalimide, K$_2$CO$_3$, DMF;
b) N$_2$H$_4$•H$_2$O, EtOH.

Similarly, reaction of bromopropylphthalimide with amine (266) gave phthalimide 298, which was reduced with hydrazine hydrate in EtOH to give diamine 299 (Scheme 47).

Scheme 47

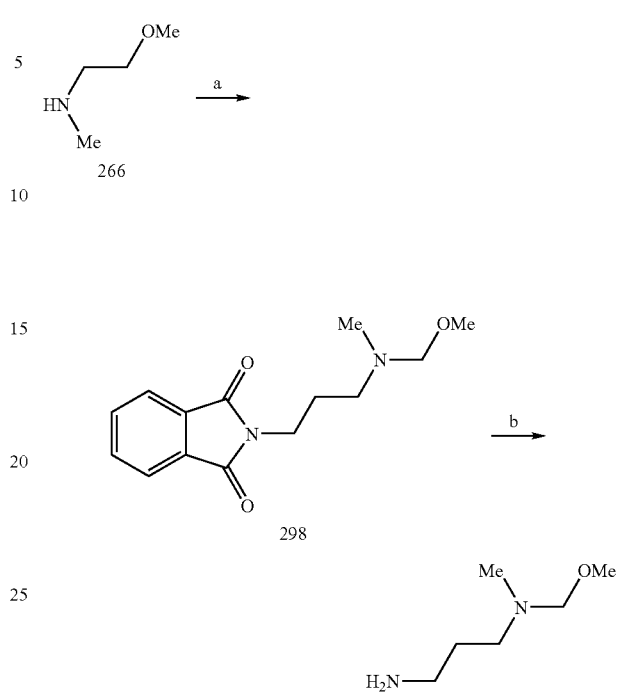

Reagents:

a) N-(2-Bromopropyl)phthalimide, K$_2$CO$_3$, DMF;
b) N$_2$H$_4$•H$_2$O, EtOH.

Similarly, reaction of bromopropylphthalimide with azetidine 275 gave phthalimide 300, which was reduced with hydrazine hydrate in EtOH to give diamine 301 (Scheme 48).

Scheme 48

Reagents:

a) N-(2-Bromopropyl)phthalimide, K$_2$CO$_3$, DMF;
b) N$_2$H$_4$•H$_2$O, EtOH.

Similarly, reaction of bromopropylphthalimide with pyrrolidine 302 gave phthalimide 303, which was reduced with hydrazine hydrate in EtOH to give diamine 304 (Scheme 49).

Scheme 49

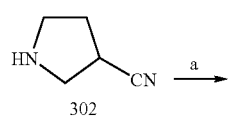

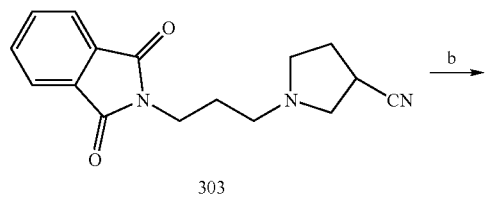

Reagents:

a) N-(2-Bromopropyl)phthalimide, K$_2$CO$_3$, DMF;
b) N$_2$H$_4$·H$_2$O, EtOH.

Similarly, reaction of bromopropylphthalimide with piperidine 286 gave phthalimide 305, which was reduced with hydrazine hydrate in EtOH to give diamine 306 (Scheme 50).

Scheme 50

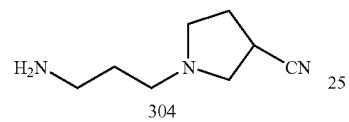

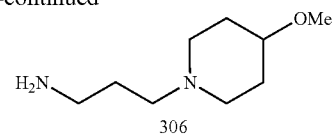

Reagents:

c) N-(2-Bromopropyl)phthalimide, K$_2$CO$_3$, DMF;
d) N$_2$H$_4$·H$_2$O, EtOH.

Similarly, reaction of bromobutylphthalimide with morpholine gave phthalimide 307, which was reduced with hydrazine hydrate in EtOH to give diamine 308 (Scheme 51).

Scheme 51

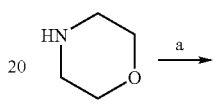

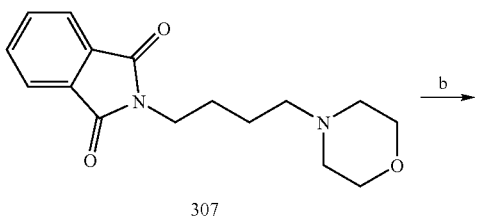

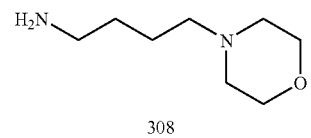

Reagents:

e) N-(2-Bromobutyl)phthalimide, K$_2$CO$_3$, DMF;
f) N$_2$H$_4$·H$_2$O, EtOH.

Reaction of the alcohol 70 with 4-(dimethylamino)butanoic acid in the presence of DCC gave 1-oxide 309 (Scheme 52). Similarly reaction of alcohol 70 with N-(tert-butoxycarbonyl)-L-valine gave carbamate 311.

Scheme 52

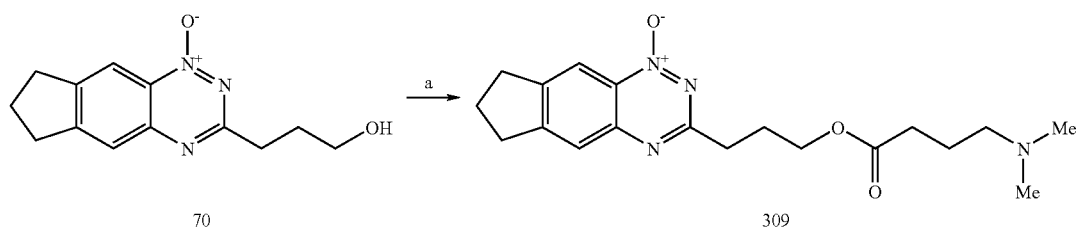

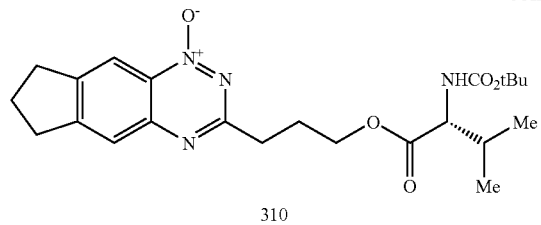

310

Reagents:

a) Me$_2$NCH$_2$CH$_2$CH$_2$CO$_2$H, DCC, DCM;
b) NBOC-L-valine, DCC, DCM;

It is to be appreciated that many variations and modifications of the reagents and starting materials in the schemes above could be readily brought about by a skilled artisan to make further compounds of Formula I without departing from the scope of the invention as defined. For example the benzo ring of the compounds of Formula I could be substituted with X groups, where X is other than H, by making or obtaining an appropriately substituted nitroaniline compound and where necessary protecting that substituent with appropriate protecting groups throughout the rest of the synthesis to ensure that the desired substitutent is carried through to the compound of Formula I.

Examples of the Compounds of the Invention

The following examples are representative of the invention and the detailed methods for preparing them; however, the scope of the invention is not to be taken as being limited to these examples.

Analyses were carried out in the Microchemical Laboratory, University of Otago, Dunedin, NZ. Melting points were determined on an Electrothermal 2300 Melting Point Apparatus. NMR spectra were obtained on a Bruker Avance 400 spectrometer at 400 MHz for $^1$H and 100 MHz for $^{13}$C spectra. Spectra were obtained in CDCl$_3$ unless otherwise specified, and were referenced to Me$_4$Si. Chemical shifts and coupling constants were recorded in units of ppm and Hz, respectively. Assignments were determined using COSY, HSQC, and HMBC two-dimensional experiments. Low resolution mass spectra were gathered by direct injection of methanolic solutions into a Surveyor MSQ mass spectrometer using an atmospheric pressure chemical ionization (APCI) mode with a corona voltage of 50 V and a source temperature of 400° C. Low resolution mass spectra were also determined on a VG-70SE mass spectrometer using an ionizing potential of 70 eV at a nominal resolution of 1000. High-resolution spectra were obtained at nominal resolutions of 3000, 5000, or 10000 as appropriate. All spectra were obtained as electron impact (EI) spectra using PFK as the reference unless otherwise stated. Solutions in organic solvents were dried with anhydrous Na$_2$SO$_4$. Solvents were evaporated under reduced pressure on a rotary evaporator. Thin-layer chromatography was carried out on aluminum-backed silica gel plates (Merck 60 F$_{254}$) with visualization of components by UV light (254 nm) or exposure to 12. Column chromatography was carried out on silica gel (Merck 230-400 mesh). Ac$_2$O refers to acetic anhydride; DCM refers to dichloromethane; DME refers to dimethoxyethane, DMF refers to dry N,N-dimethylformamide; ether refers to diethyl ether; EtOAc refers to ethyl acetate; EtOH refers to ethanol; HOAc refers to acetic acid; MeOH refers to methanol; pet. ether refers to petroleum ether, boiling range 40-60° C.; TFA refers to trifluoroacetic acid; TFAA refers to trifluoroacetic anhydride; THF refers to tetrahydrofuran dried over sodium benzophenone ketyl.

Example 1

8,9-Dihydro-7H-indeno[5,4-e][1,2,4]triazin-3-amine 1-Oxide (4)

6-Nitro-5-indanamine (2) and 4-Nitro-5-indanamine (3). Ac$_2$O (15.6 mL, 165 mmol) was added dropwise to a stirred solution of 5-aminoindan (1) (10 g, 75.1 mmol) in dioxane (40 mL) at 5° C. and the solution stirred at 20° C. for 16 h. The solution was diluted with water (100 mL) and the precipitate filtered, washed with water (2×10 mL) and dried. The solid was dissolved in cH$_2$SO$_4$ (100 mL) and cooled to 5° C. A solution of KNO$_3$ (8.35 g, 82.6 mmol) in cH$_2$SO$_4$ (15 mL) was added dropwise and the solution stirred at 5° C. for 2 h, then at 20° C. for 2 h. The solution was poured into ice/water (500 mL) and the suspension stirred for 2 h. The precipitate was filtered, washed with water (2×20 mL) and dried. The solid was purified by chromatography, eluting with a gradient (20-40%) of EtOAc/pet. ether, to give (i) N-(6-nitro-2,3-dihydro-1H-inden-5-yl)acetamide (3.97 g, 24%) as a colourless solid: mp (EtOAc/pet. ether) 105-108° C. [lit. (Schroeder, E., et al., European J. Med. Chem. 1982, 17, 35) mp 108-109° C.]; (ii) N-(4-nitro-2,3-dihydro-1H-inden-5-yl)acetamide (0.92 g, 5%) as a white solid: $^1$H NMR δ 9.51 (br s, 1H, NHCO), 8.28 (d, J=8.3 Hz, 1H, H-7), 7.41 (d, J=8.3 Hz, 1H, H-6), 3.25 (br t, J=7.5 Hz, 2H, H-1), 2.96 (br t, J=7.6 Hz, 2H, H-3), 2.22 (s, 3H, CH$_3$), 2.07-2.13 (m, 2H, H-2); $^{13}$C NMR δ 164.1, 143.3, 142.1, 134.6, 131.9, 130.9, 117.3, 35.5, 32.1, 24.9; and (iii) N-(7-nitro-2,3-dihydro-1H-inden-5-yl)acetamide (6.48 g, 39%) as a white solid: $^1$H NMR δ 7.94 (s, 1H, H-5), 7.89 (s, 1H, H-7), 7.44 (br s, 1H, NHCO), 3.36 (br t, J=7.5 Hz, 2H, H-3), 2.92 (br t, J=7.6 Hz, 2H, H-1), 2.20 (s, 3H, CH$_3$), 2.09-2.18 (m, 2H, H-2).

A suspension of N-(6-nitro-2,3-dihydro-1H-inden-5-yl)acetamide (0.90 g, 4.09 mmol) in 5 M HCl was heated at 100° C. for 16 h. The suspension was cooled to 20° C., diluted with water (100 mL), filtered, washed with water (3×15 mL) and dried to give 6-nitro-5-indanamine 2 (0.69 g, 95%) as an orange solid: $^1$H NMR δ 7.93 (s, 1H, H-7), 6.64 (s, 1H, H-4), 5.99 (br s, 2H, NH$_2$), 2.79-2.88 (m, 4H, H-1, H-3), 2.02-2.10 (m, 2H, H-2); $^{13}$C NMR δ 154.3, 144.2, 134.0, 131.3, 120.8, 113.5, 33.0, 31.4, 25.7.

A suspension of N-(4-nitro-2,3-dihydro-1H-inden-5-yl)acetamide (0.90 g, 4.09 mmol) in 5 M HCl was heated at 100° C. for 16 h. The suspension was cooled to 20° C., diluted with water (100 mL), filtered, washed with water (3×15 mL) and dried to give 4-nitro-5-indanamine 3 (Schroeder, E, et al., *European J. Med. Chem.* 1982, 17, 35) (0.69 g, 95%) as an orange solid: mp (H$_2$O) 105-107° C.; $^1$H NMR δ 7.17 (d, J=8.2 Hz, 1H, H-7), 6.62 (d, J=8.2 Hz, 1H, H-6), 5.73 (br s, 2H, NH$_2$), 3.32 (br t, J=7.5 Hz, 2H, H-3), 2.80-2.85 (m, 2H, H-1), 2.02-2.11 (m, 2H, H-2). Anal. calcd for C$_9$H$_{10}$N$_2$O$_2$: C, 60.7; H, 5.7; N, 15.7. Found: C, 60.5; H, 5.5; N, 15.8%.

8,9-Dihydro-7H-indeno[5,4-e][1,2,4]triazin-3-amine 1-Oxide (4). A mixture of 4-nitro-5-indanamine (3) (0.67 g, 3.8 mmol) and cyanamide (0.63 g, 15.0 mmol) were mixed together at 100° C., cooled to 50° C., cHCl (5 mL) added carefully and the mixture heated at 100° C. for 4 h. The mixture was cooled to 50° C., 7.5 M NaOH solution added until the mixture was strongly basic and the mixture stirred at 100° C. for 3 h. The mixture was cooled, diluted with water (100 mL), filtered, washed with water (3×20 mL), washed with ether (3×5 mL) and dried. The residue was purified by chromatography, eluting with a gradient (0-5%) of MeOH/DCM, to give amine 4 (279 mg, 37%) as a yellow powder: mp (MeOH/DCM) 270-274° C.; $^1$H NMR [(CD$_3$)$_2$SO] δ 7.56 (d, J=8.4 Hz, 1H, H-6), 7.31 (d, J=8.4 Hz, 1H, H-5), 6.79 (br s, 2H, NH$_2$), 3.55 (br t, J=7.5 Hz, 2H, H-9), 2.95 (br t, J=7.7 Hz, 2H, H-7), 2.09-2.20 (m, 2H, H-8); $^{13}$C NMR [(CD$_3$)$_2$SO] δ 159.4, 148.7, 140.9, 136.0, 131.6, 128.1, 123.9, 34.6, 32.1, 24.1. Anal. calcd for C$_{10}$H$_{10}$N$_4$O: C, 59.4; H, 5.0; N, 27.7. Found: C, 59.5; H, 5.0; N, 27.7%.

Example 2

3-Chloro-8,9-dihydro-7H-indeno[5,4-e][1,2,4]triazine 1-Oxide (5). NaNO$_2$ (167 mg, 2.4 mmol) was added in small portions to a stirred solution of amine 4 (244 mg, 1.2 mmol) in TFA (10 mL) at 5° C. and the solution stirred at 20° C. for 3 h. The solution was poured into ice/water, stirred for 30 minutes, filtered, washed with water (3×30 mL) and dried. The solid was suspended in POCl$_3$ (20 mL) and DMF (0.3 mL) and stirred at 100° C. for 1 h. The solution was cooled, poured into ice/water, stirred for 30 minutes, filtered, washed with water (3×30 mL) and dried. The solid was suspended in DCM (100 mL), dried and the solvent evaporated. The residue was purified by chromatography, eluting with 5% EtOAc/DCM, to give chloride 5 (215 mg, 80%) as a pale yellow solid: mp (DCM/EtOAc) 162-164° C.; $^1$H NMR δ 7.81 (d, J=8.4 Hz, 1H, H-6), 7.74 (d, J=8.4 Hz, 1H, H-5), 3.70 (dd, J=8.0, 7.3 Hz, 2H, H-9), 3.11 (dd, J=8.0, 7.6 Hz, 2H, H-7), 2.22-2.30 (m, 2H, H-8); $^{13}$C NMR δ 155.0, 148.4, 146.8, 137.0, 132.8, 131.5, 126.1, 34.4, 32.9, 24.3. Anal. calcd for C$_{10}$H$_8$ClN$_3$O: C, 54.2; H, 3.6; N, 19.0. Found: C, 54.2; H, 3.8; N, 18.9%.

Example 3

N$^1$,N$^1$-Dimethyl-N$^2$-(1-oxido-8,9-dihydro-7H-indeno[5,4-e][1,2,4]triazin-3-yl)-1,2-ethanediamine (6). N,N-Dimethyl-1,2-ethanediamine (0.28 mL, 2.5 mmol) was added to a stirred solution of chloride 5 (187 mg, 0.8 mmol) in DME (30 mL), and the solution stirred at reflux temperature for 2 h. The solvent was evaporated and the residue was partitioned between DCM (100 mL) and dilute aqueous NH$_3$ solution (50 mL). The organic fraction was dried and the solvent evaporated. The residue was purified by chromatography, eluting with a gradient (0-10%) of MeOH/DCM, to give 1-oxide 6 (201 mg, 88%) as a pale yellow solid: mp (MeOH/EtOAc) 186-190° C.; $^1$H NMR δ 7.54 (d, J=8.4 Hz, 1H, H-6), 7.37 (d, J=8.4 Hz, 1H, H-5), 5.80 (br s, 1H, NH), 3.63 (br t, J=7.3 Hz, 2H, H-9), 3.52-3.57 (m, 2H, CH$_2$N), 2.96 (br t, J=7 Hz, 2H, H-7), 2.57 (t, J=6.0 Hz, 2H, CH$_2$N), 2.29 [s, 6H, N(CH$_3$)$_2$], 2.12-2.21 (m, 2H, H-8); $^{13}$C NMR δ 158.5, 149.0, 142.0, 137.3, 132.2, 129.2, 124.7, 57.6, 45.0 (2), 38.7, 35.3, 32.9, 24.8. Anal. calcd for C$_{14}$H$_{19}$N$_5$O.¼H$_2$O: C, 60.5; H, 7.1; N, 25.2. Found: C, 60.6; H, 6.6; N, 25.4%.

Example 4

N$^1$,N$^1$-Dimethyl-N$^2$-(1,4-dioxido-8,9-dihydro-7H-indeno[5,4-e][1,2,4]triazin-3-yl)-1,2-ethanediamine (7). H$_2$O$_2$ (70%, 0.33 mL, ca. 6.7 mmol) was added dropwise to a stirred solution of TFAA (0.94 mL, 6.7 mmol) in DCM (10 mL) at 0° C. The solution was stirred at 0° C. for 5 min, warmed to 20° C. for 10 min, then cooled to 0° C. and added to a stirred solution of 1-oxide 6 (182 mg, 0.7 mmol) and TFA (0.10 mL, 1.3 mmol) in CHCl$_3$ (15 mL) at 0° C. The solution was stirred at 5° C. for 4 h, diluted with dilute aqueous NH$_3$ solution (10 mL) and extracted with CHCl$_3$ (4×50 mL). The combined organic fraction was dried and the solvent evaporated. The residue was purified by chromatography, eluting with a gradient (0-10%) of MeOH/DCM, to give 1,4-dioxide 7 (60 mg, 31%) as a red solid: mp (MeOH/EtOAc) 153-156° C.; $^1$H NMR δ 8.12 (d, J=8.7 Hz, 1H, H-5), 7.70 (d, J=8.7 Hz, 1H, H-6), 7.37 (br s, 1H, NH), 3.71 (br t, J=7.4 Hz, 2H, H-9), 3.60-3.64 (m, 2H, CH$_2$N), 3.03 (br t, J=7.8 Hz, 2H, H-7), 2.61 (t, J=6.0 Hz, 2H, CH$_2$N), 2.30 [s, 6H, N(CH$_3$)$_2$], 2.17-2.26 (m, 2H, H-8); $^{13}$C NMR δ 149.1, 144.7, 138.6, 138.4, 132.7, 129.1, 115.8, 57.6, 45.2 (2), 38.8, 35.1, 32.9, 24.6; MS m/z 289 (M$^+$, 0.5%), 273 (2), 256 (3), 58 (100); HRMS calcd for C$_{14}$H$_{19}$N$_5$O$_2$ (M$^+$) m/z 289.1539, found 289.1536.

Example 5

N$^1$,N$^1$-Diethyl-N$^2$-(1-oxido-8,9-dihydro-7H-indeno[5,4-e][1,2,4]triazin-3-yl)-1,2-ethanediamine (8). N,N-Diethyl-1,2-ethanediamine (0.41 mL, 2.9 mmol) was added to a stirred solution of chloride 5 (215 mg, 1.0 mmol) in DME (30 mL) and the solution stirred at reflux temperature for 5 h. The solvent was evaporated and the residue was partitioned between DCM (100 mL) and dilute aqueous NH$_3$ solution (50 mL). The organic fraction was dried and the solvent evaporated. The residue was purified by chromatography, eluting with a gradient (0-10%) of MeOH/DCM, to give 1-oxide 8 (271 mg, 93%) as a pale yellow solid: mp (MeOH/EtOAc) 126-130° C.; $^1$H NMR δ 7.54 (d, J=8.4 Hz, 1H, H-6), 7.39 (d, J=8.4 Hz, 1H, H-5), 5.93 (br s, 1H, NH), 3.63 (br dd, J=7.5, 7.4 Hz, 2H, H-9), 3.52-3.57 (m, 2H, CH$_2$N), 2.97 (br dd, J=7.8, 7.6 Hz, 2H, H-7), 2.74 (br t, J=6.0 Hz, 2H, CH$_2$N), 2.63 (q, J=7.4 Hz, 4H, 2×CH$_2$N), 2.16 (br p, J=7.6 Hz, 2H, H-8), 1.07 (t, J=7.1 Hz, 6H, 2×CH$_3$); $^{13}$C NMR δ 158.4, 149.0, 142.0, 137.3, 132.2, 129.2, 124.6, 51.2, 46.6 (2), 38.5, 35.3, 32.8, 24.8, 11.5 (2). Anal. calcd for C$_{16}$H$_{23}$N$_5$O.¼H$_2$O: C, 62.8; H, 7.7; N, 22.9. Found: C, 63.0; H, 7.6; N, 22.9%.

Example 6

N$^1$,N$^1$-Diethyl-N$^2$-(1,4-dioxido-8,9-dihydro-7H-indeno[5,4-e][1,2,4]triazin-3-yl)-1,2-ethanediamine (9). H$_2$O$_2$ (70%, 0.37 mL, ca. 7.3 mmol) was added dropwise to a stirred solution of TFM (1.0 mL, 7.3 mmol) in DCM (10 mL) at 0° C. The solution was stirred at 0° C. for 5 min, warmed to 20° C. for 10 min, then cooled to 0° C. and added to a stirred solution of 1-oxide 8 (219 mg, 0.7 mmol) and TFA (280 μL, 3.6 mmol) in DCM (15 mL) at 0° C. The solution was stirred at 20° C. for 16 h, diluted with dilute aqueous NH$_3$ solution (10 mL) and extracted with CHCl$_3$ (4×50 mL). The combined organic fraction was dried and the solvent evaporated. The residue was purified by chromatography, eluting with a gradient (0-10%) of MeOH/DCM, to give 1,4-dioxide 9 (91 mg, 31%) as a red solid: mp (MeOH) 138-141° C.; $^1$H NMR δ 8.11 (d, J=8.7 Hz, 1H, H-5), 7.70 (d, J=8.7 Hz, 1H, H-6), 7.44 (br s, 1H, NH), 3.70 (br t, J=7.4 Hz, 2H, H-9), 3.58-3.63 (m, 2H, CH$_2$N), 3.03 (br t, J=7.7 Hz, 2H, H-7), 2.77 (br dd, J=6.0, 5.8 Hz, 2H, CH$_2$N), 2.63 (q, J=7.1 Hz, 4H, 2×CH$_2$N), 2.22 (br p, J=7.7 Hz, 2H, H-8), 1.08 (t, J=7.1 Hz, 6H, 2×CH$_3$); $^{13}$C NMR δ 149.0, 144.7, 138.6, 138.3, 132.7, 129.0, 115.7, 51.2, 46.8 (2), 38.8, 35.1, 32.9, 25.6, 11.7 (2). Anal. calcd for C$_{16}$H$_{23}$N$_5$O$_2$.½H$_2$O: C, 58.9; H, 7.4; N, 21.5. Found: C, 59.2; H, 7.2; N, 21.5%.

Example 7

N$^1$-(1-Oxido-8,9-dihydro-7H-indeno[5,4-e][1,2,4]triazin-3-yl)-N$^2$,N$^2$-dipropyl-1,2-ethanediamine (10). N,N-Dipropyl-1,2-ethanediamine (297) (0.53 g, 3.7 mmol) was added to a stirred solution of chloride 5 (325 mg, 1.5 mmol) in DME (30 mL) and the solution stirred at reflux temperature for 2 h. The solvent was evaporated and the residue was partitioned between DCM (100 mL) and dilute aqueous NH$_3$ solution (50 mL). The organic fraction was dried and the solvent evaporated. The residue was purified by chromatography, eluting with a gradient (0-10%) of MeOH/DCM, to give 1-oxide 10 (454 mg, 94%) as a pale yellow solid: mp (MeOH) 148-151° C.; $^1$H NMR δ 7.54 (d, J=8.4 Hz, 1H, H-6), 7.40 (d, J=8.4 Hz, 1H, H-5), 5.77 (br s, 1H, NH), 3.63-3.68 (m, 2H, H-9), 3.48-3.52 (m, 2H, CH$_2$N), 2.95-3.00 (m, 2H, H-7), 2.68 (dd, J=6.0, 5.8 Hz, 2H, CH$_2$N), 2.40-2.45 (m, 4H, 2×CH$_2$N), 2.16-2.23 (m, 2H, H-8), 1.43-1.52 (m, 4H, 2×CH$_2$), 0.90 (t, J=7.3 Hz, 6H, 2×CH$_3$); $^{13}$C NMR δ 158.5, 149.0, 142.0, 137.3, 132.2, 129.2, 124.7, 55.9 (2), 52.6, 38.9, 35.3, 32.9, 24.8, 20.3 (2), 11.9 (2). Anal. calcd for C$_{18}$H$_{27}$N$_5$O: C, 65.6; H, 8.3; N, 21.3. Found: C, 65.7; H, 8.6; N, 21.5%.

Example 8

N$^1$-(1-Oxido-8,9-dihydro-7H-indeno[5,4-e][1,2,4]triazin-3-yl)-N$^2$,N$^2$-dipropyl-1,2-ethanediamine (11). H$_2$O$_2$ (70%, 0.53 mL, ca. 10.5 mmol) was added dropwise to a stirred solution of TFAA (1.5 mL, 10.5 mmol) in DCM (10 mL) at 0° C. The solution was stirred at 0° C. for 5 min, warmed to 20° C. for 10 min, then cooled to 0° C. and added to a stirred solution of 1-oxide 10 (364 mg, 1.1 mmol) and TFA (0.40 mL, 5.3 mmol) in DCM (15 mL) at 0° C. The solution was stirred at 20° C. for 4 h, diluted with dilute aqueous NH$_3$ solution (10 mL) and extracted with CHCl$_3$ (4×50 mL). The combined organic fraction was dried and the solvent evaporated. The residue was purified by chromatography, eluting with a gradient (0-10%) of MeOH/DCM, to give 1,4-dioxide 11 (207 mg, 57%) as a red solid: mp (MeOH/EtOAc) 133-135° C.; $^1$H NMR δ 8.11 (d, J=8.7 Hz, 1H, H-5), 7.68 (d, J=8.7 Hz, 1H, H-6), 7.48 (br s, 1H, NH), 3.68 (t, J=7.5 Hz, 2H, H-9), 3.58-3.64 (m, 2H, CH$_2$N), 3.02 (t, J=7.8 Hz, 2H, H-7), 2.76-2.81 (m, 2H, CH$_2$N), 2.46-2.55 (m, 4H, 2×CH$_2$N), 2.17-2.25 (m, 2H, H-8), 1.47-1.58 (m, 4H, 2×CH$_2$), 0.92 (t, 6H, J=7.4 Hz, 2×CH$_3$); $^{13}$C NMR δ 149.1, 144.7, 138.6, 138.4, 132.6, 129.0, 115.8, 55.9 (2), 52.5, 38.8, 35.1, 32.9, 24.6, 20.0 (2), 11.8 (2). Anal. calcd for C$_{18}$H$_{27}$N$_5$O$_2$: C, 62.6; H, 7.9; N, 20.3. Found: C, 62.7; H, 8.0; N, 20.4%.

Example 9

N-[2-(1-Piperidinyl)ethyl]-8,9-dihydro-7H-indeno[5,4-e][1,2,4]triazin-3-amine 1-Oxide (12). 2-(1-Piperidinyl)ethylamine (0.32 mL, 2.2 mmol) was added to a stirred solution of chloride 5 (165 mg, 0.7 mmol) in DME (30 mL) and the solution stirred at reflux temperature for 5 h. The solvent was evaporated and the residue was partitioned between DCM (100 mL) and dilute aqueous NH$_3$ solution (50 mL). The organic fraction was dried and the solvent evaporated. The residue was purified by chromatography, eluting with a gradient (0-10%) of MeOH/DCM, to give 1-oxide 12 (205 mg, 88%) as a pale yellow solid: mp (MeOH) 152-155° C.; $^1$H NMR δ 7.53 (d, J=8.4 Hz, 1H, H-5), 7.38 (d, J=8.4 Hz, 1H, H-6), 5.90 (br s, 1H, NH), 3.60-3.66 (m, 2H, H-9), 3.48-3.54 (m, 2H, CH$_2$N), 2.97 (br t, J=7.7 Hz, 2H, H-7), 2.57 (dd, J=6.1, 5.9 Hz, 2H, CH$_2$N), 2.38-2.45 (m, 4H, 2×CH$_2$N), 2.17 (br p, J=7.7 Hz, 2H, H-8), 1.55-1.61 (m, 4H, 2×CH$_2$), 1.41-1.48 (m, 2H, CH$_2$); $^{13}$C NMR δ 158.4, 149.0, 142.0, 137.3, 132.2, 129.1, 124.6, 56.9, 54.2 (2), 37.9, 35.3, 32.8, 25.9 (2), 24.8, 24.4. Anal. calcd for C$_{17}$H$_{23}$N$_5$O: C, 65.2; H, 7.4; N, 22.4. Found: C, 65.1; H, 7.2; N, 22.5%.

Example 10

N-[2-(1-Piperidinyl)ethyl]-8,9-dihydro-7H-indeno[5,4-e][1,2,4]triazin-3-amine 1,4-Dioxide (13). H$_2$O$_2$ (70%, 0.27 mL, ca. 5.4 mmol) was added dropwise to a stirred solution of TFM (0.8 mL, 5.4 mmol) in DCM (10 mL) at 0° C. The solution was stirred at 0° C. for 5 min, warmed to 20° C. for 10 min, then cooled to 0° C. and added to a stirred solution of 1-oxide 12 (170 mg, 0.5 mmol) and TFA (0.21 mL, 2.7 mmol) in DCM (15 mL) at 0° C. The solution was stirred at 20° C. for 16 h, diluted with dilute aqueous NH$_3$ solution (10 mL) and extracted with CHCl$_3$ (4×50 mL). The combined organic fraction was dried and the solvent evaporated. The residue was purified by chromatography, eluting with a gradient (0-10%) of MeOH/DCM, to give 1,4-dioxide 13 (89 mg, 50%) as a red solid: mp (MeOH/EtOAc) 138-141° C.; $^1$H NMR δ 8.12 (d, J=8.7 Hz, 1H, H-5), 7.70 (d, J=8.7 Hz, 1H, H-6), 7.44 (br s, 1H, NH), 3.70 (br t, J=7.6 Hz, 2H, H-9), 3.60-3.64 (m, 2H, CH$_2$N), 3.04 (br t, J=7.7 Hz, 2H, H-7), 2.64 (br t, J=6.1 Hz, 2H, CH$_2$N), 2.43-2.50 (m, 4H, 2×CH$_2$), 2.21 (br p, J=7.7 Hz, 2H, H-8), 1.59-1.65 (m, 4H, 2×CH$_2$), 1.42-1.48 (m, 2H, CH$_2$); $^{13}$C NMR δ 149.1, 144.7, 138.6, 138.4, 132.7, 129.0, 115.7, 56.9, 54.4 (2), 38.1, 35.1, 32.9, 25.9 (2), 24.6, 24.3. Anal. calcd for C$_{17}$H$_{23}$N$_5$O$_2$.½H$_2$O: C, 60.3; H, 7.2; N, 20.7. Found: C, 59.9; H, 7.0; N, 20.3%.

Example 11

N-[3-(1-Morpholinyl)propyl]-8,9-dihydro-7H-indeno[5,4-e][1,2,4]triazin-3-amine 1-Oxide (14). 3-(1-Morpholinyl)propylamine (0.31 mL, 2.1 mmol) was added to a stirred solution of chloride 5 (158 mg, 0.7 mmol) in DME (30 mL) and the solution stirred at reflux temperature for 5 h. The solvent was evaporated and the residue was partitioned between DCM (100 mL) and dilute aqueous NH$_3$ solution (50 mL). The organic fraction was dried and the solvent evaporated. The residue was purified by chromatography, eluting with a gradient (0-10%) of MeOH/DCM, to give 1-oxide 14 (212 mg, 91%) as a pale yellow solid: mp (MeOH/EtOAc) 179-181° C.; $^1$H NMR δ 7.54 (d, J=8.4 Hz, 1H, H-5), 7.37 (d, J=8.4 Hz, 1H, H-6), 6.11 (br s, 1H, NH), 3.73-3.78 (m, 4H, 2×CH$_2$O), 3.63 (br t, J=7.6 Hz, 2H, H-9), 3.55-3.60 (m, 2H, CH$_2$N), 2.97 (br t, J=7.7 Hz, 2H, H-7), 2.43-2.52 (m, 6H, 3×CH$_2$N), 2.18 (br p, J=7.7 Hz, 2H, H-8), 1.90-1.96 (m, 2H, CH$_2$); $^{13}$C NMR δ 158.5, 149.0, 142.0, 137.3, 132.2, 129.1, 124.6, 67.0 (2), 57.2, 53.7 (2), 40.7, 35.3, 32.8, 25.3, 24.8. Anal. calcd for C$_{17}$H$_{23}$N$_5$O.¼H$_2$O: C, 61.2; H, 7.1; N, 21.0. Found: C, 61.2; H, 7.0; N, 21.0%.

Example 12

N-[3-(1-Morpholinyl)propyl]-8,9-dihydro-7H-indeno[5,4-e][1,2,4]triazin-3-amine 1,4-Dioxide (15). $H_2O_2$ (70%, 0.27 mL, ca. 5.3 mmol) was added dropwise to a stirred solution of TFAA (0.8 mL, 5.3 mmol) in DCM (10 mL) at 0° C. The solution was stirred at 0° C. for 5 min, warmed to 20° C. for 10 min, then cooled to 0° C. and added to a stirred solution of 1-oxide 14 (173 mg, 0.5 mmol) and TFA (0.20 mL, 2.6 mmol) in DCM (15 mL) at 0° C. The solution was stirred at 20° C. for 16 h, diluted with dilute aqueous $NH_3$ solution (10 mL) and extracted with $CHCl_3$ (4×50 mL). The combined organic fraction was dried and the solvent evaporated. The residue was purified by chromatography, eluting with a gradient (0-10%) of MeOH/DCM, to give 1,4-dioxide 15 (42 mg, 23%) as a red solid: mp (MeOH) 172-175° C.; $^1$H NMR δ 8.28 (br s, 1H, NH), 8.12 (d, J=8.7 Hz, 1H, H-5), 7.69 (d, J=8.7 Hz, 1H, H-6), 3.81-3.85 (m, 4H, 2×$CH_2$O), 3.64-3.72 (m, 4H, $CH_2$N, H-9), 3.03 (br t, J=7.7 Hz, 2H, H-7), 2.49-2.57 (m, 6H, 3×$CH_2$N), 2.22 (br p, J=7.7 Hz, 2H, H-8), 1.84-1.91 (m, 2H, $CH_2$); $^{13}$C NMR δ 149.2, 144.6, 138.6, 138.4, 132.6, 128.9, 115.8, 66.9 (2), 57.6, 53.9 (2), 41.4, 35.1, 32.9, 24.6, 24.3. Anal. calcd for $C_{17}H_{23}N_5O_3$·¼$CH_3OH$: C, 58.6; H, 6.9; N, 19.8. Found: C, 58.6; H, 6.7; N, 19.9%.

Example 13

7,8-Dihydro-6H-indeno[5,6-e][1,2,4]triazin-3-amine 1-Oxide (19)

N-(2,3-Dihydro-1H-inden-5-yl)acetamide (16). $Ac_2O$ (44.6 mL, 473 mmol) was added dropwise to a stirred solution of 5-indanamine (1) (30 g, 225 mmol) in dioxane (120 mL) at 0° C. and the solution stirred at 20° C. for 48 h. The solution was diluted with water (500 mL), stirred 20 min and the precipitate filtered. The solid was washed with water (3×30 mL) and air-dried to give acetamide 16 (37.4 g, 95%) as a tan solid: mp 99-101° C.; $^1$H NMR δ 7.38-7.43 (m, 2H, H-4, NH), 7.10-7.16 (m, 2H, H-6, H-7), 2.85 (br q, J=7.7 Hz, 4H, H-1, H-3), 2.13 (s, 3H, $CH_3$), 2.06 (br, p, J=7.4 Hz, 2H, H-2); $^{13}$C NMR δ 168.3, 145.1, 140.3, 136.0, 124.4, 118.2, 116.6, 33.0, 32.3, 25.6, 24.4.

N-(6-Nitro-2,3-dihydro-1H-inden-5-yl)acetamide (17) and N-(4-Nitro-2,3-dihydro-1H-inden-5-yl)acetamide (18). $cHNO_3$ (70%, 40.5 mL, 639 mmol) was added dropwise to a stirred solution of acetamide 16 (37.4 g, 213 mmol) in HOAc (300 mL) at 20° C. and the solution stirred at 20° C. for 16 h. The solution was poured into ice/water (1500 mL) and the mixture stirred for 30 min. The precipitate was filtered, washed with water (3×30 mL), and air-dried to give a cream solid that was used directly. The solid was a mixture of 6-nitroacetamide 17 and 4-nitroacetamide 18 in a ratio of 20:1. A sample was separated by chromatography, eluting with 20% EtOAc/pet. ether, to give (i) 6-nitroacetamide 17 as a pale yellow solid: mp 105-108° C., [lit. (Schroeder, E.; et al., *European J. Med. Chem.* 1982, 17, 35) mp 108-109° C.], $^1$H NMR δ 10.36 (s, 1H, NHCO), 8.57 (s, 1H, H-7), 8.03 (s, 1H, H-4), 2.98 (br t, J=7.5 Hz, 2H, H-1), 2.93 (br t, J=7.4 Hz, 2H, H-3), 2.27 (s, 3H, $CH_3$), 2.10-2.17 (m, 2H, H-2); and (ii) 4-nitroacetamide 18 as a tan solid: mp 126-128° C. [lit. (Schroeder, E.; et al., *European J. Med. Chem.* 1982, 17, 35) mp 128.5° C.]; $^1$H NMR δ 9.51 (s, 1H, NHCO), 8.28 (d, J=8.3 Hz, 1H, H-7), 7.41 (d, J=8.3 Hz, 1H, H-6), 3.25 (t, J=7.5 Hz, 2H, H-1), 2.96 (br t, J=7.6 Hz, 2H, H-3), 2.22 (s, 3H, $CH_3$), 2.07-2.13 (m, 2H, H-2); $^{13}$C NMR δ 164.1, 143.3, 142.1, 134.6, 131.9, 130.9, 117.3, 35.5, 32.1, 24.9.

6-Nitro-5-indanamine (2). A suspension of the mixture of acetamides 17 and 18 in EtOH (400 mL) and cHCl (180 mL) was stirred at 80° C. for 6 h. The resulting solution was cooled and diluted with water (400 mL) and allowed to stand for 16 h. The precipitate was filtered, washed with water, and air-dried to give amine 2 (27.52 g, 73%, from 16) as an orange powder: mp 129-131° C. [lit. (Schroeder, E.; et al., *European J. Med. Chem.* 1982, 17, 35) mp (EtOH) 128.5-129.5° C.]; $^1$H NMR δ 7.93 (s, 1H, H-7), 6.55 (s, 1H, H-4), 5.99 (br s, 2H, $NH_2$), 2.79-2.88 (m, 4H, H-1, H-3), 2.02-2.10 (m, 2H, H-2); $^{13}$C NMR δ 154.3, 144.2, 134.0, 131.3, 120.8, 113.5, 33.0, 31.4, 25.7.

7,8-Dihydro-6H-indeno[5,6-e][1,2,4]triazin-3-amine 1-Oxide (19). A mixture of amine 2 (21.67 g, 121.6 mmol), cyanamide (20.45 g, 486 mmol) and $Et_2O$ (10 mL) were mixed together at 80° C., cooled to ca. 50° C., cHCl (20 mL) added dropwise, during which a vigorous reaction occurred, and the mixture was heated at 80° C. for 1 h. The mixture was cooled to 50° C., 7.5 M NaOH solution added until the mixture was strongly basic and the mixture stirred at 100° C. for 8 h. The mixture was cooled, diluted with water (500 mL), and the yellow/green precipitate filtered. The precipitate was washed with water (3×50 mL), washed with ether (3×30 mL) and dried to give crude material (20.93 g, 85%), which can be used without further purification. The material was purified by chromatography, eluting with a gradient (0-5%) of MeOH/DCM, to give 1-oxide 19 (16.72 g, 68%) as a yellow powder: mp (MeOH/DCM) 270-272° C.; $^1$H NMR [$(CD_3)_2SO$] δ 7.92 (s, 1H, H-9), 7.33 (s, 1 H, H-5), 7.11 (br s, 2H, $NH_2$), 2.91-2.99 (m, 4H, H-6, H-8), 2.01-2.09 (m, 2H, H-7); $^{13}$C NMR [$(CD_3)_2SO$] δ 159.9, 154.0, 148.5, 142.5, 128.7, 119.8, 113.8, 32.4, 31.6, 25.2. Anal. calcd for $C_{10}H_{10}N_4O$: C, 59.4; H, 5.0; N, 27.7. Found: C, 59.4; H, 5.1; N, 27.8%.

Example 14

7,8-Dihydro-6H-indeno[5,6-e][1,2,4]triazin-3-amine 1,4-Dioxide (20). $H_2O_2$ (70%, 5.0 mL, ca. 99.4 mmol) was added dropwise to a stirred solution of 1-oxide 19 (2.0 g, 9.9 mmol) in HOAc (30 mL) and the solution was stirred at 50° C. for 96 h. The mixture was cooled to 0° C., neutralised with dilute aqueous $NH_3$ solution and the mixture stirred vigorously for 30 min, then extracted with $CHCl_3$ (4×50 mL). The combined organic fraction was dried and the solvent evaporated. The residue was purified by chromatography, eluting with a gradient (0-5%) of MeOH/DCM, to give 1,4-dioxide 20 (317 mg, 15%) as a red solid: mp (MeOH/EtOAc) 190-195° C.; $^1$H NMR [$(CD_3)_2SO$] δ 8.01 (s, 1H, H-9), 7.98 (s, 1H, H-5), 7.87 (br s, 2H, $NH_2$), 3.07 (br t, J=7.4 Hz, 2H, H-6), 3.01 (br t, J=7.4 Hz, 2H, H-8), 2.10 (p, J=7.4 Hz, 2H, H-7); $^{13}$C NMR [$(CD_3)_2SO$] δ 154.3, 150.8, 144.7, 137.8, 129.6, 115.1, 111.2, 32.6, 31.7, 25.1. Anal. calcd for $C_{10}H_{10}N_4O_2$·½$CH_3OH$: C, 53.8; H, 5.2; N, 23.9. Found: C, 53.6; H, 5.2; N, 23.9%.

Example 15

3-Chloro-7,8-dihydro-6H-indeno[5,6-e][1,2,4]triazine 1-Oxide (21). $NaNO_2$ (570 mg, 8.3 mmol) was added in small portions to a stirred solution of 1-oxide 19 (837 mg, 4.1 mmol) in TFA (30 mL) at 0° C. and the solution stirred at 20° C. for 3 h. The solution was poured into ice/water, stirred for 30 min, filtered, washed with water (3×30 mL) and dried. The solid was suspended in $POCl_3$ (50 mL) and DMF (0.5 mL) and stirred at 100° C. for 1 h. The solution was cooled, poured into ice/water, stirred for 30 minutes, filtered, washed with water (3×30 mL) and dried. The solid was suspended in DCM (150 mL), dried and the solvent evaporated. The residue was purified by chromatography, eluting with 5% EtOAc/DCM, to give chloride 21 (696 mg, 76%) as a pale yellow solid: mp (DCM) 162-164° C.; $^1$H NMR δ 8.21 (s, 1H, H-9), 7.75 (s, 1H, H-5), 3.11-3.18 (m, 4H, H-6, H-8), 2.21-2.28 (m, 2H, H-7); $^{13}$C NMR δ 156.4, 156.0, 150.1, 147.3, 132.8, 122.5, 114.5, 33.3, 32.9, 25.7. Anal. calcd for $C_{10}H_8ClN_3O$: C, 54.2; H, 3.6; N, 19.0. Found: C, 54.1; H, 3.8; N, 18.7%.

Example 16

$N^1,N^1$-Dimethyl-$N^2$-(1-oxido-7,8-dihydro-6H-indeno[5,6-e][1,2,4]triazin-3-yl)-1,2-ethanediamine (22). N,N-Dimethyl-1,2-ethanediamine (0.45 mL, 4.1 mmol) was added to a stirred solution of chloride 21 (305 mg, 1.4 mmol) in DME (30 mL) and the solution stirred at reflux temperature for 2 h. The solvent was evaporated and the residue was partitioned between DCM (100 mL) and dilute aqueous $NH_3$ solution (50 mL). The organic fraction was dried and the solvent evaporated. The residue was purified by chromatography, eluting with a gradient (0-10%) of MeOH/DCM, to give 1-oxide 22 (334 mg, 88%) as a yellow solid: mp (MeOH/EtOAc) 122-124° C.; $^1$H NMR δ 8.06 (s, 1H, H-9), 7.38 (s, 1H, H-5), 5.80 (br s, 1H, NH), 3.50-3.55 (m, 2H, $CH_2N$), 2.96-3.03 (m, 4H, H-6, H-8), 2.55 (t, J=6.0 Hz, 2H, $CH_2N$), 2.27 [s, 6H, N($CH_3$)$_2$], 2.09-2.18 (m, 2H, H-7); $^{13}$C NMR δ 158.8, 154.5, 148.8, 143.2, 129.8, 120.5, 114.6, 57.6, 45.1 (2), 38.8, 33.1, 32.3, 25.7. Anal. calcd for $C_{14}H_{19}N_5O$·¼$H_2O$: C, 60.5; H, 7.1; N, 25.2. Found: C, 60.6; H, 6.8; N, 25.2%.

Example 17

$N^1$-(1,4-Dioxido-7,8-dihydro-6H-indeno[5,6-e][1,2,4]triazin-3-yl)-$N^2,N^2$-dimethyl-1,2-ethanediamine (23). $H_2O_2$ (70%, 0.54 mL, ca. 10.8 mmol) was added dropwise to a stirred solution of TFAA (1.5 mL, 10.8 mmol) in DCM (10 mL) at 0° C. The solution was stirred at 0° C. for 5 min, warmed to 20° C. for 10 min, then cooled to 0° C. and added to a stirred solution of 1-oxide 22 (294 mg, 1.1 mmol) and TFA (0.17 mL, 2.2 mmol) in $CHCl_3$ (15 mL) at 0° C. The solution was stirred at 20° C. for 6 h, diluted with dilute aqueous $NH_3$ solution (10 mL) and extracted with $CHCl_3$ (4×50 mL). The combined organic fraction was dried and the solvent evaporated. The residue was purified by chromatography, eluting with a gradient (0-10%) of MeOH/DCM, to give 1,4-dioxide 23 (173 mg, 55%) as a red solid: mp (MeOH/EtOAc) 150-153° C.; $^1$H NMR δ 8.12 (s, 1H, H-9), 8.10 (s, 1H, H-5), 7.40 (br s, 1H, NH), 3.62-3.67 (m, 2H, $CH_2N$), 3.03-3.13 (m, 4H, H-6, H-8), 2.63 (t, J=6.0 Hz, 2H, $CH_2N$), 2.31 [s, 6H, N($CH_3$)$_2$], 2.17-2.23 (m, 2H, H-7); $^{13}$C NMR δ 155.6, 149.5, 145.8, 138.0, 129.7, 115.7, 111.6, 57.5, 45.2 (2), 38.8, 33.6, 32.4, 25.6; MS m/z 289 (M$^+$, 0.5%), 272 (5), 58 (100); HRMS calcd for $C_{14}H_{19}N_5O_2$ (M$^+$) m/z 289.1539, found 289.1536. The hydrochloride salt was crystallised from MeOH/EtOAc. Anal. calcd for $C_{14}H_{20}ClN_5O_2$·½$CH_3OH$: C, 49.7; H, 6.8; N, 19.3. Found: C, 49.4; H, 7.0; N, 19.8%.

Example 18

2-[(1-Oxido-7,8-dihydro-6H-indeno[5,6-e][1,2,4]triazin-3-yl)amino]ethanol (24). 2-Aminoethanol (1.80 mL, 30.0 mmol) was added to a stirred solution of chloride 21 (2.21 g, 10.0 mmol) in DME (100 mL) and the solution stirred at reflux temperature for 90 min. The solvent was evaporated and the residue stirred with water (150 mL) at 20° C. for 30 min. The solid was filtered, washed with water several times and dried to give alcohol 24 (2.44 g, 99%) as an orange solid: mp (DME/water) 222-224° C.; $^1$H NMR [($CD_3$)$_2$SO] δ 7.92 (s, 1H, H-9), 7.54 (br t, J=6.0 Hz, 1H, NH), 7.36 (s, 1H, H-5), 4.68 (t, J=6.0 Hz, 1H, OH)), 3.56 (q, J=6.0 Hz, 2H, $CH_2O$), 3.40 (q, J=6.0 Hz, 2H, $CH_2N$), 2.89-3.00 (m, 4H, H-6, H-8), 2.00-2.08 (m, 2H, H-7); $^{13}$C NMR [($CD_3$)$_2$SO] δ 158.7, 154.0 148.0, 142.3, 128.8, 120.0, 113.9, 59.3, 43.2, 32.4, 31.6, 25.2. Anal. calcd for $C_{12}H_{14}N_4O_2$: C, 58.5; H, 5.7; N, 22.8. Found: C, 58.8; H, 5.9; N, 22.9%.

Example 19

2-[(1,4-Dioxido-7,8-dihydro-6H-indeno[5,6-e][1,2,4]triazin-3-yl)amino]ethanol (25). $H_2O_2$ (70%, 0.5 mL, ca. 10 mmol) was added dropwise to a stirred solution of TFAA (1.4 mL, 10 mmol) in DCM (20 mL) at 0° C. The solution was stirred at 0° C. for 5 min, warmed to 20° C. for 10 min, then cooled to 0° C. and added to a stirred solution of 1-oxide 24 (246 mg, 1.0 mmol) and TFA (0.28 mL, 2.0 mmol) in DCM (20 mL) at 0° C. The solution was stirred at 0° C. for 1 h and then at 20° C. for 30 h, diluted with dilute aqueous $NH_3$ solution (10 mL) and extracted with DCM (5×50 mL). The combined organic fraction was dried and the solvent evaporated. The residue was purified by chromatography, eluting with a gradient (0-4%) of MeOH/DCM, to give 1,4-dioxide 25 (106 mg, 40%) as a red solid: mp (MeOH/DCM) 187-188° C.; $^1$H NMR [($CD_3$)$_2$SO] δ 7.99 (s, 1H, H-9), 7.92-7.98 (m, 2H, NH, H-5), 4.84 (t, J=6.0 Hz, 1H, OH)), 3.61 (q, J=6.0 Hz, 2H, $CH_2O$), 3.46 (q, J=6.0 Hz, 2H, $CH_2N$), 2.98-3.10 (m, 4H, H-6, H-8), 2.05-2.14 (m, 2H, H-7); $^{13}$C NMR [($CD_3$)$_2$SO] δ 154.5, 149.4 144.9, 137.6, 129.0, 115.0, 110.9, 59.1, 43.1, 32.6, 31.7, 25.1. Anal. calcd for $C_{12}H_{14}N_4O_3$: C, 55.0; H, 5.4; N, 21.4. Found: C, 54.8; H, 5.4; N, 21.1%.

Example 20

$N^1$-(1-Oxido-7,8-dihydro-6H-indeno[5,6-e][1,2,4]triazin-3-yl)-$N^2,N^2$-diethyl-1,2-ethanediamine (26). $N^1,N^1$-Diethyl-1,2-ethanediamine (0.50 mL, 3.5 mmol) was added to a stirred solution of chloride 21 (314 mg, 1.4 mmol) in DME (50 mL) and the solution stirred at reflux temperature for 2 h. The solvent was evaporated and the residue partitioned between DCM (100 mL) and dilute aqueous $NH_3$ solution (50 mL). The organic fraction was dried and the solvent evaporated. The residue was purified by chromatography, eluting with a gradient (0-10%) of MeOH/DCM, to give 1-oxide 26 (406 mg, 95%) as a yellow solid: mp (MeOH/EtOAc) 109-112° C.; $^1$H NMR δ 7.93 (s, 1H, H-9), 7.31 (s, 1H, H-5), 7.14 (br s, 1H, NH), 3.97-4.03 (m, 2H, $CH_2N$), 3.42-3.46 (m, 2H, $CH_2N$), 3.25-3.33 (m, 4H, 2×$CH_2N$), 2.19-2.29 (m, 4H, H-6, H-8), 2.08-2.14 (m, 2H, H-7), 1.45 (t, J=7.3 Hz, 6H, 2×$CH_3$); $^{13}$C NMR δ 158.2, 154.6, 148.4, 143.7, 129.8, 120.7, 114.4, 50.8, 47.7 (2), 36.3, 33.1, 32.3, 25.7, 8.8 (2). Anal. calcd for $C_{16}H_{23}N_5O$: C, 63.8; H, 7.7; N, 23.2. Found: C, 63.9; H, 7.7; N, 23.3%.

Example 21

$N^1$-(1,4-Dioxido-7,8-dihydro-6H-indeno[5,6-e][1,2,4]triazin-3-yl)-$N^2,N^2$-diethyl-1,2-ethanediamine (27). $H_2O_2$ (70%, 0.52 mL, ca. 10.4 mmol) was added dropwise to a stirred solution of TFAA (1.5 mL, 10.4 mmol) in DCM (15 mL) at 0° C. The solution was stirred at 0° C. for 5 min, warmed to 20° C. for 10 min, then cooled to 0° C. and added to a stirred solution of 1-oxide 26 (312 mg, 1.0 mmol) and TFA (0.40 mL, 5.2 mmol) in DCM (20 mL) at 0° C. The solution was stirred at 5° C. for 4 h, diluted with dilute aqueous $NH_3$ solution (10 mL) and extracted with $CHCl_3$ (4×50 mL). The combined organic fraction was dried and the solvent evaporated. The residue was purified by chromatography, eluting with a gradient (0-10%) of MeOH/DCM, to give 1,4-dioxide 27 (179 mg, 54%) as a red gum: $^1$H NMR δ 8.11 (br s, 2H, H-5, H-9), 7.73 (br s, 1H, NH), 3.64-3.69 (m, 2H, CH$_2$N), 3.01-3.10 (m, 4H, H-6, H-8), 2.81-2.85 (m, 2H, CH$_2$N), 2.64-2.73 (m, 4H, 2×CH$_2$N), 2.14-2.22 (m, 2H, H-7), 1.09 (t, J=7.1 Hz, 6H, 2×CH$_3$); $^{13}$C NMR δ 156.0, 149.5, 145.8, 138.1, 129.8, 115.7, 111.7, 51.1, 46.6 (2), 38.5, 33.4, 32.3, 25.6, 11.0 (2); MS (FAB$^+$) m/z 318 (MH$^+$, 70%), 302 (20); HRMS (FAB$^+$) calcd for C$_{16}$H$_{24}$N$_5$O$_2$ (MH$^+$) m/z 318.1930, found 318.1933.

Example 22

N$^1$-(1-Oxido-7,8-dihydro-6H-indeno[5,6-e][1,2,4]triazin-3-yl)-N$^2$,N$^2$-dipropyl-1,2-ethanediamine (28). N$^1$,N$^1$-Dipropyl-1,2-ethanediamine (297) (0.27 g, 1.9 mmol) was added to a stirred solution of chloride 21 (298 mg, 1.3 mmol) in DME (50 mL) and the solution stirred at reflux temperature for 2 h. The solvent was evaporated and the residue partitioned between DCM (100 mL) and dilute aqueous NH$_3$ solution (50 mL). The organic fraction was dried and the solvent evaporated. The residue was purified by chromatography, eluting with a gradient (0-10%) of MeOH/DCM, to give 1-oxide 28 (325 mg, 74%) as a yellow powder: mp (MeOH/EtOAc) 95-97° C.; $^1$H NMR δ 8.07 (s, 1H, H-9), 7.39 (s, 1H, H-5), 5.80 (br s, 1H, NH), 3.46-3.53 (m, 2H, CH$_2$N), 2.96-3.03 (m, 4H, 2×CH$_2$N), 2.68 (dd, J=6.0, 5.8 Hz, 2H, CH$_2$N), 2.38-2.45 (m, 4H, H-6, H-8), 2.10-2.18 (m, 2H, H-7), 1.41-1.51 (m, 4H, 2×CH$_2$), 0.87 (t, J=7.1 Hz, 6H, 2×CH$_3$); $^{13}$C NMR δ 158.7, 154.4, 148.8, 143.0, 129.8, 120.5, 114.7, 55.9 (2), 52.6, 38.9, 31.1, 32.3, 25.7, 20.3 (2), 11.9 (2). Anal. calcd for C$_{18}$H$_{27}$N$_5$O: C, 65.6; H, 8.3; N, 21.3. Found: C, 65.4; H, 8.4; N, 21.3%.

Example 23

N$^1$-(1,4-Dioxido-7,8-dihydro-6H-indeno[5,6-e][1,2,4]triazin-3-yl)-N$^2$,N$^2$-dipropyl-1,2-ethanediamine (29). H$_2$O$_2$ (70%, 0.39 mL, ca. 7.7 mmol) was added dropwise to a stirred solution of TFAA (1.1 mL, 7.7 mmol) in DCM (15 mL) at 0° C. The solution was stirred at 0° C. for 5 min, warmed to 20° C. for 10 min, then cooled to 0° C. and added to a stirred solution of 1-oxide 28 (253 mg, 0.8 mmol) and TFA (0.30 mL, 3.8 mmol) in DCM (20 mL) at 0° C. The solution was stirred at 5° C. for 4 h, diluted with dilute aqueous NH$_3$ solution (10 mL) and extracted with CHCl$_3$ (4×50 mL). The combined organic fraction was dried and the solvent evaporated. The residue was purified by chromatography, eluting with a gradient (0-10%) of MeOH/DCM, to give 1,4-dioxide 29 (134 mg, 50%) as a red solid: mp (MeOH/EtOAc) 142-145° C.; $^1$H NMR δ 8.12 (s, 1H, H-9), 8.10 (s, 1H, H-5), 7.46 (br s, 1H, NH), 3.54-3.60 (m, 2H, CH$_2$N), 3.03-3.11 (m, 4H, H-6, H-8), 2.74 (dd, J=6.1, 5.9 Hz, 2H, CH$_2$N), 2.43-2.47 (m, 4H, 2×CH$_2$N), 2.16-2.24 (m, 2H, H-7), 1.45-1.54 (m, 4H, 2×CH$_2$), 0.91 (t, J=7.4 Hz, 6H, 2×CH$_3$); $^{13}$C NMR δ 155.5, 149.5, 145.7, 138.0, 129.6, 115.7, 111.6, 56.0 (2), 52.5, 39.1, 33.4, 32.4, 25.6, 20.4 (2), 11.8 (2). Anal. calcd for C$_{18}$H$_{27}$N$_5$O$_2$: C, 62.6; H, 7.9; N, 20.3. Found: C, 62.3; H, 8.0; N, 20.2%.

Example 24

N$^1$-(1-Oxido-7,8-dihydro-6H-indeno[5,6-e][1,2,4]triazin-3-yl)-N$^2$-(2-methoxyethyl)-N$^2$-methyl-1,2-ethanediamine (30). A solution of the chloride 21 (2.0 g, 9.03 mmol) and N'-(2-methoxyethyl)-N$^1$-methyl-1,2-ethanediamine (268) (2.38 g, 18.1 mmol) in DME (140 mL) was heated at reflux temperature for 22 h. The solution was cooled to 20° C., the solvent evaporated and the residue purified by column chromatography, eluting with a gradient (2-16%) of MeOH/DCM, to give 1-oxide 30 (1.89 g, 66%) as a yellow solid: mp 107-110° C.; $^1$H NMR δ 8.07 (s, 1H, H-9), 7.40 (s, 1H, H-5), 5.89 (br s, 1H, NH), 3.48-3.56 (m, 4H, CH$_2$O, CH$_2$N), 3.36 (s, 3H, OCH$_3$), 3.00 (q, J=7.6 Hz, 4H, H-6, H-8), 2.63-2.71 (m, 4H, 2×CH$_2$N), 2.33 (s, 3H, NCH$_3$), 2.14 (p, J=7.4 Hz, 2H, H-7); $^{13}$C NMR δ 158.8, 154.4, 148.8, 143.1, 129.8, 120.5, 114.7, 71.0, 58.8, 56.7, 56.0, 42.4, 38.8, 33.1, 32.3, 25.7; HRMS (FAB$^+$) calcd for C$_{16}$H$_{24}$N$_5$O$_2$ (MH$^+$) m/z 318.1930, found 318.1930.

Example 25

N$^1$-(1,4-Dioxido-7,8-dihydro-6H-indeno[5,6-e][1,2,4]triazin-3-yl)-N$^2$-(2-methoxyethyl)-N$_2$-methyl-1,2-ethanediamine (31). H$_2$O$_2$ (70%, 11×0.3 mL, ca. 60.72 mmol) was added over a period of 8 h to a solution of the chloride 21 (1.75 g, 5.52 mmol) in TFA (18 mL) and water (1.2 mL) and the solution stirred at 20° C. for 16 h, after which ice/water (100 mL) and excess Na$_2$CO$_3$ was added. The mixture was extracted with DCM (5×75 mL), the combined organic fraction dried and the solvent evaporated. The residue was purified by chromatography, eluting with a gradient (4-10%) of MeOH/DCM, to give 1,4-dioxide 31 (0.14 g, 8%) as a red solid: mp 58-61° C.; $^1$H NMR δ 8.13 (s, 1H, H-9), 8.10 (s, 1H, H-5), 7.44 (br s, 1H, NH), 3.63 (t, J=5.9 Hz, 2H, CH$_2$O), 3.53 (t, J=5.7 Hz, 2H, CH$_2$N), 3.37 (s, 3H, OCH$_3$), 3.11 (dt, J=7.4, 1.0 Hz, 2H, H-8), 3.06 (dt, J=7.5, 1.1 Hz, 2H, H-6), 2.75 (t, J=6.0 Hz, 2H, CH$_2$N), 2.67 (t, J=5.7 Hz, 2H, CH$_2$N), 2.35 (s, 3H, NCH$_3$), 2.20 (p, J=7.5 Hz, 2H, H-7); $^{13}$C NMR δ 155.5, 149.5, 145.7, 138.0, 129.7, 115.8, 111.6, 71.1, 58.9, 56.6, 56.0, 42.6, 39.0, 33.4, 32.4, 25.6; HRMS (FAB$^+$) calcd for C$_{16}$H$_{24}$N$_5$O$_3$ (MH$^+$) m/z 334.1879, found 334.1877.

Example 26

N$^1$-(3-Methoxypropyl)-N$^1$-methyl-N$^2$-(1-oxido-7,8-dihydro-6H-indeno[5,6-e][1,2,4]triazin-3-yl)-1,2-ethanediamine (32). A solution of chloride 21 (1.62 g, 7.3 mmol), Et$_3$N (2.0 mL, 14.0 mmol) and N$^1$-(3-methoxypropyl)-N$^1$-methyl-1,2-ethanediamine (274) (1.24 g, 8.8 mmol) in DME (50 mL) was heated at reflux temperature for 18 h. The solution was cooled, the solvent evaporated and the residue partitioned between dilute aqueous NH$_3$ solution (50 mL) and DCM (50 mL). The aqueous layer was extracted with DCM (4×120 mL), the combined organic fraction dried and the solvent evaporated. The residue was purified by chromatography, eluting with a gradient (0-15%) of MeOH/DCM, to give 1-oxide 32 (1.79 g, 74%) as a yellow solid: mp 41-42° C.; $^1$H NMR δ 8.07 (s, 1H, H-9), 7.39 (s, 1H, H-5), 5.83 (br s, 1H, NH), 3.55 (dt, J=5.9, 5.5 Hz, 2H, NCH$_2$), 3.43 (t, J=6.3 Hz, 2H, OCH$_2$), 3.33 (s, 3H, OCH$_3$), 3.01 (t, J=7.4 Hz, 2H, H-8), 2.99 (t, J=7.8 Hz, 2H, H-6), 2.64 (t, J=5.9 Hz, 2H, NCH$_2$), 2.50 (t, J=7.2 Hz, 2H, NCH$_2$), 2.27 (s, 3H, NCH$_3$), 2.14 (p, J=7.4 Hz, 2H, H-7), 1.76 (tt, J=7.2, 6.4 Hz, 2H, CH$_2$); $^{13}$C NMR δ 158.7, 154.5, 148.8, 143.2, 129.8, 120.5, 114.7, 70.8, 58.6, 55.8, 54.4, 41.6, 38.6, 33.1, 32.3, 27.4, 25.7; MS (APCI) m/z 332 (MH$^+$, 100%). Anal. calcd for C$_{17}$H$_{25}$N$_5$O$_2$: C, 61.6; H, 7.6; N, 21.1. Found: C, 61.4; H, 7.4; N, 21.4%.

Example 27

N[1]-(1,4-Dioxido-7,8-dihydro-6H-indeno[5,6-e][1,2,4]triazin-3-yl)-N[2]-(3-methoxypropyl)-N[2]-methyl-1,2-ethanediamine (33). $H_2O_2$ (70%, 2.5 mL, ca. 50 mmol) was added dropwise to a stirred solution of TFM (7.1 mL, 50 mmol) in DCM (50 mL) at 0° C. The solution was stirred at 20° C. for 10 min, then cooled to 0° C., added to a solution of 1-oxide 32 (1.7 g, 5.0 mmol) and TFA (1.9 mL, 25 mmol) in DCM (50 mL) at 0° C. The solution was stirred at 20° C. for 6 h, diluted with dilute aqueous $NH_3$ solution (80 mL) and extracted with DCM (4×125 mL). The combined organic fraction was dried and the solvent evaporated. The residue was purified by chromatography, eluting with a gradient (0-10%) of MeOH/DCM, to give 1,4-dioxide 33 (620 mg, 35%) as a red solid: mp 129-131° C.; $^1$H NMR δ 8.13 (s, 1H, H-9), 8.10 (s, 1H, H-5), 7.39 (br s, 1H, NH), 3.57-3.66 (m, 2H, NCH$_2$), 3.46 (t, J=6.3 Hz, 2H, OCH$_2$), 3.33 (s, 3H, OCH$_3$), 3.11 (dt, J=7.4, 0.9 Hz, 2H, H-8), 3.06 (dt, J=7.4, 1.1 Hz, 2H, H-6), 2.68 (t, J=6.0 Hz, 2H, NCH$_2$), 2.52 (t, J=7.2 Hz, 2H, NCH$_2$), 2.28 (s, 3H, NCH$_3$), 2.20 (p, J=7.4 Hz, 2H, H-7), 1.77 (tt, J=7.2, 6.4 Hz, 2H, CH$_2$); $^{13}$C NMR δ 155.6, 149.5, 145.7, 138.0, 129.7, 115.8, 111.6, 70.7, 58.6, 55.8, 54.3, 41.7, 38.8, 33.4, 32.4, 27.4, 25.6; MS (APCI) m/z 348 (MH$^+$, 100%). Anal. calcd for $C_{17}H_{25}N_5O_3$: C, 58.8; H, 7.3; N, 20.2. Found: C, 58.8; H, 7.0; N, 20.0%.

Example 28

N-[2-(3-Methoxy-1-azetidinyl)ethyl]-7,8-dihydro-6H-indeno[5,6-e][1,2,4]triazin-3-amine 1-Oxide (34). A solution of chloride 21 (1.32 g, 6.0 mmol), $Et_3N$ (1.65 mL, 11.8 mmol) and 2-(3-methoxy-1-azetidinyl)ethylamine (277) (950 mg, 7.3 mmol) in DME (30 mL) was heated at reflux temperature for 18 h. The solution was cooled, the solvent evaporated and the residue partitioned between dilute aqueous $NH_3$ solution (50 mL) and DCM (50 mL). The aqueous layer was extracted with DCM (4×50 mL), the combined organic fraction dried and the solvent evaporated. The residue was purified by chromatography, eluting with a gradient (0-10%) of MeOH/DCM, to give 1-oxide 34 (890 mg, 48%) as a yellow solid: mp 139-141° C.; $^1$H NMR δ 8.06 (s, 1H, H-9), 7.38 (s, 1H, H-5), 5.67 (br s, 1H, NH), 4.04 (p, J=5.8 Hz, 1H, CHO), 3.63-3.69 (m, 2H, CH$_2$N), 3.47 (dt, J=5.9, 5.6 Hz, 2H, CH$_2$N), 3.26 (s, 3H, OCH$_3$), 2.93-3.03 (m, 6H, H-6, H-8, CH$_2$N), 2.74 (t, J=5.9 Hz, 2H, NCH$_2$), 2.14 (p, J=7.4 Hz, 2H, H-7); $^{13}$C NMR δ 158.7, 154.5, 148.7, 143.3, 129.8, 120.6, 114.6, 70.0, 61.4 (2), 58.0, 56.0, 39.3, 33.1, 32.3, 25.7; MS (APCI) m/z 316 (MH$^+$, 100%). Anal. calcd for $C_{16}H_{21}N_5O_2 \cdot \frac{1}{4}H_2O$: C, 60.1; H, 6.8; N, 21.9. Found: C, 60.0; H, 6.6; N, 21.7%.

Example 29

N-[2-(3-Methoxy-1-azetidinyl)ethyl]-7,8-dihydro-6H-indeno[5,6-e][1,2,4]triazin-3-amine 1,4-Dioxide (35). $H_2O_2$ (70%, 1.4 mL, ca. 28 mmol) was added dropwise to a stirred solution of TFAA (4.0 mL, 28 mmol) in DCM (30 mL) at 0° C. The solution was stirred at 20° C. for 10 min, then cooled to 0° C., added to a solution of 1-oxide 34 (890 mg, 2.8 mmol) and TFA (1.1 mL, 14 mmol) in DCM (35 mL) at 0° C. The solution was stirred at 20° C. for 6 h, diluted with dilute aqueous $NH_3$ solution (80 mL) and extracted with DCM (4×125 mL). The combined organic fraction was dried and the solvent evaporated. The residue was purified by chromatography, eluting with a gradient (0-10%) of MeOH/DCM, to give 1,4-dioxide 35 (390 mg, 42%) as a red solid: mp 152° C. (dec.); $^1$H NMR δ 8.12 (s, 1H, H-9), 8.10 (s, 1H, H-5), 7.30 (br s, 1H, NH), 4.04 (p, J=5.8 Hz, 1H, CHO), 3.67-3.72 (m, 2H, CH$_2$N), 3.54 (dt, J=5.9, 5.5 Hz, 2H, CH$_2$N), 3.25 (s, 3H, OCH$_3$), 3.11 (dt, J=7.4, 0.9 Hz, 2H, H-6), 3.06 (dt, J=7.4, 1.1 Hz, 2H, H-8), 2.95-2.99 (m, 2H, CH$_2$N), 2.78 (t, J=5.9 Hz, 2H, CH$_2$N), 2.20 (p, J=7.5 Hz, 2H, H-7); $^{13}$C NMR δ 155.6, 149.4, 145.8, 138.0, 129.8, 115.8, 111.6, 69.9, 61.5 (2), 58.0, 56.0, 39.5, 33.4, 32.4, 25.6; MS (APCI) m/z 332 (MH$^+$, 100%). Anal. calcd for $C_{16}H_{21}N_5O_3 \cdot 0.15CH_2Cl_2$: C, 56.4; H, 6.2; N, 20.4. Found: C, 56.2; H, 6.1; N, 20.4%.

Example 30

N-[2-(1-Piperidinyl)ethyl]-7,8-dihydro-6H-indeno[5,6-e][1,2,4]triazin-3-amine 1-Oxide (36). 2-(1-Piperidinyl)ethylamine (0.67 mL, 4.7 mmol) was added to a stirred solution of chloride 21 (348 mg, 1.6 mmol) in DME (50 mL) and the solution stirred at reflux temperature for 2 h. The solvent was evaporated and the residue partitioned between DCM (100 mL) and dilute aqueous $NH_3$ solution (50 mL). The organic fraction was dried and the solvent evaporated. The residue was purified by chromatography, eluting with a gradient (0-10%) of MeOH/DCM, to give 1-oxide 36 (465 mg, 95%) as a yellow solid: mp (MeOH/EtOAc) 151-153° C.; $^1$H NMR δ 8.06 (s, 1H, H-9), 7.39 (s, 1H, H-5), 5.91 (br s, 1H, NH), 3.52-3.57 (m, 2H, CH$_2$N), 2.97-3.03 (m, 4H, H-6, H-8), 2.58 (t, J=6.0 Hz, 2H, CH$_2$N), 2.40-2.47 (m, 4H, 2×CH$_2$N), 2.10-2.18 (m, 2H, H-7), 1.55-1.63 (m, 4H, 2×CH$_2$), 1.42-1.48 (m, 2H, CH$_2$); $^{13}$C NMR δ 158.7, 154.5, 148.8, 143.1, 129.7, 120.5, 114.6, 57.0, 54.3 (2), 37.9, 33.1, 32.3, 25.9 (2), 25.7, 24.4. Anal. calcd for $C_{17}H_{23}N_5O \cdot \frac{1}{4}H_2O$: C, 64.2; H, 7.5; N, 22.0. Found: C, 64.6; H, 6.9; N, 22.1%.

Example 31

N-[2-(1-Piperidinyl)ethyl]-7,8-dihydro-6H-indeno[5,6-e][1,2,4]triazin-3-amine 1,4-Dioxide (37). $H_2O_2$ (70%, 0.63 mL, ca. 12.7 mmol) was added dropwise to a stirred solution of TFM (1.8 mL, 12.7 mmol) in DCM (15 mL) at 0° C. The solution was stirred at 0° C. for 5 min, warmed to 20° C. for 10 min, then cooled to 0° C. and added to a stirred solution of 1-oxide 36 (397 mg, 1.3 mmol) and TFA (0.20 mL, 2.5 mmol) in DCM (20 mL) at 0° C. The solution was stirred at 5° C. for 4 h, diluted with dilute aqueous $NH_3$ solution (10 mL) and extracted with CHCl$_3$ (4×50 mL). The combined organic fraction was dried and the solvent evaporated. The residue was purified by chromatography, eluting with a gradient (0-10%) of MeOH/DCM, to give 1,4-dioxide 37 (241 mg, 57%) as a red solid: mp (MeOH/EtOAc) 165-168° C.; $^1$H NMR δ 8.11 (s, 1H, H-9), 8.08 (s, 1H, H-5), 7.43 (br s, 1H, NH), 3.60-3.64 (m, 2H, CH$_2$N), 3.03-3.11 (m, 4H, H-6, H-8), 2.62 (t, J=6.0 Hz, 2H, CH$_2$N), 2.42-2.47 (m, 4H, 2×CH$_2$), 2.15-2.22 (m, 2H, H-7), 1.57-1.63 (m, 4H, 2×CH$_2$), 1.41-1.47 (m, 2H, CH$_2$); $^{13}$C NMR δ 155.6, 149.5, 145.7, 138.0, 129.7, 115.8, 111.6, 56.9, 54.4 (2), 38.2, 33.4, 32.4, 25.9 (2), 25.6, 24.3. Anal. calcd for $C_{17}H_{23}N_5O_2 \cdot \frac{1}{4}H_2O$: C, 61.2; H, 7.1; N, 21.0. Found: C, 60.7; H, 7.0; N, 21.0%.

Example 32

N-[2-(2,6-Dimethyl-1-piperidinyl)ethyl]-7,8-dihydro-6H-indeno[5,6-e][1,2,4]triazin-3-amine 1-Oxide (38). 2-(2,6-Dimethyl-1-piperidinyl)ethylamine (280) (0.66 g, 4.3 mmol) was added to a stirred solution of chloride 21 (314 mg, 1.4 mmol) in DME (50 mL) and the solution stirred at reflux temperature for 3 h. The solvent was evaporated and the residue partitioned between DCM (100 mL) and dilute aqueous $NH_3$ solution (50 mL). The organic fraction was dried and the solvent evaporated. The residue was purified by chromatography, eluting with a gradient (0-10%) of MeOH/DCM, to give 1-oxide 38 (389 mg, 80%) as a yellow solid: mp (MeOH) 173-175° C.; $^1$H NMR δ 8.07 (s, 1H, H-9), 7.38 (s, 1H, H-5), 5.47 (br s, 1H, NH), 3.50-3.55 (m, 2H, CH$_2$N), 2.96-3.03 (m, 4H, CH$_2$N, CH$_2$), 2.87-2.91 (m, 2H, CH$_2$), 2.48-2.57 (m, 2H, CH$_2$N), 2.10-2.18 (m, 2H, CH$_2$), 1.64-1.69 (m, 1H, CH$_2$), 1.53-1.58 (m, 2H, CH$_2$), 1.33-1.38 (m, 1H, CH$_2$), 1.24-1.31 (m, 2H, CH$_2$), 1.20 (d, J=6.3 Hz, 6H, 2×CH$_3$); $^{13}$C NMR δ 158.8, 154.5, 148.8, 143.2, 129.8, 120.6, 114.7, 57.2 (2), 47.5, 39.4, 34.3, 33.1 (2), 32.3, 25.8, 24.4, 21.7 (2). Anal. calcd for C$_{19}$H$_{27}$N$_5$O: C, 66.8; H, 8.0; N, 20.5. Found: C, 66.8; H, 7.8; N, 20.6%.

Example 33

N-[2-(2,6-Dimethyl-1-piperidinyl)ethyl]-7,8-dihydro-6H-indeno[5,6-e][1,2,4]triazin-3-amine 1,4-Dioxide (39). H$_2$O$_2$ (70%, 0.46 mL, ca. 9.2 mmol) was added dropwise to a stirred solution of TFAA (1.3 mL, 9.2 mmol) in DCM (20 mL) at 0° C. The solution was stirred at 0° C. for 5 min, warmed to 20° C. for 10 min, then cooled to 0° C. and added to a stirred solution of 1-oxide 38 (314 mg, 0.9 mmol) and TFA (0.35 mL, 4.6 mmol) in DCM (20 mL) at 0° C. The solution was stirred at 20° C. for 6 h, diluted with dilute aqueous NH$_3$ solution (10 mL) and extracted with CHCl$_3$ (4×50 mL). The combined organic fraction was dried and the solvent evaporated. The residue was purified by chromatography, eluting with a gradient (0-10%) of MeOH/DCM, to give 1,4-dioxide 39 (118 mg, 36%) as a red solid: mp (MeOH) 170-172° C.; $^1$H NMR δ 8.12 (s, 1H, H-9), 8.10 (s, 1H, H-5), 7.21 (br s, 1H, NH), 3.56-3.63 (m, 2H, CH$_2$N), 3.12 (br dd, J=7.6, 7.3 Hz, 2H, CH$_2$), 3.07 (br dd, J=7.5, 7.4 Hz, 2H, CH$_2$N), 2.95 (br dd, J=7.5, 7.1 Hz, 2H, CH$_2$N), 2.49-2.57 (m, 2H, CH$_2$N), 2.20 (p, J=7.5 Hz, 2H, CH$_2$), 1.65-1.70 (m, 1H, CH$_2$), 1.53-1.59 (m, 2H, CH$_2$), 1.25-1.40 (m, 3H, CH$_2$), 1.18 (d, J=6.3 Hz, 6H, 2×CH$_3$); $^{13}$C NMR δ 155.7, 149.4, 145.7, 137.9, 129.7, 115.8, 111.5, 57.1 (2), 47.2, 39.3, 34.2, 33.4 (2), 32.4, 25.6, 24.4, 21.7 (2). Anal. calcd for C$_{19}$H$_{27}$N$_5$O$_2$: C, 63.8; H, 7.6; N, 19.6. Found: C, 64.0; H, 7.6; N, 19.8%.

Example 34

N-[2-(3-Methoxy-1-piperidinyl)ethyl]-7,8-dihydro-6H-indeno[5,6-e][1,2,4]triazin-3-amine 1-Oxide (40). A solution of the chloride 21 (2.0 g, 9.0 mmol), 2-(3-methoxy-1-piperidinyl)ethylamine (283) (1.8 g, 11.4 mmol) and Et$_3$N (1.5 mL, 9.9 mmol) in DME (140 mL) was stirred at reflux temperature for 22 h. The solution was cooled to 20° C., the solvent evaporated and the residue purified by chromatography, eluting with 5% MeOH/DCM to give (i) starting material 21 (0.6 g, 30%) and (ii) 1-oxide 40 (1.9 g, 61%) as a yellow solid: mp 123-124° C.; $^1$H NMR δ 8.07 (s, 1H, H-9), 7.39 (s, 1H, H-5), 5.81 (br s, 1H, NH), 3.54-3.58 (m, 2H, CH$_2$N), 3.35 (s, 3H, OCH$_3$), 3.24-3.31 (m, 1H, CHO), 2.97-3.03 (m, 5H, H-6, H-8, CH$_2$), 2.68-2.74 (m, 1H, CH$_2$), 2.63 (dt, J=6.1, 2.4 Hz, 2H, CH$_2$N), 2.14 (p, J=7.4 Hz, 2H, H-7), 1.96-2.07 (m, 3H, CH$_2$), 1.71-1.78 (m, 1H, CH$_2$), 1.45-1.58 (m, 1H, CH$_2$), 1.17-1.27 (m, 1H, CH$_2$); $^{13}$C NMR δ 158.6, 154.5, 148.7, 143.2, 129.8, 120.5, 114.6, 76.2, 57.8, 56.5, 56.1, 53.2, 38.0, 33.1, 32.3, 29.9, 25.7, 23.2; HRMS (FAB$^+$) calcd for C$_{18}$H$_{26}$N$_5$O$_2$ (MH$^+$) m/z 344.2087, found 344.2090.

Example 35

N-[2-(3-Methoxy-1-piperidinyl)ethyl]-7,8-dihydro-6H-indeno[5,6-e][1,2,4]triazin-3-amine 1,4-Dioxide (41). H$_2$O$_2$ (70%, 2.5 mL, ca. 51 mmol) was added dropwise to a stirred solution of TFAA (7.1 mL, 51 mmol) in DCM (70 mL) at 0° C. The solution was stirred at 20° C. for 10 min, then cooled to 0° C., added to a solution of 1-oxide 40 (1.75 g, 5.1 mmol) and TFA (0.84 mL, 11 mmol) in CHCl$_3$ (70 mL) at 0° C. The solution was stirred at 20° C. for 5 h, diluted with dilute aqueous NH$_3$ solution until basic and extracted with CHCl$_3$ (3×80 mL). The combined organic fraction was dried and the solvent evaporated. The residue was purified by column chromatography, eluting with a gradient (4-20%) of MeOH/DCM, to give 1,4-dioxide 41 (0.15 g, 8%) as a red gum: $^1$H NMR δ 8.91 (br s, 1H, NH), 8.05 (s, 2H, H-5, H-9), 4.09 (t, J=5.8 Hz, 2H, CH$_2$N), 3.84 (td, J=12.8, 1.9 Hz, 1H, CHO), 3.57-3.66 (m, 4H, 2×CH$_2$), 3.57 (s, 3H, OMe), 3.40 (td, J=13.3, 3.5 Hz, 1H, CH$_2$), 3.01-3.12 (m, 5H, H-6, H-8, CH$_2$), 2.19 (p, J=7.4 Hz, 2H, H-7), 2.16-2.23 (m, 1H, CH$_2$), 2.02-2.08 (m, 1H, CH$_2$), 1.62-1.72 (m, 1H, CH$_2$), 1.37-1.48 (m, 1H, CH$_2$); $^{13}$C NMR δ 155.6, 149.4, 146.1, 138.1, 129.7, 115.5, 111.7, 73.2, 69.7, 67.6, 61.4, 56.9, 36.5, 33.3, 32.4, 28.5, 25.6, 20.3; HRMS (FAB$^+$) calcd for C$_{18}$H$_{26}$N$_5$O$_3$ (MH$^+$) m/z 360.2036, found 360.2039.

Example 36

N-[2-(4-Methoxy-1-piperidinyl)ethyl]-7,8-dihydro-6H-indeno[5,6-e][1,2,4]triazin-3-amine 1-Oxide (42). Crude 2-(4-methoxy-1-piperidinyl)ethylamine (288) (3.8 g, 23.9 mmol) was added to a stirred solution of chloride 21 (1.77 g, 8.0 mmol) and Et$_3$N (2.2 mL, 16.0 mmol) in DME (80 mL) and the solution stirred at reflux temperature for 6 h. The solvent was evaporated and the residue partitioned between DCM (100 mL) and dilute aqueous NH$_3$ solution (50 mL). The organic fraction was dried and the solvent evaporated. The residue was purified by chromatography, eluting with a gradient (0-15%) of MeOH/DCM, to give 1-oxide 42 (2.16 g, 79%) as a yellow solid: mp (MeOH/EtOAc) 131-133° C.; $^1$H NMR δ 8.07 (s, 1H, H-9), 7.39 (s, 1H, H-5), 5.82 (br s, 1H, NH), 3.50-3.56 (m, 2H, CH$_2$N), 3.33 (s, 3H, OCH$_3$), 3.21-3.26 (m, 1H, CHO), 2.97-3.03 (m, 4H, H-6, H-8), 2.72-2.82 (m, 2H, CH$_2$N), 2.60 (dd, J=6.0, 5.8 Hz, 2H, CH$_2$N), 2.20-2.26 (m, 2H, CH$_2$N), 2.15 (br p, J=7.4 Hz, 2H, H-7), 1.84-1.92 (m, 2H, CH$_2$), 1.57-1.65 (m, 2H, CH$_2$); $^{13}$C NMR δ 158.7, 154.5, 148.8, 143.2, 129.8, 120.5, 114.7, 76.2, 56.3, 55.5, 50.7 (2), 38.2, 33.1, 32.3, 30.8 (2), 25.7. Anal. calcd for C$_{18}$H$_{25}$N$_5$O$_2$: C, 63.0; H, 7.3; N, 20.4. Found: C, 63.0; H, 7.4; N, 20.4%.

Example 37

N-[2-(4-Methoxy-1-piperidinyl)ethyl]-7,8-dihydro-6H-indeno[5,6-e][1,2,4]triazin-3-amine 1,4-Dioxide (43). H$_2$O$_2$ (70%, 3.1 mL, ca. 62.6 mmol) was added dropwise to a stirred solution of TFAA (8.8 mL, 62.6 mmol) in DCM (40 mL) at 0° C. The solution was stirred at 0° C. for 5 min, warmed to 20° C. for 10 min, then cooled to 0° C. and added to a stirred solution of 1-oxide 42 (2.15 g, 6.3 mmol) and TFA (2.4 mL, 31.3 mmol) in DCM (50 mL) at 0° C. The solution was stirred at 20° C. for 8 h, diluted with dilute aqueous NH$_3$ solution (10 mL) and extracted with DCM (4×50 mL). The combined organic fraction was dried and the solvent evaporated. The residue was purified by chromatography, eluting with a gradient (0-15%) of MeOH/DCM, to give (i) starting material 42 (204 mg, 9%); and (ii) 1,4-dioxide 43 (1.0 g, 44%) as a red solid: mp (MeOH/EtOAc) 148-151° C.; $^1$H NMR δ 8.11 (s, 1H, H-9), 8.10 (s, 1H, H-5), 7.44 (br s, 1H, NH), 3.61-3.66 (m, 2H, CH$_2$N), 3.33 (s, 3H, OCH$_3$), 3.22-3.29 (m, 1H, CHO), 3.10 (br t, J=7.5 Hz, 2H, H-6), 3.05 (br t, J=7.5 Hz, 2H, H-8), 2.75-2.81 (m, 2H, CH$_2$N), 2.68 (br t, J=6.0 Hz, 2H, CH$_2$N), 2.27-2.34 (m, 2H, CH$_2$N), 2.20 (p, J=7.5 Hz, 2H, H-7), 1.87-1.95 (m, 2H, CH$_2$), 1.61-1.70 (m, 2H, CH$_2$); $^{13}$C NMR δ 155.6, 149.4, 145.8, 138.0, 129.7, 115.7, 111.6, 75.8, 56.3, 55.5, 50.7 (2), 38.3, 33.4, 32.4, 30.6 (2), 25.6. Anal. calcd for C$_{18}$H$_{25}$N$_5$O$_3$.¼H$_2$O: C, 59.4; H, 7.1; N, 19.2. Found: C, 59.2; H, 6.8; N, 19.1%.

Example 38

N-[2-(4-Morpholinyl)ethyl]-7,8-dihydro-6H-indeno[5,6-e][1,2,4]triazin-3-amine 1-Oxide (44). 2-(4-Morpholinyl) ethylamine (3.93 mL, 30.0 mmol) was added to a stirred solution of chloride 21 (2.21 g, 10.0 mmol) in DME (50 mL) and the solution stirred at reflux temperature for 3 h. The solvent was evaporated and the residue stirred with water (150 mL) at room temperature for 30 min. The solid was filtered, washed with water (3×10 mL) and dried to give 1-oxide 44 (3.08 g, 98%) as an orange solid: mp (water) 178-179° C.; $^1$H NMR δ 8.07 (s, 1H, H-9), 7.39 (s, 1H, H-5), 5.79 (br s, 1H, NH), 3.72 (br t, J=4.6 Hz, 4H, CH$_2$O), 3.59 (q, J=5.6 Hz, 2H, CH$_2$N), 2.97-3.05 (m, 4H, H-6, H-8), 2.63 (t, J=5.9 Hz, 2H, CH$_2$N), 2.51 (br t, J=4.6 Hz, 4H, CH$_2$N), 2.10-2.19 (m, 2H, H-7); $^{13}$C NMR δ 158.6, 154.6, 148.7, 143.3, 129.8, 120.5, 114.6, 66.9 (2), 56.8, 53.3 (2), 37.5, 33.1, 32.3, 25.7. Anal. calcd for C$_{16}$H$_{21}$N$_5$O$_2$: C, 60.9; H, 6.7; N, 22.2. Found: C, 61.0; H, 6.8; N, 22.3%.

Example 39

N-[2-(4-Morpholinyl)ethyl]-7,8-dihydro-6H-indeno[5,6-e][1,2,4]triazin-3-amine 1,4-Dioxide (45). H$_2$O$_2$ (70%, 0.50 mL, ca. 10.0 mmol) was added to a stirred solution of 1-oxide 44 (3.00 g, 9.52 mmol) in a mixture of TFA (30 mL) and water (2 mL) at 20° C. Ten more aliquots of 70% H$_2$O$_2$ (0.5 mL) were added in 30 min intervals and the reaction mixture was stirred at 20° C. for 26 h. Water (100 mL) was added and the mixture made basic with Na$_2$CO$_3$. The mixture was extracted with DCM (4×200 mL) and the combined organic fraction was dried and the solvent evaporated. The residue was purified by chromatography, eluting with a gradient (0-5%) of MeOH/DCM, to give 1,4-dioxide 45 (1.13 g, 36%) as a red solid: $^1$H NMR δ 8.13 (s, 1H, H-9), 8.10 (s, 1H, H-5), 7.38 (br s, 1H, NH), 3.73 (t, J=4.5 Hz, 4H, CH$_2$O), 3.67 (m, 2H, CH$_2$N), 3.03-3.15 (m, 4H, H-6, H-8), 2.68 (t, J=6.0 Hz, 2H, CH$_2$N), 2.53 (t, J=4.5 Hz, 4H, CH$_2$N), 2.17-2.25 (m, 2H, H-7); $^{13}$C NMR δ 155.7, 149.4, 145.9, 137.9, 129.7, 115.8, 111.6, 65.9 (2), 56.8, 53.4 (2), 37.7, 33.4, 32.4, 25.6. The hydrochloride salt was crystallised as a red solid: mp (MeOH/DCM) 184-185° C. Anal. calcd for C$_{16}$H$_{21}$N$_5$O$_3$.¾HCl: C, 53.5; H, 6.2; N, 19.5. Found: C, 53.9; H, 6.3; N, 19.6%.

Example 40

N-[2-(1-Azepanyl)ethyl]-7,8-dihydro-6H-indeno[5,6-e][1,2,4]triazin-3-amine 1-Oxide (46). 2-(1-Azepanyl)ethylamine (289) (0.52 g, 3.6 mmol) was added to a stirred solution of chloride 21 (322 mg, 1.5 mmol) in DME (30 mL) and the solution stirred at reflux temperature for 3 h. The solvent was evaporated and the residue partitioned between DCM (100 mL) and dilute aqueous NH$_3$ solution (50 mL). The organic fraction was dried and the solvent evaporated. The residue was purified by chromatography, eluting with a gradient (0-10%) of MeOH/DCM, to give 1-oxide 46 (264 mg, 56%) as a yellow solid: mp (MeOH) 121-123° C.; $^1$H NMR δ 8.08 (s, 1H, H-9), 7.40 (s, 1H, H-5), 5.93 (br s, 1H, NH), 3.47-3.52 (m, 2H, CH$_2$N), 2.97-3.03 (m, 4H, H-6, H-8), 2.74 (dd, J=6.0, 5.8 Hz, 2H, CH$_2$N), 2.65-2.68 (m, 4H, 2×CH$_2$N), 2.15 (p, J=7.4 Hz, 2H, H-7), 1.58-1.68 (m, 8H, 4×CH$_2$); $^{13}$C NMR δ 158.8, 154.5, 148.8, 143.1, 129.7, 120.5, 114.6, 55.9, 55.1 (2), 38.8, 33.1, 32.3, 28.4 (2), 26.9 (2), 25.7. Anal. calcd for C$_{18}$H$_{25}$N$_5$O: C, 66.0; H, 7.7; N, 21.4. Found: C, 66.0; H, 7.6; N, 21.5%.

Example 41

N-[2-(1-Azepanyl)ethyl]-7,8-dihydro-6H-indeno[5,6-e][1,2,4]triazin-3-amine 1,4-Dioxide (47). H$_2$O$_2$ (70%, 0.37 mL, ca. 7.3 mmol) was added dropwise to a stirred solution of TFAA (1.0 mL, 7.3 mmol) in DCM (20 mL) at 0° C. The solution was stirred at 0° C. for 5 min, warmed to 20° C. for 10 min, then cooled to 0° C. and added to a stirred solution of 1-oxide 46 (240 mg, 0.7 mmol) and TFA (0.28 mL, 3.7 mmol) in DCM (20 mL) at 0° C. The solution was stirred at 20° C. for 6 h, diluted with dilute aqueous NH$_3$ solution (10 mL) and extracted with CHCl$_3$ (4×50 mL). The combined organic fraction was dried and the solvent evaporated. The residue was purified by chromatography, eluting with a gradient (0-10%) of MeOH/DCM, to give 1,4-dioxide 47 (146 mg, 61%) as a red solid: mp (MeOH) 181-184° C.; $^1$H NMR δ 8.13 (s, 1H, H-9), 8.10 (s, 1H, H-5), 7.55 (br s, 1H, NH), 3.56-3.60 (m, 2H, CH$_2$N), 3.03-3.07 (m, 4H, H-6, H-8), 2.81 (dd, J=6.1, 6.0 Hz, 2H, CH$_2$N), 2.67-2.72 (m, 4H, 2×CH$_2$N), 2.20 (p, J=7.5 Hz, 2H, H-7), 1.60-1.71 (m, 8H, 4×CH$_2$); $^{13}$C NMR δ 155.6, 149.4, 145.7, 138.0, 129.6, 115.7, 111.5, 55.9, 55.1 (2), 39.0, 33.4, 32.3, 28.5 (2), 27.0 (2), 25.5. Anal. calcd for C$_{18}$H$_{25}$N$_5$O$_2$: C, 63.0; H, 7.3; N, 20.4. Found: C, 62.9; H, 7.2; N, 20.3%.

Example 42

N-[2-(1,4-Oxazepan-4-yl)ethyl]-7,8-dihydro-6H-indeno[5,6-e][1,2,4]triazin-3-amine 1-Oxide (48). A solution of chloride 21 (2.0 g, 9.0 mmol), 2-(1,4-oxazepan-4-yl)ethylamine (292) (1.63 g, 11.3 mmol) and Et$_3$N (1.3 mL, 9.9 mmol) in DME (140 mL) was stirred at reflux temperature for 20 h. The solution was cooled to 20° C., the solvent evaporated and the residue purified by column chromatography, eluting with a gradient (2-6%) of MeOH/DCM, to give (i) starting material 21 (0.5 g, 25%) and (ii) 1-oxide 48 (1.24 g, 42%) as a yellow solid: mp 119-120° C.; $^1$H NMR δ 8.08 (s, 1H, H-9), 7.40 (s, 1H, H-5), 5.82 (br s, 1H, NH), 3.81 (t, J=6.1 Hz, 2H, CH$_2$O), 3.74 (t, J=4.7 Hz, 2H, CH$_2$), 3.51-3.56 (m, 2H, CH$_2$), 2.97-3.04 (m, 4H, H-6, H-8), 2.73-2.80 (m, 6H, 3×CH$_2$), 2.15 (p, J=7.4 Hz, 2H, H-7), 1.88-1.94 (m, 2H, CH$_2$); $^{13}$C NMR δ 158.7, 154.6, 148.8, 143.3, 129.8, 120.5, 114.7, 69.3, 68.7, 57.5, 55.8, 53.6, 38.7, 33.1, 32.3, 30.0, 25.7; HRMS (FAB$^+$) calcd for C$_{17}$H$_{24}$N$_5$O$_2$ (MH$^+$) m/z 330.1930, found 330.1937.

Example 43

N-[2-(1,4-Oxazepan-4-yl)ethyl]-7,8-dihydro-6H-indeno[5,6-e][1,2,4]triazin-3-amine 1,4-Dioxide (49). H$_2$O$_2$ (70%, 1.25 mL, ca. 25.8 mmol) was added dropwise to a stirred solution of TFAA (3.6 mL, 25.8 mmol) in DCM (35 mL) at 0° C. The solution was stirred at 20° C. for 10 min, then cooled to 0° C., added to a solution of 1-oxide 48 (0.85 g, 2.58 mmol) and TFA (0.43 mL, 5.50 mmol) in CHCl$_3$ (35 mL) at 0° C. The solution was stirred at 20° C. for 5 h, diluted with dilute aqueous $NH_3$ solution until basic and extracted with $CHCl_3$ (4×60 mL). The combined organic fraction was dried and the solvent evaporated. The residue was purified by chromatography, eluting with a gradient (3-6%) of MeOH/DCM, to give 1,4-dioxide 49 (0.37 g, 42%) as a red gum: $^1$H NMR δ 8.13 (s, 1H, H-9), 8.10 (s, 1H, H-5), 7.45 (br s, 1H, NH), 3.82 (t, J=6.1 Hz, 2H, $CH_2O$), 3.74 (t, J=4.6 Hz, 2H, $CH_2O$), 3.54 (q, J=5.7 Hz, 2H, $NCH_2$), 2.97-3.04 (m, 4H, H-6, H-8), 2.73-2.80 (m, 6H, $CH_2$), 2.15 (p, J=7.4 Hz, 2H, H-7), 1.91 (p, J=5.9 Hz, 2H, $CH_2$); $^{13}$C NMR δ 158.7, 154.6, 148.8, 143.3, 129.8, 120.5, 114.7, 69.3, 68.7, 57.4, 55.8, 53.6, 38.7, 33.1, 32.3, 29.9, 25.7; HRMS ($FAB^+$) calcd for $C_{17}H_{24}N_5O_3$ ($MH^+$) m/z 346.1879, found 346.1877.

Example 44

3-[(1-Oxido-7,8-dihydro-6H-indeno[5,6-e][1,2,4]triazin-3-yl)amino]-1-propanol (50). 3-Aminopropanol (0.99 mL, 12.9 mmol) was added to a stirred solution of chloride 21 (956 mg, 4.3 mmol) in DME (80 mL) and the solution stirred at reflux temperature for 6 h. The solvent was evaporated and the residue partitioned between DCM (100 mL) and dilute aqueous $NH_3$ solution (50 mL). The organic fraction was dried and the solvent evaporated. The residue was purified by chromatography, eluting with a gradient (0-10%) of MeOH/DCM, to give 1-oxide 50 (1.09 g, 98%) as a yellow solid: mp (MeOH/DCM) 190-190.5° C.; $^1$H NMR δ 8.07 (s, 1H, H-9), 7.40 (s, 1H, H-5), 5.61 (br s, 1H, NH), 3.78 (br s, 1H, OH), 3.67-3.73 (m, 4H, $CH_2O$, $CH_2N$), 2.97-3.03 (m, 4H, H-6, H-8), 2.15 (p, J=7.5 Hz, 2H, H-7), 1.82-1.88 (m, 2H, $CH_2$); $^{13}$C NMR δ 159.2, 155.0, 147.9, 143.6, 130.0, 120.3, 114.8, 59.0, 37.7, 33.1, 33.0, 32.3, 25.7. Anal. calcd for $C_{13}H_{16}N_4O_2$: C, 60.0; H, 6.2; N, 21.5. Found: C, 59.8; H, 6.2; N, 21.6%.

Example 45

3-[(1,4-Dioxido-7,8-dihydro-6H-indeno[5,6-e][1,2,4]triazin-3-yl)amino]-1-propanol (51). TFM (0.44 mL, 2.4 mmol) was added to a stirred solution of 1-oxide 50 (486 mg, 2.2 mmol) in DCM (20 mL) at 0° C. and the solution stirred at 20° C. for 16 h. $H_2O_2$ (70%, 1.1 mL, ca. 21.9 mmol) was added dropwise to a stirred solution of TFAA (3.1 mL, 21.9 mmol) in DCM (20 mL) at 0° C. The solution was stirred at 0° C. for 5 min, warmed to 20° C. for 10 min, then cooled to 0° C. and added to the solution of 1-oxide 50 prepared above and the resulting solution was stirred at 20° C. for 16 h. Dilute aqueous $NH_3$ solution (40 mL) was added and the mixture stirred vigorously for 4 h, then the mixture extracted with DCM (4×50 mL). The combined organic fraction was dried and the solvent evaporated. The residue was purified by chromatography, eluting with a gradient (0-10%) of MeOH/DCM, to give (i) starting material 50 (254 mg, 52%); and (ii) 1,4-dioxide 51 (166 mg, 27%) as a red solid: mp (MeOH/DCM) 182-184° C.; $^1$H NMR δ 8.05 (s, 1H, H-9), 8.03 (s, 1H, H-5), 7.61 (br t, J=5.7 Hz, 1H, NH), 3.82 (br t, J=5.7 Hz, 2H, $CH_2O$), 3.78 (br s, 1H, OH), 3.71-3.77 (m, 2H, $CH_2N$), 3.10 (br t, J=7.5 Hz, 2H, H-6), 3.04 (br t, J=7.5 Hz, 2H, H-8), 2.20 (p, J=7.5 Hz, 2H, H-7), 1.97 (br p, J=6.0 Hz, 2H, $CH_2$); $^{13}$C NMR δ 156.1, 149.5, 145.8, 137.8, 129.7, 115.7, 111.3, 60.2, 39.1, 33.4, 32.3, 31.5, 25.5. Anal. calcd for $C_{13}H_{16}N_4O_3$: C, 56.5; H, 5.8; N, 20.3. Found: C, 56.8; H, 5.9; N, 20.2%.

Example 46

$N^1$-(2-Methoxyethyl)-$N^1$-methyl-$N^3$-(1-oxido-7,8-dihydro-6H-indeno[5,6-e][1,2,4]triazin-3-yl)-1,3-propanediamine (52). A solution of chloride 21 (2.0 g, 9.03 mmol) and $N^1$-(2-methoxyethyl)-$N^1$-methylpropane-1,3-diamine (297) (2.0 g, 13.6 mmol) in DME (140 mL) was stirred at 20° C. for 18 h, the solvent evaporated and the residue purified by column chromatography, eluting with a gradient (2-15%) of MeOH/DCM, to give 1-oxide 52 (2.3 g, 79%) as a yellow solid: mp 59-61° C.; $^1$H NMR [$(CH_3)_2SO$] δ 7.94 (s, 1H, H-9), 7.68 (br s, 1H, NH), 7.38 (s, 1H, H-5), 3.24-3.44 (m, 6H, $CH_2$), 3.23 (s, 3H, $OCH_3$), 2.92-2.99 (m, 4H, H-6, H-8), 2.56 (br t, J=5.8 Hz, 2H, $CH_2N$), 2.24 (s, 3H, $NCH_3$), 2.03-2.07 (m, 2H, H-7), 1.70-1.74 (m, 2H, $CH_2$); HRMS ($FAB^+$): calcd for $C_{17}H_{26}N_5O_2$ ($MH^+$) m/z 332.2087, found, 332.2089.

Example 47

$N^1$-(1,4-Dioxido-7,8-dihydro-6H-indeno[5,6-e][1,2,4]triazin-3-yl)-$N^3$-(2-methoxyethyl)-$N^3$-methyl-1,3-propanediamine (53). $H_2O_2$ (70%, 3.0 mL, ca. 60.4 mmol) was added dropwise to a stirred solution of TFM (8.4 mL, 60.4 mmol) in DCM (80 mL) at 0° C. The solution was stirred at 20° C. for 10 min, then cooled to 0° C., and added to a solution of 1-oxide 52 (2.0 g, 6.04 mmol) and TFA (1.0 mL, 13.0 mmol) in $CHCl_3$ (80 mL) at 0° C. and the solution stirred at 20° C. for 18 h. The solution was made basic with dilute aqueous $NH_3$ solution and extracted with $CHCl_3$ (3×100 mL). The combined organic fraction was dried and the solvent evaporated. The residue was purified by chromatography, eluting with a gradient (2-18%) of MeOH/DCM, to give 1,4-dioxide 53 (99 mg, 5%) as a red solid: mp 77-79° C.; $^1$H NMR δ 8.12 (s, 1H, H-9), 8.10 (s, 1H, H-5), 7.26 (br s, 1H, NH), 3.66 (t, J=6.3 Hz, 2H, $CH_2$), 3.59 (t, J=5.6 Hz, 2H, $CH_2$), 3.36 (s, 3H, $OCH_3$), 3.03-3.12 (m, 4H, H-6, H-8), 2.66-2.71 (m, 4H, 2×$CH_2$), 2.39 (s, 3H, $NCH_3$), 2.19 (p, J=7.4 Hz, 2H, H-7), 1.91 (p, J=6.6 Hz, 2H, $CH_2$); $^{13}$C NMR δ 155.6, 149.5, 145.7, 138.0, 129.7, 115.8, 111.6, 70.5, 58.9, 56.8, 55.9, 42.5, 40.5, 33.4, 32.4, 25.9, 25.6; HRMS ($FAB^+$) calcd for $C_{17}H_{26}N_5O_3$ ($MH^+$) m/z 348.2036, found 348.2032.

Example 48

N-[3-(3-Methoxy-1-azetidinyl)propyl]-7,8-dihydro-6H-indeno[5,6-e][1,2,4]triazin-3-amine 1-Oxide (54). A solution of chloride 21 (1.33 g, 6.0 mmol), $Et_3N$ (1.7 mL, 12 mmol) and 3-(3-methoxy-1-azetidinyl)propylamine (299) (1.2 g, 8.4 mmol) in DME (30 mL) was heated at reflux temperature for 18 h. The solution was cooled, the solvent evaporated and the residue partitioned between dilute aqueous $NH_3$ solution (50 mL) and DCM (50 mL). The aqueous layer was extracted with DCM (2×25 mL), the combined organic fraction dried and the solvent evaporated. The residue was purified by chromatography, eluting with a gradient (0-15%) of MeOH/DCM, to give 1-oxide 54 (1.32 g, 66%) as a yellow solid: mp 101-102° C.; $^1$H NMR δ 8.07 (s, 1H, H-9), 7.39 (s, 1H, H-5), 6.18 (br s, 1H, NH), 4.07 (p, J=5.9 Hz, 1H, CHO), 3.65-3.71 (m, 2H, $CH_2N$), 3.54 (dt, J=6.2, 5.8 Hz, 2H, $CH_2N$), 3.26 (s, 3H, $OCH_3$), 2.94-3.04 (m, 4H, H-6, H-8), 2.82-2.88 (m, 2H, $CH_2N$), 2.63 (t, J=6.4 Hz, 2H, $CH_2N$), 2.14 (p, J=7.1 Hz, 2H, H-7), 1.70 (p, J=6.4 Hz, 2H, $CH_2$); $^{13}$C NMR δ 158.8, 154.5, 148.8, 143.1, 129.8, 120.6, 114.7, 69.7, 61.5 (2), 58.6, 56.0, 40.8, 33.1, 32.3, 26.6, 25.8; MS (APCI) m/z 330 ($MH^+$, 100%). Anal. calcd for $C_{17}H_{23}N_5O_2$: C, 62.0; H, 7.0; N, 21.3. Found: C, 61.7; H, 7.2; N, 21.2%.

Example 49

N-[3-(3-Methoxy-1-azetidinyl)propyl]-7,8-dihydro-6H-indeno[5,6-e][1,2,4]triazin-3-amine 1,4-Dioxide (55). $H_2O_2$ (70%, 2.0 mL, ca. 40 mmol) was added dropwise to a stirred solution of TFM (5.6 mL, 40 mmol) in DCM (50 mL) at 0° C. The solution was stirred at 20° C. for 10 min, then cooled to 0° C., added to a solution of 1-oxide 54 (1.3 g, 4.0 mmol) and TFA (1.5 mL, 20 mmol) in DCM (50 mL) at 0° C. The solution was stirred at 20° C. for 26 h, diluted with dilute aqueous $NH_3$ solution (80 mL) and extracted with DCM (4×125 mL). The combined organic fraction was dried and the solvent evaporated. The residue was purified by chromatography, eluting with a gradient (0-15%) of MeOH/DCM, to give 1,4-dioxide 55 (400 mg, 30%) as a red solid: mp 150-152° C.; $^1$H NMR δ 8.12 (s, 1H, H-9), 8.10 (s, 1H, H-5), 8.06 (br s, 1H, NH), 4.18 (p, J=5.9 Hz, 1H, CHO), 3.91 (br s, 2H, $CH_2N$), 3.64 (t, J=6.4 Hz, 2H, $CH_2N$), 3.28 (s, 3H, $OCH_3$), 2.98-3.13 (m, 6H, H-6, H-8, $CH_2N$), 2.80 (t, J=6.3 Hz, 2H, $CH_2N$), 2.20 (p, J=7.5 Hz, 2H, H-7), 1.82 (p, J=6.4 Hz, 2H, $CH_2$); $^{13}$C NMR δ 155.7, 149.4, 145.7, 138.0, 129.7, 115.8, 111.6, 69.3, 61.4 (2), 57.3, 56.2, 40.4, 33.4, 32.4, 26.0, 25.6; MS (APCI) m/z 346 ($MH^+$, 100%); HRMS ($FAB^+$) calcd for $C_{17}H_{24}N_5O_3$ ($MH^+$) m/z 346.1879, found 346.1878.

Example 50

1-{3-[(1-Oxido-7,8-dihydro-6H-indeno[5,6-e][1,2,4]triazin-3-yl)amino]propyl}-3-pyrrolidinecarbonitrile (56). 1-(3-Aminopropyl)-3-pyrrolidinecarbonitrile (302) (0.36 g, 2.4 mmol) was added to a stirred solution of chloride 21 (402 mg, 1.8 mmol) and $Et_3N$ (0.76 mL, 5.4 mmol) in DME (50 mL) and the solution stirred at reflux temperature for 16 h. The solvent was evaporated and the residue partitioned between DCM (100 mL) and dilute aqueous $NH_3$ solution (50 mL). The organic fraction was dried and the solvent evaporated. The residue was purified by chromatography, eluting with a gradient (0-10%) of MeOH/DCM, to give 1-oxide 56 (476 mg, 78%) as a yellow solid: mp (EtOAc/pet. ether) 111-112° C.; $^1$H NMR δ 8.07 (s, 1H, H-9), 7.39 (s, 1H, H-5), 5.72 (br t, J=5.3 Hz, 1H, NH), 3.58 (q, J=6.4 Hz, 2H, $CH_2N$), 2.95-3.07 (m, 6H, H-6, H-8, $CH_2N$), 2.73-2.80 (m, 1H, CHCN), 2.55-2.68 (m, 4H, 2×$CH_2$), 2.23-2.32 (m, 1H, $CH_2$), 2.10-2.18 (m, 3H, $CH_2$, H-7), 1.85 (p, J=6.7 Hz, 2H, $CH_2$); $^{13}$C NMR δ 158.7, 154.6, 148.7, 143.3, 129.8, 122.1, 120.6, 114.6, 57.4, 53.3, 52.9, 40.2, 33.3, 33.1, 32.3, 29.2, 27.7, 26.3, 25.7. Anal. calcd for $C_{18}H_{22}N_6O$: C, 63.9; H, 6.6; N, 24.8. Found: C, 64.0; H, 6.4; N, 24.8%.

Example 51

1-{3-[(1,4-Dioxido-7,8-dihydro-6H-indeno[5,6-e][1,2,4]triazin-3-yl)amino]propyl}-3-pyrrolidinecarbonitrile (57). $H_2O_2$ (70%, 0.67 mL, ca. 13.3 mmol) was added dropwise to a stirred solution of TFAA (1.9 mL, 13.3 mmol) in DCM (20 mL) at 0° C. The solution was stirred at 0° C. for 5 min, warmed to 20° C. for 10 min, then cooled to 0° C. and added to a stirred solution of 1-oxide 56 (449 mg, 1.3 mmol) and TFA (0.51 mL, 6.6 mmol) in DCM (20 mL) at 0° C. The solution was stirred at 20° C. for 8 h, diluted with dilute aqueous $NH_3$ solution (10 mL) and extracted with DCM (4×50 mL). The combined organic fraction was dried and the solvent evaporated. The residue was purified by chromatography, eluting with a gradient (0-10%) of MeOH/DCM, to give (i) starting material 56 (198 mg, 44%) and (ii) 1,4-dioxide 57 (70 mg, 15%) as a red gum: $^1$H NMR δ 8.15 (br t, J=5.3 Hz, 1H, NH), 8.12 (s, 1H, H-9), 8.08 (s, 1H, H-5), 3.62-3.68 (m, 2H, $CH_2N$), 3.15-3.23 (m, 2H, $CH_2N$), 3.11 (br t, J=7.5 Hz, 2H, H-6), 3.07 (br t, J=7.5 Hz, 2H, H-8), 2.90-2.95 (m, 1H, CHCN), 2.73 (t, J=6.3 Hz, 2H, $CH_2N$), 2.50-2.61 (m, 2H, $CH_2N$), 2.33-2.43 (m, 1H, $CH_2$), 2.11-2.24 (m, 3H, $CH_2$, H-7), 1.91 (p, J=6.3 Hz, 2H, $CH_2$); $^{13}$C NMR δ 155.7, 149.4, 145.7, 138.0, 129.6, 122.0, 115.8, 111.5, 57.3, 53.5, 52.8, 41.0, 33.4, 32.3, 29.1, 26.9, 26.1, 25.3; MS ($FAB^+$) m/z 355 ($MH^+$, 30%), 339 (10); HRMS ($FAB^+$) calcd for $C_{18}H_{23}N_6O_2$ ($MH^+$) m/z 355.1883, found 355.1893.

Example 52

N-[3-(4-Methoxy-1-piperidinyl)propyl]-7,8-dihydro-6H-indeno[5,6-e][1,2,4]triazin-3-amine 1-Oxide (58). 3-(4-Methoxy-1-piperidinyl)propylamine (304) (0.59 g, 3.4 mmol) was added to a stirred solution of chloride 21 (505 mg, 2.3 mmol) and $Et_3N$ (0.64 mL, 2.6 mmol) in DME (50 mL) and the solution stirred at reflux temperature for 16 h. The solvent was evaporated and the residue partitioned between DCM (100 mL) and dilute aqueous $NH_3$ solution (50 mL). The organic fraction was dried and the solvent evaporated. The residue was purified by chromatography, eluting with a gradient (0-10%) of MeOH/DCM, to give 1-oxide 58 (681 mg, 84%) as a yellow solid: mp (EtOAc/pet. ether) 120-121° C.; $^1$H NMR δ 8.07 (s, 1H, H-9), 7.38 (s, 1H, H-5), 6.25 (br s, 1H, NH), 3.56-3.61 (m, 2H, $CH_2N$), 3.33 (s, 3H, $OCH_3$), 3.24-3.30 (m, 1H, CHO), 2.97-3.03 (m, 4H, H-6, H-8), 2.71-2.78 (m, 2H, $CH_2N$), 2.52 (br t, J=6.6 Hz, 2H, $CH_2N$), 2.21-2.30 (m, 2H, $CH_2$), 2.15 (br p, J=7.5 Hz, 2H, H-7), 1.91-1.98 (m, 2H, $CH_2$), 1.85 (br p, J=6.5 Hz, 2H, $CH_2$), 1.65-1.73 (m, 2H, $CH_2$); $^{13}$C NMR δ 158.8, 154.4, 148.8, 143.0, 129.8, 120.5, 114.7, 75.8, 56.8, 55.5, 50.9 (2), 40.9, 33.1, 32.3, 30.5 (2), 25.7 (2). Anal. calcd for $C_{19}H_{27}N_5O_2$: C, 63.8; H, 7.6; N, 19.6. Found: C, 63.6; H, 7.6; N, 19.4%.

Example 53

N-[3-(4-Methoxy-1-piperidinyl)propyl]-7,8-dihydro-6H-indeno[5,6-e][1,2,4]triazin-3-amine 1,4-Dioxide (59). $H_2O_2$ (70%, 0.92 mL, ca. 18.3 mmol) was added dropwise to a stirred solution of TFM (2.6 mL, 18.3 mmol) in DCM (20 mL) at 0° C. The solution was stirred at 0° C. for 5 min, warmed to 20° C. for 10 min, then cooled to 0° C. and added to a stirred solution of 1-oxide 58 (655 mg, 1.8 mmol) and TFA (0.71 mL, 9.2 mmol) in DCM (20 mL) at 0° C. The solution was stirred at 20° C. for 8 h, diluted with dilute aqueous $NH_3$ solution (10 mL) and extracted with DCM (4×50 mL). The combined organic fraction was dried and the solvent evaporated. The residue was purified by chromatography, eluting with a gradient (0-10%) of MeOH/DCM, to give (i) starting material 58 (360 mg, 55%) and (ii) 1,4-dioxide 59 (213 mg, 31%) as a red solid: mp (MeOH/EtOAc) 128-130° C.; $^1$H NMR δ 8.42 (br s, 1H, NH), 8.11 (s, 1H, H-9), 8.10 (s, 1H, H-5), 3.62-3.68 (m, 2H, $CH_2N$), 3.28-3.36 (m, 4H, $OCH_3$, CHO), 3.08 (dt, J=7.5, 1.1 Hz, 2H, H-6), 3.03 (dt, J=7.5, 1.1 Hz, 2H, H-8), 2.69-2.76 (m, 2H, $CH_2N$), 2.55 (br t, J=6.2 Hz, 2H, $CH_2N$), 2.26-2.34 (m, 2H, $CH_2N$), 2.17 (p, J=7.5 Hz, 2H, H-7), 1.94-2.03 (m, 2H, $CH_2$), 1.88 (p, J=6.2 Hz, 2H, $CH_2$), 1.72-1.81 (m, 2H, $CH_2$); $^{13}$C NMR δ 155.4, 149.5, 145.5, 138.1, 129.5, 115.7, 111.7, 75.8, 57.2, 55.4, 50.8 (2), 41.6, 33.3, 32.3, 30.3 (2), 25.5, 25.1. Anal. calcd for $C_{19}H_{27}N_5O_3 \cdot H_2O$: C, 58.3; H, 7.5; N, 17.9. Found: C, 58.4; H, 6.8; N, 17.6%.

Example 54

N-[3-(4-Morpholinyl)propyl]-7,8-dihydro-6H-indeno[5,6-e][1,2,4]triazin-3-amine 1-Oxide (60). 3-(1-Morpholinyl)propylamine (0.76 mL, 5.2 mmol) was added to a stirred solution of chloride 21 (382 mg, 1.7 mmol) in DME (50 mL) and the solution stirred at reflux temperature for 3 h. The solvent was evaporated and the residue was partitioned between DCM (100 mL) and dilute aqueous $NH_3$ solution (50 mL). The organic fraction was dried and the solvent evaporated. The residue was purified by chromatography, eluting with a gradient (0-10%) of MeOH/DCM, to give 1-oxide 60 (553 mg, 98%) as a yellow solid: mp (MeOH/EtOAc) 139-141° C.; $^1$H NMR δ 8.06 (s, 1H, H-9), 7.38 (s, 1H, H-5), 6.10 (br s, 1H, NH), 3.72-3.77 (m, 4H, 2×CH$_2$O), 3.55-3.60 (m, 2H, CH$_2$N), 2.95-3.02 (m, 4H, H-6, H-8), 2.45-2.52 (m, 6H, 3×CH$_2$N), 2.09-2.17 (m, 2H, CH$_2$), 1.79-1.86 (m, 2H, CH$_2$); $^{13}$C NMR δ 158.8, 154.5, 148.8, 143.2, 129.8, 120.5, 114.7, 67.0 (2), 57.3, 53.8 (2), 40.8, 33.1, 32.3, 25.7, 25.3. Anal. calcd for $C_{17}H_{23}N_5O_2$: C, 62.0; H, 7.0; N, 21.3. Found: C, 62.2; H, 6.9; N, 21.3%.

Example 55

N-[3-(4-Morpholinyl)propyl]-7,8-dihydro-6H-indeno[5,6-e][1,2,4]triazin-3-amine 1,4-Dioxide (61). $H_2O_2$ (70%, 0.60 mL, ca. 11.9 mmol) was added dropwise to a stirred solution of TFAA (1.7 mL, 11.9 mmol) in DCM (15 mL) at 0° C. The solution was stirred at 0° C. for 5 min, warmed to 20° C. for 10 min, then cooled to 0° C. and added to a stirred solution of 1-oxide 60 (412 mg, 1.2 mmol) and TFA (0.46 mL, 6.0 mmol) in DCM (20 mL) at 0° C. The solution was stirred at 20° C. for 4 h, diluted with dilute aqueous $NH_3$ solution (10 mL) and extracted with CHCl$_3$ (4×50 mL). The combined organic fraction was dried and the solvent evaporated. The residue was purified by chromatography, eluting with a gradient (0-10%) of MeOH/DCM, to give (i) starting material 60 (208 mg, 50%) and (ii) 1,4-dioxide 61 (122 mg, 30%) as a red solid: mp (MeOH) 158-160° C.; $^1$H NMR δ 8.37 (br s, 1H, NH), 8.11 (s, 1H, H-5), 8.09 (s, 1H, H-9), 3.80-3.84 (m, 4H, 2×CH$_2$O), 3.64-3.69 (m, 2H, CH$_2$N), 3.02-3.10 (m, 4H, H-6, H-8), 2.56 (dd, J=6.2, 6.1 Hz, 2H, CH$_2$N), 2.48-2.52 (m, 4H, 2×CH$_2$N), 2.15-2.22 (m, 2H, H-7), 1.85-1.91 (m, 2H, CH$_2$); $^{13}$C NMR δ 155.5, 149.5, 145.6, 138.0, 129.6, 115.8, 111.6, 66.9 (2), 57.7, 53.8 (2), 41.6, 33.3, 32.3, 25.5, 24.5. Anal. calcd for $C_{17}H_{23}N_5O_3 \cdot \frac{1}{4}CH_3OH$: C, 58.6; H, 6.9; N, 19.8. Found: C, 58.4; H, 6.7; N, 19.9%.

Example 56

N-[4-(4-Morpholinyl)butyl]-7,8-dihydro-6H-indeno[5,6-e][1,2,4]triazin-3-amine 1-Oxide (62). 4-(4-Morpholinyl)butylamine (306) (2.02 g, 12.8 mmol) was added to a stirred solution of chloride 21 (1.89 g, 8.5 mmol) and Et$_3$N (1.8 mL, 12.8 mmol) in DME (80 mL) and the solution stirred at reflux temperature for 16 h. The solvent was evaporated and the residue was partitioned between DCM (100 mL) and dilute aqueous $NH_3$ solution (50 mL). The organic fraction was dried and the solvent evaporated. The residue was purified by chromatography, eluting with a gradient (0-10%) of MeOH/DCM, to give 1-oxide 62 (2.57 g, 88%) as pale yellow solid: mp (MeOH/EtOAc) 151-152° C.; $^1$H NMR δ 8.07 (s, 1H, H-9), 7.38 (s, 1H, H-5), 5.78 (br s, 1H, NH), 3.78 (br t, J=4.6 Hz, 4H, 2×CH$_2$O), 3.50 (br dd, J=6.6, 5.9 Hz, 2H, CH$_2$N), 2.95-3.02 (m, 4H, H-6, H-8), 2.45 (br t, J=4.4 Hz, 4H, 2×CH$_2$N), 2.40 (t, J=7.0 Hz, 2H, CH$_2$N), 2.15 (p, J=7.5 Hz, 2H, H-7), 1.67-1.74 (m, 2H, CH$_2$), 1.58-1.64 (m, 2H, CH$_2$); $^{13}$C NMR δ 158.8, 154.5, 148.8, 143.2, 129.8, 120.5, 114.7, 66.9 (2), 58.5, 53.7 (2), 41.3, 33.1, 32.3, 27.4, 25.7, 24.0. Anal. Calcd for $C_{18}H_{25}N_5O_2$: C, 63.0; H, 7.3; N, 20.4. Found: C, 62.9; H, 7.2; N, 20.5%.

Example 57

N-[4-(4-Morpholinyl)butyl]-7,8-dihydro-6H-indeno[5,6-e][1,2,4]triazin-3-amine 1,4-Dioxide (63). $H_2O_2$ (70%, 3.6 mL, ca. 72 mmol) was added dropwise to a stirred solution of TFAA (10.2 mL, 72 mmol) in DCM (25 mL) at 0° C. The solution was stirred at 0° C. for 5 min, warmed to 20° C. for 10 min, then cooled to 0° C. and added to a stirred solution of 1-oxide 62 (2.48 g, 7.2 mmol) and TFA (2.8 mL, 36 mmol) in DCM (25 mL) at 0° C. The solution was stirred at 20° C. for 16 h, cooled to 0° C. and made basic with dilute aqueous $NH_3$ solution and stirred vigorously for 30 min. The mixture was extracted with CHCl$_3$ (4×50 mL), the combined organic fraction was dried and the solvent evaporated. The residue was purified by chromatography, eluting with a gradient (0-10%) of MeOH/DCM, to give (i) starting material 62 (981 mg, 40%) and (ii) 1,4-dioxide 63 (504 mg, 19%) as a red solid: mp (MeOH) 140-141° C.; $^1$H NMR δ 8.09 (s, 2H, H-5, H-9), 7.32 (br s, 1H, NH), 3.74 (br t, J=4.6 Hz, 4H, 2×CH$_2$O), 3.57-3.63 (m, 2H, CH$_2$N), 3.09 (br t, J=7.5 Hz, 2H, H-6), 3.05 (br t, J=7.5 Hz, 2H, H-8), 2.50-2.55 (m, 4H, 2×CH$_2$N), 2.47 (br t, J=7.1 Hz, 2H, CH$_2$N), 2.20 (p, J=7.5 Hz, 2H, H-7), 1.71-1.79 (m, 2H, CH$_2$), 1.61-1.69 (m, 2H, CH$_2$); $^{13}$C NMR δ 155.9, 149.5, 145.8, 137.9, 129.8, 115.7, 111.6, 66.6 (2), 58.1, 53.5 (2), 41.2, 33.4, 32.4, 27.1, 25.5, 23.4; HRMS (FAB$^+$) calcd for $C_{18}H_{26}N_5O_3$ (MH$^+$) m/z 360.2036, found 360.2039.

Example 58

7,8-Dihydro-6H-indeno[5,6-e][1,2,4]triazine 1-Oxide (64). tert-Butyl nitrite (90%, 2 mL, 14.8 mmol) was added to a stirred solution of amine 19 (1.0 g, 4.95 mmol) in DMF (50 mL) at 60° C. and the solution stirred at 60° C. for 2 h. The solution was cooled to 20° C. and the solvent evaporated. The residue was partitioned between EtOAc (150 mL) and water (150 mL), the organic fraction was washed with water (2×50 mL), washed with brine (50 mL) and dried and the solvent evaporated. The residue was purified by chromatography, eluting with 10% EtOAc/DCM, to give 1-oxide 64 (401 mg, 43%) as a white solid: mp (EtOAc/pet. ether) 130-131° C.; $^1$H NMR δ 8.91 (s, 1H, H-3), 8.28 (s, 1H, H-9), 7.82 (s, 1H, H-5), 3.11-3.19 (m, 4H, H-6, H-8), 2.24 (p, J=7.5 Hz, 2H, H-7); $^{13}$C NMR δ 154.9, 153.0, 150.0, 147.3, 134.6, 123.2, 114.4, 33.2, 32.9, 25.7. Anal. calcd for $C_{10}H_9N_3O$: C, 64.2; H, 4.9; N, 22.5. Found: C, 64.1; H, 4.9; N, 22.5%.

Example 59

7,8-Dihydro-6H-indeno[5,6-e][1,2,4]triazine 1,4-Dioxide (65). $H_2O_2$ (70%, 1.1 mL, ca. 21 mmol) was added dropwise to a stirred solution of TFAA (3.0 mL, 21 mmol) in DCM (20 mL) at 0° C. The solution was stirred at 0° C. for 5 min, warmed to 20° C. for 10 min, then cooled to 0° C. and added to a solution of 1-oxide 64 (0.40 g, 2.1 mmol) in DCM (20 mL) at 0° C. and the solution was stirred at 20° C. for 4 h. Dilute aqueous $NH_3$ solution (10 mL) was added and the mixture stirred vigorously for 30 min and then extracted with DCM (4×50 mL). The combined organic fraction was dried and the solvent evaporated. The residue was purified by chromatography, eluting with a gradient (10-30%) of EtOAc/DCM, to give (i) starting material 64 (68 mg, 17%) and (ii) 1,4-dioxide 65 (213 mg, 49%) as a tan solid: mp (EtOAc/pet.

ether) 179-181° C.; $^1$H NMR δ 8.81 (s, 1H, H-3), 8.31 (s, 1H, H-9), 8.28 (s, 1H, H-5), 3.13-3.22 (m, 4H, H-6, H-8), 2.26 (p, J=7.5 Hz, 2H, H-7); $^{13}$C NMR δ 155.2, 152.0, 141.0, 139.1, 134.5, 116.1, 114.1, 33.4, 33.0, 25.5. Anal. calcd for $C_{10}H_9N_3O_2$: C, 59.1; H, 4.5; N, 20.7. Found: C, 58.9; H, 4.6; N, 20.5%.

Example 60

3-Iodo-7,8-dihydro-6H-indeno[5,6-e][1,2,4]triazine 1-Oxide (66). tert-BuNO$_2$ (9.1 mL, 68.8 mmol) was added to a stirred solution of 1-oxide 19 (4.49 g, 22.2 mmol), diiodomethane (17.9 mL, 222 mmol), and CuI (4.44 g, 23.3 mmol) in THF (200 mL) and the mixture was stirred at reflux temperature for 2.5 h. The mixture was cooled to 20° C., the solvent was evaporated and the residue purified by chromatography, eluting with a gradient (0-50% EtOAc/pet. ether), to give (i) iodide 66 (4.04 g, 58%) as pale yellow needles: mp (EtOAc/pet. ether) 189-190° C.; $^1$H NMR δ 8.18 (s, 1H, H-9), 7.72 (s, 1H, H-5), 3.07-3.15 (m, 4H, H-6, H-8), 2.23 (m, 2H, H-7); $^{13}$C NMR δ 155.9, 150.2, 147.5, 133.4, 122.3, 121.7, 114.4, 33.3, 33.0, 25.6. Anal. calcd for $C_{10}H_{81}N_3O$: C, 38.4; H, 2.6; N, 13.4. Found: C, 38.6; H, 2.6; N, 13.4%; and (ii) 1-oxide 64 (0.38 g, 9%) as a white solid: mp 130-131° C., spectroscopically identical to the sample prepared above.

Example 61

Ethyl-7,8-dihydro-6H-indeno[5,6-e][1,2,4]triazine 1-Oxide (67). A solution of EtMgBr in Et$_2$O (3 M, 15 mL, 45 mmol) was added to a stirred solution of ZnCl$_2$-Et$_2$O (45% in DCM, 15 mL, 42 mmol) in THF (100 mL) at 0° C. under N$_2$ and the solution stirred at 0° C. for 10 min. Pd(PPh$_3$)$_4$ (578 mg, 0.5 mmol) and iodide 66 (3.15 g, 10.1 mmol) were added and the mixture stirred at 0° C. for 1 h. The mixture was poured into ice/water (200 mL) and extracted with EtOAc (3×100 mL). The combined organic fraction was dried and the solvent evaporated. The residue was purified by chromatography, eluting with 30% EtOAc, to give 1-oxide 67 (1.20 g, 56%) as a pale yellow solid: mp (MeOH) 80-81° C.; $^1$H NMR δ 8.26 (s, 1H, H-9), 7.26 (s, 1H, H-5), 3.11 (q, J=7.2 Hz, 4H, H-6, H-8), 3.02 (q, J=7.6 Hz, 2H, CH$_2$), 2.21 (p, J=7.2 Hz, 2H, H-7), 1.43 (t, J=7.6 Hz, 3H, CH$_3$); $^{13}$C NMR δ 167.0, 154.6, 148.7, 147.6, 132.3, 122.7, 114.3, 33.2, 32.8, 30.6, 25.8, 12.4. Anal. calcd for $C_{12}H_{13}N_3O.¼CH_3OH$: C, 65.9; H, 6.3; N, 18.8. Found: C, 66.0; H, 6.1; N, 18.5%.

Example 62

Alternative Preparation of Ethyl-7,8-dihydro-6H-indeno [5,6-e][1,2,4]triazine 1-Oxide (67). Pd(dppf)Cl$_2$ (130 mg, 0.08 mmol) was added under N$_2$ to a N$_2$-purged solution of chloride 21 (350 mg, 1.6 mmol) and SnEt$_4$ (455 mg, 1.9 mmol) in DME (20 mL) and the mixture was stirred at 85° C. for 16 h. The mixture was cooled, the solvent evaporated and the residue purified by chromatography, eluting with 20% EtOAc/pet. ether, to give (i) starting material 21 (148 mg, 42%) and (ii) 1-oxide 67 (84 mg, 25%) as a yellow solid: mp 79-81° C., spectroscopically identical to the sample prepared above.

Example 63

3-Ethyl-7,8-dihydro-6H-indeno[5,6-e][1,2,4]triazine 1,4-Dioxide (68). H$_2$O$_2$ (70%, 0.15 mL, ca. 2.9 mmol) was added dropwise to a stirred solution of TFAA (0.40 mL, 2.9 mmol) in DCM (5 mL) at 0° C. The solution was stirred at 20° C. for 10 min, then cooled to 0° C., and added to a solution of 1-oxide 67 (60 mg, 0.29 mmol) and TFA (0.05 mL, 0.63 mmol) in CHCl$_3$ (5 mL) at 0° C. Another aliquot of H$_2$O$_2$ (0.15 mL) was added after 24 h, and the solution stirred at 20° C. for another 24 h. The solution was made basic with dilute aqueous NH$_3$ solution and extracted with CHCl$_3$ (3×10 mL). The combined organic fraction was dried and the solvent evaporated. The residue was purified by chromatography, eluting with 5% EtOAc/DCM, to give (i) starting material 67 (18 mg, 30%) and (ii) 1,4-dioxide 68 (32 mg, 48%) as a yellow solid: mp 140-142° C.; $^1$H NMR δ 8.32 (s, 1H, H-9), 8.27 (s, 1H, H-5), 3.13-3.23 (m, 6H, H-6, H-8, CH$_2$), 2.26 (q, J=7.5 Hz, 2H, H-7), 1.43 (t, J=7.5 Hz, 3H, CH$_3$); $^{13}$C NMR δ 155.7, 155.1, 150.6, 139.1, 133.8, 115.9, 113.9, 33.4, 32.8, 25.6, 23.9, 9.31. Anal. calcd for $C_{12}H_{13}N_3O_2.½CH_3OH$: C, 60.7; H, 6.1; N, 17.0. Found: C, 60.3; H, 5.7; N, 16.8%.

Example 64

3-Allyl-7,8-dihydro-6H-indeno[5,6-e][1,2,4]triazine 1-Oxide (69). Pd(PPh$_3$)$_4$ (0.89 g, 0.77 mmol) was added to a stirred, degassed solution of iodide 66 (4.80 g, 15.3 mmol) and allyltributyltin (5.2 mL, 16.9 mmol) in DME (100 mL), and the mixture stirred at reflux temperature for 8 h. The solvent was evaporated and the residue purified by chromatography, eluting with 10% EtOAc/pet. ether, to give 1-oxide 69 (2.96 g, 85%) as white solid: mp (EtOAc/pet. ether) 60-61° C.; $^1$H NMR δ 8.26 (s, 1H, H-9), 7.77 (s, 1H, H-5), 6.12-6.23 (m, 1H, H-2'), 5.29 (dd, J=17.1, 1.5 Hz, 1H, H-3'), 5.22 (dd, J=10.1, 1.3 Hz, 1H, H-3'), 3.77 (br d, J=6.9 Hz, 2H, H-1'), 3.08-3.14 (m, 4H, H-6, H-8), 2.21 (p, J=7.5 Hz, 2H, H-7); $^{13}$C NMR δ 164.1, 154.8, 149.0, 147.5, 133.0, 132.3, 122.7, 118.2, 114.3, 41.6, 33.2, 32.8, 25.7. Anal. calcd for $C_{13}H_{13}N_3O$: C, 68.7; H, 5.8; N, 18.5. Found: C, 68.7; H, 5.9; N, 18.7%.

Example 65

3-(1-Oxido-7,8-dihydro-6H-indeno[5,6-e][1,2,4]triazin-3-yl)-1-propanol (70). A solution of 9-BBN in THF (31.1 mL, 15.6 mmol) was added dropwise to a stirred solution of alkene (2.95 g, 13.0 mmol) in THF (150 mL) and the solution stirred at 20° C. for 3 h. A solution of NaOH (3M, 6.5 mL, 19.5 mmol) was added carefully, followed by the dropwise addition of 35% aqueous H$_2$O$_2$ (5.8 mL, 58.4 mmol) and the mixture stirred at 20° C. for 1 h. The mixture was diluted with brine (100 mL), extracted with EtOAc (3×100 mL), the combined organic fraction dried and the solvent evaporated. The residue was purified by chromatography, eluting with a gradient (20-30%) of EtOAc/pet. ether, to give alcohol 70 (1.77 g, 55%) as a white solid: mp (EtOAc/pet. ether) 131-133° C.; $^1$H NMR δ 8.24 (s, 1H, H-9), 7.74 (s, 1H, H-5), 3.78 (br dt, J=5.8, 5.5 Hz, 2H, CH$_2$O), 3.08-3.14 (m, 4H, H-6, H-8, CH$_2$), 2.36 (br t, J=5.5 Hz, 1H, OH), 2.21 (p, J=7.4 Hz, 2H, H-7), 2.12-2.17 (m, 2H, CH$_2$); $^{13}$C NMR δ 165.7, 154.9, 149.0, 147.2, 132.3, 122.5, 114.3, 62.1, 34.0, 33.2, 32.8, 30.5, 25.7. Anal. calcd for $C_{13}H_{15}N_3O_2$: C, 63.7; H, 6.2; N, 17.1. Found: C, 63.7; H, 6.2; N, 17.3%.

Example 66

3-(1-Oxido-7,8-dihydro-6H-indeno[5,6-e][1,2,4]triazin-3-yl)-1-propanol (70). Pd(OAc)$_2$ (18 mg, 0.08 mmol) was added to a degassed solution of iodide 66 (250 mg, 0.80 mmol), allyl alcohol (0.27 mL, 3.40 mmol), tetrabutylammonium chloride (182 mg, 0.80 mmol) and NaHCO$_3$ (147 mg, 1.76 mmol) in acetonitrile (12.5 mL) and the solution irradiated in a Milestone MicroSYNTH reactor for 15 min at 150° C. (max. 400 watt). After cooling, the mixture was quenched with saturated aqueous NH$_4$Cl solution (10 ml) and filtered. The filtrate was extracted with EtOAc (3×20 ml), dried and the solvent evaporated. The crude residue was dissolved in MeOH (20 mL), cooled to −40° C. and NaBH$_4$ (2×40 mg, 2.12 mmol) in MeOH (20 mL) added to it. The solution was stirred at −40° C. for 1, then HOAc (0.1 mL) added, warmed to 20° C. and the solvent evaporated. The residue was purified by chromatography, eluting with a gradient (80-100%) EtOAc/pet. ether, to give alcohol 70 (89 mg, 45%) as an off-white solid; spectroscopically identical to the sample prepared above.

Example 67

3-(1,4-Dioxido-7,8-dihydro-6H-indeno[5,6-e][1,2,4]triazin-3-yl)-1-propanol (71). H$_2$O$_2$ (70%, 1.6 mL, ca. 33 mmol) was added dropwise to a stirred solution of TFAA (4.6 mL, 33 mmol) in DCM (30 mL) at 0° C. The solution was stirred at 0° C. for 5 min, warmed to 20° C. for 10 min, then cooled to 0° C. The solution was added to a solution of 1-oxide 70 (0.86 g, 3.3 mmol) in DCM (50 mL) at 0° C. and the solution was stirred at 20° C. for 16 h. Dilute aqueous NH$_3$ solution (30 mL) was added and the mixture stirred vigorously for 30 min and then extracted with DCM (4×50 mL). The combined organic fraction was dried and the solvent evaporated. The residue was purified by chromatography, eluting with a gradient (0-5%) of MeOH/DCM, to give (i) starting material 70 (283 mg, 33%) and (ii) 1,4-dioxide 71 (347 mg, 40%) as a yellow solid: mp (MeOH/EtOAc) 153-155° C.; $^1$H NMR δ 8.33 (s, 1H, H-9), 8.26 (s, 1H, H-5), 3.68 (br dt, J=6.1, 5.7 Hz, 2H, CH$_2$O), 3.33 (t, J=6.9 Hz, 2H, CH$_2$), 3.13-3.20 (m, 4H, H-6, H-8), 3.09 (br t, J=6.1 Hz, 1H, OH), 2.26 (p, J=7.5 Hz, 2H, H-7), 2.10-2.18 (m, 2H, CH$_2$); $^{13}$C NMR δ 155.5, 155.0, 150.9, 138.8, 134.0, 115.8, 114.1, 61.2, 33.4, 32.9, 29.6, 26.8, 25.6. Anal. calcd for C$_{13}$H$_{15}$N$_3$O$_3$: C, 59.8; H, 5.8; N, 16.1. Found: C, 60.0; H, 5.7; N, 16.1%.

Example 68

3-(3-(Di-tert-butoxyphosphoryloxy)propyl)-7,8-dihydro-6H-indeno[5,6-e][1,2,4]triazine 1-Oxide (72). Tetrazole (428 mg, 6.1 mmol) was added to a stirred solution of alcohol 70 (500 mg, 2.0 mmol) and di-tert-butyldiethylphoshoramidite (0.77 mL, 2.5 mmol) in dry THF (30 mL) and the solution stirred at 20° C. under N$_2$ for 22 h. The solution was cooled to 40° C. (MeCN/dry ice) and a dried solution of MCPBA (985 mg, 2.9 mmol) in DCM (10 mL) was added, and the solution stirred at −40° C. for 15 min. A solution of NaHSO$_3$ (10%, 2 mL) was added and the mixture partitioned between water and DCM. The organic fraction was washed with dilute aqueous NH$_3$ solution (3×20 mL), dried and the solvent evaporated. The residue was purified by chromatography, eluting with a gradient (0-4%) of MeOH/DCM, to give crude phosphate ester 72 (764 mg, 86%) as a thick pale-brown oil: $^1$H NMR δ 8.25 (s, 1H, H-9), 7.74 (s, 1H, H-5), 4.08-4.13 (m, 2H, CH$_2$O), 3.09-3.14 (m, 6H, H-6, H-8, CH$_2$), 2.18-2.31 (m, 4H, H-7, CH$_2$), 1.48 [s, 18H, 2×OC(CH$_3$)$_3$]; HRMS (FAB$^+$) calcd for C$_{21}$H$_{33}$N$_3$O$_5$P (MH$^+$) m/z 438.2158, found 438.2154.

Example 69

3-(3-(Di-tert-butoxyphosphoryloxy)propyl)-7,8-dihydro-6H-indeno[5,6-e][1,2,4]triazine 1,4-Dioxide (73). A dried solution of MCPBA (2.29 g, 6.63 mmol) in DCM (25 mL) was added to a mixture of 1-oxide 72 (ca. 70%, 580 mg, 0.928 mmol) and NaHCO$_3$ (557 mg, 6.63 mmol) in DCM (30 mL) and the solution stirred at 20° C. for 16 h. The solution was diluted with DCM (100 mL) and washed with diluted with dilute aqueous NH$_3$ solution (3×60 mL) and extracted with DCM (3×20 mL). The combined organic fraction was dried and the solvent evaporated. The residue was purified by chromatography, eluting with 10% MeOH/EtOAc. to give (i) starting material 72 (224 mg, 55%) and (ii) 1,4-dioxide 73 (103 mg, 25%) as a yellow solid: mp 129-131° C.; $^1$H NMR δ 8.31 (s, 1H, H-9), 8.26 (s, 1H, H-5), 4.09-4.16 (m, 2H, CH$_2$O), 3.27-3.31 (m, 2H, CH$_2$), 3.09-3.19 (m, 4H, H-6, H-8), 2.20-2.30 (m, 4H, H-7, CH$_2$), 1.48 [s, 18H, 2×OC(CH$_3$)$_3$]; $^{13}$C NMR δ 155.1, 154.0, 150.7, 139.1, 133.9, 115.9, 113.9, 82.2 (d, J=8.0 Hz, 2), 65.8 (d, J=6.0 Hz), 33.4, 32.9, 29.9 (d, J=5.0 Hz, 6), 27.0, 25.6, 25.6. HRMS (FAB$^+$) calcd for C$_{21}$H$_{33}$N$_3$O$_6$P (MH$^+$) m/z 454.2107, found 454.2101.

Example 70

3-(1,4-Dioxido-7,8-dihydro-4H-indeno[5,6-e][1,2,4]triazin-3-yl)propyl Dihydrogen Phosphate (74). TFA (0.16 mL) was added to a stirred solution of phosphate diester 73 (92 mg, 0.20 mmol) in DCM (15 mL) and the solution stirred at 20° C. for 4 h. The solvent was evaporated, the residue dissolved in CHCl$_3$ and filtered. The filtrate was concentrated and freeze dried to give phosphate 74 as a hygroscopic brown gum (77 mg, 100%); $^1$H NMR δ 8.24 (br s, 1H, H-9), 8.17 (br s, 1H, H-5), 4.13 (br m, 2H, CH$_2$O), 3.36 (br s, 2H, 2×OH), 3.12-3.21 (m, 6H, H-6, H-8, CH$_2$), 2.08-2.27 (m, 4H, H-7, CH$_2$); HRMS (FAB$^+$) calcd for C$_{13}$H$_{17}$N$_3$O$_6$P (MH$^+$) m/z 342.0855, found 342.0854.

Example 71

3-[3-(4-Morpholinyl)propyl]-7,8-dihydro-6H-indeno[5,6-e][1,2,4]triazine 1-Oxide (76). Iodide 66 (3.98 g, 12.7 mmol) was added to a degassed solution of allyl alcohol (1.95 g, 33 mmol), Pd(OAc)$_2$ (120 mg, 0.53 mmol), tetrabutylammonium bromide (3.4 g, 11 mmol) and NaHCO$_3$ (2.3 g, 27 mmol) in DMF (70 mL) and the solution was stirred at 50° C. for 24 h. The mixture was quenched with saturated aqueous NH$_4$Cl solution (100 ml) and filtered. The filtrate was extracted with EtOAc (5×200 mL), dried and the solvent evaporated. The residue was purified by chromatography, eluting with 50% EtOAc/pet. ether, to give a dark oil (2.7 g, 87%) that was used without further purification. Purification of a small sample by chromatography, eluting with a gradient (20-50%) EtOAc/pet. ether, gave 3-(1-oxido-7,8-dihydro-6H-indeno[5,6-e][1,2,4]triazin-3-yl)propanal (75) as an orange solid: mp (EtOAc/pet. ether) 72-74° C.; $^1$H NMR δ 9.93 (t, J=0.9 Hz, 1H, CHO), 8.25 (s, 1H, H-9), 7.73 (s, 1H, H-5), 3.35 (t, J=7.0 Hz, 2H, CH$_2$), 3.07-3.14 (m, 6H, H-6, H-8, CH$_2$), 2.21 (p, J=7.5 Hz, 2H, H-7); $^{13}$C NMR δ 200.4, 163.9, 154.8, 149.1, 147.2, 132.3, 122.7, 114.2, 40.5, 33.1, 32.8, 29.4, 25.7; MS (Cl, CH$_3$OH) m/z 244 (MH$^+$, 100%); HRMS (Cl, CH$_3$OH) calcd for C$_{13}$H$_{14}$N$_3$O$_2$ (MH$^+$) m/z 244.1086, found 244.1088. Anal. calcd for C$_{13}$H$_{13}$N$_3$O$_2$: C, 64.2; H, 5.4; N, 17.3. Found: C, 63.9; H, 5.5; N, 17.0%. Morpholine (3.9 mL, 44 mmol) was added to a solution of aldehyde (2.7 g, 11.1 mmol) in EtOH (100 mL) at 0° C. and the solution stirred for 20 min. NaCHBH$_3$ (2.1 g, 33 mmol) was added and the mixture stirred at 0° C. for 30 min, then HOAc (0.5 mL) was added and the mixture stirred at 20° C. for 16 h. The solvent was evaporated and the residue partitioned between DCM and water, the organic phase was dried and the solvent evaporated. The residue purified by chromatography, eluting with 10% MeOH/EtOAc, to give 1-oxide 76 (1.8 g, 52%) as a pale yellow oil: $^1$H NMR δ 8.25 (s, 1H, H-9), 7.73 (s, 1H, H-5), 3.58 (br t, J=4.6 Hz, 4H, 2×CH$_2$O), 3.09-3.15 (m, 4H, H-6, H-8), 3.04 (br t, J=7.4 Hz, 2H, CH$_2$), 2.48 (br dd, J=7.3, 7.0 Hz, 2H, CH$_2$N), 2.43 (br t, J=4.6 Hz, 4H, 2×CH$_2$N), 2.22 (p, J=7.4 Hz, 2H, H-7), 2.06-2.14 (m, 2H, CH$_2$). Formation of the hydrochloride salt gave a tan solid: mp (MeOH/EtOAc) 193-195° C.; $^1$H NMR [(CD$_3$)$_2$SO] δ 11.16 (br s, 1H, NH$^+$Cr$^-$), 8.19 (s, 1H, H-9), 7.83 (s, 1H, H-5), 3.75-3.90 (m, 4H, 2×CH$_2$O), 3.25-3.35 (m, 4H, 2×CH$_2$N), 3.05-3.15 (m, 6H, H-6, H-8, CH$_2$N), 3.00 (t, J=7.4 Hz, 2H, CH$_2$), 2.19-2.28 (m, 2H, CH$_2$), 2.12 (p, J=7.5 Hz, 2H, H-7); $^{13}$C NMR [(CD$_3$)$_2$SO] δ 163.8, 154.7, 148.9, 146.6, 131.8, 122.3, 113.6, 63.2 (2), 55.1, 51.0 (2), 33.2, 32.5, 32.2, 25.3, 21.0. Anal. calcd for C$_{17}$H$_{23}$ClN$_4$O$_2$·½H$_2$O: C, 56.7; H, 6.7; N, 15.6. Found: C, 56.6; H, 6.7; N, 15.4%.

Example 72

3-[3-(4-Morpholinyl)propyl]-7,8-dihydro-6H-indeno[5,6-e][1,2,4]triazine 1,4-Dioxide (77). H$_2$O$_2$ (70%, 2.8 mL, ca. 56 mmol) was added dropwise to a stirred solution of TFM (7.9 mL, 56 mmol) in DCM (20 mL) at 0° C. The solution was stirred at 0° C. for 5 min, warmed to 20° C. for 10 min, then cooled to 0° C. The solution was added to a solution of 1-oxide 76 (1.76 g, 5.6 mmol) and TFA (2.2 mL, 28 mmol) in DCM (40 mL) at 0° C. and the solution was stirred at 20° C. for 6 h. Dilute aqueous NH$_3$ solution (40 mL) was added and the mixture stirred vigorously for 30 min and then extracted with DCM (4×50 mL). The combined organic fraction was dried and the solvent evaporated. The residue was purified by chromatography, eluting with a gradient (0-10%) of MeOH/DCM, to give (i) starting material 76 (173 mg, 10%); and (ii) 1,4-dioxide 77 (868 mg, 47%) as a yellow solid: mp (MeOH/DCM) 109-110° C.; $^1$H NMR δ 8.30 (s, 1H, H-9), 8.27 (s, 1H, H-5), 3.44 (br t, J=4.4 Hz, 4H, 2×CH$_2$O), 3.24 (br t, J=7.3 Hz, 2H, CH$_2$), 3.13-3.19 (m, 4H, H-6, H-8), 2.50 (t, J=6.5 Hz, 2H, CH$_2$N), 2.38 (br t, J=4.3 Hz, 4H, 2×CH$_2$N), 2.27 (p, J=7.5 Hz, 2H, H-7), 2.06-2.12 (m, 2H, CH$_2$); $^{13}$C NMR δ 155.2, 155.1, 150.5, 139.0, 133.7, 115.8, 113.8, 67.0 (2), 58.0, 53.5 (2), 33.3, 32.8, 28.5, 25.5, 21.8. Anal. calcd for C$_{17}$H$_{22}$N$_4$O$_3$: C, 61.8; H, 6.7; N, 17.0. Found: C, 62.0; H, 6.8; N, 17.2%.

Example 73

N,N-Dimethyl-3-(1-oxido-7,8-dihydro-6H-indeno[5,6-e][1,2,4]triazin-3-yl)-1-propanamine (78). A solution of anhydrous Me$_2$NH (2.4 g, 52 mmol) in MeOH (50 mL) was added to a solution of propanal 75 (1.5 g, 6.2 mmol) in MeOH (50 ml) at 0° C. and the solution stirred for 20 min. NaCNBH$_3$ (1.5 g, 24 mmol) was added and the solution stirred for 30 min, then HOAc (2 ml) was added and the mixture was stirred at 20° C. for 16 h. The solvent was evaporated and the residue was partitioned between DCM (200 mL) and water (200 mL). The aqueous phase was extracted with DCM (2×200 ml), the combined organic phase was dried and the solvent evaporated. The residue was purified by chromatography, eluting with 10% MeOH/EtOAc, to give 1-oxide 78 (930 mg, 55%) as a yellow oil: $^1$H NMR [(CD$_3$)$_2$SO] δ 8.17 (s, 1H, H-9), 7.81 (s, 1H, H-5), 3.06-3.12 (m, 4H, H-6, H-8), 2.94-3.03 (m, 4H, 2×CH$_2$), 2.66 [s, 6H, N(CH$_3$)$_2$], 2.07-2.18 (m, 4H, H-7, CH$_2$); $^{13}$C NMR δ 164.1, 155.0, 149.2, 146.8, 131.9, 122.4, 113.7, 56.6, 43.0 (2), 33.3, 32.7, 32.4, 25.4, 22.7; HRMS (FAB$^+$) calcd for C$_{15}$H$_{21}$N$_4$O (MH$^+$) m/z 273.1715, found 273.1714.

Example 74

N-[3-(1,4-Dioxido-7,8-dihydro-6H-indeno[5,6-e][1,2,4]triazin-3-yl)propyl]-N,N-dimethylamine (79). H$_2$O$_2$ (70%, 0.65 mL, 13 mmol) was added dropwise to a stirred solution of TFAA (1.8 mL, 13 mmol) in DCM (20 mL) at 0° C. The solution was stirred at 0° C. for 5 min, warmed to 20° C. for 10 min, then cooled to 0° C. and added to a stirred solution of 1-oxide 78 (353 mg, 1.3 mmol) and TFA (0.7 mL, 9.1 mmol) in DCM (20 mL) at 0° C. The solution was stirred at 20° C. for 8 h, diluted with dilute aqueous NH$_3$ solution (12 mL) and extracted with DCM (4×50 mL). The combined organic fraction was dried and the solvent evaporated. The residue was purified by chromatography, eluting with a gradient (0-10%) of MeOH/DCM, to give 1,4-dioxide 79 (154 mg, 41%) as a red solid: $^1$H NMR δ 8.30 (s, 1H, H-9), 8.26 (s, 1H, H-5), 3.25-3.09 (m, 6H, H-6, H-8, CH$_2$), 2.75 (t, J=7.3 Hz, 2H, CH$_2$), 2.70 [s, 6H, N(CH$_3$)$_2$], 2.29-2.14 (m, 4H, H-7, CH$_2$); $^{13}$C NMR δ 155.2, 153.9, 150.8, 139.1, 133.9, 115.9, 113.9, 58.0, 44.3 (2), 33.4, 32.9, 27.9, 25.6, 21.7; HRMS (FAB$^+$) calcd for C$_{15}$H$_{21}$N$_4$O$_2$ (MH$^+$) m/z 289.1665, found 289.1669.

Example 75

N,N-Bis(2-methoxyethyl)-3-(1-oxido-7,8-dihydro-6H-indeno[5,6-e][1,2,4]triazin-3-yl)-1-propanamine (80). Bis-(2-methoxyethyl)amine (3.0 g, 22.5 mmol) was added to a stirred solution of propanal 75 (1.2 g, 4.9 mmol) in MeOH (100 ml) at 0° C. and the solution stirred for 30 min. NaCNBH$_3$ (1.5 g, 24 mmol) was added and the solution stirred at 0° C. for 30 min and then HOAc (2 mL) was added and the mixture was stirred at 20° C. for 16 h. The solvent was evaporated and the residue was partitioned between DCM (200 mL) and water (200 mL). The aqueous phase was extracted with DCM (2×200 ml), the combined organic phase was dried and the solvent evaporated. The residue was purified by chromatography, eluting with 10% MeOH/EtOAc, to give 1-oxide 80 (1.1 g, 50%) as a yellow oil: $^1$H NMR [(CD$_3$)$_2$SO] δ 8.19 (s, 1H, H-9), 7.83 (s, 1H, H-5), 3.61-3.68 (m, 4H, 2×CH$_2$O), 3.31-3.38 (m, 4H, 2×CH$_2$N), 3.26 (s, 6H, 2×OCH$_3$), 3.20-3.14 (m, 4H, 2×CH$_2$), 3.07-3.12 (m, 4H, H-6, H-8), 2.15-2.10 (m, 4H, H-7, CH$_2$); $^{13}$C NMR δ 163.9, 154.7, 149.0, 146.7, 131.8, 122.2, 113.6, 58.0 (2), 57.4 (2), 52.4, 52.3, 32.5, 32.2, 25.3, 23.0 (2), 19.1; HRMS (FAB$^+$) calcd for C$_{19}$H$_{29}$N$_4$O$_3$ (MH$^+$) m/z 361.2240, found 361.2243.

Example 76

N-[3-(1,4-Dioxido-7,8-dihydro-6H-indeno[5,6-e][1,2,4]triazin-3-yl)propyl]-N,N-bis(2-methoxyethyl)amine (81). H$_2$O$_2$ (70%, 2.0 mL, 39 mmol) was added dropwise to a stirred solution of TFM (5.4 mL, 39 mmol) in DCM (50 mL) at 0° C. The solution was stirred at 0° C. for 5 min, warmed to 20° C. for 10 min, then cooled to 0° C. and added to a stirred solution of 1-oxide 80 (1.50 g, 4.2 mmol) and TFA (1.5 mL, 1.95 mmol) in DCM (50 mL) at 0° C. The solution was stirred at 20° C. for 6 h, diluted with dilute aqueous NH$_3$ solution (36 mL) and extracted with DCM (3×150 mL). The combined organic fraction was dried and the solvent evaporated. The residue was purified by chromatography, eluting with a gradient (0-10%) of MeOH/DCM, to give 1,4-dioxide 81 (533 mg, 35%) as a red gum: $^1$H NMR δ 8.28 (s, 1H, H-9), 8.24 (s, 1H, H-5), 3.78 (br t, J=4.7 Hz, 4H, 2×CH$_2$O), 3.40-3.45 (m, 6H, 3×CH$_2$), 3.33 [s, 6H, 2×OCH$_3$), 3.19-3.23 (m, 2H, CH$_2$), 3.12-3.17 (m, 4H, H-6, H-8), 2.34-2.38 (m, 2H, CH$_2$), 2.22-2.28 (m, 2H, H-7); $^{13}$C NMR δ 155.5, 152.5, 151.1, 139.0, 134.0, 115.8, 113.8, 67.2 (2), 58.9 (2), 52.9 (3), 33.4, 32.9, 27.2, 25.5, 18.8; HRMS (FAB$^+$) calcd for $C_{19}H_{29}N_4O_4$ (MH$^+$) m/z 377.2189, found 377.2185.

Example 77

3-[3-(3-Methoxy-1-azetidinyl)propyl]-7,8-dihydro-6H-indeno[5,6-e][1,2,4]triazine 1-Oxide (82). 3-Azetidinyl methyl ether hydrochloride (275) (MacKenzie et al., PCT Int Appl. WO 9605193, 1996) (0.60 g, 4.9 mmol) was added to a stirred solution of propanal 75 (1.2 g, 4.9 mmol) in MeOH (100 mL) at 0° C. and the solution stirred for 30 min. NaCNBH$_3$ (1.5 g, 24 mmol) was added and the solution stirred at 0° C. for 30 min and then HOAc (2 mL) was added and the mixture was stirred at 20° C. for 16 h. The solvent was evaporated and the residue was partitioned between DCM (200 mL) and water (200 mL). The aqueous phase was extracted with DCM (2×200 mL), the combined organic phase was dried and the solvent evaporated. The residue was purified by chromatography, eluting with 10% MeOH/EtOAc, to give 1-oxide 82 (930 mg, 60%) as a yellow oil: $^1$H NMR δ 8.24 (s, 1H, H-9), 7.74 (s, 1H, H-5), 4.27-4.39 (m, 3H, CH$_2$N, CHO), 3.49-3.53 (m, 2H, CH$_2$N), 3.30 (s, 3H, OCH$_3$), 3.21-3.27 (m, 2H, CH$_2$N), 3.09-3.16 (m, 4H, H-6, H-8), 3.05 (t, J=7.2 Hz, 2H, CH$_2$), 2.14-2.26 (m, 4H, H-7, CH$_2$); $^{13}$C NMR δ 163.9, 155.1, 149.3, 147.3, 132.3, 122.7, 144.2, 68.3, 60.9, 58.7, 56.6, 56.5, 33.5, 33.1, 32.8, 25.7, 23.8; HRMS calcd for $C_{17}H_{22}N_4O_2$ (M$^+$) m/z 314.1743, found 314.1742.

Example 78

3-[3-(3-Methoxy-1-azetidinyl)propyl]-7,8-dihydro-6H-indeno[5,6-e][1,2,4]triazine 1,4-Dioxide (83). H$_2$O$_2$ (70%, 2.0 mL, 39 mmol) was added dropwise to a stirred solution of TFAA (5.4 mL, 39 mmol) in DCM (50 mL) at 0° C. The solution was stirred at 0° C. for 5 min, warmed to 20° C. for 10 min, then cooled to 0° C. and added to a stirred solution of 1-oxide 82 (0.93 g, 3.0 mmol) and TFA (1.5 mL, 19.5 mmol) in DCM (50 mL) at 0° C. The solution was stirred at 20° C. for 8 h, diluted with dilute aqueous NH$_3$ solution (30 mL) and extracted with DCM (3×150 mL). The combined organic fraction was dried and the solvent evaporated. The residue was purified by chromatography, eluting with a gradient (0-10%) of MeOH/DCM, to give 1,4-dioxide 83 (0.60 g, 60%) as a red gum: $^1$H NMR δ 8.31 (s, 1H, H-9), 8.28 (s, 1H, H-5), 4.60-4.70 (m, 2H, CH$_2$N), 4.33-4.40 (m, 1H, CHO), 3.60-3.75 (m, 2H, CH$_2$N), 3.33 (s, 3H, CH$_3$O), 3.25-3.32 (m, 2H, CH$_2$N), 3.12-3.25 (m, 6H, H-6, H-8, CH$_2$), 2.27-2.33 (m, 4H, H-7, CH$_2$); $^{13}$C NMR δ 155.5, 152.3, 151.2, 139.1, 134.1, 115.9, 113.9, 67.8, 61.0, 58.9, 56.9, 55.6, 32.9, 32.4, 26.9, 25.6, 22.9; HRMS (FAB$^+$) calcd for $C_{17}H_{23}N_4O_3$ (MH$^+$) m/z 331.1770, found 331.1771.

Example 79

3-[3-(1-Pyrrolidinyl)propyl]-7,8-dihydro-6H-indeno[5,6-e][1,2,4]triazine 1-Oxide (84). Pyrrolidine (3.0 g, 42 mmol) was added to a stirred solution of propanal 75 (1.5 g, 6.2 mmol) in MeOH (100 mL) at 0° C. and the solution stirred for 30 min. NaCNBH$_3$ (1.5 g, 24 mmol) was added and the solution stirred at 0° C. for 30 min and then HOAc (2 mL) was added and the mixture was stirred at 20° C. for 16 h. The solvent was evaporated and the residue was partitioned between DCM (200 mL) and water (200 mL). The aqueous phase was extracted with DCM (2×200 mL), the combined organic phase was dried and the solvent evaporated. The residue was purified by chromatography, eluting with 10% MeOH/EtOAc, to give 1-oxide 84 (1.5 g, 84%) as a yellow oil: $^1$H NMR [(CD$_3$)$_2$SO] δ 8.25 (s, 1H, H-9), 7.74 (s, 1H, H-5), 3.10-3.16 (m, 4H, H-6, H-8), 3.02-3.09 (m, 2H, CH$_2$N), 2.80-2.88 (m, 6H, 3×CH$_2$), 2.17-2.28 (m, 4H, H-7, CH$_2$), 1.82-1.90 (m, 4H, 2×CH$_2$); $^{13}$C NMR δ 165.0, 154.8, 149.2, 147.2, 132.3, 122.7, 114.3, 55.0, 53.4 (2), 34.8, 33.2, 32.8, 25.7, 25.5, 23.4 (2); HRMS calcd for $C_{17}H_{22}N_4O$ (M$^+$) m/z 298.1794, found 298.1794.

Example 80

3-[3-(1-Pyrrolidinyl)propyl]-7,8-dihydro-6H-indeno[5,6-e][1,2,4]triazine 1,4-Dioxide (85). H$_2$O$_2$ (70%, 2.0 mL, 39 mmol) was added dropwise to a stirred solution of TFAA (5.4 mL, 39 mmol) in DCM (50 mL) at 0° C. The solution was stirred at 0° C. for 5 min, warmed to 20° C. for 10 min, then cooled to 0° C. and added to a stirred solution of 1-oxide 84 (1.50 g, 4.6 mmol) and TFA (1.5 mL, 19.5 mmol) in DCM (50 mL) at 0° C. The solution was stirred at 20° C. for 6 h, diluted with dilute aqueous NH$_3$ solution (30 mL) and extracted with DCM (3×150 mL). The combined organic fraction was dried and the solvent evaporated. The residue was purified by chromatography, eluting with a gradient (0-10%) of MeOH/DCM, to give 1,4-dioxide 85 (846 mg, 35%) as a red gum: $^1$H NMR δ 8.25 (s, 1H, H-9), 8.20 (s, 1H, H-5), 3.22-3.22 (m, 6H, 3×CH$_2$), 3.11-3.20 (m, 4H, H-6, H-8), 2.80-3.05 (m, 2H, CH$_2$), 2.33-2.43 (m, 2H, CH$_2$), 2.21-2.30 (m, 2H, H-7), 2.13 (br s, 4H, 2×CH$_2$); $^{13}$C NMR δ 155.4, 152.4, 151.0, 139.0, 133.9, 115.7, 113.7, 54.2, 53.5 (2), 33.3, 32.8, 27.1, 25.4, 23.8, 23.2 (2); HRMS (FAB$^+$) calcd for $C_{17}H_{23}N_4O_2$ (MH$^+$) m/z 315.1821, found 315.1820.

Example 81

3-[3-(1-Piperidinyl)propyl]-7,8-dihydro-6H-indeno[5,6-e][1,2,4]triazine 1-Oxide (86). Piperidine (3.0 g, 35 mmol) was added to a stirred solution of propanal 75 (1.5 g, 6.2 mmol) in MeOH (100 mL) at 0° C. and the solution stirred for 30 min. NaCNBH$_3$ (1.5 g, 24 mmol) was added and the solution stirred at 0° C. for 30 min and then HOAc (2 mL) was added and the mixture was stirred at 20° C. for 16 h. The solvent was evaporated and the residue was partitioned between DCM (200 mL) and water (200 mL). The aqueous phase was extracted with DCM (2×200 mL), the combined organic phase was dried and the solvent evaporated. The residue was purified by chromatography, eluting with 10% MeOH/EtOAc, to give 1-oxide 86 (1.33 g, 69%) as a yellow oil: $^1$H NMR δ 8.24 (s, 1H, H-9), 7.74 (s, 1H, H-5), 3.09-3.15 (m, 4H, H-6, H-8), 3.02-3.07 (m, 2H, CH$_2$), 2.82-2.95 (m, 6H, 3×CH$_2$), 2.27-2.38 (m, 2H, CH$_2$), 2.17-2.26 (m, 2H, H-7), 1.76-1.87 (m, 4H, 2×CH$_2$), 1.50-1.60 (m, 2H, CH$_2$); $^{13}$C NMR δ 164.3, 155.0, 149.2, 147.4, 132.3, 122.7, 114.2, 57.1, 53.5 (2), 34.3, 33.2, 32.8, 25.7 (2), 23.7, 22.9, 22.6; HRMS (FAB$^+$) calcd for $C_{18}H_{25}N_4O$ (MH$^+$) m/z 313.2025, found 313.2025.

Example 82

3-[3-(1-Piperidinyl)propyl]-7,8-dihydro-6H-indeno[5,6-e][1,2,4]triazine 1,4-Dioxide (87). H$_2$O$_2$ (70%, 2.0 mL, 39 mmol) was added dropwise to a stirred solution of TFAA (5.4 mL, 39 mmol) in DCM (50 mL) at 0° C. The solution was stirred at 0° C. for 5 min, warmed to 20° C. for 10 min, then cooled to 0° C. and added to a stirred solution of 1-oxide 86 (1.33 g, 4.2 mmol) and TFA (1.5 mL, 19.5 mmol) in DCM (50 mL) at 0° C. The solution was stirred at 20° C. for 4 h, diluted with dilute aqueous NH$_3$ solution (40 mL) and extracted with DCM (3×150 mL). The combined organic fraction was dried and the solvent evaporated. The residue was purified by chromatography, eluting with a gradient (0-10%) of MeOH/DCM, to give 1,4-dioxide 87 (1.05 g, 76%) as a red gum: $^1$H NMR δ 8.30 (s, 1H, H-9), 8.26 (s, 1H, H-5), 3.34-3.40 (m, 4H, 2×CH$_2$), 3.27 (t, J=7.1 Hz, 2H, CH$_2$N), 3.12-3.21 (m, 4H, H-6, H-8), 3.05-3.12 (m, 2H, CH$_2$), 2.42-2.51 (m, 2H, CH$_2$), 2.22-2.32 (m, 2H, H-7), 1.64-1.73 (m, 4H, 2×CH$_2$), 1.40-1.51 (m, 2H, CH$_2$); $^{13}$C NMR δ 161.8, 155.2, 150.8, 139.1, 134.0, 115.8, 113.9, 58.9, 53.7, 53.4, 33.4, 32.9, 28.0, 25.6, 24.0 (2), 19.7, 13.6; HRMS (FAB$^+$) calcd for C$_{18}$H$_{25}$N$_4$O$_2$ (MH$^+$) m/z 329.1974, found 329.1974.

Example 83

7-Methyl-7,8-dihydro-6H-indeno[5,6-e][1,2,4]triazin-3-amine 1 Oxide (94). 2-Methyl-6-nitro-1-indanone (89). 2-Methyl-1-indanone (88) (18.74 g, 128 mmol) was added dropwise to stirred fuming HNO$_3$ (100 mL) at −10° C. over 1 h. The mixture was stirred at −10° C. for 10 min then poured into ice/water (1 L) and the mixture stirred for 1 h. The precipitate was filtered and the filtrate extracted with DCM (4×80 mL). The combined organic fraction was dried and the solvent evaporated. The combined residue was purified by chromatography, eluting with a gradient (10-20%) of EtOAc/pet. ether, to give (i) 2-methyl-4-nitro-1-indanone (89) (1.89 g, 8%) as a tan solid: mp 61-63° C. [lit. Murray, R. J. & Cromwell, N. H., *J. Org. Chem.* 1976, 41, 3540) mp (Et$_2$O/pet. ether) 74-75° C.]; $^1$H NMR δ 8.46 (dd, J=8.0, 1.1 Hz, 1H, H-5), 8.08 (br d, J=7.5 Hz, 1H, H-7), 7.60 (br dd, J=8.0, 7.5 Hz, 1H, H-6), 3.93 (dd, J=19.2, 8.0 Hz, 1H, H-3), 3.20 (dd, J=19.2, 4.0 Hz, 1H, H-3), 2.76-2.85 (m, 1H, H-2), 1.37 (d, J=7.5 Hz, 3H, CH$_3$); and (ii) 2-methyl-6-nitro-1-indanone (90) (10.76 g, 44%) as a tan solid: mp 60-61° C.; $^1$H NMR δ 8.56 (d, J=2.0 Hz, 1H, H-7), 8.44 (dd, J=8.4, 2.2 Hz, 1H, H-5), 7.63 (d, J=8.4 Hz, 1H, H-4), 3.48-3.54 (m, 1H, H-2), 2.81-2.90 (m, 2H, H-3), 1.36 (d, J=7.3 Hz, 3H, CH$_3$). Anal. calcd for C$_{10}$H$_9$NO$_3$: C, 62.8; H, 4.7; N, 7.3. Found: C, 62.7; H, 4.8; N, 7.4%.

N-(2-Methyl-2,3-dihydro-1H-inden-5-yl)acetamide (91). A solution of nitroindanone 90 (2.08 g, 10.9 mmol) in EtOH (100 mL), water (10 mL) and cHCl (1 mL) with Pd/C (200 mg) was vigorously stirred under H$_2$ (60 psi) for 16 h. The mixture was filtered through Celite and the solvent was evaporated. The residue was partitioned between dilute aqueous NH$_3$ solution and DCM, and the organic fraction dried and the solvent evaporated. The residue was suspended in dioxane (30 mL), and Ac$_2$O (1.6 mL, 17.0 mmol) added dropwise. The mixture was stirred at 20° C. for 16 h, and then quenched with MeOH (20 mL) and the solvent evaporated. The residue was purified by chromatography, eluting with a gradient (20-50%) of EtOAc/pet. ether, to give acetamide 91 (1.03 g, 50%) as a white solid: mp (EtOAc/pet. ether) 90-91° C.; $^1$H NMR δ 7.41 (br d, J=1.7 Hz, 1H, H-4), 7.35 (br s, 1H, NH), 7.15 (br dd, J=8.0, 1.7 Hz, 1H, H-6), 7.10 (br d, J=8.0 Hz, 1H, H-7), 2.97-3.05 (m, 2H, CH$_2$), 2.45-2.61 (m, 3H, H-2, CH$_2$), 2.16 (s, 3H, COCH$_3$), 1.13 (d, J=6.4 Hz, 3H, CH$_3$); $^{13}$C NMR δ 168.3, 144.7, 139.9, 136.0, 124.5, 118.2, 116.7, 41.2, 40.6, 34.7, 24.5, 20.7. Anal. calcd for C$_{12}$H$_{15}$NO: C, 76.2; H, 8.0; N, 7.4. Found: C, 76.3; H, 7.9; N, 7.4%.

N-(2-Methyl-6-nitro-2,3-dihydro-1H-inden-5-yl)acetamide (92). A solution of nitric acid (70%, 3.2 mL, 50.3 mmol) in TFA (5 mL) was added dropwise to a stirred solution of acetamide 91 (3.93 g, 16.8 mmol) in TFA (40 mL) and the solution stirred at 20° C. for 2 h. The solution was poured into ice/water (400 mL) and stirred for 30 min. The precipitate was filtered, washed with water (3×30 mL), and dried. The solid was purified by chromatography, eluting with 10% EtOAc/pet. ether, to give nitroacetamide 92 (3.79 g, 96%) as a red solid: mp (EtOAc/pet. ether) 99-100° C.; $^1$H NMR δ 10.41 (br s, 1H, NH), 8.50 (s, 1H, H-7), 8.00 (s, 1H, H-4), 3.03-3.13 (m, 2H, CH$_2$), 2.51-2.67 (m, 3H, H-2, CH$_2$), 2.29 (s, 3H, COCH$_3$), 1.14 (d, J=6.4 Hz, 3H, CH$_3$); $^{13}$C NMR δ 169.0, 153.9, 139.4, 135.3, 133.7, 121.1, 117.7, 41.6, 40.2, 34.7, 25.6, 20.4. Anal. calcd for C$_{12}$H$_{14}$N$_2$O$_3$: C, 61.5; H, 6.0; N, 12.0. Found: C, 61.6; H, 6.2; N, 11.5%.

2-Methyl-6-nitro-5-indanamine (93). A suspension of nitroacetamide 92 (3.79 g, 16.2 mmol) in EtOH (100 mL) and cHCl (14 mL) was stirred at reflux temperature for 4 h. The mixture was cooled and the EtOH evaporated. The mixture was diluted with water (100 mL) and the pH adjusted to 9 with cNH$_3$. The mixture was extracted with DCM (3×50 mL) and the combined organic fraction dried and the solvent evaporated. The residue was purified by chromatography, eluting with 20% EtOAc/pet. ether, to give nitroaniline 93 (3.01 g, 97%) as a red solid: mp (EtOAc/pet. ether) 100-101° C.; $^1$H NMR δ 7.89 (s, 1H, H-7), 6.61 (s, 1H, H-4), 5.99 (br s, 2H, NH$_2$), 2.92-2.99 (m, 2H, CH$_2$), 2.40-2.58 (m, 3H, H-2, CH$_2$), 1.12 (d, J=6.5 Hz, 3H, CH$_3$); $^{13}$C NMR δ 153.9, 144.3, 133.6, 131.3, 120.9, 113.6, 41.1, 39.6, 34.8, 20.4. Anal. calcd for C$_{10}$H$_{12}$N$_2$O$_2$: C, 62.5; H, 6.3; N, 14.6. Found: C, 62.6; H, 6.3; N, 14.5%.

7-Methyl-7,8-dihydro-6H-indeno[5,6-e][1,2,4]triazin-3-amine 1-Oxide (94). A mixture of nitroaniline 93 (3.0 g, 15.7 mmol) and cyanamide (2.6 g, 62.6 mmol) was mixed together at 80° C., cHCl (5 mL) added dropwise and the mixture heated at 100° C. for 3 h. A further three aliquots of cyanamide (0.5 g, 11.9 mmol) and cHCl (0.5 mL) were added over two hours. The mixture was cooled to 50° C., 7.5 M NaOH solution added until the mixture was strongly basic and the mixture stirred at 100° C. for 3 h. The mixture was cooled, diluted with water (100 mL), filtered, washed with water (2×30 mL), and dried. The residue was purified by chromatography, eluting with a gradient (0-15%) of MeOH/DCM, to give 1-oxide 94 (3.06 g, 90%) as a yellow powder: mp (MeOH/DCM) 275-277° C.; $^1$H NMR [(CD$_3$)$_2$SO] δ 7.90 (s, 1H, H-9), 7.31 (s, 1H, H-5), 7.10 (br s, 2H, NH$_2$), 3.05-3.14 (m, 2H, CH$_2$), 2.48-2.62 (m, 3H, H-7, CH$_2$), 1.09 (d, J=6.3 Hz, 3H, CH$_3$); $^{13}$C NMR [(CD$_3$)$_2$SO] δ 159.9, 153.7, 148.6, 142.1, 128.7, 120.0, 113.9, 41.4, 39.6, 34.3, 19.9. Anal. calcd for C$_{11}$H$_{12}$N$_4$O: C, 61.1; H, 5.6; N, 25.9. Found: C, 61.3; H, 5.6; N, 26.2%.

Example 84

3-Chloro-7-methyl-7,8-dihydro-6H-indeno[5,6-e][1,2,4]triazine 1-Oxide (95). NaNO$_2$ (0.43 g, 6.2 mmol) was added in small portions to a stirred solution of amine 94 (1.23 g, 5.7 mmol) in TFA (50 mL) at 0° C. and the solution stirred at 20° C. for 1 h. The solution was poured into ice/water (500 mL) and stirred for 30 minutes. The solvent was evaporated and the residue dried. The solid was suspended in POCl$_3$ (40 mL) and DMF (0.4 mL) and stirred at 80° C. for 1 h. The solution was cooled, poured into ice/water, stirred for 30 minutes, filtered, washed with water (3×30 mL) and dried. The filtrate was neutralized with cNH$_3$, extracted with CHCl$_3$ (4×30 mL), the combined organic fraction dried and the solvent evaporated. The combined residue was purified by chromatography, eluting with 5% EtOAc/DCM, to give chloride 95 (1.06 g, 79%) as a pale yellow solid: mp (DCM/pet. ether) 121-122° C.; $^1$H NMR δ 8.18 (s, 1H, H-9), 7.71 (s, 1H, H-5), 3.21-3.30

(m, 2H, CH$_2$), 2.65-2.80 (m, 3H, H-7, CH$_2$), 1.20 (d, J=6.4 Hz, 3H, CH$_3$); $^{13}$C NMR δ 156.0, 155.9, 149.8, 147.4, 132.8, 122.6, 114.6, 41.3, 40.9, 35.0, 20.2. Anal. calcd for C$_{11}$H$_{10}$ClN$_3$O: C, 56.1; H, 4.3; N, 17.8. Found: C, 56.0; H, 4.2; N, 17.8%.

Example 85

N$^1$,N$^1$-Dimethyl-N$^2$-(7-methyl-1 oxido-7,8-dihydro-6H-indeno[5,6-e][1,2,4]triazin-3-yl)-1,2-ethanediamine (96). A solution of chloride 95 (240 mg, 0.9 mmol), N$^1$,N$^1$-dimethyl-1,2-ethanediamine (0.26 mL, 2.4 mmol) and Et$_3$N (0.33 mL, 2.4 mmol) in DME (50 mL) was stirred at reflux temperature for 4 h. The solvent was evaporated and the residue partitioned between DCM (100 mL) and dilute aqueous NH$_3$ solution (50 mL). The organic fraction was dried and the solvent evaporated. The residue was purified by chromatography, eluting with a gradient (0-10%) of MeOH/DCM, to give 1-oxide 96 (389 mg, 86%) as a yellow solid: mp (MeOH/EtOAc) 119-121° C.; $^1$H NMR δ 8.03 (s, 1H, H-9), 7.35 (s, 1H, H-5), 5.82 (br s, 1H, NH), 3.52-3.58 (m, 2H, CH$_2$N), 3.07-3.17 (m, 2H, CH$_2$), 2.55-2.67 (m, 5H, CH, CH$_2$, CH$_2$N), 2.28 [s, 6H, N(CH$_3$)$_2$], 1.15 (d, J=6.1 Hz, 3H, CH$_3$); $^{13}$C NMR δ 158.7, 154.2, 148.9, 142.9, 129.8, 120.7, 114.8, 57.6, 45.1 (2), 41.2, 40.4, 38.7, 34.9, 20.2. Anal. calcd for C$_{15}$H$_{21}$N$_5$O: C, 62.7; H, 7.4; N, 24.4. Found: C, 62.4; H, 7.1; N, 24.1%.

Example 86

N$^1$,N$^1$-Dimethyl-N$^2$-(7-methyl-1,4-dioxido-7,8-dihydro-6H-indeno[5,6-e][1,2,4]triazin-3-yl)-1,2-ethanediamine (97). H$_2$O$_2$ (70%, 0.65 mL, ca. 12.9 mmol) was added dropwise to a stirred solution of TFAA (1.8 mL, 12.9 mmol) in DCM (20 mL) at 0° C. The solution was stirred at 0° C. for 5 min, warmed to 20° C. for 10 min, then cooled to 0° C. and added to a stirred solution of 1-oxide 96 (371 mg, 1.3 mmol) and TFA (0.50 mL, 6.5 mmol) in DCM (20 mL) at 0° C. The solution was stirred at 20° C. for 6 h, diluted with dilute aqueous NH$_3$ solution (10 mL) and extracted with CHCl$_3$ (4×30 mL). The combined organic fraction was dried and the solvent evaporated. The residue was purified by chromatography, eluting with a gradient (0-10%) of MeOH/DCM, to give (i) starting material 96 (181 mg, 49%) and (ii) 1,4-dioxide 97 (103 mg, 26%) as a red solid: mp (MeOH/DCM) 149-151° C.; $^1$H NMR δ 8.09 (s, 1H, H-9), 8.07 (s, 1H, H-5), 7.52 (br s, 1H, NH), 3.58-3.64 (m, 2H, CH$_2$N), 3.14-3.27 (m, 2H, CH$_2$), 2.63-2.75 (m, 3H, CH, CH$_2$), 2.59 (br t, J=6.0 Hz, 2H, CH$_2$), 2.28 [s, 6H, N(CH$_3$)$_2$], 1.18 (d, J=6.2 Hz, 3H, CH$_3$); $^{13}$C NMR δ 155.6, 149.4, 145.5, 138.0, 128.9, 115.8, 111.8, 57.4, 45.0 (2), 41.4, 40.4, 38.7, 34.8, 20.1. Anal. calcd for C$_{15}$H$_{21}$N$_5$O$_2$·½CH$_2$Cl$_2$: C, 54.6; H, 6.3; N, 19.9. Found: C, 54.4; H, 6.0; N, 19.8%.

Example 87

7-Methyl-N-[3-(4-morpholinyl)propyl]-7,8-dihydro-6H-indeno[5,6-e][1,2,4]triazin-3-amine 1-Oxide (98). A solution of chloride 95 (367 mg, 1.6 mmol), 3-(4-morpholinyl)propylamine (0.34 mL, 2.3 mmol) and Et$_3$N (0.33 mL, 2.3 mmol) in DME (50 mL) was stirred at reflux temperature for 8 h. The solvent was evaporated and the residue partitioned between DCM (100 mL) and dilute aqueous NH$_3$ solution (50 mL). The organic fraction was dried and the solvent evaporated. The residue was purified by chromatography, eluting with a gradient (0-10%) of MeOH/DCM, to give 1-oxide 98 (525 mg, 98%) as a yellow solid: mp (MeOH/DCM) 138-140° C.; $^1$H NMR δ 8.04 (s, 1H, H-9), 7.35 (s, 1H, H-5), 6.10 (br t, J=5.0 Hz, 1H, NH), 3.75 (br t, J=4.7 Hz, 4H, 2×CH$_2$O), 3.56-3.61 (m, 2H, CH$_2$N), 3.08-3.18 (m, 2H, CH$_2$), 2.56-2.65 (m, 3H, CH, CH$_2$), 2.44-2.52 (m, 6H, 3×CH$_2$N), 1.83 (br p, J=6.5 Hz, 2H, CH$_2$), 1.15 (d, J=6.1 Hz, 3H, CH$_3$); $^{13}$C NMR δ 158.8, 154.2, 148.9, 142.8, 129.8, 120.7, 114.8, 67.0 (2), 57.3, 53.8 (2), 41.2, 40.8, 40.4, 34.9, 25.3, 20.4. Anal. calcd for C$_{18}$H$_{25}$N$_5$O$_2$: C, 63.0; H, 7.3; N, 20.4. Found: C, 63.2; H, 7.2; N, 20.4%.

Example 88

7-Methyl-N-[3-(4-morpholinyl)propyl]-7,8-dihydro-6H-indeno[5,6-e][1,2,4]triazin-3-amine 1,4-Dioxide (99). H$_2$O$_2$ (70%, 0.72 mL, ca. 14.3 mmol) was added dropwise to a stirred solution of TFAA (2.0 mL, 14.3 mmol) in DCM (20 mL) at 0° C. The solution was stirred at 0° C. for 5 min, warmed to 20° C. for 10 min, then cooled to 0° C. and added to a stirred solution of 1-oxide 98 (490 mg, 1.4 mmol) and TFA (0.55 mL, 7.1 mmol) in DCM (20 mL) at 0° C. The solution was stirred at 20° C. for 6 h, diluted with dilute aqueous NH$_3$ solution (10 mL) and extracted with CHCl$_3$ (4×30 mL). The combined organic fraction was dried and the solvent evaporated. The residue was purified by chromatography, eluting with a gradient (0-10%) of MeOH/DCM, to give (i) starting material 98 (280 mg, 57%) and (ii) 1,4-dioxide 99 (88 mg, 17%) as a red solid: mp (MeOH/DCM) 161-163 DC; $^1$H NMR δ 8.30 (br s, 1H, NH), 8.08 (br s, 2H, H-5, H-9), 3.82 (br t, J=4.5 Hz, 4H, 2×CH$_2$O), 3.58-3.63 (m, 2H, CH$_2$N), 3.15-3.25 (m, 2H, CH$_2$), 2.61-2.74 (m, 3H, CH, CH$_2$), 2.57 (br t, J=6.1 Hz, 2H, CH$_2$N), 2.47-2.53 (m, 4H, 2×CH$_2$N), 1.83-1.90 (m, 2H, CH$_2$), 1.18 (d, J=6.2 Hz, 3H, CH$_3$); $^{13}$C NMR δ 155.2, 149.5, 145.2, 138.1, 129.5, 115.8, 111.7, 66.9 (2), 57.7, 53.8 (2), 41.6, 41.4, 40.4, 34.9, 24.5, 20.2. Anal. calcd for C$_{18}$H$_{25}$N$_5$O$_3$: C, 60.2; H, 7.0; N, 19.5. Found: C, 60.6; H, 7.0; N, 18.3%.

Example 89

3-Iodo-7-methyl-7,8-dihydro-6H-indeno[5,6-e][1,2,4]triazine 1-Oxide (100). tert-Butyl nitrite (2.5 mL, 18.6 mmol) was added a stirred mixture of amine 94 (1.30 g, 6.0 mmol), diiodomethane (4.8 mL, 60 mmol) and CuI (1.2 g, 6.3 mmol) in THF (50 mL) and the mixture stirred at reflux temperature for 3 h. The solution was cooled and the solvent evaporated. The residue was purified by chromatography, eluting with a gradient (20-50%) of EtOAc/pet. ether, to give chloride 100 (1.31 g, 67%) as a pale yellow solid: mp (EtOAc/pet. ether) 140-142° C.; $^1$H NMR δ 8.15 (s, 1H, H-9), 7.70 (s, 1H, H-5), 3.20-3.30 (m, 2H, CH$_2$), 2.65-2.79 (m, 3H, H-7, CH$_2$), 1.20 (d, J=6.4 Hz, 3H, CH$_3$); $^{13}$C NMR δ 155.5, 149.9, 147.6, 133.4, 122.5, 121.7, 114.6, 41.3, 41.0, 35.0, 20.2. Anal. calcd for C$_{11}$H$_{10}$IN$_3$O: C, 40.4; H, 3.1; N, 12.9. Found: C, 40.6; H, 3.0; N, 12.7%.

Example 90

3-(7-Methyl-1-oxido-7,8-dihydro-6H-indeno[5,6-e][1,2,4]triazin-3-yl)propanal (101). Iodide 100 (1.53 g, 4.7 mmol) was added to a degassed solution of allyl alcohol (0.89 mL, 13.1 mmol), Pd(OAc)$_2$ (52 mg, 0.23 mmol), nBu$_4$NBr (1.35 g, 4.2 mmol) and NaHCO$_3$ (0.86 g, 10.3 mmol) in DMF (40 mL) and the solution was stirred at 50° C. for 24 h under N$_2$. The mixture was quenched with saturated aqueous NH$_4$Cl solution (50 mL) and filtered. The filtrate was extracted with EtOAc (5×50 mL), dried and the solvent evaporated. The residue was purified by chromatography, eluting with a gradient (20-50%) of EtOAc/pet. ether, to give (i) starting material 100 (0.86 g, 56%) and (ii) aldehyde 101 as an orange gum: $^1$H NMR δ 9.93 (s, 1H, CHO), 8.21 (s, 1H, H-9), 7.69 (s, 1H, H-5), 3.35 (t, J=7.0 Hz, 2H, CH$_2$), 3.20-3.27 (m, 2H, CH$_2$), 3.19 (br dd, J=7.2, 6.7 Hz, 2H, CH$_2$), 2.64-2.76 (m, 3H, H-7, CH$_2$), 1.19 (d, J=6.4 Hz, 3H, CH$_3$); $^{13}$C NMR δ 200.5, 163.9, 154.5, 148.7, 147.3, 132.4, 122.8, 114.4, 41.2, 40.9, 40.5, 35.0, 29.4, 20.2; MS (FAB$^+$) m/z 258 (MH$^+$, 60%), 242 (10); HRMS (FAB$^+$) calcd for C$_{14}$H$_{16}$N$_3$O$_2$ (MH$^+$) m/z 258.1243, found 258.1242.

Example 91

7-Methyl-3-[3-(4-morpholinyl)propyl]-7,8-dihydro-6H-indeno[5,6-e][1,2,4]triazine 1-Oxide (102). Morpholine (0.64 mL, 7.3 mmol) was added to a solution of aldehyde 101 (0.47 g, 1.8 mmol) in EtOH (20 mL) at 0° C. and the solution stirred for 30 min. NaCNBH$_3$ (0.35 g, 5.5 mmol) was added and the mixture stirred at 0° C. for 30 min, then HOAc (0.5 mL) was added and the mixture stirred at 20° C. for 30 min. The solvent was evaporated and the residue partitioned between DCM and water, the organic phase was dried, the solvent evaporated and the residue purified by chromatography, eluting with a gradient (0-10%) of MeOH/EtOAc, to give (i) starting material 101 (83 mg, 17%) and (ii) alcohol 103 (134 mg, 28%) as a white solid: mp (MeOH/EtOAc) 70-71° C.; $^1$H NMR δ 8.21 (s, 1H, H-9), 7.71 (s, 1H, H-5), 3.78 (t, J=6.1 Hz, 2H, CH$_2$O), 3.20-3.28 (m, 2H, CH$_2$), 3.15 (t, J=7.2 Hz, 2H, CH$_2$), 2.64-2.78 (m, 3H, H-7, CH$_2$), 2.35 (br s, 1H, OH), 2.12-2.19 (m, 2H, CH$_2$), 1.19 (d, J=6.4 Hz, 3H, CH$_3$); $^{13}$C NMR δ 165.7, 154.6, 148.7, 147.3, 132.3, 122.6, 114.4, 62.1, 41.2, 40.9, 35.0, 30.6, 24.7, 20.2. Anal. calcd for C$_{14}$H$_{17}$N$_3$O$_2$.¼H$_2$O: C, 63.7; H, 6.7; N, 15.9. Found: C, 63.7; H, 6.6; N, 15.9%; and (iii) 1-oxide 102 (331 mg, 55%) as a yellow gum: $^1$H NMR δ 8.22 (s, 1H, H-9), 7.70 (s, 1H, H-5), 3.60 (br t, J=4.7 Hz, 4H, 2×CH$_2$O), 3.21-3.28 (m, 2H, CH$_2$), 3.05 (br t, J=7.4 Hz, 2H, CH$_2$), 2.65-2.77 (m, 3H, H-7, CH$_2$), 2.47-2.54 (m, 6H, 3×CH$_2$N), 2.11 (p, J=7.3 Hz, 2H, CH$_2$), 1.19 (d, J=6.4 Hz, 3H, CH$_3$); $^{13}$C NMR δ 165.7, 154.4, 148.5, 147.5, 132.3, 122.7, 114.4, 66.7 (2), 55.1, 53.5 (2), 41.2, 40.9, 35.2, 35.0, 24.7, 20.2; MS (FAB$^+$) m/z 392 (MH$^+$, 100%), 311 (20); HRMS (FAB$^+$) calcd for C$_{18}$H$_{25}$N$_4$O$_2$ (MH$^+$) m/z 329.1978, found 329.1978.

Example 92

7-Methyl-3-[3-(4-morpholinyl)propyl]-7,8-dihydro-6H-indeno[5,6-e][1,2,4]triazine 1,4-Dioxide (104). H$_2$O$_2$ (70%, 0.49 mL, ca. 9.7 mmol) was added dropwise to a stirred solution of TFAA (1.4 mL, 9.7 mmol) in DCM (10 mL) at 0° C. The solution was stirred at 0° C. for 5 min, warmed to 20° C. for 10 min, then cooled to 0° C. and added to a stirred solution of 1-oxide 102 (320 mg, 1.0 mmol) and TFA (0.38 mL, 4.9 mmol) in DCM (20 mL) at 0° C. The solution was stirred at 20° C. for 4 h, diluted with dilute aqueous NH$_3$ solution (10 mL) and extracted with CHCl$_3$ (4×30 mL). The combined organic fraction was dried and the solvent evaporated. The residue was purified by chromatography, eluting with a gradient (0-5%) of MeOH/DCM, to give 1,4-dioxide 104 (148 mg, 44%) as a red solid: mp (MeOH/DCM) 119-121° C.; $^1$H NMR δ 8.27 (s, 1H, H-9), 8.23 (s, 1H, H-5), 3.45 (br t, J=4.5 Hz, 4H, 2×CH$_2$O), 3.21-3.33 (m, 4H, 2×CH$_2$), 2.68-2.81 (m, 3H, H-7, CH$_2$), 2.48 (t, J=6.5 Hz, 2H, CH$_2$N), 2.37 (br t, J=4.5 Hz, 4H, 2×CH$_2$N), 2.06-2.13 (m, 2H, CH$_2$), 1.20 (d, J=6.4 Hz, 3H, CH$_3$); $^{13}$C NMR δ 155.2, 154.7, 150.2, 139.1, 133.8, 115.9, 113.9, 67.0 (2), 58.0, 53.5 (2), 41.4, 40.8, 35.0, 28.8, 21.8, 20.1. Anal. calcd for C$_{18}$H$_{24}$N$_4$O$_3$.¼CH$_3$OH: C, 62.2; H, 7.2; N, 15.9. Found: C, 62.3; H, 7.0; N, 16.0%.

Example 93

3-(7-Methyl-1,4-dioxido-7,8-dihydro-6H-indeno[5,6-e][1,2,4]triazin-3-yl)-1-propanol (105). H$_2$O$_2$ (70%, 0.25 mL, ca. 5.0 mmol) was added dropwise to a stirred solution of TFAA (0.7 mL, 5.0 mmol) in DCM (10 mL) at 0° C. The solution was stirred at 0° C. for 5 min, warmed to 20° C. for 10 min, then cooled to 0° C. and added to a stirred solution of 1-oxide 103 (130 mg, 0.5 mmol) in DCM (10 mL) at 0° C. The solution was stirred at 20° C. for 4 h, diluted with dilute aqueous NH$_3$ solution (10 mL) and stirred vigorously for 1 h. The mixture was extracted with CHCl$_3$ (4×30 mL) and the combined organic fraction was dried and the solvent evaporated. The residue was purified by chromatography, eluting with EtOAc, to give 1,4-dioxide 105 (68 mg, 49%) as a red solid: mp (EtOAc/pet. ether) 130-131° C.; $^1$H NMR δ 8.30 (s, 1H, H-9), 8.22 (s, 1H, H-5), 3.69 (br t, J=5.8 Hz, 2H, CH$_2$O), 3.24-3.35 (m, 4H, 2×CH$_2$), 3.10 (br s, 1H, OH), 2.68-2.83 (m, 3H, H-7, CH$_2$), 2.10-2.17 (m, 2H, CH$_2$), 1.21 (d, J=6.5 Hz, 3H, CH$_3$); $^{13}$C NMR δ 155.2, 155.0, 150.5, 138.9, 134.0, 115.9, 114.2, 61.2, 41.4, 40.9, 34.9, 29.6, 26.8, 20.1. Anal. calcd for C$_{14}$H$_{17}$N$_3$O$_3$: C, 61.1; H, 6.2; N, 15.3. Found: C, 61.4; H, 6.3; N, 15.0%.

Example 94

N$^7$,N$^7$-Dimethyl-7,8-dihydro-6H-indeno[5,6-e][1,2,4]triazine-3,7-diamine 1-Oxide (111). N,N-Dimethyl-2-indanamine (107). Methanesulfonyl chloride (11.5 mL, 149 mmol) was added dropwise to a stirred solution of 2-indanol (106) (20 g, 149 mmol) and iPr$_2$NEt (28.6 mL, 164 mmol) in DCM (300 mL) at 0° C., and the solution stirred at 20° C. for 16 h. The solution was washed with 1 M HCl (80 mL), aqueous saturated NaHCO$_3$ solution (80 mL) and brine (100 mL), dried and the solvent evaporated. The residue was recrystallised from EtOH to give 2,3-dihydro-1H-inden-2-yl methanesulfonate (31.14 g, 98%) as a white solid. Aqueous HNMe$_2$ (40%, 180 mL, 1.42 mol) was added slowly to a stirred solution of mesylate (30.25 g, 143 mmol) in DMF (200 mL) and the solution stirred at 20° C. for 16 h. The solution was partitioned between EtOAc (400 mL) and water (800 mL) and the organic fraction washed with water (3×80 mL), brine (100 mL), dried and the solvent evaporated. The residue was suspended in 1 M HCl (400 mL) and washed with DCM (3×80 mL). The pH of the aqueous fraction was adjusted to 14 with NaOH, the mixture chilled at 5° C. for 8 h and the precipitate filtered. The precipitate was washed with water (50 mL) and dried to give amine 107 (21.54 g, 93%) as a light gray solid: $^1$H NMR δ 7.10-7.17 (m, 4H, H$_{arom}$), 3.01-3.08 (m, 3H, H-2, CH$_2$), 2.82-2.91 (m, 2H, CH$_2$), 2.31 [s, 6H, N(CH$_3$)$_2$].

N,N-Dimethyl-5-nitro-2-indanamine (108). cHNO$_3$ (70%, 22.6 mL, 357 mmol) was added dropwise to a stirred solution of indane 107 (15.54 g, 95.8 mmol) in TFA (90 mL) and the solution stirred at 20° C. for 48 h. The solution was poured into ice/water (1 L) and the pH adjusted to 10 with cNH$_3$. The mixture was extracted with DCM (4×150 mL), the combined organic fraction dried and the solvent evaporated to give crude 5-nitroindanamine 108 containing ca. 5% of the corresponding 4-nitro isomer. A small portion was purified by chromatography, eluting with a gradient (0-5%) of MeOH/DCM, to give 5-nitroindanamine 108 as an oil: $^1$H NMR δ 8.03-8.06 (m, 2H, H-4, H-6), 7.30 (d, J=8.9 Hz, 1H, H-7), 3.23-3.30 (m, 1H, H-2), 3.12-3.20 (m, 2H, CH$_2$), 2.97-3.03

(m, 2H. CH$_2$), 2.38 [s, 6H, N(CH$_3$)$_2$]. The hydrochloride salt crystallised as a tan powder, mp 223-227° C. Anal. calcd for C$_{11}$H$_{15}$ClN$_2$O$_2$: C, 54.4; H, 6.2; N, 11.5. Found: C, 55.0; H, 6.3; N, 11.4%.

N-[2-(Dimethylamino)-2,3-dihydro-1H-inden-5-yl]acetamide (109). A solution of crude nitroindanamine 108 (19.82 g, 95.8 mmol) in EtOH (200 mL) and Pd/C (500 mg) was stirred in 2×100 mL batches under H$_2$ (60 psi) for 16 h. The combined batches were filtered through Celite, and washed with warm EtOH (1 L) and then DMF (100 mL). The solvent was evaporated and the residue suspended in dioxane (130 mL), and Ac$_2$O (19 mL, 190 mmol) added dropwise. The mixture was stirred at 20° C. for 16 h, diluted with water (200 mL), the pH adjusted to 10 with cNH$_3$, and the mixture stirred for 30 min. The precipitate was filtered, washed with water (50 mL) and dried to give pure 5-acetamide 109 (15.38 g, 73%) as tan powder: mp 94-96° C.; $^1$H NMR δ 7.42 (br s, 1H, NH), 7.08-7.14 (m, 3H, H-4, H-6, H-7), 2.97-3.08 (m, 3H, H-2, CH$_2$), 2.78-2.89 (m, 2H, CH$_2$), 2.30 [s, 6H, N(CH$_3$)$_2$], 2.15 (s, 3H, COCH$_3$); $^{13}$C NMR δ 168.3, 142.8, 137.9, 136.3, 124.5, 118.5, 116.6, 68.1, 43.8 (2), 37.7, 37.1, 24.5. Anal. calcd for C$_{13}$H$_{18}$N$_2$O.H$_2$O: C, 66.1; H, 8.5; N, 11.9. Found: C, 66.1; H, 8.5; N, 11.9%.

N$^2$,N$^2$-Dimethyl-6-nitro-2,5-indanediamine (110). A solution of cHNO$_3$ (70%, 13.4 mL, 211 mmol) in TFA (15 mL) was added dropwise to a stirred solution of acetamide 109 (15.38 g, 70.5 mmol) in TFA (120 mL) and the solution stirred at 20° C. for 16 h. The solution was poured into ice/water (1.2 L) and the pH adjusted to 10 with cNH$_3$. The mixture was extracted with DCM (4×150 mL), the combined organic fraction dried and the solvent evaporated. The residue was filtered through a short column of silica, eluting with a gradient (0-15%) of MeOH/DCM, to give a 6:1 mixture of N-[2-(dimethylamino)-6-nitro-2,3-dihydro-1H-inden-5-yl]acetamide and N-[2-(dimethylamino)-4-nitro-2,3-dihydro-1H-inden-5-yl]acetamide (16.7 g, 90%). A solution of the acetamide mixture (16.7 g, 63.4 mmol) in EtOH (300 mL) and cHCl (70 mL) was stirred at reflux temperature for 4 h. The mixture was cooled and the EtOH evaporated. The mixture was diluted with water (200 mL) and the pH adjusted to 9 with cNH$_3$. The precipitate was filtered, washed with water (40 mL), dried and recrystallised from EtOAc/pet. ether to give pure 6-nitroaniline 110 (8.12 g, 52%) as a red solid: mp 19-121° C.; $^1$H NMR δ 7.91 (s, 1H, H-7), 6.61 (s, 1H, H-4), 6.00 (br s, 2H, NH$_2$), 2.95-3.06 (m, 3H, H-2, CH$_2$), 2.74-2.84 (m, 2H, CH$_2$), 2.29 [s, 6H, N(CH$_3$)$_2$]; $^{13}$C NMR δ 151.8, 144.4, 131.6, 131.4, 121.0, 113.6, 67.8, 43.8 (2), 37.9, 36.2. Anal. calcd for C$_{11}$H$_{15}$N$_3$O$_2$: C, 59.7; H, 6.8; N, 19.0. Found: C, 59.5; H, 6.9; N, 18.9%.

N$^7$,N$^7$-Dimethyl-7,8-dihydro-6H-indeno[5,6-e][1,2,4]triazine-3,7-diamine 1-Oxide (111). A mixture of nitroaniline 110 (0.50 g, 2.3 mmol) and cyanamide (0.4 g, 9.0 mmol) were mixed together at 80° C., cHCl (5 mL) added dropwise and the mixture heated at 100° C. for 3 h. A further aliquot of cyanamide (0.4 g, 9.0 mmol) and cHCl (1 mL) was added and the mixture stirred at 100° C. for 1 h. The mixture was cooled to 50° C., 7.5 M NaOH solution added until the mixture was strongly basic and the mixture stirred at 100° C. for 3 h. The mixture was cooled, diluted with water (30 mL), filtered, washed with water (2×10 mL), and dried. The residue was filtered through a short plug of silica, eluting with 10% MeOH/DCM, and the solvent evaporated to give 1-oxide 111 (246 mg, 44%) as a yellow powder: mp (MeOH/DCM) 212-216° C.; $^1$H NMR [(CD$_3$)$_2$SO] δ 7.93 (s, 1H, H-9), 7.34 (s, 1H, H-5), 7.11 (br s, 2H, NH$_2$), 3.03-3.18 (m, 3H, H-7, CH$_2$), 2.79-2.89 (m, 2H, CH$_2$), 2.22 [s, 6H, N(CH$_3$)$_2$]; $^{13}$C NMR [(CD$_3$)$_2$SO] δ 159.9, 152.0, 148.6, 140.5, 128.9, 120.0, 114.1, 67.0, 43.2 (2), 37.0, 36.1. Anal. calcd for C$_{12}$H$_{15}$N$_5$O.½H$_2$O: C, 56.7; H, 6.3; N, 27.5. Found: C, 56.9; H, 6.0; N, 27.4%.

Example 95

3-Chloro-N,N-dimethyl-7,8-dihydro-6H-indeno[5,6-e][1,2,4]triazin-7-amine 1-Oxide (112). NaNO$_2$ (100 mg, 1.4 mmol) was added in small portions to a stirred solution of amine 111 (320 mg, 1.3 mmol) in TFA (10 mL) at 0° C. and the solution stirred at 20° C. for 1 h. The solution was poured into ice/water (50 mL) and stirred for 30 minutes. The solvent was evaporated and the residue dried. The solid was suspended in POCl$_3$ (5 mL) and DMF (3 drops) and stirred at 80° C. for 1 h. The solution was cooled, poured into ice/water, stirred for 30 minutes, filtered, washed with water (3×30 mL) and dried. The filtrate was neutralised with cNH$_3$, extracted with CHCl$_3$ (4×30 mL), the combined organic fraction dried and the solvent evaporated. The combined residue was purified by chromatography, eluting with 5% MeOH/DCM, to give chloride 112 (245 mg, 71%) as a pale yellow solid: mp (DCM) 160-165° C.; $^1$H NMR δ 8.19 (s, 1H, H-9), 7.73 (s, 1H, H-5), 3.25-3.34 (m, 2H, CH$_2$), 3.15-3.23 (m, 1H, H-7), 3.02-3.11 (m, 2H, CH$_2$), 2.34 [s, 6H, N(CH$_3$)$_2$]; $^{13}$C NMR δ 156.1, 154.0, 147.8, 147.4, 133.0, 122.7, 114.8, 67.5, 43.8 (2), 38.1, 37.7. Anal. calcd for C$_{12}$H$_{13}$ClN$_4$O: C, 54.5; H, 5.0; N, 21.2. Found: C, 54.6; H, 4.9; N, 21.3%.

Example 96

N$^3$-Ethyl-N$^7$,N$^7$-dimethyl-7,8-dihydro-6H-indeno[5,6-e][1,2,4]triazine-3,7-diamine 1-Oxide (113). Aqueous ethylamine (70%, 0.35 mL, 4.4 mmol) was added to a stirred solution of chloride 112 (240 mg, 0.9 mmol) in DME (20 mL) and the solution stirred at reflux temperature for 4 h. The solvent was evaporated and the residue purified by chromatography, eluting with a gradient (0-10%) of MeOH/DCM, to give 1-oxide 113 (203 mg, 84%) as a yellow solid: mp (MeOH/EtOAc) 187-190° C.; $^1$H NMR δ 8.05 (s, 1H, H-9), 7.37 (s, 1H, H-5), 5.14 (br s, 1H, NH), 3.54 (dq, J=7.2, 1.3 Hz, 2H, CH$_2$N), 3.06-3.21 (m, 3H, CH, CH$_2$), 2.89-2.99 (m, 2H, CH$_2$), 2.32 [s, 6H, N(CH$_3$)$_2$], 1.28 (t, J=7.2 Hz, 3H, CH$_3$); $^{13}$C NMR δ 158.7, 152.1, 148.9, 140.9, 130.0, 120.8, 115.0, 67.7, 43.9 (2), 38.0, 37.1, 36.3, 14.8. Anal. calcd for C$_{14}$H$_{19}$N$_5$O: C, 61.5; H, 7.0; N, 25.6. Found: C, 61.3; H, 7.1; N, 25.5%.

Example 97

N$^3$-Ethyl-N$^7$,N$^7$-dimethyl-7,8-dihydro-6H-indeno[5,6-e][1,2,4]triazine-3,7-diamine 1,4-Dioxide (114). H$_2$O$_2$ (70%, 0.35 mL, ca. 6.9 mmol) was added dropwise to a stirred solution of TFAA (1.0 mL, 6.9 mmol) in DCM (10 mL) at 0° C. The solution was stirred at 0° C. for 5 min, warmed to 20° C. for 10 min, then cooled to 0° C. and added to a stirred solution of 1-oxide 113 (188 mg, 0.7 mmol) and TFA (0.26 mL, 3.4 mmol) in DCM (10 mL) at 0° C. The solution was stirred at 20° C. for 6 h, diluted with dilute aqueous NH$_3$ solution (10 mL) and extracted with CHCl$_3$ (4×30 mL). The combined organic fraction was dried and the solvent evaporated. The residue was purified by chromatography, eluting with a gradient (0-10%) of MeOH/DCM, to give (i) starting material 113 (175 mg, 93%) and (ii) 1,4-dioxide 114 (8 mg, 4%) as a red gum: $^1$H NMR δ 8.11 (s, 1H, H-9), 8.08 (s, 1H, H-5), 6.98 (br s, 1H, NH), 3.63 (dq, J=7.2, 1.0 Hz, 2H, CH$_2$N), 3.15-3.30 (m, 3H, CH, CH$_2$), 2.95-3.07 (m, 2H, CH$_2$), 2.33 [s, 6H, N(CH$_3$)$_2$], 1.36 (t, J=7.2 Hz, 3H, CH$_3$); MS (FAB$^+$) m/z 290 (MH$^+$, 20%), 274 (5); HRMS (FAB$^+$) calcd for C$_{14}$H$_{20}$N$_5$O$_2$ (MH$^+$) m/z 290.1617, found 290.1607.

Example 98

7-(Dimethylamino)-3-ethyl-7,8-dihydro-6H-indeno[5,6-e][1,2,4]triazine 1-Oxide (115). Pd(PPh$_3$)$_4$ (240 mg, 0.21 mmol) was added to a N$_2$-purged, stirred solution of chloride 112 (550 mg, 1.9 mmol) and SnEt$_4$ (800 mg, 3.4 mmol) in DME (55 mL), and the mixture stirred at 85° C. under N$_2$ for 16 h. The mixture was cooled, the solvent evaporated and the residue purified by chromatography, eluting with a gradient (0-10%) of MeOH/DCM, to give 1-oxide 115 (250 mg, 47%) as an unstable brown solid: $^1$H NMR δ 8.23 (s, 1H, H-9), 7.73 (s, 1H, H-5), 3.04-3.33 (m, 5H, H-6, H-7, H-8) 3.02 (q, J=7.6 Hz, 2H, CH$_2$), 2.35 [s, 6H, N(CH$_3$)$_2$], 1.43 (t, J=7.6 Hz, 3H, CH$_3$); $^{13}$C NMR δ 167.2, 152.2, 147.6, 146.3, 132.4, 122.9, 114.6, 67.6, 43.8 (2), 38.0, 37.6, 30.6, 12.3; HRMS calcd for C$_{14}$H$_{18}$N$_4$O (M$^+$) m/z 258.1481, found 258.1473.

Example 99

7-(Dimethylamino)-3-ethyl-7,8-dihydro-6H-indeno[5,6-e][1,2,4]triazine 1,4-Dioxide (116). H$_2$O$_2$ (70%, 0.47 mL, ca. 9.7 mmol) was added dropwise to a stirred solution of TFM (1.35 mL, 9.7 mmol) in DCM (15 mL) at 0° C. The solution was stirred at 20° C. for 10 min, then cooled to 0° C. and added to a solution of 1-oxide 115 (250 mg, 0.97 mmol) and TFA (0.16 mL, 2.07 mmol) in CHCl$_3$ (15 mL) at 0° C. The solution was stirred at 20° C. for 5 h. The solution was made basic with dilute aqueous NH$_3$ solution and extracted with CHCl$_3$ (3×30 mL). The combined organic fraction was dried and the solvent evaporated. The residue was purified by column chromatography, eluting with a gradient (0-10%) of MeOH/DCM, to give 1,4-dioxide 116 (55 mg, 21%) as an unstable brown solid: $^1$H NMR δ 8.30 (s, 1H, H-9), 8.25 (s, 1H, H-5), 3.07-3.37 (m, 7H, H-6, H-7, H-8, CH$_2$), 2.36 [s, 6H, N(CH$_3$)$_2$], 1.43 (t, J=7.5 Hz, 3H, CH$_3$); HRMS calcd for C$_{14}$H$_{18}$N$_4$O$_2$ (M$^+$) m/z 274.1430, found 274.1428.

Example 100

(3-Amino-1-oxido-7,8-dihydro-6H-indeno[5,6-e][1,2,4]triazin-7-yl)methanol (124). 1,2-Bis(bromomethyl)-4-nitrobenzene (118). KNO$_3$ (33.0 g, 330 mmol) was added in small portions, over 1 h, to a stirred solution of 1,2-bis(bromomethyl)benzene (117) (72.2 g, 300 mmol) in cH$_2$SO$_4$ (600 mL) at 0° C. After the addition was completed, the mixture was stirred at 0° C. for 3 h. The mixture was poured onto ice and stirred at 0° C. for 2 h. The solid was filtered, washed with water several times and dried to give nitrobenzene 118 (63.1 g, 68%) as a white solid: mp (EtOAc/pet. ether) 73-74° C.; $^1$H NMR δ 8.25 (d, J=2.3 Hz, 1H, H-3), 8.15 (dd, J=8.4, 2.3 Hz, 1H, H-5), 7.56 (d, J=8.4 Hz, 1H, H-6), 4.67 (s, 2H, CH$_2$Br), 4.66 (s, 2H, CH$_2$Br); $^{13}$C NMR δ 148.0, 143.4138.3, 132.1, 125.9, 124.1, 28.0, 27.5. Anal. calcd for C$_8$H$_7$NBr$_2$O$_2$: C, 31.1; H, 2.3; N, 4.5. Found: C, 31.1; H, 2.3; N, 4.5%.

5-Nitro-2-indanecarboxylic Acid (119). Diethyl malonate (9.10 mL, 60.0 mmol) was added to a stirred suspension of NaH (60% in oil, 3.02 g, 126 mmol) in dry Et$_2$O (500 mL) at 20° C. under N$_2$ and the mixture was stirred for 30 min. 1,2-Bis(bromomethyl)-4-nitrobenzene (118) (18.5 g, 60.0 mmol) was added and the mixture was stirred at 20° C. for 24 h. The reaction was diluted with EtOAc (200 mL) and washed with 1 M HCl. The solvent was evaporated to give a brown oil that was treated with 2 M NaOH (100 mL) in EtOH (100 mL) at 20° C. for 15 h. Most of the solvent was evaporated and DCM (300 mL) was added and the mixture was acidified with 1 M HCl. The organic fraction was dried and the solvent evaporated to give a brown solid that was suspended in xylene (200 mL) and stirred at reflux temperature for 90 min. The solvent was evaporated to give a brown oil which was purified by chromatography, eluting with a gradient (0-20%) of EtOAc/pet. ether, to give acid 119 (2.44 g, 20%) as a pale yellow solid: mp (EtOAc/pet. ether) 115-117° C.; $^1$H NMR δ 9.10 (br s, 1H, CO$_2$H), 8.06-8.11 (m, 2H, H-4, H-6), 7.36 (d, J=9.0 Hz, 1H, H-7), 3.30-3.56 (m, 5H, H-1, H-2, H-3); $^{13}$C NMR δ 180.0, 149.0, 147.6, 143.1, 124.8, 122.7, 119.6, 43.3, 35.9, 35.7. Anal. calcd for C$_{10}$H$_9$NO$_4$: C, 58.0; H, 4.4; N, 6.8. Found: C, 58.2; H, 4.5; N, 6.8%.

(5-Nitro-2,3-dihydro-1H-inden-2-yl)methanol (120). BH$_3$-DMS (10 M, 1.30 mL, 13.0 mmol) was added to a stirred solution of acid 119 (2.07 g, 10.0 mmol) in dry THF (30 mL) at 20° C. under N$_2$ and the mixture was stirred at 20° C. for 30 min. The reaction was quenched with MeOH and the solvent evaporated to give a brown oil which was purified by chromatography, eluting with a gradient (0-20%) of EtOAc/pet. ether, to give alcohol 120 (1.13 g, 59%) as an oil: $^1$H NMR δ 8.01-8.07 (m, 2H, H-4, H-6), 7.32 (d, J=8.0 Hz, 1H, H-7), 3.68 (d, J=5.8 Hz, 2H, CH$_2$O), 3.09-3.20 (m, 2H, CH$_2$), 2.76-2.91 (m, 3H, CH$_2$, CH); HRMS calcd for C$_{10}$H$_{11}$NO$_3$ (M$^+$) m/z 193.0739, found 193.0733.

[5-(Acetylamino)-2,3-dihydro-1H-inden-2-yl]methyl Acetate (121). A solution of nitroindanol 120 (0.54 g, 2.77 mmol) in MeOH (70 mL) and 5% Pd/C (100 mg) was stirred under H$_2$ (60 psi) for 16 h. The mixture was filtered through Celite, washed with MeOH and the solvent evaporated to give the corresponding aniline derivative, which was treated with Ac$_2$O (5 mL, 53.0 mmol) and Et$_3$N (5 mL, 36.0 mmol) in DCM (50 mL) at 20° C. for 28 h. The mixture was partitioned between EtOAc and water and the organic fraction was washed with water, dried and the solvent evaporated to give a brown oil which was purified by chromatography, eluting with a gradient (30-50%) of EtOAc/pet. ether, to give acetate 121 (0.38 g, 56%) as an oil: $^1$H NMR δ 7.44 (s, 1H, H-4), 7.26 (br s, 1H, NH), 7.09-7.17 (m, 2H, H-6, H-7), 4.08 (d, J=7.0 Hz, 2H, CH$_2$O), 2.99-3.09 (m, 2H, CH$_2$), 2.65-2.87 (m, 3H, CH, CH$_2$), 2.16 (s, 3H, COCH$_3$) 2.06 (s, 3H, CH$_3$); $^{13}$C NMR δ 171.2, 168.2, 143.3, 138.4, 136.4, 124.7, 118.5, 116.7, 67.5, 38.5, 36.0, 35.4, 24.5, 20.9; HRMS calcd for C$_{14}$H$_{17}$NO$_3$ (M$^+$) m/z 247.1208, found 247.1204.

[5-(Acetylamino)-6-nitro-2,3-dihydro-1H-inden-2-yl]methyl Acetate (122). cHNO$_3$ (70%, 3.0 mL, 33.3 mmol) was added dropwise (over 20 min) to a stirred solution of 121 (1.45 g, 5.85 mmol) in TFA (30 mL) at 20° C. and the reaction mixture stirred for 15 min at 20° C. The mixture was poured into ice/water (300 mL), stirred 30 min and extracted with DCM (3×100 mL). Evaporation of the solvent gave crude acetate 122 (1.60 g, 94%), containing ca. 8% of the 4-nitro isomer which was removed by recrystallisation from ether, to give acetate 122 as a tan solid: mp (ether) 106-107° C.; $^1$H NMR δ 10.36 (br s, 1H, NH), 8.58 (s, 1H, H-7), 8.03 (s, 1H, H-4), 4.05-4.13 (m, 2H, CH$_2$O), 3.06-3.22 (m, 2H, CH$_2$), 2.73-2.94 (m, 3H, CH$_2$, CH), 2.27 (s, 3H, COCH$_3$), 2.06 (s, 3H, COCH$_3$); $^{13}$C NMR δ 171.0, 169.0, 152.3, 137.9, 135.5, 134.0, 121.4, 117.8, 66.7, 38.5, 36.5, 35.1, 25.6, 20.8. Anal. calcd for C$_{14}$H$_{16}$N$_2$O$_5$: C, 57.5; H, 5.5; N, 9.6. Found: C, 57.7; H, 5.4; N, 9.7%.

(5-Amino-6-nitro-2,3-dihydro-1H-inden-2-yl)methanol (123). A mixture of acetate 122 (5.60 g, 19.2 mmol) and 5 M HCl (80 mL) in MeOH (80 mL) was stirred at reflux temperature for 30 min. The solvent was evaporated to give the hydrochloride salt of 123 (4.42 g, 94%) as an orange solid: mp (MeOH) 143-145° C.; $^1$H NMR [(CD$_3$)$_2$SO] δ 7.73 (s, 1H, H-7), 7.43 (br s, 4H, NH$_2$, OH, HCl), 6.84 (s, 1H, H-4), 3.31-3.38 (m, 2H, CH$_2$O), 2.77-2.90 (m, 2H, CH$_2$), 2.44-2.64 (m, 3H, CH$_2$, CH); $^{13}$C NMR [(CD$_3$)$_2$SO] δ 153.2, 145.7 131.4, 129.1, 119.8, 113.7, 63.8, 41.5, 35.2, 33.6; HRMS calcd for C$_{10}$H$_{12}$N$_2$O$_3$ (M$^+$) m/z 208.0848, found 208.0850. Anal. calcd for C$_{10}$H$_{12}$N$_2$O$_3$.HCl: C, 49.1; H, 5.4; N, 11.5. Found: C, 49.4; H, 5.4; N, 11.5%.

(3-Amino-1-oxido-7,8-dihydro-6H-indeno[5,6-e][1,2,4] triazin-7-yl)methanol (124). A mixture of nitroaniline 123 (4.43 g, 17.8 mmol) and cyanamide (3.51 g, 83.6 mmol) were mixed together at 100° C., cooled to 50° C., cHCl (8.21 mL) added carefully and the mixture stirred at 65-70° C. for 90 min. A solution of 7.5 M NaOH (72 mL) was added until the mixture was strongly basic and the mixture stirred at 90-98° C. for 45 min. The mixture was cooled, diluted with water (50 mL), filtered, washed with water (3×20 mL) and dried to give 1-oxide 124 (3.67 g, 89%) as a green-yellow solid: mp (DCM/MeOH) 255-257° C.; $^1$H NMR [(CD$_3$)$_2$SO] δ 7.93 (s, 1H, H-9), 7.33 (s, 1H, H-5), 7.10 (s, 2H, NH$_2$), 4.67 (t, J=5.2 Hz, 1H, OH), 3.40 (dd, J=6.5 Hz, 5.2 Hz, 2H, CH$_2$O), 2.99-3.10 (m, 2H, CH$_2$), 2.73-2.85 (m, 2H, CH$_2$), 2.52-2.63 (m, 1H, CH); $^{13}$C NMR [(CD$_3$)$_2$SO] δ 159.9, 153.5, 148.6, 141.9, 128.8, 120.1, 114.1, 63.7, 41.6, 35.3, 34.6. Anal. calcd for C$_{11}$H$_{12}$N$_4$O$_2$.¼CH$_3$OH: C, 56.2; H, 5.5; N, 23.3. Found: C, 56.7; H, 5.4; N, 23.2%.

Example 101

(3-Bromo-1-oxido-7,8-dihydro-6H-indeno[5,6-e][1,2,4] triazin-7-yl)methanol (125). NaNO$_2$ (23 mg, 0.33 mmol) was added to a stirred mixture of amine 124 (77 mg, 0.33 mmol), HBr (48%, 2 mL) and DMF (2 mL) at 20° C. and the mixture stirred at 20° C. for 1 h. CuBr (57 mg, 0.40 mmol) was added and the reaction mixture stirred at 20° C. for 90 min. The mixture was diluted with EtOAc (50 mL) and washed with water (3×20 mL). The organic solution was dried and the solvent evaporated to give an orange oil, that was purified by chromatography, eluting with a gradient (0-30%) of EtOAc/pet. ether, to give bromide 125 (40 mg, 41%) as an oil: $^1$H NMR δ 8.19 (s, 1H, H-9), 7.74 (s, 1H, H-5), 3.72 (d, J=6.5 Hz, 2H, CH$_2$O), 3.22-3.33 (m, 2H, CH$_2$), 2.96-3.08 (m, 2H, CH$_2$), 2.80-2.89 (m, 1H, CH), OH not observed; HRMS calcd for C$_{11}$H$_{10}$$^{79}$BrN$_3$O$_2$ (M$^+$) m/z 294.9956, found 294.9949; calcd for C$_{11}$H$_{10}$$^{81}$BrN$_3$O$_2$ (M$^+$) m/z 296.9936, found 296.9943.

Example 102

[3-(Ethylamino)-1-oxido-7,8-dihydro-6H-indeno[5,6-e] [1,2,4]triazin-7-yl]methanol (126). A mixture of bromide 125 (91 mg, 0.31 mmol), 70% ethylamine (0.5 mL) and DME (3 mL) was stirred at 20° C. for 3 h. The mixture was partitioned between EtOAc and aqueous Na$_2$CO$_3$ solution. The organic layer was separated, dried and the solvent evaporated to give compound 126 (74 mg, 92%) as yellow solid: mp (EtOAc) 150° C.; $^1$H NMR δ 8.07 (s, 1H, H-9), 7.40 (s, 1H, H-5), 5.07 (br s, 1H, NH), 3.64-3.72 (m, 2H, CH$_2$O), 3.50-3.58 (m, 2H, CH$_2$N), 3.11-3.21 (m, 2H, CH$_2$), 2.71-2.93 (m, 3H, CH$_2$, CH), 1.29 (t, J=7.2 Hz, 3H, CH$_3$), OH not observed; HRMS calcd for C$_{13}$H$_{16}$N$_4$O$_2$ (M$^+$) m/z 260.1271, found 260.1273.

Example 103

[3-(Ethylamino)-1,4-dioxido-7,8-dihydro-6H-indeno[5, 6-e][1,2,4]triazin-7-yl]methanol (127). H$_2$O$_2$ (70%, 1.0 mL, ca. 20.0 mmol) was added dropwise to a stirred solution of 1-oxide 126 (71 mg, 0.27 mmol) in HOAc (3 mL) at 50° C. and the reaction was stirred at 50° C. for 20 h. The mixture was diluted with aqueous NaHCO$_3$ solution and extracted with DCM (5×50 mL). The combined organic fraction was dried and the solvent evaporated. The residue was purified by chromatography, eluting with a gradient (0-4%) of MeOH/DCM, to give 1,4-dioxide 127 (11 mg, 15%) as a red solid: mp (MeOH/DCM) 153-155° C.; $^1$H NMR δ 8.10 (s, 1H, H-9), 8.05 (s, 1H, H-5), 7.01 (br s, 1H, NH), 3.69 (d, J=6.5 Hz, 2H, CH$_2$O), 3.59-3.67 (m, 2H, CH$_2$N), 3.15-3.28 (m, 2H, CH$_2$), 2.90-3.03 (m, 2H, CH$_2$), 2.72-2.86 (m, 1H, CH), 1.35 (t, J=7.2 Hz, 3H, CH$_3$), OH not observed; HRMS calcd for C$_{13}$H$_{16}$N$_4$O$_3$ (M$^+$) m/z 276.1222, found 276.1222.

Example 104

Alternative Preparation of (3-Amino-1-oxido-7,8-dihydro-6H-indeno[5,6-e][1,2,4]triazin-7-yl)methanol (124)

2-Indanecarboxylic Acid (129). A mixture of 2-indanecarbonitrile (128) (Ksander, G. M. et al., *J. Med. Chem.* 2001, 44, 4677) (55.1 g, 0.385 mol), cHCl (100 mL) and dioxane (500 mL) was stirred at 60-70° C. for 41 h. The mixture was cooled and dioxane evaporated to give a residue, which was suspended in 1 M HCl (300 mL) and stirred at 20° C. for 15 h. The solid was filtered, washed with water and dried to give acid 129 (54.1 g, 87%) as a white solid: mp (EtOAc/pet. ether) 128° C. [lit. (Baeyer, A. & Perkin W. H., *Chem. Ber.* 1884, 17, 122) mp 130.2° C.]; $^1$H NMR δ 10.50 (br s, 1H, CO$_2$H), 7.14-7.25 (m, 4H, H-4, H-5, H-6, H-7), 3.21-3.43 (m, 5H, H-1, H-2, H-3).

5-Nitro-2-indanecarboxylic Acid (119) and 4-Nitro-2-indanecarboxylic Acid (130). 70% HNO$_3$ (46 mL, 798 mmol) was added dropwise (over 2 h 40 min) to a stirred solution of acid 129 (21.6 g, 133 mmol) in TFA (240 mL) at 0° C. and the solution stirred at 0° C. for 2 h 30 min. The mixture was poured onto ice (1.5 L) and stirred for 30 min. The mixture was extracted with DCM (3×200 mL), the combined organic fraction dried and the solvent evaporated. The residue was purified by chromatography, eluting with a gradient (0-30%) of EtOAc/pet. ether, to give a mixture (2.2:1 ratio) of 5-nitroindane 119 and 4-nitroindane 130 isomers (23.4 g, 85%) as a yellow solid. Chromatography of a small sample gave (i) 119 as a yellow solid: spectroscopically identical to the previously reported data (see Example 99); and (ii) 4-nitroindane 130 as needles: mp (EtOAc/pet. ether) 151-153° C.; $^1$H NMR δ 8.04 (dd, J=8.2 Hz, 0.6 Hz, 1H, H-5), 7.52 (dd, J=7.4 Hz, 0.6 Hz, 1H, H-7), 7.36 (br t, J=7.8 Hz, 1H, H-6), 3.72-3.86 (m, 2H, H-3), 3.31-3.52 (m, 3H, H-1, H-2), CO$_2$H not observed. Anal. calcd for C$_{10}$H$_9$NO$_4$: C, 58.0; H, 4.4; N, 6.8. Found: C, 58.1; H, 4.4; N, 6.8%.

(5-Nitro-2,3-dihydro-1H-inden-2-yl)methanol (120) and (4-Nitro-2,3-dihydro-1H-inden-2-yl)methanol (131). BH$_3$.DMS (10 M, 14.7 mL, 147 mmol) was added dropwise (over 20 min) to a stirred solution of acids 119 and 130 (ratio 2.2:1) (23.4 g, 113 mmol) in THF (150 mL) at 20° C. under N$_2$ and the solution was stirred for 90 min. The reaction was quenched with MeOH (150 mL) and the solvent evaporated. The residue was purified by chromatography, eluting with a gradient (10-30%) of EtOAc/pet. ether, to give a mixture (2.0:1 ratio) of alcohols 120 and 131 (20.9 g, 96%) as an oil which was used without further purification.

[5-(Acetylamino)-6-nitro-2,3-dihydro-1H-inden-2-yl] methyl Acetate (122). Two batches of nitroindanes 120 and 131 (20.9 g, 109 mmol) in MeOH (200 mL) were stirred with 5% Pd/C (500 mg) under H$_2$ (60 psi) for 16 h. The mixtures were combined and filtered through Celite, washed with MeOH and the solvent evaporated to give the corresponding aniline derivative, which was treated with Ac₂O (103 mL, 1.09 mol) and Et₃N (182 mL, 1.31 mol) in DCM (400 mL) at 20° C. for 25 h. The solvent was evaporated and the residue partitioned between EtOAc and water. The organic fraction was washed with water, dried and the solvent evaporated. The residue was dissolved in TFA (200 mL) and 70% HNO₃ (20.0 mL, 222 mmol) was added dropwise (over 1 h) at 0° C. and the reaction mixture was stirred at 20° C. for a further 30 min. The mixture was poured into ice/water (800 mL) and extracted with DCM (3×200 mL). The combined organic fraction was dried and the solvent evaporated. The residue was purified by chromatography, eluting with a gradient (0-25%) of EtOAc/pet. ether, to give acetate 122 (16.5 g, 52%) as a tan solid: spectroscopically identical to the sample prepared above (Example 99).

(5-Amino-6-nitro-2,3-dihydro-1H-inden-2-yl)methanol (123). See Example 100.

(3-Amino-1-oxido-7,8-dihydro-6H-indeno[5,6-e][1,2,4] triazin-7-yl)methanol (124). See Example 100.

Example 105

7-({[tert-Butyl(dimethyl)silyl]oxy}methyl)-7,8-dihydro-6H-indeno[5,6-e][1,2,4]triazin-3-amine 1-Oxide (132). iPr₂NEt (22.1 mL, 127 mmol) was added dropwise (over 30 min) to a mixture of alcohol 124 (8.56 g, 36.9 mmol) and TBDMSCl (8.34 g, 55.3 mmol) in DMF (100 mL) at 20° C. and the mixture was stirred at 20° C. for 1 h. The solvent was evaporated, the residue suspended in water (400 mL) and stirred at 0° C. for 1 h. The solid was filtered, washed with water (3×50 mL) and dried to give silylether 132 (12.1 g, 94%): mp (MeOH/EtOAc) 169-171° C.; $^1$H NMR [(CD₃)₂SO] δ 7.93 (s, 1H, H-9), 7.34 (s, 1H, H-5), 7.10 (s, 2H, NH₂), 3.55-3.63 (m, 2H, CH₂O), 3.20-3.12 (m, 2H, CH₂), 2.72-2.84 (m, 2H, CH₂), 2.58-2.68 (m, 1H, H-7), 0.83 [s, 9H, SiC(CH₃)₃], 0.02 [s, 6H, Si(CH₃)₂]; $^{13}$C NMR [(CD₃)₂SO] δ 159.8, 153.2, 148.6, 141.6, 128.7, 120.1, 114.1, 65.2, 41.3, 35.1, 34.3, 25.6 (3), 17.8, −5.52 (2). Anal. calcd for C₁₇H₂₆N₄O₂Si: C, 58.9; H, 7.6; N, 16.2. Found: C, 58.7; H, 7.6; N, 16.6%.

Example 106

7-({[tert-Butyl(dimethyl)silyl]oxy}methyl)-3-iodo-7,8-dihydro-6H-indeno[5,6-e][1,2,4]triazine 1-Oxide (133) and 7-({[tert-Butyl(dimethyl)silyl]oxy}methyl)-7,8-dihydro-6H-indeno[5,6-e][1,2,4]triazine 1-Oxide (134). tert-Butyl nitrite (3.26 mL, 27.4 mmol) was added to a stirred suspension of amine 132 (2.82 g, 8.15 mmol) in THF (100 mL) at 20° C. and the mixture stirred for 5 min. Diiodomethane (3.26 mL, 40.4 mmol) and CuI (164 mg, 0.82 mmol) were added and the mixture was stirred at reflux temperature for 95 min. The mixture was cooled and partitioned between EtOAc and water. The organic solution was dried and the solvent evaporated to give a brown oil which was purified by chromatography, eluting with a gradient (0-10%) of EtOAc/pet. ether, to give (i) iodide 133 (2.27 g, 61%) as a yellow solid: mp (EtOAc/pet. ether) 108-109° C.; $^1$H NMR δ 8.15 (s, 1H, H-9), 7.70 (s, 1H, H-5), 3.59-3.67 (m, 2H, CH₂O), 3.13-3.25 (m, 2H, CH₂), 2.93-3.05 (m, 2H, CH₂), 2.73-2.84 (m, 1H, H-7), 0.86 [s, 9H, SiC(CH₃)₃], 0.04 [s, 6H, Si(CH₃)₂]; $^{13}$C NMR δ 155.2, 149.6, 147.6, 133.5, 122.5, 121.7, 114.6, 65.3, 41.9, 36.0, 35.7, 25.8 (3), 18.2, −5.43 (2). Anal. calcd for C₁₇H₂₄IN₃O₂Si: C, 44.6; H, 5.3; N, 9.2. Found: C, 45.1; H, 5.4; N, 9.2%; and (ii) 1-oxide 134 (0.32 g, 12%) as a yellow solid: mp (EtOAc/pet. ether) 120-122° C.; $^1$H NMR δ 8.91 (s, 1H, H-3), 8.26 (s, 1H, H-9), 7.80 (s, 1H, H-5), 3.61-3.69 (m, 2H, CH₂O), 3.16-3.27 (m, 2H, CH₂), 2.96-3.07 (m, 2H, CH₂), 2.74-2.85 (m, 1H, H-7), 0.86 [s, 9H, SiC(CH₃)₃], 0.04 [s, 6H, Si(CH₃)₂]; $^{13}$C NMR δ 154.2, 153.0, 149.4, 147.3, 134.6, 123.4, 114.6, 65.3, 41.9, 35.9, 35.6, 25.8 (3), 18.2, −5.43 (2). Anal. calcd for C₁₇H₂₅N₃O₂Si·¼H₂O: C, 60.8; H, 7.7; N, 12.5. Found: C, 60.8; H, 7.4; N, 12.5%.

Example 107

7-({[tert-Butyl(dimethyl)silyl]oxy}methyl)-3-ethyl-7,8-dihydro-6H-indeno[5,6-e][1,2,4]triazine 1-Oxide (135). Et₄Sn (1.47 mL, 7.5 mmol) and Pd(PPh₃)₄ (154 mg, 0.99 mmol) were added to a N₂-purged, stirred solution of iodide 133 (2.27 g, 4.97 mmol) in dry dioxane (30 mL) at 20° C. and the reaction mixture was stirred at reflux temperature under N₂. After 5 h more Et₄Sn (1.5 mL, 7.5 mmol) and Pd(PPh₃)₄ (150 mg, 0.98 mmol) were added and the mixture stirred at reflux temperature for 5 h. The mixture was cooled and partitioned between EtOAc and water. The organic layer was separated, dried and the solvent evaporated. The residue was purified by chromatography, eluting with a gradient (0-5%) of EtOAc/pet. ether, to give 1-oxide 135 (1.57 g, 88%) as a yellow solid: mp (EtOAc/pet. ether) 63-65° C.; $^1$H NMR δ 8.23 (s, 1H, H-9), 7.72 (s, 1H, H-5), 3.59-3.66 (m, 2H, CH₂O), 3.14-3.24 (m, 2H, CH₂), 2.92-3.06 (m, 4H, H-6, H-8), 2.72-2.83 (m, 1H, H-7), 1.43 (t, J=7.5 Hz, 3H, CH₃), 0.87 [s, 9H, SiC(CH₃)₃], 0.04 [s, 6H, Si(CH₃)₂]. Anal. calcd for C₁₉H₂₉N₃O₂Si: C, 63.5; H, 8.1; N, 11.7. Found: C, 63.3; H, 8.2; N, 11.4%.

Example 108

(3-Ethyl-1,4-dioxido-7,8-dihydro-6H-indeno[5,6-e][1,2,4]triazin-7-yl)methanol (136). H₂O₂ (70%, 1.5 mL, ca. 30.0 mmol) was added dropwise to a stirred solution of 1-oxide 135 (273 mg, 0.76 mmol) and HOAc (6 mL) at 50° C. and the reaction was stirred at 80° C. for 20 h. The mixture was cooled, water (50 mL) was added and the mixture was extracted with DCM (5×50 mL). The combined organic fraction was dried and the solvent evaporated to give a yellow oil which was treated with Et₃N (3 mL) in MeOH (20 mL) at 20° C. for 66 h. The solvent was evaporated and the residue was purified by chromatography, eluting with a gradient (0-5%) of MeOH/DCM, to give 1,4-dioxide 136 (35 mg, 18%) as a yellow solid: mp (MeOH/DCM) 157-158° C.; $^1$H NMR δ 8.31 (s, 1H, H-9), 8.26 (s, 1H, H-5), 3.72 (br d, J=5.8 Hz, 2H, CH₂O), 3.25-3.35 (m, 2H, CH₂), 3.20 (q, J=7.5 Hz, 2H, CH₂), 3.00-3.10 (m, 2H, CH₂), 2.81-2.92 (m, 1H, H-7H), 1.43 (t, J=7.5 Hz, 3H, CH₃), OH not observed; HRMS calcd for C₁₃H₁₅N₃O₃ (M⁺) m/z 261.1113, found 261.1115. Anal. calcd for C₁₃H₁₅N₃O₃: C, 59.8; H, 5.8; N, 16.1. Found: C, 59.6; H, 5.9; N, 15.9%.

Example 109

3-Allyl-7-({[tert-butyl(dimethyl)silyl]oxy}methyl)-7,8-dihydro-6H-indeno[5,6-e][1,2,4]triazine 1-Oxide (137). Allyltributyltin (4.35 mL, 14.1 mmol) and Pd(PPh₃)₄ (0.72 g, 0.64 mmol) were added to a N₂-purged, stirred solution of iodide 133 (5.88 g, 12.9 mmol) in DME (80 mL) at 20° C. and the reaction mixture was stirred at reflux temperature under N₂ for 8 h. The reaction mixture was cooled and partitioned between EtOAc and brine. The organic layer was separated, dried, and the solvent evaporated. The residue was purified by chromatography, eluting with a gradient (0-5%) of EtOAc/pet. ether, to give alkene 137 (4.75 g, 99%) as a yellow solid: mp (EtOAc/pet. ether) 49-52° C.; $^1$H NMR δ 8.23 (s, 1H, H-9), 7.74 (s, 1H, H-5), 6.17-6.24 (m, 1H, CH), 5.20-5.34 (m, 2H, CH$_2$), 3.75-3.80 (m, 2H, CH$_2$), 3.59-3.67 (m, 2H, CH$_2$O), 3.13-3.25 (m, 2H, CH$_2$), 2.92-3.04 (m, 2H, CH$_2$), 2.72-2.84 (m, 1H, H-7), 0.87 [s, 9H, SiC(CH$_3$)$_3$], 0.04 [s, 6H, Si(CH$_3$)$_2$]; $^{13}$C NMR δ 164.1, 154.1, 148.3, 147.6, 133.0, 132.4, 123.0, 118.2, 114.5, 65.4, 42.0, 41.7, 35.8, 35.5, 25.8 (3), 18.3, −5.41 (2); HRMS (FAB$^+$) calcd for C$_{20}$H$_{30}$N$_3$O$_2$Si (MH$^+$) m/z 372.2107, found 372.2110. Anal. calcd for C$_{20}$H$_{29}$N$_3$O$_2$Si.¼H$_2$O: C, 63.9; H, 7.9; N, 11.2. Found: C, 63.9; H, 7.7; N, 10.8%.

Example 110

3-[7-({[tert-Butyl(dimethyl)silyl]oxy}methyl)-1-oxido-7,8-dihydro-6H-indeno[5,6-e][1,2,4]triazin-3-yl]-1-propanol (138). A solution of 9-BBN (0.5 M, 32.5 mL, 16.3 mmol) in THF was added to a stirred solution of alkene 137 (4.02 g, 10.8 mmol) in THF (50 mL) at 20° C. under N$_2$ and the mixture was stirred at 20° C. for 30 min. The mixture was cooled to 0° C., a solution of sodium acetate (3 M, 25 mL, 75 mmol) and then H$_2$O$_2$ (70%, 25 mL, 468 mmol) were added carefully and stirred for 10 min. MeOH (100 mL) was added and the mixture stirred at 20° C. for 20 min. The mixture was partitioned between aqueous Na$_2$CO$_3$ solution and EtOAc. The combined organic fraction was dried and the solvent evaporated. The residue was purified by chromatography, using a gradient (50-70%) of EtOAc/pet. ether, to give alcohol 138 (2.08 g, 49%) as a pale yellow solid: mp (EtOAc/pet. ether) 93-94° C.; $^1$H NMR δ 8.22 (s, 1H, H-9), 7.72 (s, 1H, H-5), 3.79 (br q, J=5.1 Hz, 2H, CH$_2$O), 3.59-3.67 (m, 2H, CH$_2$OSi), 3.12-3.24 (m, 4H, CH$_2$), 2.93-3.03 (m, 2H, CH$_2$), 2.73-2.84 (m, 1H, H-7), 2.30 (br s, 1H, OH), 2.11-2.21 (m, 2H, CH$_2$), 0.87 [s, 9H, SiC(CH$_3$)$_3$], 0.04 [s, 6H, Si(CH$_3$)$_2$]; $^{13}$C NMR δ 165.7, 154.2, 148.3, 147.3, 132.3, 122.8, 114.5, 65.4, 62.2, 42.0, 35.8, 35.5, 34.0, 30.6, 25.8 (3), 18.3, −5.41 (2). Anal. calcd for C$_{20}$H$_{31}$N$_3$O$_3$S.¼H$_2$O: C, 61.7; H, 8.0; N, 10.8. Found: C, 61.5; H, 7.8; N, 10.9%.

Example 111

7-({[tert-Butyl(dimethyl)silyl]oxy}methyl)-3-[3-(4-morpholinyl)propyl]-7,8-dihydro-6H-indeno[5,6-e][1,2,4]triazine 1-Oxide (139). Methanesulfonyl chloride (54 μL, 1.32 mmol) was added dropwise to a stirred solution of alcohol 138 (467 mg, 1.20 mmol), and iPr$_2$NEt (0.42 mL, 2.40 mmol) in DCM (15 mL) at 0° C., and the solution was stirred at 0° C. for 20 min. Water (15 mL) was added and the mixture extracted with EtOAc (3×30 mL). The organic fraction was washed with dilute. Na$_2$CO$_3$ solution (30 mL) and water (30 mL). The organic solution was dried and the solvent evaporated to give a brown oil to which morpholine (1.05 mL, 12.0 mmol) in DMF (10 mL) was added and the solution stirred at 20° C. for 70 h. The solution was diluted with EtOAc (200 mL) and washed with Na$_2$CO$_3$ solution (30 mL) and water (30 mL). The organic solution was dried and the solvent evaporated. The residue was purified by chromatography, eluting with a gradient (0-30%) of EtOAc/DCM, to give 1-oxide 139 (492 mg, 67%) as an oil: $^1$H NMR δ 8.23 (s, 1H, H-9), 7.70 (s, 1H, H-5), 3.55-3.67 (m, 6H, CH$_2$OSi, 2×CH$_2$O), 3.14-3.24 (m, 2H, H-8), 2.93-3.07 (m, 4H, CH$_2$, H-6), 2.72-2.84 (m, 1H, H-7), 2.38-2.51 (m, 6H, 2×CH$_2$N), 2.03-2.14 (m, 2H, CH$_2$), 0.87 [s, 9H, SiC(CH$_3$)$_3$], 0.04 [s, 6H, Si(CH$_3$)$_2$]; HRMS (FAB$^+$) calcd for C$_{24}$H$_{39}$N$_4$O$_3$Si (MH$^+$) m/z 459.2791, found 459.2784.

Example 112

{3-[3-(4-Morpholinyl)propyl]-1-oxido-7,8-dihydro-6H-indeno[5,6-e][1,2,4]triazin-7-yl}methanol (140). A solution of silyl ether 139 (488 mg, 1.07 mmol), and 1 M HCl (1.18 mL) in MeOH (30 mL) was stirred at 20° C. for 3 h. The solvent was evaporated and the residue was crystallised from MeOH/EtOAc to give alcohol 140 (357 mg, 88%) as the hydrochloride salt: mp (MeOH/EtOAc) 210-212° C.; $^1$H NMR [(CD$_3$)$_2$SO] δ 11.19 (s, 1H, HCl), 8.16 (s, 1H, H-9), 7.80 (s, 1H, H-5), 4.70 (br s, 1H, OH), 3.75-3.99 (m, 4H, 2×CH$_2$O), 3.41 (d, J=6.6 Hz, 2H, CH$_2$O), 3.33-3.51 (m, 2H, CH$_2$N), 3.11-3.27 (m, 4H, CH$_2$N, H-8), 2.87-3.11 (m, 6H, 2×CH$_2$N, CH$_2$), 2.59-2.71 (m, 1H, H-7), 2.22-2.32 (m, 2H, CH$_2$); $^{13}$C NMR [(CD$_3$)$_2$SO] δ 163.6, 154.2, 148.4, 146.7, 131.8, 122.5, 113.8, 63.5, 63.0 (2), 55.0, 50.9 (2), 41.6, 35.4, 35.1, 33.1, 20.8. Anal. calcd for C$_{18}$H$_{24}$N$_4$O$_3$.HCl.¼CH$_3$OH: C, 56.4; H, 6.7; N, 14.4. Found: C, 56.3; H, 6.4; N, 14.6%.

Example 113

{3-[3-(4-Morpholinyl)propyl]-1,4-dioxido-7,8-dihydro-6H-indeno[5,6-e][1,2,4]triazin-7-yl}methanol (141). H$_2$O$_2$ (70%, 0.46 mL, 7.7 mmol) was added drop-wise (over 5 min) to a stirred solution of 1-oxide 140 (292 mg, 0.77 mmol), TFA (0.32 mL, 3.9 mmol), and TFAA (1.24 mL, 7.7 mmol) in DCM (25 mL) at 20° C. and the mixture stirred at 20° C. for 17 h. Another aliquot of H$_2$O$_2$ (70%, 0.46 mL, 7.7 mmol) and TFAA (1.24 mL, 7.7 mmol) were added and the mixture was stirred for 1 h. Aqueous NH$_3$ solution (2 M, 30 mL) was added at 0° C. and the mixture stirred at 0° C. for 10 min, then stirred at 20° C. for 20 min. The mixture was extracted with DCM (5×80 mL), the combined organic fraction was dried and the solvent evaporated. The residue was purified by chromatography, eluting with a gradient (0-5%) of MeOH/DCM, to give 1,4-dioxide 141 (169 mg, 61%) as a dull orange solid: mp (MeOH/DCM) 112-114° C.; $^1$H NMR δ 8.30 (s, 1H, H-9), 8.26 (s, 1H, H-5), 3.73 (d, J=6.4 Hz, 2H, CH$_2$O), 3.45 (br s, 4H, 2×CH$_2$O), 3.21-3.37 (m, 4H, H-8, CH$_2$), 3.00-3.09 (m, 2H, CH$_2$), 2.83-2.92 (m, 1H, H-7), 2.50 (t, J=6.4 Hz, 2H, CH$_2$N), 2.39 (br s, 4H, 2×CH$_2$N), 2.07-2.15 (m, 2H, CH$_2$), OH not observed; $^{13}$C NMR [(CD$_3$)$_2$SO] δ 154.1, 153.7, 149.3, 138.7, 133.5, 115.3, 113.3, 66.0 (2), 63.4, 57.2, 53.0 (2), 41.5, 35.6, 35.1, 28.0, 21.0. HRMS (FAB$^+$) calcd for C$_{18}$H$_{25}$N$_4$O$_4$ (MH$^+$) m/z 361.1876, found 361.1878.

Example 114

(3-Ethyl-1-oxido-7,8-dihydro-6H-indeno[5,6-e][1,2,4]triazin-7-yl)methanol (142). A solution of silylether 135 (1.57 g, 4.37 mmol), and 1 N HCl (5 mL) in MeOH (40 mL) was stirred at 20° C. for 1 h. The solution was partitioned between EtOAc and water. The organic layer was dried, the solvent evaporated and the residue was purified by chromatography, eluting with a gradient (0-2%) of MeOH/DCM, to give alcohol 142 (0.84 g, 79%) as a yellow solid: mp (MeOH/EtOAc) 122-123° C.; $^1$H NMR [(CD$_3$)$_2$SO] δ 8.13 (s, 1H, H-9), 7.77 (s, 1H, H-5), 4.71 (t, J=5.2 Hz, 1H, OH), 3.42 (dd, J=6.4 Hz, 5.2 Hz, 2H, CH$_2$O), 3.11-3.20 (m, 2H, CH$_2$), 2.86-2.96 (m, 4H, CH$_2$), 2.59-2.71 (m, 1H, H-7), 1.32 (t, J=7.5 Hz, 3H, CH$_3$); $^{13}$C NMR [(CD$_3$)$_2$SO] δ 165.9, 153.9, 148.1, 146.8, 131.6, 122.5, 113.8, 63.5, 41.6, 35.3, 35.0, 29.6, 11.8. Anal. calcd for C$_{13}$H$_{15}$N$_3$O$_2$: C, 63.7; H, 6.2; N, 17.1. Found: C, 63.9; H, 6.2; N, 17.4%.

Example 115

3-Ethyl-7-(4-morpholinylmethyl)-7,8-dihydro-6H-indeno[5,6-e][1,2,4]triazine 1-Oxide (143). Methanesulfonyl chloride (0.14 mL, 1.7 mmol) was added drop-wise to a stirred solution of alcohol 142 (347 mg, 1.42 mmol) and iPr$_2$NEt (0.49 mL, 2.84 mmol) in DCM (25 mL) at 0° C., and the solution was stirred at 0° C. for 1 h. Water (25 mL) was added and the mixture extracted with EtOAc (3×30 mL). The organic fraction was washed with dilute Na$_2$CO$_3$ solution (25 mL) and water (25 mL). The organic solution was dried and the solvent evaporated to give a yellow solid, which was treated with morpholine (0.37 mL, 4.3 mmol) in DMF (10 mL) at 100-110° C. for 10 h. The solution was diluted with EtOAc (200 mL) and washed with Na$_2$CO$_3$ solution (50 mL) and water (30 mL). The organic solution was dried and the solvent evaporated. The residue was purified by chromatography, eluting with a gradient (50-70%) of EtOAc/pet. ether, to give 1-oxide 143 (398 mg, 89%) as a pale yellow solid: mp (EtOAc) 111-112° C.; $^1$H NMR δ 8.24 (s, 1H, H-9), 7.73 (s, 1H, H-5), 3.73 (t, J=4.6 Hz, 4H, 2×CH$_2$O), 3.19-3.29 (m, 2H, CH$_2$), 3.02 (q, J=7.6 Hz, 2H, CH$_2$), 2.88-2.99 (m, 2H, CH$_2$), 2.77-2.88 (m, 1H, H-7), 2.47 (t, J=4.6 Hz, 4H, 2×CH$_2$N), 2.38 (d, J=7.6 Hz, 2H, CH$_2$), 1.43 (t, J=7.6 Hz, 3H, CH$_3$); $^{13}$C NMR δ 167.1, 153.6, 147.7, 147.6, 132.3, 123.1, 114.7, 67.0 (2), 63.3, 53.9 (2), 37.6, 37.3, 36.7, 30.6, 12.3. Anal. calcd for C$_{17}$H$_{22}$N$_4$O$_2$: C, 65.0; H, 7.1; N, 17.8. Found: C, 64.9; H, 7.1; N, 17.9%.

Example 116

3-Ethyl-7-(4-morpholinylmethyl)-7,8-dihydro-6H-indeno[5,6-e][1,2,4]triazine 1,4-Dioxide (144). H$_2$O$_2$ (70%, 0.95 mL, ca 16 mmol) was added drop-wise (over 10 min) to a stirred solution of 1-oxide 143 (503 mg, 1.6 mmol), TFAA (2.56 mL, 16.0 mmol) and TFA (0.66 mL, 8.0 mmol) in DCM (60 mL) at 20° C. and the mixture was stirred at 20° C. for 7 h. Dilute Na$_2$CO$_3$ solution (40 mL) was added and the mixture was extracted with DCM (5×80 mL). The combined organic fraction was dried and the solvent evaporated to give an oil which was purified by chromatography, eluting with a gradient (0-2%) of MeOH/DCM, to give 1,4-dioxide 144 (87 mg, 21%) as a yellow solid: mp (MeOH/DCM) 164-165° C.; $^1$H NMR δ 8.31 (s, 1H, H-9), 8.25 (s, 1H, H-5), 3.72 (t, J=4.6 Hz, 4H, 2×CH$_2$O), 3.17-3.34 (m, 4H, CH$_2$), 2.80-2.95 (m, 3H, CH$_2$, H-7), 2.45 (t, J=4.6 Hz, 4H, 2×CH$_2$N), 2.38 (d, J=7.7 Hz, 2H, CH$_2$), 1.43 (t, J=7.5 Hz, 3H, CH$_3$); $^{13}$C NMR δ 155.7, 154.1, 149.5, 139.2, 134.0, 116.3, 114.3, 67.0 (2), 63.1, 53.9 (2), 37.7, 37.2, 36.6, 23.8, 9.2. Anal. calcd for C$_{17}$H$_{22}$N$_4$O$_3$: C, 61.8; H, 6.7; N, 17.0. Found: C, 62.1; H, 6.7; N, 16.8%.

Example 117

2-(3-Amino-1-oxido-7,8-dihydro-6H-indeno[5,6-e][1,2,4]triazin-7-yl)ethanol (157)

(E)-2-(1-Oxo-1H-inden-2(3H)-ylidene)acetic Acid (146). A mixture of 1-indanone (145) (25 g, 190 mmol), glyoxylic acid (50% aqueous solution, 70 g, 470 mmol), and CH$_2$SO$_4$ (6.25 mL) in dioxane (25 mL) were stirred at reflux temperature for 4 h. The mixture was cooled, the product filtered off, washed with water and dried to give acid 146 (32.8 g, 92%) as a white solid: mp 201-203° C. [lit. (Nagasawa et al., Japanese Patent 04338358, 1992) 205-206° C.]; $^1$H NMR [(CD$_3$)$_2$SO] δ 12.00 (br s, 1H, OH), 7.73-7.80 (m, 2H, H-5, H-7), 7.68 (br d, J=7.7 Hz, 1H, H-4), 7.49 (t, J=7.9 Hz, 1H, H-6), 6.55 (t, J=2.4 Hz, 1H, CHCO$_2$), 4.08 (d, J=1.8 Hz, 2H, H-3).

2-(2,3-Dihydro-1H-inden-2-yl)acetic Acid (147). A solution of acid 146 (10.0 g, 53.1 mmol) in MeOH (45 mL) and dioxane (150 mL) with Pd/C (10%, 1.0 g) was stirred under H$_2$ (40 psi) for 16 h. The mixture was filtered through Celite and the solvent evaporated to give acid 147 as an off-white solid: mp 85-88° C. [lit. (Nagasawa et al., Japanese Patent 04338358, 1992) 89-91° C.]; $^1$H NMR δ 8.47 (br s, 1H, OH), 7.08-7.18 (m, 4H, H-4, H-5, H-6, H-7), 2.99-3.06 (m, 2H, H-1, H-3), 2.69-2.74 (m, 1H, H-2), 2.53-2.60 (m, 2H, H-1, H-3), 2.48 (d, J=7.4 Hz, 2H, CH$_2$CO$_2$).

Ethyl 2-(2,3-Dihydro-1H-inden-2-yl)acetate (148). A solution of acid 147 (32.0 g, 180 mmol) in dry EtOH (250 mL) and CH$_2$SO$_4$ (2.0 mL) was stirred at reflux temperature under N$_2$ for 16 h. The solvent was evaporated, the residue partitioned between ice/water (200 mL) and DCM (50 mL) and the aqueous layer extracted with DCM (2×40 mL). The combined organic layer was washed with saturated aqueous NaHCO$_3$ solution and water, dried and the solvent evaporated to yield ester 148 (33.3 g, 90%) (lit. Tanaka, et. al., *J. Med. Chem.* 1994, 37, 2071-2078) as a brown oil: $^1$H NMR δ 7.10-7.21 (m, 4H, H-4, H-5, H-6, H-7), 4.15 (q, J=7.1 Hz, 2H, CH$_2$), 3.10-3.45 (m, 2H, H-1, H-3), 2.82-2.94 (m, 1H, H-2), 2.62-2.68 (m, 2H, H-1, H-3), 4.48 (d, J=7.4 Hz, 2H, CH$_2$CO$_2$), 1.27 (t, J=7.1 Hz, 2H, CH$_3$).

2-(2,3-Dihydro-1H-inden-2-yl)ethanol (149). A solution of ester 148 (68.8 g, 337 mmol) in dry THF (250 mL) was added to dropwise to a suspension of LiAlH$_4$ (20.0 g, 501 mmol) in dry THF (500 mL) at 0° C. and the resulting mixture was stirred for 1.5 h. EtOAc was added to quench excess LiAlH$_4$ and then aqueous H$_2$SO$_4$ solution (10%, 1 L) was added and the organic fraction separated. The aqueous solution was extracted with EtOAc (3×250 mL), and the combined organic fraction dried and the solvent evaporated to give alcohol 149 (54.5 g, 100%) (lit. Tanaka, et. al., *J. Med. Chem.* 1994, 37, 2071-2078) as a yellow oil: $^1$H NMR δ 7.16-7.25 (m, 2H, H$_{arom}$), 7.09-7.14 (m, 2H, H$_{arom}$), 3.74 (t, J=6.8 Hz, 2H, CH$_2$O), 3.03-3.10 (m, 2H, CH$_2$), 2.53-2.66 (m, 3H, CH$_2$, CH), 1.82 (q, J=6.8 Hz, 2H, CH$_2$), OH not observed.

2-(2,3-Dihydro-1H-inden-2-yl)ethyl Acetate (150). Ac$_2$O (47 mL, 505 mmol) in DCM (50 mL) was added over 1 h to a stirred solution of alcohol 149 (54.5 g, 337 mmol), pyridine (52 mL, 981 mmol) and DMAP (1.65 g, 13 mol) in DCM (400 mL) and the resulting solution was stirred at 20° C. for 16 h. H$_2$O (200 mL) was added, and the mixture stirred for 1 h. The organic fraction was washed with aqueous HCl solution (1 M, 100 mL) and H$_2$O (150 mL), dried and the solvent evaporated to give acetate 150 (68.4 g, 99%) as a pale brown oil: $^1$H NMR δ 7.16-7.19 (m, 2H, H$_{arom}$), 7.09-7.14 (m, 2H, H$_{arom}$), 4.16 (t, J=6.8 Hz, 2H, CH$_2$O), 3.04-3.10 (m, 2H, CH$_2$), 2.48-2.66 (m, 3H, CH$_2$, CH), 2.05 (s, 3H, COCH$_3$), 1.85 (q, J=6.8 Hz, 2H, CH$_2$); $^{13}$C NMR δ 171.1, 143.0 (2), 126.2 (2), 124.4 (2), 63.5, 39.1 (2), 37.0, 34.3, 21.0. Anal calcd for C$_{13}$H$_{16}$O$_2$: C, 76.4; H, 7.9. Found: C, 76.6; H, 7.9%.

Mixture of 2-(5-Nitro-2,3-dihydro-1H-inden-2-yl)ethyl Acetate (151) and 2-(4-Nitro-2,3-dihydro-1H-inden-2-yl)ethyl Acetate (152). Cu(NO$_3$)$_2$.3H$_2$O (71 g, 294 mmol) was added in portions to a stirred solution of the acetate 150 (30 g, 147 mmol) in DCM (500 mL) and Ac$_2$O (500 mL) at 0° C., the resulting mixture allowed to warm to 20° C. and stirred for 16 h. The reaction mixture was poured into ice-water/cNH$_3$ (2.5:1, 3.5 L) and the layers separated. The aqueous layer was extracted with EtOAc (2×500 mL), the combined organic layer dried, the solvent evaporated and the residue was purified by chromatography, eluting with 20% EtOAc/pet. ether, to give an inseparable mixture of 2-(5-nitro-2,3-dihydro-1H- inden-2-yl)ethyl acetate (151) and 2-(4-nitro-2,3-dihydro-1H-inden-2-yl)ethyl acetate (152) (ratio 151:152=3:1) (26.5 g, 72%) as a yellow oil which was used without further purification: Anal. calcd for $C_{13}H_{15}NO_4$: C, 62.6; H, 6.1; N, 5.6. Found: C, 62.9; H, 6.1; N, 5.4%.

Mixture of 2-(5-Acetamido-2,3-dihydro-1H-inden-2-yl) ethyl Acetate (153) and 244-Acetamido-2,3-dihydro-1H-inden-2-yl)ethyl Acetate (154). A solution of the nitro-compounds (151 and 152) (13.0 g, 52 mmol) in EtOH (50 mL) and MeOH (50 mL) with Pd/C (10%, 250 mg) was stirred under $H_2$ (45 psi) for 5 h. The solution was filtered through Celite and the solvent evaporated. The residue was dissolved in dioxane (130 mL), $Ac_2O$ (12.3 mL, 130 mmol) added, and the mixture stirred at 20° C. for 16 h. $H_2O$ (60 mL) and then aqueous $NH_3$ solution (ca 7 M, ca. 50 mL) was added until the solution was basic. The mixture was extracted with EtOAc (3×120 mL), the combined organic layer dried and the solvent evaporated to give an inseparable mixture of acetates 153 and 154 (ratio 153:154=3:1) (13.5 g, 99%) as an orange oil which was used without further purification: HRMS (FAB$^+$) calcd for $C_{15}H_{20}NO_3$ (MH$^+$) m/z 262.1443, found 262.1443.

2-(5-Acetamido-6-nitro-2,3-dihydro-1H-inden-2-yl)ethyl Acetate (155). $HNO_3$ (70%, 13.6 mL, 214 mmol) was added dropwise to a solution of the acetates (153 and 154) (27 g, 103 mmol) in TFA (120 mL) at 0° C. and the solution allowed to warm to 20° C. over 1.5 h. The mixture was poured into ice/water (500 mL) and made basic with $cNH_3$ (ca. 150 mL). The mixture was extracted with DCM (3×250 mL), the combined organic layer dried and the solvent evaporated. The residue was filtered through a plug of silica, eluting with 50% EtOAc/pet. ether, the solvent evaporated and the residue recrystallised from EtOAc/pet. ether to give acetamide 155 (18.2 g, 55%) as a pale yellow solid: mp 89-91° C.; $^1$H NMR δ 10.36 (br s, 1H, NH), 8.55 (s, 1H, H-4), 8.01 (s, 1H, H-7), 4.16 (t, J=6.6 Hz, 2H, $CH_2O$), 3.06-3.18 (m, 2H, H-1, H-3), 2.57-2.73 (m, 3H, H-1, H-2, H-3), 2.27 (s, 3H, $COCH_3$), 2.07 (s, 3H, $COCH_3$), 1.85 (q, J=6.6 Hz, 2H, $CH_2$); $^{13}$C NMR δ 171.0, 167.0, 153.0, 138.6, 135.4, 133.9, 121.1, 117.6, 63.1, 39.7, 38.2, 37.4, 34.1, 25.6, 21.0. Anal calcd for $C_{15}H_{18}N_2O_5$: C, 58.8; H, 5.9; N, 9.1. Found: C, 59.2; H, 6.0; N, 8.9%.

2-(5-Amino-6-nitro-2,3-dihydro-1H-inden-2-yl)ethanol (156). Acetamide 155 (24.0 g, 78 mmol) was suspended in MeOH (350 mL), $H_2O$ (180 mL) and cHCl (150 mL), and stirred at reflux temperature for 1 h. The resulting orange solution was cooled to 20° C. and the solvent evaporated to give nitroaniline 156 (17.4 g, 100%) as an orange solid: mp 89-91° C.; $^1$H NMR δ 7.90 (s, 1H, H-4), 6.62 (s, 1H, H-7), 6.02 (br s, 2H, $NH_2$), 3.74 (t, J=6.6 Hz, 2H, $CH_2O$), 2.96-3.04 (m, 2H, H-1, H-3), 2.49-2.60 (m, 3H, H-1, H-2, H-3), 1.77 (q, J=6.6 Hz, 2H, $CH_2$), 1.40 (br s, 1H, OH); $^{13}$C NMR δ 153.4, 144.3, 133.0, 131.2, 120.9, 113.5, 61.7, 39.3, 38.2, 37.7, 37.2. Anal. calcd for $C_{11}H_{14}N_2O_3$: C, 59.5; H, 6.4; N, 12.6. Found: C, 59.7; H, 6.3; N, 12.2%.

2-(3-Amino-1-oxido-7,8-dihydro-6H-indeno[5,6-e][1,2,4]triazin-7-yl)ethanol (157). A mixture of nitroaniline 156 (17.6 g, 79 mmol) and cyanamide (19.8 g, 471 mmol) were melted together at 60° C. and cHCl (35 mL) was added dropwise. The solution was heated to 100° C., stirred for 1 h, cooled to ca. 50° C. and the mixture made strongly basic with 7.5 M NaOH solution. The mixture was heated to 100° C. for 3 h, cooled to 20° C. and diluted with ice/water. The resulting precipitate was filtered, washed with $H_2O$ (100 mL) and $Et_2O$ (30 mL), and dried to give 1-oxide 157 (18.4 g, 94%) as a yellow-green solid: mp 230-235° C.; $^1$H NMR [(CD$_3$)$_2$SO] δ 7.92 (s, 1H, H-9), 7.33 (s, 1H, H-5), 7.11 (br s, 2H, $NH_2$), 4.45 (br s, 1H, OH), 3.49 (t, J=6.6 Hz, 2H, $CH_2O$), 3.06-3.15 (m, 2H, H-6, H-8), 2.59-2.69 (m, 2H, H-6, H-8), 2.49-2.54 (m, 1H, H-7), 1.63 (q, J=6.6 Hz, 2H, $CH_2$); HRMS calcd for $C_{12}H_{14}N_4O_2$ (M$^+$) m/z 246.1117, found 246.1115.

Example 118

2-(3-Iodo-1-oxido-7,8-dihydro-6H-indeno[5,6-e][1,2,4]triazin-7-yl)ethanol (158). tert-BuNO$_2$ (4.0 mL, 30.6 mmol) was added to a suspension of amine 157 (2.5 g, 10.2 mmol), CuI (2.04 g, 10.7 mmol) and I2 (1.42 g, 5.6 mmol) in THF (50 mL) and the mixture stirred at reflux temperature for 4 h. The mixture was cooled to 20° C., filtered and the solvent evaporated. The residue was dissolved in EtOAc (50 mL), washed with aqueous $Na_2S_2O_4$ (5%, 2×25 mL), dried, and the solvent evaporated. The residue was purified by chromatography, eluting with 5% MeOH/DCM, to give iodide 158 (1.49 g, 41%) as a pale yellow solid: mp 96-99° C.; $^1$H NMR δ 8.15 (s, 1H, H-9), 7.70 (s, 1H, H-5), 3.79 (t, J=6.5 Hz, 2H, $CH_2O$), 3.25-3.33 (m, 2H, H-6, H-8), 2.68-2.86 (m, 3H, H-6, H-7, H-8), 1.84 (q, J=6.5 Hz, 2H, $CH_2$), 1.42 (br s, 1H, OH); $^{13}$C NMR δ 155.1, 149.4, 147.6, 133.5, 122.4, 121.8, 114.5, 61.4, 39.5, 39.2, 37.8, 37.5; HRMS (FAB$^+$) calcd for $C_{12}H_{13}IN_3O_2$ (MH$^+$) m/z 358.0053, found 358.0053.

Example 119

3-Iodo-7-(2-(tetrahydro-2H-pyran-2-yloxy)ethyl)-7,8-dihydro-6H-indeno[5,6-e][1,2,4]triazine 1-Oxide (159). Dihydropyran (2.6 mL, 28.6 mmol) was added dropwise to a solution of alcohol 158 (3.4 g, 9.5 mmol) and PPTS (0.60 g, 2.4 mmol) in DCM (150 mL) and the resulting solution stirred at 20° C. for 1 h. The solvent was evaporated and the residue purified by chromatography, eluting with 50% EtOAc/pet. ether, to give a mixture of diastereoisomers of iodide 159 (4.1 g, 98%) as a pale yellow solid: mp 80-82° C.; $^1$H NMR δ 8.15 (s, 1H, H-9), 7.70 (s, 1H, H-5), 4.58-4.60 (m, 1H, CHO), 3.84-3.86 (m, 2H, $CH_2O$), 3.48-3.54 (m, 2H, $CH_2O$), 3.24-3.29 (m, 2H, H-6, H-8), 2.72-2.86 (m, 3H, H-6, H-7, H-8), 1.72-1.88 (m, 4H, $CH_2$), 1.52-1.61 (m, 4H, $CH_2$); $^{13}$C NMR δ 155.2, 149.6, 147.6, 133.5, 122.41 and 122.40, 121.8, 114.52 and 114.50, 99.1, 66.0, 62.6, 39.7 and 39.5, 39.4 and 39.2, 38.0, 35.1, 30.8, 25.4, 19.7; HRMS (FAB$^+$) calcd for $C_{17}H_{21}IN_3O_3$ (MH$^+$) m/z 442.0628, found 442.0630.

Example 120

3-Ethyl-7-(2-(tetrahydro-2H-pyran-2-yloxy)ethyl)-7,8-dihydro-6H-indeno[5,6-e][1,2,4]triazine 1-Oxide (160). Pd(PPh$_3$)$_4$ (0.65 g, 0.57 mmol) was added to a N$_2$-flushed solution of iodide 159 (2.5 g, 5.7 mmol) and SnEt$_4$ (1.7 mL, 8.5 mmol) in DME (150 mL) under N$_2$ and the mixture heated to 85° C. for 16 h. The reaction mixture was cooled, the solvent evaporated and the residue purified by chromatography, eluting with 20% EtOAc/pet. ether, to give to give a mixture of diastereoisomers of 1-oxide 160 (1.56 g, 80%) as a pale green oil: $^1$H NMR δ 8.22 (s, 1H, H-9), 7.71 (s, 1H, H-5), 4.59-4.61 (m, 1H, CHO), 3.85-3.89 (m, 2H, $OCH_2$), 3.49-3.53 (m, 2H, $CH_2$), 3.24-3.31 (m, 2H, H-6, H-8), 3.02 (q, J=7.6 Hz, 2H, $CH_2$), 2.64-2.87 (m, 3H, H-6, H-7, H-8), 1.53-1.87 (m, 8H, 4×$CH_2$), 1.43 (t, J=7.6 Hz, 3H, $CH_3$); $^{13}$C NMR δ 166.5, 153.4, 147.5, 147.1, 131.7, 122.16 and 122.15, 113.8, 98.5, 65.6, 62.0, 39.0 and 38.9, 38.6 and 38.5, 37.4, 34.6, 30.2, 30.1, 24.9, 19.2, 11.8.

Example 121

2-(3-Ethyl-1-oxido-7,8-dihydro-6H-indeno[5,6-e][1,2,4]triazin-7-yl)ethanol (161). Methanesulfonic acid (3 drops) was added to a stirred solution of tetrahydropyranyl ether 160 (1.10 g, 3.2 mmol) in MeOH (30 mL) and the mixture was stirred at 20° C. for 1 h. The solvent was evaporated and the residue purified by chromatography, eluting with 5% MeOH/DCM, to give 1-oxide 161 (783 mg, 94%) as a yellow solid: mp 96-99° C.; $^1$H NMR δ 8.23 (s, 1H, H-9), 7.72 (s, 1H, H-5), 3.80 (t, J=6.5 Hz, 2H, $CH_2O$), 3.25-3.33 (m, 2H, H-6, H-8), 3.02 (q, J=7.6 Hz, 2H, $CH_2$), 2.68-2.86 (m, 3H, H-6, H-7, H-8), 1.84 (q, J=6.5 Hz, 2H, $CH_2$), 1.43 (t, J=7.6 Hz, 3H, $CH_3$), 1.40-1.45 (m, 1H, OH); $^{13}$C NMR δ 167.1, 153.8, 147.9, 147.6, 132.3, 122.7, 114.3, 61.5, 39.4, 39.1, 37.9, 37.5, 30.6, 12.3; HRMS (FAB$^+$) calcd for $C_{14}H_{18}N_3O_2$ (MH$^+$) m/z 260.1399, found 260.1397.

Example 122

2(3-Ethyl-1,4-dioxido-7,8-dihydro-6H-indeno[5,6-e][1,2,4]triazin-7-yl)ethanol (162). $H_2O_2$ (70%, 0.27 mL, ca. 5.6 mmol) was added dropwise to a stirred solution of TFAA (0.77 mL, 5.6 mmol) in DCM (10 mL) at 0° C. The solution was stirred at 20° C. for 10 min, then cooled to 0° C. and added to a solution of 1-oxide 161 (144 mg, 0.56 mmol) and TFA (0.1 mL, 1.2 mmol) in $CHCl_3$ (10 mL) at 0° C. The solution was stirred at 20° C. for 22 h, diluted with dilute aqueous $NH_3$ solution until basic and extracted with $CHCl_3$ (3×20 mL). The combined organic fraction was stirred with $Et_3N$ for 45 min, dried and the solvent evaporated. The residue was purified by chromatography, eluting with EtOAc/pet. ether, to give (i) starting material 161 (35 mg, 24%) and (ii) 1,4-dioxide 162 (92 mg, 60%) as a yellow solid: mp 152-155° C.; $^1$H NMR δ 8.29 (s, 1H, H-9), 8.24 (s, 1H, H-5), 3.77-3.82 (m, 2H, $CH_2O$), 3.29-3.38 (m, 2H, H-6, H-8), 3.20 (q, J=7.5 Hz, 2H, $CH_2$), 2.73-2.90 (m, 3H, H-6, H-7, H-8), 1.84 (q, J=6.6 Hz, 2H, $CH_2$), 1.43 (t, J=7.5 Hz, 3H, $CH_3$), 1.34 (t, J=4.9 Hz, 1H, OH); $^{13}$C NMR δ 155.8, 154.3, 149.8, 139.2, 133.8, 115.9, 113.9, 61.3, 39.6, 39.1, 37.8, 37.5, 23.9, 9.3. Anal. calcd for $C_{14}H_{17}N_3O_3$: C, 61.1; H, 6.2; N, 15.3. Found: C, 60.8; H, 6.3; N, 14.9%.

Example 123

3-Ethyl-7-[2-(4-morpholinyl)ethyl]-7,8-dihydro-6H-indeno[5,6-e][1,2,4]triazine 1-Oxide (163). Methanesulfonyl chloride (0.18 mL, 2.3 mmol) was added to a solution of alcohol 161 (457 mg, 1.76 mmol) and $Et_3N$ (0.37 mL, 2.6 mmol) in DCM (30 mL) at 0° C., and the mixture was stirred for 1 h. Saturated aqueous $KHCO_3$ solution (20 mL) was added and the aqueous layer extracted with DCM (20 mL). The combined organic layer was dried and the solvent evaporated to give a pale yellow solid (560 mg, 94%) that was used without further purification. The mesylate (560 mg, 1.7 mmol) was dissolved in dry DMF (15 mL), and morpholine (0.22 mL, 2.5 mmol) and $Et_3N$ (0.35 mL, 2.5 mmol) added. The solution was stirred at 100° C. for 3.5 h, cooled and the solvent evaporated. The residue was purified by chromatography, eluting with 5% MeOH/DCM, to give 1-oxide 163 (265 mg, 50%) as a brown oil: $^1$H NMR δ 8.22 (s, 1H, H-9), 7.71 (s, 1H, H-5), 3.73 (t, J=4.7 Hz, 4H, 2×$CH_2O$), 3.23-3.30 (m, 2H, H-6, H-8), 3.01 (q, J=7.6 Hz, 2H, $CH_2$), 2.75-2.84 (m, 2H, H-6, H-8), 2.58-2.62 (m, 1H, H-7), 2.43-2.48 (m, 6H, 3×$CH_2N$), 1.73-1.79 (m, 2H, $CH_2$), 1.43 (t, J=7.6 Hz, 3H, $CH_3$); $^{13}$C NMR δ 167.1, 153.8, 147.9, 147.6, 132.3, 122.7, 114.4, 66.9 (2), 57.5, 53.8 (2), 39.4, 39.1, 38.8, 32.0, 30.6, 12.3; HRMS (FAB$^+$) calcd for $C_{18}H_{24}N_4O_2$ (MH$^+$) m/z 328.1899, found 328.1899.

Example 124

3-Ethyl-7-[2-(4-morpholinyl)ethyl]-7,8-dihydro-6H-indeno[5,6-e][1,2,4]triazine 1,4-Dioxide (164). $H_2O_2$ (70%, 0.39 mL, ca. 8.1 mmol) was added dropwise to a stirred solution of TFAA (1.12 mL, 8.1 mmol) in DCM (15 mL) at 0° C. The solution was stirred at 20° C. for 10 min, then cooled to 0° C., added to a solution of 1-oxide 163 (265 mg, 0.81 mmol) and TFA (0.13 mL, 1.7 mmol) in $CHCl_3$ (15 mL) at 0° C. The solution was stirred at 20° C. for 4.5 h, diluted with dilute aqueous $NH_3$ solution until basic and extracted with $CHCl_3$ (3×30 mL). The combined organic fraction was dried and the solvent evaporated. The residue was purified by chromatography, eluting with a gradient (1-10%) of MeOH/DCM, to give (i) starting material 163 (62 mg, 23%) and (ii) 1,4-dioxide 164 (83 mg, 30%) as a yellow solid which was converted to the hydrochloride salt: mp 131-133° C.; $^1$H NMR δ 13.40 (br s, 1H, HCl), 8.30 (s, 1H, H-9), 8.25 (s, 1H, H-5), 4.32 (t, J=12.0 Hz, 2H, $CH_2$), 4.00 (dd, J=12.0, 3.0 Hz, 2H, H-6, H-8), 3.48 (d, J=12.0 Hz, 2H, H-6, H-8), 3.32-3.39 (m, 2H, $CH_2$), 3.20 (q, J=7.5 Hz, 2H, $CH_2$), 3.06-3.09 (m, 2H, $CH_2$), 2.88-2.94 (m, 4H, 2×$CH_2$), 2.67-2.73 (m, 1H, H-7), 2.25-2.28 (m, 2H, $CH_2$), 1.43 (t, J=7.5 Hz, 3H, $CH_3$); $^{13}$C NMR δ 156.0, 152.6, 148.2, 139.3, 133.9, 116.3, 114.3, 63.6 (2), 56.5, 52.0 (2), 39.1, 38.6, 37.8, 28.5, 23.9, 9.3; HRMS (FAB$^+$) calcd for $C_{18}H_{25}N_4O_3$ (MH$^+$) m/z 344.1848, found 344.1846.

Example 125

7,8,9,10-Tetrahydronaphtho[2,1-e][1,2,4]triazin-3-amine 1-Oxide (170)

N-(5,6,7,8-Tetrahydro-2-naphthalenyl)acetamide (166). fHNO$_3$ (8.6 mL, 144 mmol) in $CH_2SO_4$ (50 mL) was added dropwise to a stirred solution of α-tetralone (165) (20 g, 137 mmol) in $CH_2SO_4$ (300 mL) at 0° C. and the solution stirred for 1 h. The solution was poured into ice/water (2 L), stirred for 30 min, filtered and washed with water. The solid was dried and purified by chromatography, eluting with 20% EtOAc/pet. ether, to give (i) 5-nitro-3,4-dihydro-1(2H)-naphthalenone (4.1 g, 16%) as a white solid: $^1$H NMR δ 8.35 (dd, J=7.8, 1.4 Hz, 1H, H-6), 8.09 (dd, J=8.0, 1.4 Hz, 1H, H-8), 7.48 (br t, J=7.9 Hz, 1H, H-7), 3.22 (t, J=6.1 Hz, 2H, H-4), 2.74 (dd, J=6.8, 6.4 Hz, 2H, H-2), 2.13-2.21 (m, 2H, H-3); and (ii) 7-nitro-3,4-dihydro-1(2H)-naphthalenone (20.1 g, 77%) as a white solid: $^1$H NMR δ 8.86 (d, J=2.5 Hz, 1H, H-4), 8.30 (dd, J=8.4, 2.5 Hz, 1H, H-6), 7.46 (d, J=8.4 Hz, 1H, H-5), 3.09 (t, J=6.1 Hz, 2H, H-4), 2.74 (dd, J=7.0, 6.2 Hz, 2H, H-2), 2.17-2.25 (m, 2H, H-3).

A solution of 7-nitro-3,4-dihydro-1(2H)-naphthalenone (1.67 g, 8.7 mmol) in EtOAc/EtOH (1:1, 150 mL), water (15 mL) and cHCl (2 mL) with Pd/C (5%, 500 mg) was stirred vigorously under $H_2$ (60 psi) for 16 h. The suspension was filtered through Celite, washed with EtOH (4×10 mL) and the organic solvent evaporated. The aqueous residue was partitioned between DCM and dilute aqueous $NH_3$ solution and the organic fraction dried and the solvent evaporated. The residue was dissolved in dioxane (20 mL), and AcO (1.8 mL, 19.2 mmol) was added dropwise to the solution at 0° C. The solution was stirred at 20° C. for 16 h, diluted with water (50 mL), and partitioned between EtOAc and dilute aqueous $NH_3$ solution. The organic fraction was washed with water (3×20 mL), dried and the solvent evaporated to give N-(5,6,7,8-tetrahydro-2-naphthalenyl)acetamide 166 (1.57 g, 95%) as a white solid: $^1$H NMR δ 7.18-7.25 (m, 2H, H-1, NH), 7.15 (dd, J=8.2, 2.1 Hz, 1H, H-3), 7.00 (d, J=8.2 Hz, 1H, H-4), 2.69-2.77 (m, 4H, 2×CH$_2$), 2.15 (s, 3H, CH$_3$), 1.74-1.80 (m, 4H, 2×CH$_2$). The procedure was repeated a number of times to give N-(5,6,7,8-tetrahydro-2-naphthalenyl)acetamide 166 (10.21 g, 88% overall).

N-(3-Nitro-5,6,7,8-tetrahydro-2-naphthalenyl)acetamide (167) and N(1-Nitro-5,6,7,8-tetrahydro-2-naphthalenyl)acetamide (168). A solution of KNO$_3$ (5.73 g, 56.6 mmol) in CH$_2$SO$_4$ (25 mL) was added dropwise to a stirred solution of acetanilide 166 (10.21 g, 53.9 mmol) in CH$_2$SO$_4$ (150 mL) at 0° C. and the mixture stirred at 0° C. for 2 h. The mixture was poured into ice/water (1.5 L) and the suspension stirred for 30 min. The precipitate was filtered, washed with water and dried. The solid was purified by chromatography, eluting with a gradient (20-70%) of EtOAc/pet. ether, to give (i) N-(3-nitro-5,6,7,8-tetrahydro-2-naphthalenyl)acetamide (167) (840 mg, 7%) as a white solid: $^1$H NMR δ 10.24 (br s, 1H, NH), 8.44 (s, 1H, H-4), 7.93 (s, 1H, H-1), 2.82-2.86 (m, 2H, CH$_2$), 2.75-2.79 (m, 2H, CH$_2$), 2.27 (s, 3H, CH$_3$), 1.78-1.83 (m, 4H, 2×CH$_2$); and (ii) N-(1-nitro-5,6,7,8-tetrahydro-2-naphthalenyl)acetamide (168) (1.65, 9, 13%) as a white solid: $^1$H NMR δ 8.04 (br s, 1H, NH), 7.91 (br d, J=8.4 Hz, 1H, H-3), 7.24 (d, J=8.4 Hz, 1H, H-4), 2.78-2.82 (m, 2H, CH$_2$), 2.72-2.76 (m, 2H, CH$_2$), 2.18 (s, 3H, CH$_3$), 1.76-1.83 (m, 4H, 2×CH$_2$); and (iii) N-(4-nitro-5,6,7,8-tetrahydro-2-naphthalenyl)acetamide (7.58 g, 60%) as a white solid: $^1$H NMR δ 7.79 (d, J=2.0 Hz, 1H, H-3), 7.56 (d, J=2.0 Hz, 1H, H-1), 7.22 (br s, 1H, NH), 2.87-2.93 (m, 2H, CH$_2$), 2.80-2.84 (m, 2H, CH$_2$), 2.20 (s, 3H, CH$_3$), 1.76-1.83 (m, 4H, 2×CH$_2$).

1-Nitro-5,6,7,8-tetrahydro-2-naphthalenamine (169). A suspension of acetamide 168 (835 mg, 4.4 mmol) in 6 M HCl (50 mL) was stirred at 100° C. for 16 h. The suspension was cooled to 20° C., diluted with water (50 mL) and the pH adjusted to 8 with dilute aqueous NH$_3$ solution. The mixture was extracted with DCM (3×50 mL), the combined organic fraction dried and the solvent evaporated. The residue was purified by chromatography, eluting with 20% EtOAc/pet. ether, to give amine 169 (755 mg, 56%) as an orange solid: mp (EtOAc/pet. ether) 76-78° C.; $^1$H NMR δ 6.98 (d, J=8.4 Hz, 1H, H-4), 6.58 (d, J=8.4 Hz, 1H, H-3), 4.73 (br s, 2H, NH$_2$), 2.76-2.81 (m, 2H, CH$_2$), 2.65-2.69 (m, 2H, CH$_2$), 1.69-1.78 (m, 2H, CH$_2$). Anal. calcd for C$_{10}$H$_{12}$N$_2$O$_2$: C, 62.5; H, 6.3; N, 14.6. Found: C, 62.8; H, 6.1; N, 14.6%.

7,8,9,10-Tetrahydronaphtho[2,1-e][1,2,4]triazin-3-amine 1-Oxide (170). A mixture of nitroaniline 169 (0.73 g, 3.8 mmol) and cyanamide (0.63 g, 15.1 mmol) were mixed together at 100° C., cooled to 50° C., cHCl (5 mL) added carefully and the mixture heated at 100° C. for 2 h. The mixture was cooled to 50° C., 7.5 M NaOH solution added until the mixture was strongly basic and the mixture stirred at 100° C. for 3 h. The mixture was cooled, diluted with water (50 mL), filtered, washed with water (2×25 mL) and dried. The residue was purified by chromatography, eluting with a gradient (0-5%) of MeOH/DCM, to give amine 170 (124 mg, 15%) as a yellow powder: mp (MeOH) 271° C. (dec.); $^1$H NMR [(CD$_3$)$_2$SO] δ 7.43 (d, J=8.6 Hz, 1H, H-6), 7.26 (d, J=8.6 Hz, 1H, H-5), 7.00 (br s, 2H, NH$_2$), 3.36-3.40 (m, 2H, CH$_2$), 2.75-2.80 (m, 2H, CH$_2$), 1.67-1.75 (m, 4H, 2×CH$_2$); $^{13}$C NMR [(CD$_3$)$_2$SO] δ 159.5, 149.5, 137.3, 133.8, 131.1, 129.9, 123.0, 29.8, 28.7, 22.5, 21.0. Anal. calcd for C$_{11}$H$_{12}$N$_4$O: C, 61.1; H, 5.6; N, 25.9. Found: C, 61.0; H, 5.6; N, 26.0%.

Example 126

3-Chloro-7,8,9,10-tetrahydronaphtho[2,1-e][1,2,4]triazine 1-Oxide (171). NaNO$_2$ (73 mg, 1.0 mmol) was added in small portions to a stirred solution of amine 170 (114 mg, 0.5 mmol) in TFA (5 mL) at 0° C. and the solution stirred at 20° C. for 3 h. The solution was poured into ice/water, stirred 30 minutes, filtered, washed with water (3×30 mL) and dried. The solid was suspended in POCl$_3$ (10 mL) and DMF (0.2 mL) and stirred at 100° C. for 1 h. The solution was cooled, poured into ice/water, stirred for 30 minutes, filtered, washed with water (3×30 mL) and dried. The solid was suspended in DCM (100 mL), dried and the solvent evaporated. The residue was purified by chromatography, eluting with 5% EtOAc/DCM, to give chloride 171 (95 mg, 76%) as a pale yellow solid: mp (MeOH) 165-167° C.; $^1$H NMR δ 7.68 (d, J=8.6 Hz, 1H, H-5), 7.63 (d, J=8.6 Hz, 1H, H-6), 3.48-3.53 (m, 2H, CH$_2$), 2.92-2.97 (m, 2H, CH$_2$), 1.80-1.88 (m, 4H, 2×CH$_2$); $^{13}$C NMR δ 155.6, 148.3, 141.3, 138.6, 133.9, 132.8, 125.0, 31.1, 29.0, 22.6, 21.1. Anal. calcd for C$_{11}$H$_{10}$ClN$_3$O$_2$: C, 56.0; H, 4.3; N, 17.8. Found: C, 56.3; H, 4.4; N, 17.6%.

Example 127

N$^1$,N$^1$-Dimethyl-N$^2$-(1-oxido-7,8,9,10-tetrahydronaphtho[2,1-e][1,2,4]triazin-3-yl)-1,2-ethanediamine (172). N,N-Dimethyl-1,2-ethanediamine (0.12 mL, 1.0 mmol) was added to a stirred solution of chloride 171 (83 mg, 0.4 mmol) in DME (20 mL) and the solution stirred at reflux temperature for 3 h. The solvent was evaporated and the residue partitioned between DCM (50 mL) and dilute aqueous NH$_3$ solution (50 mL). The organic fraction was dried and the solvent evaporated. The residue was purified by chromatography, eluting with a gradient (0-10%) of MeOH/DCM, to give 1-oxide 172 (84 mg, 84%) as a yellow solid: mp (MeOH) 151-153° C.; $^1$H NMR δ 7.31-7.36 (m, 2H, H-5, H-6), 5.75 (br s, 1H, NH), 3.51-3.55 (m, 2H, CH$_2$N), 3.45-3.49 (m, 2H, CH$_2$), 2.72-2.83 (m, 2H, CH$_2$), 2.57 (br dd, J=6.0, 5.8 Hz, 2H, CH$_2$N), 2.29 [s, 6H, N(CH$_3$)$_2$], 1.75-1.82 (m, 4H, 2×CH$_2$); $^{13}$C NMR δ 158.4, 149.8, 137.4, 134.7, 132.4, 129.1, 123.5, 57.7, 45.0 (2), 38.6, 30.7, 29.3, 23.1, 21.6. Anal. calcd for C$_{15}$H$_{21}$N$_5$O.½CH$_3$OH: C, 61.4; H, 7.6; N, 23.1. Found: C, 61.2; H, 7.4; N, 23.4%.

Example 128

N$^1$-(1,4-Dioxido-7,8,9,10-tetrahydronaphtho[2,1-e][1,2,4]triazin-3-yl)-N$^2$,N$^2$-dimethyl-1,2-ethanediamine (173). H$_2$O$_2$ (70%, 0.12 mL, ca. 2.4 mmol) was added dropwise to a stirred solution of TFAA (0.34 mL, 2.4 mmol) in DCM (10 mL) at 0° C. The solution was stirred at 0° C. for 5 min, warmed to 20° C. for 10 min, then cooled to 0° C. and added to a stirred solution of 1-oxide 172 (70 mg, 0.2 mmol) and TFA (95 µL, 1.2 mmol) in DCM (10 mL) at 0° C. The solution was stirred at 20° C. for 6 h, diluted with dilute aqueous NH$_3$ solution (10 mL) and extracted with CHCl$_3$ (4×50 mL). The combined organic fraction was dried and the solvent evaporated. The residue was purified by chromatography, eluting with a gradient (0-10%) of MeOH/DCM, to give 1,4-dioxide 173 (38 mg, 52%) as a red solid: mp (MeOH/EtOAc) 139-142° C.; $^1$H NMR δ 8.06 (d, J=8.9 Hz, 1H, H-5), 7.51 (d, J=8.9 Hz, 1H, H-6), 7.38 (br s, 1H, NH), 3.59-3.66 (m, 2H, CH$_2$N), 3.49-3.55 (m, 2H, CH$_2$), 2.83-2.92 (m, 2H, CH$_2$), 2.61-2.65 (m, 2H, CH$_2$N), 2.32 [s, 6H, N(CH$_3$)$_2$], 1.80-1.88 (m, 4H, 2×CH$_2$).

Example 129

6,7,8,9-Tetrahydronaphtho[2,3-e][1,2,4]triazin-3-amine 1-Oxide (175)

3-Nitro-5,6,7,8-tetrahydro-2-naphthalenamine (174). A suspension of nitroacetamide 167 (151 mg, 0.65 mmol) in 6 M HCl (30 mL) was stirred at 100° C. for 6 h. The suspension was cooled to 20° C., diluted with water (50 mL) and the pH adjusted to 8 with aqueous $NH_3$ solution. The mixture was extracted with DCM (3×50 mL), the combined organic fraction dried, and the solvent evaporated to give amine 174 (113 mg, 100%) as an orange solid: $^1$H NMR δ 7.83 (s, 1H, H-4), 7.50 (s, 1H, H-1), 5.79 (s, 2H, $NH_2$), 2.67-2.73 (m, 4H, 2×$CH_2$), 1.78-1.83 (m, 4H, 2×$CH_2$).

6,7,8,9-Tetrahydronaphtho[2,3-e][1,2,4]triazin-3-amine 1-Oxide (175). A mixture of nitroaniline 174 (0.77 g, 4.0 mmol) and cyanamide (0.68 g, 16.0 mmol) were mixed together at 100° C., cooled to 50° C., cHCl (5 mL) added carefully and the mixture heated at 100° C. for 4 h. The mixture was cooled to 50° C., 7.5 M NaOH solution added until the mixture was strongly basic and the mixture stirred at 100° C. for 3 h. The mixture was cooled, diluted with water (100 mL) and filtered. The precipitate was washed with water (3×20 mL), washed with ether (10 mL) and dried. The residue was purified by chromatography, eluting with 5% MeOH/DCM, to give amine 175 (0.30 g, 35%) as a yellow powder: mp (MeOH/DCM) 270-274° C.; $^1$H NMR [$(CD_3)_2$SO] δ 7.83 (s, 1H, H-10), 7.23 (s, 1H, H-5), 7.11 (br s, 2H, $NH_2$), 2.82-2.89 (m, 4H, H-6, H-9), 1.72-1.77 (m, 4H, H-7, H-8); $^{13}$C NMR [$(CD_3)_2$SO] δ 159.8, 146.9, 146.8, 136.2, 128.0, 124.0, 118.1, 29.1, 28.5, 22.0, 21.8. Anal. calcd for $C_{11}H_{12}N_4O \cdot \frac{1}{4}H_2O$: C, 59.9; H, 5.7; N, 25.4. Found: C, 60.4; H, 5.5; N, 25.5%.

Example 130

3-Chloro-6,7,8,9-tetrahydronaphtho[2,3-e][1,2,4]triazine 1-Oxide (176). $NaNO_2$ (181 mg, 2.6 mmol) was added in small portions to a stirred solution of amine 175 (284 mg, 1.3 mmol) in TFA (10 mL) at 0° C. and the solution stirred at 20° C. for 2 h. The solution was poured into ice/water, stirred 30 minutes, filtered, washed with water (3×10 mL) and dried. The solid was suspended in $POCl_3$ (10 mL) and DMF (0.1 mL), and stirred at 100° C. for 1 h. The solution was cooled, poured into ice/water, stirred for 30 min, filtered, washed with water (3×10 mL) and dried. The solid was suspended in DCM (50 mL), dried and the solvent evaporated. The residue was purified by chromatography, eluting with 5% EtOAc/DCM, to give chloride 176 (173 mg, 56%) as a pale yellow solid: mp (EtOAc/DCM) 104-106° C.; $^1$H NMR δ 8.10 (s, 1H, H-10), 7.65 (s, 1H, H-5), 2.98-3.05 (m, 4H, H-6, H-9), 1.86-1.93 (m, 4H, H-7, H-8); $^{13}$C NMR δ 155.9, 149.5, 145.5, 143.1, 131.8, 126.9, 118.8, 30.2, 29.9, 22.2, 22.0. Anal. calcd for $C_{11}H_{10}ClN_3O$: C, 56.0; H, 4.3; N, 17.8. Found: C, 56.2; H, 4.3; N, 17.8%.

Example 131

$N^1$-(1-Oxido-6,7,8,9-tetrahydronaphtho[2,3-e][1,2,4]triazin-3-yl)-$N^2$,$N^2$-dimethyl-1,2-ethanediamine (177). N,N-Dimethylethanediamine (0.22 mL, 2.0 mmol) was added to a stirred solution of chloride 176 (157 mg, 0.7 mmol) in DME (30 mL) and the solution stirred at reflux temperature for 2 h. The solvent was evaporated and the residue partitioned between DCM (100 mL) and dilute aqueous $NH_3$ solution (50 mL). The organic fraction was dried and the solvent evaporated. The residue was purified by chromatography, eluting with a gradient (0-10%) of MeOH/DCM, to give 1-oxide 177 (167 mg, 87%) as a yellow solid: mp (MeOH) 149-151° C.; $^1$H NMR δ 7.96 (s, 1H, H-10), 7.29 (s, 1H, H-5), 5.81 (br s, 1H, NH), 3.50-3.55 (m, 2H, $CH_2$N), 2.85-2.92 (m, 4H, H-6, H-9), 2.56 (br t, J=6.0 Hz, 2H, $CH_2$N), 2.28 [s, 6H, N($CH_3$)$_2$], 1.81-1.85 (m, 4H, H-7, H-8); $^{13}$C NMR δ 158.7, 147.5, 147.0, 136.0, 129.1, 124.9, 119.0, 57.6, 45.1 (2), 38.7, 30.0, 29.3, 22.7, 22.5. Anal. calcd for $C_{15}H_{21}N_5O$: C, 62.7; H, 7.4; N, 24.4. Found: C, 62.5; H, 7.2; N, 24.3%.

Example 132

$N^1$-(1,4-Dioxido-6,7,8,9-tetrahydronaphtho[2,3-e][1,2,4]triazin-3-yl)-$N^2$,$N^2$-dimethyl-1,2-ethanediamine (178). $H_2O_2$ (70%, 0.27 mL, ca. 5.3 mmol) was added dropwise to a stirred solution of TFAA (0.8 mL, 5.3 mmol) in DCM (10 mL) at 0° C. The solution was stirred at 0° C. for 5 min, warmed to 20° C. for 10 min, then cooled to 0° C. and added to a stirred solution of 1-oxide 177 (153 mg, 0.5 mmol) and TFA (0.20 mL, 2.7 mmol) in DCM (10 mL) at 0° C. The solution was stirred at 20° C. for 16 h, diluted with dilute aqueous $NH_3$ solution (10 mL) and extracted with $CHCl_3$ (4×50 mL). The combined organic fraction was dried and the solvent evaporated. The residue was purified by chromatography, eluting with a gradient (0-10%) of MeOH/DCM, to give (i) starting material 177 (37 mg, 24%) and (ii) 1,4-dioxide 178 (47 mg, 29%) as a red solid: mp (MeOH) 148-151° C.; $^1$H NMR δ 8.02 (s, 1H, H-10), 7.98 (s, 1H, H-5), 7.35 (br s, 1H, NH), 3.63 (br t, J=6.0 Hz, 2H, $CH_2$N), 2.98-3.04 (m, 2H, $CH_2$), 2.91-2.96 (m, 2H, $CH_2$), 2.61 (br t, J=6.0 Hz, 2H, $CH_2$N), 2.30 [s, 6H, N($CH_3$)$_2$], 1.83-1.92 (m, 4H, H-7, H-8); $^{13}$C NMR δ 149.4, 148.7, 138.8, 136.5, 128.9, 120.1, 115.8, 57.6, 45.2 (2), 38.9, 30.3, 29.4, 22.3, 22.0. Anal. calcd for $C_{15}H_{21}N_5O_2 \cdot 1\frac{1}{2}H_2O$: C, 54.5; H, 7.3; N, 21.2. Found: C, 54.4; H, 6.3; N, 20.7%.

Example 133

N-[3-(4-Morpholinyl)propyl]-6,7,8,9-tetrahydronaphtho[2,3-e][1,2,4]triazin-3-amine 1-Oxide (179). 3-(4-Morpholinyl)propylamine (314 mg, 2.18 mmol) was added to a stirred solution of chloride 176 (171 mg, 0.73 mmol) in DME (8 mL) and the solution stirred at reflux temperature for 30 min. The solution was cooled and partitioned in between EtOAc and aqueous $Na_2CO_3$ solution. The organic fraction was washed with water, dried and the solvent evaporated to give 1-oxide 179 (250 mg, 100%) as an orange solid: mp (EtOAc) 115-116° C.; $^1$H NMR δ 7.97 (s, 1H, H-10), 7.29 (s, 1H, H-5), 6.14 (br s, 1H, NH), 3.75 (t, J=4.6 Hz, 4H, 2×$CH_2$O), 3.60 (q, J=6.2 Hz, 2H, $CH_2$N), 2.86-2.95 (m, 4H, H-6, H-9), 2.45-2.56 (m, 6H, 3×$CH_2$N), 1.80-1.88 (m, 6H, H-7, H-8, $CH_2$); $^{13}$C NMR δ 158.7, 147.5 147.0, 136.0, 129.1, 124.9, 119.0, 67.0 (2), 57.3, 53.8 (2), 40.8, 30.0, 29.3, 25.3, 22.7, 22.5. Anal. calcd for $C_{18}H_{25}N_5O_2$: C, 63.0; H, 7.3; N, 20.4. Found: C, 62.8; H, 7.4; N, 20.3%.

Example 134

N-[3-(4-Morpholinyl)propyl]-6,7,8,9-tetrahydronaphtho[2,3-e][1,2,4]triazin-3-amine 1,4-Dioxide (180). $H_2O_2$ (70%, 0.36 mL, ca. 6.0 mmol) was added dropwise to a stirred solution of TFAA (0.96 mL, 6.0 mmol) in DCM (5 mL) at 0° C. The solution was stirred at 0° C. for 5 min, warmed to 20° C. for 10 min, then added to a stirred solution of 1-oxide 179 (204 mg, 0.60 mmol) and TFA (0.24 mL, 3.0 mmol) in DCM (5 mL) at 0° C. The solution was stirred at 20° C. for 8 h, diluted with dilute aqueous $NH_3$ solution (10 mL) and extracted with DCM (5×50 mL). The combined organic fraction was dried and the solvent evaporated. The residue was purified by chromatography, eluting with a gradient (0-2%) of MeOH/DCM, to give 1,4-dioxide 180 (28 mg, 13%) as a red solid which was converted to the hydrochloride salt: mp (MeOH/DCM) 182-185° C.; $^1$H NMR [$(CD_3)_2$SO] δ 10.29 (s, 1H, HCl), 8.35 (br s, 1H, NH), 7.95 (s, 1H, H-10), 7.87 (s, 1H, H-5), 3.92-4.01 (m, 2H, $CH_2O$), 3.37 (m, 4H, $CH_2N$, $CH_2O$), 2.88-3.22 (m, 8H, 2×$CH_2N$, H-6, H-9), 2.53 (t, J=5.6 Hz, 2H, $CH_2N$), 2.00-2.09 (m, 2H, $CH_2N$), 1.74-1.83 (m, 4H, H-7, H-8); $^{13}$C NMR [$(CD_3)_2$SO] δ 149.2, 147.8, 138.0, 136.1, 128.5, 119.4, 115.0, 63.0 (2), 53.5, 50.9 (2), 37.9, 29.4, 28.5, 22.7, 21.7, 21.6. Anal. calcd for $C_{18}H_{25}N_5O_3·2HCl·2H_2O$: C, 46.2; H, 6.7; N, 15.0. Found: C, 46.3; H, 6.4; N, 15.0%.

Example 135

7,8,9,10-Tetrahydro-6H-cyclohepta[g][1,2,4]benzotriazin-3-amine 1-Oxide (186)

3-Nitro-6,7,8,9-tetrahydro-5H-benzo[a]cyclohepten-2-amine (185). A solution of fHNO$_3$ (7.5 mL) in $CH_2SO_4$ (50 mL) was added dropwise to a stirred suspension of 1-benzosuberone (181) (20 g, 124.8 mmol) in $CH_2SO_4$ (400 mL) at 0° C. The mixture was stirred a further 30 min and poured into ice/water. The slurry was extracted with ether (2×200 mL), the combined organic fraction dried, and the solvent evaporated. The residue was purified by chromatography, eluting with a gradient (10-30%) of EtOAc/pet. ether, to give 3-nitro-6,7,8,9-tetrahydro-5H-benzo[a]cyclohepten-5-one (14.75 g, 58%) as a tan powder: mp (EtOAc/pet. ether) 81-82° C.; $^1$H NMR δ 8.56 (d, J=2.5 Hz, 1H, H-4), 8.26 (dd, J=8.3, 2.5 Hz, 1H, H-2), 7.40 (d, J=8.3 Hz, 1H, H-1), 3.02-3.08 (m, 2H, H-9), 2.78-2.82 (m, 2H, H-6), 1.92-1.99 (m, 2H, H-8), 1.83-1.90 (m, 2H, H-7). A solution of ketone (14.7 g, 71.6 mmol) in EtOAc/EtOH (1:1, 100 mL) and 20% HCl (50 mL) was stirred vigorously under $H_2$ (60 psi) for 5 days. The suspension was filtered through Celite, washed with EtOH (4×20 mL) and the solvent evaporated. The residue was dissolved in DCM, washed with dilute $NH_3$, dried, and the solvent evaporated. The residue was dissolved in dioxane (300 mL), cooled to 0° C., and $Ac_2O$ (13.5 mL, 143.2 mmol) added dropwise. The solution was stirred at 20° C. for 16 h, diluted with water (500 mL) and the suspension filtered. The filtrate was extracted with EtOAc (2×100 mL); the combined organic fraction washed with water (50 mL) and dilute aqueous $NH_3$ solution (2×50 mL), dried, and the solvent evaporated. The combined solids were purified by chromatography, eluting with 50% EtOAc/pet. ether, to give N-(6,7,8,9-tetrahydro-5H-benzo[a]cyclohepten-2-yl)acetamide (10.89 g, 75%) as a tan powder: mp 112-114° C.; $^1$H NMR δ 7.20 (d, J=2.2 Hz, 1H, H-1), 7.15-7.21 (m, 2H, H-3, NH), 7.02 (d, J=8.0 Hz, 1H, H-4), 2.71-2.77 (m, 4H, H-5, H-9), 2.15 (s, 3H, $CH_3$), 1.78-1.86 (m, 2H, H-7), 1.56-1.66 (m, 4H, H-6, H-8). A solution of $KNO_3$ (5.96 g, 58.9 mmol) in $CH_2SO_4$ (25 mL) was added dropwise to a stirred suspension of amide (10.89 g, 53.6 mmol) in $CH_2SO_4$ (160 mL) at 0° C. and the mixture stirred at 0-5° C. for 2 h. The mixture was poured into ice/water, stirred 30 min, filtered, washed with water (3×30 mL) and dried. The solid was purified by chromatography, eluting with a gradient (20-50%) of EtOAc/pet. ether, to give (i) N-(3-nitro-6,7,8,9-tetrahydro-5H-benzo[a]cyclohepten-2-yl)acetamide (182) (2.62 g, 20%) as a white solid: $^1$H NMR δ 10.32 (br s, 1H, NH), 8.52 (s, 1H, H-4), 7.94 (s, 1H, H-1), 2.84-2.88 (m, 2H, H-5), 2.78-2.82 (m, 2H, H-9), 2.27 (s, 3H, $CH_3$), 1.80-1.87 (m, 2H, H-7), 1.61-1.69 (m, 4H, H-6, H-8); (ii) N-(1-nitro-6,7,8,9-tetrahydro-5H-benzo[a]cyclohepten-2-yl)acetamide (183) (0.85 g, 6%) as a white solid: $^1$H NMR δ 7.81 (br d, J=8.4 Hz, 1H, H-4), 7.77 (br s, 1H, NH), 7.23 (d, J=8.4 Hz, 1H, H-3), 2.82-2.86 (m, 2H, H-5), 2.65-2.69 (m, 2H, H-9), 2.27 (s, 3H, $CH_3$), 1.80-1.88 (m, 2H, H-7), 1.61-1.73 (m, 4H, H-6, H-8); and (iii) N-(4-nitro-6,7,8,9-tetrahydro-5H-benzo[a]cyclohepten-2-yl)acetamide (184) (6.91 g, 52%) as a white solid: $^1$H NMR δ 7.69 (br d, J=1.9 Hz, 1H, H-3), 7.45 (d, J=1.9 Hz, 1H, H-1), 7.24 (br s, 1H, NH), 2.84-2.88 (m, 2H, H-5), 2.78-2.81 (m, 2H, H-9), 2.19 (s, 3H, $CH_3$), 1.81-1.87 (m, 2H, H-7), 1.61-1.72 (m, 4H, H-6, H-8).

A suspension of 3-nitroacetamide 182 (2.62 g, 10.6 mmol) in 5 M HCl (100 mL) was stirred at reflux temperature for 16 h. The suspension was cooled, diluted with water (100 mL), filtered, washed with water (3×10 mL) and dried to give nitroaniline 185 (1.96 g, 90%) as a yellow powder: mp 137-139° C.; $^1$H NMR δ 7.83 (s, 1H, H-4), 6.55 (s, 1H, H-1), 5.96 (br s, 2H, $NH_2$), 2.67-2.73 (m, 4H, H-5, H-9), 1.76-1.81 (m, 2H, H-7), 1.59-1.67 (m, 4H, H-6, H-8); $^{13}$C NMR δ 153.1, 143.2, 133.0, 129.8, 125.1, 118.5, 36.6, 35.4, 32.1, 28.8, 28.2. Anal. calcd for $C_{11}H_{14}N_2O_2$: C, 64.1; H, 6.8; N, 13.6. Found: C, 64.0; H, 6.5; N, 13.5%.

7,8,9,10-Tetrahydro-6H-cyclohepta[g][1,2,4]benzotriazin-3-amine 1 Oxide (186). A mixture of nitroaniline 185 (2.26 g, 11.0 mmol) and cyanamide (1.84 g, 43.8 mmol) were mixed together at 100° C., cooled to 50° C., cHCl (10 mL) added carefully and the mixture heated at 100° C. for 4 h. The mixture was cooled to 50° C., 7.5 M NaOH solution added until the mixture was strongly basic and the mixture stirred at 100° C. for 3 h. The mixture was cooled, diluted with water (100 mL), filtered, washed with water (3×20 mL), washed with ether (10 mL) and dried. The residue as purified by chromatography, eluting with 5% MeOH/DCM, to give amine 186 (0.26 g, 10%) as a yellow powder: mp (MeOH) 261-265° C.; $^1$H NMR [$(CD_3)_2$SO] δ 7.86 (s, 1H, H-11), 7.29 (s, 1H, H-5), 7.13 (br s, 2H, $NH_2$), 2.84-2.90 (m, 4H, H-6, H-10), 1.74-1.80 (m, 2H, H-8), 1.58-1.67 (m, 4H, H-7, H-9); $^{13}$C NMR [$(CD_3)_2$SO] δ 160.2, 152.8, 147.8, 141.2, 127.9, 124.3, 117.8, 35.6, 35.1, 31.3, 29.3, 28.0. Anal. calcd for $C_{12}H_{14}N_4O$: C, 62.6; H, 6.1; N, 24.3. Found: C, 62.9; H, 6.2; N, 24.6%.

Example 136

3-Chloro-7,8,9,10-tetrahydro-6H-cyclohepta[g][1,2,4]benzotriazine 1-Oxide (187). $NaNO_2$ (151 mg, 2.2 mmol) was added in small portions to a stirred solution of amine 186 (252 mg, 1.1 mmol) in TFA (10 mL) at 0° C. and the solution stirred at 20° C. for 2 h. The solution was poured into ice/water, stirred for 30 min, filtered, washed with water (3×10 mL) and dried. The solid was suspended in $POCl_3$ (10 mL) and DMF (0.1 mL) and stirred at 100° C. for 1 h. The solution was cooled, poured into ice/water, stirred for 30 minutes, filtered, washed with water (3×5 mL) and dried. The solid was suspended in DCM (50 mL), dried and the solvent evaporated. The residue was purified by chromatography, eluting with 5% EtOAc/DCM, to give chloride 187 (204 mg, 75%) as a pale yellow solid: mp (EtOAc/DCM) 146-148° C.; $^1$H NMR δ 8.11 (s, 1H, H-11), 7.67 (s, 1H, H-5), 2.97-3.03 (m, 4H, H-6, H-10), 1.85-1.91 (m, 2H, H-8), 1.70-1.76 (m, 4H, H-7, H-9); $^{13}$C NMR δ 156.3, 155.2, 148.9, 146.7, 132.0, 126.8, 118.5, 36.9, 36.7, 31.9, 28.2, 28.1. Anal. calcd for $C_{12}H_{12}ClN_3O$: C, 57.7; H, 4.8; N, 16.8. Found: C, 57.6; H, 4.9; N, 16.9%.

Example 137

N$^1$,N$^1$-Dimethyl-N$^2$-(1-oxido-7,8,9,10-tetrahydro-6H-cyclohepta[g][1,2,4]benzotriazin-3-yl)-1,2-ethanediamine (188). N,N-Dimethyl-1,2-ethanediamine (0.23 mL, 2.1 mmol) was added to a stirred solution of chloride 187 (178 mg, 0.7 mmol) in DME (30 mL) and the solution stirred at reflux temperature for 2 h. The solvent was evaporated and the residue partitioned between DCM (100 mL) and dilute aqueous NH$_3$ solution (50 mL). The organic fraction was dried and the solvent evaporated. The residue was purified by chromatography, eluting with a gradient (0-10%) of MeOH/DCM, to give 1-oxide 188 (204 mg, 95%) as a yellow solid: mp (MeOH) 149-152° C.; $^1$H NMR δ 7.96 (s, 1H, H-11), 7.31 (s, 1H, H-5), 5.84 (br s, 1H, NH), 3.52-3.57 (m, 2H, CH$_2$N), 2.85-2.90 (m, 4H, H-6, H-10), 2.58 (br t, J=6.0 Hz, 2H, CH$_2$N), 2.28 [s, 6H, N(CH$_3$)$_2$], 1.79-1.85 (m, 2H, H-8), 1.65-1.74 (m, 4H, H-7, H-9); $^{13}$C NMR δ 159.0, 153.4, 148.0, 142.1, 129.0, 125.0, 118.8, 57.6, 45.1 (2), 38.7, 36.8, 36.2, 32.0, 28.7, 28.4. Anal. calcd for C$_{16}$H$_{23}$N$_5$O.½H$_2$O: C, 61.9; H, 7.8; N, 22.6. Found: C, 62.0; H, 7.8; N, 22.4%.

Example 138

N$^1$-(1,4-Dioxido-7,8,9,10-tetrahydro-6H-cyclohepta[g][1,2,4]benzotriazin-3-yl)-N$^2$,N$^2$-dimethyl-1,2-ethanediamine (189). H$_2$O$_2$ (70%, 0.31 mL, ca. 6.2 mmol) was added dropwise to a stirred solution of TFAA (0.9 mL, 6.2 mmol) in DCM (10 mL) at 0° C. The solution was stirred at 0° C. for 5 min, warmed to 20° C. for 10 min, then cooled to 0° C. and added to a stirred solution of 1-oxide 188 (186 mg, 0.6 mmol) and TFA (0.24 mL, 3.1 mmol) in DCM (10 mL) at 0° C. The solution was stirred at 20° C. for 16 h, diluted with dilute aqueous NH$_3$ solution (10 mL) and extracted with CHCl$_3$ (4×50 mL). The combined organic fraction was dried and the solvent evaporated. The residue was purified by chromatography, eluting with a gradient (0-10%) of MeOH/DCM, to give (i) starting material 188 (43 mg, 23%) and (ii) 1,4-dioxide 189 (82 mg, 42%) as a red solid: mp (MeOH) 131-133° C.; $^1$H NMR δ 8.03 (s, 1H, H-11), 7.99 (s, 1H, H-5), 7.36 (br s, 1H, NH), 3.63 (br t, J=6.0 Hz, 2H, CH$_2$N), 2.98-3.03 (m, 2H, CH$_2$), 2.91-2.95 (m, 2H, CH$_2$), 2.60 (br t, J=6.0 Hz, 2H, CH$_2$N), 2.30 [s, 6H, N(CH$_3$)$_2$], 1.82-1.89 (m, 2H, H-8), 1.68-1.76 (m, 4H, H-7, H-9); $^{13}$C NMR δ 154.4, 149.7, 144.7, 137.1, 128.7, 119.8, 115.9, 57.5, 45.2 (2), 38.9, 37.0, 36.2, 31.8, 28.4, 28.2. Anal. calcd for C$_{16}$H$_{23}$N$_5$O$_2$.¼CH$_3$OH: C, 60.0; H, 7.4; N, 21.5. Found: C, 59.9; H, 7.0; N, 21.5%.

Example 139

6,7-Dihydrofuro[3,2-g][1,2,4]benzotriazin-3-amine 1-Oxide (195)

1-(2,3-Dihydro-1-benzofuran-5-yl)ethanone (191). AlCl$_3$ (12.4 g, 93.0 mmol) was added in small portions to a stirred solution of AcCl (12.6 mL, 177.7 mmol) in dry DCM (100 mL) at −10° C. and the mixture stirred until homogeneous (15 min). The solution was added, via a cannula, to a stirred solution of 2,3-dihydro-1-benzofuran (190) (11.2 g, 93.0 mmol) in dry DCM (100 mL) at −10° C. and the solution stirred for 30 min at −10° C., and then poured into ice/cHCl (5:1 v/v, 1 L). The mixture was stirred for 2 h, extracted with DCM (3×100 mL), the combined organic fraction dried, and the solvent evaporated. The residue was purified by chromatography, eluting with a gradient (10-20%) of EtOAc/pet. ether, to give ketone 191 (14.23 g, 94%) as a white solid: mp 59-60° C. [lit. (Dun, J. P., et al., *J. Med. Chem.* 1986, 29, 2326-2329.) mp 60° C.]; $^1$H NMR δ 7.85 (d, J=1.9 Hz, 1H, H-4), 7.79 (dd, J=8.5, 1.9 Hz, 1H, H-6), 6.80 (d, J=8.5 Hz, 1H, H-7), 4.65 (t, J=8.7 Hz, 2H, H-2), 3.18 (br t, J=8.7 Hz, 2H, H-3), 2.13 (s, 3H, CH$_3$).

N-(2,3-Dihydro-1-benzofuran-5-yl)acetamide (192). NH$_2$OH.HCl (7.3 g, 105 mmol) was added to a stirred solution of ketone 191 (14.2 g, 87.7 mmol) and pyridine (9.2 mL, 114 mmol) in MeOH (100 mL) and the mixture stirred at 20° C. for 16 h. The solvent was evaporated and the residue partitioned between brine and EtOAc. The organic fraction was dried and the solvent evaporated to give crude 1-(2,3-dihydro-1-benzofuran-5-yl)ethanone oxime (15.3 g, 99%). HCl gas was bubbled through a solution of the oxime (15.3 g, 86.5 mmol) in Ac$_2$O (16.3 mL, 173 mmol) and HOAc (54 mL, 865 mmol), and the solution stood at 20° C. for 24 h. The precipitate was poured into ice/water, stirred for 2 h, the solid filtered and washed with water and dried. The aqueous fraction was extracted with DCM (2×50 mL), the combined organic extract dried and the solvent evaporated. The slurry was treated with water (20 mL) and evaporated several times to remove Ac$_2$O. The combined solids were purified by chromatography, eluting with a gradient (50-100%) of EtOAc/pet. ether, to give acetamide 192 (7.94 g, 52%) as a white solid: mp 92-93° C. [lit. (Blade-Font, A.; de Mas Rocabayera, T. *J. Chem. Soc. P1*, 1982, 814848) mp 93° C.]; $^1$H NMR δ 7.47 (br s, 1H, H-4), 7.21 (br s, 1H, NH), 6.99 (dd, J=8.5, 2.1 Hz, 1H, H-6), 6.69 (d, J=8.5 Hz, 1H, H-7), 4.55 (t, J=8.7 Hz, 2H, H-2), 3.18 (br t, J=8.7 Hz, 2H, H-3), 2.13 (s, 3H, CH$_3$).

N-(6-Nitro-2,3-dihydro-1-benzofuran-5-yl)acetamide (193). A solution of fHNO$_3$ (2.1 mL, 52.0 mmol) in HOAc (10 mL) was added dropwise to a stirred solution of acetamide 192 (6.58 g, 37.1 mmol) in HOAc (100 mL) at 15° C. The mixture was stirred at 15° C. for 1 h, then poured into ice/water (800 mL) and stirred for 30 min. The precipitate was filtered, washed with water (3×30 mL) and dried. The solid was purified by chromatography, eluting with a gradient (50-100%) of EtOAc/pet. ether, to give acetamide 193 (7.52 g, 91%) as a white solid: mp (EtOAc) 139-140° C. [lit. (Schroeder, E.; Lehman, M.; Clemens, R. U.S. Pat. No. 4,411,910, 1983.) mp 141-142° C.]; $^1$H NMR δ 10.19 (br s, 1H, NH), 8.56 (s, 1H, H-7), 7.53 (s, 1H, H-4), 4.65 (t, J=8.7 Hz, 2H, H-2), 3.30 (dt, J=8.7, 1.1 Hz, 2H, H-3), 2.26 (s, 3H, CH$_3$). Anal. calcd for C$_{10}$H$_{10}$N$_2$O$_4$: C, 54.0; H, 4.5; N, 12.6. Found: C, 54.2; H, 4.6; N, 12.6%.

6-Nitro-2,3-dihydro-1-benzofuran-5-ylamine (194). A suspension of acetamide 193 (8.98 g, 40.4 mmol) and cHCl (50 mL) in EtOH (100 mL) was heated at reflux temperature for 2 h. The solution was cooled, carefully neutralized with aqueous NH$_3$ solution, and the resulting precipitate filtered and dried to give nitroaniline 194 (7.27 g, 100%) as an orange solid: mp (H$_2$O) 148-149° C.; $^1$H NMR δ 7.44 (s, 1H, H-7), 6.68 (t, J=1.2 Hz, 1H, H-4), 5.92 (br s, 2H, NH$_2$), 4.54 (t, J=8.4 Hz, 2H, H-2), 3.18 (dt, J=8.4, 1.2 Hz, 2H, H-3); $^{13}$C NMR δ 151.8, 140.8, 139.0, 131.2, 114.4, 103.4, 71.2, 30.0. Anal. calcd for C$_8$H$_8$N$_2$O$_3$: C, 53.3; H, 4.5; N, 15.6. Found: C, 53.2; H, 4.5; N, 15.6%.

6,7-Dihydrofuro[3,2-g][1,2,4]benzotriazin-3-amine 1-Oxide (195). A mixture of nitroaniline 194 (7.27 g, 40.4 mmol) and cyanamide (6.79 g, 162 mmol) were mixed together at 100° C., cooled to 50° C., cHCl (15 mL) added carefully and the mixture heated at 100° C. for 4 h. The mixture was cooled to 50° C., 7.5 M NaOH solution added until the mixture was strongly basic and the mixture stirred at 100° C. for 3 h. The mixture was cooled, diluted with water (200 mL), filtered, washed with water (3×50 mL) and dried. The aqueous fraction was extracted with CHCl$_3$ (3×50 mL), dried and the solvent evaporated. The combined solids were purified by chromatography, eluting with a gradient (0-10%) of MeOH/DCM, to give crude amine 195 (1.87 g, 23%) as a yellow powder: mp (MeOH/DCM) 241-246° C. Anal. calcd for $C_9H_8N_4O_2$: C, 52.9; H, 4.0; N, 27.4. Found: C, 53.3; H, 3.8; N, 26.4%.

Example 140

3-Chloro-6,7-dihydrofuro[3,2-g][1,2,4]benzotriazine 1-Oxide (196). $NaNO_2$ (310 mg, 4.4 mmol) was added in small portions to a stirred solution of amine 195 (825 mg, 4.0 mmol) in TFA (20 mL) at 0° C. and the solution stirred at 0° C. for 1 h. The solution was poured into ice/water, stirred for 30 minutes, filtered, washed with water (3×10 mL) and dried. The solid was suspended in $POCl_3$ (20 mL) and DMF (0.2 mL) and stirred at 100° C. for 1 h. The solution was cooled, poured into ice/water, stirred for 30 minutes, filtered, washed with water (3×20 mL) and dried. The solid was suspended in DCM (150 mL), dried and the solvent evaporated. The aqueous fraction was extracted with EtOAc (3×40 mL), the combined organic fraction dried and the solvent evaporated. The combined solid was purified by chromatography, eluting with 5% EtOAc/DCM, to give chloride 196 (283 mg, 31%) as a pale yellow solid: mp (EtOAc/DCM) 223-224° C.; $^1$H NMR δ 7.75 (br t, J=1.4 Hz, 1H, H-5), 7.58 (s, 1H, H-9), 4.81 (t, J=8.4 Hz, 2H, H-7), 3.49 (dt, J=8.4, 1.4 Hz, 2H, H-6); $^{13}$C NMR δ 162.8, 154.9, 154.3, 144.4, 142.3, 123.8, 96.4, 72.9, 29.5. Anal. calcd for $C_9H_6ClN_3O_2$: C, 48.3; H, 2.7; N, 18.8. Found: C, 48.5; H, 2.7; N, 18.9%.

Example 141

$N^1,N^1$-Dimethyl-$N^2$-(1-oxido-6,7-dihydrofuro[3,2-g][1,2,4]benzotriazin-3-yl)-1,2-ethanediamine (197). N,N-Dimethyl-1,2-ethanediamine (0.40 mL, 3.6 mmol) was added to a stirred solution of chloride 196 (270 mg, 1.2 mmol) in DME (30 mL) and the solution stirred at reflux temperature for 4 h. The solvent was evaporated and the residue partitioned between DCM (100 mL) and dilute aqueous $NH_3$ solution (50 mL). The organic fraction was dried and the solvent evaporated. The residue was purified by chromatography, eluting with a gradient (0-10%) of MeOH/DCM, to give 1-oxide 197 (216 mg, 65%) as a yellow solid: mp (MeOH/EtOAc) 153-157° C.; $^1$H NMR δ 7.50 (s, 1H, H-9), 7.40 (t, J=1.4 Hz, 1H, H-5), 5.73 (br s, 1H, NH), 4.67 (t, J=8.3 Hz, 2H, H-7), 3.48-3.53 (m, 2H, $CH_2N$), 3.53 (dt, J=8.3, 1.4 Hz, 2H, H-6), 2.55 (dd, J=6.1, 5.9 Hz, 2H, $CH_2N$), 2.28 [s, 6H, $N(CH_3)_2$]; $^{13}$C NMR δ 158.3, 158.2, 146.1, 140.6, 130.6, 121.8, 96.6, 71.9, 57.7, 45.1 (2), 38.8, 29.7. Anal. calcd for $C_{13}H_{17}N_5O_2·¼CH_3OH$: C, 56.2; H, 6.4; N, 24.7. Found: C, 56.1; H, 6.2; N, 25.0%.

Example 142

$N^1$-(1,4-Dioxido-6,7-dihydrofuro[3,2-g][1,2,4]benzotriazin-3-yl)-$N^2,N^2$-dimethyl-1,2-ethanediamine (198). $H_2O_2$ (70%, 0.66 mL, ca. 13.2 mmol) was added dropwise to a stirred solution of TFAA (1.9 mL, 13.2 mmol) in DCM (10 mL) at 0° C. The solution was stirred at 0° C. for 5 min, warmed to 20° C. for 10 min, then cooled to 0° C. and added to a stirred solution of 1-oxide 197 (363 mg, 1.3 mmol) and TFA (0.51 mL, 6.6 mmol) in DCM (15 mL) at 0° C. The solution was stirred at 20° C. for 4 h, diluted with dilute aqueous $NH_3$ solution (10 mL) and extracted with $CHCl_3$ (4×50 mL). The combined organic fraction was dried and the solvent evaporated. The residue was purified by chromatography, eluting with a gradient (0-10%) of MeOH/DCM, to give 1,4-dioxide 198 (98 mg, 25%) as a red solid: mp (MeOH/EtOAc) 149-151° C.; $^1$H NMR δ 8.12 (s, 1H, H-5), 7.54 (s, 1H, H-9), 7.27 (br s, 1H, NH), 4.75 (t, J=8.3 Hz, 2H, H-7), 3.58-3.64 (m, 2H, $CH_2N$), 3.43 (t, J=8.2 Hz, 2H, H-6), 2.62 (t, J=6.0 Hz, 2H, $CH_2N$), 2.31 [s, 6H, $N(CH_3)_2$]; $^{13}$C NMR δ 159.9, 148.9, 141.6, 135.2, 130.9, 113.1, 97.4, 72.4, 57.5, 45.1 (2), 38.8, 29.7. Anal. calcd for $C_{13}H_{17}N_5O_3·¼H_2O$: C, 52.8; H, 6.0; N, 23.7. Found: C, 52.8; H, 5.7; N, 23.5%.

Example 143

N-[3-(4-Morpholinyl)propyl]-6,7-dihydrofuro[3,2-g][1,2,4]benzotriazin-3-amine 1-Oxide (199). A solution of chloride 196 (850 mg, 3.8 mmol) and 3-(4-morpholinyl)propylamine (1.7 mL, 11.5 mmol) in DME (30 mL) was stirred at reflux temperature for 18 h. The solution was cooled, the solvent evaporated and the residue partitioned between dilute aqueous $NH_3$ solution (50 mL) and DCM (50 mL). The aqueous layer was extracted with DCM (2×25 mL), the combined organic fraction dried and the solvent evaporated. The residue was purified by chromatography, eluting with a gradient (2-10%) of MeOH/DCM, to give 1-oxide 199 (1.08 g, 85%) as a yellow solid: mp 142-144° C.; $^1$H NMR δ 7.52 (s, 1H, H-9), 7.41 (s, 1H, H-5), 5.97 (br s, 1H, NH), 4.67 (t, J=8.3 Hz, 2H, H-7), 3.75 (t, J=4.7 Hz, 4H, 2×$CH_2O$), 3.56 (dt, J=6.4, 5.9 Hz, 2H, $CH_2N$), 3.35 (dt, J=8.3, 1.2 Hz, 2H, H-6), 2.42-2.53 (m, 6H, 2×$CH_2N$, $CH_2$), 1.83 (p, J=6.5 Hz, 2H, $CH_2$); $^{13}$C NMR δ 158.3, 151.4, 146.1, 140.5, 128.7, 121.8, 96.7, 71.9, 67.0 (2), 57.3, 53.8 (2), 40.8, 29.7, 25.4; MS (APCI) m/z 332 ($MH^+$, 100%). Anal. calcd for $C_{16}H_{21}N_5O_3$: C, 58.0; H, 6.4; N, 21.1. Found: C, 58.0; H, 6.0; N, 21.2%.

Example 144

N-[3-(4-Morpholinyl)propyl]-6,7-dihydrofuro[3,2-g][1,2,4]benzotriazin-3-amine 1,4-Dioxide (200). $H_2O_2$ (70%, 1.6 mL, ca. 32 mmol) was added dropwise to a stirred solution of TFM (4.5 mL, 32 mmol) in DCM (40 mL) at 0° C. The solution was stirred at 20° C. for 10 min, then cooled to 0° C., added to a solution of 1-oxide 199 (1.06 g, 3.2 mmol) and TFA (1.25 mL, 16 mmol) in DCM (40 mL) at 0° C. The solution was stirred at 20° C. for 4.5 h, diluted with dilute aqueous $NH_3$ solution (50 mL) and extracted with DCM (4×125 mL). The combined organic fraction was dried and the solvent evaporated. The residue was purified by chromatography, eluting with a gradient (0-10%) of MeOH/DCM to give 1,4-dioxide 200 (150 mg, 14%) as a red solid: mp 145-148° C.; $^1$H NMR δ 8.26 (br s, 1H, NH), 8.14 (s, 1H, H-9), 7.53 (s, 1H, H-5), 4.74 (t, J=8.3 Hz, 2H, H-7), 3.83 (t, J=4.6 Hz, 4H, 2×$CH_2O$), 3.65 (br q, J=5.9 Hz, 2H, $CH_2N$), 3.43 (dt, J=8.3, 1.2 Hz, 2H, H-6), 2.58 (br t, J=6.1 Hz, 2H, $CH_2$), 2.53 (br s, 4H, 2×$CH_2N$), 1.88 (p, J=6.2 Hz, 2H, $CH_2$); $^{13}$C NMR δ 159.8, 149.0, 141.5, 135.2, 130.8, 113.1, 97.4, 72.4, 66.8 (2), 57.7, 53.8 (2), 41.6, 29.7, 24.5; MS (APCI) m/z 348 ($MH^+$, 100%); HRMS ($FAB^+$) calcd for $C_{16}H_{22}N_5O_4$ ($MH^+$) m/z 348.1672, found 348.1666. Anal. calcd for $C_{16}H_{21}N_5O_4·0.4CH_2Cl_2$: C, 51.7; H, 5.8; N, 18.4. Found: C, 51.7; H, 5.4; N, 18.1%.

Example 145

3-Amino-7,8-dihydrobenzofuro[6,5-e][1,2,4]triazine 1-Oxide (204)

6-Nitro-2,3-dihydro-1-benzofuran (201). $NaNO_2$ (2.66 g, 39 mmol) was added in portions to a solution of nitroaniline 194 (6.5 g, 36 mmol) in water (150 mL) and $CH_2SO_4$ (60 mL)

at 0° C. The solution was stirred at 0° C. for 3 h, aqueous $H_3PO_2$ solution (50%, 13 mL) was added, and the mixture stood at 0° C. for 16 h and then at 20° C. for 4 d. The mixture was extracted with ether (3×300 mL), the combined organic layer washed with water (3×200 mL), dried and the solvent evaporated to yield dihydrobenzofuran 201 (4.34 g, 73%) as a red-brown solid: mp 71-72° C.; $^1$H NMR δ 7.76 (dd, J=8.1, 2.1 Hz, 1H, H-5), 7.57 (d, J=2.1 Hz, 1H, H-7), 7.29 (d, J=8.1 Hz, 1H, H-4), 4.70 (t, J=8.1 Hz, 2H, H-2), 3.30 (t, J=8.1 Hz, 2H, H-3). Anal. calcd for $C_8H_7NO_3$: C, 58.2; H, 4.3; N, 8.5. Found: C, 58.5; H, 4.3; N, 8.5%.

N-(2,3-Dihydro-1-benzofuran-6-yl)acetamide (202). A mixture of dihydrobenzofuran 201 (4.34 g, 26.3 mmol) and $PtO_2$ (420 mg, 1.9 mmol) in THF (40 mL) and EtOH (200 mL) was stirred vigorously under $H_2$ (30 psi) for 16 h. The mixture was filtered through Celite, washed with THF and the solvent evaporated. The residue was purified by chromatography, eluting with 2% MeOH/DCM, to give 6-amino-2,3-dihydrobenzofuran (2.89 g, 81%), which was dissolved in dioxane (95 mL), $Ac_2O$ (4.3 mL, 45.6 mmol) was added dropwise, and the solution stirred at 20° C. for 16 h. Water (200 mL) was added and the mixture extracted with DCM (3×120 mL). The combined organic layer was dried and the solvent evaporated to give acetamide 202 (3.56 g, 97%) as a yellow solid: mp 115-118° C.; $^1$H NMR δ 7.26 (br s, 1H, NH), 7.09 (d, J=7.9 Hz, 1H, H-4), 7.04 (s, 1H, H-7), 6.91 (d, J=7.9 Hz, 1H, H-5), 4.56 (t, J=8.6 Hz, 2H, H-2), 3.15 (t, J=8.1 Hz, 2H, H-3), 2.14 (s, 3H, $COCH_3$). Anal. calcd for $C_{10}H_{11}NO_2$: C, 67.8; H, 6.3; N, 7.9. Found: C, 67.7; H, 6.4; N, 8.0%.

5-Nitro-2,3-dihydro-1-benzofuran-6-ylamine (203). A solution of $cHNO_3$ (70%, 1.3 mL, 21 mmol) in HOAc (5 mL) was added dropwise to a stirred solution of acetamide 202 (3.56 g, 20 mmol) in HOAc (15 mL) at 20° C. and the solution stirred at 20° C. for 2 h. The solution was poured into ice/water (150 mL) and the mixture stirred for 30 min. The precipitate was filtered, washed with water, and dried to give a pale-brown solid, which was dissolved in a mixture of EtOH (35 mL) and cHCl (16 mL) and stirred at reflux temperature for 2 h. The resulting solution was cooled, the solvent evaporated, the residue diluted with water (40 mL), and then made basic with dilute aqueous $NH_3$ solution. The precipitate was filtered, washed with water, and dried to give nitroaniline 203 (2.08 g, 90%) as a yellow solid, mp 140-142° C.; $^1$H NMR δ 7.98 (s, 1H, H-4), 6.25 (br s, 2H, $NH_2$), 6.11 (s, 1H, H-7), 4.64 (t, J=8.0 Hz, 2H, H-2), 3.13 (t, J=7.8 Hz, 2H, H-3); $^{13}$C NMR δ 166.6, 147.7, 126.9, 122.8, 118.9, 96.1, 73.2, 27.9. Anal. calcd for $C_8H_8N_2O_3$: C, 53.3; H, 4.5; N, 15.6. Found: C, 53.1; H, 4.6; N, 15.5%.

7,8-Dihydrofuro[2,3-g][1,2,4]benzotriazin-3-amine 1-Oxide (204). A mixture of nitroaniline 203 (4.0 g, 22.2 mmol) and cyanamide (7.2 g, 171 mmol) were mixed together at 80° C., cooled to 50° C., cHCl (8.0 mL) added carefully and the mixture heated at 80° C. for 4 h. The mixture was cooled to 50° C., 7.5 M NaOH solution added until the mixture was strongly basic, and the mixture stirred at 100° C. for 3 h. The mixture was cooled, diluted with water (20 mL), filtered, washed with water (20 mL) and ether (5 mL), and dried to give 1-oxide 204 (8.6 g, 96%) as a yellow powder: mp (DCM) 293-296° C.; $^1$H NMR [$(CD_3)_2SO$] δ 7.71 (s, 1H, H-9), 6.23 (s, 1H, H-5), 4.59 (t, J=8.5 Hz, 2H, H-7), 3.12 (t, J=8.5 Hz, 2H, H-8), $NH_2$ not observed; HRMS (FAB$^+$) calcd for $C_9H_9N_4O_2$ (MH$^+$) m/z 205.0726, found 205.0725.

Example 146

7,8-Dihydrofuro[2,3-g][1,2,4]benzotriazin-3-amine 1,4-Dioxide (205). $H_2O_2$ (70%, 1.2 mL, ca. 24.5 mmol) was added dropwise to a stirred solution of 1-oxide 204 (500 mg, 2.45 mmol) in HOAc (10 mL) and the solution stirred at 50° C. for 24 h. The solution was cooled to 0° C. and the precipitate filtered. The solid was recrystallised from DMF to give 1,4-dioxide 205 (199 mg, 37%) as a red solid: mp>300° C. (235-240° C. dec.); $^1$H NMR [$(CD_3)_2SO$] δ 8.06 (t, J=1.6 Hz, 1H, H-9), 7.86 (br s, 2H, $NH_2$), 7.23 (s, 1H, H-5), 4.77 (t, J=8.3 Hz, 2H, H-8), 3.30-3.60 (m, 2H, H-7); HRMS calcd for $C_9H_8N_4O_3$ (M$^+$) m/z 220.0596, found 220.0601.

Example 147

3-Chloro-7,8-dihydrofuro[2,3-g][1,2,4]benzotriazine 1-Oxide (206). $NaNO_2$ (3.38 g, 49.0 mmol) was added in small portions to a stirred solution of amine 205 (5.0 g, 24.5 mmol) in TFA (50 mL) at 20° C. and the solution stirred at 20° C. for 1 h. The solution was poured into ice/water, stirred 30 min, filtered, the solid washed with water and dried. The solid was suspended in $POCl_3$ (65 mL) and DMF (0.4 mL) and stirred at 100° C. for 1 h. The solution was cooled, poured into ice/water, stirred for 30 min, filtered, washed with water and dried. The residue was purified by chromatography, eluting with a gradient (0-3%) of MeOH/DCM, to give chloride 206 (3.76 g, 69%) as a yellow solid: mp (DCM) 203-205° C.; $^1$H; $^1$H NMR [$(CD_3)_2SO$] δ 8.23 (t, J=1.6 Hz, 1H, H-9), 7.20 (s, 1H, H-5), 4.23 (t, J=8.4 Hz, 2H, H-7), 3.45 (dt, J=8.4, 1.6 Hz, 2H, H-8); $^{13}$C NMR δ 167.2, 155.3, 150.0, 137.4, 129.1, 116.0, 102.7, 73.9, 28.3; HRMS (FAB$^+$) calcd for $C_9H_7^{35}ClN_3O_2$ (MH$^+$) m/z 224.0227, found 224.0221.

Example 148

$N^1,N^1$-Dimethyl-$N^2$-(1-oxido-7,8-dihydrofuro[2,3-g][1,2,4]benzotriazin-3-yl)-1,2-ethanediamine (207). A solution of chloride 206 (100 mg, 0.45 mmol) and $N^1,N^1$-dimethylethane-1,2-diamine (0.2 mL, 1.8 mmol) in DME (10 mL) was stirred at reflux temperature for 1 h, the solvent evaporated and the residue purified by chromatography, eluting with a gradient (5-8%) of MeOH/DCM to give the 1-oxide 207 (108 mg, 88%) as a yellow solid, mp 163-165° C.; $^1$H NMR δ 8.09 (t, J=1.4 Hz, 1H, H-9), 6.79 (s, 1H, H-5), 5.83 (br s, 1H, NH), 4.72 (t, J=8.3 Hz, 2H, H-7), 3.52-3.56 (m, 2H, $CH_2N$), 3.31 (dt, J=8.3, 1.4 Hz, 2H, H-8), 2.57 (t, J=8.3 Hz, 2H, $CH_2N$), 2.29 [s, 6H, $N(CH_3)_2$]; $^{13}$C NMR δ 166.5, 159.3, 151.8, 129.3, 126.4, 116.6, 102.0, 72.9, 57.6, 45.0 (2), 38.6, 28.6. HRMS (FAB$^+$) calcd for $C_{13}H_{18}N_5O_2$ (MH$^+$) m/z 276.1461, found 276.1461.

Example 149

$N^1$-(1,4-Dioxido-7,8-dihydrofuro[2,3-g][1,2,4]benzotriazin-3-yl)-$N^2,N^2$-dimethyl-1,2-ethanediamine (208). $H_2O_2$ (70%, 0.18 mL, ca. 3.6 mmol) was added dropwise to a stirred solution of TFAA (0.51 mL, 3.6 mmol) in DCM (6 mL) at 0° C. The solution was stirred at 20° C. for 10 min, then cooled to 0° C., added to a solution of 1-oxide 207 (100 mg, 0.36 mmol) and TFA (0.06 mL, 0.78 mmol) in $CHCl_3$ (6 mL) at 0° C. and the solution stirred at 20° C. for 4.5 h. The solution was cooled to 0° C., made basic with dilute aqueous $NH_3$ solution and extracted with $CHCl_3$ (3×10 mL). The combined organic fraction was dried and the solvent evaporated. The residue was purified by chromatography, eluting with a gradient (5-16%) of MeOH/DCM to give 1,4-dioxide 208 (56 mg, 53%) as an orange solid: mp 186-189° C.; $^1$H NMR δ 8.13 (t, J=1.6 Hz, 1H, H-9), 7.48 (br s, 2H, H-5, NH), 4.81 (t, J=8.3 Hz, 2H, H-7), 3.62 (t, J=6.0 Hz, 2H, CH$_2$N), 3.37 (dt, J=8.3, 1.6 Hz, 2H, H-8), 2.62 (t, J=8.3 Hz, 2H, CH$_2$N), 2.30 [s, 6H, N(CH$_3$)$_2$]; $^{13}$C NMR δ 167.2, 149.9, 140.6, 132.0, 117.9, 93.8, 87.9, 73.4, 57.5, 45.2 (2), 38.8, 28.5. HRMS (FAB$^+$) calcd for C$_{13}$H$_{18}$N$_5$O$_3$ (MH$^+$) m/z 292.1410, found 292.1409.

Example 150

N$^1$,N$^1$-Diethyl-N$^2$-(1-oxido-7,8-dihydrofuro[2,3-g][1,2,4]benzotriazin-3-yl)-1,2-ethanediamine (209). A solution of chloride 206 (250 mg, 1.12 mmol) and N$^1$,N$^1$-diethylethane-1,2-diamine (0.63 mL, 4.48 mmol) in DME (25 mL) was stirred at reflux temperature for 2 h, the solvent evaporated and the residue purified by chromatography, eluting with a gradient (5-10%) of MeOH/DCM to give the 1-oxide 209 (255 mg, 75%) as a yellow solid: mp 150-151° C.; $^1$H NMR δ 8.09 (t, J=1.6 Hz, 1H, H-9), 6.79 (s, 1H, H-5), 5.90 (br s, 1H, NH), 4.72 (t, J=8.3 Hz, 2H, H-7), 3.48-3.54 (m, 2H, CH$_2$N), 3.30 (dt, J=8.3, 1.4 Hz, 2H, H-8), 2.69-2.72 (m, 2H, CH$_2$N), 2.59 (q, J=7.1 Hz, 4H, 2×CH$_2$), 1.05 (t, J=7.1 Hz, 6H, 2×CH$_3$); $^{13}$C NMR δ 166.5, 159.3, 151.8, 129.3, 126.3, 116.6, 102.1, 72.9, 51.3, 46.7 (2), 38.7, 28.6, 11.7 (2). Anal. calcd for C$_{15}$H$_{21}$N$_5$O$_2$·¼CH$_3$OH: C, 58.8; H, 7.1; N, 22.5. Found: C, 58.8; H, 6.7; N, 22.8%.

Example 151

N$^1$-(1,4-Dioxido-7,8-dihydrofuro[2,3-g][1,2,4]benzotriazin-3-yl)-N$^2$,N$^2$-diethyl-1,2-ethanediamine (210). H$_2$O$_2$ (70%, 0.38 mL, ca. 2.8 mmol) was added dropwise to a stirred solution of TFAA (1.1 mL, 2.8 mmol) in DCM (15 mL) at 0° C. The solution was stirred at 20° C. for 10 min, then cooled to 0° C., added to a solution of 1-oxide 209 (235 mg, 0.78 mmol) and TFA (0.13 mL, 1.7 mmol) in CHCl$_3$ (15 mL) at 0° C. The solution was stirred at 20° C. for 4 h, diluted with dilute aqueous NH$_3$ solution until basic and extracted with CHCl$_3$ (3×25 mL). The combined organic fraction was dried and the solvent evaporated. The residue was purified by chromatography, eluting with a gradient (5-10%) of MeOH/DCM, to give 1,4-dioxide 210 (95 mg, 38%) as a red solid: mp 187-190° C.; $^1$H NMR (CD$_3$OD) δ 8.16 (t, J=1.7 Hz, 1H, H-9), 7.30 (s, 1H, H-5), 4.85 (t, J=8.4 Hz, 2H, H-7), 3.90-3.94 (m, 2H, CH$_2$), 3.40-3.49 (m, 4H, H-8, CH$_2$), 3.36 (q, J=7.3 Hz, 4H, CH$_2$), 1.37 (t, J=7.3 Hz, 6H, CH$_3$), NH not observed; $^{13}$C NMR δ 169.8, 151.5, 142.3, 135.5, 128.2, 119.0, 93.7, 75.6, 51.7, 49.0 (2), 37.3, 29.4, 9.1 (2); HRMS (FAB$^+$) calcd for C$_{15}$H$_{22}$N$_5$O$_3$ (MH$^+$) m/z 320.1723, found 320.1726.

Example 152

N-[3-(4-Morpholinyl)propyl]-7,8-dihydrofuro[2,3-g][1,2,4]benzotriazin-3-amine 1-Oxide (211). A solution of chloride 206 (250 mg, 1.1 mmol) and 3-(4-morpholinyl)propylamine (0.65 mL, 4.5 mmol) in DME (25 mL) was stirred at reflux temperature for 2 h, the solvent evaporated and the residue purified by chromatography, eluting with a gradient (2-5%) of MeOH/DCM, to give 1-oxide 211 (340 mg, 92%) as a yellow solid: mp 152-154° C.; $^1$H NMR δ 8.10 (t, J=1.6 Hz, 1H, H-9), 6.79 (s, 1H, H-5), 6.09 (br s, 1H, NH), 4.42 (t, J=8.3 Hz, 2H, H-7), 3.75 (t, J=4.7 Hz, 4H, 2×CH$_2$O), 3.55-3.60 (m, 2H, CH$_2$), 3.30 (dt, J=8.3, 1.6 Hz, 2H, H-7), 2.46-2.52 (m, 6H, 2×CH$_2$N, CH$_2$), 1.82 (p, J=6.5 Hz, 2H, CH$_2$); $^{13}$C NMR δ 166.5, 159.4, 151.8, 129.2, 126.4, 116.6, 102.1, 72.9, 67.0 (2), 57.3, 53.8 (2), 40.8, 28.6, 25.3. Anal. calcd for C$_{16}$H$_{21}$N$_5$O$_3$: C, 58.0; H, 6.4; N, 21.1. Found: C, 57.8; H, 6.2; N, 21.1%.

Example 153

N-[3-(4-Morpholinyl)propyl]-7,8-dihydrofuro[2,3-g][1,2,4]benzotriazin-3-amine 1,4-Dioxide (212). H$_2$O$_2$ (70%, 0.46 mL, ca. 9.5 mmol) was added dropwise to a stirred solution of TFAA (1.32 mL, 9.5 mmol) in DCM (20 mL) at 0° C. The solution was stirred at 20° C. for 10 min, then cooled to 0° C., added to a solution of 1-oxide 211 (313 mg, 0.95 mmol) and TFA (0.16 mL, 2.0 mmol) in CHCl$_3$ (15 mL) at 0° C. The solution was stirred at 20° C. for 4 h, diluted with dilute aqueous NH$_3$ solution until basic and extracted with CHCl$_3$ (3×25 mL). The combined organic fraction was dried and the solvent evaporated. The residue was purified by chromatography, eluting with a gradient (1-12%) of MeOH/DCM, to give (i) starting material 211 (120 mg, 38%) and (ii) 1,4-dioxide 212 (68 mg, 21%) as a dark orange solid: mp 186-189° C.; $^1$H NMR [(CD$_3$)$_2$SO] δ 8.45 (t, J=1.4 Hz, 1H, H-9), 8.05 (s, 1H, H-5), 7.21 (s, 1H, NH), 4.77 (t, J=8.3 Hz, 2H, H-7), 3.33-3.64 (m, 8H, 2×CH$_2$O, H-8, CH$_2$), 2.36-2.45 (m, 6H, 2×CH$_2$N, CH$_2$), 1.77 (p, J=6.6 Hz, 2H, CH$_2$); HRMS (FAB$^+$) calcd for C$_{16}$H$_{22}$N$_5$O$_4$ (MH$^+$) m/z 348.1672, found 348.1671.

Example 154

3-Iodo-7,8-dihydrobenzofuro[6,5-e][1,2,4]triazine 1-Oxide (213). tert-BuNO$_2$ (90%, 3.8 mL, 28.8 mmol) was added to a stirred solution of 1-oxide 204 (2.0 g, 9.8 mmol), CH$_2$I$_2$ (3.8 mL, 46.7 mmol) and CuI (1.87 g, 9.8 mmol) in THF (40 mL), and the mixture was stirred at reflux temperature for 7 h. The mixture was cooled to 20° C., the solvent was evaporated and the residue purified by chromatography, eluting with a gradient (2-10%) of MeOH/DCM, to give iodide 213 (1.50 g, 49%) as a pale yellow solid: mp 192-194° C.; $^1$H NMR δ 8.19 (t, J=1.6 Hz, 1H, H-9), 7.10 (s, 1H, H-5), 4.83 (t, J=8.4 Hz, 2H, H-7), 3.44 (dt, J=8.4, 1.6 Hz, 2H, H-8); $^{13}$C NMR δ 167.0, 150.4, 136.2, 123.3, 116.4, 105.8, 103.7, 73.4, 29.0; HRMS calcd for C$_9$H$_6$IN$_3$O$_2$(M$^+$) m/z 314.9505, found 314.9501.

Example 155

3-(1-Oxido-7,8-dihydrofuro[2,3-g][1,2,4]benzotriazin-3-yl)propanal (214). Pd(OAc)$_2$ (53 mg, 0.24 mmol) was added to a N$_2$-purged solution of iodide 213 (1.50 g, 4.8 mmol), allyl alcohol (0.91 mL, 13.3 mmol), nBu$_4$NBr (1.38 g, 4.3 mmol) and NaHCO$_3$ (880 mg, 10.5 mmol) in dry DMF (40 mL) and the solution was stirred at 60° C. for 24 h under N$_2$. The mixture was quenched with saturated aqueous NH$_4$Cl solution (150 mL) and filtered. The filtrate was extracted with EtOAc (5×50 mL), dried and the solvent evaporated. The residue was purified by chromatography, eluting with a gradient (20-50%) of EtOAc/pet. ether, to give aldehyde 214 as a dark oil, which was crystallised from MeOH to give a pale purple solid (532 mg, 45%): mp 140-142° C.; $^1$H NMR δ 9.92 (s, 1H, CHO), 8.26 (t, J=1.5 Hz, 1H, H-9), 7.10 (s, 1H, H-5), 4.80 (t, J=8.4 Hz, 2H, H-7), 3.43 (dt, J=8.4, 1.5 Hz, 2H, H-8), 3.29-3.33 (m, 2H, CH$_2$), 3.06-3.10 (m, 2H, CH$_2$); $^{13}$C NMR δ 200.4, 166.5, 165.0, 150.3, 135.2, 129.0, 116.2, 104.0, 73.1, 40.5, 29.4, 29.0; HRMS (FAB$^+$) calcd for C$_{12}$H$_{12}$N$_3$O$_3$ (MH$^+$) m/z 246.0879, found 246.0881.

Example 156

3-[3-(4-Morpholinyl)propyl]-7,8-dihydrofuro[2,3-g][1,2,4]benzotriazine 1-Oxide (215). Morpholine (0.22 mL, 2.52 mmol) was added to a solution of aldehyde 214 (220 mg, 0.90 mmol) in MeOH (10 mL) and DMF (10 ml), and the solution stirred for 30 min. NaCNBH$_3$ (176 mg, 2.80 mmol) was added, followed by HOAc (0.12 mL) and the mixture stirred at 20° C. for 30 min. The solvent was evaporated and the residue partitioned between DCM (40 mL) and water (40 mL). The aqueous phase was extracted with DCM (2×40 mL), the combined organic phase was dried and the solvent evaporated. The residue was purified by chromatography, eluting with 10% MeOH/EtOAc, to give 1-oxide 215 (210 mg, 74%) as a pale brown solid, mp 96-99° C.; $^1$H NMR δ 8.27 (t, J=1.6 Hz, 1H, H-9), 7.11 (s, 1H, H-5), 4.80 (t, J=8.4 Hz, 2H, H-8), 3.59 (t, J=4.6 Hz, 4H, 2×CH$_2$O), 3.43 (dt, J=8.4, 1.6 Hz, 2H, H-7), 2.97-3.01 (m, 2H, CH$_2$), 2.44-2.48 (m, 2H, CH$_2$), 2.41 (t, J=4.5 Hz, 4H, 2×CH$_2$N), 2.03-2.11 (m, 2H, CH$_2$); $^{13}$C NMR δ 167.1, 166.4, 150.5, 134.8, 128.9, 116.2, 103.9, 73.0, 67.0 (2), 58.3, 53.5 (2), 53.4, 27.0, 24.9. Anal. calcd for C$_{16}$H$_{20}$N$_4$O$_3$: C, 60.8; H, 6.4; N, 17.7. Found: C, 60.7; H, 6.5; N, 17.7%.

Example 157

3-[3-(4-Morpholinyl)propyl]-7,8-dihydrofuro[2,3-g][1,2,4]benzotriazine 1,4-Dioxide (216). H$_2$O$_2$ (70%, 0.31 mL, ca. 6.3 mmol) was added dropwise to a stirred solution of TFAA (0.88 mL, 6.3 mmol) in DCM (12 mL) at 0° C. The solution was stirred at 0° C. for 5 min, warmed to 20° C. for 10 min, then cooled to 0° C. The solution was added to a solution of 1-oxide 215 (200 mg, 0.63 mmol) and TFA (0.10 mL, 1.4 mmol) in DCM (12 mL) at 0° C. and the solution was stirred at 20° C. for 2.5 h. Dilute aqueous NH$_3$ solution was added until the mixture was basic and then the mixture was extracted with CHCl$_3$ (3×20 mL). The combined organic fraction was dried and the solvent evaporated. The residue was purified by chromatography, eluting with a gradient (1-5%) of MeOH/DCM, to give 1,4-dioxide 216 (88 mg, 43%) as a dark yellow solid: mp 150-154° C.; $^1$H NMR δ 8.28 (t, J=1.6 Hz, 1H, H-9), 7.68 (s, 1H, H-5), 4.87 (t, J=8.5 Hz, 2H, H-7), 3.48 (dt, J=8.5, 1.5 Hz, 2H, H-8), 3.44 (t, J=4.4 Hz, 4H, 2×CH$_2$O), 3.22 (t, J=7.2 Hz, 2H, CH$_2$), 2.49 (t, J=6.5 Hz, 2H, CH$_2$), 2.38 (t, J=4.4 Hz, 4H, 2×CH$_2$N), 2.06-2.13 (m, 2H, CH$_2$); $^{13}$C NMR δ 166.7, 156.1, 141.7, 136.3, 130.2, 117.8, 96.1, 73.5, 67.0 (2), 58.0, 53.5 (2), 29.0, 28.8, 21.8. Anal. calcd for C$_{16}$H$_{20}$N$_4$O$_4$: C, 57.8; H, 6.1; N, 16.9. Found: C, 57.8; H, 6.1; N, 16.6%.

Example 158

[1,3]Dioxolo[4,5-g][1,2,4]benzotriazin-3-amine 1-Oxide (221)

N-(1,3-Benzodioxol-5-yl)acetamide (218). Ac$_2$O (21.4 mL, 226 mmol) was added dropwise to a stirred solution of 3,4-methylendioxyaniline (217) (25.87 g, 189 mmol) in dioxane (200 mL) at 0° C. and the mixture was stirred at 16° C. for 16 h. MeOH (10 mL) was added to decompose excess Ac$_2$O and the solvent evaporated. The residue was dissolved in EtOAc (200 mL), dried and the solvent evaporated. The residue was filtered through a short column of silica, eluting with a gradient (50-100%) of EtOAc/pet. ether, to give acetamide 218 (29.17 g, 86%) as a white solid: mp 133-135° C. [lit (Krasso, A. & Ramuz, H., U.S. Pat. No. 4,599,347, 1986) mp (toluene) 138-139° C.]; $^1$H NMR δ 7.09 (d, J=1.8 Hz, 1H, H-4), 7.06 (br s, 1H, NH), 6.77 (dd, J=8.3, 1.8 Hz, 1H, H-6), 6.72 (d, J=8.3 Hz, 1H, H-7), 5.94 (s, 2H, H-2), 2.14 (s, 3H, CH$_3$).

N-(6-Nitro-1,3-benzodioxol-5-yl)acetamide (219). A solution of 70% HNO$_3$ (15.5 mL, 244 mmol) in HOAc (40 mL) was added dropwise to a stirred solution of acetamide 218 (29.17 g, 163 mmol) in HOAc (150 mL) at 15-20° C. and the mixture stirred at 20° C. for 16 h. The precipitate was filtered, washed with water and dried to give nitroacetamide 219 (36.0 g, 99%) as a yellow powder: mp 207-208° C. (Krasso, A. & Ramuz, H., U.S. Pat. No. 4,599,347, 1986) mp 212-213° C.]; $^1$H NMR δ 10.78 (br s, 1H, NH), 8.36 (s, 1H, H-7), 7.66 (s, 1H, H-4), 6.10 (s, 2H, H-2), 2.27 (s, 3H, CH$_3$).

6-Nitro-1,3-benzodioxol-5-amine (220). NaOMe (4.82 g, 89.2 mmol) was added to a stirred solution of nitroacetamide 219 (5.0 g, 22.3 mmol) in MeOH (100 mL) at reflux temperature and the mixture stirred at reflux temperature for 15 min. HOAc (25 mL, 446 mmol) was added to quench the reaction and the solvent evaporated. Toluene (2×50 mL) was added and the azeotrope evaporated. The residue was dissolved in DCM (100 mL) and filtered through a short column of silica to give nitroaniline 220 (3.25 g, 80%) as an orange solid: mp 199-201° C. [lit (Krasso, A. & Ramuz, H., U.S. Pat. No. 4,599,347, 1986) mp (iPrOH) 203-204° C.]; $^1$H NMR δ 7.53 (s, 1H, H-7), 6.30 (br s, 2H, NH$_2$), 6.22 (s, 1H, H-4), 5.98 (s, 2H, H-2).

[1,3]Dioxolo[4,5-g][1,2,4]benzotriazin-3-amine 1-Oxide (221). A mixture of nitroaniline 220 (5.55 g, 30.5 mmol) and cyanamide (5.37 g, 122 mmol) were melted together at 100° C., cooled to 50° C., cHCl (15 mL) added dropwise and the mixture heated at 100° C. for 4 h. The mixture was cooled to 50° C., 7.5 M NaOH solution added until the mixture was strongly basic and the mixture stirred at 100° C. for 3 h. The mixture was cooled, diluted with water (200 mL), filtered, washed with water (3×30 mL), washed with ether (3×5 mL) and dried to give 1-oxide 221 (3.24 g, 51%) as a yellow powder: mp (MeOH/DCM) 290-295° C.; $^1$H NMR [(CD$_3$)$_2$SO] δ 7.45 (s, 1H, H-9), 7.00 (br s, 2H, NH$_2$), 6.94 (s, 1H, H-5), 6.23 (s, 2H, H-7); $^{13}$C NMR [(CD$_3$)$_2$SO] δ 160.0, 155.1, 149.0, 147.0, 125.3, 103.1, 101.3, 95.8. Anal. calcd for C$_8$H$_6$N$_4$O$_3$: C, 46.6; H, 2.9; N, 27.2. Found: C, 46.7; H, 2.9; N, 27.3%.

Example 159

3-Chloro[1,3]dioxolo[4,5-g][1,2,4]benzotriazine 1-Oxide (222). NaNO$_2$ (620 mg, 8.9 mmol) was added in small portions to a stirred solution of amine 221 (1.75 g, 8.5 mmol) in TFA (25 mL) at 0° C. and the solution stirred at 20° C. for 1 h. The solution was poured into ice/water, stirred 30 minutes, filtered, the precipitate was washed with water (3×30 mL) and dried. The solid was suspended in POCl$_3$ (50 mL) and DMF (0.5 mL) and stirred at 100° C. for 1 h. The solution was cooled, poured into ice/water, stirred for 30 min, filtered, washed with water (3×30 mL) and dried. The solid was suspended in DCM (150 mL), dried and the solvent evaporated. The residue was purified by chromatography, eluting with 5% EtOAc/DCM, to give chloride 222 (753 mg, 39%) as a pale yellow solid: mp (DCM) 253-255° C.; $^1$H NMR δ 7.69 (s, 1H, H-9), 7.45 (s, 1H, H-5), 6.42 (s, 2H, H-7); $^{13}$C NMR δ 156.6, 154.2, 152.0, 147.8, 130.6, 104.7, 103.1, 95.7. Anal. calcd for C$_8$H$_4$ClN$_3$O$_3$: C, 42.6; H, 1.8; N, 18.6. Found: C, 42.7; H, 1.7; N, 18.5%.

Example 160

N$^1$,N$^1$-Dimethyl-N$^2$-(1-oxido[1,3]dioxolo[4,5-g][1,2,4]benzotriazin-3-yl)-1,2-ethanediamine (223). N,N-Dimethyl-1,2-ethanediamine (0.52 mL, 4.8 mmol) was added to a stirred solution of chloride 222 (359 mg, 1.6 mmol) in DME (40 mL) and the solution stirred at reflux temperature for 2 h. The solvent was evaporated and the residue partitioned between DCM (100 mL) and dilute aqueous NH$_3$ solution (50 mL). The organic fraction was dried and the solvent evaporated. The residue was purified by chromatography, eluting with a gradient (0-15%) of MeOH/DCM, to give 1-oxide 223 (390 mg, 88%) as a yellow solid: mp (MeOH/DCM) 192-194° C.; $^1$H NMR δ 7.45 (s, 1H, H-9), 7.35 (br s, 1H, NH), 6.96 (s, 1H, H-5), 6.23 (s, 2H, H-7), 3.35-3.39 (m, 2H, CH$_2$N), 2.42 (t, J=6.7 Hz, 2H, CH$_2$N), 2.18 [s, 6H, N(CH$_3$)$_2$]; $^{13}$C NMR δ 158.9, 155.2, 148.7, 146.9, 125.3, 103.2, 101.6, 95.9, 57.8, 45.2 (2), 38.6. Anal. calcd for C$_{12}$H$_{15}$N$_5$O$_3$: C, 52.0; H, 5.5; N, 25.3. Found: C, 52.1; H, 5.5; N, 25.3%.

Example 161

N$^1$-(1,4-Dioxido[1,3]dioxolo[4,5-g][1,2,4]benzotriazin-3-yl)-N$^2$,N$^2$-dimethyl-1,2-ethanediamine (224). H$_2$O$_2$ (70%, 0.67 mL, ca. 13.5 mmol) was added dropwise to a stirred solution of TFAA (1.9 mL, 13.5 mmol) in DCM (20 mL) at 0° C. The solution was stirred at 0° C. for 5 min, warmed to 20° C. for 10 min, then cooled to 0° C. and added to a stirred solution of 1-oxide 223 (374 mg, 1.4 mmol) and TFA (0.52 mL, 6.7 mmol) in DCM (15 mL) at 0° C. The solution was stirred at 20° C. for 8 h, diluted with dilute aqueous NH$_3$ solution (10 mL) and extracted with CHCl$_3$ (4×50 mL). The combined organic fraction was dried and the solvent evaporated. The residue was purified by chromatography, eluting with a gradient (0-20%) of MeOH/DCM, to give 1,4-dioxide 224 (52 mg, 13%) as a red solid: mp (MeOH/EtOAc) 175-179° C.; $^1$H NMR δ 7.60 (s, 1H, H-9), 7.59 (s, 1H, H-5), 7.35 (br s, 1H, NH), 6.21 (s, 2H, H-7), 3.61 (br t, J=6.0 Hz, 2H, CH$_2$N), 2.62 (br t, J=6.0 Hz, 2H, CH$_2$N), 2.31 [s, 6H, N(CH$_3$)$_2$]; $^{13}$C NMR δ 155.9, 149.7, 148.9, 137.8, 126.7, 103.5, 97.9, 94.1, 57.4, 45.1 (2), 38.8. Anal. calcd for C$_{12}$H$_{15}$N$_5$O$_4$·½CH$_3$OH: C, 48.5; H, 5.5; N, 22.6. Found: C, 48.7; H, 5.3; N, 22.6%.

Example 162

9,10-Dihydro-8H-chromeno[6,5-e][1,2,4]triazin-3-amine 1-Oxide (234)

N-(3,4-Dihydro-2H-chromen-6-yl)acetamide (228). A solution of KNO$_3$ (2.25 g, 22.3 mmol) in CH$_2$SO$_4$ (10 mL) was added dropwise to a stirred solution of 4-chromanone (225) (3.0 g, 20.2 mmol) in CH$_2$SO$_4$ (50 mL) at 0° C. and the mixture stirred at 0° C. for 2 h. The mixture was poured into ice/water (500 mL), stirred 30 min and the precipitate filtered. The solid was washed with water (3×10 mL) and dried. The solid was purified by chromatography, eluting with 20% EtOAc/pet. ether, to give (i) 8-nitro-2,3-dihydro-4H-chromen-4-one (226) (369 mg, 9%) as a white solid: mp (EtOAc/pet. ether) 120-121° C.; $^1$H NMR δ 8.17 (dd, J=7.8, 1.8 Hz, 1H, H-7), 8.10 (dd, J=8.0, 1.8 Hz, 1H, H-5), 7.12 (dd, J=8.0, 7.8 Hz, 1H, H-6), 4.73 (dd, J=6.5, 6.4 Hz, 2H, H-2), 2.95 (br t, J=6.5 Hz, 2H, H-3). Anal. calcd for C$_9$H$_7$NO$_4$: C, 56.0; H, 3.7; N, 7.3. Found: C, 56.1; H, 3.7; N, 7.3%; and (ii) 6-nitro-2,3-dihydro-4H-chromen-4-one (227) (3.17 g, 81%) as a white solid: mp (EtOAc/pet. ether) 169-171° C.; $^1$H NMR δ 8.78 (d, J=2.8 Hz, 1H, H-5), 8.32 (dd, J=9.1, 2.8 Hz, 1H, H-7), 7.11 (d, J=9.1 Hz, 1H, H-8), 4.67 (dd, J=6.6, 6.4 Hz, 2H, H-2), 2.91 (dd, J=6.6, 6.4 Hz, 2H, H-3); $^{13}$C NMR δ 189.4, 165.7, 142.1, 130.3, 123.7, 120.8, 119.3, 67.6, 37.1. Anal. calcd for C$_9$H$_7$NO$_4$: C, 56.0; H, 3.7; N, 7.3. Found: C, 56.1; H, 3.7; N, 7.4%.

A mixture of nitrochromanone 227 (2.0 g, 13.4 mmol) and Pd/C (5%, 100 mg) in EtOH/EtOAc (4:1, 150 mL), water (10 mL), and cHCl (1 mL) was stirred under H$_2$ (60 psi) for 16 h. The mixture was filtered through celite, washed with EtOH (3×25 mL) and the solvent evaporated. The residue was partitioned between dilute aqueous NH$_3$ solution and DCM, the organic fraction dried, and the solvent evaporated. The residue was dissolved in dry dioxane (100 mL) and Ac$_2$O (2.8 mL, 29.4 mmol) added dropwise. The solution was stirred at 20° C. for 16 h, diluted with water and the solvent evaporated. The residue was purified by chromatography, eluting with a gradient (50-100%) of EtOAc/pet. ether, to give acetamide 228 (2.09 g, 70%) as a white solid: mp 111-113° C. [lit. (Hach, V. Coll. Czech. Chem. Commun. 1959, 24, 3136-3140) mp (EtOH) 118° C.]; $^1$H NMR δ 7.28 (d, J=2.2 Hz, 1H, H-5), 7.02 (dd, J=8.6, 2.2 Hz, 1H, H-7), 6.72 (d, J=8.6 Hz, 1H, H-8), 4.15 (br dd, J=5.2, 5.0 Hz, 2H, H-2), 2.77 (br t, J=6.5 Hz, 2H, H-4), 2.13 (s, 3H, CH$_3$), 1.95-2.02 (m, 2H, H-3).

Alternative Preparation of N-(3,4-Dihydro-2H-chromen-6-yl)acetamide (228). A solution of 4-chromanone (225) (14.82 g, 0.1 mol) in HOAc (50 mL) was added to a stirred suspension of Zn dust (10 eq. w/w, 148 g) in HOAc (200 mL) and the mixture stirred at 100° C. for 16 h. The mixture was cooled, filtered, washed with HOAc (3×100 mL) and the solvent from the combined filtrate evaporated. The residue was suspended in water (200 mL) and the suspension made basic with NaOH, extracted with EtOAc (3×100 mL), the combined extracts dried and the solvent evaporated to give chroman (229) (11.83 g, 88%) as a white solid.

AlCl$_3$ (11.8 g, 88.2 mmol) was added in small portions to a stirred solution of AcCl (11.9 mL, 167.5 mmol) in dry DCM (250 mL) at −10° C. and the mixture stirred until homogeneous (15 min). The solution was added, via a cannula, to a stirred solution of chroman (229) (11.8 g, 88.2 mmol) in dry DCM (200 mL) at −10° C. and the solution stirred for 30 min at −10° C. and then poured into ice/cHCl (5:1 v/v, 1.5 L). The mixture was stirred for 2 h, extracted with DCM (3×100 mL), the combined organic fraction dried and the solvent evaporated. The residue was purified by chromatography, eluting with a gradient (10-20%) of EtOAc/pet. ether, to give 1-(3,4-dihydro-2H-chromen-6-yl)ethanone (230) (12.45 g, 80%) as a white solid: $^1$H NMR δ 7.68-7.22 (m, 2H, H-5, H-7), 6.82 (d, J=9.2 Hz, 1H, H-8), 4.24 (br dd, J=5.3, 5.2 Hz, 2H, H 2), 2.83 (br t, J=6.5 Hz, 2H, H-4), 2.53 (s, 3H, CH$_3$), 2.00-2.06 (m, 2H, H-3).

Hydroxylamine.HCl (2.9 g, 41.9 mmol) was added to a stirred solution of ketone 230 (6.15 g, 34.9 mmol) and pyridine (3.7 mL, 45.4 mmol) in MeOH (30 mL) and the mixture stirred at 20° C. for 16 h. The solvent was evaporated and the residue partitioned between brine and EtOAc. The organic fraction was dried and the solvent evaporated to give crude 1-(3,4-dihydro-2H-chromen-6-yl)ethanone oxime (6.3 g, 94%). HCl gas was bubbled through a solution of oxime (6.3 g, 32.5 mmol) in Ac$_2$O (6.1 mL, 65 mmol) and HOAc (40 mL, 650 mmol), and the solution stood at 20° C. for 24 h. The precipitate was poured into ice/water, stirred for 2 h, the solid filtered and washed with water and dried. The aqueous fraction was extracted with DCM (2×50 mL), the combined extract dried and the solvent evaporated. The slurry was treated with water (20 mL) and evaporated several times to remove Ac$_2$O. The combined solids were purified by chromatography, eluting with a gradient (50-100%) of EtOAc/pet.

ether, to give acetamide 228 (3.74 g, 59%) as a white solid: spectroscopically identical to the sample prepared above.

N-(7-Nitro-3,4-dihydro-2H-chromen-6-yl)acetamide (232) and N-(5-Nitro-3,4-dihydro-2H-chromen-6-yl)acetamide (231). A solution of fHNO$_3$ (2.5 mL, 63.2 mmol) in HOAc (10 mL) was added dropwise to a stirred solution of acetamide 228 (8.63 g, 45.1 mmol) in HOAc (100 mL) at 15° C. The mixture was stirred at 15° C. for 1 h, then poured into ice/water (800 mL) and stirred for 30 min. The precipitate was filtered, washed with water (3×30 mL) and dried. The solid was purified by chromatography, eluting with a gradient (30-100%) of EtOAc/pet. ether, to give (i) 7-nitro-6-acetamide 232 (2.49 g, 23%) as a white solid: mp (EtOAc) 141-143° C. [lit., (Brancaccio, G.; Lotteiri, G.; Viterbo, R. *J. Het. Chem.* 1973, 10, 623-629.) mp (EtOH) 139-142° C.]; $^1$H NMR δ 10.0 (br s, 1H, NH), 8.40 (s, 1H, H-8), 7.61 (s, 1H, H-5), 4.21 (br t, J=5.2 Hz, 2H, H-2), 2.87 (br t, J=6.5 Hz, 2H, H-4), 2.24 (s, 3H, CH$_3$), 2.00-2.06 (m, 2H, H-3); and (ii) 5-nitro-6-acetamide 231 (2.08 g, 19%) as a white solid: mp (EtOAc) 191-192° C. [lit. (Brancaccio, G.; Lotteiri, G.; Viterbo, R. *J. Het Chem.* 1973, 10, 623-629.) mp (EtOH) 177-180° C.]; $^1$H NMR δ 8.07 (br s, 1H, NH), 7.83 (br d, J=9.1 Hz, 1H, H-7), 6.99 (d, J=9.1 Hz, 1H, H-8), 4.20 (br t, J=5.2 Hz, 2H, H-2), 2.80 (br t, J=6.5 Hz, 2H, H-4), 2.16 (s, 3H, CH$_3$); 1.96-2.02 (m, 2H, H-3); and (iii) N-(8-nitro-3,4-dihydro-2H-chromen-6-yl)acetamide (0.85 g, 8%), as a white solid: mp (EtOAc) 200-201° C. [lit. (Brancaccio, G.; Lotteiri, G.; Viterbo, R. *J. Het. Chem.* 1973, 10, 623-629.) mp (EtOH) 188-191° C.]; $^1$H NMR δ 7.67 (br s, 1H, H-6), 7.61 (br s, 1H, H-5), 7.16 (br s, 1H, NH), 4.30 (br t, J=5.2 Hz, 2H, H-2), 2.86 (br t, J=6.5 Hz, 2H, H-4), 2.17 (s, 3H, CH$_3$); 2.04-2.10 (m, 2H, H-3).

5-Nitro-3,4-dihydro-2H-chromen-6-ylamine (233). A solution of acetamide 231 (1.24 g, 5.25 mmol) in 95% EtOH (50 mL) and NaOH (0.63 g, 15.7 mmol) was stirred at reflux temperature for 16 h. The mixture was cooled and the solvent evaporated. The residue was partitioned between Et$_2$O and water, the organic fraction dried and the solvent evaporated. The residue was purified by chromatography, eluting with 20% EtOAc/pet. ether, to give nitroaniline 233 (1.54 g, 85%) as red oil: $^1$H NMR δ 6.85 (d, J=9.0 Hz, 1H, H-8), 6.60 (d, J=9.0 Hz, 1H, H-7), 4.90 (br s, 2H, NH$_2$), 4.13 (dd, J=5.3, 5.1 Hz, 2H, H-2), 2.90 (br t, J=6.5 Hz, 2H, H-4), 1.91-1.96 (m, 2H, H-3).

9,10-Dihydro-8H-chromeno[6,5-e][1,2,4]triazin-3-amine 1-Oxide (234). A mixture of nitroaniline 233 (1.52 g, 7.8 mmol) and cyanamide (1.32 g, 31.3 mmol) were mixed together at 100° C., cooled to 50° C., cHCl (10 mL) added carefully and the mixture heated at 100° C. for 4 h. The mixture was cooled to 50° C., 7.5 M NaOH solution added until the mixture was strongly basic and the mixture stirred at 100° C. for 3 h. The mixture was cooled, diluted with water (100 mL), filtered, washed with water (3×20 mL) and dried. The aqueous fraction was extracted with CHCl$_3$ (3×50 mL), the combined organic fraction dried and the solvent evaporated. The combined solids were purified by chromatography, eluting with a gradient (0-5%) of MeOH/DCM, to give (i) starting nitroaniline 233 (470 mg, 31%) and (ii) amine 234 (246 mg, 14%) as a yellow powder: mp (MeOH/DCM) 275-279° C. (dec.); $^1$H NMR [(CD$_3$)$_2$SO] δ 7.26-7.31 (m, 2H, H-5, H-6), 6.90 (br s, 2H, NH$_2$), 4.12-4.17 (m, 2H, H-8), 3.30-3.33 (m, 2H, H-10), 1.87-1.93 (m, 2H, H-9); $^{13}$C NMR [(CD$_3$)$_2$SO] δ 159.0, 151.2, 146.3, 129.5, 128.0, 124.6, 113.5, 65.3, 24.4, 21.5. Anal. calcd for C$_{10}$H$_{10}$N$_4$O$_2$: C, 55.0; H, 4.6; N, 25.6. Found: C, 55.0; H, 4.6; N, 25.6%.

Example 163

3-Chloro-9,10-dihydro-8H-chromeno[6,5-e][1,2,4]triazine 1-Oxide (235). NaNO$_2$ (134 mg, 1.9 mmol) was added in small portions to a stirred solution of amine 234 (231 mg, 1.0 mmol) in TFA (10 mL) at 0° C. and the solution stirred at 20° C. for 3 h. The solution was poured into ice/water, stirred for 30 min, filtered, washed with water (3×10 mL) and dried. The solid was suspended in POCl$_3$ (20 mL) and DMF (0.3 mL), and stirred at 100° C. for 1 h. The solution was cooled, poured into ice/water, stirred for 30 min, filtered, washed with water (3×20 mL) and dried. The solid was suspended in DCM (100 mL), dried and the solvent evaporated. The aqueous fraction was extracted with EtOAc (3×30 mL), the combined organic fraction dried and the solvent evaporated. The combined solids were purified by chromatography, eluting with 5% EtOAc/DCM, to give chloride 235 (63 mg, 27%) as a pale yellow solid: mp (EtOAc) 160-162° C.; $^1$H NMR δ 7.70 (d, J=9.2 Hz, 1H, H-6), 7.47 (d, J=9.2 Hz, 1H, H-5), 4.29 (br dd, J=5.2, 5.2 Hz, 2H, H-8), 3.54 (t, J=6.5 Hz, 2H, H-10), 2.03-2.09 (m, 2H, H-9); $^{13}$C NMR δ 156.6, 154.0, 145.0, 133.9, 129.5, 126.9, 114.0, 66.4, 24.6, 21.6. Anal. calcd for C$_{10}$H$_8$ClN$_3$O$_2$: C, 50.5; H, 3.4; N, 17.7. Found: C, 50.7; H, 3.4; N, 17.8%.

Example 164

N$^1$,N$^1$-Dimethyl-N$^2$-(1-oxido-9,10-dihydro-8H-chromeno[6,5-e][1,2,4]triazin-3-yl)-1,2-ethanediamine (236). N,N-Dimethyl-1,2-ethanediamine (65 μL, 0.6 mmol) was added to a stirred solution of chloride 235 (47 mg, 0.2 mmol) in DME (20 mL) and the solution stirred at reflux temperature for 2 h. The solvent was evaporated and the residue was partitioned between DCM (50 mL) and dilute aqueous NH$_3$ solution (20 mL). The organic fraction was dried and the solvent evaporated. The residue was purified by chromatography, eluting with a gradient (0-10%) of MeOH/DCM, to give 1-oxide 236 (55 mg, 95%) as a pale yellow solid: mp (MeOH/EtOAc) 119-120° C.; $^1$H NMR δ 7.35 (d, J=9.2 Hz, 1H, H-6), 7.23 (d, J=9.2 Hz, 1H, H-5), 5.66 (br s, 1H, NH), 4.19 (br dd, J=5.1, 5.0 Hz, 2H, H-8), 3.47-3.53 (m, 4H, H-10, CH$_2$N), 2.54 (br t, J=6.0 Hz, 2H, CH$_2$N), 2.27 [s, 6H, N(CH$_3$)$_2$], 1.97-2.04 (m, 2H, H-9); $^{13}$C NMR δ 158.0, 152.2, 146.7, 130.3, 128.4, 125.2, 114.0, 65.9, 57.7, 45.1 (2), 38.7, 24.9, 22.2. Anal. calcd for C$_{14}$H$_{19}$N$_5$O$_2$·¼H$_2$O: C, 57.2; H, 6.7; N, 23.8. Found: C, 57.5; H, 6.6; N, 23.8%.

Example 165

N$^1$-(1,4-Dioxido-9,10-dihydro-8H-chromeno[6,5-e][1,2,4]triazin-3-yl)-N$^2$,N$^2$-dimethyl-1,2-ethanediamine (237). H$_2$O$_2$ (70%, 0.16 mL, ca. 3.2 mmol) was added dropwise to a stirred solution of TFAA (0.45 mL, 3.2 mmol) in DCM (10 mL) at 0° C. The solution was stirred at 0° C. for 5 min, warmed to 20° C. for 10 min, then cooled to 0° C. and added to a stirred solution of 1-oxide 236 (50 mg, 0.17 mmol) and TFA (0.12 mL, 1.6 mmol) in DCM (15 mL) at 0° C. The solution was stirred at 20° C. for 4 h, diluted with dilute aqueous NH$_3$ solution (10 mL) and extracted with CHCl$_3$ (4×50 mL). The combined organic fraction was dried and the solvent evaporated. The residue was purified by chromatography, eluting with a gradient (0-10%) of MeOH/DCM, to give 1,4-dioxide 237 (28 mg, 54%) as a red gum: $^1$H NMR δ 8.11 (d, J=9.5 Hz, 1H, H-5), 7.36 (d, J=9.5 Hz, 1H, H-6), 7.23 (br s, 1H, NH), 4.21-4.25 (m, 2H, H-8), 3.61 (br t, J=5.8 Hz, 2H, CH$_2$N), 3.56 (br t, J=6.5 Hz, 2H, H-10), 2.62 (br t, J=6.0 Hz, 2H, CH$_2$N), 2.31 [s, 6H, N(CH$_3$)$_2$], 2.00-2.07 (m, 2H, H-9); $^{13}$C NMR δ 154.0, 148.4, 135.8, 130.6, 128.9, 116.0, 114.9, 66.2, 57.5, 45.1 (2), 38.7, 24.5, 21.9; MS (FAB$^+$) m/z 306 (MH$^+$, 60%), 290 (20), 176 (100); HRMS (FAB$^+$) calcd for $C_{14}H_{20}N_5O_3$ (MH$^+$) m/z 306.1566, found 306.1568. Anal. calcd for $C_{14}H_{19}N_5O_3 \cdot \frac{1}{2}H_2O \cdot \frac{1}{2}MeOH$: C, 52.7; H, 6.7; N, 21.2. Found: C, 52.8; H, 6.7; N, 21.2%.

Example 166

7,8-Dihydro-6H-chromeno[6,7-e][1,2,4]triazin-3-amine 1-Oxide (239)

7-Nitro-3,4-dihydro-2H-chromen-6-ylamine (238). A suspension of acetamide 232 (2.49 g, 10.5 mmol) and cHCl (10 mL) in EtOH (50 mL) was heated at reflux temperature for 16 h. The solution was cooled, carefully neutralized with aqueous NH$_3$ solution, extracted with EtOAc (2×50 mL), the combined organic fraction dried and the solvent evaporated to give nitroaniline 238 (2.05 g, 100%) as an orange solid: mp (EtOAc) 145-148° C. [lit. (Brancaccio, G.; Lotteiri, G.; Viterbo, R. *J. Het. Chem.* 1973, 10, 623-629) mp (H$_2$O) 139-140° C.]; $^1$H NMR δ 7.54 (s, 1H, H-8), 6.50 (s, 1H, H-5), 5.62 (br s, 2H, NH$_2$), 4.14 (br t, J=5.2 Hz, 2H, H-2), 2.77 (br t, J=6.5 Hz, 2H, H-4), 1.95-2.02 (m, 2H, H-3).

7,8-Dihydro-6H-chromeno[6,7-e][1,2,4]triazin-3-amine 1-Oxide (239). A mixture of nitroaniline 238 (2.05 g, 10.6 mmol) and cyanamide (1.78 g, 42.3 mmol) were mixed together at 100° C., cooled to 50° C., cHCl (10 mL) added carefully and the mixture heated at 100° C. for 4 h. The mixture was cooled to 50° C., 7.5 M NaOH solution added until the mixture was strongly basic and the mixture stirred at 100° C. for 3 h. The mixture was cooled, diluted with water (200 mL), filtered, washed with water (3×50 mL) and dried. The aqueous fraction was extracted with CHCl$_3$ (3×50 mL), dried and the solvent evaporated. The combined solids were purified by chromatography, eluting with a gradient (0-10%) of MeOH/DCM, to give amine 239 (1.30 g, 56%) as a yellow powder: mp (MeOH/DCM) 280-283° C.; $^1$H NMR [(CD$_3$)$_2$SO] δ 7.32 (s, 1H, H-10), 7.31 (s, 1H, H-5), 6.96 (br s, 2H, NH$_2$), 4.22 (dd, J=5.3, 5.2 Hz, 2H, H-8), 2.95 (br t, J=6.3 Hz, 2H, H-6), 1.92-1.98 (m, 2H, H-7); $^{13}$C NMR [(CD$_3$)$_2$SO] δ 159.1, 152.2, 143.4, 135.8, 128.7, 125.7, 102.6, 66.5, 25.0, 21.0. Anal. calcd for $C_{10}H_{10}N_4O_2$: C, 55.0; H, 4.6; N, 25.7. Found: C, 55.1; H, 4.6; N, 25.5%.

Example 167

3-Chloro-7,8-dihydro-6H-chromeno[6,7-e][1,2,4]triazine 1-Oxide (240). NaNO$_2$ (320 mg, 4.6 mmol) was added in small portions to a stirred solution of amine 239 (963 mg, 4.4 mmol) in TFA (20 mL) at 0° C. and the solution stirred at 0° C. for 1 h. The solution was poured into ice/water, stirred for 30 min, filtered, washed with water (3×10 mL) and dried. The solid was suspended in POCl$_3$ (20 mL) and DMF (0.2 mL) and stirred at 100° C. for 1 h. The solution was cooled, poured into ice/water, stirred for 30 minutes, filtered, washed with water (3×20 mL) and dried. The solid was suspended in DCM (150 mL), dried and the solvent evaporated. The aqueous fraction was extracted with EtOAc (3×40 mL), the combined organic fraction dried and the solvent evaporated. The combined solid was purified by chromatography, eluting with 5% EtOAc/DCM, to give chloride 240 (939 mg, 66%) as a pale yellow solid: mp (EtOAc/DCM) 192-195° C.; $^1$H NMR δ 7.64-7.67 (m, 2H, H-5, H-10), 4.34-4.39 (m, 2H, H-8), 3.08 (br dd, J=6.6, 6.1 Hz, 2H, H-6), 2.09-2.15 (m, 2H, H-7); $^{13}$C NMR δ 157.6, 154.1, 141.9, 136.7, 133.2, 128.3, 104.0, 67.4, 26.0, 21.1. Anal. calcd for $C_{10}H_8ClN_3O_2$: C, 50.5; H, 3.4; N, 17.7. Found: C, 50.8; H, 3.3; N, 17.7%.

Example 168

N$^1$,N$^1$-Dimethyl-N$^2$-(1-oxido-7,8-dihydro-6H-chromeno[6,7-e][1,2,4]triazin-3-yl)-1,2-ethanediamine (241). N,N-Dimethyl-1,2-ethanediamine (0.47 mL, 4.3 mmol) was added to a stirred solution of chloride 240 (341 mg, 1.4 mmol) in DME (30 mL) and the solution stirred at reflux temperature for 4 h. The solvent was evaporated and the residue partitioned between DCM (100 mL) and dilute aqueous NH$_3$ solution (50 mL). The organic fraction was dried and the solvent evaporated. The residue was purified by chromatography, eluting with a gradient (0-10%) of MeOH/DCM, to give 1-oxide 241 (343 mg, 83%) as a yellow solid: mp (MeOH/EtOAc) 150-152° C.; $^1$H NMR δ 7.58 (s, 1H, H-10), 7.30 (s, 1H, H-5), 5.79 (br s, 1H, NH), 4.25 (br dd, J=5.3, 5.2 Hz, 2H, H-8), 3.51-3.56 (m, 2H, CH$_2$N), 2.96 (br t, J=6.0 Hz, 2H, H-6), 2.60 (br t, J=6.0 Hz, 2H, CH$_2$N), 2.31 [s, 6H, N(CH$_3$)$_2$], 2.02-2.09 (m, 2H, H-7); $^{13}$C NMR δ 158.0, 152.9, 143.6, 135.1, 130.0, 126.1, 104.3, 66.9, 57.6, 45.0 (2), 38.7, 25.9, 21.7. Anal. calcd for $C_{14}H_{19}N_5O_2 \cdot \frac{1}{2}H_2O$: C, 57.2; H, 6.7; N, 23.8. Found: C, 57.1; H, 6.5; N, 23.9%.

Example 169

N$^1$-(1,4-Dioxido-7,8-dihydro-6H-chromeno[6,7-e][1,2,4]triazin-3-yl)-N$^2$,N$^2$-dimethyl-1,2-ethanediamine (242). H$_2$O$_2$ (70%, 0.47 mL, ca. 9.3 mmol) was added dropwise to a stirred solution of TFAA (1.3 mL, 9.3 mmol) in DCM (10 mL) at 0° C. The solution was stirred at 0° C. for 5 min, warmed to 20° C. for 10 min, then cooled to 0° C. and added to a stirred solution of 1-oxide 241 (270 mg, 0.9 mmol) and TFA (0.36 mL, 4.7 mmol) in DCM (15 mL) at 0° C. The solution was stirred at 20° C. for 4 h, diluted with dilute aqueous NH$_3$ solution (10 mL) and extracted with CHCl$_3$ (4×50 mL). The combined organic fraction was dried and the solvent evaporated. The residue was purified by chromatography, eluting with a gradient (0-10%) of MeOH/DCM, to give 1,4-dioxide 242 (71 mg, 22%) as a red solid: mp (MeOH/EtOAc) 152-154° C.; $^1$H NMR δ 7.99 (s, 1H, H-5), 7.61 (s, 1H, H-10), 7.27 (br s, 1H, NH), 4.30 (br dd, J=5.3, 5.2 Hz, 2H, H-8), 3.62 (br t, J=5.9 Hz, 2H, CH$_2$N), 3.05 (br t, J=6.3 Hz, 2H, H-6), 2.62 (t, J=6.0 Hz, 2H, CH$_2$N), 2.31 [s, 6H, N(CH$_3$)$_2$], 2.05-2.12 (m, 2H, H-7); $^{13}$C NMR δ 154.7, 148.7, 136.2, 133.2, 130.1, 117.4, 105.2, 67.1, 57.6, 45.1 (2), 38.8, 26.1, 21.3. Anal. calcd for $C_{14}H_{19}N_5O_3 \cdot \frac{1}{2}H_2O$: C, 52.7; H, 6.5; N, 22.0. Found: C, 53.0; H, 5.9, 21.6%.

Example 170

N-[3-(4-Morpholinyl)propyl]-7,8-dihydro-6H-chromeno[6,7-e][1,2,4]triazin-3-amine 1-Oxide (243). 3-(4-Morpholinyl)propylamine (0.71 mL, 4.8 mmol) was added to a stirred solution of chloride 240 (380 mg, 1.6 mmol) in DME (40 mL) and the solution stirred at reflux temperature for 4 h. The solvent was evaporated and the residue partitioned between DCM (100 mL) and dilute aqueous NH$_3$ solution (50 mL). The organic fraction was dried and the solvent evaporated. The residue was purified by chromatography, eluting with a gradient (0-10%) of MeOH/DCM, to give 1-oxide 243 (514 mg, 93%) as a yellow solid: mp (MeOH/EtOAc) 151-152° C.; $^1$H NMR δ 7.60 (s, 1H, H-10), 7.30 (s, 1H, H-5), 6.00 (br s, 1H, NH), 4.26 (br dd, J=5.3, 5.2 Hz, 2H, H-8), 3.75 (br t, J=4.7 Hz, 4H, 2×CH$_2$O), 3.55 (dt, J=6.3, 5.9 Hz, 2H, CH$_2$N), 2.97 (br t, J=6.3 Hz, 2H, H-6), 2.45-2.52 (m, 6H, 3×CH$_2$N), 2.02-

2.08 (m, 2H, H-7), 1.79-1.86 (m, 2H, CH$_2$); $^{13}$C NMR δ 158.1, 152.9, 143.6, 135.1, 130.0, 126.1, 104.4, 67.0 (2), 66.9, 57.3 (2), 53.8, 40.7, 25.9, 25.3, 21.7. Anal. calcd for C$_{17}$H$_{23}$N$_5$O$_3$: C, 59.1; H, 6.7; N, 20.3. Found: C, 59.4; H, 6.6; N, 20.3%.

Example 171

N-[3-(4-Morpholinyl)propyl]-7,8-dihydro-6H-chromeno[6,7-e][1,2,4]triazin-3-amine 1,4-Dioxide (244). H$_2$O$_2$ (70%, 0.74 mL, ca. 14.7 mmol) was added dropwise to a stirred solution of TFM (2.1 mL, 14.7 mmol) in DCM (20 mL) at 0° C. The solution was stirred at 0° C. for 5 min, warmed to 20° C. for 10 min, then cooled to 0° C. and added to a stirred solution of 1-oxide 243 (509 mg, 1.5 mmol) and TFA (0.57 mL, 7.4 mmol) in DCM (15 mL) at 0° C. The solution was stirred at 20° C. for 4 h, diluted with dilute aqueous NH$_3$ solution (10 mL) and extracted with CHCl$_3$ (4×50 mL). The combined organic fraction was dried and the solvent evaporated. The residue was purified by chromatography, eluting with a gradient (0-10%) of MeOH/DCM, to give (i) starting material 243 (80 mg, 16%) and (ii) 1,4-dioxide 244 (75 mg, 16%) as a red solid: mp (MeOH/EtOAc) 173-176° C.; $^1$H NMR δ 8.33 (br t, J=4.9 Hz, 1H, NH), 8.01 (s, 1H, H-5), 7.62 (s, 1H, H-10), 4.31 (br dd, J=5.3, 5.2 Hz, 2H, H-8), 3.83 (br t, J=4.6 Hz, 4H, 2×CH$_2$O), 3.62-3.68 (m, 2H, CH$_2$N), 3.03-3.08 (m, 2H, H-6), 2.58 (br dd, J=6.2, 6.0 Hz, 2H, CH$_2$N), 2.50 (m, 4H, 2×CH$_2$N), 2.07-2.13 (m, 2H, H-7), 1.84-1.91 (m, 2H, CH$_2$); $^{13}$C NMR δ 154.5, 148.7, 136.1, 133.2, 129.9, 117.3, 105.2, 67.1, 66.9 (2), 57.8, 53.8 (2), 41.6, 26.1, 24.4, 21.3. Anal. calcd for C$_{17}$H$_{23}$N$_5$O$_3$.¼H$_2$O: C, 55.8; H, 6.5; N, 19.1. Found: C, 55.8; H, 6.5, 18.8%.

Example 172

7-Ethyl-7,8-dihydro-6H-[1,2,4]triazino[5,6-f]isoindol-3-amine 1-Oxide (247)

2-Ethyl-5-nitroisoindoline (245). A mixture of dibromide 118 (9.27 g, 30.0 mmol), ethylamine hydrochloride (2.45 g, 30.0 mmol) and Et$_3$N (21 mL, 150 mmol) in DMF (100 mL) was stirred at 20° C. for 90 min. The mixture was partitioned between EtOAc and aqueous Na$_2$CO$_3$ solution. The organic fraction was washed with water, dried and the solvent evaporated to give isoindole 245 (3.21 g, 56%) as a dark oil: $^1$H NMR δ 8.11 (dd, J=8.1, 2.1 Hz, 1H, H-6), 8.05 (d, J=2.1 Hz, 1H, H-4), 7.34 (d, J=8.1 Hz, 1H, H-7), 3.99 (s, 4H, H-1, H-3), 2.82 (q, J=7.2 Hz, 2H, CH$_2$), 1.22 (t, J=7.2 Hz, 3H, CH$_3$); HRMS (FAB$^+$) calcd for C$_{10}$H$_{13}$N$_2$O$_2$ (MH$^+$) m/z 193.0977, found 193.0983.

N-(2-Ethyl-2,3-dihydro-1H-isoindol-5-yl)acetamide (246). A solution of isoindole 245 (3.20 g, 16.7 mmol) in MeOH (100 mL) was stirred with Pd/C (5%, 300 mg) under H$_2$ (60 psi) for 16 h. The solution was filtered through Celite, washed with MeOH (3×20 mL) and the solvent evaporated. The residue was dissolved in DCM (130 mL) and Et$_3$N (13 mL, 93 mmol), Ac$_2$O (13 mL, 138 mmol) was added dropwise and the solution stirred at 20° C. for 15 h. The mixture was partitioned between DCM and aqueous Na$_2$CO$_3$ solution. The organic solution was washed with water, dried and the solvent was evaporated to give acetamide 246 (3.00 g, 88%) as a dark oil: $^1$H NMR δ 7.45 (br s, 1H, H-4), 7.30 (br s, 1H, NH), 7.18 (br d, J=8.0 Hz, 1H, H-6), 7.12 (d, J=8.0 Hz, 1H, H-7), 3.90 (s, 4H, H-1), 3.87 (s, 2H, H-3), 2.76 (q, J=7.2 Hz, 2H, CH$_2$), 2.15 (s, 3H, COCH$_3$) 1.19 (t, J=7.2 Hz, 3H, CH$_3$); HRMS (FAB$^+$) calcd for C$_{12}$H$_{17}$N$_2$O (MH$^+$) m/z 203.1184, found 203.1188.

N-(2-Ethyl-6-nitro-2,3-dihydro-1H-isoindol-5-yl)acetamide (247). KNO$_3$ (1.33 g, 13.2 mmol) was added in small portions, over 10 min, to a stirred solution of acetamide 246 (2.45 g, 12.0 mmol) in CH$_2$SO$_4$ (50 mL) at 0° C. and the reaction mixture was stirred at 0° C. for a further 45 min. The mixture was poured onto ice, made basic with cNH$_3$ and extracted with DCM (3×100 mL). The solvent was evaporated to give a brown oil which was purified by chromatography on neutral Al$_2$O$_3$, eluting with a gradient (0-20%) of EtOAc/pet. ether, to give nitroacetamide 247 (1.49 g, 50%) as a yellow solid: mp EtOAc/pet. ether) 85-87° C.; $^1$H NMR δ 10.43 (br s, 1H, NH), 8.62 (s, 1H, H-7), 8.03 (s, 1H, H-4), 3.96 (s, 2H, CH$_2$N), 3.92 (s, 2H, CH$_2$N), 2.79 (q, J=7.2 Hz, 2H, CH$_2$N), 2.28 (s, 3H, COCH$_3$), 1.21 (t, J=7.2 Hz, 3H, CH$_3$); HRMS (FAB$^+$) calcd for C$_{12}$H$_{16}$N$_3$O$_3$ (MH$^+$) m/z 250.1192, found 250.1195. Anal. calcd for C$_{12}$H$_{15}$N$_3$O$_3$: C, 57.8; H, 6.0; N, 16.9. Found: C, 57.9; H, 5.9; N, 16.7%.

2-Ethyl-6-nitro-5-isoindolinamine (246). A mixture of nitroacetamide 247 (1.52 g, 6.1 mmol) and 5 M HCl (12 mL) was stirred at reflux temperature for 20 min. The suspension was diluted with water (40 mL), cooled to 0° C., and made basic with cNH$_3$. The precipitate was filtered, washed with water and dried to give nitroaniline 248 (1.13 g, 89%); mp 121-123° C.; $^1$H NMR δ 7.94 (s, 1H, H-7), 6.64 (s, 1H, H-4), 6.06 (br s, 2H, NH$_2$), 3.83 (br s, 2H, CH$_2$N), 3.81 (br s, 2H, CH$_2$N), 2.75 (q, J=7.2 Hz, 2H, CH$_2$N), 1.19 (t, J=7.2 Hz, 3H, CH$_3$); $^{13}$C NMR δ 149.7, 144.6, 131.5, 130.0, 119.3, 111.7, 58.4, 57.3, 49.9, 13.9. Anal. calcd for C$_{10}$H$_{13}$N$_3$O$_2$: C, 58.0; H, 6.2; N, 20.3. Found: C, 57.8; H, 6.2; N, 20.0%.

7-Ethyl-7,8-dihydro-6H-[1,2,4]triazino[5,6-f]isoindol-3-amine 1-Oxide (249). A mixture of nitroaniline 248 (414 mg, 2.0 mmol) and cyanamide (336 mg, 8.0 mmol) were mixed together at 100° C., cooled to 50° C., cHCl (0.78 mL) added carefully and the mixture stirred at 70-80° C. for 45 min. The mixture was cooled to ca. 50° C. and 7.5 M NaOH solution (5 mL) added until the mixture was strongly basic and the mixture stirred at 80-90° C. for 15 min. The mixture was cooled, diluted with water (100 mL), filtered, washed with water (3×20 mL) and dried to give 1-oxide 249 (404 mg, 87%) as a greenish-yellow solid: mp 218° C.; $^1$H NMR [(CD$_3$)$_2$SO] δ 7.98 (s, 1H, H-9), 7.38 (s, 1H, H-5), 7.18 (s, 2H, NH$_2$), 3.89 (s, 2H, CH$_2$N), 3.86 (s, 2H, CH$_2$N), 2.70 (q, J=7.2 Hz, 2H, CH$_2$N), 1.11 (t, J=7.2 Hz, 3H, CH$_3$); $^{13}$C NMR [(CD$_3$)$_2$SO] δ 160.0, 149.8, 148.7, 138.5, 128.9, 118.2, 112.5, 57.5, 57.0, 49.0, 13.5. Anal. calcd for C$_{11}$H$_{13}$N$_5$O: C, 57.1; H, 5.7; N, 30.3. Found: C, 57.1; H, 5.6; N, 30.3%.

Example 173

7-Ethyl-7,8-dihydro-6H-[1,2,4]triazino[5,6-f]isoindol-3-amine 1,4-Dioxide (250). H$_2$O$_2$ (70%, 0.50 mL, ca. 10 mmol) was added dropwise to a stirred mixture of 1-oxide 249 (328 mg, 1.4 mmol), TFA (4 mL) and water (0.3 mL) at 0° C. and the mixture was stirred at 20° C. Two more aliquots of H$_2$O$_2$ (70%, 0.50 mL, ca. 10 mmol) were added at 3 h and 20 h. After 28 h at 20° C., the mixture was diluted with aqueous NH$_3$ solution (20 mL) and extracted with DCM (5×50 mL). The combined organic fraction was dried and the solvent evaporated. The residue was purified by chromatography, eluting with a gradient (0-10%) of MeOH/DCM, to give 1,4-dioxide 250 (68 mg, 19%) as a red solid which was crystallised as the hydrochloride salt: mp (MeOH/DCM) 230° C.; $^1$H NMR [(CD$_3$)$_2$SO] δ 11.84 (br s, 1H, HCl), 8.27 (s, 1H, H-9), 8.20 (s, 1H, H-5), 8.14 (br s, 2H, NH$_2$), 4.88-5.05 (m, 2H, CH$_2$N), 4.50-4.73 (m, 2H, CH$_2$N), 3.42 (q, J=7.2 Hz, 2H, CH$_2$N), 1.32 (t, J=7.2 Hz, 3H, CH$_3$); $^{13}$C NMR [(CD$_3$)$_2$SO] δ 151.4, 143.0, 138.5, 134.0, 130.6, 115.6, 111.4, 56.5, 56.1, 49.1, 10.3; HRMS (FAB$^+$) calcd for $C_{11}H_{14}N_5O_2$ (MH$^+$) m/z 248.1148, found 248.1154.

Example 174

7-Methyl-6,7,8,9-tetrahydro[1,2,4]triazino[6,5-g] isoquinolin-3-amine 1-Oxide (256)

2-Methyl-7-nitro-1,2,3,4-tetrahydroisoquinoline (252). Formic acid (9.4 mL, 250 mmol) was added dropwise to Ac$_2$O (19 mL, 202 mmol) at 0° C. The solution was stirred at 50° C. for 45 min, then cooled to −18° C., diluted with THF (100 mL) and a solution of 7-nitro-1,2,3,4-tetrahydroisoquinoline [(a) Tercel, M.; et al., *J. Med. Chem.* 1996, 39, 1084-1094; (b) Zhu, Z., et al., *J. Med. Chem.* 2003, 46, 831-837] (251) (13.8 g, 5.0 mmol) in THF (100 mL) was added and stirred at −15 to −18° C. for 30 min. The solution was warmed to 20° C., the solvent evaporated and the residue partitioned between saturated aqueous NaHCO$_3$ solution (250 mL) and EtOAc (250 mL). The aqueous fraction was extracted with EtOAc (3×250 mL), dried and the solvent evaporated. The residue was dissolved in THF (200 mL), cooled to 10° C. and BH$_3$-DMS solution (10 M, 19.4 mL, 194 mmol) was added. The solution was stirred at 20° C. for 1 h, diluted with MeOH (30 mL) and acidified with HCl solution (1 M, 45 mL). The solution was stirred at 40° C. for 15 min, the solvent evaporated and the residue partitioned between saturated aqueous NaHCO$_3$ solution (250 mL) and EtOAc (250 mL). The aqueous fraction was extracted with EtOAc (3×250 mL), dried and the solvent evaporated. The residue was purified by chromatography, eluting with a gradient (2-5%) of MeOH/DCM, to give isoquinoline 252 (12.6 g, 85%) as an orange solid: $^1$H NMR δ 8.09 (dd, J=8.4, 2.3 Hz, 1H, H-6), 7.95 (d, J=2.3 Hz, 1H, H-8), 7.37 (d, J=8.4 Hz, 1H, H-5), 4.27 (d, J=16.1 Hz, 1H, H-1), 3.94 (d, J=16.1 Hz, 1H, H-1), 3.23-3.34 (m, 2H, CH$_2$), 2.99-3.18 (m, 2H, CH$_2$), 2.17 (s, 3H, NCH$_3$); MS (APCI) m/z 193 (MH$^+$, 100%).

N-(2-Methyl-1,2,3,4-tetrahydro-7-isoquinolinyl)acetamide (253). A solution of isoquinoline 252 (2.5 g, 13.0 mmol) in EtOH (200 mL) was stirred with Pd/C (5%, 200 mg) under H$_2$ (35 psi) for 4 h. The solution was filtered through Celite, washed with EtOH (50 mL) and the solvent was evaporated. The residue was dissolved in dioxane (50 mL), Ac$_2$O (2.7 mL, 28.6 mmol) was added and the solution stirred at 20° C. for 16 h. The solvent was evaporated and the residue was partitioned between dilute aqueous NH$_3$ solution (50 mL) and DCM (50 mL). The aqueous layer was extracted with DCM (4×125 mL), the combined organic fraction dried and the solvent evaporated. The residue was purified by chromatography, eluting with 5% MeOH/DCM, to give acetamide 253 (2.1 g, 77%) as a brown solid: mp 157-159° C.; $^1$H NMR δ 7.29 (br s, 1H, H-8), 7.27 (br s, 1H, H-6), 7.22 (br s, 1H, NH), 7.12 (br d, J=8.1 Hz, 1H, H-5), 4.18 (d, J=16.2 Hz, 1H, H-1), 3.82 (d, J=16.1 Hz, 1H, H-1), 3.11-3.25 (m, 2H, H-3), 2.91-3.00 (m, 2H, H-4), 2.61 (s, 3H, NCH$_3$), 2.16 (s, 3H, COCH$_3$); $^{13}$C NMR δ 168.3, 136.6, 131.0, 129.2, 126.6, 119.2, 118.1, 61.5, 56.6, 47.3, 24.5, 24.0; MS (APCI) m/z 205 (MH$^+$, 100%). Anal. calcd for $C_{12}H_{16}N_2O \cdot \frac{1}{2}CH_3OH \cdot \frac{1}{2}H_2O$: C, 65.5; H, 8.4; N, 12.2. Found: C, 65.8; H, 8.8; N, 12.6%.

2-Methyl-8-nitro-1,2,3,4-tetrahydro-7-isoquinolinamine (254) and 2-Methyl-6-nitro-1,2,3,4-tetrahydro-7-isoquinolinamine (255). A solution of KNO$_3$ (7.9 g, 78.4 mmol) in CH$_2$SO$_4$ (30 mL) was added dropwise to a stirred solution of acetamide 253 (14.6 g, 71.3 mmol) in cH$_2$SO$_4$ (200 mL) at 0° C. The solution was stirred at 0° C. for 90 min, then poured into ice/water (1 L), the pH adjusted to 10 with cNH$_3$ and the mixture extracted with DCM (4×250 mL). The solvent was evaporated, the residue dissolved in HCl (5 M, 150 mL) and heated at reflux temperature for 3 h. The solution was cooled and partitioned between cNH$_3$ (70 mL) and DCM (250 mL). The aqueous layer was extracted with DCM (3×250 mL), the combined organic fraction dried and the solvent evaporated. The residue was purified by chromatography, eluting with a gradient (5-20%) of MeOH/DCM, to give (i) 8-nitroaniline 254 (1.9 g, 12%) as an orange solid: mp 122-123° C., $^1$H NMR δ 7.05 (d, J=8.5 Hz, 1H, H-6), 6.64 (d, J=8.5 Hz, 1H, H-5), 5.24 (br s, 2H, NH$_2$), 3.69 (s, 2H, H-1), 2.84 (t, J=6.0 Hz, 2H, H-3), 2.66 (t, J=6.0 Hz, 2H, H-4), 2.46 (s, 3H, NCH$_3$); $^{13}$C NMR δ 141.5, 134.5, 134.0, 131.6, 124.6, 116.6, 56.3, 51.9, 46.0, 28.7; MS (APCI) m/z 208 (MH$^+$, 100%). Anal. calcd for $C_{10}H_{13}N_3O_2 \cdot \frac{1}{4}H_2O$: C, 56.7; H, 6.4; N, 19.9. Found: C, 56.5; H, 6.8; N, 20.0%; and (ii) 6-nitroaniline 255 (2.8 g, 18%) as an orange solid: mp 171-172° C., $^1$H NMR δ 7.89 (s, 1H, H-5), 6.46 (s, 1H, H-8), 5.85 (br s, 2H, NH$_2$), 3.50 (s, 2H, H-1), 2.84 (t, J=6.0 Hz, 2H, H-3), 2.66 (t, J=6.0 Hz, 2H, H-4), 2.43 (s, 3H, NCH$_3$); $^{13}$C NMR δ 144.0, 142.5, 131.4, 125.5, 123.5, 115.4, 57.7, 52.8, 45.8, 28.0; MS (APCI) m/z 208 (MH$^+$, 100%). Anal. calcd for $C_{10}H_{13}N_3O_2$: C, 58.0; H, 6.3; N, 20.3. Found: C, 57.9; H, 6.3; N, 20.4%.

7-Methyl-6,7,8,9-tetrahydro[1,2,4]triazino[6,5-g]isoquinolin-3-amine 1-Oxide (256). A mixture of 6-nitroaniline 255 (2.3 g, 10.7 mmol) and cyanamide (2.0 g, 46.6 mmol) was melted at 100° C. The mixture was cooled to 60° C. and cHCl (5 mL) was slowly added. The solution was heated at 100° C. for 90 min, then a further three aliquots of cyanamide (2.1 g) and cHCl (5 mL) were added over 3 h. The solution was cooled to 50° C. and made basic with NaOH solution (7.5 M, 20 mL). The solution was heated at 100° C. for another 90 min, cooled and diluted with water (50 mL). The solid was filtered and washed with water to give 1-oxide 256 (1.70 g, 66%) as a brown solid: mp 170-175° C.; $^1$H NMR [(CD$_3$)$_2$SO] δ 7.90 (s, 1H, H-10), 7.25 (s, 1H, H-5), 7.15 (br s, 2H, NH$_2$), 3.62 (s, 2H, H-6), 2.96 (t, J=5.9 Hz, 2H, H-8), 2.62 (t, J=5.9 Hz, 2H, H-9), 2.35 (s, 3H, NCH$_3$); $^{13}$C NMR δ 159.8, 146.8, 144.3, 132.0, 128.4, 121.9, 118.3, 57.3, 51.9, 45.4, 28.3; MS (APCI) m/z 232 (MH$^+$, 100%). Anal. calcd for $C_{11}H_{13}N_5O \cdot \frac{1}{2}H_2O$: C, 55.0; H, 5.9; N, 29.1. Found: C, 55.6; H, 5.5; N, 28.7%.

Example 175

3-Chloro-7-methyl-6,7,8,9-tetrahydro[1,2,4]triazino[6,5-g]isoquinoline 1-Oxide (257). NaNO$_2$ (570 mg, 8.2 mmol) was added in portions to a solution of 1-oxide 256 (1.8 g, 7.8 mmol) in TFA (20 mL) and the mixture was stirred at 0° C. for 4 h. The solution was poured into ice/water (100 mL), made basic with dilute aqueous NH$_3$ solution (50 mL) and extracted with DCM (150 mL). The aqueous fraction was concentrated and the residue dried. The residue was dissolved in POCl$_3$ (40 mL) and DMF (3 drops) and heated at 100° C. for 3 h. The solution was cooled, poured into ice/water (400 mL), basified with dilute aqueous NH$_3$ solution (50 mL) and the aqueous layer was extracted with DCM (3×200 mL). The combined organic fraction was dried and the solvent evaporated. The residue was purified by chromatography, eluting with 5% MeOH/DCM, to give chloride 257 (1.47 g, 75%) as a yellow solid: mp 179° C. (dec.); $^1$H NMR δ 8.17 (s, 1H, H-10), 7.63 (s, 1H, H-5), 3.80 (s, 2H, H-6), 3.17 (t, J=6.0 Hz, 2H, H-8), 2.77 (t, J=5.9 Hz, 2H, H-9), 2.51 (s, 3H, NCH$_3$); $^{13}$C NMR δ 156.2, 146.3, 145.5, 139.7, 128.0, 124.8, 119.0, 58.0, 52.0, 45.8, 29.7; MS (APCI) m/z 251 (MH$^+$, 100%), 253 (MH$^+$, 30%). Anal. calcd for $C_{11}H_{11}ClN_4O$: C, 52.7; H, 4.4; N, 22.4; Cl, 14.1. Found: C, 52.7; H, 4.4; N, 22.3; Cl, 14.2%.

Example 176

N-Ethyl-7-methyl-6,7,8,9-tetrahydro[1,2,4]triazino[6,5-g]isoquinolin-3-amine 1-Oxide (258). A solution of chloride 257 (500 mg, 2.0 mmol) and ethylamine (0.4 mL, 6.0 mmol) in DME (15 mL) was heated at 60° C. for 4 h in a sealed pressure tube. The solution was cooled to 20° C., the solid filtered off and solvent evaporated. The combined residue was purified by chromatography, eluting with a gradient (2-4%) of MeOH/DCM, to give 1-oxide 258 (460 mg, 88%) as a yellow solid: mp 193-196° C.; $^1$H NMR δ 8.03 (s, 1H, H-10), 7.27 (s, 1H, H-5), 5.07 (br s, 1H, NH), 3.69 (s, 2H, H-6), 3.53 (dq, J=7.2, 5.8 Hz, 2H, $CH_2N$), 3.05 (t, J=6.0 Hz, 2H, H-8), 2.72 (t, J=6.0 Hz, 2H, H-9), 2.48 (s, 3H, $NCH_3$), 1.29 (t, J=7.2 Hz, 3H, $CH_3$); $^{13}$C NMR δ 158.6, 147.0, 144.4, 132.5, 129.6, 122.8, 119.3, 58.2, 52.6, 46.0, 36.3, 29.1, 14.8; MS (APCI) m/z 260 (MH$^+$, 100%). Anal. calcd for $C_{13}H_{17}N_5O$: C, 60.2; H, 6.6; N, 27.0. Found: C, 59.9; H, 6.6; N, 26.9%.

Example 177

N-Ethyl-7-methyl-6,7,8,9-tetrahydro[1,2,4]triazino[6,5-g]isoquinolin-3-amine 1,4-Dioxide (259). $H_2O_2$ (70%, 1.7 mL, ca. 17 mmol) was added dropwise to a stirred solution of TFAA (2.4 mL, 17 mmol) in DCM (15 mL) at 0° C. The solution was stirred at 20° C. for 10 min, then cooled to 0° C., added to a solution of 1-oxide 258 (440 mg, 1.7 mmol) and TFA (0.66 mL, 8.5 mmol) in DCM (15 mL) at 0° C. The solution was stirred at 20° C. for 4 h, diluted with dilute aqueous $NH_3$ solution (80 mL) and extracted with DCM (4×125 mL). The combined organic fraction was dried and the solvent evaporated. The residue was purified by chromatography, eluting with a gradient (1-10%) of MeOH/DCM, to give 1,4-dioxide 259 (35 mg, 8%) as a red solid: mp 120-124° C.; $^1$H NMR δ 8.10 (s, 1H, H-10), 7.96 (s, 1H, H-5), 6.95 (br s, 1H, NH), 3.78 (s, 2H, H-6), 3.63 (dq, J=7.2, 6.0 Hz, 2H, $CH_2N$), 3.10 (t, J=6.0 Hz, 2H, H-8), 2.75 (t, J=6.0 Hz, 2H, H-9), 2.50 (s, 3H, $NCH_3$), 1.36 (t, J=7.2 Hz, 3H, $CH_3$); $^{13}$C NMR δ 149.3, 145.5, 136.5, 135.3, 129.3, 120.5, 113.9, 58.1, 52.1, 45.8, 36.5, 29.1, 14.8; MS (APCI) m/z 276. (MH$^+$, 100%); HRMS (FAB$^+$) calcd for $C_{13}H_{18}N_5O_2$ (MH$^+$) m/z 276.1461, found 276.1456.

Example 178

3-Ethyl-7-methyl-6,7,8,9-tetrahydro[1,2,4]triazino[6,5-g]isoquinoline 1-Oxide (260). Pd(PPh$_3$)$_4$ (350 mg, 0.3 mmol) was added to a N$_2$-purged, stirred solution of chloride 257 (750 mg, 3.0 mmol) and Et$_4$Sn (1.2 mL, 6.0 mmol) in DME (35 mL), and the mixture was stirred at 85° C. for 18 h under N$_2$. The solution was cooled to 20° C. and the solvent evaporated. The residue was purified by chromatography, eluting with a gradient (2-5%) of MeOH/DCM, to give 1-oxide 260 (590 mg, 81%) as a brown solid: mp 129-131° C.; $^1$H NMR δ 8.21 (s, 1H, H-10), 7.63 (s, 1H, H-5), 3.79 (s, 2H, H-6), 3.16 (t, J=6.0 Hz, 2H, H-8), 3.02 (q, J=7.6 Hz, 2H, $CH_2$), 2.77 (t, J=6.0 Hz, 2H, H-9), 2.51 (s, 3H, $NCH_3$), 1.43 (t, J=7.6 Hz, 3H, $CH_3$); $^{13}$C NMR δ 167.3, 145.8144.6, 138.2, 131.7, 125.0, 118.8, 58.1, 52.3, 45.9, 30.7, 29.6, 12.2; MS (APCI) m/z 245 (MH$^+$, 100%). Anal. calcd for $C_{13}H_{16}N_4O \cdot \frac{1}{4}H_2O$: C, 62.5; H, 6.7; N, 22.4. Found: C, 62.6; H, 6.6; N, 22.4%.

Example 179

3-Ethyl-7-methyl-6,7,8,9-tetrahydro[1,2,4]triazino[6,5-g]isoquinoline 1,4-Dioxide (261). $H_2O_2$ (70%, 2.4 mL, ca. 25 mmol) was added dropwise to a stirred solution of TFAA (3.5 mL, 25 mmol) in DCM (20 mL) at 0° C. The solution was stirred at 20° C. for 10 min, then cooled to 0° C., added to a solution of 1-oxide 260 (590 mg, 2.4 mmol) and TFA (0.96 mL, 12.2 mmol) in DCM (20 mL) at 0° C. The solution was stirred at 20° C. for 4 h, diluted with dilute aqueous $NH_3$ solution (80 mL) and extracted with DCM (4×150 mL). The combined organic fraction was dried and the solvent evaporated. The residue was purified by chromatography, eluting with a gradient (2-5%) of MeOH/DCM, to give 1,4-dioxide 261 (107 mg, 17%) as a yellow solid: mp 124-128° C.; $^1$H NMR δ 8.23 (s, 1H, H-10), 8.18 (s, 1H, H-5), 3.83 (s, 2H, H-6), 3.15-3.24 (m, 4H, $CH_2$, H-8), 2.78 (t, J=6.0 Hz, 2H, H-9), 2.51 (s, 3H, $NCH_3$), 1.43 (t, J=7.5 Hz, 3H, $CH_3$); $^{13}$C NMR δ 149.3, 145.5, 136.5, 135.3, 129.3, 120.5, 116.3, 58.1, 51.9, 45.8, 29.6, 23.9, 9.3; MS (APCI) m/z 261 (MH$^+$, 100%). Anal. calcd for $C_{13}H_{16}N_4O_2 \cdot \frac{1}{4}CH_2Cl_2$: C, 56.5; H, 5.9; N, 19.9. Found: C, 56.6; H, 5.9; N, 19.7%.

Example 180

9-Methyl-7,8,9,10-tetrahydro[1,2,4]triazino[5,6-h]isoquinolin-3-amine 1-Oxide (262). A mixture of 8-nitroaniline 254 (510 mg, 2.5 mmol) and cyanamide (460 mg, 10.9 mmol) was melted at 100° C. The mixture was cooled to 60° C. and cHCl (4 mL) was added slowly. The solution was heated at 100° C. for 1 h, then three more aliquots of cyanamide (460 mg, 10.9 mmol) and cHCl (5 mL) were added over 3 h. The solution was cooled to 60° C. and the solution made basic with NaOH solution (7.5 M, 10 mL). The solution was heated at 100° C. for another 1 h, cooled and diluted with water (50 mL). The solid was filtered and washed with water (30 mL) to give 1-oxide 262 (360 mg, 63%) as a brown solid: mp 226-229° C.; $^1$H NMR [(CD$_3$)$_2$SO] δ 7.50 (d, J=8.6 Hz, 1H, H-5), 7.32 (d, J=8.6 Hz, 1H, H-6), 7.09 (br s, 2H, $NH_2$), 4.09 (s, 2H, H-10), 2.88 (t, J=5.7 Hz, 2H, H-7), 2.58 (t, J=5.7 Hz, 2H, H-8), 2.40 (s, 3H, $NCH_3$); MS (APCI) m/z 232 (MH$^+$, 100%). Anal. calcd for $C_{11}H_{13}N_5O \cdot \frac{1}{4}CH_3OH$: C, 56.5; H, 5.9; N, 29.3. Found: C, 56.6; H, 5.6; N, 29.1%.

Example 181

3-Chloro-9-methyl-7,8,9,10-tetrahydro[1,2,4]triazino[5,6-h]isoquinoline 1 Oxide (263). NaNO$_2$ (105 mg, 1.5 mmol) was added to a stirred solution of 1-oxide 262-(295 mg, 1.3 mmol) in TFA (10 mL) and the mixture stirred at 0° C. for 3 h. The solution was poured into ice/water (50 mL), concentrated and the residue dried. The residue was dissolved in POCl$_3$ (10 mL) and DMF (2 drops) and heated at 100° C. for 4 h. The solution was cooled, poured into ice/water (100 mL), and made basic with dilute aqueous NH$_3$ solution (20 mL). The mixture was extracted with DCM (3×200 mL), the combined organic fraction dried and the solvent evaporated. The residue was purified by chromatography, eluting with a gradient (3-5%) of MeOH/DCM, to give chloride 263 (240 mg, 75%) as a yellow solid: mp 200-205° C.; $^1$H NMR δ 7.75 (d, J=8.6 Hz, 1H, H-5), 7.69 (d, J=8.6 Hz, 1H, H-6), 4.32 (s, 2H, H-10), 3.07-3.13 (m, 2H, H-7), 2.74 (t, J=5.9 Hz, 2H, H-8), 2.57 (s, 3H, $NCH_3$); $^{13}$C NMR δ 155.9, 148.1, 138.7, 138.1, 132.5, 130.4, 125.7, 57.2, 50.3, 45.8, 30.9; MS (APCI) m/z 251 (MH$^+$, 100%), 253 (MH$^+$, 35%). Anal. calcd for $C_{11}H_{11}ClN_4O$: C, 52.7; H, 4.4; N, 22.4; Cl, 14.1. Found: C, 52.7; H, 4.4; N, 22.2; Cl, 14.4%.

Example 182

3-Ethyl-9-methyl-7,8,9,10-tetrahydro[1,2,4]triazino[5,6-h]isoquinoline 1 Oxide (264). Pd(PPh$_3$)$_4$ (108 mg, 0.09 mmol) was added to a N$_2$-purged, stirred solution of chloride 263 (225 mg, 0.9 mmol) and Et$_4$Sn (0.36 mL, 1.8 mmol) in DME (15 mL) and the mixture was stirred at 85° C. for 18 h under N$_2$. The solution was cooled to 20° C. and the solvent evaporated. The residue was purified by chromatography, eluting with a gradient (2-10%) of MeOH/DCM, to give 1-oxide 264 (130 mg, 60%) as a brown solid: mp 99-102° C.; $^1$H NMR δ 7.75 (d, J=8.6 Hz, 1H, H-5), 7.62 (d, J=8.6 Hz, 1H, H-6), 4.38 (s, 2H, H-10), 3.05-3.11 (m, 2H, H-7), 2.98 (q, J=7.6 Hz, 2H, CH$_2$), 2.73 (t, J=5.9 Hz, 2H, H-8), 2.57 (s, 3H, NCH$_3$), 1.42 (t, J=7.6 Hz, 3H, CH$_3$); $^{13}$C NMR δ 167.1, 148.4, 137.1, 136.9, 136.3, 129.7, 126.1, 57.4, 50.5, 45.9, 30.7, 30.2, 12.2; MS (APCI) m/z (MH$^+$, 100%). HRMS (FAB$^+$) calcd for $C_{13}H_{17}N_4O$ (MH$^+$) m/z 245.1402, found 245.1403.

Example 183

3-Ethyl-9-methyl-7,8,9,10-tetrahydro[1,2,4]triazino[5,6-h]isoquinoline 1,4-Dioxide (265). H$_2$O$_2$ (70%, 0.5 mL, ca. 5 mmol) was added dropwise to a stirred solution of TFM (0.7 mL, 5 mmol) in DCM (10 mL) at 0° C. The solution was stirred at 20° C. for 10 min, then cooled to 0° C., added to a solution of 1-oxide 264 (120 mg, 0.5 mmol) and TFA (0.19 mL, 2.5 mmol) in DCM (10 mL) at 0° C. The solution was stirred at 20° C. for 4 h, diluted with dilute aqueous NH$_3$ solution (20 mL) and extracted with DCM (4×100 mL). The combined organic fraction was dried and the solvent evaporated. The residue was purified by chromatography, eluting with a gradient (2-8%) of MeOH/DCM, to give 1,4-dioxide 265 (24 mg, 19%) as a red solid: mp 117-121° C.; $^1$H NMR δ 8.35 (d, J=8.8 Hz, 1H, H-5), 7.70 (d, J=8.8 Hz, 1H, H-6), 4.41 (s, 2H, H-10), 3.18 (q, J=7.5 Hz, 2H, CH$_2$), 3.12 (br t, J=5.8 Hz, 2H, H-7), 2.74 (t, J=5.8 Hz, 2H, H-8), 2.58 (s, 3H, NCH$_3$), 1.42 (t, J=7.5 Hz, 3H, CH$_3$); MS (APCI) m/z 261 (MH$^+$, 100%); HRMS (FAB$^+$) calcd for $C_{13}H_{17}N_4O_2$ (MH$^+$) m/z 261.1352, found: 261.1354.

Example 184

Synthesis of Amine Sidechains $N^1$-(2-Methoxyethyl)-$N^1$-methyl-1,2-ethanediamine (268)

[(2-Methoxyethyl)(methyl)amino]acetonitrile (267). 2-Methoxy-N-methylethanamine 266 (10.0 g, 112 mmol) was added dropwise to a stirred aqueous solution of glycolonitrile (55%, 12.0 mL, 123 mmol) at 0° C. and the mixture stirred at 70° C. for 1 h. The solution was cooled to 20° C., and Et$_2$O (150 mL) and water (100 mL) were added. The aqueous layer was extracted with Et$_2$O (3×40 mL), the combined organic fraction dried and the solvent evaporated to give nitrile 267 (6.46 g, 45%) as a colourless oil: $^1$H NMR [(CD$_3$)$_2$SO] δ 3.63 (s, 2H, CH$_2$CN), 3.50 (t, J=5.1 Hz, 2H, CH$_2$O), 3.37 (s, 3H, OCH$_3$), 2.69 (t, J=5.1 Hz, 2H, CH$_2$N), 2.42 (s, 3H, NCH$_3$); HRMS calcd for $C_6H_{12}N_2O$ (M$^+$) m/z 128.0947, found 128.0946.

$N^1$-(2-Methoxyethyl)-$N^1$-methylethane-1,2-diamine (268). A mixture of nitrile 267 (3.06 g, 23.4 mmol) and Raney-Nickel (50% slurry in water, 15 g) in EtOH (100 mL) and cNH$_3$ (10 mL) was stirred vigorously under H$_2$ (60 psi) for 5 h. The mixture was filtered through Celite, washed with EtOH (60 mL) and the solvent evaporated, keeping the bath temperature below 35° C. to give crude diamine 268 (Pasini, C.; et al., Farmaco, Edizione Scientifica 1965, 20, 673-685) (2.45 g, 79%) as a colourless oil, which was used without further purification: $^1$H NMR [(CD$_3$)$_2$SO] δ 3.39 (t, J=6.0 Hz, 2H, CH$_2$O), 3.22 (s, 3H, OCH$_3$), 2.61 (br s, 2H, CH$_2$N), 2.49 (t, J=6.0 Hz, 2H, CH$_2$N), 2.36 (t, J=6.7 Hz, 2H, CH$_2$N), 2.17 (s, 3H, NCH$_3$), NH$_2$ not observed; $^{13}$C NMR δ 59.4, 57.9, 56.3, 42.4, 38.6, 20.2.

$N^1$-(3-Methoxypropyl)-$N^1$-methyl-1,2-ethanediamine (274)

tert-Butyl 3-Methoxypropylcarbamate (270). A solution of 3-methoxy-1-propanamine (269) (20 mL, 195 mmol) and di-tert-butyldicarbonate (43.5 g, 199 mmol) in CHCl$_3$ (400 mL) was heated at reflux temperature for 16 h. The solution was cooled, the solvent evaporated and the residue dried to give carbamate 270 (42.3 g, quant.) as a colourless oil: $^1$H NMR δ 4.81 (br s, 1H, NH), 3.44 (t, J=6.0 Hz, 2H, CH$_2$N), 3.33 (s, 3H, OCH$_3$), 3.18-3.25 (m, 2H, OCH$_2$), 1.75 (p, J=6.3 Hz, 2H, CH$_2$), 1.44 [s, 9H, C(CH$_3$)$_3$].

tert-Butyl 3-Methoxypropyl(methyl)carbamate (271). A suspension of carbamate 270 (5.0 g, 26.4 mmol), crushed KOH (3.8 g, 67.7 mmol) in MeI (15 mL) was stirred at 20° C. for 72 h under N$_2$. The solution was filtered through Celite, washed with DCM (2×50 mL) and the solvent evaporated. The residue was purified by chromatography, eluting with a gradient (30-50%) of EtOAc/pet. ether, to give carbamate 271 (2.0 g, 37%) as a colourless oil: $^1$H NMR δ 3.38 (t, J=6.3 Hz, 2H, CH$_2$N), 3.33 (s, 3H, OCH$_3$), 3.28 (t, J=7.0 Hz, 2H, CH$_2$O), 2.85 (s, 3H, NCH$_3$), 1.78 (tt, J=7.0, 6.3 Hz, 2H, CH$_2$), 1.46 [s, 9H, C(CH$_3$)$_3$]; MS (APCI) m/z 104 (MH$^+$-tBuCO$_2$, 100%); HRMS (FAB$^+$) calcd for $C_{10}H_{22}NO_3$ (MH$^+$) m/z 204.1600, found 204.1605.

N-(3-Methoxypropyl)-N-methylamine (272). A solution of HCl in dioxane (4 M, 15 mL, 60 mmol) was added to a solution of carbamate 271 (3.8 g, 18.7 mmol) in dioxane (50 mL) was stirred at 20° C. for 24 h. The solvent was evaporated to give crude amine 272 as the HCl salt: (2.6 g, quant.) as a colourless oil; $^1$H NMR δ 9.39 (br s, 2H, NH$_2$$^+$Cl$^-$), 3.54 (t, J=5.7 Hz, 2H, CH$_2$N), 3.36 (s, 3H, OCH$_3$), 3.10 (tt, J=7.1, 6.8 Hz, 2H, CH$_2$), 2.71 (t, J=5.6 Hz, 3H, NCH$_3$), 2.12 (tt, J=7.0, 6.0 Hz, 2H, CH$_2$); MS (APCI) m/z 104 (MH$^+$, 100%); HRMS calcd for $C_5H_{13}NO$ (M$^+$) m/z 103.0997, found 103.0996.

[(3-Methoxypropyl)(methyl)amino]acetonitrile (273). A solution of amine hydrochloride 272 (2.6 g, 18.7 mmol), aqueous glycolonitrile (55%, 2.4 mL, 24.7 mmol) and Et$_3$N (4.0 mL, 28.1 mmol) was stirred at 50° C. for 3 h. The solution was cooled and partitioned between water (50 mL) and Et$_2$O (50 mL). The organic fraction was washed with water (2×50 mL) and brine (50 mL), dried and the solvent evaporated to give nitrile 273 (1.94 g, 73%) as a colourless oil; $^1$H NMR δ 3.53 (s, 2H, CH$_2$CN), 3.42 (t, J=6.3 Hz, 2H, CH$_2$N), 3.33 (s, 3H, OCH$_3$), 2.54 (t, J=7.1 Hz, 2H, CH$_2$), 2.36 (s, 3H, NCH$_3$), 1.73 (tt, J=7.1, 6.3 Hz, 2H, CH$_2$); MS (APCI) m/z 143 (MH$^+$, 100%).

$N^1$-(3-Methoxypropyl)-$N^1$-methyl-1,2-ethanediamine (274). A mixture of nitrile 273 (1.94 g, 14.0 mmol), cNH$_3$ (8 mL) and Raney Nickel (50% slurry in water, 5.3 g) in EtOH (100 mL) was stirred under H$_2$ (60 psi) for 4 h. The mixture was filtered through Celite, washed with EtOH (50 mL) and the solvent was evaporated to give crude diamine 274 (1.65 g, 83%) as a yellow oil, which was used without further purification: $^1$H NMR δ 3.42 (t, J=6.4 Hz, 2H, CH$_2$N), 3.33 (s, 3H, OCH$_3$), 2.76 (t, J=6.1 Hz, 2H, CH$_2$), 2.43 (t, J=7.2 Hz, 2H, CH$_2$), 2.40 (t, J=6.2 Hz, 2H, CH$_2$), 2.21 (s, 3H, NCH$_3$), 1.74 (tt, J=7.2, 6.2 Hz, 2H, CH$_2$), NH$_2$ not observed; MS (APCI) m/z 147 (MH$^+$, 100%); HRMS calcd for C$_7$H$_{18}$N$_2$O (M$^+$) m/z 146.1419, found 146.1424.

2(3-Methoxy-1-azetidinyl)ethylamine (277)

(3-Methoxy-1-azetidinyl)acetonitrile (276). A solution of 3-methoxyazetidine hydrochloride (275) (MacKenzie et al., PCT Int Appl. WO 9605193, 1996) (3.0 g, 24.4 mmol), aqueous glycolonitrile (55%, 3.4 mL, 34.3 mmol) and Et$_3$N (5.2 mL, 37.3 mmol) was stirred at 20° C. for 3 h, then heated at 50° C. for 1 h. The solution was cooled and partitioned between water (50 mL) and Et$_2$O (50 mL). The organic fraction was washed with water (2×50 mL) and brine (50 mL), dried and the solvent evaporated to give nitrile 276 (1.76 g, 57%) as a colourless oil: $^1$H NMR δ 4.06 (p, J=5.7 Hz, 1H, CHO), 3.61-3.66 (m, 2H, CH$_2$N), 3.49 (s, 2H, CH$_2$CN), 3.28 (s, 3H, OCH$_3$), 3.22-3.27 (m, 2H, CH$_2$N); MS (APCI) m/z 127 (MH$^+$, 100%).

2(3-Methoxy-1-azetidinyl)ethylamine (277). A mixture of nitrile 276 (1.76 g, 14.0 mmol), cNH$_3$ (7 mL) and Raney Nickel (50% slurry in water, 4.6 g) in EtOH (100 mL) was stirred under H$_2$ (60 psi) for 5 h. The mixture was filtered through Celite, washed with EtOH (50 mL) and the solvent was evaporated to give crude diamine 277 (950 mg, 52%) as a yellow oil, which was used without further purification: $^1$H NMR δ 4.03 (p, J=5.8 Hz, 1H, CHO), 3.58-3.63 (m, 2H, CH$_2$N), 3.25 (s, 3H, OCH$_3$), 2.88-2.93 (m, 2H, CH$_2$N), 2.67 (t, J=6.0 Hz, 2H, CH$_2$N), 2.52 (t, J=6.0 Hz, 2H, CH$_2$N), NH$_2$ not observed; MS (APCI) m/z 131 (MH$^+$, 100%); HRMS (FAB$^+$) calcd for C$_6$H$_{15}$N$_2$O (MH$^+$) m/z 131.1184, found 131.1183.

2-(2,6-Dimethyl-1-piperidinyl)ethylamine (280)

(2,6-Dimethyl-1-piperidinyl)acetonitrile (279). Dimethylpiperidine (278) (5.9 mL, 43.8 mmol) was added to a stirred aqueous solution of glycolonitrile (55%, 5 g, 48.2 mmol) at 5° C. and the solution stirred at 70° C. for 30 min. The solution was cooled, diluted with ether (50 mL), washed with water (2×20 mL), dried and the solvent evaporated to give nitrile 279 (3.97 g, 60%) as a clear oil: $^1$H NMR δ 3.78 (s, 2H, CH$_2$N), 2.41-2.50 (m, 2H, 2×CH), 1.65-1.70 (m, 2H, CH$_2$), 1.25-1.42 (m, 4H, 2×CH$_2$), 1.13 (d, J=6.2 Hz, 6H, 2×CH$_3$); MS m/z 153 (MH$^+$, 100%).

2-(2,6-Dimethyl-1-piperidinyl)ethylamine (280). A mixture of nitrile 279 (3.13 g, 20.6 mmol) and Raney Nickel (50% w/w suspension in water, ca. 2 mL) in EtOH (30 mL) and cNH$_3$ (2 mL) was stirred under H$_2$ (60 psi) for 5 h. The suspension was filtered through Celite, washed with EtOH (3×10 mL) and the solvent evaporated to give diamine 280 (2.52 g, 78%) as a colourless oil which was used without further purification: $^1$H NMR δ 2.71-2.76 (m, 2H, CH$_2$N), 2.63-2.68 (m, 2H, CH$_2$N), 2.41-2.47 (m, 2H, 2×CH), 1.49-1.55 (m, 2H, CH$_2$), 1.43 (br s, 2H, NH$_2$), 1.25-1.42 (m, 4H, 2×CH$_2$), 1.11 (d, J=6.3 Hz, 6H, 2×CH$_3$); MS m/z 157 (MH$^+$, 100%).

2-(3-Methoxy-1-piperidinyl)ethylamine (283)

(3-Methoxy-1-piperidinyl)acetonitrile (282). Et$_3$N (7.0 mL, 50 mmol) was added to a suspension of 3-methoxypiperidine hydrochloride (281) (McManus, J. M. et al., *J. Med. Chem.* 1965, 8, 766-776) (3.80 g, 25.0 mmol) and aqueous glycolonitrile (55%, 2.7 mL, 27.6 mmol), and the resulting solution stirred at 70° C. for 1.5 h. The solution was cooled to 20° C. and diluted with water (40 mL). The aqueous layer was extracted with Et$_2$O (4×50 mL), the combined organic fraction dried and the solvent evaporated to give nitrile 282 (3.76 g, 97%) as a colourless oil, which was used without further purification: $^1$H NMR δ 3.54 (s, 2H, CH$_2$CN), 3.36-3.40 (m, 1H, H-3), 3.37 (s, 3H, OCH$_3$), 2.77 (dd, J=10.9, 3.2 Hz, 1H, H-2), 2.44-2.56 (m, 3H, H-2, H-6), 1.75-1.85 (m, 2H, H-4, H-5), 1.52-1.57 (m, 2H, H-4, H-5).

2-(3-Methoxy-1-piperidinyl)ethylamine (283). A mixture of nitrile 282 (3.5 g, 22.7 mmol) and Raney Nickel (50% w/w suspension in water, 8 g) in EtOH (100 mL) and cNH$_3$ (10 mL) was stirred under H$_2$ (60 psi) for 22 h. The mixture was filtered through Celite, the solid washed with EtOH (60 mL) and the solvent evaporated to give diamine 283 as a crude colourless oil (3.48 g, 97%) which was used without further purification: HRMS (FAB$^+$) calcd for C$_8$H$_{19}$N$_2$O (MH$^+$) m/z 159.14974, found 159.14976.

2-(4-Methoxy-1-piperidinyl)ethylamine (288)

4-Methoxypiperidine (286). A mixture of tert-butyl 4-hydroxy-1-piperidinecarboxylate (284) (Dailewicz, J. C.; et al., *J. Med. Chem.* 2002, 45, 2432-2453) (19.7 g, 98 mmol), crushed KOH (11.0 g, 196 mmol) and MeI (7.3 mL, 118 mmol) in DMSO (100 mL) was stirred at 20° C. for 16 h under N$_2$. The mixture was poured into water (500 mL) and extracted with Et$_2$O (2×150 mL). The combined organic fraction was washed with water (2×50 mL), dried and the solvent evaporated to give methyl ether 285 (19.1 g, 91%) as a white solid: $^1$H NMR δ 3.71-3.78 (m, 2H, CH$_2$N), 3.31-3.39 (m, 4H, CHO, OCH$_3$), 3.06-3.12 (m, 2H, CH$_2$N), 1.80-1.85 (m, 2H, CH$_2$), 1.45-1.54 (m, 2H, CH$_2$), 1.43 [s, 9H, C(CH$_3$)$_3$]. A solution of HCl in dioxane (4 M, 67 mL, 266 mmol) was added to a stirred solution of methyl ether 285 (19.1 g, 88.7 mmol) in dioxane (100 mL) and the mixture stirred at 20° C. for 96 h. The solvent was evaporated and the residue dried to give the amine hydrochloride 286 as a white solid: $^1$H NMR [(CD$_3$)$_2$SO] δ 8.99 (br s, 2H, NH.HCl), 3.40-3.46 (m, 1H, CHO), 3.25 (s, 3H, OCH$_3$), 3.07-3.12 (m, 2H, CH$_2$N), 2.88-2.94 (m, 2H, CH$_2$N), 1.91-1.99 (m, 2H, CH$_2$), 1.63-1.74 (m, 2H, CH$_2$). The hydrochloride was dissolved in water (50 mL), the pH adjusted to 10 with cNH$_3$ and the mixture extracted with CHCl$_3$ (4×50 mL) to give the free base, which was used without further purification.

(4-Methoxy-1-piperidinyl)acetonitrile (287). 4-Methoxypiperidine (286) (10.1 g, 87.6 mmol) was added dropwise to a stirred aqueous solution of glycolonitrile (55%, 10.0 g, 96.4 mmol) at 5° C. and the solution was stirred at 70° C. for 1 h. The solution was cooled, diluted with Et$_2$O (50 mL) and washed with water (2×20 mL). The organic fraction was dried and the solvent evaporated. The residue was purified by chromatography, eluting with a gradient (0-5%) of MeOH/DCM, to give nitrile 287 (10.25 g, 76%) as a colourless oil: $^1$H NMR δ 3.51 (s, 2H, CH$_2$CN), 3.35 (s, 3H, OCH$_3$), 3.21-3.28 (m, 1H, CHO), 2.72-2.78 (m, 2H, CH$_2$N), 2.40-2.46 (m, 2H, CH$_2$N), 1.90-1.98 (m, 2H, CH$_2$N), 1.60-1.69 (m, 2H, CH$_2$).

2-(4-Methoxy-1-piperidinyl)ethylamine (288). A mixture of nitrile 287 (10.25 g, 66.5 mmol) and Raney Nickel (50% w/w in water, ca. 10 mL) in EtOH (150 mL) and cNH$_3$ (10 mL) was stirred under H$_2$ (60 psi) for 16 h. The mixture was filtered through Celite, washed with EtOH (3×10 mL) and the solvent evaporated to give crude diamine 288 as an oil which was used directly.

2-(1-Azepanyl)ethylamine (291)

1-Azepanylacetonitrile (290). Azepane (289) (4.9 mL, 43.8 mmol) was added dropwise to a stirred aqueous solution of glycolonitrile (55%, 5.0 g, 48.2 mmol) at 5° C. and the solution was stirred at 70° C. for 30 min. The solution was cooled, diluted with water (20 mL), washed with $Et_2O$ (3×50 mL). The organic fraction was dried and the solvent evaporated to give nitrile 290 (5.58 g, 92%) as a colourless oil: $^1H$ NMR δ 3.56 (s, 2H, $CH_2CN$), 2.71 (br dd, J=5.8, 5.5 Hz, 4H, 2×$CH_2N$), 1.67-1.73 (m, 4H, 2×$CH_2$), 1.59-1.64 (m, 4H, 2×$CH_2$).

2-(1-Azepanyl)ethylamine (291). A mixture of nitrile 290 (5.58 g, 40.4 mmol) and Raney Nickel (50% w/w in water, ca. 5 mL) in EtOH (50 mL) and $cNH_3$ (4 mL) was stirred under $H_2$ (60 psi) for 16 h. The mixture was filtered through Celite, washed with EtOH (3×10 mL) and the solvent evaporated to give crude diamine 291 as an oil (2.03 g, 35%) which was used without further purification: $^1H$ NMR δ 2.72 (t, J=6.1 Hz, 2H, $CH_2N$), 2.60-2.68 (m, 4H, 2×$CH_2N$), 2.53 (t, J=6.1 Hz, 2H, $CH_2N$), 1.55-1.66 (m, 10H, 4×$CH_2$, $NH_2$).

2-(1,4-Oxazepan-4-yl)ethylamine (294)

2-(1,4-Oxazepan-4-yl)acetonitrile (293). 1,4-Oxazepane (292) (Turner, S. R. et al., PCT Int. Appl. WO 2000 040561, 2000) (4.95 g, 49.0 mmol) was added dropwise to a stirred aqueous solution of glycolonitrile (55%, 5.3 mL, 53.8 mmol) at 5° C. and stirred at 70° C. for 1 h. More aqueous glycolonitrile (55%, 0.96 mL, 6.13 mmol) was added and the mixture stirred for 30 min, cooled to 20° C. and $Et_2O$ (100 mL) and water (50 mL) were added. The aqueous layer was extracted with $Et_2O$ (4×30 mL), the combined organic fraction dried and the solvent evaporated to give nitrile 293 (3.24 g, 47%) as a pale yellow oil: $^1H$ NMR δ 3.80-3.84 (m, 2H, H-5), 3.74-3.77 (m, 2H, H-3), 3.60 (s, 2H, $CH_2CN$), 2.79-2.84 (m, 4H, H-2, H-7), 1.92-1.99 (m, 2H, H-6); HRMS calcd for $C_7H_{12}N_2O$ ($M^+$) m/z 140.0950, found 140.0947.

2-(1,4-Oxazepan-4-yl)ethanamine (294). A mixture of nitrile 293 (3.2 g, 22.8 mmol) and Raney-Nickel (50% w/w in water, ca. 12 g) in EtOH (100 mL) and $cNH_3$ (10 mL) was stirred under $H_2$ (60 psi) for 16 h. The mixture was filtered through Celite, washed with EtOH (3×10 mL) and the solvent evaporated to give crude diamine 294 (2.98 g, 91%) as a pale yellow oil, which was used without further purification: $^1H$ NMR [$(CD_3)_2SO$] δ 3.64-3.67 (m, 2H, H-3), 3.57-3.59 (m, 2H, H-5), 2.49-2.62 (m, 8H, H-2, H-7, 2×$CH_2$), 1.71-1.80 (m, 2H, H-6), $NH_2$ not observed; HRMS ($FAB^+$) calcd for $C_7H_{17}N_2O$ ($MH^+$) m/z 145.13409, found 145.13439.

$N^1,N^1$-Dipropyl-1,2-ethanediamine (297)

2-[2-Dipropylamino)ethyl]-1H-isoindole-1,3(2H)-dione (296). A mixture of N,N-dipropylamine (295) (12.6 g, 125 mmol), N-(2-bromoethyl)phthalimide (15.8 g, 62.4 mmol) and $K_2CO_3$ (10.4 g, 74.9 mmol) in DMF (150 mL) was stirred at 100° C. for 3 h. The solution was cooled and the solvent evaporated. The residue was partitioned between EtOAc (200 mL) and water (200 mL) and the organic fraction extracted with 1 M HCl (200 mL). The acidic fraction was washed with ether (2×50 mL), made basic with $cNH_3$ and then extracted with DCM (3×100 mL). The combined organic fraction was dried and the solvent evaporated. The residue was purified by chromatography, eluting with EtOAc, to give phthalamide 296 (10.4 g, 60%) as a colourless oil, which was used without further purification: $^1H$ NMR δ 7.81-7.85 (m, 2H, $H_{arom}$), 7.67-7.73 (m, 2H, $H_{arom}$), 3.75 (dd, J=7.1, 6.8 Hz, 2H, $CH_2N$), 3.69 (dd, J=7.1, 6.8 Hz, 2H, $CH_2N$), 2.39-2.44 (m, 4H, 2×$CH_2N$), 1.35-1.45 (m, 4H, 2×$CH_2$), 0.81 (t, J=7.3 Hz, 6H, 2×$CH_3$).

$N^1,N^1$-Dipropyl-1,2-ethanediamine (297). A solution of phthalimide 296 (10.4 g, 37.8 mmol) and $N_2H_4.H_2O$ (3.7 mL, 75.5 mmol) in EtOH (100 mL) was stirred at reflux temperature for 2 h. The solution was cooled to 5° C. for 2 h, the precipitate filtered, washed with EtOH (5 mL) and the filtrate evaporated to half volume. The solution was cooled at 5° C. for a further 2 h, the precipitate filtered, washed with EtOH (5 mL) and the filtrate evaporated. The residue was dissolved in 1 M HCl (50 mL), washed with $Et_2O$ (2×50 mL) and the pH of the aqueous fraction adjusted to 10 with dilute aqueous $NH_3$ solution. The mixture was extracted with $CHCl_3$ (4×50 mL), the combined organic fraction dried and the solvent evaporated to give diamine 297 as a pale yellow oil (4.06 g, 74%) which was used without further purification: $^1H$ NMR δ 2.70 (dd, J=6.2, 5.9 Hz, 2H, $CH_2N$), 2.44 (dd, J=6.2, 5.9 Hz, 2H, $CH_2N$), 2.32-2.37 (m, 4H, 2×$CH_2N$), 1.50 (br s, 2H, $NH_2$), 1.38-1.47 (m, 4H, 2×$CH_2$), 0.87 (t, J=7.3 Hz, 6H, 2×$CH_3$).

$N^1$-(2-Methoxyethyl)-$N^1$-methylpropane-1,3-diamine (299)

2-{3-[(2-Methoxyethyl)(methyl)amino]propyl}-1H-isoindole-1,3(2H)-dione (298). A suspension of 2-methoxy-N-methylethanamine (266) (20.0 g, 224 mmol), N-(3-bromopropyl)phthalimide (50.1 g, 187 mmol) and $K_2CO_3$ (31.0 g, 224 mmol) in DMF (200 mL) was stirred at 100° C. for 3 h. The solution was cooled and the solvent evaporated to give phthalimide 298 (51.7 g, 100%) as a colourless oil, which was used without further purification: $^1H$ NMR δ 7.82-7.86 (m, 2H, $H_{arom}$), 7.68-7.73 (m, 2H, $H_{arom}$), 3.73 (t, J=7.2 Hz, 2H, $CH_2N$), 3.42-3.46 (m, 2H, $CH_2O$), 3.32 (s, 3H, $OCH_3$), 2.53-2.56 (m, 2H, $CH_2N$), 2.44-2.49 (m, 2H, $CH_2N$), 2.25 (s, 3H, $NCH_3$), 1.82-1.90 (m, 2H, $CH_2$); HRMS ($CI^+$) calcd for $C_{15}H_{21}N_2O_3$ ($MH^+$) m/z 277.1552, found 277.1557.

$N^1$-(2-Methoxyethyl)-$N^1$-methylpropane-1,3-diamine (299). A solution of phthalimide 298 (50.0 g, 181 mmol) and $N_2H_4$—$H_2O$ (17.5 mL, 362 mmol) in EtOH (500 mL) was stirred at reflux temperature for 2 h. The solution was cooled to 5° C. for 2 h, the precipitate filtered, washed with EtOH (5 mL) and the filtrate evaporated to half volume. The solution was cooled at 5° C. for a further 2 h, the precipitate filtered, washed with EtOH (5 mL) and the filtrate evaporated. The residue was dissolved in 1 M HCl (50 mL), washed with $Et_2O$ (2×50 mL) and the pH of the aqueous fraction adjusted to 10 with dilute aqueous $NH_3$ solution. The mixture was extracted with $CHCl_3$ (4×50 mL), the combined organic fraction dried and the solvent evaporated to give diamine 299 (Sandberg, R., et al., *Acta Pharmaceutica Suecica* 1979, 16, 386-395) as a pale yellow oil (25.2 g, 95%) which was used without further purification: $^1H$ NMR [$(CD_3)_2SO$] δ 3.38 (t, J=6.0 Hz, 2H, $CH_2O$), 3.21 (s, 3H, $OCH_3$), 2.60 (t, J=6.8 Hz, 2H, $CH_2N$), 2.46 (t, J=6.0 Hz, 2H, $CH_2N$), 2.36 (t, J=7.0 Hz, 2H, $CH_2N$), 2.14 (s, 3H, $NCH_3$), 1.50 (p, J=7.0 Hz, 2H, $CH_2$), $NH_2$ not observed; HRMS ($CI^+$) calcd for $C_7H_{17}N_2O$ ($M-H^+$) m/z 145.1341, found 145.1337.

3-(3-Methoxy-1-azetidinyl)propylamine (301)

2-[3-(3-Methoxy-1-azetidinyl)propyl]-1H-isoindole-1,3(2H)-dione (300). A suspension of 3-methoxyazetidine (275) (MacKenzie et al., PCT Int. Appl. WO 9605193, 1996) (1.6 g, 18.8 mmol), 2-(3-bromopropyl)phthalimide (4.8 g, 17.9 mmol) and $K_2CO_3$ (3.7 g, 26.9 mmol) in THF (150 mL) was stirred at reflux temperature for 18 h. The solution was cooled, the solvent evaporated and the residue partitioned between water (50 mL) and EtOAc (100 mL). The aqueous layer was extracted with EtOAc (2×150 mL), the combined organic fraction washed with water (2×100 mL) and brine (100 mL), dried and the solvent evaporated. The residue was purified by chromatography, eluting with a gradient (0-5%) of MeOH/DCM, to give phthalimide 300 (5.2 g, 65%) as a colourless oil: $^1$H NMR δ 7.84 (dd, J=5.4, 3.1 Hz, 2H, H$_{arom}$), 7.70 (dd, J=5.4, 3.1 Hz, 2H, H$_{arom}$), 3.95 (p, J=5.8 Hz, 1H, CHO), 3.73 (t, J=7.1 Hz, 2H, CH$_2$N), 3.55-3.60 (m, 2H, CH$_2$N), 3.22 (s, 3H, OCH$_3$), 2.78-2.84 (m, 2H, CH$_2$N), 2.51 (t, J=7.1 Hz, 2H, CH$_2$N), 1.72 (p, J=7.1 Hz, 2H, CH$_2$); MS (APCI) m/z 275 (MH$^+$, 100%); HRMS (FAB$^+$) calcd for C$_{15}$H$_{19}$N$_2$O$_3$ (MH$^+$) m/z 275.1396, found 275.1391.

3-(3-Methoxy-1-azetidinyl)propylamine (301). A solution of phthalimide 300 (5.2 g, 18.9 mmol) and N$_2$H$_4$.H$_2$O (1.9 g, 37.8 mmol) in EtOH (100 mL) was heated at reflux temperature for 3 h. The solution was cooled to 0° C., the solid filtered off and washed with cold EtOH (20 mL) and EtOAc (100 mL). The solvent was evaporated to half volume, stored at −20° C. for 16 h and the suspension filtered. The filtrate was evaporated, the residue was dissolved in Et$_2$O, the solid filtered off and the solvent was evaporated to give crude diamine 301 (1.8 g, 66%) as a yellow oil, which was used without further purification: $^1$H NMR δ 4.02 (p, J=5.8 Hz, 1H, CHO), 3.58-3.63 (m, 2H, CH$_2$N), 3.25 (s, 3H, OCH$_3$), 2.82-2.87 (m, 2H, CH$_2$N), 2.72 (t, J=6.9 Hz, 2H, NCH$_2$), 2.50 (t, J=7.1 Hz, 2H, NCH$_2$), 1.40-1.60 (m, 4H, NH$_2$, CH$_2$); MS (APCI) m/z 145 (MH$^+$, 100%).

1-(3-Aminopropyl)-3-pyrrolidinecarbonitrile (304)

1-[3-(1,3-Dioxo-1,3-dihydro-2H-isoindol-2-yl)propyl]-3-pyrrolidinecarbonitrile (303). A suspension of 3-pyrrolidinecarbonitrile (302) (Swidinsky, J., et al., *J. Pharm. Sci.* 1967, 56, 192-196) (4.5 g, 15.6 mmol), N-(3-bromopropyl)phthalimide (3.48 g, 13.0 mmol), and K$_2$CO$_3$ (2.16 g, 15.6 mmol) in DMF (20 mL) was stirred at 100° C. for 1.5 h. The solution was cooled, the solvent evaporated and the residue partitioned between water (50 mL) and EtOAc (50 mL). The organic fraction was extracted with 1 M HCl (2×50 mL) and the acidic fraction washed with Et$_2$O (2×20 mL). The acidic fraction was made basic with dilute aqueous NH$_3$ solution and the alkaline solution was extracted with DCM (3×25 mL), the combined organic fraction dried and the solvent evaporated. The residue was purified by chromatography, eluting with EtOAc, to give phthalimide 303 (1.70 g, 46%) as a colourless oil: $^1$H NMR δ 7.82-7.87 (m, 2H, H$_{arom}$), 7.69-7.74 (m, 2H, H$_{arom}$), 3.75-3.79 (m, 2H, CH$_2$), 2.87-2.93 (m, 2H, CH$_2$N), 2.52-2.60 (m, 5H, CH$_2$, CH$_2$N, CH), 2.06-2.15 (m, 1H, CH$_2$), 1.96-2.04 (m, 1H, CH$_2$), 1.87 (p, J=7.0 Hz, 2H, CH$_2$); $^{13}$C NMR δ 168.4 (2), 133.9 (2), 132.2 (2), 123.1 (2), 122.1, 57.2, 52.6 (2), 36.3, 29.1, 27.2, 26.1; HRMS (FAB$^+$) calcd for C$_{16}$H$_{17}$N$_3$O$_2$ (M$^+$) m/z 283.1321, found 283.1318.

1-(3-Aminopropyl)-3-pyrrolidinecarbonitrile (304). A solution of phthalimide 303 (5.96 g, 21.0 mmol) and N$_2$H$_4$.H$_2$O (2.04 mL, 42.0 mmol in EtOH (60 mL) was stirred at reflux temperature for 2 h. The solution was cooled to 5° C. for 2 h, the precipitate filtered, washed with EtOH (5 mL) and the filtrate evaporated to half volume. The solution was cooled at 5° C. for a further 2 h, the precipitate filtered, washed with EtOH (5 mL) and the filtrate evaporated to give diamine 304 which was used without further purification: $^1$H NMR δ 2.94-3.02 (m, 1H, CHCN), 2.90 (dd, J=9.0, 7.9 Hz, 1H, CH$_2$), 2.82 (t, J=6.8 Hz, 2H, CH$_2$N), 2.61-2.68 (m, 2H, CH$_2$N), 2.48-2.58 (m, 3H, CH$_2$N), 2.05-2.15 (m, 1H, CH$_2$), 2.03-2.11 (m, 1H, CH$_2$), 1.68 (p, J=7.0 Hz, 2H, CH$_2$), NH$_2$ not observed.

3-(4-Methoxy-1-piperidinyl)propylamine (306)

2-[3-(4-Methoxy-1-piperidinyl)propyl]-1H-isoindole-1,3 (2H)-dione (305). A suspension of 4-methoxypiperidine (286) (4.1 g, 35.3 mmol), N-(3-bromopropyl)phthalimide (9.0 g, 33.6 mmol) and K$_2$CO$_3$ (7.0 g, 50.4 mmol) in DMF (80 mL) was stirred at 50° C. for 16 h. The solution was cooled, the solvent evaporated and the residue partitioned between water (150 mL) and EtOAc (150 mL). The organic fraction was washed with water (2×50 mL) and brine (50 mL), dried and the solvent evaporated. The residue was purified by chromatography, eluting with a gradient (0-5%) of MeOH/DCM, to give phthalimide 305 (6.0 g, 59%) as a white solid: $^1$H NMR δ 7.81-7.86 (m, 2H, H$_{arom}$), 7.67-7.73 (m, 2H, H$_{arom}$), 3.75-3.79 (t, J=7.0 Hz, 2H, CH$_2$N), 3.28 (s, 3H, OCH$_3$), 3.09-3.17 (m, 1H, CHO), 2.63-2.70 (m, 2H, CH$_2$N), 2.39 (t, J=7.0 Hz, 2H, CH$_2$N), 2.01-2.08 (m, 2H, CH$_2$N), 1.85 (p, J=7.0 Hz, 2H, CH$_2$), 1.74-1.81 (m, 2H, CH$_2$), 1.37-1.46 (m, 2H, CH$_2$). Anal. calcd for C$_{17}$H$_{22}$N$_2$O$_3$: C, 67.5; H, 7.3; N, 9.3. Found: C, 67.3; H, 7.4; N, 9.3%.

3-(4-Methoxy-1-piperidinyl)propylamine (306). A solution of phthalimide 305 (6.0 g, 19.8 mmol) and N$_2$H$_4$.H$_2$O (1.9 mL, 40 mmol) in EtOH (100 mL) was stirred at reflux temperature for 2 h. The solution was cooled to 5° C. for 2 h, the precipitate filtered, washed with EtOH (5 mL) and the filtrate evaporated to half volume. The solution was cooled at 5° C. for a further 2 h, the precipitate filtered, washed with EtOH (5 mL) and the filtrate evaporated. The residue was dissolved in 1 M HCl (50 mL), washed with Et$_2$O (2×50 mL) and the pH of the aqueous fraction adjusted to 10 with dilute aqueous NH$_3$ solution. The mixture was extracted with CHCl$_3$ (4×50 mL), the combined organic fraction dried and the solvent evaporated to give diamine 306 (1.85 g, 54%) as a pale yellow oil: $^1$H NMR δ 3.33 (s, 3H, OCH$_3$), 3.17-3.24 (m, 1H, CHO), 2.71-2.78 (m, 4H, 2×CH$_2$N), 2.37 (dd, J=7.5, 7.2 Hz, 2H, CH$_2$N), 2.08-2.13 (m, 2H, CH$_2$N), 1.85-1.93 (m, 2H, CH$_2$), 1.50-1.67 (m, 6H, 2×CH$_2$, NH$_2$); MS m/z 172 (M$^+$, 5%), 128 (60), 57 (100); HRMS calcd for C$_9$H$_{20}$N$_2$O (M$^+$) m/z 172.1576, found 172.1571.

4-(4-Morpholinyl)butylamine (308)

2-[4-(4-Morpholinyl)butyl]-1H-isoindole-1,3(2H)-dione (307). A mixture of 4-bromobutylphthalimide (10.0 g, 35.4 mmol), K$_2$CO$_3$ (5.88 g, 42.5 mmol) and morpholine (4.6 mL, 53.1 mmol) in DMF (100 mL) was stirred at 100° C. for 8 h, cooled to 20° C. and the solvent evaporated. The residue was partitioned between EtOAc (300 mL) and water (300 mL), the organic fraction washed with water (2×50 mL) and brine (50 mL), dried and the solvent evaporated. The residue was purified by chromatography, eluting with EtOAc, to give phthalimide 307 (9.59 g, 94%) as a clear oil: $^1$H NMR δ 7.81-7.86 (m, 2H, H$_{arom}$), 7.68-7.73 (m, 2H, H$_{arom}$), 3.66-3.72 (m, 6H, 2×CH$_2$O, CH$_2$N), 2.41 (br t, J=4.5 Hz, 4H, 2×CH$_2$N), 2.35 (br dd, J=7.6, 7.4 Hz, 2H, CH$_2$N), 1.69-1.76 (m, 2H, CH$_2$), 1.50-1.58 (m, 2H, CH$_2$).

4-(4-Morpholinyl)butylamine (308). A solution of phthalimide 307 (9.42 g, 32.7 mmol) and N$_2$H$_4$—H$_2$O (3.2 mL, 65.3 mmol) in EtOH (140 mL) was stirred at reflux temperature for 2 h. The mixture was cooled to 0° C., filtered, the filtrate cooled at 0° C. for 3 h, and filtered. The filtrate was evaporated and the residue dissolved in 1 M HCl. The solution was washed with ether (2×50 mL) and the pH adjusted to 10 with aqueous $NH_3$ solution. The resulting mixture was extracted with $CHCl_3$ (4×50 mL), the combined organic fraction dried and the solvent evaporated to give diamine 308 (Thompson, A. M.; et. al., *J. Med. Chem.*, 1997, 40, 3915-3925) (2.0 g, 39%) as a colourless oil: $^1$H NMR δ 3.72 (br t, J=4.7 Hz, 4H, 2×$CH_2$O), 2.71 (br dd, J=6.9, 6.7 Hz, 2H, $CH_2$N), 2.44 (br t, J=4.6 Hz, 4H, 2×$CH_2$N), 2.34 (br dd, J=7.8, 7.0 Hz, 2H, $CH_2$N), 1.62 (br s, 2H, $NH_2$), 1.42-1.59 (m, 4H, 2×$CH_2$)—

Example 185

3-(3-(4-(Dimethylamino)butanoyloxy)propyl)-7,8-dihydro-6H-indeno[5,6-e][1,2,4]triazine 1-Oxide (309). A mixture of alcohol 70 (100 mg, 0.41 mmol), 4-(dimethylamino)butanoic acid hydrochloride (68 mg, 0.41 mmol), DCC (93 mg, 0.45 mmol), DMAP (5 mg, 0.04 mmol) and $Et_3$N (0.06 mL, 0.41 mmol) in DCM (20 mL) was stirred at 20° C. for 16 h. The solvent was evaporated and the residue purified by chromatography, eluting with a gradient (0-10%) of MeOH/20% EtOAc/DCM, to give the ester 309 (137 mg, 94%) as a pale-brown oil: $^1$H NMR δ 8.25 (s, 1H, H-9), 7.74 (s, 1H, H-5), 4.21 (t, J=6.3 Hz, 2H, $CH_2$O), 3.06-3.15 (m, 6H, H-6, H-8, $CH_2$), 2.73 (br s, 2H, H-7), 2.56 [s, 6H, N($CH_3$)$_2$], 2.37 (t, J=7.0 Hz, 2H, $CH_2$), 2.18-2.29 (m, 4H, $CH_2$), 1.92-1.99 (m, 2H, $CH_2$); $^{13}$C NMR δ 172.6, 164.9, 154.9, 149.1, 147.4, 132.3, 122.7, 114.2, 63.7, 57.7, 43.9 (2), 33.6, 33.2, 32.8, 31.3, 26.8, 25.7, 21.0; HRMS calcd for $C_{19}H_{26}N_4O_3$ ($M^+$) m/z 358.2005, found 358.2006.

Example 186

3-(3-(2-(tert-Butoxycarbonylamino)-3-methylbutanoyloxy)propyl)-7,8-dihydro-6H-indeno[5,6-e][1,2,4]triazine 1-Oxide (310). A mixture of alcohol 70 (50 mg, 0.20 mmol), N-Boc Valine (44 mg, 0.20 mmol), DCC (46 mg, 0.22 mmol) and DMAP (2.5 mg, 0.02 mmol) in DCM (10 mL) was stirred at 20° C. for 1 h. The solvent was evaporated and the residue purified by chromatography, eluting with a gradient (0-5%) of MeOH/DCM, to give the crude ester, which was suspended in DCM (2 mL) and filtered to remove urea by-products. The filtrate was concentrated to give crude ester 310 (84 mg, 93%) as a pale-brown gum: $^1$H NMR δ 8.27 (s, 1H, H-9); 7.76 (s, 1H, H-5), 4.96-5.03 (m, 1H, CH), 4.28 (t, J=6.5 Hz, 2H, $CH_2$O), 3.08-3.16 (m, 6H, H-6, H-8, $CH_2$), 2.21-2.31 (m, 4H, H-7, $CH_2$), 2.08-2.17 (br m, 1H, CH), 1.46 [s, 9H, C($CH_3$)$_3$], 0.97 (d, J=6.9 Hz, 3H, $CH_3$), 0.91 (d, J=6.9 Hz, 3H, $CH_3$), NH not observed; HRMS calcd for $C_{23}H_{32}N_4O_5$ ($M^+$) m/z 444.2373, found 444.2382.

Example 189

Evaluation of the Cytotoxicity of Compounds by Proliferation Assay ($IC_{50}$) Under Aerobic and Hypoxic Conditions Compounds representative of the invention were evaluated under both aerobic and hypoxic conditions in a proliferation assay ($IC_{50}$), using two cell lines: human colon carcinoma HT29, and human cervical carcinoma SiHa (Table 1).

Drug exposures were performed in 96-well plates (Nunc) either using a 37 DC humidified incubator (20% $O_2$, 5% $CO_2$) or in the incubator compartment (37° C.) of an anaerobic chamber (Shell Lab) where palladium catalyst scrubbed gas (90% $N_2$, 5% $H_2$, 5% $CO_2$) ensures severe anoxia (<0.001% $O_2$). For each experiment, compounds were simultaneously tested under both oxic and hypoxic conditions and included TPZ as an internal control. An 8-methyl-5-nitroquinoline derivative, SN 24349, known to require very low oxygen concentrations for bioactivation (Siim et al., *Br. J. Cancer* 1994, 70, 596-603) was used to confirm that strict hypoxia was present during the experiment. The assay acceptance criteria based on SN 24349 were: anoxic $IC_{50}$<3 μM for HT29 and <1 μM for SiHa; HCR>30 for HT29 and >100 for SiHa. Cell cultures were grown in αMEM (Gibco) containing 5% heat inactivated FCS and maintained in exponential growth phase. For each individual experiment an appropriate number of cells were seeded (HT29=1100; SiHa=1500) into wells in αMEM+10% FCS+10 mM added glucose+100 μM 2'-deoxycytidine (2'dCyd), and allowed to attach for 2-3 h. High glucose (final concentration 17 mM) and the presence of 2'-dCyd minimize hypoxia-induced cell cycle arrest. Cultures were then exposed to drugs, using 3-fold serial dilutions in duplicate, for a further 4 h. Subsequently cells were washed free of compound using complete media (without glucose/2'-dCyd) and allowed to grow for 5 (oxic) or 6 (anoxic) days. Plates were stained with sulforhodamine B as described previously (Wilson et al., *J. Med. Chem.* 1989, 32, 31-38) and $IC_{50}$ values determined.

$IC_{50}$=The concentration of drug to reduce viable cell numbers to 50% of control cell cultures grown under the same conditions but not exposed to drug.

HCR=Hypoxic cytotoxicity ratio is defined as the ratio of $IC_{50}$ values under aerobic and hypoxic conditions ($IC_{50}$ aerobic/$IC_{50}$ hypoxic).

TABLE 1

Cytotoxicities of compounds of the invention under oxic and hypoxic conditions, and hypoxic selectivity (HCR) in proliferation assay.

| | HT29 | | | SiHa | | |
|---|---|---|---|---|---|---|
| No | $IC_{50}$ (μM) hypoxic | $IC_{50}$ (μM) oxic | HCR | $IC_{50}$ (μM) hypoxic | $IC_{50}$ (μM) oxic | HCR |
| 7 | 3.0 | 255 ± 53 | 67 | 1.6 + 1.1 | 226 ± 46 | 99 |
| 9 | 4.2 ± 1.5 | 72 ± 22 | 17 ± 5 | 0.9 ± 0.2 | 59 ± 4 | 64 ± 4 |
| 11 | 12.4 | 99 ± 9 | 7 | 3.3 ± 0.3 | 74 ± 27 | 23 ± 10 |
| 13 | 4.9 ± 0.6 | 251 ± 24 | 53 ± 11 | 1.0 ± 0.1 | 52 ± 8 | 51 ± 1 |
| 15 | 37.6 | 902 | 24 | 13.9 | 460 | 33 |
| 20 | 15 ± 6 | 387 ± 108 | 27 ± 2 | 8.3 ± 0.4 | 253 ± 30 | 31 ± 5 |
| 23 | 2.3 ± 0.6 | 318 ± 14 | 152 ± 35 | 0.7 ± 0.3 | 105 ± 21 | 111 ± 5 |
| 25 | 47 ± 4 | 1520 | 32 | 17.7 ± 0.6 | 751 | 42 |
| 27 | 4.2 | 254 | 61 | 1.1 | 143 | 133 |
| 29 | 2.5 | 196 | 77 | 0.7 | 63 | 91 |
| 31 | 5.9 ± 0.8 | 172 ± 100 | 26 ± 12 | 2.5 ± 0.8 | 162 ± 48 | 67 ± 2 |

TABLE 1-continued

Cytotoxicities of compounds of the invention under oxic and hypoxic conditions, and hypoxic selectivity (HCR) in proliferation assay.

| | HT29 | | | SiHa | | |
|---|---|---|---|---|---|---|
| No | $IC_{50}$ (μM) hypoxic | $IC_{50}$ (μM) oxic | HCR | $IC_{50}$ (μM) hypoxic | $IC_{50}$ (μM) oxic | HCR |
| 33 | 6.3 ± 2.1 | 315 ± 84 | 52 ± 4 | 2.0 ± 1.1 | 152 ± 38 | 92 ± 30 |
| 35 | 3.4 ± 0.1 | 165 ± 10 | 49 ± 5 | 1.8 ± 0.2 | 108 ± 8 | 61 ± 10 |
| 37 | 5.8 ± 2.9 | 186 ± 58 | 49 ± 35 | 1.3 ± 0.4 | 101 ± 25 | 143 |
| 39 | 2.7 ± 0.2 | 117 ± 47 | 42 ± 15 | 1.1 ± 0.1 | 73 ± 14 | 65 ± 13 |
| 41 | 93 ± 11 | 1390 ± 349 | 19 ± 0.3 | 46 ± 11 | 1750 ± 148 | 46 ± 17 |
| 43 | 3.5 ± 0.3 | 187 ± 98 | 56 ± 33 | 1.2 ± 0.1 | 91 ± 3 | 78 ± 11 |
| 45 | 19 ± 2 | 310 ± 109 | 17 ± 6 | 9.9 ± 1.4 | 245 ± 60 | 28 ± 11 |
| 47 | 1.4 ± 0.1 | 72 ± 2 | 52 ± 1 | 0.71 ± 0.01 | 67 ± 5 | 95 ± 6 |
| 49 | 7.1 ± 0.6 | 399 ± 148 | 58 ± 26 | 2.8 ± 1.2 | 217 ± 52 | 86 ± 18 |
| 51 | >50 | 1610 | | 20.5 ± 3.3 | 455 ± 25 | 22 ± 1 |
| 53 | 5.4 ± 2.8 | 261 ± 90 | 81 ± 60 | 2.6 ± 0.4 | 142 ± 6 | 55 ± 6 |
| 55 | 2.4 ± 0.3 | 233 ± 19 | 102 ± 22 | 1.4 ± 0.4 | 99 ± 14 | 83 ± 34 |
| 57 | 22 ± 1 | 87 ± 3 | 4 ± 0.1 | 10.4 ± 0.6 | 231 ± 64 | 22 ± 6 |
| 59 | 7.1 ± 0.8 | 494 ± 36 | 70 ± 5 | 2.0 ± 0.2 | 114 ± 2 | 57 ± 1 |
| 61 | 21 ± 8 | 385 ± 14 | 20 ± 5 | 8.8 ± 1.7 | 357 ± 35 | 44 ± 12 |
| 63 | 14.2 | 325 ± 70 | 28 | 5.3 ± 0.4 | 239 ± 22 | 46 ± 8 |
| 65 | 2.4 ± 0.4 | 401 ± 236 | 226 ± 153 | 1.0 ± 0.5 | 80 ± 7 | 155 ± 117 |
| 68 | 48 ± 8 | 289 ± 3 | 6.0 ± 0.05 | 37 ± 2 | 326 ± 7 | 8.8 ± 0.2 |
| 71 | 15 ± 3 | 874 ± 119 | 57 ± 1 | 6.9 ± 3.3 | 680 ± 95 | 114 ± 31 |
| 77 | 2.8 ± 0.6 | 349 ± 62 | 127 ± 12 | 1.4 ± 0.3 | 302 ± 48 | 223 ± 14 |
| 79 | 0.54 ± 0.07 | 195 ± 99 | 386 ± 213 | 0.32 ± 0.09 | 194 ± 120 | 738 ± 523 |
| 83 | 1.3 ± 0.2 | 262 ± 83 | 249 ± 129 | 0.58 ± 0.19 | 300 ± 162 | 640 ± 411 |
| 85 | 0.63 ± 0.05 | 161 ± 48 | 249 ± 55 | 0.35 ± 0.01 | 133 ± 42 | 385 ± 125 |
| 87 | 0.37 ± 0.05 | 202 ± 72 | 598 ± 233 | 0.26 ± 0.08 | 219 ± 96 | 1000 ± 431 |
| 97 | 3.5 ± 0.4 | 185 ± 27 | 54 ± 14 | 1.4 ± 0.3 | 123 ± 17 | 97 ± 33 |
| 99 | 19 ± 6 | 459 ± 93 | 25 ± 2 | 8.4 ± 3.2 | 415 ± 133 | 50 ± 3 |
| 104 | 2.9 ± 0.1 | 210 ± 38 | 72 ± 13 | 1.7 ± 0.2 | 226 ± 14 | 134 ± 4 |
| 105 | 13.0 ± 1.3 | 1040 ± 28 | 80 ± 2 | 8.0 ± 0.4 | 831 ± 30 | 104 ± 4 |
| 136 | 17.1 | 774 ± 8 | 45 | 6.5 ± 0.2 | 314 ± 60 | 48 ± 8 |
| 141 | 2.4 ± 0.1 | 294 ± 34 | 121 ± 14 | 1.8 ± 0.2 | 377 | 206 |
| 144 | 4.8 ± 1.3 | 154 ± 51 | 31 ± 2 | 2.4 ± 0.1 | 147 ± 37 | 62 ± 19 |
| 162 | 7.7 ± 1.2 | 717 ± 320 | 102 ± 57 | 2.9 ± 0.4 | 283 | 86 |
| 164 | 3.6 ± 1.1 | 121 ± 21 | 36 ± 5 | 1.3 | 95 ± 12 | 84 |
| 173 | 3.4 | 60.5 | 18 | 1.0 | 62 | 64 |
| 180 | 6.3 ± 0.8 | 158 ± 19 | 25 ± 3 | 2.6 ± 0.5 | 127 ± 14 | 54 ± 16 |
| 189 | 5.2 ± 0.9 | 250 ± 119 | 54 ± 32 | 1.2 ± 0.1 | 99 ± 32 | 88 ± 32 |
| 198 | 2.4 ± 0.1 | 61 ± 6 | 23 ± 0.2 | 0.30 ± 0.02 | 36 ± 10 | 87 ± 9 |
| 200 | 22.0 ± 4.2 | 177 ± 80 | 8 ± 3 | 3.4 ± 0.8 | 90 ± 24 | 28 ± 6 |
| 205 | 117 | 495 | 4 | 23 | >500 | |
| 208 | 5.2 ± 0.3 | 258 ± 207 | 46 ± 36 | 1.9 ± 0.2 | 176 ± 70 | 128 ± 3 |
| 210 | 9.6 ± 3.6 | 708 ± 178 | 113 ± 53 | 3.4 ± 0.7 | 376 ± 10 | 122 ± 25 |
| 212 | 48.6 ± 12.2 | 225 ± 136 | 6 ± 4 | 29.4 ± 4.2 | 355 ± 240 | 14 ± 10 |
| 216 | 8.9 ± 0.4 | 218 ± 54 | 25 ± 6 | 5.05 ± 0.01 | 216 | 43 |
| 224 | 13 ± 7 | 471 ± 443 | 26 ± 21 | 4.7 ± 3.3 | 304 ± 254 | 53 ± 17 |
| 237 | 4.1 | 59.1 | 14 | 0.67 | 43.8 | 66 |
| 242 | 1.5 | 38 ± 10 | 19 | 0.31 | 25 ± 6 | 60 |
| 244 | 11 ± 3 | 188 ± 51 | 19 ± 5 | 3.6 ± 0.5 | 145 ± 29 | 41 ± 10 |
| 250 | 1.5 | 6.2 | | 0.85 | 36 ± 32 | 80 |
| 259 | 2.60 ± 0.03 | 154 ± 19 | 59 ± 7 | 1.1 ± 0.5 | 111 ± 51 | 100 ± 2 |
| 261 | 13 ± 1 | 24 ± 2 | 2 ± 0.2 | 3.1 ± 0.1 | 18 ± 1 | 6 ± 0.2 |

Example 188

HT29 Excision assay. In vivo activity of single dose of compound 77 in combination with radiation. The activity of compound 77 against hypoxic cells in HT29 tumours is illustrated in FIG. 1. Subcutaneous HT29 tumours (average of two largest diameters 8-10 mm) were grown by inoculating $10^7$ cells (obtained by enzymatic dissociation of multicellular spheroids) into CD-1 nude mice. Cmpd 77 was administered as a single i.p. dose (560 μmol/kg, which is 75% of the maximum tolerated dose) alone or 5 min after radiation (20 Gy). Tumours were excised 18 h after treatment and plated to determine the number of clonogens/g tumour tissue. Hypoxic cytotoxicity of compound 77 is demonstrated by the difference between the radiation-only and radiation+drug groups. This difference was statistically significant (p<0.05) using ANOVA and Dunnett's test. Selectivity for hypoxic cells is demonstrated by the greater activity of 77 with radiation than as a single agent.

The activity of single doses of TPZ and compounds 61 and 77 against hypoxic cells in HT29 and an additional two human tumour models is illustrated in FIG. 2. The drugs were administered i.p. at the stated doses 5 minutes after irradiation in experiments similar to that described above. All drugs were administered at 0.75×MTD. The activity is measured as logs of cell kill in addition to the cell kill observed for radiation alone.

Example 189

Fractionated Tumour Excision Assays. In Vivo Activity of Multiple Doses of Drug in Combination with Fractionated Radiation The activity of multiple doses of compound 77 and TPZ against hypoxic cells in three human tumour xenografts is illustrated in FIG. 3. Subcutaneous tumours (average of two largest diameters 8-10 mm) were grown by inoculating $10^7$ cells into the midline of the back in CD-1 nude mice. Drugs were administered by i.p. injection at 100% of the MTD for twice daily (9 am, 3 pm) administration for 4 days, either alone or 30 min before each of 8×2.5 Gy local irradiation of the tumour. Tumours were excised 18 hr after treatment and plated to determine the number of clonogens/g tumour tissue. Antitumour activity is measured as logs of cell kill in addition to the cell kill observed for radiation alone. In each of the three tumour models investigated, administration of compound 77 or TPZ, 30 min before each radiation dose, gave significantly (P<0.05) greater log cell kill compared to radiation alone (FIG. 3). Compound 77 gave greater killing than TPZ in each tumour model. In SiHa tumours the log cell kill in addition to radiation alone was significantly greater (p<0.05, Student's t-test) for 77 plus radiation relative to TPZ plus radiation.

Wherein the foregoing description reference has been made to reagents, or integers having known equivalents thereof, then those equivalents are herein incorporated as if individually set forth.

While this invention has been described with reference to certain embodiments and examples, it is to be appreciated that further modifications and variations can be made to embodiments and examples without departing from the scope of the invention.

The invention claimed is:

1. A compound of Formula I or a pharmacologically acceptable salt thereof,

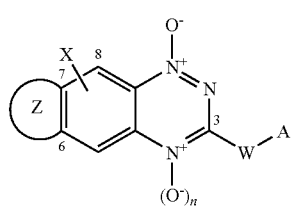

Formula I wherein n=0 or 1; and

X at one of the available carbons 5-8 on the benzo ring is selected from the following groups, H, halo, R, OH, OR, OC(O)H, OC(O)R, OC(O)NH$_2$, OC(O)NHR, OC(O)NRR, OP(O)(OH)$_2$, OP(O)(OR)$_2$, NO$_2$, NH$_2$, NHR, NRR, NHC(O)H, NHC(O)R, NRC(O)R, NHC(O)NH$_2$, NHC(O)NRR, NRC(O)NHR, SH, SR, S(O)H, S(O)R, SO$_2$R, SO$_2$NH$_2$, SO$_2$NHR, SO$_2$NRR, CF$_3$, CN, CO$_2$H, CO$_2$R, CHO, C(O)R, C(O)NH$_2$, C(O)NHR, C(O)NRR, CONHSO$_2$H, CONHSO$_2$R, CONRSO$_2$R, cyclic C$_3$-C$_7$ alkylamino, imidazolyl, C$_1$-C$_6$-alkylpiperazinyl and morpholinyl;

wherein each R is independently selected from a C$_{1-6}$ alkyl group, a C$_{2-4}$ alkenyl group and a C$_{3-7}$ cyclic alkyl group;

wherein W represents NH, NMe or CH$_2$; and

A represents H or an optionally substituted C$_{1-6}$ alkyl group or an optionally substituted C$_{2-6}$ alkenyl group or an optionally substituted C$_{3-7}$ cyclic alkyl group wherein the one or more optional substituents are each independently selected from halo, OH, OR$^3$, OC(O)R$^3$, OC(O)NH$_2$, OC(O)NHR$^3$, OC(O)NR$^3$R$^3$, OP(O)(OH)$_2$, OP(O)(OR$^3$)$_2$, NO$_2$, NH$_2$, NHR$^3$, NR$^3$R$^3$, N$^+$(—O$^-$)R$^3$R$^3$, NHC(O)H, NHC(O)R$^3$, NR$^2$C(O)R$^3$, NHC(O)NH$_2$, NHC(O)NR$^3$R$^3$, NR$^2$C(O)NHR$^3$, SH, SR$^3$, S(O)H, S(O)R$^3$, SO$_2$R$^3$, SO$_2$NH$_2$, SO$_2$NHR$^3$, SO$_2$NR$^3$R$^3$, CF$_3$, CN, CO$_2$H, CO$_2$R, CHO, C(O)R$^3$, C(O)NH$_2$, C(O)NHR$^3$, C(O)NR$^3$R$^3$, CONHSO$_2$H, C(O)NHSO$_2$R$^3$, C(O)NR$^3$SO$_2$R$^3$, cyclic C$_3$-C$_7$ alkylamino, imidazolyl, piperazinyl, morpholinyl, piperidinyl, azepanyl, pyrrolidinyl and azetidinyl; wherein each of the groups imidazolyl, piperazinyl, morpholinyl, piperidinyl, azepanyl, pyrrolidinyl and azetidinyl are optionally substituted by one or more R$^3$ groups, halo, OH, OR$^3$, OC(O)R$^3$, OC(O)NH$_2$, OC(O)NHR$^3$, OC(O)NR$^3$R$^3$, OP(O)(OH)$_2$, OP(O)(OR$^3$)$_2$, NO$_2$, NH$_2$, NHR$^3$, NR$^3$R$^3$, N$^+$(—O$^-$)R$^3$R$^3$, NHC(O)H, NHC(O)R$^3$, NR$^3$C(O)R$^3$, NHC(O)NH$_2$, NHC(O)NR$^3$R$^3$, NR$^3$C(O)NHR$^3$, SH, SR$^3$, S(O)H, S(O)R$^3$, SO$_2$R$^3$, SO$_2$NH$_2$, SO$_2$NHR$^3$, SO$_2$NR$^3$R$^3$, CF$_3$, CN, CO$_2$H, CO$_2$R$^3$, CHO, C(O)R$^3$, C(O)NH$_2$, C(O)NHR$^3$, C(O)NR$^3$R$^3$, CONHSO$_2$H, C(O)NHSO$_2$R$^3$, and C(O)NR$^3$SO$_2$R$^3$; or A represents an optionally substituted C$_4$-C$_8$ aryl or an optionally substituted heteroaryl group having up to 12 carbon atoms, and wherein the one or more optional substituents are each independently selected from; halo, OH, OR$^3$, OC(O)R$^3$, OC(O)NH$_2$, OC(O)NHR$^3$, OC(O)NR$^3$R$^3$, OP(O)(OH)$_2$, OP(O)(OR$^3$)$_2$, NO$_2$, NH$_2$, NHR$^3$, NR$^3$R$^3$, N$^+$(—O$^+$)R$^3$R$^3$, NHC(O)H, NHC(O)R$^3$, NR$^2$C(O)R$^3$, NHC(O)NH$_2$, NHC(O)NR$^3$R$^3$, NR$^2$C(O)NHR$^3$, SH, SR$^3$, S(O)H, S(O)R$^3$, SO$_2$R$^3$, SO$_2$NH$_2$, SO$_2$NHR$^3$, SO$_2$NR$^3$R$^3$, CF$_3$, CN, CO$_2$H, CO$_2$R, CHO, C(O)R$^3$, C(O)NH$_2$, C(O)NHR$^3$, C(O)NR$^3$R$^3$, CONHSO$_2$H, C(O)NHSO$_2$R$^3$, C(O)NR$^3$SO$_2$R$^3$, cyclic C$_3$-C$_7$ alkylamino, imidazolyl, piperazinyl, morpholinyl, piperidinyl, azepanyl, pyrrolidinyl and azetidinyl; wherein each of the groups imidazolyl, piperazinyl, morpholinyl, piperidinyl, azepanyl, pyrrolidinyl and azetidinyl are optionally substituted by one or more R$^3$ groups, halo, OH, OR$^3$, OC(O)R$^3$, OC(O)NH$_2$, OC(O)NHR$^3$, OC(O)NR$^3$R$^3$, OP(O)(OH)$_2$, OP(O)(OR$^3$)$_2$, NO$_2$, NH$_2$, NHR$^3$, NR$^3$R$^3$, N$^+$(—O$^-$)R$^3$R$^3$, NHC(O)H, NHC(O)R$^3$, NR$^3$C(O)R$^3$, NHC(O)NH$_2$, NHC(O)NR$^3$R$^3$, NR$^3$C(O)NHR$^3$, SH, SR$^3$, S(O)H, S(O)R$^3$, SO$_2$R$^3$, SO$_2$NH$_2$, SO$_2$NHR$^3$, SO$_2$NR$^3$R$^3$, CF$_3$, CN, CO$_2$H, CO$_2$R$^3$, CHO, C(O)R$^3$, C(O)NH$_2$, C(O)NHR$^3$, C(O)NR$^3$R$^3$, CONHSO$_2$H, C(O)NHSO$_2$R$^3$ and C(O)NR$^3$SO$_2$R$^3$; and each heteroaryl group includes one or more heteroatoms in its ring system which are each independently selected from O, N or S;

wherein each R$^3$ is independently selected from an optionally substituted C$_{1-6}$ alkyl or an optionally substituted C$_{2-6}$ alkenyl group and wherein the one or more optional substituents are each independently selected from; halo, OH, OR$^4$, OC(O)R$^4$, OC(O)NH$_2$, OC(O)NHR$^4$, OC(O)NR$^4$R$^4$, OP(O)(OH)$_2$, OP(O)(OR$^4$)$_2$, NO$_2$, NH$_2$, NHR$^4$, NR$^4$R$^4$, N$^+$(—O$^-$)R$^4$R$^4$, NHC(O)H, NHC(O)R$^4$, NR$^4$C(O)R$^4$, NHC(O)NH$_2$, NHC(O)NR$^4$R$^4$, NR$^4$C(O)NHR$^4$, SH, SR$^4$, S(O)H, S(O)R$^4$, SO$_2$R$^4$, SO$_2$NH$_2$, SO$_2$NHR$^4$, SO$_2$NR$^4$R$^4$, CF₃, CN, CO₂H, CO₂R, CHO, C(O)R⁴, C(O)NH₂, C(O)NHR⁴, C(O)NR⁴R⁴, CONHSO₂H, C(O)NHSO₂R⁴, C(O)NR⁴SO₂R⁴, cyclic C₃-C₇ alkylamino, imidazolyl, piperazinyl, morpholinyl, piperidinyl, azepanyl, pyrrolidinyl and azetidinyl; wherein each of the groups imidazolyl, piperazinyl, morpholinyl, piperidinyl, azepanyl, pyrrolidinyl and azetidinyl are optionally substituted by one or more R⁴ groups, halo, OH, OR⁴, OC(O)R⁴, OC(O)NH2, OC(O)NHR⁴, OC(O)NR⁴R⁴, OP(O)(OH)₂, OP(O)(OR⁴)₂, NO₂. NH₂, NHR⁴, NR⁴R⁴, N⁺(—O⁻)R⁴R⁴, NHC(O)H, NHC(O)R⁴, NR⁴C(O)R⁴, NHC(O)NH₂, NHC(O)NR⁴R⁴, NR⁴C(O)NHR⁴, SH, SR⁴, S(O)H, S(O)R⁴, SO₂R⁴, SO₂NH₂, SO₂NHR⁴, SO₂NR⁴R⁴, CF₃, CN, CO₂H, CO₂R, CHO, C(O)R⁴, C(O)NH₂, C(O)NHR⁴, C(O)NR⁴R⁴, CONHSO₂H, C(O)NHSO₂R⁴ and C(O)NR⁴SO₂R⁴; wherein each R⁴ is independently selected from C₁₋₄ alkyl, C₂₋₄ alkenyl, halo, OH, OC₁-C₄, NO₂, NH₂, CF₃, CN, CO₂H, COCN or SH;

or wherein W and A together represent H or halo;

Z represents an optionally substituted 4-8 membered saturated ring system fused to the benzo ring in the 6,7-positions or the 7,8-positions;

wherein the one or more optional substituents of the ring system are each independently selected from halo, R⁵, OH, OR⁵, OC(O)R⁵, OC(O)NH₂OC(O)NHR⁵, OC(O)NR⁵R⁵, OP(O)(OH)₂, OP(O)(OR⁵)₂, NO₂, NH₂, NHR⁵, NR⁵R⁵, N⁺(—O⁻)R⁵R⁵, NHC(O)H, NHC(O)R⁵, NR⁵C(O)R⁵, NHC(O)NH₂, NHC(O)NR⁵R⁵, NR⁵C(O)NHR⁵, SH, SR⁵, S(O)H, S(O)R⁵, SO₂R⁵, SO₂NH₂, SO₂NHR⁵, SO₂NR⁵R⁵, CF₃, CN, CO₂H, CO₂R, CHO, C(O)R⁵, C(O)NH₂, C(O)NHR⁵, C(O)NR⁵R⁵, C(O)NHSO₂H, C(O)NHSO₂R⁵, C(O)NR⁵SO₂R⁵, cyclic C₃-C₇ alkylamino, imidazolyl, piperazinyl, morpholinyl, piperidinyl, azepanyl, pyrrolidinyl and azetidinyl; wherein each of the groups imidazolyl, piperazinyl, morpholinyl, piperidinyl, azepanyl, pyrrolidinyl and azetidinyl are optionally substituted by one or more R⁵ groups halo, R⁵, OH, OR⁵, OC(O)R⁵, OC(O)NH₂OC(O)NHR⁵, OC(O)NR⁵R⁵, OP(O)(OH)₂, OP(O)(OR⁵)₂, NO₂, NH₂, NHR⁵, NR⁵R⁵, N⁺(—O⁻)R⁵R⁵, NHC(O)H, NHC(O)R⁵, NR⁵C(O)R⁵, NHC(O)NH₂, NHC(O)NR⁵R⁵, NR⁵C(O)NHR⁵, SH, SR⁵, S(O)H, S(O)R⁵, SO₂R⁵, SO₂NH₂, SO₂NHR⁵, SO₂NR⁵R⁵, CF₃, CN, CO₂H, CO₂R, CHO, C(O)R⁵, C(O)NH₂, C(O)NHR⁵, C(O)NR⁵R⁵, C(O)NHSO₂H, C(O)NHSO₂R⁵ and C(O)NR⁵SO₂R⁵ wherein each R⁵ is independently selected from an optionally substituted C₁₋₆ alkyl or an optionally substituted C₂₋₆ alkenyl group or an optionally substituted C₃₋₇ cyclic alkyl group and wherein the one or more optional substituents are each independently selected from; halo, R⁶, OH, OR⁶, OC(O)R⁶, OC(O)NHR⁶, OC(O)NR⁶R⁶, OP(O)(OH)₂, OP(O)(OR⁶)₂, NO₂, NH₂, NHR⁶, NR⁶R⁶, N⁺(—O⁻)R⁶R⁶, NHC(O)R⁶, NR⁶C(O)R⁶, NHC(O)NR⁶R⁶, NR⁶C(O)NHR⁶, SH, SR⁶, S(O)R⁶, SO₂R⁶, SO₂NHR⁶, SO₂NR⁶R⁶, CF₃, CN, CO₂H, CO₂R, CHO, C(O)R⁶, C(O)NH₂, C(O)NHR⁶, C(O)NR⁶R⁶, C(O)NHSO₂R⁶, C(O)NR⁶SO₂R⁶, cyclic C₃-C₇ alkylamino, imidazolyl, piperazinyl, morpholinyl, piperidinyl, azepanyl, pyrrolidinyl and azetidinyl; wherein each of the groups imidazolyl, piperazinyl, morpholinyl, piperidinyl, azepanyl, pyrrolidinyl and azetidinyl are optionally substituted by one or more R⁶ groups, halo, OH, OR⁶, OC(O)R⁶, OC(O)NH₂, OC(O)NHR⁶, OC(O)NR⁶R⁶, OP(O)(OH)₂, OP(O)(OR⁶)₂, NO₂, NH₂, NHR⁶, NR⁶R⁶, N⁺(—O⁻)R⁶R⁶, NHC(O)H, NHC(O)R⁶, NR⁶C(O)R⁶, NHC(O)NH₂, NHC(O)NR⁶R⁶, NR⁶C(O)NHR⁶, SH, SR⁶, S(O)H, S(O)R⁶, SO₂R⁶, SO₂NH₂, SO₂NHR⁶, SO₂NR⁶R⁶, CF₃, CN, CO₂H, CO₂R⁶, CHO, C(O)R⁶, C(O)NH₂, C(O)NHR⁶, C(O)NR⁶R⁶, C(O)NHSO₂H, C(O)NHSO₂R⁶ and C(O)NR⁶SO₂R⁶ wherein each R⁶ is independently selected from C₁₋₆ alkyl, C₂₋₆ alkenyl, halo, OH, OMe, NO₂, NH₂, CF₃, CN, CO₂H or SH; and wherein the optionally substituted 4-8 membered ring system includes one or more carbon atoms and/or one or more ring system moieties selected from O, NH, NR⁷, CONH, CONR⁷, NHCO, NR⁷CO, wherein each R⁷ is independently selected from an optionally substituted C₁₋₆ alkyl, an optionally substituted C₂₋₆ alkenyl group or an optionally substituted C₃₋₇ cyclic alkyl group and wherein the one or more optional substituents are each independently selected from halo, R⁸, OH, OR⁸, OC(O)R⁸, OC(O)NH₂, OC(O)NHR⁸, OC(O)NR⁸R⁸, OP(O)(OH)₂, OP(O)(OR⁵)₂, NO₂, NH₂, NHR⁸, NR⁸R⁸, N⁺(—O⁻)R⁸R⁸, NHC(O)H, NHC(O)R⁸, NR⁸C(O)R⁸, NHC(O)NH₂, NHC(O)NR⁸R⁸, NR⁸C(O)NHR⁸, SH, SR⁸, S(O)H, S(O)R⁸, SO₂R⁸, SO₂NH₂, SO₂NHR⁸, SO₂NR⁸R⁸, CF₃, CN, CO₂H, CO₂R, CHO, C(O)R⁸, C(O)NH₂, C(O)NHR⁸, C(O)NR⁸R⁸, C(O)NHSO₂H, C(O)NHSO₂R⁸, C(O)NR⁸SO₂R⁸, cyclic C₃-C₇ alkylamino, imidazolyl, piperazinyl, morpholinyl, piperidinyl, azepanyl, pyrrolidinyl and azetidinyl; wherein each of the groups imidazolyl, piperazinyl, morpholinyl, piperidinyl, azepanyl, pyrrolidinyl and azetidinyl are optionally substituted by one or more R⁸ groups, halo, R⁸, OH, OR⁸, OC(O)R⁸, OC(O)NH₂, OC(O)NHR⁸, OC(O)NR⁸R⁸, OP(O)(OH)₂, OP(O)(OR⁵)₂, NO₂, NH₂, NHR⁸, NR⁸R⁸, N⁺(—O⁻)R⁸R⁸, NHC(O)H, NHC(O)R⁸, NR⁸C(O)R⁸, NHC(O)NH₂, NHC(O)NR⁸R⁸, NR⁸C(O)NHR⁸, SH, SR⁸, S(O)H, S(O)R⁸, SO₂R⁸, SO₂NH₂, SO₂NHR⁸, SO₂NR⁸R⁸, CF₃, CN, CO₂H, CO₂R, CHO, C(O)R⁸, C(O)NH₂, C(O)NHR⁸, C(O)NR⁸R⁸, C(O)NHSO₂H, C(O)NHSO₂R⁸ and C(O)NR⁸SO₂R⁸; wherein each R⁸ is independently selected from an optionally substituted C₁₋₆ alkyl, an optionally substituted C₂₋₆ alkenyl group or an optionally substituted C₃₋₇ cyclic alkyl group and wherein the one or more optional substituents is each independently selected from; halo, OH, OR⁹, OC(O)R⁹, OC(O)NH₂, OC(O)NHR⁹, OC(O)NR⁹R⁹, OP(O)(OH)₂, OP(O)(OR⁹)₂, NO₂, NH₂, NHR⁹, NR⁹R⁹, N⁺(—O⁻)R⁹R⁹, NHC(O)H, NHC(O)R⁹, NR⁹C(O)R⁹, NHC(O)NH₂, NHC(O)NR⁹R⁹, NR⁹C(O)NHR⁹, SH, SR⁹, S(O)H, S(O)R⁹, SO₂R⁹, SO₂NH₂, SO₂NHR⁹, SO₂NR⁹R⁹, CF₃, CN, CO₂H, CO₂R, CHO, C(O)R⁹, C(O)NH₂, C(O)NHR⁹, C(O)NR⁹R⁹, C(O)NHSO₂H, C(O)NHSO₂R⁹, C(O)NR⁹SO₂R⁹, cyclic C₃-C₇ alkylamino, imidazolyl, piperazinyl, morpholinyl, piperidinyl, azepanyl, pyrrolidinyl and azetidinyl; wherein each of the groups imidazolyl, piperazinyl, morpholinyl, piperidinyl, azepanyl, pyrrolidinyl and azetidinyl are optionally substituted by one or more R⁹ groups, halo, OH, OR⁹, OC(O)R⁹, OC(O)NH₂, OC(O)NHR⁹, OC(O)NR⁹R⁹, OP(O)(OH)₂, OP(O)(OR⁹)₂, NO₂, NH₂, NHR⁹, NR⁹R⁹, N⁺(—O⁻)R⁹R⁹, NHC(O)H, NHC(O)R⁹, NR⁹C(O)R⁹, NHC(O)NH₂, NHC(O)NR⁹R⁹, NR⁹C(O)NHR⁹, SH, SR⁹, S(O)H, S(O)R⁹, SO₂R⁹, SO₂NH₂, SO₂NHR⁹, SO₂NR⁹R⁹, CF₃, CN, CO₂H, CO₂R, CHO, C(O)R⁹, C(O)NH₂, C(O)NHR⁹, C(O)NR⁹R⁹, C(O)NHSO₂H, C(O)NHSO₂R⁹, and C(O)NR⁹SO₂R⁹; wherein each R⁹ is independently selected from C₁₋₆ alkyl, C₂₋₆ alkenyl, halo, OH, OMe, NO₂, NH₂, CF₃, CN, CO₂H or SH.

2. A compound as claimed in claim 1 wherein Z represents an optionally substituted 5-7 membered saturated ring system fused to the benzo ring in the 6,7-positions or the 7,8-positions; wherein the one or more optional substituents of the ring system are each independently selected from halo, $C_1$-$C_6$ alkyl, OH, $OC_1$-$C_6$alkyl, $OC(O)C_1$-$C_6$alkyl, $OC(O)NH_2$, $OC(O)NHC_1$-$C_6$alkyl, $OC(O)N(C_1$-$C_6$alkyl$)_2$, $OP(O)(OH)_2$, $OP(O)(OC_1$-$C_6$alkyl$)_2$, $NO_2$, $NH_2$, $NHC_1$-$C_6$alkyl, $N(C_1$-$C_6$alkyl$)_2$, $N^+(—O^-)(C_1$-$C_6$ alkyl$)_2$, $NHC(O)H$, $NHC(O)C_1$-$C_6$alkyl, $N(C_1$-$C_6$alkyl$)C(O)C_1$-$C_6$ alkyl, $NHC(O)NH_2$, $NHC(O)N(C_1$-$C_6$alkyl$)_2$, $NC_1$-$C_6$ alkyl$C(O)NHC_1$-$C_6$ alkyl, SH, $SC_1$-$C_6$ alkyl, $S(O)H$, $S(O)C_1$-$C_6$alkyl, $SO_2C_1$-$C_6$alkyl, $SO_2NH_2$, $SO_2NHC_1$-$C_6$ alkyl, $SO_2N(C_1$-$C_6$ alkyl$)_2$, $CF_3$, CN, $CO_2H$, $CO_2C_1$-$C_6$ alkyl, CHO, $C(O)C_1$-$C_6$ alkyl, $C(O)NH_2$, $C(O)NHC_1$-$C_6$alkyl, $C(O)N(C_1$-$C_6$ alkyl$)_2$, $C(O)NHSO_2H$, $C(O)NHSO_2C_1$-$C_6$ alkyl, $C(O)N(C_1$-$C_6$ alkyl$)SO_2(C_1$-$C_6$ alkyl), cyclic $C_3$-$C_7$ alkylamino, imidazolyl, piperazinyl, morpholinyl, piperidinyl, azepanyl, pyrrolidinyl and azetidinyl; wherein each of the substituents are optionally substituted by one or more halo, $C_1$-$C_6$ alkyl, OH, $OC_1$-$C_6$ alkyl, and wherein the optionally substituted ring system includes one or more carbon atoms and/or one or more ring system moieties selected from O, NH, $N(C_1$-$C_6$ alkyl), CONH, $CON(C_1$-$C_6$ alkyl), NHCO, $N(C_1$-$C_6$ alkyl)CO, wherein each $C_1$-$C_6$ alkyl is optionally substituted with one or more halo, $C_1$-$C_6$ alkyl, OH, $OC_1$-$C_6$ alkyl, $OP(O)(OH)_2$, $OP(O)(OC_1$-$C_6$ alkyl$)_2$, $NO_2$, $NH_2$, $NHC_1$-$C_6$ alkyl, $N(C_1$-$C_6$ alkyl$)_2$, SH, $S(C_1$-$C_6$ alkyl), $S(O)H$, $S(O)C_1$-$C_6$ alkyl, $SO_2C_1$-$C_6$ alkyl, $SO_2NH_2$, $CF_3$, CN, $CO_2H$, $CO_2R$, CHO, $C(O)C_1$-$C_6$ alkyl, $C(O)NH_2$, $C(O)NHC_1$-$C_6$ alkyl, $C(O)N(C_1$-$C_6$ alkyl$)_2$, $C(O)NHSO_2H$, $C(O)NHSO_2R^8$, $C(O)NR^8SO_2R^8$, cyclic $C_3$-$C_7$ alkylamino, imidazolyl, piperazinyl, morpholinyl, piperidinyl, azepanyl, pyrrolidinyl and azetidinyl; wherein each of the groups imidazolyl, piperazinyl, morpholinyl, piperidinyl, azepanyl, pyrrolidinyl and azetidinyl.

3. A compound as claimed in claim 1 wherein Z represents a 5, 6 or 7 membered ring, optionally substituted with one or more substituents selected from $C_{1-6}$ alkyl wherein the alkyl is optionally substituted with one or more OH, NH and $N(C_1$-$C_6$ alkyl$)_2$, and wherein the ring optionally includes one or more O, NH or $N(C_1$-$C_6$ alkyl) moieties.

4. A compound as claimed in claim 1 wherein Z represents a 5, 6 or 7 membered ring, optionally substituted with $CH_3$, $CH_2OH$, $N(CH_3)_2$, $CH_2CH_3$, $(CH_2)_2OH$, and wherein the ring optionally includes one or more O, NH or $N(C_1$-$C_6$ alkyl) moieties.

5. A compound as claimed in claim 1 wherein Z represents a 5 or 6 membered ring optionally substituted with $CH_3$, $CH_2OH$, $N(CH_3)_2$, $CH_2CH_3$, $(CH_2)_2OH$, and wherein the 5 or 6 membered ring is selected from the following:

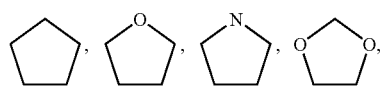

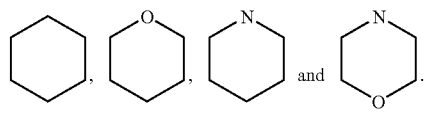 and

6. A compound of claim 1 wherein Z represents an unsubstituted 5 membered carbon ring.

7. A compound of claim 1 wherein W represents —NH, or —$CH_2$.

8. A compound of claim 1 wherein A represents H or an optionally substituted $C_{1-6}$ alkyl group or an optionally substituted $C_{2-6}$ alkenyl group wherein the one or more optional substituents are each independently selected from halo, OH, $OC_{1-6}$ alkyl, $OC(O)C_{1-6}$ alkyl, $OC(O)NH_2$, $OC(O)NHC_{1-6}$ alkyl, $OC(O)N(C_{1-6}$ alkyl$)_2$, $OP(O)(OH)_2$, $OP(O)(OC_{1-6}$ alkyl$)_2$, $NO_2$, $NH_2$, $NHC_{1-6}$ alkyl, $N(C_{1-6}$ alkyl$)_2$, $NHC(O)H$, $NHC(O)C_{1-6}$ alkyl, $NR^2C(O)C_{1-6}$ alkyl, $NHC(O)NH_2$, $NHC(O)N(C_{1-6}$ alkyl$)_2$, $N(C_{1-6}$alkyl$)C(O)NHC_{1-6}$ alkyl, $CF_3$, CN, $CO_2H$, $CO_2C_{1-6}$ alkyl, CHO, $C(O)C_{1-6}$ alkyl, $C(O)NH_2$, $C(O)NHC_{1-6}$ alkyl, $C(O)N(C_{1-6}$alkyl$)_2$, $CONHSO_2H$, $C(O)NHSO_2C_{1-6}$ alkyl, $C(O)NC_{1-6}$ alkyl$SO_2C_{1-6}$ alkyl, cyclic $C_3$-$C_7$ alkylamino, imidazolyl, piperazinyl, morpholinyl, piperidinyl, azepanyl, pyrrolidinyl and azetidinyl; wherein each of the groups imidazolyl, piperazinyl, morpholinyl, piperidinyl, azepanyl, pyrrolidinyl and azetidinyl are optionally substituted by one or more groups selected from halo, OH, $OC_{1-6}$ alkyl, $OC(O)C_{1-6}$ alkyl, $OC(O)NH_2$, $OC(O)NHC_{1-6}$ alkyl, $OC(O)N(C_{1-6}$ alkyl$)_2$, $OP(O)(OH)_2$, $OP(O)(OC_{1-6}$ alkyl$)_2$, $NO_2$, $NH_2$, $NHC_{1-6}$ alkyl, $N(C_{1-6}$ alkyl$)_2$, $NHC(O)H$, $NHC(O)C_{1-6}$ alkyl, $NC_{1-6}$ alkyl$C(O)C_{1-6}$ alkyl, $NHC(O)NH_2$, $NHC(O)N(C_{1-6}$ alkyl$)_2$, $NC_{1-6}$ alkyl$C(O)NHC_{1-6}$ alkyl, $CF_3$, CN, $CO_2H$, $CO_2C_{1-6}$ alkyl, CHO, $C(O)C_{1-6}$ alkyl, $C(O)NH_2$, $C(O)NHC_{1-6}$ alkyl, $C(O)N(C_{1-6}$ alkyl), $CONHSO_2H$, $C(O)NHSO_2(C_{1-6}$ alkyl), and $C(O)NC_{1-6}$ alkyl$SO_2C_{1-6}$ alkyl.

9. A compound of claim 1 wherein A represents an optionally substituted —$C_1$-$C_6$alkyl, $C_1$-$C_6$alkyl OH, —$N(C_1$-$C_6$alkyl$)_2$, —$N(C_1$-$C_6$alkyl$)OC_1$-$C_6$alkyl, —$C_1$-$C_6$alkylN$(C_1$-$C_6$alkyl$)_2$, —$C_1$-$C_6$alkylN$(C_1$-$C_6$alkyl), $C_1$-$C_6$alkyl$OC_1$-$C_6$alkyl, —$C_1$-$C_6$alkyl$OC_1$-$C_6$alkyl, —$C_1$-$C_6$alkylNazetidine, —$C_1$-$C_6$alkylOP(O)(OH$)_2$, —$C_1$-$C_6$alkylNpyrrolidine, —$C_1$-$C_6$alkylNpiperidine, —$C_1$-$C_6$alkyl N(2,6-(di $C_1$-$C_6$alkyl)piperidine), —$C_1$-$C_6$alkylNmorpholine, —$C_1$-$C_6$alkylazepane, —$C_1$-$C_6$alkylNoxazepine, $C_1$-$C_6$alkylOC(O) $C_1$-$C_6$alkylN$(C_1$-$C_6$alkyl$)_2$, $C_1$-$C_6$alkylOC(O)$C_1$-$C_6$alkyl(NCO$_2C_1$-$C_6$alkyl) $C_1$-$C_6$alkyl, wherein the one or more substituents are each independently selected from OH, $C_1$-$C_6$alkyl, $OC_1$-$C_6$alkyl or CN.

10. A compound of claim 1 wherein W and A together represent H, halo, $NH_2$, $NHCH_2CH_3$, —$CH_2CH_2CH_2NMe_2$, —$CH_2CH_2CH_2OH$, —$NH(CH_2)_2N(Me)_2$, —$NHCH_2CH_2OH$,
—$NHCH_2CH_2NEt_2$, —$NHCH_2CH_2NPr_2$,
—$CH_2CH_2CH_2N(Me)CH_2CH_2OMe$,
—$N(CH_2CH_2OMe)_2$,
—$NHCH_2CH_2N(Me)CH_2CH_2CH_2OMe$,
—$NHCH_2CH_2Nazetidine-3-OMe$,
—$CH_2CH_2CH_2OP(O)(OH)_2$,
—$CH_2CH_2CH_2Npyrrolidine$,
—$NHCH_2CH_2Npiperidine$,
—$NHCH_2CH_2N-(2,6-diMepiperidine)$,
—$CH_2CH_2CH_2Nazetidine-3-OMe$,
—$NHCH_2CH_2Npiperidine-3-OMe$,
—$NHCH_2CH_2Npiperidine-4-OMe$,
—$CH_2CH_2CH_2Npiperidine$,
—$NHCH_2CH_2Nmorpholine$, —$NHCH_2CH_2Nazepane$,
—$NHCH_2CH_2Noxazepine$, —$NHCH_2CH_2CH_2OH$,
—$NHCH_2CH_2CH_2N(Me)CH_2CH_2OMe$,
—$NHCH_2CH_2CH_2NazetidineOMe$,
—$NHCH_2CH_2CH_2N(pyrrolidine-3-CN)$,
—$NHCH_2CH_2CH_2Npiperidine-4-OMe$, —NHCH₂CH₂CH₂Nmorpholine,
—NHCH₂CH₂CH₂CH₂Nmorpholine,
—CH₂CH₂CH₂OC(O)CH₂CH₂CHN(Me)₂, and
—CH₂CH₂CH₂OC(O)CH(NHCO₂tBu)CH₂Me₂.

11. A compound as claimed in claim 1 wherein W and A together represent halo, —NHCH₂CH₂CH₂Nmorpholine, —NHCH₂CH₂N(Me)₂ or —CH₂CH₂CH₂NMe₂.

12. A compound as claimed in claim 1 wherein X on the benzo ring is H.

13. A compound or a pharmacologically acceptable salt thereof selected from the following:

8,9-Dihydro-7H-indeno[5,4-e][1,2,4]triazin-3-amine 1-oxide;
3-Chloro-8,9-dihydro-7H-indeno[5,4-e][1,2,4]triazine 1-oxide;
N¹,N¹-Dimethyl-N²-(1-oxido-8,9-dihydro-7H-indeno[5,4-e][1,2,4]triazin-3-yl)-1,2-ethanediamine;
N¹,N¹-Dimethyl-N²-(1,4-dioxido-8,9-dihydro-7H-indeno[5,4-e][1,2,4]triazin-3-yl)-1,2-ethanediamine;
N¹,N¹-Diethyl-N²-(1-oxido-8,9-dihydro-7H-indeno[5,4-e][1,2,4]triazin-3-yl)-1,2-ethanediamine;
N¹,N¹-Diethyl-N²-(1,4-dioxido-8,9-dihydro-7H-indeno[5,4-e][1,2,4]triazin-3-yl)-1,2-ethanediamine;
N¹-(1-Oxido-8,9-dihydro-7H-indeno[5,4-e][1,2,4]triazin-3-yl)-N²,N²-dipropyl-1,2-ethanediamine;
N-[2-(1-Piperidinyl)ethyl]-8,9-dihydro-7H-indeno[5,4-e][1,2,4]triazin-3-amine 1-oxide;
N-[2-(1-Piperidinyl)ethyl]-8,9-dihydro-7H-indeno[5,4-e][1,2,4]triazin-3-amine 1,4-dioxide;
N-[3-(1-Morpholinyl)propyl]-8,9-dihydro-7H-indeno[5,4-e][1,2,4]triazin-3-amine 1-oxide;
N-[3-(1-Morpholinyl)propyl]-8,9-dihydro-7H-indeno[5,4-e][1,2,4]triazin-3-amine 1,4-dioxide;
7,8-Dihydro-6H-indeno[5,6-e][1,2,4]triazin-3-amine 1-oxide;
7,8-Dihydro-6H-indeno[5,6-e][1,2,4]triazin-3-amine 1,4-dioxide;
3-Chloro-7,8-dihydro-6H-indeno[5,6-e][1,2,4]triazine 1-oxide;
N¹,N¹-Dimethyl-N²-(1-oxido-7,8-dihydro-6H-indeno[5,6-e][1,2,4]triazin-3-yl)-1,2-ethanediamine;
N¹-(1,4-Dioxido-7,8-dihydro-6H-indeno[5,6-e][1,2,4]triazin-3-yl)-N²,N²-dimethyl-1,2-ethanediamine;
2-[(1-Oxido-7,8-dihydro-6H-indeno[5,6-e][1,2,4]triazin-3-yl)amino]ethanol;
2-[(1,4-Dioxido-7,8-dihydro-6H-indeno[5,6-e][1,2,4]triazin-3-yl)amino]ethanol;
N¹-(1-Oxido-7,8-dihydro-6H-indeno[5,6-e][1,2,4]triazin-3-yl)-N²,N²-diethyl-1,2-ethanediamine;
N¹-(1,4-Dioxido-7,8-dihydro-6H-indeno[5,6-e][1,2,4]triazin-3-yl)-N²,N²-diethyl-1,2-ethanediamine;
N¹-(1-Oxido-7,8-dihydro-6H-indeno[5,6-e][1,2,4]triazin-3-yl)-N²,N²-dipropyl-1,2-ethanediamine;
N¹-(1,4-Dioxido-7,8-dihydro-6H-indeno[5,6-e][1,2,4]triazin-3-yl)-N²,N²-dipropyl-1,2-ethanediamine;
N¹-(1-Oxido-7,8-dihydro-6H-indeno[5,6-e][1,2,4]triazin-3-yl)-N²-(2-methoxyethyl)-N²-methyl-1,2-ethanediamine;
N¹-(1,4-dioxido-7,8-dihydro-6H-indeno[5,6-e][1,2,4]triazin-3-yl)-N²-(2-methoxyethyl)-N²-methyl-1,2-ethanediamine;
N¹-(3-Methoxypropyl)-N¹-methyl-N²-(1-oxido-7,8-dihydro-6H-indeno[5,6-e][1,2,4]triazin-3-yl)-1,2-ethanediamine;
N¹-(1,4-Dioxido-7,8-dihydro-6H-indeno[5,6-e][1,2,4]triazin-3-yl)-N²-(3-methoxypropyl)-N²-methyl-1,2-ethanediamine;
N-[2-(3-Methoxy-1-azetidinyl)ethyl]-7,8-dihydro-6H-indeno[5,6-e][1,2,4]triazin-3-amine 1-oxide;
N-[2-(3-Methoxy-1-azetidinyl)ethyl]-7,8-dihydro-6H-indeno[5,6-e][1,2,4]triazin-3-amine 1,4-dioxide;
N-[2-(1-Piperidinyl)ethyl]-7,8-dihydro-6H-indeno[5,6-e][1,2,4]triazin-3-amine 1-oxide;
N-[2-(1-Piperidinyl)ethyl]-7,8-dihydro-6H-indeno[5,6-e][1,2,4]triazin-3-amine 1,4-dioxide;
N-[2-(2,6-Dimethyl-1-piperidinyl)ethyl]-7,8-dihydro-6H-indeno[5,6-e][1,2,4]triazin-3-amine 1-oxide;
N-[2-(2,6-Dimethyl-1-piperidinyl)ethyl]-7,8-dihydro-6H-indeno[5,6-e][1,2,4]triazin-3-amine 1,4-dioxide;
N-[2-(3-Methoxy-1-piperidinyl)ethyl]-7,8-dihydro-6H-indeno[5,6-e][1,2,4]triazin-3-amine 1-oxide;
N-[2-(3-Methoxy-1-piperidinyl)ethyl]-7,8-dihydro-6H-indeno[5,6-e][1,2,4]triazin-3-amine 1,4-dioxide;
N-[2-(4-Methoxy-1-piperidinyl)ethyl]-7,8-dihydro-6H-indeno[5,6-e][1,2,4]triazin-3-amine 1-oxide;
N-[2-(4-Methoxy-1-piperidinyl)ethyl]-7,8-dihydro-6H-indeno[5,6-e][1,2,4]triazin-3-amine 1,4-dioxide;
N-[2-(4-Morpholinyl)ethyl]-7,8-dihydro-6H-indeno[5,6-e][1,2,4]triazin-3-amine 1-oxide;
N-[2-(4-Morpholinyl)ethyl]-7,8-dihydro-6H-indeno[5,6-e][1,2,4]triazin-3-amine 1,4-dioxide;
N-[2-(1-Azepanyl)ethyl]-7,8-dihydro-6H-indeno[5,6-e][1,2,4]triazin-3-amine 1-oxide;
N-[2-(1-Azepanyl)ethyl]-7,8-dihydro-6H-indeno[5,6-e][1,2,4]triazin-3-amine 1,4-dioxide;
N-[2-(1,4-Oxazepan-4-yl)ethyl]-7,8-dihydro-6H-indeno[5,6-e][1,2,4]triazin-3-amine 1-oxide;
N-[2-(1,4-Oxazepan-4-yl)ethyl]-7,8-dihydro-6H-indeno[5,6-e][1,2,4]triazin-3-amine 1,4-dioxide;
3-[(1-Oxido-7,8-dihydro-6H-indeno[5,6-e][1,2,4]triazin-3-yl)amino]-1-propanol;
3-[(1,4-Dioxido-7,8-dihydro-6H-indeno[5,6-e][1,2,4]triazin-3-yl)amino]-1-propanol;
N¹-(1-Oxido-7,8-dihydro-6H-indeno[5,6-e][1,2,4]triazin-3-yl)-N³-(2-methoxyethyl)-N³-methyl-1,3-propanediamine;
N¹-(1,4-Dioxido-7,8-dihydro-6H-indeno[5,6-e][1,2,4]triazin-3-yl)-N³-(2-methoxyethyl)-N³-methyl-1,3-propanediamine;
N-[3-(3-Methoxy-1-azetidinyl)propyl]-7,8-dihydro-6H-indeno[5,6-e][1,2,4]triazin-3-amine 1-oxide;
N-[3-(3-Methoxy-1-azetidinyl)propyl]-7,8-dihydro-6H-indeno[5,6-e][1,2,4]triazin-3-amine 1,4-dioxide;
1-{3-[(1-Oxido-7,8-dihydro-6H-indeno[5,6-e][1,2,4]triazin-3-yl)amino]propyl}-3-pyrrolidinecarbonitrile;
1-{3-[(1,4-Dioxido-7,8-dihydro-6H-indeno[5,6-e][1,2,4]triazin-3-yl)amino]propyl}-3-pyrrolidinecarbonitrile;
N-[3-(4-Methoxy-1-piperidinyl)propyl]-7,8-dihydro-6H-indeno[5,6-e][1,2,4]triazin-3-amine 1-oxide;
N-[3-(4-Methoxy-1-piperidinyl)propyl]-7,8-dihydro-6H-indeno[5,6-e][1,2,4]triazin-3-amine 1,4-dioxide;
N-[3-(4-Morpholinyl)propyl]-7,8-dihydro-6H-indeno[5,6-e][1,2,4]triazin-3-amine 1-oxide;
N-[3-(4-Morpholinyl)propyl]-7,8-dihydro-6H-indeno[5,6-e][1,2,4]triazin-3-amine 1,4-dioxide;
N-[4-(4-Morpholinyl)butyl]-7,8-dihydro-6H-indeno[5,6-e][1,2,4]triazin-3-amine 1-oxide;
N-[4-(4-Morpholinyl)butyl]-7,8-dihydro-6H-indeno[5,6-e][1,2,4]triazin-3-amine 1,4-dioxide;
7,8-Dihydro-6H-indeno[5,6-e][1,2,4]triazine 1-oxide;
7,8-Dihydro-6H-indeno[5,6-e][1,2,4]triazine 1,4-dioxide;
3-Iodo-7,8-dihydro-6H-indeno[5,6-e][1,2,4]triazine 1-oxide;

Ethyl-7,8-dihydro-6H-indeno[5,6-e][1,2,4]triazine 1-oxide;
3-Ethyl-7,8-dihydro-6H-indeno[5,6-e][1,2,4]triazine 1,4-dioxide;
3-Allyl-7,8-dihydro-6H-indeno[5,6-e][1,2,4]triazine 1-oxide;
3-(1-Oxido-7,8-dihydro-6H-indeno[5,6-e][1,2,4]triazin-3-yl)-1-propanol;
3-(1,4-Dioxido-7,8-dihydro-6H-indeno[5,6-e][1,2,4]triazin-3-yl)-1-propanol;
3-(3-(Di-tert-butoxyphosphoryloxy)propyl)-7,8-dihydro-6H-indeno[5,6-e][1,2,4]triazine 1-oxide;
3-(3-(Di-tert-butoxyphosphoryloxy)propyl)-7,8-dihydro-6H-indeno[5,6-e][1,2,4]triazine 1,4-dioxide;
3-(1,4-Dioxido-7,8-dihydro-6H-indeno[5,6-e][1,2,4]triazin-3-yl)propyl dihydrogen phosphate;
3-[3-(4-Morpholinyl)propyl]-7,8-dihydro-6H-indeno[5,6-e][1,2,4]triazine 1-oxide;
3-[3-(4-Morpholinyl)propyl]-7,8-dihydro-6H-indeno[5,6-e][1,2,4]triazine 1,4-dioxide;
N,N-Dimethyl-3-(1-oxido-7,8-dihydro-6H-indeno[5,6-e][1,2,4]triazin-3-yl)-1-propanamine;
N-[3-(1,4-Dioxido-7,8-dihydro-6H-indeno[5,6-e][1,2,4]triazin-3-yl)propyl]-N,N-dimethylamine;
N,N-Bis(2-methoxyethyl)-3-(1-oxido-7,8-dihydro-6H-indeno[5,6-e][1,2,4]triazin-3-yl)-1-propanamine;
N-[3-(1,4-Dioxido-7,8-dihydro-6H-indeno[5,6-e][1,2,4]triazin-3-yl)propyl]-N,N-bis(2-methoxyethyl)amine;
3-[3-(3-Methoxy-1-azetidinyl)propyl]-7,8-dihydro-6H-indeno[5,6-e][1,2,4]triazine 1-oxide;
3-[3-(3-Methoxy-1-azetidinyl)propyl]-7,8-dihydro-6H-indeno[5,6-e][1,2,4]triazine 1,4-dioxide;
3-[3-(1-Pyrrolidinyl)propyl]-7,8-dihydro-6H-indeno[5,6-e][1,2,4]triazine 1-oxide;
3-[3-(1-Pyrrolidinyl)propyl]-7,8-dihydro-6H-indeno[5,6-e][1,2,4]triazine 1,4-dioxide;
3-[3-(1-Piperidinyl)propyl]-7,8-dihydro-6H-indeno[5,6-e][1,2,4]triazine 1-oxide;
3-[3-(1-Piperidinyl)propyl]-7,8-dihydro-6H-indeno[5,6-e][1,2,4]triazine 1,4-dioxide;
7-Methyl-7,8-dihydro-6H-indeno[5,6-e][1,2,4]triazin-3-amine 1-oxide;
3-Chloro-7-methyl-7,8-dihydro-6H-indeno[5,6-e][1,2,4]triazine 1-oxide;
$N^1,N^1$-Dimethyl-$N^2$-(7-methyl-1-oxido-7,8-dihydro-6H-indeno[5,6-e][1,2,4]triazin-3-yl)-1,2-ethanediamine;
$N^1,N^1$-Dimethyl-$N^2$-(7-methyl-1,4-dioxido-7,8-dihydro-6H-indeno[5,6-e][1,2,4]triazin-3-yl)-1,2-ethanediamine;
7-Methyl-N-[3-(4-morpholinyl)propyl]-7,8-dihydro-6H-indeno[5,6-e][1,2,4]triazin-3-amine 1-oxide;
7-Methyl-N-[3-(4-morpholinyl)propyl]-7,8-dihydro-6H-indeno[5,6-e][1,2,4]triazin-3-amine 1,4-dioxide;
3-Iodo-7-methyl-7,8-dihydro-6H-indeno[5,6-e][1,2,4]triazine 1-oxide;
3-(7-Methyl-1-oxido-7,8-dihydro-6H-indeno[5,6-e][1,2,4]triazin-3-yl)propanal;
7-Methyl-3-[3-(4-morpholinyl)propyl]-7,8-dihydro-6H-indeno[5,6-e][1,2,4]triazine 1-oxide;
7-Methyl-3-[3-(4-morpholinyl)propyl]-7,8-dihydro-6H-indeno[5,6-e][1,2,4]triazine 1,4-dioxide;
3-(7-Methyl-1,4-dioxido-7,8-dihydro-6H-indeno[5,6-e][1,2,4]triazin-3-yl)-1-propanol;
$N^7,N^7$-Dimethyl-7,8-dihydro-6H-indeno[5,6-e][1,2,4]triazine-3,7-diamine 1-oxide;
3-Chloro-N,N-dimethyl-7,8-dihydro-6H-indeno[5,6-e][1,2,4]triazin-7-amine 1-oxide;
$N^3$-Ethyl-$N^7,N^7$-dimethyl-7,8-dihydro-6H-indeno[5,6-e][1,2,4]triazine-3,7-diamine 1-oxide;
$N^3$-Ethyl-$N^7,N^7$-dimethyl-7,8-dihydro-6H-indeno[5,6-e][1,2,4]triazine-3,7-diamine 1,4-dioxide;
7-(Dimethylamino)-3-ethyl-7,8-dihydro-6H-indeno[5,6-e][1,2,4]triazine 1-oxide;
7-(Dimethylamino)-3-ethyl-7,8-dihydro-6H-indeno[5,6-e][1,2,4]triazine 1,4-dioxide;
(3-Amino-1-oxido-7,8-dihydro-6H-indeno[5,6-e][1,2,4]triazin-7-yl)methanol;
(3-Bromo-1-oxido-7,8-dihydro-6H-indeno[5,6-e][1,2,4]triazin-7-yl)methanol;
[3-(Ethylamino)-1-oxido-7,8-dihydro-6H-indeno[5,6-e][1,2,4]triazin-7-yl]methanol;
[3-(Ethylamino)-1,4-dioxido-7,8-dihydro-6H-indeno[5,6-e][1,2,4]triazin-7-yl]methanol;
7-({[tert-Butyl(dimethyl)silyl]oxy}methyl)-7,8-dihydro-6H-indeno[5,6-e][1,2,4]triazin-3-amine 1-oxide;
7-({[tert-Butyl(dimethyl)silyl]oxy}methyl)-3-iodo-7,8-dihydro-6H-indeno[5,6-e][1,2,4]triazine 1-oxide;
7-({[tert-Butyl(dimethyl)silyl]oxy}methyl)-3-ethyl-7,8-dihydro-6H-indeno[5,6-e][1,2,4]triazine 1-oxide;
(3-Ethyl-1,4-dioxido-7,8-dihydro-6H-indeno[5,6-e][1,2,4]triazin-7-yl)methanol;
3-Allyl-7-({[tert-butyl(dimethyl)silyl]oxy}methyl)-7,8-dihydro-6H-indeno[5,6-e][1,2,4]triazine 1-oxide;
3-[7-({[tert-Butyl(dimethyl)silyl]oxy}methyl)-1-oxido-7,8-dihydro-6H-indeno[5,6-e][1,2,4]triazin-3-yl]-1-propanol;
7-({[tert-Butyl(dimethyl)silyl]oxy}methyl)-3-[3-(4-morpholinyl)propyl]-7,8-dihydro-6H-indeno[5,6-e][1,2,4]triazine 1-oxide;
{3-[3-(4-Morpholinyl)propyl]-1-oxido-7,8-dihydro-6H-indeno[5,6-e][1,2,4]triazin-7-yl}methanol;
{3-[3-(4-Morpholinyl)propyl]-1,4-dioxido-7,8-dihydro-6H-indeno[5,6-e][1,2,4]triazin-7-yl}methanol;
(3-Ethyl-1-oxido-7,8-dihydro-6H-indeno[5,6-e][1,2,4]triazin-7-yl)methanol;
3-Ethyl-7-(4-morpholinylmethyl)-7,8-dihydro-6H-indeno[5,6-e][1,2,4]triazine 1-oxide;
3-Ethyl-7-(4-morpholinylmethyl)-7,8-dihydro-6H-indeno[5,6-e][1,2,4]triazine 1,4-dioxide;
2-(3-Amino-1-oxido-7,8-dihydro-6H-indeno[5,6-e][1,2,4]triazin-7-yl)ethanol;
2-(3-Iodo-1-oxido-7,8-dihydro-6H-indeno[5,6-e][1,2,4]triazin-7-yl)ethanol;
3-Iodo-7-(2-(tetrahydro-2H-pyran-2-yloxy)ethyl)-7,8-dihydro-6H-indeno[5,6-e][1,2,4]triazine 1-oxide;
3-Ethyl-7-(2-(tetrahydro-2H-pyran-2-yloxy)ethyl)-7,8-dihydro-6H-indeno[5,6-e][1,2,4]triazine 1-oxide;
2-(3-Ethyl-1-oxido-7,8-dihydro-6H-indeno[5,6-e][1,2,4]triazin-7-yl)ethanol;
2-(3-Ethyl-1,4-dioxido-7,8-dihydro-6H-indeno[5,6-e][1,2,4]triazin-7-yl)ethanol;
3-Ethyl-7-[2-(4-morpholinyl)ethyl]-7,8-dihydro-6H-indeno[5,6-e][1,2,4]triazine 1-oxide;
3-Ethyl-7-[2-(4-morpholinyl)ethyl]-7,8-dihydro-6H-indeno[5,6-e][1,2,4]triazine 1,4-dioxide;
7,8,9,10-Tetrahydronaphtho[2,1-e][1,2,4]triazin-3-amine 1-oxide;
3-Chloro-7,8,9,10-tetrahydronaphtho[2,1-e][1,2,4]triazine 1-oxide;
$N^1,N^1$-Dimethyl-$N^2$-(1-oxido-7,8,9,10-tetrahydronaphtho[2,1-e][1,2,4]triazin-3-yl)-1,2-ethanediamine;
$N^1$-(1,4-Dioxido-7,8,9,10-tetrahydronaphtho[2,1-e][1,2,4]triazin-3-yl)-$N^2,N^2$-dimethyl-1,2-ethanediamine;

6,7,8,9-Tetrahydronaphtho[2,3-e][1,2,4]triazin-3-amine 1-oxide;

3-Chloro-6,7,8,9-tetrahydronaphtho[2,3-e][1,2,4]triazine 1-oxide;

$N^1$-(1-Oxido-6,7,8,9-tetrahydronaphtho[2,3-e][1,2,4]triazin-3-yl)-$N^2$,$N^2$-dimethyl-1,2-ethanediamine;

$N^1$-(1,4-Dioxido-6,7,8,9-tetrahydronaphtho[2,3-e][1,2,4]triazin-3-yl)-$N^2$,$N^2$-dimethyl-1,2-ethanediamine;

N-[3-(4-Morpholinyl)propyl]-6,7,8,9-tetrahydronaphtho[2,3-e][1,2,4]triazin-3-amine 1-oxide;

N-[3-(4-Morpholinyl)propyl]-6,7,8,9-tetrahydronaphtho[2,3-e][1,2,4]triazin-3-amine 1,4-dioxide;

7,8,9,10-Tetrahydro-6H-cyclohepta[g][1,2,4]benzotriazin-3-amine 1-oxide;

3-Chloro-7,8,9,10-tetrahydro-6H-cyclohepta[g][1,2,4]benzotriazine 1-oxide;

$N^1$,$N^1$-Dimethyl-$N^2$-(1-oxido-7,8,9,10-tetrahydro-6H-cyclohepta[g][1,2,4]benzotriazin-3-yl)-1,2-ethanediamine;

$N^1$-(1,4-Dioxido-7,8,9,10-tetrahydro-6H-cyclohepta[g][1,2,4]benzotriazin-3-yl)-$N^2$,$N^2$-dimethyl-1,2-ethanediamine;

6,7-Dihydrofuro[3,2-g][1,2,4]benzotriazin-3-amine 1-oxide;

3-Chloro-6,7-dihydrofuro[3,2-g][1,2,4]benzotriazine 1-oxide;

$N^1$,$N^1$-Dimethyl-$N^2$-(1-oxido-6,7-dihydrofuro[3,2-g][1,2,4]benzotriazin-3-yl)-1,2-ethanediamine;

$N^1$-(1,4-Dioxido-6,7-dihydrofuro[3,2-g][1,2,4]benzotriazin-3-yl)-$N^2$,$N^2$-dimethyl-1,2-ethanediamine;

N-[3-(4-Morpholinyl)propyl]-6,7-dihydrofuro[3,2-g][1,2,4]benzotriazin-3-amine 1-oxide;

N-[3-(4-Morpholinyl)propyl]-6,7-dihydrofuro[3,2-g][1,2,4]benzotriazin-3-amine 1,4-dioxide;

3-Amino-7,8-dihydrobenzofuro[6,5-e][1,2,4]triazine 1-oxide;

1,4-Dioxido-7,8-dihydrofuro[2,3-g][1,2,4]benzotriazin-3-ylamine;

3-Chloro-7,8-dihydro-6H-indeno[5,6-e][1,2,4]triazine 1-oxide;

$N^1$-(1-Oxido-7,8-dihydrofuro[2,3-g][1,2,4]benzotriazin-3-yl)-$N^2$,$N^2$-dimethyl-1,2-ethanediamine;

$N^1$-(1,4-Dioxido-7,8-dihydrofuro[2,3-g][1,2,4]benzotriazin-3-yl)-$N^2$,$N^2$-dimethyl-1,2-ethanediamine;

$N^1$-(1-Oxido-7,8-dihydrofuro[2,3-g][1,2,4]benzotriazin-3-yl)-$N^2$,$N^2$-diethyl-1,2-ethanediamine;

$N^1$-(1,4-Dioxido-7,8-dihydrofuro[2,3-g][1,2,4]benzotriazin-3-yl)-$N^2$,$N^2$-diethyl-1,2-ethanediamine;

N-[3-(4-Morpholinyl)propyl]-7,8-dihydrofuro[2,3-g][1,2,4]benzotriazin-3-amine 1-oxide;

N-[3-(4-Morpholinyl)propyl]-7,8-dihydrofuro[2,3-g][1,2,4]benzotriazin-3-amine 1,4-dioxide;

3-Iodo-7,8-dihydrobenzofuro[6,5-e][1,2,4]triazine 1-oxide;

3-(1-Oxido-7,8-dihydrofuro[2,3-g][1,2,4]benzotriazin-3-yl)propanal;

3-[3-(4-Morpholinyl)propyl]-7,8-dihydrofuro[2,3-g][1,2,4]benzotriazine 1-oxide;

3-[3-(4-Morpholinyl)propyl]-7,8-dihydrofuro[2,3-g][1,2,4]benzotriazine 1,4-dioxide;

[1,3]Dioxolo[4,5-g][1,2,4]benzotriazin-3-amine 1-oxide;

3-Chloro[1,3]dioxolo[4,5-g][1,2,4]benzotriazine 1-oxide;

$N^1$,$N^1$-Dimethyl-$N^2$-(1-oxido[1,3]dioxolo[4,5-g][1,2,4]benzotriazin-3-yl)-1,2-ethanediamine;

$N^1$-(1,4-Dioxido[1,3]dioxolo[4,5-g][1,2,4]benzotriazin-3-yl)-$N^2$,$N^2$-dimethyl-1,2-ethanediamine;

9,10-Dihydro-8H-chromeno[6,5-e][1,2,4]triazin-3-amine 1-oxide;

3-Chloro-9,10-dihydro-8H-chromeno[6,5-e][1,2,4]triazine 1-oxide;

$N^1$,$N^1$-Dimethyl-$N^2$-(1-oxido-9,10-dihydro-8H-chromeno[6,5-e][1,2,4]triazin-3-yl)-1,2-ethanediamine;

$N^1$-(1,4-Dioxido-9,10-dihydro-8H-chromeno[6,5-e][1,2,4]triazin-3-yl)-$N^2$,$N^2$-dimethyl-1,2-ethanediamine;

7,8-Dihydro-6H-chromeno[6,7-e][1,2,4]triazin-3-amine 1-oxide;

3-Chloro-7,8-dihydro-6H-chromeno[6,7-e][1,2,4]triazine 1-oxide;

$N^1$,$N^1$-Dimethyl-$N^2$-(1-oxido-7,8-dihydro-6H-chromeno[6,7-e][1,2,4]triazin-3-yl)-1,2-ethanediamine;

$N^1$-(1,4-Dioxido-7,8-dihydro-6H-chromeno[6,7-e][1,2,4]triazin-3-yl)-$N^2$,$N^2$-dimethyl-1,2-ethanediamine;

N-[3-(4-Morpholinyl)propyl]-7,8-dihydro-6H-chromeno[6,7-e][1,2,4]triazin-3-amine 1-oxide;

N-[3-(4-Morpholinyl)propyl]-7,8-dihydro-6H-chromeno[6,7-e][1,2,4]triazin-3-amine 1,4-dioxide;

7-Ethyl-1-oxido-7,8-dihydro-6H-[1,2,4]triazino[5,6-f]isoindol-3-ylamine;

7-Ethyl-1,4-dioxido-7,8-dihydro-6H-[1,2,4]triazino[5,6-f]isoindol-3-ylamine;

7-Methyl-6,7,8,9-tetrahydro[1,2,4]triazino[6,5-g]isoquinolin-3-amine 1-oxide;

3-Chloro-7-methyl-6,7,8,9-tetrahydro[1,2,4]triazino[6,5-g]isoquinoline 1-oxide;

N-Ethyl-7-methyl-6,7,8,9-tetrahydro[1,2,4]triazino[6,5-g]isoquinolin-3-amine 1-oxide;

N-Ethyl-7-methyl-6,7,8,9-tetrahydro[1,2,4]triazino[6,5-g]isoquinolin-3-amine 1,4-dioxide;

3-Ethyl-7-methyl-6,7,8,9-tetrahydro[1,2,4]triazino[6,5-g]isoquinoline 1-oxide;

3-Ethyl-7-methyl-6,7,8,9-tetrahydro[1,2,4]triazino[6,5-g]isoquinoline 1,4-dioxide;

9-Methyl-7,8,9,10-tetrahydro[1,2,4]triazino[5,6-h]isoquinolin-3-amine 1-oxide;

3-Chloro-9-methyl-7,8,9,10-tetrahydro[1,2,4]triazino[5,6-h]isoquinoline 1-oxide;

3-Ethyl-9-methyl-7,8,9,10-tetrahydro[1,2,4]triazino[5,6-h]isoquinoline 1-oxide;

3-Ethyl-9-methyl-7,8,9,10-tetrahydro[1,2,4]triazino[5,6-h]isoquinoline 1,4-dioxide;

3-(3-(4-(Dimethylamino)butanoyloxy)propyl)-7,8-dihydro-6H-indeno[5,6-e][1,2,4]triazine 1-oxide; and 3-(3-(2-(tert-Butoxycarbonylamino)-3-methylbutanoyloxy)propyl)-7,8-dihydro-6H-indeno[5,6-e][1,2,4]triazine 1-oxide.

14. A compound of Formula I as claimed in claim 1 selected from 3-[3-(4-Morpholinyl)propyl]-7,8-dihydro-6H-indeno[5,6-e][1,2,4]triazine 1,4-Dioxide or N-[3-(4-Morpholinyl)propyl]-7,8-dihydro-6H-indeno[5,6-e][1,2,4]triazin-3-amine 1,4-dioxide.

15. A method of therapy for treating cancers comprising the steps of:
administering a compound of Formula I as defined in claim 1 in a therapeutically effective amount to a subject having tumour cells, wherein the subject's tumour cells are in a hypoxic environment; and administering radiotherapy to the subject before, during or after the administration of the compound of Formula I.

16. The method as claimed in claim 15 further including the step of administering one or more chemotherapeutic agents to the subject before, during or after the administration of the compound of Formula I.

17. The method as claimed in claim 16 wherein the one or more chemotherapeutic agents are selected from Cisplatin or other platinum-based derivatives, Temozolomide or other DNA methylating agents, Cyclophosphamide or other DNA alkylating agents, Doxorubicin, mitoxantrone, camptothecin or other topoisomerase inhibitors, Methotrexate, gemcitabine or other antimetabolites and Docetaxel or other taxanes.

18. The method as claimed in claim 15 wherein the subject is human.

19. A pharmaceutical composition including a therapeutically effective amount of a compound of formula I as defined in claim 1 and a pharmaceutically acceptable excipient, adjuvant, carrier, buffer or stabiliser.

20. A method of improving the response of a tumour in a subject to radiotherapy, comprising the steps of:

(a) administering to the subject a pharmaceutical composition comprising a compound of Formula I as defined in claim 1 in an amount sufficient to kill or radiosensitise hypoxic cells in tumours, and (b) subjecting the tumour to radiation either before or after administration of the said pharmaceutical composition.

21. The method as claimed in claim 20 wherein the subject is human.

22. A method of making a compound of Formula I or a pharmacologically acceptable salt thereof,

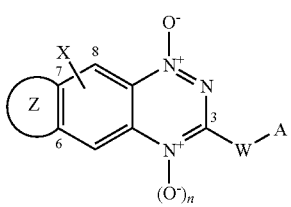

Formula I wherein, n, X, Z, W and A are as defined in claim 1, the method including the steps of reacting a nitroaniline compound of Formula II

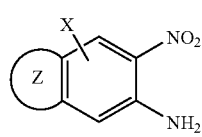

Formula II wherein X and Z are as defined above for a compound of Formula I, with cyanamide followed by a cyclisation step under basic conditions to give a mono-oxide compound of Formula I where n represents 0 and of optionally oxidising the mono-oxide compound of Formula I to form a dioxide compound of Formula I where n represents 1.

23. The method as claimed in claim 22 further including the steps of converting a monoxide of Formula III

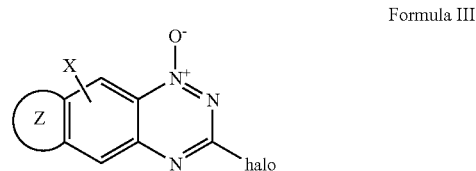

Formula III wherein X and Z are as defined above for a compound of Formula I; to a mono-oxide compound of Formula IV

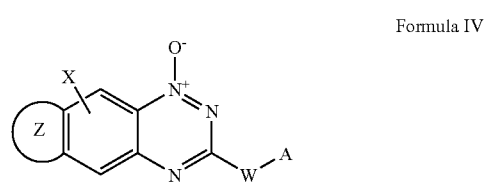

Formula IV wherein X and Z are as defined above for a compound of Formula III and W and A are as defined in claim 22 and together represent other than halo; and of optionally oxidising the resulting mono-oxide compound to form a dioxide compound of Formula I

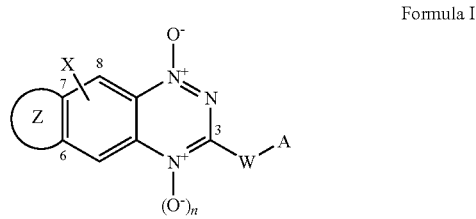

Formula I where n represents 1 and X, Z, W and A are as defined in claim 22.

24. The method as claimed in claim 23, wherein halo of Formula III represents chloro, bromo or iodo.

25. A method of making a compound of Formula I as defined in claim 1 including the step of reacting a nitroaniline compound of Formula II

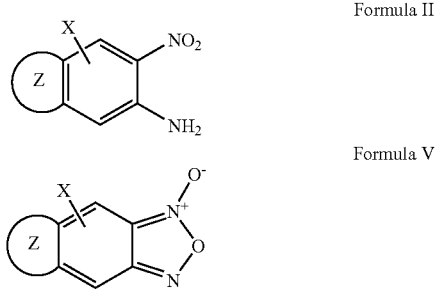

Formula II

Formula V wherein X and Z are as defined in claim 1 for a compound of Formula I, with sodium hypochlorite in the presence of a base to form a furoxan of Formula V wherein X and Z are as defined in claim 1 for a compound of Formula I, and reacting the compound of Formula V with a substituted cyanamide to give a dioxide compound of Formula I where n represents 1.

26. A method of making a compound of Formula I as defined in claim 22 with reference to Schemes 1 to 37 and 52 respectively set forth below:

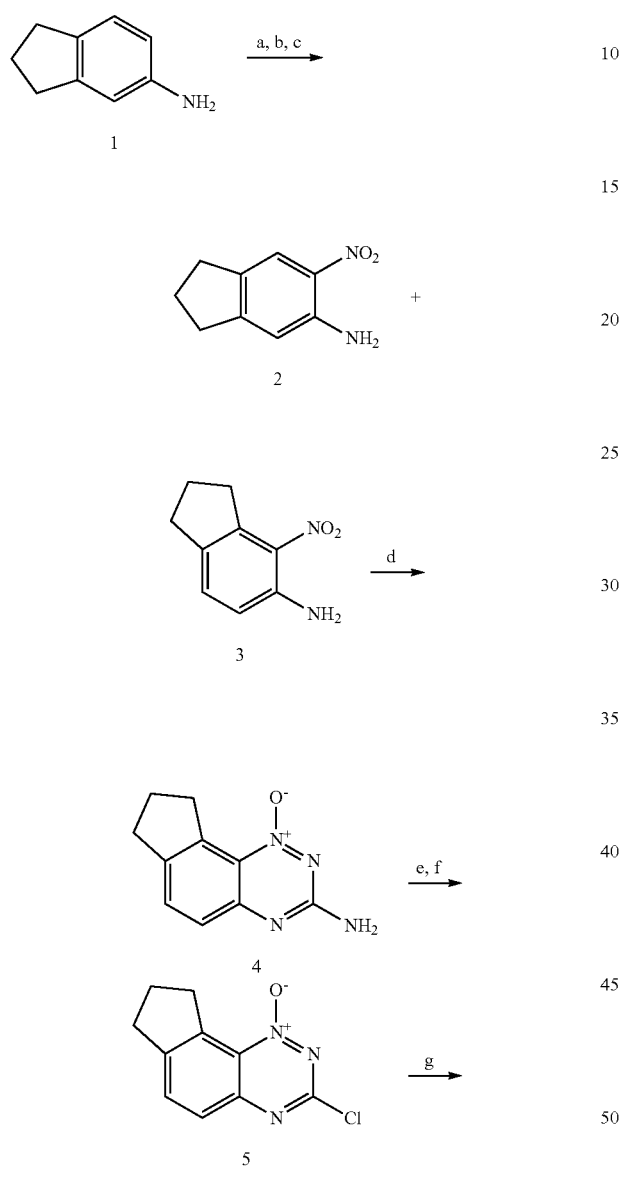

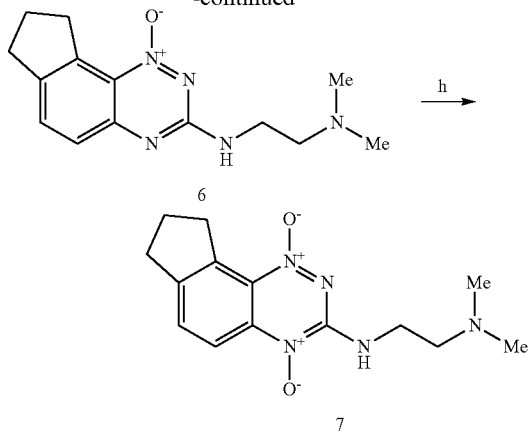

wherein a-h are reagents as follows:
  a) Ac$_2$O, dioxane;
  b) KNO$_3$, cH$_2$SO$_4$;
  c) 5 M HCl;
  d) NH$_2$CN, HCl; then NaOH;
  e) NaNO$_2$; TFA;
  f) POCl$_3$, DMF;
  g) NH$_2$CH$_2$CH$_2$NMe$_2$, DME;
  h) CF$_3$CO$_3$H, CF$_3$CO$_2$H, DCM;

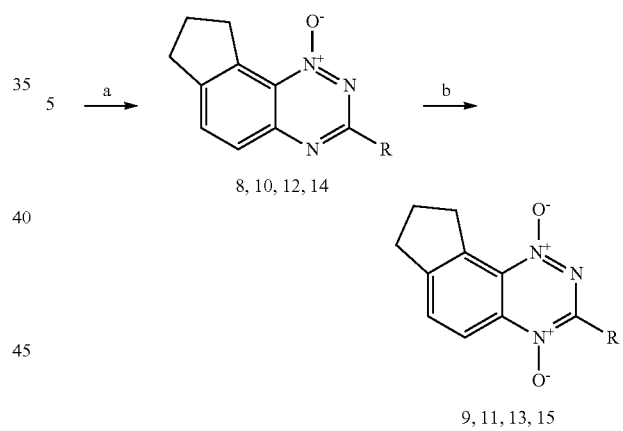

wherein a and b are reagents as follows:
  a) amine, DME;
  b) CF$_3$CO$_3$H, CF$_3$CO$_2$H, DCM;

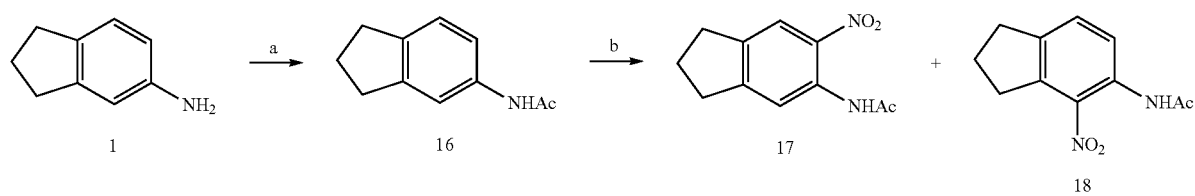

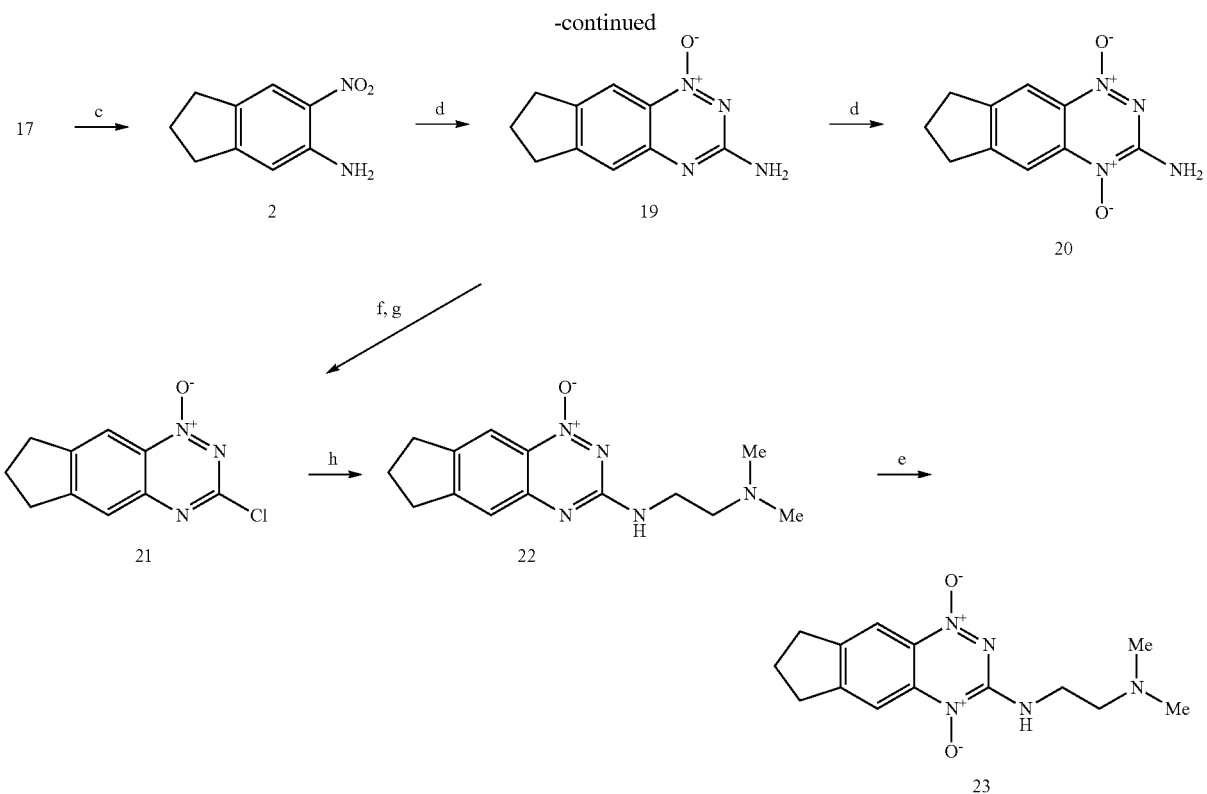
wherein a-h are reagents as follows:
a) Ac$_2$O, dioxane;
b) cHNO$_3$, HOAc;
c) cHCl, EtOH;
d) NH$_2$CN, HCl; then NaOH;
e) CF$_3$CO$_3$H, CF$_3$CO$_2$H, DCM;
d) NaNO$_2$, TFA;
g) POCl$_3$, DMF;
h) NH$_2$CH$_2$CH$_2$NMe$_2$, DME;
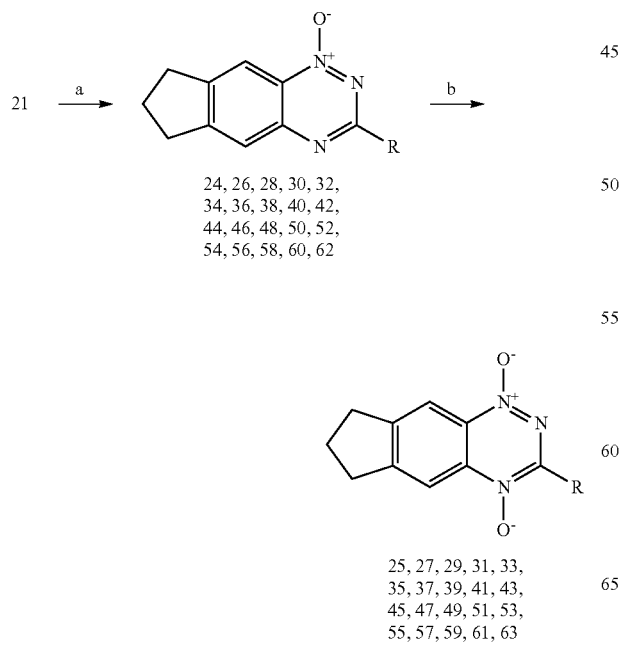
24, 26, 28, 30, 32, 34, 36, 38, 40, 42, 44, 46, 48, 50, 52, 54, 56, 58, 60, 62
25, 27, 29, 31, 33, 35, 37, 39, 41, 43, 45, 47, 49, 51, 53, 55, 57, 59, 61, 63
wherein a and b are reagents as follows:
a) amine, DME; or amine, Et$_3$N, DME;
b) CF$_3$CO$_3$H, CF$_3$CO$_2$H, DCM;
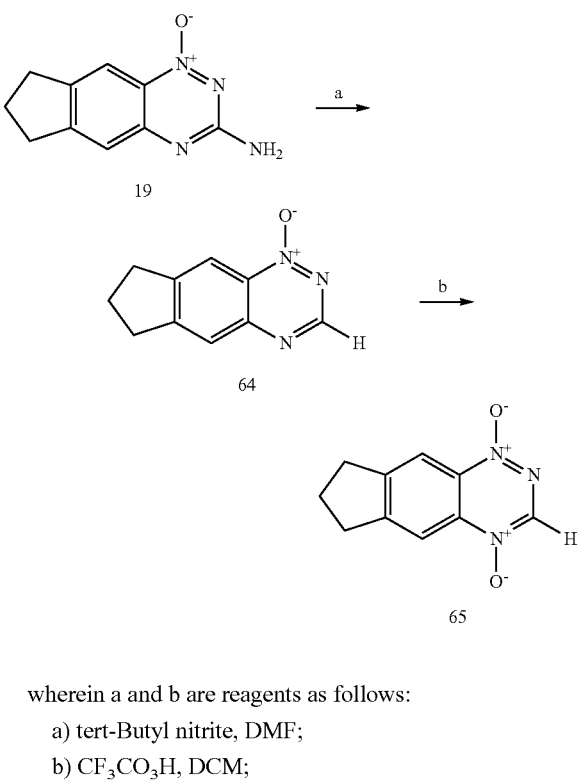
wherein a and b are reagents as follows:
a) tert-Butyl nitrite, DMF;
b) CF$_3$CO$_3$H, DCM;

183 184
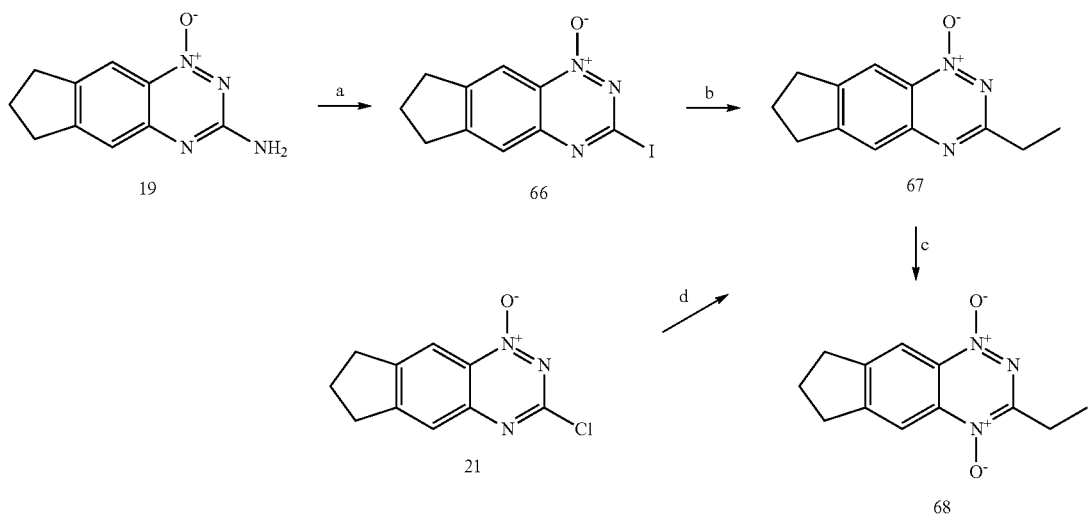
wherein a-d are reagents as follows:
 a) tert-BuNO$_2$, CH$_2$I$_2$, CuI, THF;
 b) EtMgBr, ZnCl$_2$.Et$_2$O, Pd(PPh$_3$)$_4$, THF;
 c) CF$_3$CO$_3$H, DCM
 d) Et$_4$Sn, Pd(dppf)Cl$_2$, THF;
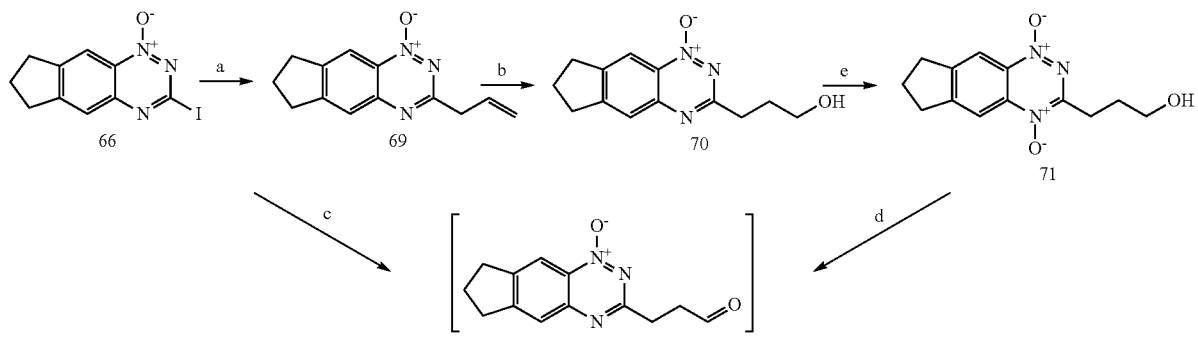
wherein a-e are reagents as follows:
 a) AllylSnBu$_3$, Pd(PPh$_3$)$_4$, THF;
 b) 9-BBN, THF; NaOH, H$_2$O$_2$;
 c) Allyl alcohol, Pd(OAc)$_2$, nBu$_4$NCl, NaHCO$_3$, MeCN;
 d) NaBH$_4$, MeOH, −40° C.;
 e) CF$_3$CO$_3$H, DCM;
-continued
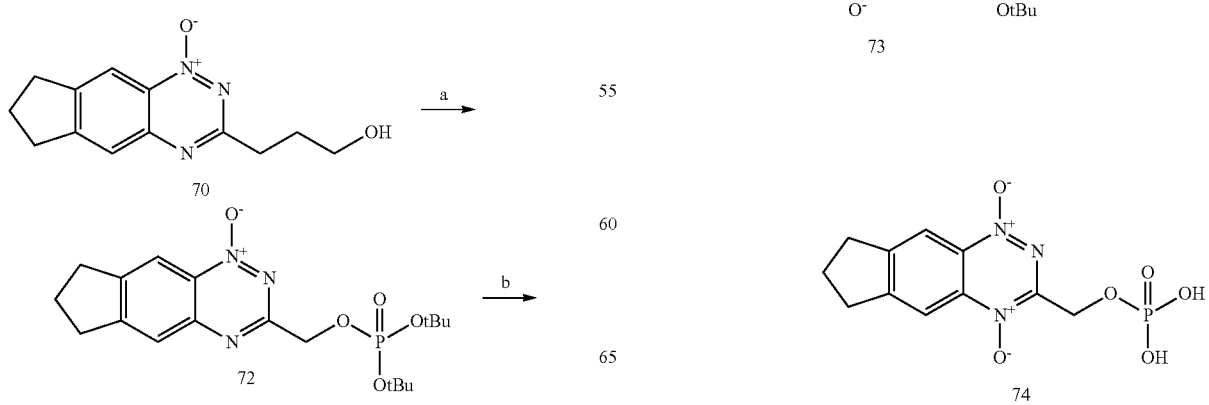

wherein a-c are reagents as follows:
  a) Di-tert-butyldiethylphosphoramidite, tetrazole, THF, then MCPBA;
  b) MCPBA, NaHCO₃, DCM;
  c) CF₃CO₂H, DCM;

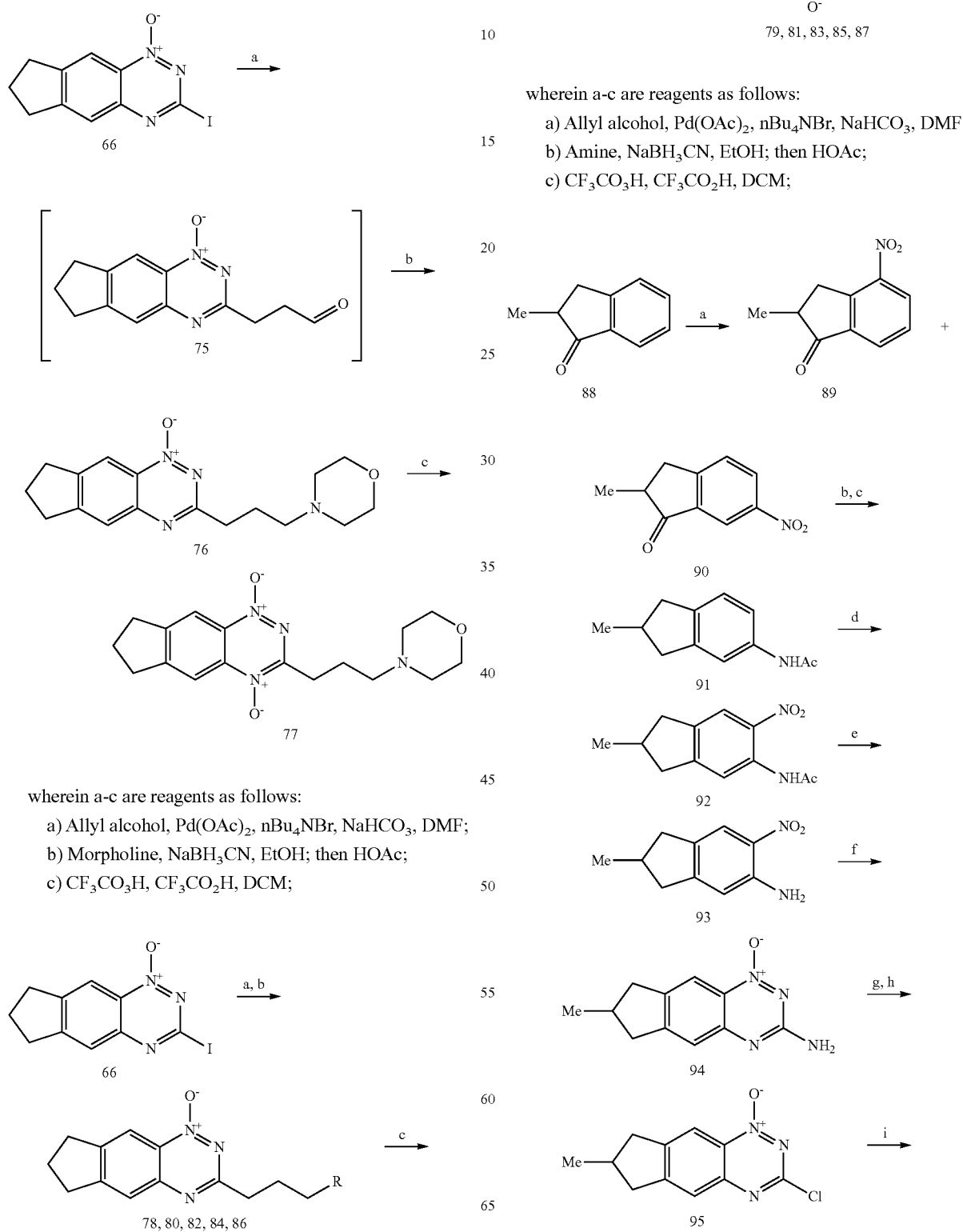

wherein a-c are reagents as follows:
  a) Allyl alcohol, Pd(OAc)₂, nBu₄NBr, NaHCO₃, DMF;
  b) Amine, NaBH₃CN, EtOH; then HOAc;
  c) CF₃CO₃H, CF₃CO₂H, DCM;

wherein a-c are reagents as follows:
  a) Allyl alcohol, Pd(OAc)₂, nBu₄NBr, NaHCO₃, DMF;
  b) Morpholine, NaBH₃CN, EtOH; then HOAc;
  c) CF₃CO₃H, CF₃CO₂H, DCM;

187 188
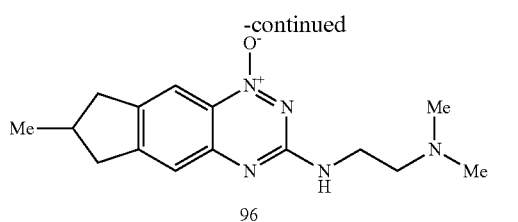
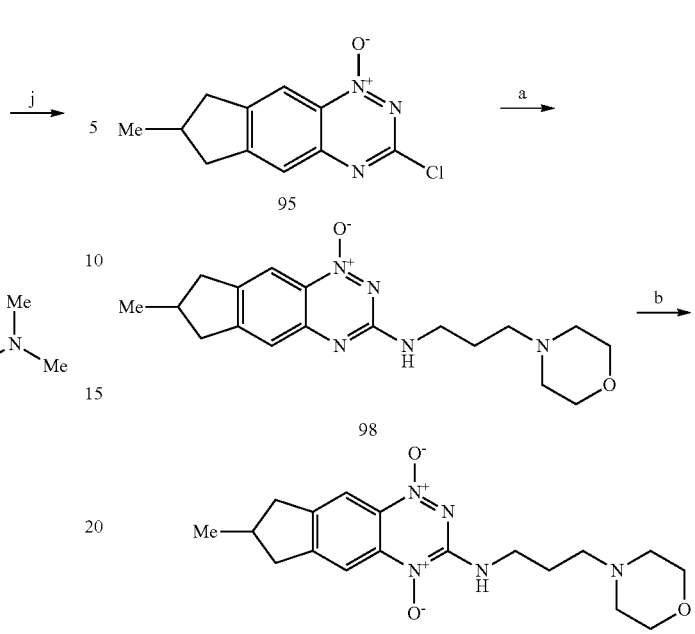
wherein a-j are reagents as follows:
a) fHNO₃;
b) H₂, Pd/C, EtOH, aq HCl;
c) Ac₂O, dioxane;
d) HNO₃, CF₃CO₂H;
e) cHCl, EtOH;
f) NH₂CN, HCl; then NaOH;
g) NaNO$_a$, TFA;
h) POCl₃, DMF;
i) NH₂CH₂CH₂NMe₂, DME;
CF₃CO₃H, CF₃CO₂H, DCM;
wherein a and b are reagents as follows:
a) NH₂CH₂CH₂CH₂Nmorpholine, Et₃N, DME;
b) CF₃CO₃H, CF₃CO₂H, DCM;
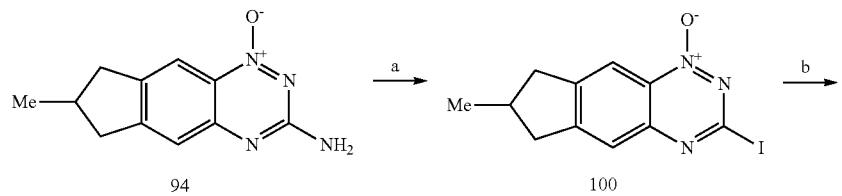
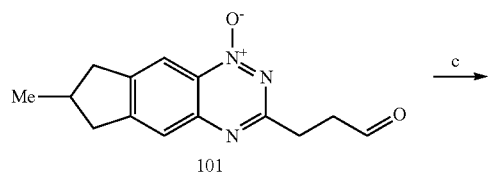
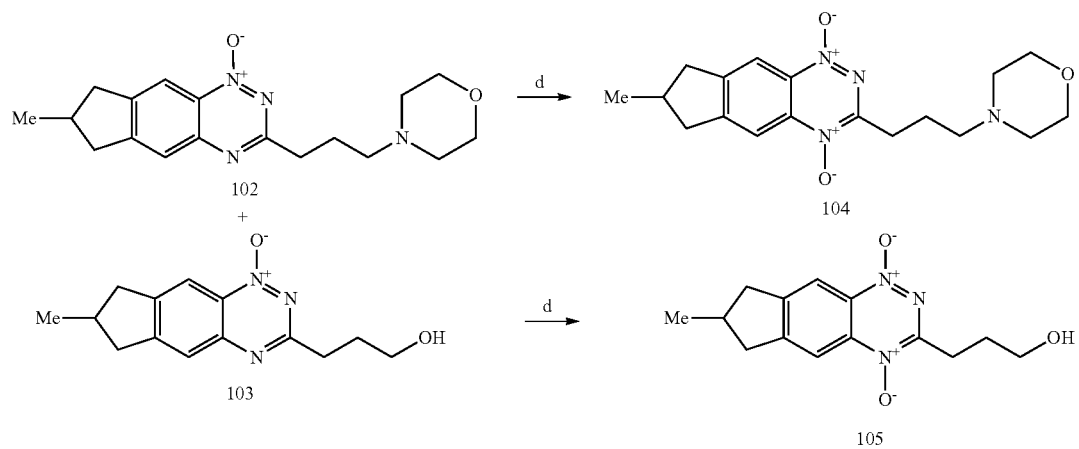

wherein a-d are reagents as follows:
 a) tBuNO$_2$, CH$_2$I$_2$, CuI, THF;
 b) Allyl alcohol, Pd(OAc)$_2$, nBu$_4$NBr, NaHCO$_3$, DMF;
 c) Morpholine, NaBH$_3$CN, EtOH; then HOAc;
 c) CF$_3$CO$_3$H, CF$_3$CO$_2$H, DCM;

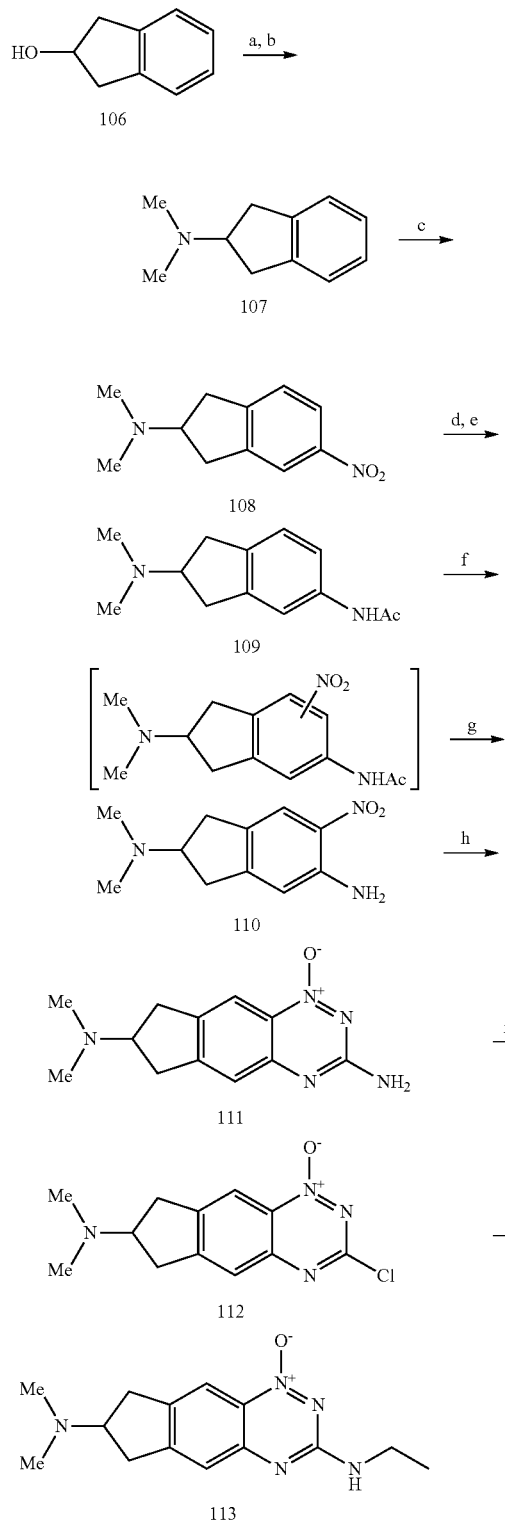

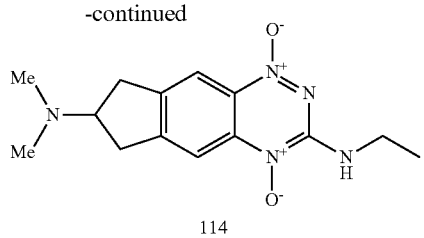

wherein a-l are reagents as follows:
 a) MsCl, iPr$_2$NEt, DCM;
 b) aq. HNMe$_2$, DMF;
 c) cHNO$_3$, CF$_3$CO$_2$H;
 d) H$_2$, Pd/C, EtOH;
 e) Ac$_2$O, dioxane;
 f) cHNO$_3$, CF$_3$CO$_2$H;
 g) cHCl, EtOH;
 h) NH$_2$CN, HCl; then NaOH;
 i) NaNO$_2$, TFA;
 j) POCl$_3$, DMF;
 k) aq. EtNH$_2$, DME;
 l) CF$_3$CO$_3$H, DCM;

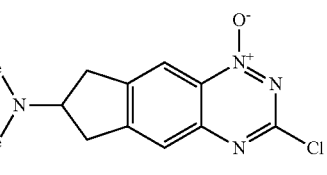

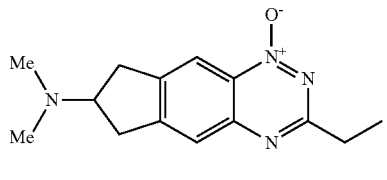

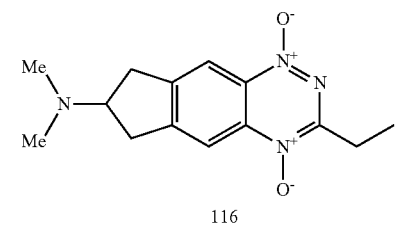

wherein a and b are reagents as follows:
 a) Et$_4$Sn, Pd(PPh$_3$)$_4$, DME;
 b) CF$_3$CO$_3$H, CF$_3$CO$_2$H, DCM;

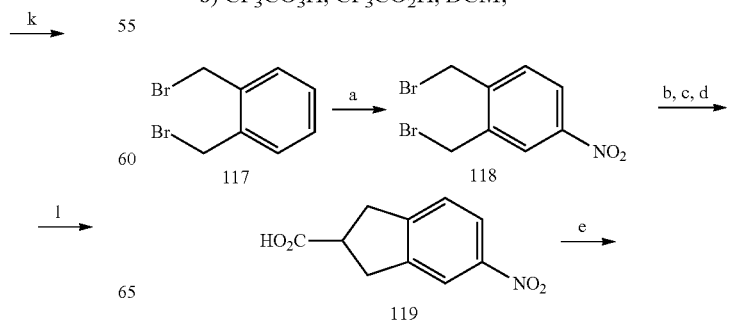

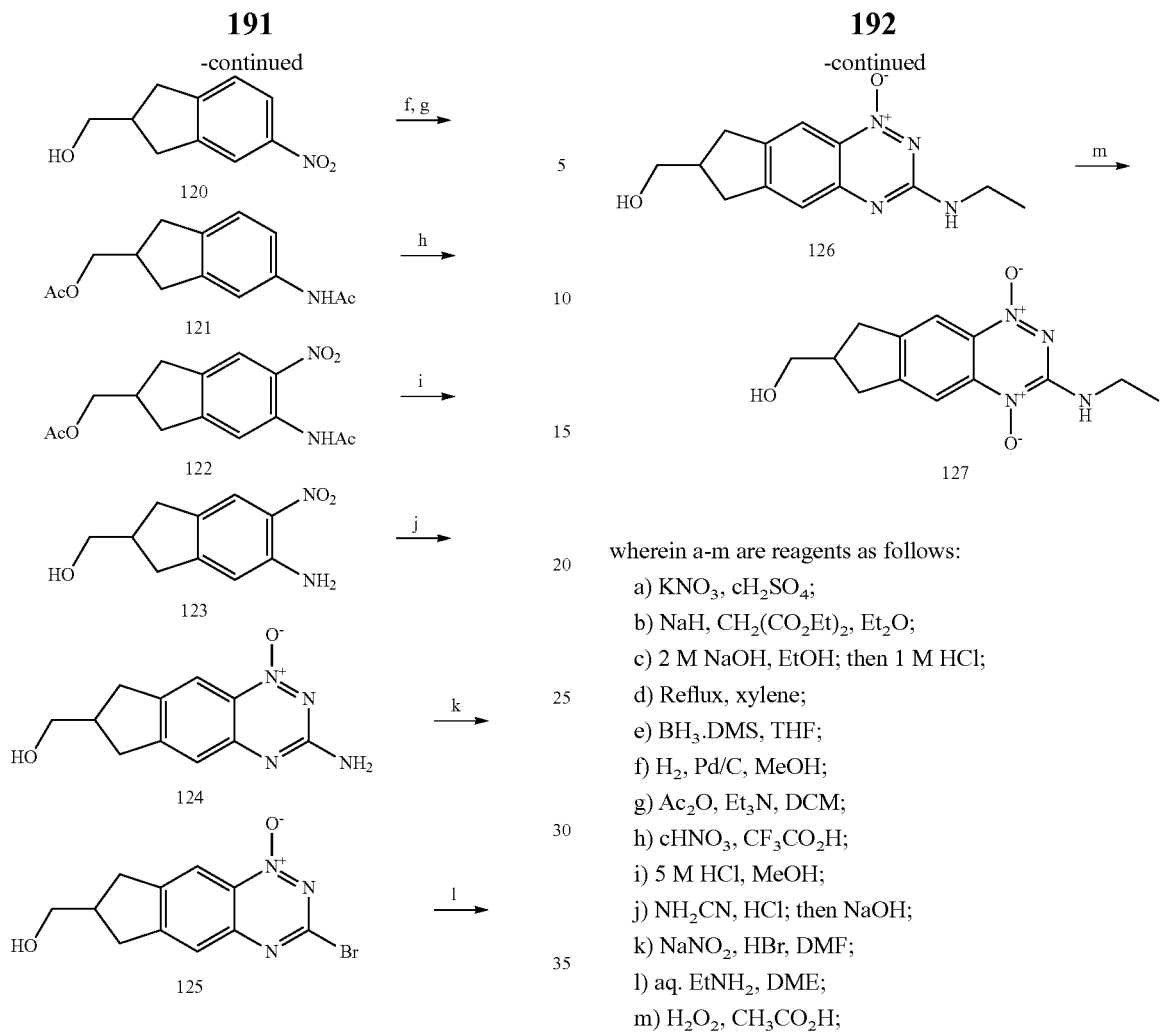
wherein a-m are reagents as follows:
  a) KNO$_3$, cH$_2$SO$_4$;
  b) NaH, CH$_2$(CO$_2$Et)$_2$, Et$_2$O;
  c) 2 M NaOH, EtOH; then 1 M HCl;
  d) Reflux, xylene;
  e) BH$_3$.DMS, THF;
  f) H$_2$, Pd/C, MeOH;
  g) Ac$_2$O, Et$_3$N, DCM;
  h) cHNO$_3$, CF$_3$CO$_2$H;
  i) 5 M HCl, MeOH;
  j) NH$_2$CN, HCl; then NaOH;
  k) NaNO$_2$, HBr, DMF;
  l) aq. EtNH$_2$, DME;
  m) H$_2$O$_2$, CH$_3$CO$_2$H;
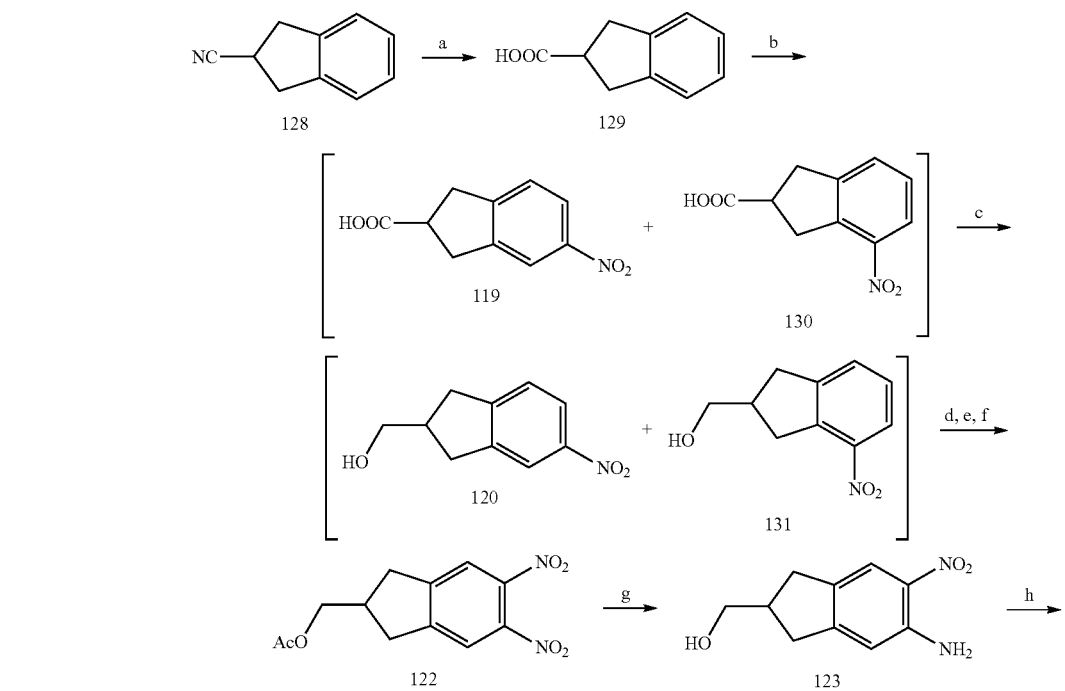

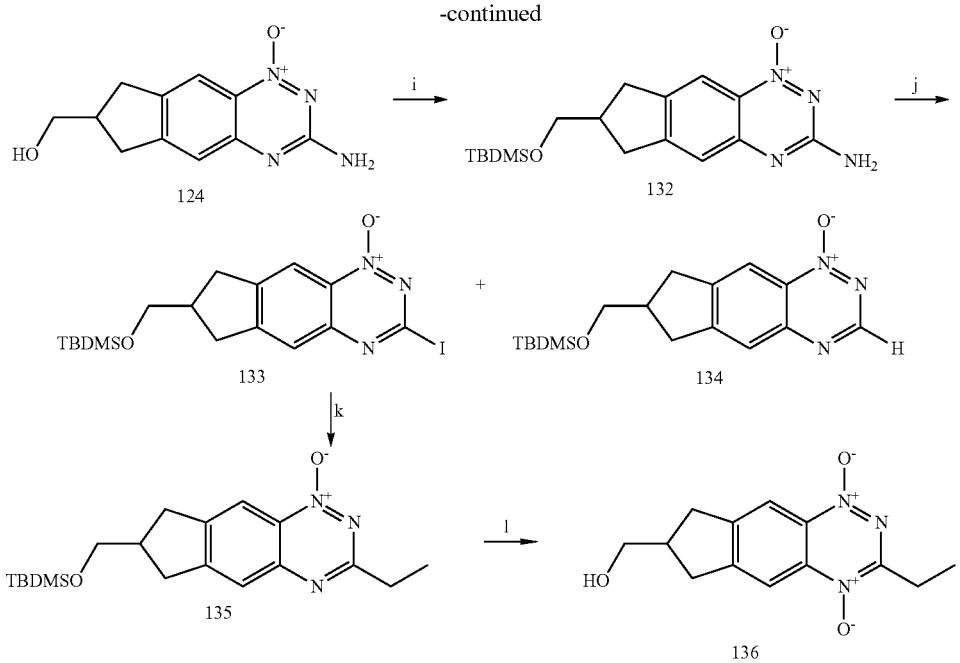

wherein a-l are reagents as follows:
a) cHCl, dioxane;
b) cHNO$_3$, CF$_3$CO$_2$H;
c) BH$_3$.DMS, THF;
d) H$_2$, Pd/C, MeOH;
e) Ac$_2$O, Et$_3$N, DCM;
g) 5 M HCl; MeOH;
h) NH$_2$CN, HCl; then NaOH;
i) TBDMSCl, iPr$_2$NEt, DMF;
j) tert-BuNO$_2$, CH$_2$I$_2$, CuI, THF;
k) Et$_4$Sn, Pd(PPh$_3$)$_4$, DME;
l) H$_2$O$_2$, CH$_3$CO$_2$H;

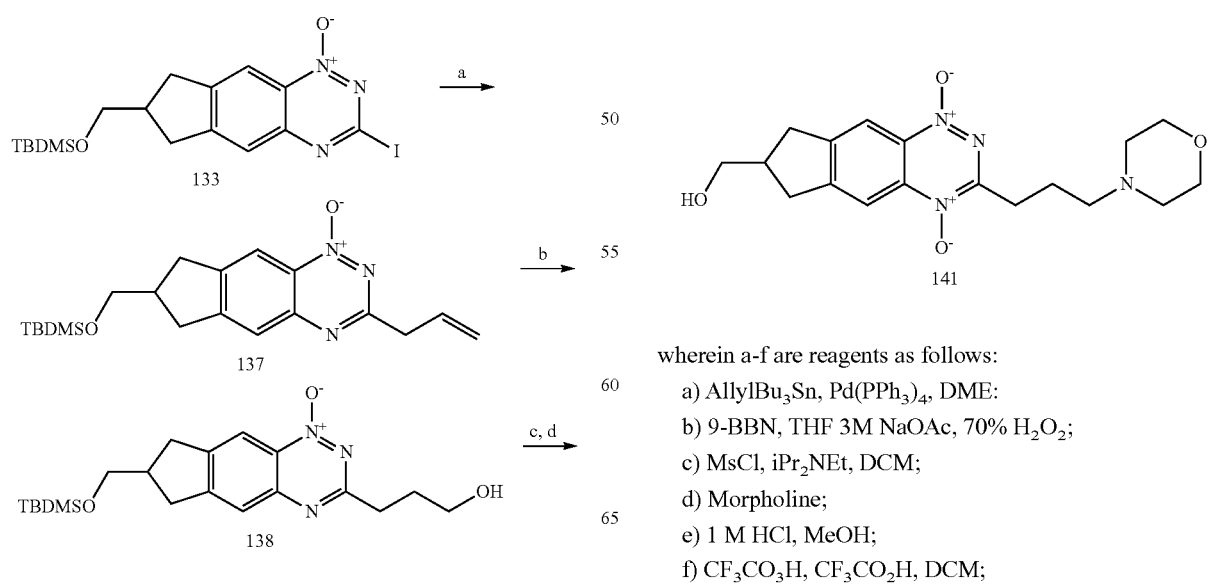

wherein a-f are reagents as follows:
a) AllylBu$_3$Sn, Pd(PPh$_3$)$_4$, DME:
b) 9-BBN, THF 3M NaOAc, 70% H$_2$O$_2$;
c) MsCl, iPr$_2$NEt, DCM;
d) Morpholine;
e) 1 M HCl, MeOH;
f) CF$_3$CO$_3$H, CF$_3$CO$_2$H, DCM;

195
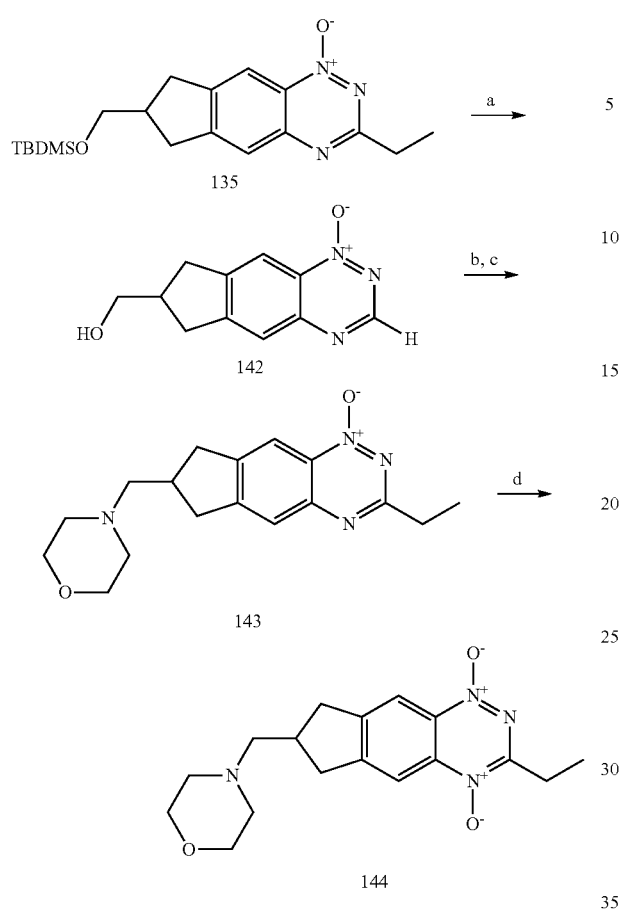
wherein a-d are reagents as follows:
 a) 1 M HCl, MeOH;
 b) MsCl, iPr$_2$NEt, DCM;
 c) Morpholine;
 d) CH$_3$CO$_3$H, CH$_3$CO$_2$H, DCM;
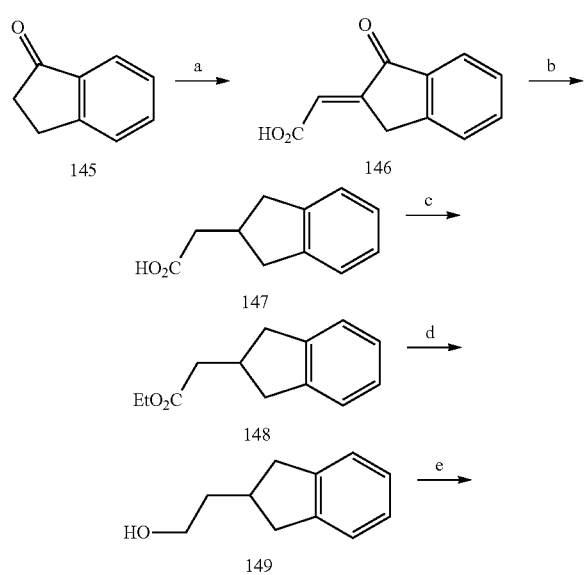
196
-continued
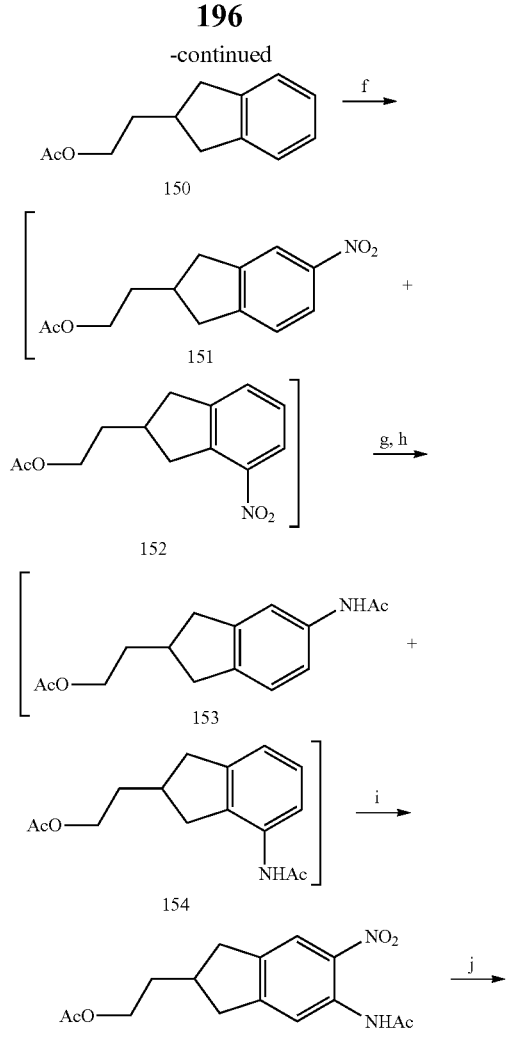
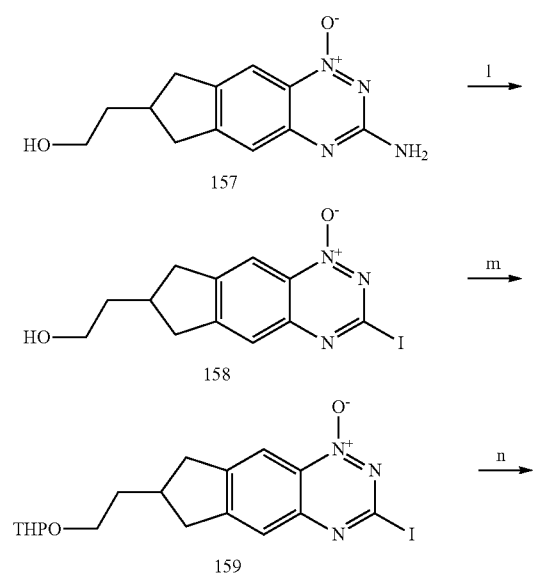

wherein a-p are reagents as follows:
a) aq. glyoxylic acid, cH$_2$SO$_4$;
b) H$_2$, Pd/C, MeOH, dioxane;
c) cH$_2$SO$_4$, EtOH;
d) LiAlH$_4$, THF;
e) Ac$_2$O, pyridine, DMAP, DCM;
f) Ac$_2$O, Cu(NO$_3$)$_2$.3H$_2$O, DCM;
g) H$_2$, Pd/C, MeOH;
h) Ac$_2$O, dioxane;
i) cHNO$_3$, CF$_3$CO$_2$H;
j) 5 M HCl, MeOH;
k) NH$_2$CN, HCl; then NaOH;
l) tert-BuNO$_2$, I$_2$, CuI, THF;
m) Dihydropyran, PPTS, DCM;
n) Et$_4$Sn, Pd(PPh$_3$)$_4$, DME;
o) MeSO$_3$H, MeOH;
p) CF$_3$CO$_2$H, DCM;

wherein a-c are reagents as follows:
a) MsCl, NEt$_3$, DCM;
b) morpholine;
c) CF$_3$CO$_3$H, CF$_3$CO$_2$H, DCM;

199
-continued

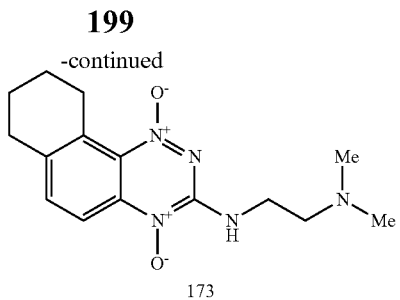
173 where a-k are reagents as follows:
a) KNO$_3$, cH$_2$SO$_4$;
b) H$_2$, Pd/C, EtOH, EtOAc, HCl;
c) Ac$_2$O, dioxane;
d) KNO$_3$, cH$_2$SO$_4$;
e) 6 M HCl;
f) NH$_2$CN, HCl;
g) NaOH;
h) NaNO$_2$, TFA;
i) POCl$_3$, DMF;
j) NH$_2$CH$_2$CH$_2$NMe$_2$, DME;
k) CF$_3$CO$_3$H, CF$_3$CO$_2$H, DCM;

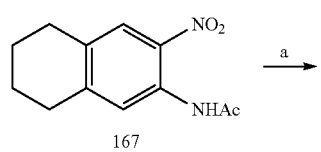
167

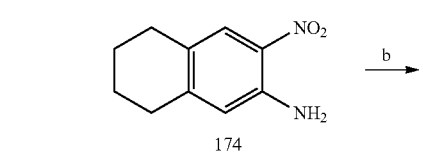
174

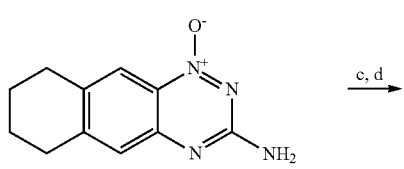
175

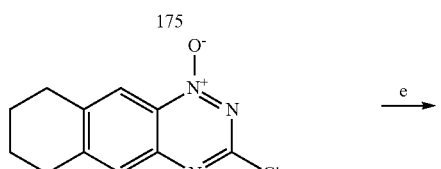
176

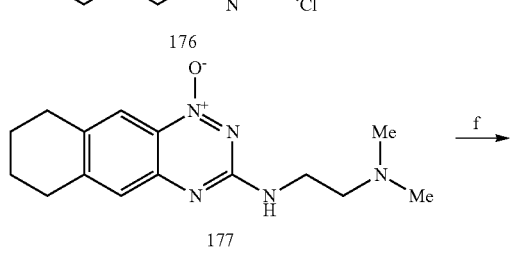
177

200
-continued

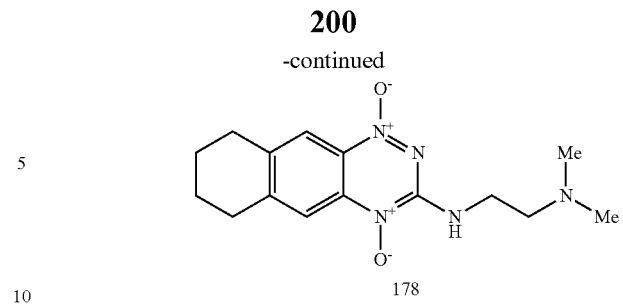
178 wherein a-f are reagents as follows:
a) HCl;
b) NH$_2$CN, HCl; then NaOH;
c) NaNO$_2$, TFA;
d) POCl$_3$, DMF;
e) NH$_2$CH$_2$CH$_2$NMe$_2$, DME;
f) CF$_3$CO$_3$H, CF$_3$CO$_2$H, DCM;

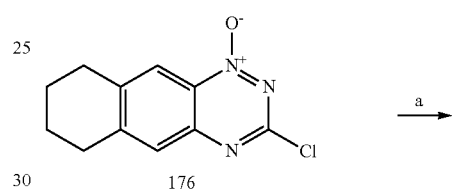
176

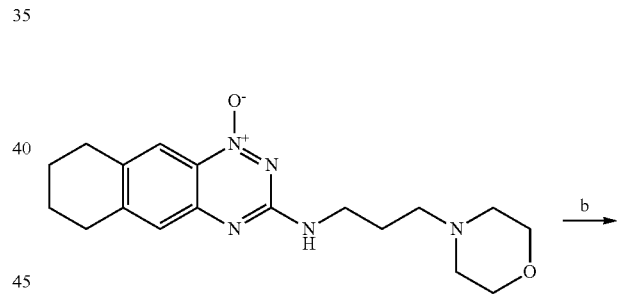
179

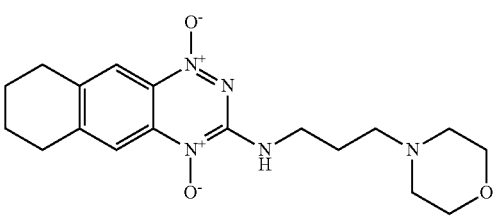
180 wherein a and b are reagents as follows:
a) NH$_2$CH$_2$CH$_2$Nmorpholine, Et$_3$N, DME;
b) CF$_3$CO$_3$H, CF$_3$CO$_2$H, DCM;

201
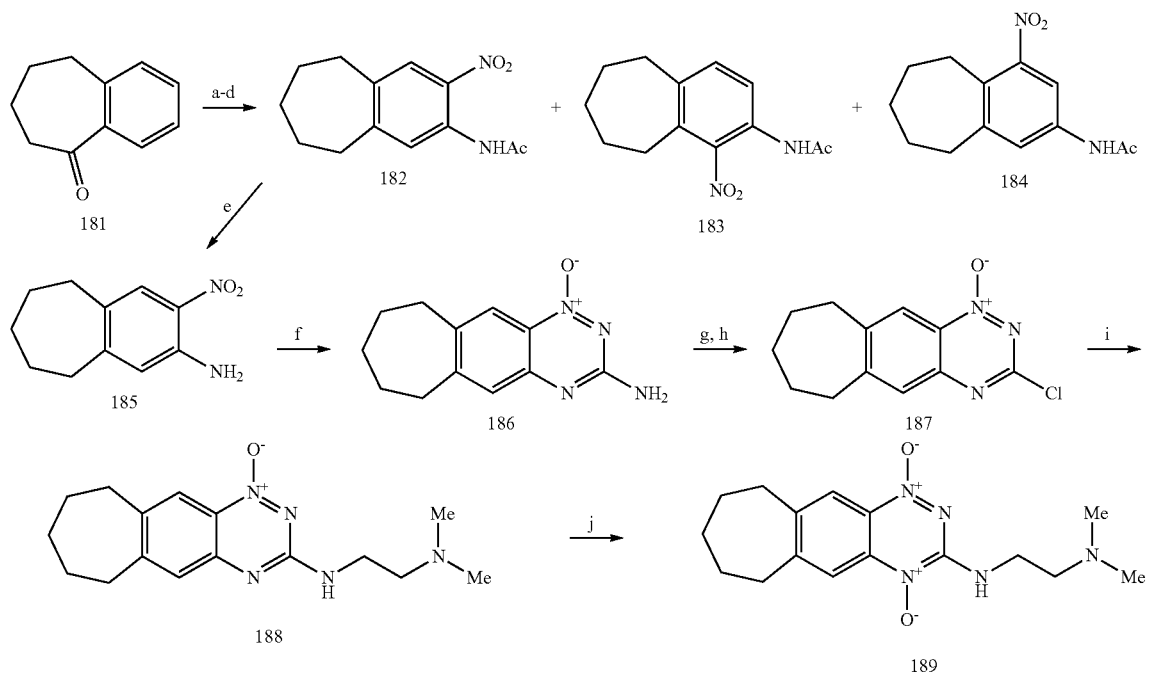
wherein a-j are reagents as follows:
a) fHNO$_3$, cH$_2$SO$_4$;
b) H$_2$, Pd/C, EtOH/EtOAc;
c) Ac$_2$O, dioxane;
d) KNO$_3$, cH$_2$SO$_4$;
e) 5 M HCl;
f) NH$_2$CN, HCl; then NaOH;
g) NaNO$_2$, TFA;
i) NH$_2$CH$_2$CH$_2$NMe$_2$, DME;
j) CF$_3$CO$_3$H, CF$_3$CO$_2$H, DCM;
202
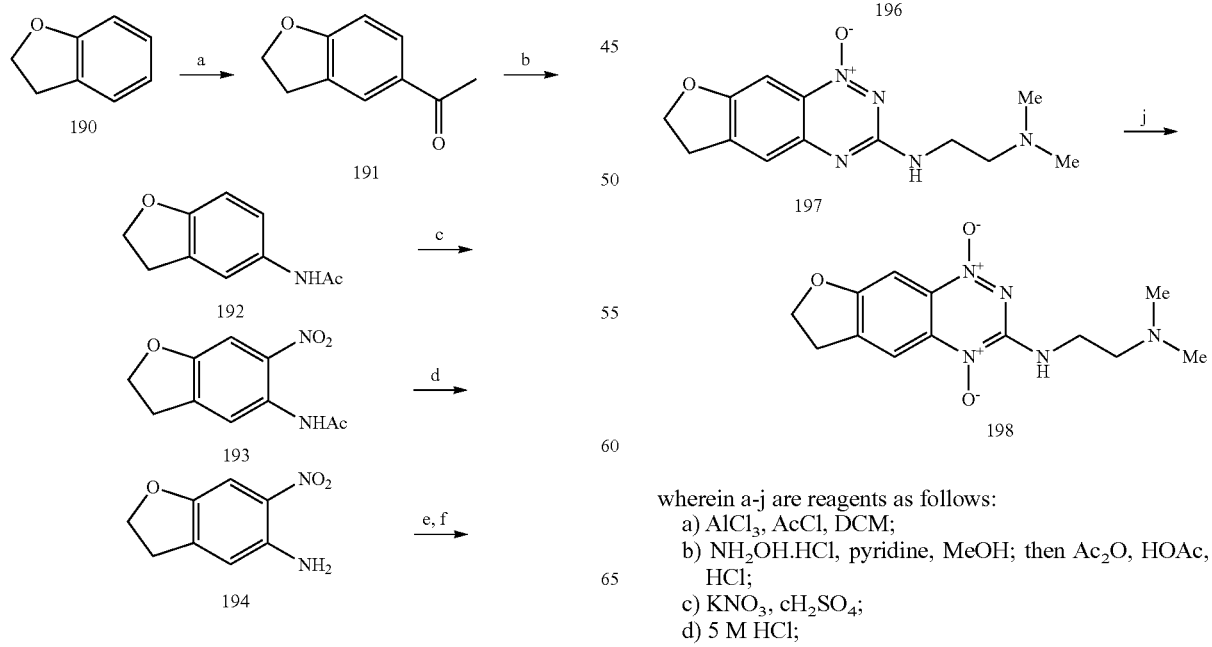
wherein a-j are reagents as follows:
a) AlCl$_3$, AcCl, DCM;
b) NH$_2$OH.HCl, pyridine, MeOH; then Ac$_2$O, HOAc, HCl;
c) KNO$_3$, cH$_2$SO$_4$;
d) 5 M HCl;

e) NH$_2$CN, HCl;
f) NaOH;
g) NaNO$_2$, TFA;
h) POCl$_3$
i) NH$_2$CH$_2$CH$_2$NMe$_2$, DME;
j) CF$_3$CO$_3$H, CF$_3$CO$_2$H, DCM;

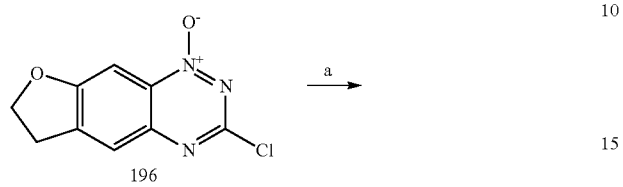
196

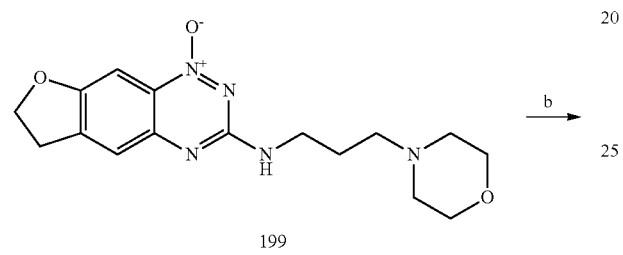
199

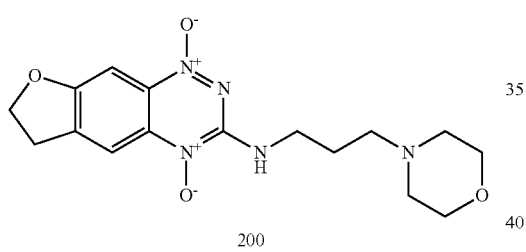
200 wherein a and b are reagents as follows:
a) NH$_2$CH$_2$CH$_2$Nmorpholine, DME;
b) CF$_3$CO$_3$H, CF$_3$CO$_2$H, DCM;

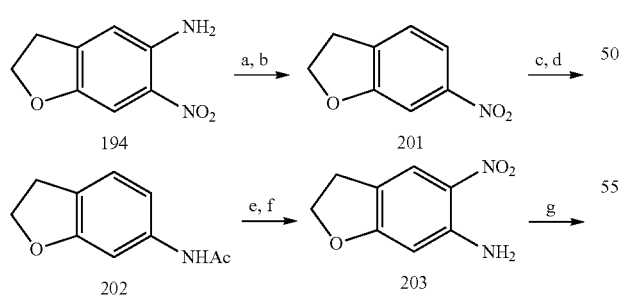
194   201
202   203

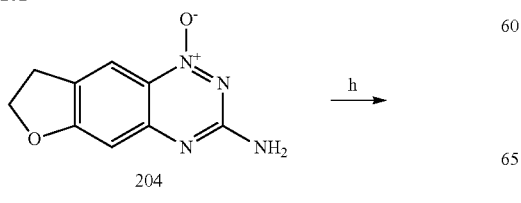
204

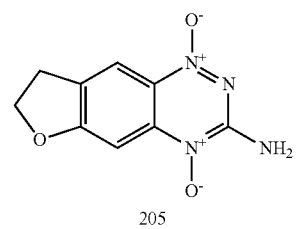
205 wherein a-h are reagents as follows:
a) NaNO$_2$, cH$_2$SO$_4$;
b) 50% aq. H$_3$PO$_2$;
c) H$_2$, PtO$_2$, EtOH;
d) Ac$_2$O, dioxane;
e) 70% HNO$_3$, HOAc;
f) cHCl, EtOH;
g) NH$_2$CN, HCl; then NaOH
h) CF$_3$CO$_3$H, CF$_3$CO$_2$H, DCM;

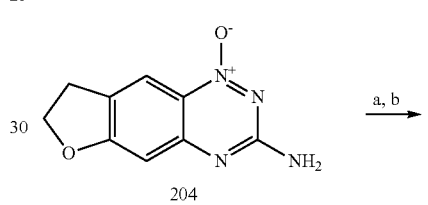
204

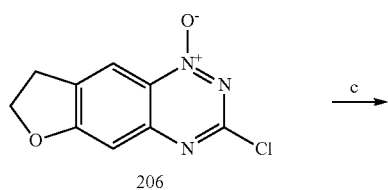
206

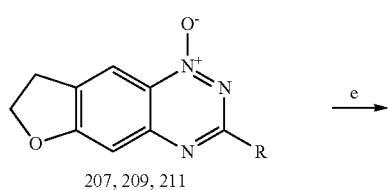
207, 209, 211

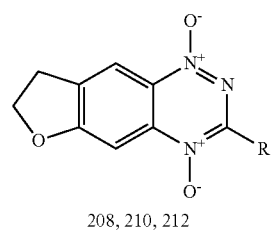
208, 210, 212 wherein a-d are reagents as follows:
a) NaNO$_2$, TFA;
b) POCl$_3$, DMF;
c) Amine, DME;
d) CF$_3$CO$_3$H, CF$_3$CO$_2$H, DCM;

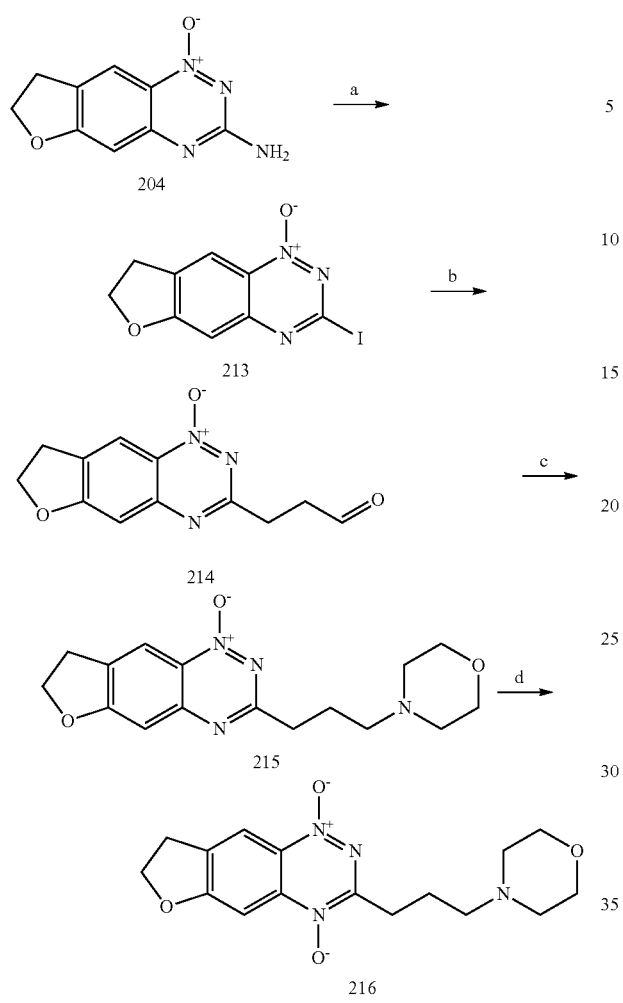
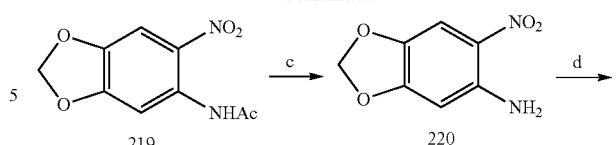
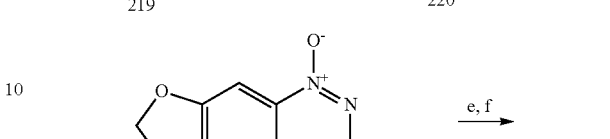
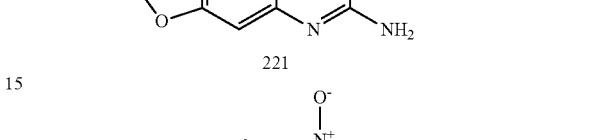
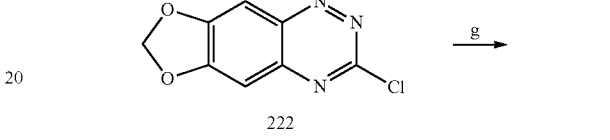
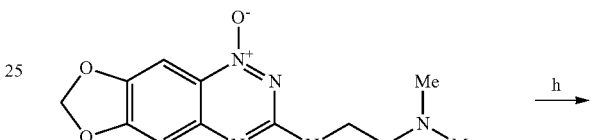
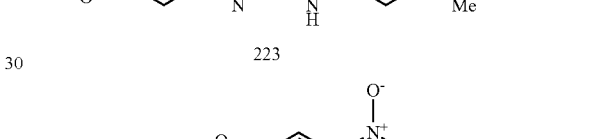
wherein a-d are reagents as follows:
  a) tert-BuNO₂, CH₂I₂, CuI, THF;
  b) allyl alcohol, Pd(OAc)₂, nBu₄NBr, NaHCO₃, DMF;
  c) morpholine, NaBH₃CN, EtOH; then HOAc;
  d) CF₃CO₃H, CF₃CO₂H, DCM;
wherein a-h are reagents as follows:
  a) Ac₂O, dioxane;
  b) cHNO₃, HOAc;
  c) NaOMe, MeOH;
  d) NH₂CN, HCl; then NaOH;
  e) NaNO₂, TFA;
  f) POCl₃, DMF;
  g) NH₂CH₂CH₂NMe₂, DME;
  h) CF₃CO₃H, CF₃CO₂H, DCM;
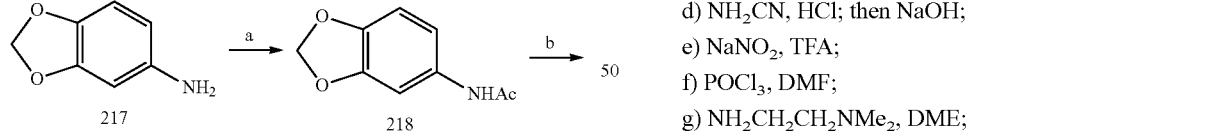
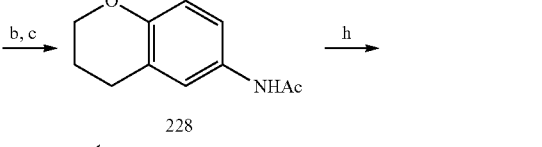

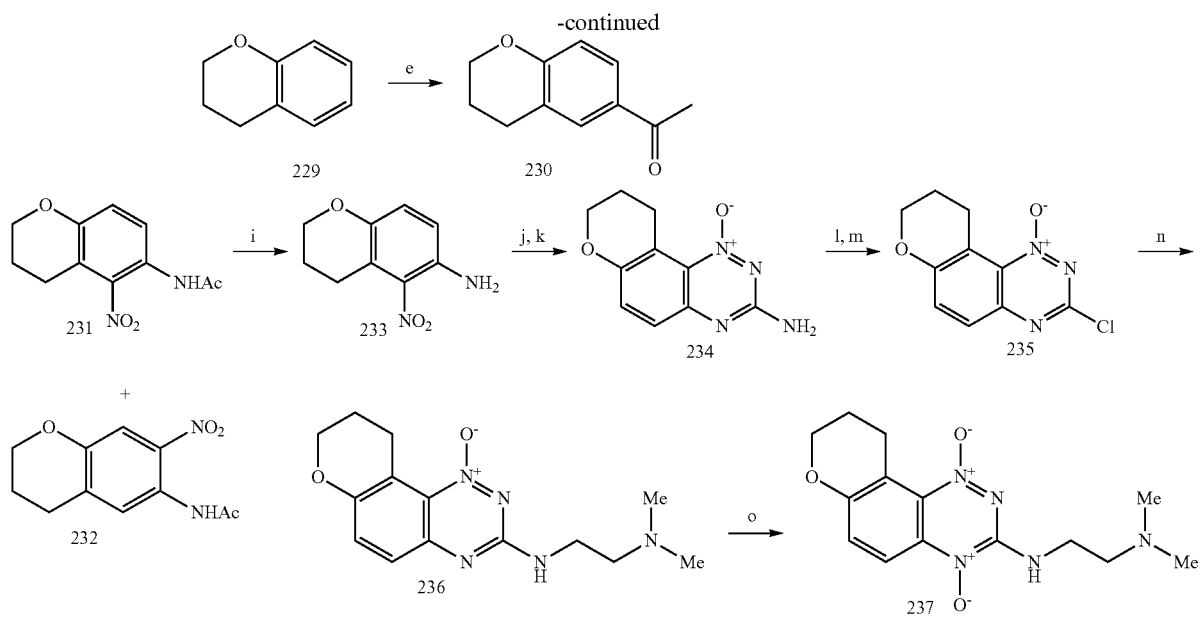
wherein a-o are reagents as follows:
a) KNO₃, cH₂SO₄;
b) H₂, Pd/C, EtOH/EtOAc, HCl;
c) Ac₂O, dioxane;
d) Zn, HOAc;
e) AlCl₃, AcCl, DCM;
f) NH₂OH.HCl, pyridine, MeOH;
g) Ac₂O, HOAc, HCl;
h) KNO₃, cH₂SO₄;
i) NaOH, aq EtOH;
j) NH₂CN, HCl;
k) NaOH:
l) NaNO₂, TFA;
m) POCl₃, DMF;
n) NH₂CH₂CH₂NMe₂, DME;
o) CF₃CO₃H, CF₃CO₂H, DCM;
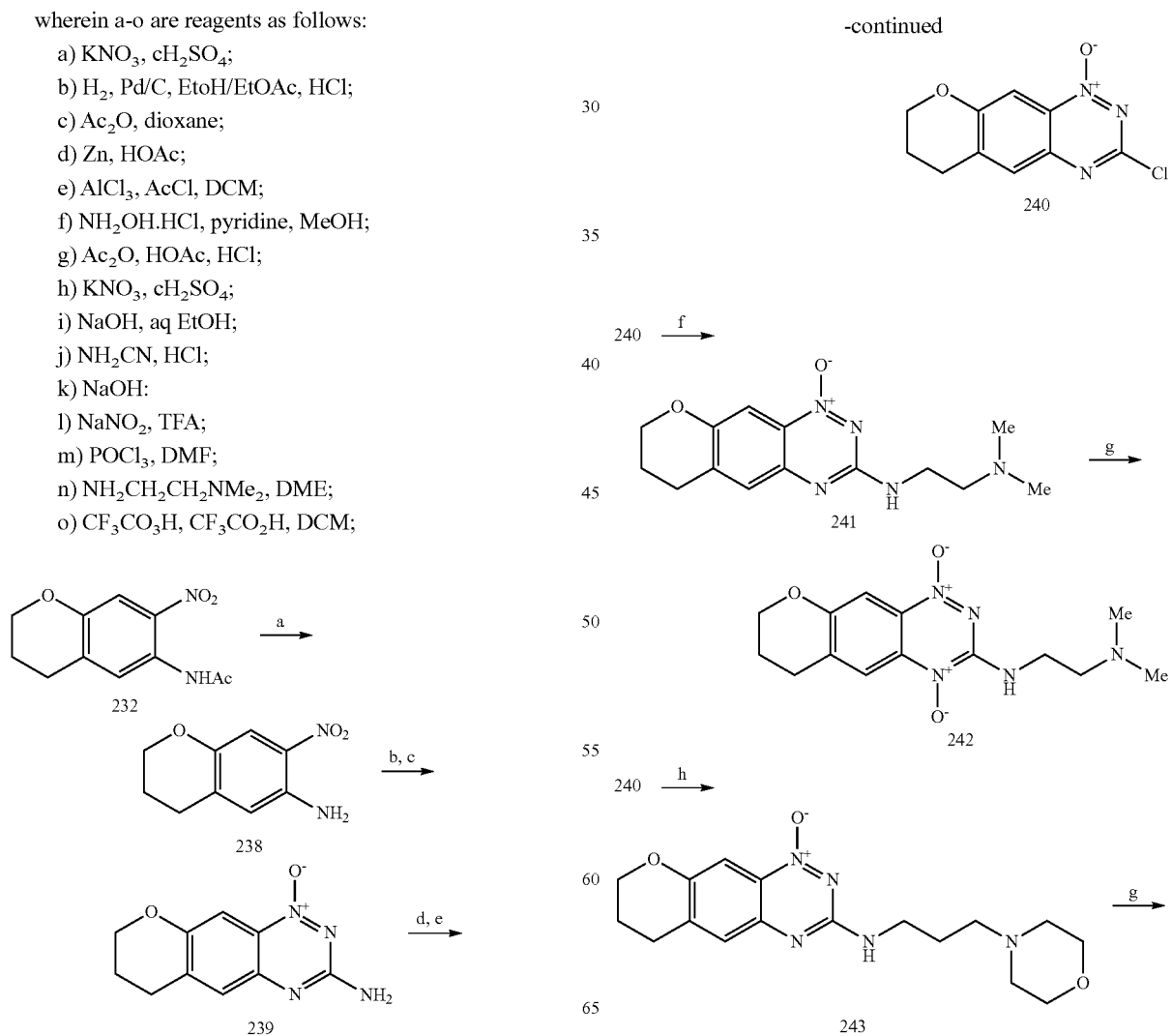

209
-continued
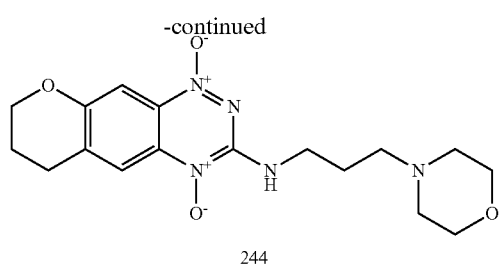
244
wherein a-h are reagents as follows:
 a) HCl, aq EtOH;
 b) NH$_2$CN, HCl;
 c) NaOH;
 d) NaNO$_2$, TFA;
 e) POCl$_3$, DMF;
 f) NH$_2$CH$_2$CH$_2$NMe$_2$, DME;
 g) CF$_3$CO$_3$H, CF$_3$CO$_2$H, DCM;
 h) NH$_2$CH$_2$CH$_2$Nmorpholine, DME;
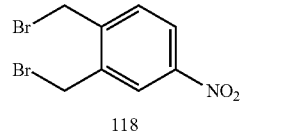
118
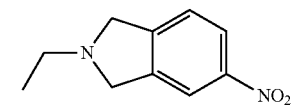
245
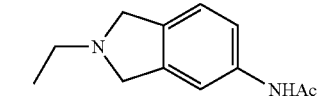
246
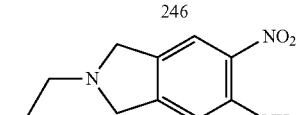
247
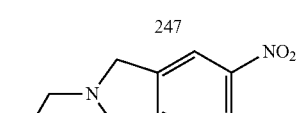
248
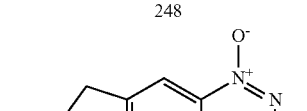
249
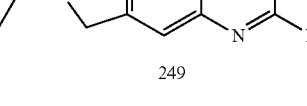
250
210
wherein a-q are reagents as follows:
 a) EtNH$_2$, Et$_3$N, DMF;
 b) H$_2$, Pd/C, MeOH;
 c) Ac$_2$O, dioxane;
 d) KNO$_3$, cH$_2$SO$_4$;
 e) 5 M HCl;
 f) NH$_2$CN, HCl, then NaOH;
 g) H$_2$O$_2$, CF$_3$CO$_2$H, DCM;
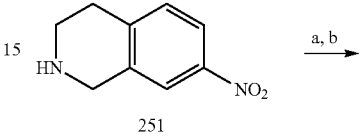
251
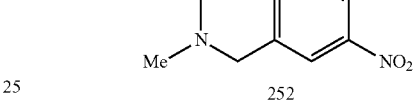
252
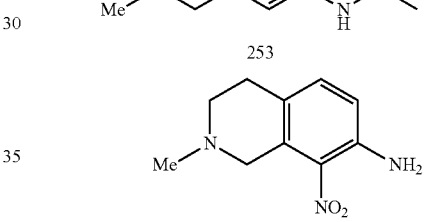
253
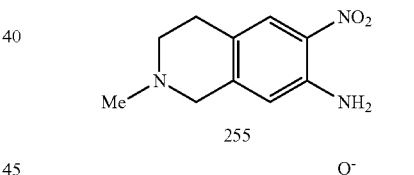
254
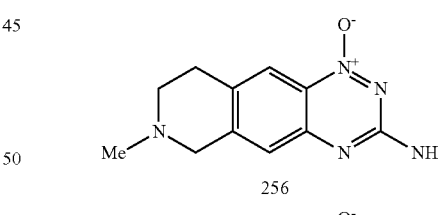
255
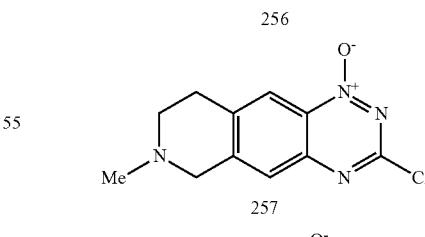
256
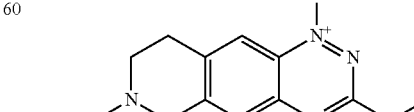
257
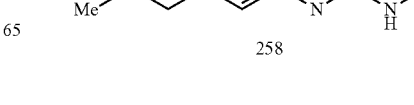
258

211

-continued

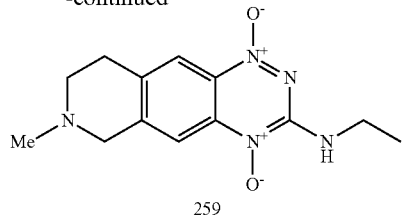
259 wherein a-k are reagents as follows:
  a) Ac₂O, HCO₂H, THF;
  b) BH₃.DMS, THF;
  c) H₂, Pd/C, EtOH;
  d) Ac₂O, dioxane;
  e) KNO₃, cH₂SO₄;
  f) 5 M HCl;
  g) NH₂CN, HCl; then NaOH;
  h) NaNO₂, TFA;
  i) POCl₃, DMF;
  j) EtNH₂, DME;
  k) CF₃CO₃, CF₃CO₂H, DCM;

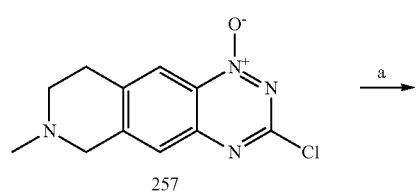
257

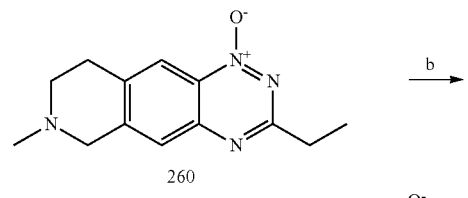
260

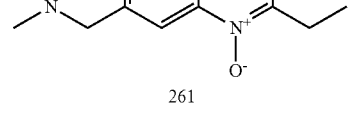
261 wherein a and b are reagents as follows:
  a) Et₄Sn, Pd(PPh₃)₄, DME;
  b) CF₃CO₃H, CF₃CO₂H, DCM;

212

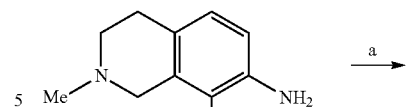
254

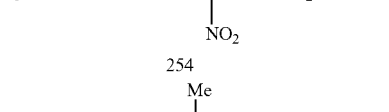
262

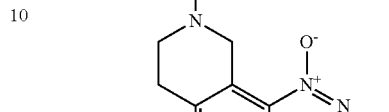
263

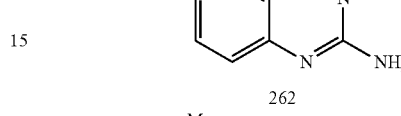
264

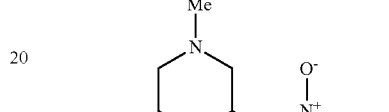
265 wherein a-e are reagents as follows:
  a) NH₂CN, HCl; then NaOH;
  b) NaNO₂, TFA;
  c) POCl₃, DMF;
  d) Et₄Sn, Pd(PPh₃)₄, DME;
  e) CF₃CO₃H, CF₃CO₂H, DCM;

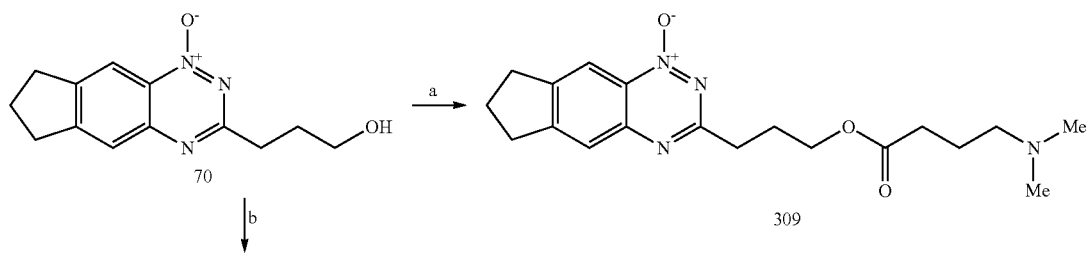

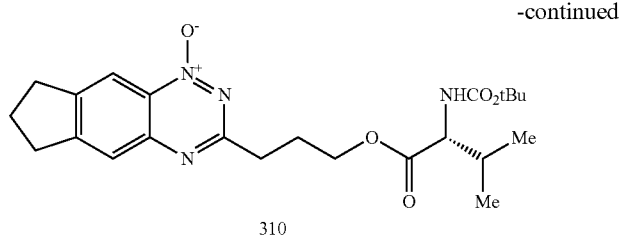
310 wherein a and b are reagents as follows:
  a) Me₂NCH₂CH₂CH₂CO₂H, DCC, DCM;
  b) NBOC-L-valine, DCC, DCM.

27. A compound of Formula I obtained by the method as claimed in claim 22.

28. A compound of claim 1, which is 3-[3-(4-Morpholinyl)propyl]-7,8-dihydro-6H-indeno[5,6-e][1,2,4]triazine 1,4-dioxide.

29. A pharmaceutical composition of claim 19, wherein the compound of Formula I is 3-[3-(4-Morpholinyl)propyl]-7,8-dihydro-6H-indeno[5,6-e][1,2,4]triazine 1,4-dioxide.

30. A method of claim 15, wherein the compound of Formula I is 3-[3-(4-Morpholinyl)propyl]-7,8-dihydro-6H-indeno[5,6-e][1,2,4]triazine 1,4-dioxide.

\* \* \* \* \*